(12) United States Patent
Tsuji et al.

(10) Patent No.: US 9,382,544 B2
(45) Date of Patent: Jul. 5, 2016

(54) APTAMER THAT RECOGNIZES PEPTIDE

(75) Inventors: Shotaro Tsuji, Setagaya-ku (JP); Jou Akitomi, Koto-ku (JP); Shintarou Katou, Koto-ku (JP); Iwao Waga, Koto-ku (JP); Takashi Ohtsu, Yokohama (JP)

(73) Assignee: NEC Solution Innovators, Ltd., Tokyo (JP)

(*) Notice: Subject to any disclaimer, the term of this patent is extended or adjusted under 35 U.S.C. 154(b) by 1268 days.

(21) Appl. No.: 13/320,462

(22) PCT Filed: May 14, 2010

(86) PCT No.: PCT/JP2010/058221
§ 371 (c)(1),
(2), (4) Date: Jan. 11, 2012

(87) PCT Pub. No.: WO2010/131748
PCT Pub. Date: Nov. 18, 2010

(65) Prior Publication Data
US 2012/0129720 A1      May 24, 2012

(30) Foreign Application Priority Data

May 15, 2009 (JP) .................................. 2009-119269

(51) Int. Cl.
| *C12N 15/115* | (2010.01) |
| *C07H 21/02* | (2006.01) |
| *C12N 15/113* | (2010.01) |
| *C12N 15/10* | (2006.01) |

(52) U.S. Cl.
CPC ............... *C12N 15/115* (2013.01); *C07H 21/02* (2013.01); *C12N 15/113* (2013.01); *C12N 15/1048* (2013.01); *C12N 2310/113* (2013.01); *C12N 2310/16* (2013.01); *C12N 2320/50* (2013.01)

(58) Field of Classification Search
CPC ............... C12N 15/115; C12N 15/113; C12N 15/1048; C12N 2310/113; C12N 2310/16; C12N 2320/50; C07H 21/02
See application file for complete search history.

(56) References Cited

U.S. PATENT DOCUMENTS

| 2005/0142582 A1* | 6/2005 | Doyle et al. ...................... 435/6 |
| 2010/0036106 A1 | 2/2010 | Yoshida et al. |

FOREIGN PATENT DOCUMENTS

| EP | 2554672 A1 | 2/2013 |
| WO | 2005/024042 A2 | 3/2005 |
| WO | 2005/030989 A1 | 4/2005 |
| WO | 2006-103772 A1 | 10/2006 |

(Continued)

OTHER PUBLICATIONS

Walter et al., "Systematic Investigation of Optimal Aptamer Immobilization for Protein-Microarray Applications", Anal. Chem., vol. 80. No. 19, pp. 7372-7378 (2008).

(Continued)

*Primary Examiner* — Jeremy C Flinders
(74) *Attorney, Agent, or Firm* — Sughrue Mion, PLLC

(57) ABSTRACT

An aptamer capable of binding to a histidine peptide is provided. A nucleic acid used as the aptamer capable of binding to a histidine peptide may be a nucleic acid containing the base sequence of SEQ ID NO: 17, SEQ ID NO: 18, or containing a base sequence obtained by substitution, deletion, addition, or insertion of one or more bases in SEQ ID NO: 17 or 18.

3 Claims, 7 Drawing Sheets

(56) References Cited

FOREIGN PATENT DOCUMENTS

WO   2008/066231 A1   6/2008
WO   2011125852 A1   10/2011

OTHER PUBLICATIONS

Extended European Search Report dated May 31, 2013 issued by the European Patent Office in counterpart European Patent Application No. 10775005.1.

Eiichiro Fukusaki et al., "Obtainment of Nucleic Acid Aptamer by SELEX Method", Journal of Bioscience and Bioengineering, 2001, pp. 350-354, vol. 79, No. 9.

Tsuji, S. et al., "RNA Aptamer Binding to Polyhistidine-Tag", Biochemical and Biophysical Research Communications, 2009, pp. 227-231, vol. 386.

Nimjee S.M. et al., "The potential of Aptamers as Anticoagulants", Trends Cardiovasc. Med., 2005, pp. 41-45 vol. 15, No. 1.

Nimjee S.M. et al., "Aptamers: An Emerging Class of Therapeutics", Annu., Rev., Med., 2005, pp. 555-583, vol. 56.

Eugene W.M. et al., "Pegaptanib, a Targeted anti-VEGF Aptamer for Ocular Vascular Disease", Nat. Rev. Drug Discov., 2006, pp. 123-132, vol. 5.

Huang Y.C. et al. "Immobilized DNA Switches as Electronic Sensors for Picomolar Detection of Plasma Proteins", J. Am. Chem. Soc., 2008, pp. 8023-8029, vol. 130, No. 25.

Deng C. et al., "Impedimetric Aptasensor with Femtomolar Sensitivity Based on the Enlargement of Surface-Charged Gold Nanoparticles", Anal. Chem., 2009, pp. 739-745, vol. 81, No. 2.

Xu H. et al., "Aptamer-Functionalized Gold Nanoparticles as Probes in a Dry-Reagent Strip Biosensor for Protein Analysis", Anal. Chem., 2009, pp. 669-675, vol. 81, No. 2.

Mairal T. et al., "Aptamers: Molecular Tools for Analytical Application", Anal. Bioanal. Chem., 2008, pp. 989-1007, vol. 390.

Bunka et al., "Aptamers Come of Age—At Last", Nat. Rev. Microbiol., 2006, pp. 588-596, vol. 4.

"Application of RNA aptamer against a peptide tag," Proceedings of the 31st Annual Meeting of the Molecular Biology Society of Japan and the 81st Annual Meeting of the Japanese Biochemical Society, p. 508, 2P-1435 (2008).

Communication dated Aug. 28, 2014 from the Japanese Patent Office in counterpart application No. 2011-513393.

* cited by examiner

SEQUENCE LISTING

```
<160> NUMBER OF SEQ ID NOS: 2347

<210> SEQ ID NO 1
<211> LENGTH: 80
<212> TYPE: RNA
<213> ORGANISM: Artificial
<220> FEATURE:
<223> OTHER INFORMATION: Aptamer

<400> SEQUENCE: 1
gggacgcuca cguacgcuca ccggguuauu ggcgcaauau gguauccug uauuggucug      60 ucagugccug gacgugcagu                                                80

<210> SEQ ID NO 2
<211> LENGTH: 80
<212> TYPE: RNA
<213> ORGANISM: Artificial
<220> FEATURE:
<223> OTHER INFORMATION: Aptamer

<400> SEQUENCE: 2
gggacgcuca cguacgcuca cguccgaucg auacugguau auuggcgccu ucguggaaug      60
ucagugccug gacgugcagu                                                80

<210> SEQ ID NO 3
<211> LENGTH: 80
<212> TYPE: RNA
<213> ORGANISM: Artificial
<220> FEATURE:
<223> OTHER INFORMATION: Aptamer

<400> SEQUENCE: 3
gggacgcuca cguacgcuca ccuguuuugu cuagguuuau ggcgcuuau uccuggaaug       60 ucagugccug gacgugcagu                                                80

<210> SEQ ID NO 4
<211> LENGTH: 80
<212> TYPE: RNA
<213> ORGANISM: Artificial
<220> FEATURE:
<223> OTHER INFORMATION: Aptamer

<400> SEQUENCE: 4
gggacgcuca cguacgcuca cucaggugau uggcgcuauu uaucgaucga uaauugaaug      60
ucagugccug gacgugcagu                                                80

<210> SEQ ID NO 5
<211> LENGTH: 80
<212> TYPE: RNA
<213> ORGANISM: Artificial
<220> FEATURE:
<223> OTHER INFORMATION: Aptamer

<400> SEQUENCE: 5
gggacgcuca cguacgcuca uguuccuuug gguuauggc uccuuguuga ccaggggaug       60
ucagugccug gacgugcagu                                                80

<210> SEQ ID NO 6
<211> LENGTH: 80
<212> TYPE: RNA
```

```
<213> ORGANISM: Artificial
<220> FEATURE:
<223> OTHER INFORMATION: Aptamer

<400> SEQUENCE: 6
gggacgcuca cguacgcuca caacacucga aggguuuauu ggccccacca ugguggaaug    60
ucagugccug gacgugcagu                                                80

<210> SEQ ID NO 7
<211> LENGTH: 80
<212> TYPE: RNA
<213> ORGANISM: Artificial
<220> FEATURE:
<223> OTHER INFORMATION: Aptamer

<400> SEQUENCE: 7
gggacgcuca cguacgcuca cgguuauugg cggaggaucu gcauggcau gccucgacug      60 ucagugccug gacgugcagu                                                80

<210> SEQ ID NO 8
<211> LENGTH: 80
<212> TYPE: RNA
<213> ORGANISM: Artificial
<220> FEATURE:
<223> OTHER INFORMATION: Aptamer

<400> SEQUENCE: 8
gggacgcuca cguacgcuca cuucuuuccc acucacgucu cgguuuuauu gguccaguuu    60
ucagugccug gacgugcagu                                                80

<210> SEQ ID NO 9
<211> LENGTH: 80
<212> TYPE: RNA
<213> ORGANISM: Artificial
<220> FEATURE:
<223> OTHER INFORMATION: Aptamer

<400> SEQUENCE: 9
gggacgcuca cguacgcuca ggugaauugg cacuucuuua ucuacggauc gagucggaug    60
ucagugccug gacgugcagu                                                80

<210> SEQ ID NO 10
<211> LENGTH: 67
<212> TYPE: RNA
<213> ORGANISM: Artificial
<220> FEATURE:
<223> OTHER INFORMATION: Aptamer

<400> SEQUENCE: 10
gggacgcuca cguacgcuca gguuuauugg ugccguguag uggaauauca gugccuggac    60
gugcagu                                                              67

<210> SEQ ID NO 11
<211> LENGTH: 80
<212> TYPE: RNA
<213> ORGANISM: Artificial
<220> FEATURE:
<223> OTHER INFORMATION: Aptamer

<400> SEQUENCE: 11
gggacgcuca cguacgcuca cuucccuaga cccuccaggu uacaggcgcc gcccggaaug    60
ucagugccug gacgugcagu                                                80
```

```
<210> SEQ ID NO 12
<211> LENGTH: 56
<212> TYPE: RNA
<213> ORGANISM: Artificial
<220> FEATURE:
<223> OTHER INFORMATION: Aptamer

<400> SEQUENCE: 12
ggguacgcuc agguauauug gcgccuucgu ggaaugucag ugccuggacg ugcagu        56

<210> SEQ ID NO 13
<211> LENGTH: 54
<212> TYPE: RNA
<213> ORGANISM: Artificial
<220> FEATURE:
<223> OTHER INFORMATION: Aptamer

<400> SEQUENCE: 13
ggguacgcuc agguauauug gcgccucggg aaugucagug ccuggacgug cagu          54

<210> SEQ ID NO 14
<211> LENGTH: 37
<212> TYPE: RNA
<213> ORGANISM: Artificial
<220> FEATURE:
<223> OTHER INFORMATION: Aptamer

<400> SEQUENCE: 14
ggguauauug gcgccuucgu ggaaugucag ugccugg                             37

<210> SEQ ID NO 15
<211> LENGTH: 38
<212> TYPE: RNA
<213> ORGANISM: Artificial
<220> FEATURE:
<223> OTHER INFORMATION: Aptamer

<400> SEQUENCE: 15
ggguacuggu auauggcgc cuucguggaa ugucagug                             38

<210> SEQ ID NO 16
<211> LENGTH: 35
<212> TYPE: RNA
<213> ORGANISM: Artificial
<220> FEATURE:
<223> OTHER INFORMATION: Aptamer

<400> SEQUENCE: 16
ggguauauug gcgccucggg aaugucagug ccugg                               35

<210> SEQ ID NO 17
<211> LENGTH: 10
<212> TYPE: RNA
<213> ORGANISM: Artificial
<220> FEATURE:
<223> OTHER INFORMATION: consensus sequence of Aptamers
<220> FEATURE:
<221> NAME/KEY: misc_feature
<222> LOCATION: (4)..(4)
<223> OTHER INFORMATION: n represents 1 to 3 of n which represents a,
      g, c, u or t

<400> SEQUENCE: 17 ggunayuggh                                                           10
```

```
<210> SEQ ID NO 18
<211> LENGTH: 19
<212> TYPE: RNA
<213> ORGANISM: Artificial
<220> FEATURE:
<223> OTHER INFORMATION: partial sequence of Aptamer

<400> SEQUENCE: 18
ggcgccuucg uggaauguc                                                        19

<210> SEQ ID NO 19
<211> LENGTH: 80
<212> TYPE: RNA
<213> ORGANISM: Artificial
<220> FEATURE:
<223> OTHER INFORMATION: Aptamer

<400> SEQUENCE: 19
gggacgcuca cguacgcuca uuuuacuuuu ccuacgaccg ggugaacugg cucuuggaug          60
ucagugccug gacgugcagu                                                      80

<210> SEQ ID NO 20
<211> LENGTH: 80
<212> TYPE: RNA
<213> ORGANISM: Artificial
<220> FEATURE:
<223> OTHER INFORMATION: Aptamer

<400> SEQUENCE: 20
gggacgcuca cguacgcuca aaaugcuguu gcagguuauu uggcucucgg ucugagaaug          60
ucagugccug gacgugcagu                                                      80

<210> SEQ ID NO 21
<211> LENGTH: 80
<212> TYPE: RNA
<213> ORGANISM: Artificial
<220> FEATURE:
<223> OTHER INFORMATION: Aptamer

<400> SEQUENCE: 21
gggacgcuca cguacgcuca uguccgggu cgacuggcug uuagagaucu cugauguagg           60
ucagugccug gacgugcagu                                                      80

<210> SEQ ID NO 22
<211> LENGTH: 80
<212> TYPE: RNA
<213> ORGANISM: Artificial
<220> FEATURE:
<223> OTHER INFORMATION: Aptamer

<400> SEQUENCE: 22
gggacgcuca cguacgcuca gcuccgggua uacuggcgac gaccguuauu gugucgcaug          60
ucagugccug gacgugcagu                                                      80

<210> SEQ ID NO 23
<211> LENGTH: 80
<212> TYPE: RNA
<213> ORGANISM: Artificial
<220> FEATURE:
<223> OTHER INFORMATION: Aptamer

<400> SEQUENCE: 23
gggacgcuca cguacgcuca ggguacugg cacuacugaa auucauuug aguaggucug            60
```

```
ucagugccug gacgugcagu                                              80

<210> SEQ ID NO 24
<211> LENGTH: 80
<212> TYPE: RNA
<213> ORGANISM: Artificial
<220> FEATURE:
<223> OTHER INFORMATION: Aptamer

<400> SEQUENCE: 24
gggacgcuca cguacgcuca ggugaacugg uccgcauuua gcuucuuau uugcgggau     60 ucagugccug gacgugcagu                                              80

<210> SEQ ID NO 25
<211> LENGTH: 80
<212> TYPE: RNA
<213> ORGANISM: Artificial
<220> FEATURE:
<223> OTHER INFORMATION: Aptamer

<400> SEQUENCE: 25
gggacgcuca cguacgcuca gguguauugg augcuuuaag caggucucug cuucagcaau   60
ucagugccug gacgugcagu                                              80

<210> SEQ ID NO 26
<211> LENGTH: 80
<212> TYPE: RNA
<213> ORGANISM: Artificial
<220> FEATURE:
<223> OTHER INFORMATION: Aptamer

<400> SEQUENCE: 26
gggacgcuca cguacgcuca uucgaccggg uuauggcug cucccucug guuugugaug     60 ucagugccug gacgugcagu                                              80

<210> SEQ ID NO 27
<211> LENGTH: 80
<212> TYPE: RNA
<213> ORGANISM: Artificial
<220> FEATURE:
<223> OTHER INFORMATION: Aptamer

<400> SEQUENCE: 27
gggacgcuca cguacgcuca acacuugcuu uuucuugucc ggguuuauug gucguuguau   60
ucagugccug gacgugcagu                                              80

<210> SEQ ID NO 28
<211> LENGTH: 80
<212> TYPE: RNA
<213> ORGANISM: Artificial
<220> FEATURE:
<223> OTHER INFORMATION: Aptamer

<400> SEQUENCE: 28
gggacgcuca cguacgcuca gagaucguuc ugguuauugg cgccuucuga uaaaggaaug   60
ucagugccug gacgugcagu                                              80

<210> SEQ ID NO 29
<211> LENGTH: 80
<212> TYPE: RNA
<213> ORGANISM: Artificial
<220> FEATURE:
<223> OTHER INFORMATION: Aptamer
```

<400> SEQUENCE: 29
gggacgcuca cguacgcuca uugucuuggu guauugguua cuguccaaug ggcgguguau    60
ucagugccug gacgugcagu                                                80

<210> SEQ ID NO 30
<211> LENGTH: 80
<212> TYPE: RNA
<213> ORGANISM: Artificial
<220> FEATURE:
<223> OTHER INFORMATION: Aptamer

<400> SEQUENCE: 30
gggacgcuca cguacgcuca aaaugcuguu gcagguuauu uggcucucgg ucugagaaug    60
ucagugccug gacgugcagu                                                80

<210> SEQ ID NO 31
<211> LENGTH: 80
<212> TYPE: RNA
<213> ORGANISM: Artificial
<220> FEATURE:
<223> OTHER INFORMATION: Aptamer

<400> SEQUENCE: 31
gggacgcuca cguacgcuca cgguggauug gcgacgauga ccuugauagu ccucguaaug    60
ucagugccug gacgugcagu                                                80

<210> SEQ ID NO 32
<211> LENGTH: 80
<212> TYPE: RNA
<213> ORGANISM: Artificial
<220> FEATURE:
<223> OTHER INFORMATION: Aptamer

<400> SEQUENCE: 32
gggacgcuca cguacgcuca uagaguguau uuguaccagg uauacuggcg cgaacgaaug    60
ucagugccug gacgugcagu                                                80

<210> SEQ ID NO 33
<211> LENGTH: 80
<212> TYPE: RNA
<213> ORGANISM: Artificial
<220> FEATURE:
<223> OTHER INFORMATION: Aptamer

<400> SEQUENCE: 33
gggacgcuca cguacgcuca gcucucuuac uuccugggug acuggcucuu ucggguaug    60 ucagugccug gacgugcagu                                                80

<210> SEQ ID NO 34
<211> LENGTH: 80
<212> TYPE: RNA
<213> ORGANISM: Artificial
<220> FEATURE:
<223> OTHER INFORMATION: Aptamer

<400> SEQUENCE: 34
gggacgcuca cguacgcuca gguuauuggc gcccucgaac caaaauggau gccgggaaug    60
ucagugccug gacgugcagu                                                80

<210> SEQ ID NO 35

```
<211> LENGTH: 80
<212> TYPE: RNA
<213> ORGANISM: Artificial
<220> FEATURE:
<223> OTHER INFORMATION: Aptamer

<400> SEQUENCE: 35
gggacgcuca cguacgcuca cauguccggg uggauuggau cgauuacuug uuuucguuua    60
ucagugccug gacgugcagu                                                80

<210> SEQ ID NO 36
<211> LENGTH: 80
<212> TYPE: RNA
<213> ORGANISM: Artificial
<220> FEATURE:
<223> OTHER INFORMATION: Aptamer

<400> SEQUENCE: 36
gggacgcuca cguacgcuca ccucaagucg ggucuauugu cuccggcgaa gcauggacug    60
ucagugccug gacgugcagu                                                80

<210> SEQ ID NO 37
<211> LENGTH: 80
<212> TYPE: RNA
<213> ORGANISM: Artificial
<220> FEATURE:
<223> OTHER INFORMATION: Aptamer

<400> SEQUENCE: 37
gggacgcuca cguacgcuca gagccacggg uuuacuggcg cuaaacaaau guuuaggaug    60
ucagugccug gacgugcagu                                                80

<210> SEQ ID NO 38
<211> LENGTH: 80
<212> TYPE: RNA
<213> ORGANISM: Artificial
<220> FEATURE:
<223> OTHER INFORMATION: Aptamer

<400> SEQUENCE: 38
gggacgcuca cguacgcuca gcgcuucucg uuugcuuucc ggguucauug guccauguuu    60
ucagugccug gacgugcagu                                                80

<210> SEQ ID NO 39
<211> LENGTH: 80
<212> TYPE: RNA
<213> ORGANISM: Artificial
<220> FEATURE:
<223> OTHER INFORMATION: Aptamer

<400> SEQUENCE: 39
gggacgcuca cguacgcuca ggcguucuuc gcuguaguuc cgguuuauug gucuuuguuu    60
ucagugccug gacgugcagu                                                80

<210> SEQ ID NO 40
<211> LENGTH: 80
<212> TYPE: RNA
<213> ORGANISM: Artificial
<220> FEATURE:
<223> OTHER INFORMATION: Aptamer

<400> SEQUENCE: 40
gggacgcuca cguacgcuca ugucucgguu uauuggcggu cggacuuuug cccugcgaug    60
```
ucagugccug gacgugcagu                                           80

<210> SEQ ID NO 41
<211> LENGTH: 80
<212> TYPE: RNA
<213> ORGANISM: Artificial
<220> FEATURE:
<223> OTHER INFORMATION: Aptamer

<400> SEQUENCE: 41
gggacgcuca cguacgcuca cgaaauccag guuugauugg cguggcaccc uugccaagug    60
ucagugccug gacgugcagu                                           80

<210> SEQ ID NO 42
<211> LENGTH: 80
<212> TYPE: RNA
<213> ORGANISM: Artificial
<220> FEATURE:
<223> OTHER INFORMATION: Aptamer

<400> SEQUENCE: 42
gggacgcuca cguacgcuca augagcucac cuggguaauu ggcgccaauu caagggucug    60
ucagugccug gacgugcagu                                           80

<210> SEQ ID NO 43
<211> LENGTH: 80
<212> TYPE: RNA
<213> ORGANISM: Artificial
<220> FEATURE:
<223> OTHER INFORMATION: Aptamer

<400> SEQUENCE: 43
gggacgcuca cguacgcuca cgcucaggug aauugguuac guuucucug acaaugugga    60 ucagugccug gacgugcagu                                           80

<210> SEQ ID NO 44
<211> LENGTH: 80
<212> TYPE: RNA
<213> ORGANISM: Artificial
<220> FEATURE:
<223> OTHER INFORMATION: Aptamer

<400> SEQUENCE: 44
gggacgcuca cguacgcuca auucuguucu gucucuccgg guuuacuggc gcuaugaaug    60
ucagugccug gacgugcagu                                           80

<210> SEQ ID NO 45
<211> LENGTH: 80
<212> TYPE: RNA
<213> ORGANISM: Artificial
<220> FEATURE:
<223> OTHER INFORMATION: Aptamer

<400> SEQUENCE: 45
gggacgcuca cguacgcuca aagugucugc aagcuaccg guuuauuggc cacuccguuu    60
ucagugccug gacgugcagu                                           80

<210> SEQ ID NO 46
<211> LENGTH: 80
<212> TYPE: RNA
<213> ORGANISM: Artificial
<220> FEATURE:

<223> OTHER INFORMATION: Aptamer

<400> SEQUENCE: 46
gggacgcuca cguacgcuca ugauugaaug ggcgaaucga ccuuaccggu uuucugcaac    60
ucagugccug gacgugcagu    80

<210> SEQ ID NO 47
<211> LENGTH: 79
<212> TYPE: RNA
<213> ORGANISM: Artificial
<220> FEATURE:
<223> OTHER INFORMATION: Aptamer

<400> SEQUENCE: 47
gggacgcuca cguacgcuca ucucgccgca uuccagguu uuuggcgcu uaugaaugau    60 cagugccugg acgugcagu    79

<210> SEQ ID NO 48
<211> LENGTH: 80
<212> TYPE: RNA
<213> ORGANISM: Artificial
<220> FEATURE:
<223> OTHER INFORMATION: Aptamer

<400> SEQUENCE: 48
gggacgcuca cguacgcuca auucuguucu gucucuccgg guuuacuggc gcuaugaaug    60
ucagugccug gacgugcagu    80

<210> SEQ ID NO 49
<211> LENGTH: 77
<212> TYPE: RNA
<213> ORGANISM: Artificial
<220> FEATURE:
<223> OTHER INFORMATION: Aptamer

<400> SEQUENCE: 49
gggacgcuca cguacgcuca ggggacugg uuucuaagug cuuugacugc uggaggauca    60
gugccuggac gugcagu    77

<210> SEQ ID NO 50
<211> LENGTH: 66
<212> TYPE: RNA
<213> ORGANISM: Artificial
<220> FEATURE:
<223> OTHER INFORMATION: Aptamer

<400> SEQUENCE: 50
gggacgcuca cguacgcuca gguuauuggc uuuccgagcg aagaugucag ugccuggacg    60
ugcagu    66

<210> SEQ ID NO 51
<211> LENGTH: 80
<212> TYPE: RNA
<213> ORGANISM: Artificial
<220> FEATURE:
<223> OTHER INFORMATION: Aptamer

<400> SEQUENCE: 51
gggacgcuca cguacgcuca gguguauugg auaacagcug cuucuuggaa cguugucguu    60
ucagugccug gacgugcagu    80

```
<210> SEQ ID NO 52
<211> LENGTH: 80
<212> TYPE: RNA
<213> ORGANISM: Artificial
<220> FEATURE:
<223> OTHER INFORMATION: Aptamer

<400> SEQUENCE: 52
gggacgcuca cguacgcuca gguuuauugg auguuugucu cccguucggg acauucguuu      60
ucagugccug gacgugcagu                                                 80

<210> SEQ ID NO 53
<211> LENGTH: 80
<212> TYPE: RNA
<213> ORGANISM: Artificial
<220> FEATURE:
<223> OTHER INFORMATION: Aptamer

<400> SEQUENCE: 53
gggacgcuca cguacgcuca gguugauccc guucuucuug acuggcgccu ucauggagug      60
ucagugccug gacgugcagu                                                 80

<210> SEQ ID NO 54
<211> LENGTH: 58
<212> TYPE: RNA
<213> ORGANISM: Artificial
<220> FEATURE:
<223> OTHER INFORMATION: Aptamer

<400> SEQUENCE: 54
ggguacgcuc agguuuauug gugccgugua guggaauguc agugccugga cgugcagu       58

<210> SEQ ID NO 55
<211> LENGTH: 42
<212> TYPE: RNA
<213> ORGANISM: Artificial
<220> FEATURE:
<223> OTHER INFORMATION: Aptamer

<400> SEQUENCE: 55
gggucaggua uauuggcgcc uucguggaau gucagugccu gg                        42

<210> SEQ ID NO 56
<211> LENGTH: 40
<212> TYPE: RNA
<213> ORGANISM: Artificial
<220> FEATURE:
<223> OTHER INFORMATION: Aptamer

<400> SEQUENCE: 56
gggucaggua uauuggcgcc ucgggaaugu cagugccugg                           40

<210> SEQ ID NO 57
<211> LENGTH: 176
<212> TYPE: DNA
<213> ORGANISM: Artificial
<220> FEATURE:
<223> OTHER INFORMATION: sense strand

<400> SEQUENCE: 57
atgcggggtt ctcatcatca tcatcatcat ggtatggcta gcatgactgg tggacagcaa     60
atgggatccg gatcctctag agtcgactgg taccgatatc agatctatcg atgaattcgc    120
ggcgctaagt ggtgaggtat attggcgcct tcgtggaatg tcagtgcctc accata        176
```

<210> SEQ ID NO 58
<211> LENGTH: 153
<212> TYPE: DNA
<213> ORGANISM: Artificial
<220> FEATURE:
<223> OTHER INFORMATION: partial sequence of pCold IV

<400> SEQUENCE: 58
catatgcggg gttctcatca tcatcatcat catggtatgg ctagcatgac tggtggacag    60
caaatgggat cccccgggag cggccgctaa tctagatagg taatctctgc ttaaaagcac    120
agaatctaag atccctgcca tttggcgggg att    153

<210> SEQ ID NO 59
<211> LENGTH: 181
<212> TYPE: DNA
<213> ORGANISM: Artificial
<220> FEATURE:
<223> OTHER INFORMATION: partial sequence of sense strand

<400> SEQUENCE: 59
atgcggggtt ctcatcatca tcatcatcat ggtatggcta gcatgactgg tggacagcaa    60
atgggatccc ccgggagcgg cgctaatcta gataggtaat ctctgcttaa aagcacagaa    120
tctaagatcc ctgccaggta tattggcgcc ttcgtggaat gtcagtgcct ggcgggatt    180 t    181

<210> SEQ ID NO 60
<211> LENGTH: 100
<212> TYPE: DNA
<213> ORGANISM: Artificial
<220> FEATURE:
<223> OTHER INFORMATION: polynucleotide having random sequences
<220> FEATURE:
<221> NAME/KEY: misc_feature
<222> LOCATION: (10)..(69)
<223> OTHER INFORMATION: n represents a, g, c, t or u

<400> SEQUENCE: 60
cacggatccn nnnnnnnnn nnnnnnnnnn nnnnnnnnnn nnnnnnnnnn nnnnnnnnnn    60
nnnnnnnnng gtggaggcgg gtctgggggc ggaggttcag    100

<210> SEQ ID NO 61
<211> LENGTH: 33
<212> TYPE: DNA
<213> ORGANISM: Artificial
<220> FEATURE:
<223> OTHER INFORMATION: polynucleotide

<400> SEQUENCE: 61
cgtctagcgg ccgcctgaac ctccgccccc aga    33

<210> SEQ ID NO 62
<211> LENGTH: 21
<212> TYPE: DNA
<213> ORGANISM: Artificial
<220> FEATURE:
<223> OTHER INFORMATION: polynucleotide

<400> SEQUENCE: 62
caaatgggat ccgaatctgg t    21

<210> SEQ ID NO 63
<211> LENGTH: 100

```
<212> TYPE: DNA
<213> ORGANISM: Artificial
<220> FEATURE:
<223> OTHER INFORMATION: polynucleotide having random sequences
<220> FEATURE:
<221> NAME/KEY: misc_feature
<222> LOCATION: (15)..(34)
<223> OTHER INFORMATION: n represents a, g, c, t or u
<220> FEATURE:
<221> NAME/KEY: misc_feature
<222> LOCATION: (60)..(79)
<223> OTHER INFORMATION: n represents a, g, c, t or u

<400> SEQUENCE: 63
cttagcggcc gctmnnmnnm nnmnmnnmnn nmnnagaagc tttaccgtta atgctaccmn      60
nmnnmnnmnn mnnmnnmnna ccagattcgg atcccatttg                          100

<210> SEQ ID NO 64
<211> LENGTH: 88
<212> TYPE: DNA
<213> ORGANISM: Artificial
<220> FEATURE:
<223> OTHER INFORMATION: polynucleotide having random sequences
<220> FEATURE:
<221> NAME/KEY: misc_feature
<222> LOCATION: (15)..(34)
<223> OTHER INFORMATION: n represents a, g, c, t or u
<220> FEATURE:
<221> NAME/KEY: misc_feature
<222> LOCATION: (48)..(67)
<223> OTHER INFORMATION: n represents a, g, c, t or u

<400> SEQUENCE: 64
cttagcggcc gctmnnmnnm nnmnmnnmnn nmnntttacc gttaatmnnm nnmnnmnnmn      60
nmnnmnnacc agattcggat cccatttg                                        88

<210> SEQ ID NO 65
<211> LENGTH: 54
<212> TYPE: RNA
<213> ORGANISM: Artificial
<220> FEATURE:
<223> OTHER INFORMATION: Aptamer

<400> SEQUENCE: 65
ggguacgcuc agguauauug gcgccccggg aaugucagug ccuggacgug cagu            54

<210> SEQ ID NO 66
<211> LENGTH: 55
<212> TYPE: RNA
<213> ORGANISM: Artificial
<220> FEATURE:
<223> OTHER INFORMATION: Aptamer

<400> SEQUENCE: 66
ggguacgcuc agguauauug gcgccuucgu ggaugucagu gccuggacgu gcagu           55

<210> SEQ ID NO 67
<211> LENGTH: 54
<212> TYPE: RNA
<213> ORGANISM: Artificial
<220> FEATURE:
<223> OTHER INFORMATION: Aptamer

<400> SEQUENCE: 67
ggguacgcuc agguauauug gcgccuucgu ggugucagug ccuggacgug cagu            54

<210> SEQ ID NO 68
```

```
<211> LENGTH: 52
<212> TYPE: RNA
<213> ORGANISM: Artificial
<220> FEATURE:
<223> OTHER INFORMATION: Aptamer

<400> SEQUENCE: 68
ggguacgcuc agguauauug gcgccucggg ugucagugcc uggacgugca gu            52

<210> SEQ ID NO 69
<211> LENGTH: 117
<212> TYPE: DNA
<213> ORGANISM: Artificial
<220> FEATURE:
<223> OTHER INFORMATION: DNA encoding a tag region of tagged protein

<400> SEQUENCE: 69
atgcggggtt ctcatcatca tcatcatcat ggtatggcta gcatgactgg tggacagcaa    60
atgggtcggg atctgtacga cgatgacgat aaggatcgat ggggatccat gccgatg      117

<210> SEQ ID NO 70
<211> LENGTH: 39
<212> TYPE: PRT
<213> ORGANISM: Artificial
<220> FEATURE:
<223> OTHER INFORMATION: Tag region of tagged protein

<400> SEQUENCE: 70

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Met Pro Met
        35

<210> SEQ ID NO 71
<211> LENGTH: 117
<212> TYPE: DNA
<213> ORGANISM: Artificial
<220> FEATURE:
<223> OTHER INFORMATION: DNA encoding a tag region of tagged protein

<400> SEQUENCE: 71
atgcggggtt ctcatcatca tcatcatcat ggtatggcta gcatgactgg tggacagcaa    60
atgggtcggg atctgtacga cgatgacgat aaggatcgat ggggatccat cgccacc      117

<210> SEQ ID NO 72
<211> LENGTH: 39
<212> TYPE: PRT
<213> ORGANISM: Artificial
<220> FEATURE:
<223> OTHER INFORMATION: Tag region of tagged protein

<400> SEQUENCE: 72

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Ile Ala Thr
        35

<210> SEQ ID NO 73
<211> LENGTH: 81
```

<212> TYPE: DNA
<213> ORGANISM: Artificial
<220> FEATURE:
<223> OTHER INFORMATION: DNA encoding a tag region of tagged protein

<400> SEQUENCE: 73
atgcggggtt ctcatcatca tcatcatcat ggtatggcta gcatgactgg tggacagcaa    60
atgggtggat ccatcgccac c                                              81

<210> SEQ ID NO 74
<211> LENGTH: 27
<212> TYPE: PRT
<213> ORGANISM: Artificial
<220> FEATURE:
<223> OTHER INFORMATION: Tag region of tagged protein

<400> SEQUENCE: 74

Met Arg Gly Ser His His His His His His Gly Met Ala Ser Met Thr
1               5                   10                  15

Gly Gly Gln Gln Met Gly Gly Ser Ile Ala Thr
            20                  25

<210> SEQ ID NO 75
<211> LENGTH: 48
<212> TYPE: DNA
<213> ORGANISM: Artificial
<220> FEATURE:
<223> OTHER INFORMATION: DNA encoding a tag region of tagged protein

<400> SEQUENCE: 75
atgcggggtt ctcatcatca tcatcatcat ggtggatcca tcgccacc                 48

<210> SEQ ID NO 76
<211> LENGTH: 16
<212> TYPE: PRT
<213> ORGANISM: Artificial
<220> FEATURE:
<223> OTHER INFORMATION: Tag region of tagged protein

<400> SEQUENCE: 76

Met Arg Gly Ser His His His His His His Gly Gly Ser Ile Ala Thr
1               5                   10                  15

<210> SEQ ID NO 77
<211> LENGTH: 84
<212> TYPE: DNA
<213> ORGANISM: Artificial
<220> FEATURE:
<223> OTHER INFORMATION: DNA encoding a tag region of tagged protein

<400> SEQUENCE: 77
atggctagca tgactggtgg acagcaaatg ggtcgggatc tgtacgacga tgacgataag    60
gatcgatggg gatccatcgc cacc                                           84

<210> SEQ ID NO 78
<211> LENGTH: 28
<212> TYPE: PRT
<213> ORGANISM: Artificial
<220> FEATURE:
<223> OTHER INFORMATION: Tag region of tagged protein

<400> SEQUENCE: 78

Met Ala Ser Met Thr Gly Gly Gln Gln Met Gly Arg Asp Leu Tyr Asp
1               5                   10                  15

Asp Asp Asp Lys Asp Arg Trp Gly Ser Ile Ala Thr
            20                  25

<210> SEQ ID NO 79
<211> LENGTH: 48
<212> TYPE: DNA
<213> ORGANISM: Artificial
<220> FEATURE:
<223> OTHER INFORMATION: DNA encoding a tag region of tagged protein

<400> SEQUENCE: 79
atggctagca tgactggtgg acagcaaatg ggtggatcca tcgccacc          48

<210> SEQ ID NO 80
<211> LENGTH: 16
<212> TYPE: PRT
<213> ORGANISM: Artificial
<220> FEATURE:
<223> OTHER INFORMATION: Tag region of tagged protein

<400> SEQUENCE: 80

Met Ala Ser Met Thr Gly Gly Gln Gln Met Gly Gly Ser Ile Ala Thr
1               5                   10                  15

<210> SEQ ID NO 81
<211> LENGTH: 82
<212> TYPE: DNA
<213> ORGANISM: Artificial
<220> FEATURE:
<223> OTHER INFORMATION: polynucleotide having random sequences
<220> FEATURE:
<221> NAME/KEY: misc_feature
<222> LOCATION: (15)..(34)
<223> OTHER INFORMATION: n represents a, g, c, t or u
<220> FEATURE:
<221> NAME/KEY: misc_feature
<222> LOCATION: (42)..(61)
<223> OTHER INFORMATION: n represents a, g, c, t or u

<400> SEQUENCE: 81
cttagcggcc gctmnnmnnm nnmnnmnnmn nmnnacccgg mnnmnnmnnm nnmnnmnnmn    60
naccagattc ggatcccatt tg                                            82

<210> SEQ ID NO 82
<211> LENGTH: 76
<212> TYPE: DNA
<213> ORGANISM: Artificial
<220> FEATURE:
<223> OTHER INFORMATION: polynucleotide having random sequences
<220> FEATURE:
<221> NAME/KEY: misc_feature
<222> LOCATION: (15)..(55)
<223> OTHER INFORMATION: n represents a, g, c, t or u

<400> SEQUENCE: 82
cttagcggcc gctmnnmnnm nnmnnmnnmn nmnnmnnmnn mnnmnnmnnm nnmnnaccag    60
attcggatcc catttg                                                   76

<210> SEQ ID NO 83
<211> LENGTH: 21
<212> TYPE: DNA
<213> ORGANISM: Artificial
<220> FEATURE:
<223> OTHER INFORMATION: polynucleotide

<400> SEQUENCE: 83
caaatgggat ccgaaatcaa a                                             21

```
<210> SEQ ID NO 84
<211> LENGTH: 100
<212> TYPE: DNA
<213> ORGANISM: Artificial
<220> FEATURE:
<223> OTHER INFORMATION: polynucleotide having random sequences
<220> FEATURE:
<221> NAME/KEY: misc_feature
<222> LOCATION: (21)..(25)
<223> OTHER INFORMATION: n represents a, g, c, t or u
<220> FEATURE:
<221> NAME/KEY: misc_feature
<222> LOCATION: (30)..(46)
<223> OTHER INFORMATION: n represents a, g, c, t or u
<220> FEATURE:
<221> NAME/KEY: misc_feature
<222> LOCATION: (60)..(79)
<223> OTHER INFORMATION: n represents a, g, c, t or u

<400> SEQUENCE: 84
cttagcggcc gctctgatam nnmnngccmn nmnnmnnmnn mnmnnatac aggccatcmn    60 nmnnmnnmnn mnnmnnmnnt ttgatttcgg atcccatttg                       100

<210> SEQ ID NO 85
<211> LENGTH: 26
<212> TYPE: DNA
<213> ORGANISM: Artificial
<220> FEATURE:
<223> OTHER INFORMATION: forward primer

<400> SEQUENCE: 85
ggctagcatg actggtggac agcaaa                                       26

<210> SEQ ID NO 86
<211> LENGTH: 25
<212> TYPE: DNA
<213> ORGANISM: Artificial
<220> FEATURE:
<223> OTHER INFORMATION: reverse primer

<400> SEQUENCE: 86
ctgacattcc acgaaggcgc caata                                        25

<210> SEQ ID NO 87
<211> LENGTH: 22
<212> TYPE: DNA
<213> ORGANISM: Artificial
<220> FEATURE:
<223> OTHER INFORMATION: forward primer

<400> SEQUENCE: 87
gtaaggcaag tcccttcaag ag                                           22

<210> SEQ ID NO 88
<211> LENGTH: 20
<212> TYPE: DNA
<213> ORGANISM: Artificial
<220> FEATURE:
<223> OTHER INFORMATION: reverse primer

<400> SEQUENCE: 88
ggcagggatc ttagattctg                                              20

<210> SEQ ID NO 89
<211> LENGTH: 40
<212> TYPE: RNA
```

<213> ORGANISM: Artificial
<220> FEATURE:
<223> OTHER INFORMATION: aptamer

<400> SEQUENCE: 89
ccggguuauu ggcgcaauau ugguauccug uauuggucug                              40

<210> SEQ ID NO 90
<211> LENGTH: 40
<212> TYPE: RNA
<213> ORGANISM: Artificial
<220> FEATURE:
<223> OTHER INFORMATION: aptamer

<400> SEQUENCE: 90
cguccgaucg auacugguau auuggcgccu ucguggaaug                              40

<210> SEQ ID NO 91
<211> LENGTH: 40
<212> TYPE: RNA
<213> ORGANISM: Artificial
<220> FEATURE:
<223> OTHER INFORMATION: aptamer

<400> SEQUENCE: 91
ccuguuuugu cuagguuuau uggcgcuuau uccuggaaug                              40

<210> SEQ ID NO 92
<211> LENGTH: 40
<212> TYPE: RNA
<213> ORGANISM: Artificial
<220> FEATURE:
<223> OTHER INFORMATION: aptamer

<400> SEQUENCE: 92
cucaggugau uggcgcuauu uaucgaucga uaauugaaug                              40

<210> SEQ ID NO 93
<211> LENGTH: 40
<212> TYPE: RNA
<213> ORGANISM: Artificial
<220> FEATURE:
<223> OTHER INFORMATION: aptamer

<400> SEQUENCE: 93
uguuccuuug gguuauuggc uccuuguuga ccaggggaug                              40

<210> SEQ ID NO 94
<211> LENGTH: 40
<212> TYPE: RNA
<213> ORGANISM: Artificial
<220> FEATURE:
<223> OTHER INFORMATION: aptamer

<400> SEQUENCE: 94
caacacucga agguuuauu ggccccacca ugguggaaug                               40

<210> SEQ ID NO 95
<211> LENGTH: 40
<212> TYPE: RNA
<213> ORGANISM: Artificial
<220> FEATURE:
<223> OTHER INFORMATION: aptamer

<400> SEQUENCE: 95
cgguuauugg cggaggaucu gucauggcau gccucgacug                              40

<210> SEQ ID NO 96
<211> LENGTH: 40
<212> TYPE: RNA
<213> ORGANISM: Artificial
<220> FEATURE:
<223> OTHER INFORMATION: aptamer

<400> SEQUENCE: 96
cuucuuuccc acucacgucu cgguuuuauu gguccaguuu       40

<210> SEQ ID NO 97
<211> LENGTH: 40
<212> TYPE: RNA
<213> ORGANISM: Artificial
<220> FEATURE:
<223> OTHER INFORMATION: aptamer

<400> SEQUENCE: 97
ggugaauugg cacuucuuua ucuacggauc gagucggaug       40

<210> SEQ ID NO 98
<211> LENGTH: 27
<212> TYPE: RNA
<213> ORGANISM: Artificial
<220> FEATURE:
<223> OTHER INFORMATION: aptamer

<400> SEQUENCE: 98
gguuuauugg ugccguguag uggaaua       27

<210> SEQ ID NO 99
<211> LENGTH: 40
<212> TYPE: RNA
<213> ORGANISM: Artificial
<220> FEATURE:
<223> OTHER INFORMATION: aptamer

<400> SEQUENCE: 99
cuucccuaga cccuccaggu uacaggcgcc gcccggaaug       40

<210> SEQ ID NO 100
<211> LENGTH: 25
<212> TYPE: RNA
<213> ORGANISM: Artificial
<220> FEATURE:
<223> OTHER INFORMATION: aptamer

<400> SEQUENCE: 100
gguauauugg cgccuucgug gaaug       25

<210> SEQ ID NO 101
<211> LENGTH: 23
<212> TYPE: RNA
<213> ORGANISM: Artificial
<220> FEATURE:
<223> OTHER INFORMATION: aptamer

<400> SEQUENCE: 101
gguauauugg cgccucggga aug       23

<210> SEQ ID NO 102
<211> LENGTH: 25
<212> TYPE: RNA
<213> ORGANISM: Artificial
<220> FEATURE:

```
<223> OTHER INFORMATION: aptamer

<400> SEQUENCE: 102
gguauauugg cgccuucgug gaaug                                              25

<210> SEQ ID NO 103
<211> LENGTH: 29
<212> TYPE: RNA
<213> ORGANISM: Artificial
<220> FEATURE:
<223> OTHER INFORMATION: aptamer

<400> SEQUENCE: 103
uacugguaua uuggcgccuu cguggaaug                                          29

<210> SEQ ID NO 104
<211> LENGTH: 23
<212> TYPE: RNA
<213> ORGANISM: Artificial
<220> FEATURE:
<223> OTHER INFORMATION: aptamer

<400> SEQUENCE: 104
gguauauugg cgccucggga aug                                                23

<210> SEQ ID NO 105
<211> LENGTH: 40
<212> TYPE: RNA
<213> ORGANISM: Artificial
<220> FEATURE:
<223> OTHER INFORMATION: aptamer

<400> SEQUENCE: 105
uucgaccggg uuauuggcug cucuccucug guuugugaug                              40

<210> SEQ ID NO 106
<211> LENGTH: 40
<212> TYPE: RNA
<213> ORGANISM: Artificial
<220> FEATURE:
<223> OTHER INFORMATION: aptamer

<400> SEQUENCE: 106
acacuugcuu uuucuugucc ggguuuauug gucguuguau                              40

<210> SEQ ID NO 107
<211> LENGTH: 40
<212> TYPE: RNA
<213> ORGANISM: Artificial
<220> FEATURE:
<223> OTHER INFORMATION: aptamer

<400> SEQUENCE: 107
gagaucguuc ugguuauugg cgccuucuga uaaaggaaug                              40

<210> SEQ ID NO 108
<211> LENGTH: 40
<212> TYPE: RNA
<213> ORGANISM: Artificial
<220> FEATURE:
<223> OTHER INFORMATION: aptamer

<400> SEQUENCE: 108
uugucuuggu guauugguua cuguccaaug ggcgguguau                              40
```

```
<210> SEQ ID NO 109
<211> LENGTH: 40
<212> TYPE: RNA
<213> ORGANISM: Artificial
<220> FEATURE:
<223> OTHER INFORMATION: aptamer

<400> SEQUENCE: 109
aaaugcuguu gcagguuauu uggcucucgg ucgagaaug                                40

<210> SEQ ID NO 110
<211> LENGTH: 40
<212> TYPE: RNA
<213> ORGANISM: Artificial
<220> FEATURE:
<223> OTHER INFORMATION: aptamer

<400> SEQUENCE: 110
cgguggauug gcgacgauga ccuugauagu ccucguaaug                              40

<210> SEQ ID NO 111
<211> LENGTH: 40
<212> TYPE: RNA
<213> ORGANISM: Artificial
<220> FEATURE:
<223> OTHER INFORMATION: aptamer

<400> SEQUENCE: 111
uagaguguau uuguaccagg uauacuggcg cgaacgaaug                              40

<210> SEQ ID NO 112
<211> LENGTH: 40
<212> TYPE: RNA
<213> ORGANISM: Artificial
<220> FEATURE:
<223> OTHER INFORMATION: aptamer

<400> SEQUENCE: 112
gcucucuuac uuccugggug acuggcucuu ucgggguaug                              40

<210> SEQ ID NO 113
<211> LENGTH: 40
<212> TYPE: RNA
<213> ORGANISM: Artificial
<220> FEATURE:
<223> OTHER INFORMATION: aptamer

<400> SEQUENCE: 113
gguuauuggc gcccucgaac caaaauggau gccgggaaug                              40

<210> SEQ ID NO 114
<211> LENGTH: 40
<212> TYPE: RNA
<213> ORGANISM: Artificial
<220> FEATURE:
<223> OTHER INFORMATION: aptamer

<400> SEQUENCE: 114
cauguccggg uggauuggau cgauuacuug uuuucguuua                              40

<210> SEQ ID NO 115
<211> LENGTH: 40
<212> TYPE: RNA
<213> ORGANISM: Artificial
<220> FEATURE:
<223> OTHER INFORMATION: aptamer
```

```
<400> SEQUENCE: 115
ccucaagucg ggucuauugu cuccggcgaa gcauggacug                                    40

<210> SEQ ID NO 116
<211> LENGTH: 40
<212> TYPE: RNA
<213> ORGANISM: Artificial
<220> FEATURE:
<223> OTHER INFORMATION: aptamer

<400> SEQUENCE: 116
gagccacggg uuuacuggcg cuaaacaaau guuuaggaug                                    40

<210> SEQ ID NO 117
<211> LENGTH: 40
<212> TYPE: RNA
<213> ORGANISM: Artificial
<220> FEATURE:
<223> OTHER INFORMATION: aptamer

<400> SEQUENCE: 117
gcgcuucucg uuugcuuucc ggguucauug guccauguuu                                    40

<210> SEQ ID NO 118
<211> LENGTH: 40
<212> TYPE: RNA
<213> ORGANISM: Artificial
<220> FEATURE:
<223> OTHER INFORMATION: aptamer

<400> SEQUENCE: 118
ggcguucuuc gcuguaguuc cgguuuauug gucuuuguuu                                    40

<210> SEQ ID NO 119
<211> LENGTH: 40
<212> TYPE: RNA
<213> ORGANISM: Artificial
<220> FEATURE:
<223> OTHER INFORMATION: aptamer

<400> SEQUENCE: 119
ugucucgguu uauuggcggu cggacuuuug cccugcgaug                                    40

<210> SEQ ID NO 120
<211> LENGTH: 40
<212> TYPE: RNA
<213> ORGANISM: Artificial
<220> FEATURE:
<223> OTHER INFORMATION: aptamer

<400> SEQUENCE: 120
cgaaauccag guuugauugg cguggcaccc uugccaagug                                    40

<210> SEQ ID NO 121
<211> LENGTH: 40
<212> TYPE: RNA
<213> ORGANISM: Artificial
<220> FEATURE:
<223> OTHER INFORMATION: aptamer

<400> SEQUENCE: 121
augagcucac cugggulaauu ggcgccaauu caagggucug                                   40

<210> SEQ ID NO 122
<211> LENGTH: 40
```

```
<212> TYPE: RNA
<213> ORGANISM: Artificial
<220> FEATURE:
<223> OTHER INFORMATION: aptamer

<400> SEQUENCE: 122
cgcucaggug aauugguuac guuucucug acaaugugga                              40

<210> SEQ ID NO 123
<211> LENGTH: 40
<212> TYPE: RNA
<213> ORGANISM: Artificial
<220> FEATURE:
<223> OTHER INFORMATION: aptamer

<400> SEQUENCE: 123
auucuguucu gucucuccgg guuuacuggc gcaugaaug                              40

<210> SEQ ID NO 124
<211> LENGTH: 40
<212> TYPE: RNA
<213> ORGANISM: Artificial
<220> FEATURE:
<223> OTHER INFORMATION: aptamer

<400> SEQUENCE: 124
aagugucugc aagucuaccg guuuauuggc cacuccguuu                             40

<210> SEQ ID NO 125
<211> LENGTH: 40
<212> TYPE: RNA
<213> ORGANISM: Artificial
<220> FEATURE:
<223> OTHER INFORMATION: aptamer

<400> SEQUENCE: 125
ugauugaaug ggcgaaucga ccuuaccggu uuucugcaac                             40

<210> SEQ ID NO 126
<211> LENGTH: 39
<212> TYPE: RNA
<213> ORGANISM: Artificial
<220> FEATURE:
<223> OTHER INFORMATION: aptamer

<400> SEQUENCE: 126
ucucgccgca uuccagguu uuuggcgcu uaugaauga                                39

<210> SEQ ID NO 127
<211> LENGTH: 23
<212> TYPE: RNA
<213> ORGANISM: Artificial
<220> FEATURE:
<223> OTHER INFORMATION: aptamer

<400> SEQUENCE: 127
gguauauugg cgccccggga aug                                               23

<210> SEQ ID NO 128
<211> LENGTH: 24
<212> TYPE: RNA
<213> ORGANISM: Artificial
<220> FEATURE:
<223> OTHER INFORMATION: aptamer

<400> SEQUENCE: 128
```

```
gguauauugg cgccuucgug gaug                                              24
```

<210> SEQ ID NO 129
<211> LENGTH: 23
<212> TYPE: RNA
<213> ORGANISM: Artificial
<220> FEATURE:
<223> OTHER INFORMATION: aptamer

<400> SEQUENCE: 129

```
gguauauugg cgccuucgug gug                                               23
```

<210> SEQ ID NO 130
<211> LENGTH: 21
<212> TYPE: RNA
<213> ORGANISM: Artificial
<220> FEATURE:
<223> OTHER INFORMATION: aptamer

<400> SEQUENCE: 130

```
gguauauugg cgccucgggu g                                                 21
```

<210> SEQ ID NO 131
<211> LENGTH: 40
<212> TYPE: RNA
<213> ORGANISM: Artificial
<220> FEATURE:
<223> OTHER INFORMATION: aptamer

<400> SEQUENCE: 131

```
uuuuacuuuu ccuacgaccg ggugaacugg cucuuggaug                             40
```

<210> SEQ ID NO 132
<211> LENGTH: 40
<212> TYPE: RNA
<213> ORGANISM: Artificial
<220> FEATURE:
<223> OTHER INFORMATION: aptamer

<400> SEQUENCE: 132

```
aaaugcuguu gcagguuauu uggcucucgg ucugagaaug                             40
```

<210> SEQ ID NO 133
<211> LENGTH: 40
<212> TYPE: RNA
<213> ORGANISM: Artificial
<220> FEATURE:
<223> OTHER INFORMATION: aptamer

<400> SEQUENCE: 133

```
uguuccgggu cgacuggcug uuagagaucu cugauguagg                             40
```

<210> SEQ ID NO 134
<211> LENGTH: 40
<212> TYPE: RNA
<213> ORGANISM: Artificial
<220> FEATURE:
<223> OTHER INFORMATION: aptamer

<400> SEQUENCE: 134

```
gcuccgggua uacuggcgac gaccguuauu gugucgcaug                             40
```

<210> SEQ ID NO 135
<211> LENGTH: 40
<212> TYPE: RNA
<213> ORGANISM: Artificial

```
<220> FEATURE:
<223> OTHER INFORMATION: aptamer

<400> SEQUENCE: 135
gguguacugg cacuacugaa auuucauuug aguaggucug                               40

<210> SEQ ID NO 136
<211> LENGTH: 40
<212> TYPE: RNA
<213> ORGANISM: Artificial
<220> FEATURE:
<223> OTHER INFORMATION: aptamer

<400> SEQUENCE: 136
ggugaacugg uccgcauuua gcuuucuuau uugcggguau                               40

<210> SEQ ID NO 137
<211> LENGTH: 40
<212> TYPE: RNA
<213> ORGANISM: Artificial
<220> FEATURE:
<223> OTHER INFORMATION: aptamer

<400> SEQUENCE: 137
gguguauugg augcuuuaag caggucucug cuucagcaau                               40

<210> SEQ ID NO 138
<211> LENGTH: 40
<212> TYPE: RNA
<213> ORGANISM: Artificial
<220> FEATURE:
<223> OTHER INFORMATION: aptamer

<400> SEQUENCE: 138
auucuguucu gucucuccgg guuuacuggc gcuaugaaug                               40

<210> SEQ ID NO 139
<211> LENGTH: 37
<212> TYPE: RNA
<213> ORGANISM: Artificial
<220> FEATURE:
<223> OTHER INFORMATION: aptamer

<400> SEQUENCE: 139 ggugggacugg uuucuaagug cuuugacugc uggagga                                 37

<210> SEQ ID NO 140
<211> LENGTH: 26
<212> TYPE: RNA
<213> ORGANISM: Artificial
<220> FEATURE:
<223> OTHER INFORMATION: aptamer

<400> SEQUENCE: 140 gguuauggc uuuccgagcg aagaug                                               26

<210> SEQ ID NO 141
<211> LENGTH: 40
<212> TYPE: RNA
<213> ORGANISM: Artificial
<220> FEATURE:
<223> OTHER INFORMATION: aptamer

<400> SEQUENCE: 141
gguguauugg auaacagcug cuucuuggaa cguugucguu                               40
```

```
<210> SEQ ID NO 142
<211> LENGTH: 40
<212> TYPE: RNA
<213> ORGANISM: Artificial
<220> FEATURE:
<223> OTHER INFORMATION: aptamer

<400> SEQUENCE: 142
gguuuauugg auguuugucu cccguucggg acauucguuu                              40

<210> SEQ ID NO 143
<211> LENGTH: 40
<212> TYPE: RNA
<213> ORGANISM: Artificial
<220> FEATURE:
<223> OTHER INFORMATION: aptamer

<400> SEQUENCE: 143
gguugauccc guucuucuug acuggcgccu ucauggagug                              40

<210> SEQ ID NO 144
<211> LENGTH: 27
<212> TYPE: RNA
<213> ORGANISM: Artificial
<220> FEATURE:
<223> OTHER INFORMATION: aptamer

<400> SEQUENCE: 144
gguuuauugg ugccguguag uggaaug                                            27

<210> SEQ ID NO 145
<211> LENGTH: 25
<212> TYPE: RNA
<213> ORGANISM: Artificial
<220> FEATURE:
<223> OTHER INFORMATION: aptamer

<400> SEQUENCE: 145
gguauauugg cgccuucgug gaaug                                              25

<210> SEQ ID NO 146
<211> LENGTH: 23
<212> TYPE: RNA
<213> ORGANISM: Artificial
<220> FEATURE:
<223> OTHER INFORMATION: aptamer

<400> SEQUENCE: 146
gguauauugg cgccucggga aug                                                23

<210> SEQ ID NO 147
<211> LENGTH: 26
<212> TYPE: RNA
<213> ORGANISM: Artificial
<220> FEATURE:
<223> OTHER INFORMATION: aptamer
<220> FEATURE:
<221> NAME/KEY: misc_feature
<222> LOCATION: (4)..(4)
<223> OTHER INFORMATION: n stands for any base.

<400> SEQUENCE: 147
ggunayuggh gccuucgugg aauguc                                             26

<210> SEQ ID NO 148
<211> LENGTH: 27
```

```
<212> TYPE: RNA
<213> ORGANISM: Artificial
<220> FEATURE:
<223> OTHER INFORMATION: aptamer

<400> SEQUENCE: 148
gguauauugg cgccuucgug gaauguc                                            27

<210> SEQ ID NO 149
<211> LENGTH: 20
<212> TYPE: RNA
<213> ORGANISM: Artificial
<220> FEATURE:
<223> OTHER INFORMATION: aptamer

<400> SEQUENCE: 149
gggacgcuca cguacgcuca                                                    20

<210> SEQ ID NO 150
<211> LENGTH: 20
<212> TYPE: RNA
<213> ORGANISM: Artificial
<220> FEATURE:
<223> OTHER INFORMATION: aptamer

<400> SEQUENCE: 150
ucagugccug gacgugcagu                                                    20

<210> SEQ ID NO 151
<211> LENGTH: 97
<212> TYPE: DNA
<213> ORGANISM: Artificial
<220> FEATURE:
<223> OTHER INFORMATION: library
<220> FEATURE:
<221> NAME/KEY: misc_feature
<222> LOCATION: (21)..(60)
<223> OTHER INFORMATION: n stands for any base.

<400> SEQUENCE: 151
actgcacgtc caggcactga nnnnnnnnnn nnnnnnnnnn nnnnnnnnnn nnnnnnnnnn         60
tgagcgtacg tgagcgtccc tatagtgagt cgtatta                                 97

<210> SEQ ID NO 152
<211> LENGTH: 20
<212> TYPE: DNA
<213> ORGANISM: Artificial
<220> FEATURE:
<223> OTHER INFORMATION: promoter

<400> SEQUENCE: 152
taatacgact cactataggg                                                    20

<210> SEQ ID NO 153
<211> LENGTH: 37
<212> TYPE: DNA
<213> ORGANISM: Artificial
<220> FEATURE:
<223> OTHER INFORMATION: primer

<400> SEQUENCE: 153
taatacgact cactataggg acgctcacgt acgctca                                 37

<210> SEQ ID NO 154
<211> LENGTH: 20
<212> TYPE: DNA
```

<213> ORGANISM: Artificial
<220> FEATURE:
<223> OTHER INFORMATION: primer

<400> SEQUENCE: 154
actgcacgtc caggcactga                                          20

<210> SEQ ID NO 155
<211> LENGTH: 17
<212> TYPE: DNA
<213> ORGANISM: Artificial
<220> FEATURE:
<223> OTHER INFORMATION: primer

<400> SEQUENCE: 155
taatacgact cactata                                             17

<210> SEQ ID NO 156
<211> LENGTH: 41
<212> TYPE: DNA
<213> ORGANISM: Artificial
<220> FEATURE:
<223> OTHER INFORMATION: primer

<400> SEQUENCE: 156
tcgacctcga gaaaaaaaaa agggacgctc acgtacgctc a                  41

<210> SEQ ID NO 157
<211> LENGTH: 43
<212> TYPE: DNA
<213> ORGANISM: Artificial
<220> FEATURE:
<223> OTHER INFORMATION: primer

<400> SEQUENCE: 157
gagtcgcggc cgctttttttt tttactgcac gtccaggcac tga               43

<210> SEQ ID NO 158
<211> LENGTH: 40
<212> TYPE: RNA
<213> ORGANISM: Artificial
<220> FEATURE:
<223> OTHER INFORMATION: Aptamer

<400> SEQUENCE: 158
ggugaauugg cacuucuuua ucuacggauc gagucggaug                    40

<210> SEQ ID NO 159
<211> LENGTH: 40
<212> TYPE: RNA
<213> ORGANISM: Artificial
<220> FEATURE:
<223> OTHER INFORMATION: Aptamer

<400> SEQUENCE: 159
ccuguuuugu cuagguucau uggcgcuuau uccuggaaug                    40

<210> SEQ ID NO 160
<211> LENGTH: 40
<212> TYPE: RNA
<213> ORGANISM: Artificial
<220> FEATURE:
<223> OTHER INFORMATION: Aptamer

<400> SEQUENCE: 160
ccggguuauu ggcgcaauau gguauccug uauuggucug                     40

<210> SEQ ID NO 161
<211> LENGTH: 40
<212> TYPE: RNA
<213> ORGANISM: Artificial
<220> FEATURE:
<223> OTHER INFORMATION: Aptamer

<400> SEQUENCE: 161
ggugaacugg uccgcauuua gcuucuuau uugcgggguau                    40

<210> SEQ ID NO 162
<211> LENGTH: 40
<212> TYPE: RNA
<213> ORGANISM: Artificial
<220> FEATURE:
<223> OTHER INFORMATION: Aptamer

<400> SEQUENCE: 162
uguuccgggu cgacuggcug uuagagaucu cugauguagg                    40

<210> SEQ ID NO 163
<211> LENGTH: 40
<212> TYPE: RNA
<213> ORGANISM: Artificial
<220> FEATURE:
<223> OTHER INFORMATION: Aptamer

<400> SEQUENCE: 163
gguguacugg cacuacugaa auuucauuug aguaggucug                    40

<210> SEQ ID NO 164
<211> LENGTH: 40
<212> TYPE: RNA
<213> ORGANISM: Artificial
<220> FEATURE:
<223> OTHER INFORMATION: Aptamer

<400> SEQUENCE: 164
cucaggugau uggcgcuauu uaucgaucga uaauugaaug                    40

<210> SEQ ID NO 165
<211> LENGTH: 40
<212> TYPE: RNA
<213> ORGANISM: Artificial
<220> FEATURE:
<223> OTHER INFORMATION: Aptamer

<400> SEQUENCE: 165
auucuguucu gucucuccgg guuuacuggc gcuaugaaug                    40

<210> SEQ ID NO 166
<211> LENGTH: 40
<212> TYPE: RNA
<213> ORGANISM: Artificial
<220> FEATURE:
<223> OTHER INFORMATION: Aptamer

<400> SEQUENCE: 166
acacuugcuu uucuugucc ggguuuauug gucguugugu                     40

<210> SEQ ID NO 167
<211> LENGTH: 40
<212> TYPE: RNA
<213> ORGANISM: Artificial
<220> FEATURE:

<223> OTHER INFORMATION: Aptamer

<400> SEQUENCE: 167
gcuccgggua uacuggcgac gaccguuauu gugucgcaug          40

<210> SEQ ID NO 168
<211> LENGTH: 40
<212> TYPE: RNA
<213> ORGANISM: Artificial
<220> FEATURE:
<223> OTHER INFORMATION: Aptamer

<400> SEQUENCE: 168
uagaguguau uuguaccagg uauacuggcg cgaacgaaug          40

<210> SEQ ID NO 169
<211> LENGTH: 40
<212> TYPE: RNA
<213> ORGANISM: Artificial
<220> FEATURE:
<223> OTHER INFORMATION: Aptamer

<400> SEQUENCE: 169
ccgcuugauu cgcuacaccu agguuauugg cguucggcug          40

<210> SEQ ID NO 170
<211> LENGTH: 40
<212> TYPE: RNA
<213> ORGANISM: Artificial
<220> FEATURE:
<223> OTHER INFORMATION: Aptamer

<400> SEQUENCE: 170
ugucucgguu uauuggcggu cggacuuuug cccugcgaug          40

<210> SEQ ID NO 171
<211> LENGTH: 40
<212> TYPE: RNA
<213> ORGANISM: Artificial
<220> FEATURE:
<223> OTHER INFORMATION: Aptamer

<400> SEQUENCE: 171
cauccagguu gauuggcggc augccuaugg guagcgacug          40

<210> SEQ ID NO 172
<211> LENGTH: 39
<212> TYPE: RNA
<213> ORGANISM: Artificial
<220> FEATURE:
<223> OTHER INFORMATION: Aptamer

<400> SEQUENCE: 172
agguuuacug gcucugccuu caguugggaa ugcagcgug          39

<210> SEQ ID NO 173
<211> LENGTH: 40
<212> TYPE: RNA
<213> ORGANISM: Artificial
<220> FEATURE:
<223> OTHER INFORMATION: Aptamer

<400> SEQUENCE: 173 ggguguauugg uuagcagauu cguuccucca uuugcugaga          40

<210> SEQ ID NO 174
<211> LENGTH: 40
<212> TYPE: RNA
<213> ORGANISM: Artificial
<220> FEATURE:
<223> OTHER INFORMATION: Aptamer

<400> SEQUENCE: 174
gguaauuggc gcacuuucau uauugauggu aguggcucug                                40

<210> SEQ ID NO 175
<211> LENGTH: 40
<212> TYPE: RNA
<213> ORGANISM: Artificial
<220> FEATURE:
<223> OTHER INFORMATION: Aptamer

<400> SEQUENCE: 175
ggcuucacuc uagguucgac uggcuccuuc ccacggcaug                                40

<210> SEQ ID NO 176
<211> LENGTH: 40
<212> TYPE: RNA
<213> ORGANISM: Artificial
<220> FEATURE:
<223> OTHER INFORMATION: Aptamer

<400> SEQUENCE: 176
gguguauugg uggcuagcc ggacugaauc ggacgacuua                                 40

<210> SEQ ID NO 177
<211> LENGTH: 40
<212> TYPE: RNA
<213> ORGANISM: Artificial
<220> FEATURE:
<223> OTHER INFORMATION: Aptamer

<400> SEQUENCE: 177
cugcuugucu cucagguuua uggcgucau uuuucgauug                                 40

<210> SEQ ID NO 178
<211> LENGTH: 40
<212> TYPE: RNA
<213> ORGANISM: Artificial
<220> FEATURE:
<223> OTHER INFORMATION: Aptamer

<400> SEQUENCE: 178
uuccgcaugu ggguaaacug gcgccugauu uuuuggagug                                40

<210> SEQ ID NO 179
<211> LENGTH: 40
<212> TYPE: RNA
<213> ORGANISM: Artificial
<220> FEATURE:
<223> OTHER INFORMATION: Aptamer

<400> SEQUENCE: 179
ggugaacugg cucgagauuu gucgcuuguu gaucgguaug                                40

<210> SEQ ID NO 180
<211> LENGTH: 40
<212> TYPE: RNA
<213> ORGANISM: Artificial
<220> FEATURE:
<223> OTHER INFORMATION: Aptamer

```
<400> SEQUENCE: 180
uguuccuuug gguuauuggc uccuuguuga ccagggaug                                40

<210> SEQ ID NO 181
<211> LENGTH: 40
<212> TYPE: RNA
<213> ORGANISM: Artificial
<220> FEATURE:
<223> OTHER INFORMATION: Aptamer

<400> SEQUENCE: 181
ccuguuuugu cuagguuuau uggcgcuuau uccuggaaug                                40

<210> SEQ ID NO 182
<211> LENGTH: 40
<212> TYPE: RNA
<213> ORGANISM: Artificial
<220> FEATURE:
<223> OTHER INFORMATION: Aptamer

<400> SEQUENCE: 182
cagcacuuuc cgagguguac ugguuugagu uauucaggga                                40

<210> SEQ ID NO 183
<211> LENGTH: 29
<212> TYPE: RNA
<213> ORGANISM: Artificial
<220> FEATURE:
<223> OTHER INFORMATION: Aptamer

<400> SEQUENCE: 183 ggugauugg uuacgcucca aguguggua                                             29

<210> SEQ ID NO 184
<211> LENGTH: 40
<212> TYPE: RNA
<213> ORGANISM: Artificial
<220> FEATURE:
<223> OTHER INFORMATION: Aptamer

<400> SEQUENCE: 184
gguucauugg cguugcuagu cucaugauca agcaagucug                                40

<210> SEQ ID NO 185
<211> LENGTH: 40
<212> TYPE: RNA
<213> ORGANISM: Artificial
<220> FEATURE:
<223> OTHER INFORMATION: Aptamer

<400> SEQUENCE: 185
accggguuac uggcgucguu acgauuaccg ugucgaagug                                40

<210> SEQ ID NO 186
<211> LENGTH: 39
<212> TYPE: RNA
<213> ORGANISM: Artificial
<220> FEATURE:
<223> OTHER INFORMATION: Aptamer

<400> SEQUENCE: 186
aggucaacug gcgccugcua cuuuaauguu augggagug                                 39

<210> SEQ ID NO 187
<211> LENGTH: 40
```

```
<212> TYPE: RNA
<213> ORGANISM: Artificial
<220> FEATURE:
<223> OTHER INFORMATION: Aptamer

<400> SEQUENCE: 187
gguuuauugg cucucucuua ucuccccguc ugagagcgug                    40

<210> SEQ ID NO 188
<211> LENGTH: 40
<212> TYPE: RNA
<213> ORGANISM: Artificial
<220> FEATURE:
<223> OTHER INFORMATION: Aptamer

<400> SEQUENCE: 188
uuacucuuuu ucggcgucac gguugauugg ccuuugggug                    40

<210> SEQ ID NO 189
<211> LENGTH: 40
<212> TYPE: RNA
<213> ORGANISM: Artificial
<220> FEATURE:
<223> OTHER INFORMATION: Aptamer

<400> SEQUENCE: 189
ggucuauugg ugccuguucc cguccguugg aaucggaaua                    40

<210> SEQ ID NO 190
<211> LENGTH: 40
<212> TYPE: RNA
<213> ORGANISM: Artificial
<220> FEATURE:
<223> OTHER INFORMATION: Aptamer

<400> SEQUENCE: 190
cgcucaggug aauugguuac guuuucucug acaaugugga                    40

<210> SEQ ID NO 191
<211> LENGTH: 40
<212> TYPE: RNA
<213> ORGANISM: Artificial
<220> FEATURE:
<223> OTHER INFORMATION: Aptamer

<400> SEQUENCE: 191
gguauauugg cggaguucuc ugaccgguag guucucgcug                    40

<210> SEQ ID NO 192
<211> LENGTH: 40
<212> TYPE: RNA
<213> ORGANISM: Artificial
<220> FEATURE:
<223> OTHER INFORMATION: Aptamer

<400> SEQUENCE: 192
gguaauuggc acuaggaucu guugacuacc ccuagguuug                    40

<210> SEQ ID NO 193
<211> LENGTH: 40
<212> TYPE: RNA
<213> ORGANISM: Artificial
<220> FEATURE:
<223> OTHER INFORMATION: Aptamer

<400> SEQUENCE: 193
``` cucuuuccc acucacgucu cgguuuuauu gguccaguuu              40

<210> SEQ ID NO 194
<211> LENGTH: 40
<212> TYPE: RNA
<213> ORGANISM: Artificial
<220> FEATURE:
<223> OTHER INFORMATION: Aptamer

<400> SEQUENCE: 194
ggugaacugg uuacguguag uugaaaauug cugcugugua              40

<210> SEQ ID NO 195
<211> LENGTH: 40
<212> TYPE: RNA
<213> ORGANISM: Artificial
<220> FEATURE:
<223> OTHER INFORMATION: Aptamer

<400> SEQUENCE: 195
ccagucgugu ccggguguau gguugcuug ucgaaacgga              40

<210> SEQ ID NO 196
<211> LENGTH: 40
<212> TYPE: RNA
<213> ORGANISM: Artificial
<220> FEATURE:
<223> OTHER INFORMATION: Aptamer

<400> SEQUENCE: 196
gguuuauugg cacuuggaau gacguuauuc cauggcuuug              40

<210> SEQ ID NO 197
<211> LENGTH: 40
<212> TYPE: RNA
<213> ORGANISM: Artificial
<220> FEATURE:
<223> OTHER INFORMATION: Aptamer

<400> SEQUENCE: 197
ucugggugua uuggucgaua aagaaguugu ucuuuucgga              40

<210> SEQ ID NO 198
<211> LENGTH: 40
<212> TYPE: RNA
<213> ORGANISM: Artificial
<220> FEATURE:
<223> OTHER INFORMATION: Aptamer

<400> SEQUENCE: 198
uucagguuau uggcccaggc uuuuuccaaa acccggugug              40

<210> SEQ ID NO 199
<211> LENGTH: 40
<212> TYPE: RNA
<213> ORGANISM: Artificial
<220> FEATURE:
<223> OTHER INFORMATION: Aptamer

<400> SEQUENCE: 199
uucgaccggg uuauuggcug cucuccucug guuugugaug              40

<210> SEQ ID NO 200
<211> LENGTH: 40
<212> TYPE: RNA
<213> ORGANISM: Artificial

```
<220> FEATURE:
<223> OTHER INFORMATION: Aptamer

<400> SEQUENCE: 200
gguguacugg ccuucaucuc cauucggaua cggaacgucg                              40

<210> SEQ ID NO 201
<211> LENGTH: 40
<212> TYPE: RNA
<213> ORGANISM: Artificial
<220> FEATURE:
<223> OTHER INFORMATION: Aptamer

<400> SEQUENCE: 201
agguguacug gucgguaauu gucugaaauu ugcuucguua                              40

<210> SEQ ID NO 202
<211> LENGTH: 37
<212> TYPE: RNA
<213> ORGANISM: Artificial
<220> FEATURE:
<223> OTHER INFORMATION: Aptamer

<400> SEQUENCE: 202
gguggacugg uuucuaagug cuuugacugc uggagga                                 37

<210> SEQ ID NO 203
<211> LENGTH: 40
<212> TYPE: RNA
<213> ORGANISM: Artificial
<220> FEATURE:
<223> OTHER INFORMATION: Aptamer

<400> SEQUENCE: 203
gcgcuucucg uuugcuuucc ggguucauug guccauguuu                              40

<210> SEQ ID NO 204
<211> LENGTH: 40
<212> TYPE: RNA
<213> ORGANISM: Artificial
<220> FEATURE:
<223> OTHER INFORMATION: Aptamer

<400> SEQUENCE: 204
cggucccagg uguacugguu guccguuuc gguugcguua                               40

<210> SEQ ID NO 205
<211> LENGTH: 40
<212> TYPE: RNA
<213> ORGANISM: Artificial
<220> FEATURE:
<223> OTHER INFORMATION: Aptamer

<400> SEQUENCE: 205
ucgccguucu gguuuacugg cuucagguuu cuuugaaaug                              40

<210> SEQ ID NO 206
<211> LENGTH: 40
<212> TYPE: RNA
<213> ORGANISM: Artificial
<220> FEATURE:
<223> OTHER INFORMATION: Aptamer

<400> SEQUENCE: 206
cgccugggua auuggugccu cgugucaucc acgucgaaua                              40
```

```
<210> SEQ ID NO 207
<211> LENGTH: 40
<212> TYPE: RNA
<213> ORGANISM: Artificial
<220> FEATURE:
<223> OTHER INFORMATION: Aptamer

<400> SEQUENCE: 207
gguaaauugg caccguuugg auucgcuuuc cauggauuug                           40

<210> SEQ ID NO 208
<211> LENGTH: 40
<212> TYPE: RNA
<213> ORGANISM: Artificial
<220> FEATURE:
<223> OTHER INFORMATION: Aptamer

<400> SEQUENCE: 208
agucuugggu guacuggcga aguugcguuu uaacuugcug                           40

<210> SEQ ID NO 209
<211> LENGTH: 40
<212> TYPE: RNA
<213> ORGANISM: Artificial
<220> FEATURE:
<223> OTHER INFORMATION: Aptamer

<400> SEQUENCE: 209
aggguaauug gcgcugucug uuuugaaucu gggcuggcug                           40

<210> SEQ ID NO 210
<211> LENGTH: 40
<212> TYPE: RNA
<213> ORGANISM: Artificial
<220> FEATURE:
<223> OTHER INFORMATION: Aptamer

<400> SEQUENCE: 210
cgaaauccag guuugauugg cguggcaccc uugccaagug                           40

<210> SEQ ID NO 211
<211> LENGTH: 40
<212> TYPE: RNA
<213> ORGANISM: Artificial
<220> FEATURE:
<223> OTHER INFORMATION: Aptamer

<400> SEQUENCE: 211
cggguggacu ggucaccacc gacucgaucu gguggagaga                           40

<210> SEQ ID NO 212
<211> LENGTH: 40
<212> TYPE: RNA
<213> ORGANISM: Artificial
<220> FEATURE:
<223> OTHER INFORMATION: Aptamer

<400> SEQUENCE: 212
gagaucguuc ugguuauugg cgccuucuga uaaaggaaug                           40

<210> SEQ ID NO 213
<211> LENGTH: 40
<212> TYPE: RNA
<213> ORGANISM: Artificial
<220> FEATURE:
<223> OTHER INFORMATION: Aptamer
```

```
<400> SEQUENCE: 213
ggugaauugg cugaaggucu ucguucuga cauuucgugu                    40

<210> SEQ ID NO 214
<211> LENGTH: 40
<212> TYPE: RNA
<213> ORGANISM: Artificial
<220> FEATURE:
<223> OTHER INFORMATION: Aptamer

<400> SEQUENCE: 214
gugucuuugu uccaggugga cuggcugcuc ggugcguaug                   40

<210> SEQ ID NO 215
<211> LENGTH: 40
<212> TYPE: RNA
<213> ORGANISM: Artificial
<220> FEATURE:
<223> OTHER INFORMATION: Aptamer

<400> SEQUENCE: 215
gguuuauugg uguucgccua ucgauuuuuu gggcuuuuua                   40

<210> SEQ ID NO 216
<211> LENGTH: 37
<212> TYPE: RNA
<213> ORGANISM: Artificial
<220> FEATURE:
<223> OTHER INFORMATION: Aptamer

<400> SEQUENCE: 216
aacgguguau uggucuucag auuuuuucug acguuga                      37

<210> SEQ ID NO 217
<211> LENGTH: 40
<212> TYPE: RNA
<213> ORGANISM: Artificial
<220> FEATURE:
<223> OTHER INFORMATION: Aptamer

<400> SEQUENCE: 217
gcucucuuac uuccugggug acuggcucuu ucgggguaug                   40

<210> SEQ ID NO 218
<211> LENGTH: 40
<212> TYPE: RNA
<213> ORGANISM: Artificial
<220> FEATURE:
<223> OTHER INFORMATION: Aptamer

<400> SEQUENCE: 218
uugcucaaaa agguguauug guucaacagg gggguuagua                   40

<210> SEQ ID NO 219
<211> LENGTH: 40
<212> TYPE: RNA
<213> ORGANISM: Artificial
<220> FEATURE:
<223> OTHER INFORMATION: Aptamer

<400> SEQUENCE: 219
gugcauuucu gggguggacug guauaguauc gacuaugugu                  40

<210> SEQ ID NO 220
```

```
<211> LENGTH: 40
<212> TYPE: RNA
<213> ORGANISM: Artificial
<220> FEATURE:
<223> OTHER INFORMATION: Aptamer

<400> SEQUENCE: 220
caacacucga aggguuuauu ggccccacca ugguggaaug                              40

<210> SEQ ID NO 221
<211> LENGTH: 40
<212> TYPE: RNA
<213> ORGANISM: Artificial
<220> FEATURE:
<223> OTHER INFORMATION: Aptamer

<400> SEQUENCE: 221
cugaaggguu gauuggcggc uuccagggga cgaagcgcug                              40

<210> SEQ ID NO 222
<211> LENGTH: 40
<212> TYPE: RNA
<213> ORGANISM: Artificial
<220> FEATURE:
<223> OTHER INFORMATION: Aptamer

<400> SEQUENCE: 222
cgguuauugg cggaggaucu gucauggcau gccucgacug                              40

<210> SEQ ID NO 223
<211> LENGTH: 40
<212> TYPE: RNA
<213> ORGANISM: Artificial
<220> FEATURE:
<223> OTHER INFORMATION: Aptamer

<400> SEQUENCE: 223
gguuuauugg uggucauccu uugcaaugug cuuugacuua                              40

<210> SEQ ID NO 224
<211> LENGTH: 40
<212> TYPE: RNA
<213> ORGANISM: Artificial
<220> FEATURE:
<223> OTHER INFORMATION: Aptamer

<400> SEQUENCE: 224
gauuuugguu uauuggcuuu gccguuugaa gugcaaaaug                              40

<210> SEQ ID NO 225
<211> LENGTH: 40
<212> TYPE: RNA
<213> ORGANISM: Artificial
<220> FEATURE:
<223> OTHER INFORMATION: Aptamer

<400> SEQUENCE: 225
ucggucuaau guucgccguu cagguuuauu ggucucguuu                              40

<210> SEQ ID NO 226
<211> LENGTH: 40
<212> TYPE: RNA
<213> ORGANISM: Artificial
<220> FEATURE:
<223> OTHER INFORMATION: Aptamer

<400> SEQUENCE: 226
```

```
gguguacugg cccucuuacg cucaaugcuc aggugguguq                              40

<210> SEQ ID NO 227
<211> LENGTH: 40
<212> TYPE: RNA
<213> ORGANISM: Artificial
<220> FEATURE:
<223> OTHER INFORMATION: Aptamer

<400> SEQUENCE: 227
cacguucuac gguugauugg ucuggcacuc ugucgguaua                              40

<210> SEQ ID NO 228
<211> LENGTH: 39
<212> TYPE: RNA
<213> ORGANISM: Artificial
<220> FEATURE:
<223> OTHER INFORMATION: Aptamer

<400> SEQUENCE: 228
gguguauugg cgacaugaag ggaauuucuc guugguuug                               39

<210> SEQ ID NO 229
<211> LENGTH: 40
<212> TYPE: RNA
<213> ORGANISM: Artificial
<220> FEATURE:
<223> OTHER INFORMATION: Aptamer

<400> SEQUENCE: 229
ucgucucagg uguauuggcu ggcgcugcga ggagucgagg                              40

<210> SEQ ID NO 230
<211> LENGTH: 40
<212> TYPE: RNA
<213> ORGANISM: Artificial
<220> FEATURE:
<223> OTHER INFORMATION: Aptamer

<400> SEQUENCE: 230 ugucccucu ugcguuucgg guguauuggu ccuuucggga                               40

<210> SEQ ID NO 231
<211> LENGTH: 40
<212> TYPE: RNA
<213> ORGANISM: Artificial
<220> FEATURE:
<223> OTHER INFORMATION: Aptamer

<400> SEQUENCE: 231
ucuucuaggu uauuggcgcg uugaucacau cuaccggcug                              40

<210> SEQ ID NO 232
<211> LENGTH: 40
<212> TYPE: RNA
<213> ORGANISM: Artificial
<220> FEATURE:
<223> OTHER INFORMATION: Aptamer

<400> SEQUENCE: 232
uguccgcugg guguacuggc cgguuucguu gccauguugu                              40

<210> SEQ ID NO 233
<211> LENGTH: 40
<212> TYPE: RNA
```

```
<213> ORGANISM: Artificial
<220> FEATURE:
<223> OTHER INFORMATION: Aptamer

<400> SEQUENCE: 233
aggguguauu ggcacaguuu ugcuuacggc uaauugguug                              40

<210> SEQ ID NO 234
<211> LENGTH: 40
<212> TYPE: RNA
<213> ORGANISM: Artificial
<220> FEATURE:
<223> OTHER INFORMATION: Aptamer

<400> SEQUENCE: 234
cacacuuuuc ucgguaauug gcgcuacuuc ccguagaaug                              40

<210> SEQ ID NO 235
<211> LENGTH: 40
<212> TYPE: RNA
<213> ORGANISM: Artificial
<220> FEATURE:
<223> OTHER INFORMATION: Aptamer

<400> SEQUENCE: 235
uuguugucgu ugguuauugg cgcaucggac cgauuggcug                              40

<210> SEQ ID NO 236
<211> LENGTH: 40
<212> TYPE: RNA
<213> ORGANISM: Artificial
<220> FEATURE:
<223> OTHER INFORMATION: Aptamer

<400> SEQUENCE: 236
ucuucgcaac gcuugguuau uggcggaucc ucgaucgcug                              40

<210> SEQ ID NO 237
<211> LENGTH: 40
<212> TYPE: RNA
<213> ORGANISM: Artificial
<220> FEATURE:
<223> OTHER INFORMATION: Aptamer

<400> SEQUENCE: 237
gguauauugg cgccacuucc cccgcgacua guggaacuug                              40

<210> SEQ ID NO 238
<211> LENGTH: 40
<212> TYPE: RNA
<213> ORGANISM: Artificial
<220> FEATURE:
<223> OTHER INFORMATION: Aptamer

<400> SEQUENCE: 238
ucacguccac uccugguuau uggcgucauu uucugagcug                              40

<210> SEQ ID NO 239
<211> LENGTH: 40
<212> TYPE: RNA
<213> ORGANISM: Artificial
<220> FEATURE:
<223> OTHER INFORMATION: Aptamer

<400> SEQUENCE: 239
gguaaauugg ucuuguuauu gcgauuuugc ggacuugugu                              40
```

```
<210> SEQ ID NO 240
<211> LENGTH: 40
<212> TYPE: RNA
<213> ORGANISM: Artificial
<220> FEATURE:
<223> OTHER INFORMATION: Aptamer

<400> SEQUENCE: 240
aauccuguug ucucaggugg auugguugua uucuuacgga                              40

<210> SEQ ID NO 241
<211> LENGTH: 39
<212> TYPE: RNA
<213> ORGANISM: Artificial
<220> FEATURE:
<223> OTHER INFORMATION: Aptamer

<400> SEQUENCE: 241
aggugaauug gcuuugcgc uauuuuugg ugcuuaggg                                 39

<210> SEQ ID NO 242
<211> LENGTH: 40
<212> TYPE: RNA
<213> ORGANISM: Artificial
<220> FEATURE:
<223> OTHER INFORMATION: Aptamer

<400> SEQUENCE: 242 cuucggggu uauuggcaca gguucuucgc accugguuug                               40

<210> SEQ ID NO 243
<211> LENGTH: 40
<212> TYPE: RNA
<213> ORGANISM: Artificial
<220> FEATURE:
<223> OTHER INFORMATION: Aptamer

<400> SEQUENCE: 243
gagccacggg uuuacuggcg cuaaacaaau guuuaguaug                              40

<210> SEQ ID NO 244
<211> LENGTH: 40
<212> TYPE: RNA
<213> ORGANISM: Artificial
<220> FEATURE:
<223> OTHER INFORMATION: Aptamer

<400> SEQUENCE: 244
uccacuguau cucucgggug uacuggcgcg auacugaaug                              40

<210> SEQ ID NO 245
<211> LENGTH: 40
<212> TYPE: RNA
<213> ORGANISM: Artificial
<220> FEATURE:
<223> OTHER INFORMATION: Aptamer

<400> SEQUENCE: 245
ugugguuacu ggcgccuagc acuucuccgu gcacggaaug                              40

<210> SEQ ID NO 246
<211> LENGTH: 40
<212> TYPE: RNA
<213> ORGANISM: Artificial
<220> FEATURE:
```

<223> OTHER INFORMATION: Aptamer

<400> SEQUENCE: 246
aacuuccggg uggauugguu acugucacug ugauugugga                              40

<210> SEQ ID NO 247
<211> LENGTH: 40
<212> TYPE: RNA
<213> ORGANISM: Artificial
<220> FEATURE:
<223> OTHER INFORMATION: Aptamer

<400> SEQUENCE: 247
aauuccacgu uaucaggugu auuggcgacu aauugucaug                              40

<210> SEQ ID NO 248
<211> LENGTH: 40
<212> TYPE: RNA
<213> ORGANISM: Artificial
<220> FEATURE:
<223> OTHER INFORMATION: Aptamer

<400> SEQUENCE: 248
cccucugggu auacuggcga auucauucuc guuuugucug                              40

<210> SEQ ID NO 249
<211> LENGTH: 41
<212> TYPE: RNA
<213> ORGANISM: Artificial
<220> FEATURE:
<223> OTHER INFORMATION: Aptamer

<400> SEQUENCE: 249
ccgcucucga cuuucguccu ggguuaauug gccuaacggu g                            41

<210> SEQ ID NO 250
<211> LENGTH: 40
<212> TYPE: RNA
<213> ORGANISM: Artificial
<220> FEATURE:
<223> OTHER INFORMATION: Aptamer

<400> SEQUENCE: 250
uguucgggug uauuggcaac ugcauguuug caguaauugg                              40

<210> SEQ ID NO 251
<211> LENGTH: 40
<212> TYPE: RNA
<213> ORGANISM: Artificial
<220> FEATURE:
<223> OTHER INFORMATION: Aptamer

<400> SEQUENCE: 251
gguuuauugg ugcuacaagu ugcuucacaa cccguaguua                              40

<210> SEQ ID NO 252
<211> LENGTH: 40
<212> TYPE: RNA
<213> ORGANISM: Artificial
<220> FEATURE:
<223> OTHER INFORMATION: Aptamer

<400> SEQUENCE: 252
aacgugaugc uaugucggug ccacugguga uucggccgcg                              40

```
<210> SEQ ID NO 253
<211> LENGTH: 40
<212> TYPE: RNA
<213> ORGANISM: Artificial
<220> FEATURE:
<223> OTHER INFORMATION: Aptamer

<400> SEQUENCE: 253
agagcucgcc accucucgcc cggguucauu ggucucguuu                           40

<210> SEQ ID NO 254
<211> LENGTH: 40
<212> TYPE: RNA
<213> ORGANISM: Artificial
<220> FEATURE:
<223> OTHER INFORMATION: Aptamer

<400> SEQUENCE: 254
guuguucagg ugauuggcgc ugguucugug ggcccgaaug                           40

<210> SEQ ID NO 255
<211> LENGTH: 26
<212> TYPE: RNA
<213> ORGANISM: Artificial
<220> FEATURE:
<223> OTHER INFORMATION: Aptamer

<400> SEQUENCE: 255
gguuauuggc uuuccgagcg aagaug                                         26

<210> SEQ ID NO 256
<211> LENGTH: 40
<212> TYPE: RNA
<213> ORGANISM: Artificial
<220> FEATURE:
<223> OTHER INFORMATION: Aptamer

<400> SEQUENCE: 256
aacgucuuuc ggguacugg uguugauuuu aggacaauua                           40

<210> SEQ ID NO 257
<211> LENGTH: 40
<212> TYPE: RNA
<213> ORGANISM: Artificial
<220> FEATURE:
<223> OTHER INFORMATION: Aptamer

<400> SEQUENCE: 257
gaauggugua uuggucguca uccgugugcc ggcugaugga                          40

<210> SEQ ID NO 258
<211> LENGTH: 39
<212> TYPE: RNA
<213> ORGANISM: Artificial
<220> FEATURE:
<223> OTHER INFORMATION: Aptamer

<400> SEQUENCE: 258 uccccggaa aacaugccca gguugauugg ucauugugu                            39

<210> SEQ ID NO 259
<211> LENGTH: 40
<212> TYPE: RNA
<213> ORGANISM: Artificial
<220> FEATURE:
<223> OTHER INFORMATION: Aptamer
```

<400> SEQUENCE: 259
ucgaucguuu cagguuauug gcgacacauu cgugggacug         40

<210> SEQ ID NO 260
<211> LENGTH: 40
<212> TYPE: RNA
<213> ORGANISM: Artificial
<220> FEATURE:
<223> OTHER INFORMATION: Aptamer

<400> SEQUENCE: 260
uuccccugcg aacagguuua uuggcggugc aguuacagug         40

<210> SEQ ID NO 261
<211> LENGTH: 40
<212> TYPE: RNA
<213> ORGANISM: Artificial
<220> FEATURE:
<223> OTHER INFORMATION: Aptamer

<400> SEQUENCE: 261
gguuuacugg cgcuagcggc uguuggaccg cuuugaacug         40

<210> SEQ ID NO 262
<211> LENGTH: 40
<212> TYPE: RNA
<213> ORGANISM: Artificial
<220> FEATURE:
<223> OTHER INFORMATION: Aptamer

<400> SEQUENCE: 262
cggugaacug guuacgucgg acuggccuuu cuugcgugua         40

<210> SEQ ID NO 263
<211> LENGTH: 40
<212> TYPE: RNA
<213> ORGANISM: Artificial
<220> FEATURE:
<223> OTHER INFORMATION: Aptamer

<400> SEQUENCE: 263
uuguuggccg ccugguuuac uggcucucau uccgagcaug         40

<210> SEQ ID NO 264
<211> LENGTH: 40
<212> TYPE: RNA
<213> ORGANISM: Artificial
<220> FEATURE:
<223> OTHER INFORMATION: Aptamer

<400> SEQUENCE: 264
ggugaauugg cuuucgguug auguagaguc uagggagaug         40

<210> SEQ ID NO 265
<211> LENGTH: 40
<212> TYPE: RNA
<213> ORGANISM: Artificial
<220> FEATURE:
<223> OTHER INFORMATION: Aptamer

<400> SEQUENCE: 265
gguuaauugg ccgggguucu agauaauacu uccuugugug         40

<210> SEQ ID NO 266
<211> LENGTH: 40

```
<212> TYPE: RNA
<213> ORGANISM: Artificial
<220> FEATURE:
<223> OTHER INFORMATION: Aptamer

<400> SEQUENCE: 266
gguuuacugg cggccagaau gcuuugcuga augguggugg                                40

<210> SEQ ID NO 267
<211> LENGTH: 39
<212> TYPE: RNA
<213> ORGANISM: Artificial
<220> FEATURE:
<223> OTHER INFORMATION: Aptamer

<400> SEQUENCE: 267
acguuggcgc uuucgagguu auuggcuccu uuuggcgug                                 39

<210> SEQ ID NO 268
<211> LENGTH: 40
<212> TYPE: RNA
<213> ORGANISM: Artificial
<220> FEATURE:
<223> OTHER INFORMATION: Aptamer

<400> SEQUENCE: 268
cauuugcguu ucggguuuac uggcacauuc uccugcguua                                40

<210> SEQ ID NO 269
<211> LENGTH: 40
<212> TYPE: RNA
<213> ORGANISM: Artificial
<220> FEATURE:
<223> OTHER INFORMATION: Aptamer

<400> SEQUENCE: 269
cgguuuauug gcugauuuac cggcuccuug uauuugaug                                 40

<210> SEQ ID NO 270
<211> LENGTH: 40
<212> TYPE: RNA
<213> ORGANISM: Artificial
<220> FEATURE:
<223> OTHER INFORMATION: Aptamer

<400> SEQUENCE: 270
gcguaucuag gugaacuggc gcuauacucc gcguggaaug                                40

<210> SEQ ID NO 271
<211> LENGTH: 40
<212> TYPE: RNA
<213> ORGANISM: Artificial
<220> FEATURE:
<223> OTHER INFORMATION: Aptamer

<400> SEQUENCE: 271
ucgccauccc uggugaacug guuacuaucu ucuuggugua                                40

<210> SEQ ID NO 272
<211> LENGTH: 40
<212> TYPE: RNA
<213> ORGANISM: Artificial
<220> FEATURE:
<223> OTHER INFORMATION: Aptamer

<400> SEQUENCE: 272
```

```
ucuaggugua uuggucaguu gaacgguguu caucuuguuu                    40

<210> SEQ ID NO 273
<211> LENGTH: 40
<212> TYPE: RNA
<213> ORGANISM: Artificial
<220> FEATURE:
<223> OTHER INFORMATION: Aptamer

<400> SEQUENCE: 273
ucucuguugc uuaucuaggu guauggcua gccucuugug                     40

<210> SEQ ID NO 274
<211> LENGTH: 40
<212> TYPE: RNA
<213> ORGANISM: Artificial
<220> FEATURE:
<223> OTHER INFORMATION: Aptamer

<400> SEQUENCE: 274
uugucuuggu guauggguua cguccaaug ggcgguguau                     40

<210> SEQ ID NO 275
<211> LENGTH: 40
<212> TYPE: RNA
<213> ORGANISM: Artificial
<220> FEATURE:
<223> OTHER INFORMATION: Aptamer

<400> SEQUENCE: 275
acugcgucgg cuacgguuua cuggcuccuc aucgggcagg                    40

<210> SEQ ID NO 276
<211> LENGTH: 40
<212> TYPE: RNA
<213> ORGANISM: Artificial
<220> FEATURE:
<223> OTHER INFORMATION: Aptamer

<400> SEQUENCE: 276
augcauuuuu uggguggacu ggcagcucuu gacgcgguaa                    40

<210> SEQ ID NO 277
<211> LENGTH: 40
<212> TYPE: RNA
<213> ORGANISM: Artificial
<220> FEATURE:
<223> OTHER INFORMATION: Aptamer

<400> SEQUENCE: 277
gguguacugg cugaucacug auuugcaauc gauuaucgug                    40

<210> SEQ ID NO 278
<211> LENGTH: 38
<212> TYPE: RNA
<213> ORGANISM: Artificial
<220> FEATURE:
<223> OTHER INFORMATION: Aptamer

<400> SEQUENCE: 278
gguuuauugg uggucucugc cuuucauagg ccgauuua                      38

<210> SEQ ID NO 279
<211> LENGTH: 40
<212> TYPE: RNA
<213> ORGANISM: Artificial
```

```
<220> FEATURE:
<223> OTHER INFORMATION: Aptamer

<400> SEQUENCE: 279
agucugcauc aaggugaauu ggcgaugccc cccaugucug                           40

<210> SEQ ID NO 280
<211> LENGTH: 40
<212> TYPE: RNA
<213> ORGANISM: Artificial
<220> FEATURE:
<223> OTHER INFORMATION: Aptamer

<400> SEQUENCE: 280
agugucuucu uggguaauug gcuuucggga uccgaaaaug                           40

<210> SEQ ID NO 281
<211> LENGTH: 40
<212> TYPE: RNA
<213> ORGANISM: Artificial
<220> FEATURE:
<223> OTHER INFORMATION: Aptamer

<400> SEQUENCE: 281
aucgcauuuu gucuaggugu auuggcuaag cucguugugu                           40

<210> SEQ ID NO 282
<211> LENGTH: 40
<212> TYPE: RNA
<213> ORGANISM: Artificial
<220> FEATURE:
<223> OTHER INFORMATION: Aptamer

<400> SEQUENCE: 282
aucgcugcug ucauucguac cggguuuauu ggucucgugu                           40

<210> SEQ ID NO 283
<211> LENGTH: 40
<212> TYPE: RNA
<213> ORGANISM: Artificial
<220> FEATURE:
<223> OTHER INFORMATION: Aptamer

<400> SEQUENCE: 283
ccucgauguu caggugcauu gguuuccacg uauuggagga                           40

<210> SEQ ID NO 284
<211> LENGTH: 40
<212> TYPE: RNA
<213> ORGANISM: Artificial
<220> FEATURE:
<223> OTHER INFORMATION: Aptamer

<400> SEQUENCE: 284
ggugaauugg uguucugaug uuguaugaaa cauagauuua                           40

<210> SEQ ID NO 285
<211> LENGTH: 40
<212> TYPE: RNA
<213> ORGANISM: Artificial
<220> FEATURE:
<223> OTHER INFORMATION: Aptamer

<400> SEQUENCE: 285
gguguacugg uaacggcgaa acagauguuu ggucguuuca                           40
```

```
<210> SEQ ID NO 286
<211> LENGTH: 40
<212> TYPE: RNA
<213> ORGANISM: Artificial
<220> FEATURE:
<223> OTHER INFORMATION: Aptamer

<400> SEQUENCE: 286
augucgccca ucucugcauu cugggucauu ggucucguuu                                40

<210> SEQ ID NO 287
<211> LENGTH: 40
<212> TYPE: RNA
<213> ORGANISM: Artificial
<220> FEATURE:
<223> OTHER INFORMATION: Aptamer

<400> SEQUENCE: 287
cgucaugggu guauugguua uaucacuccg aagauacaaa                                40

<210> SEQ ID NO 288
<211> LENGTH: 40
<212> TYPE: RNA
<213> ORGANISM: Artificial
<220> FEATURE:
<223> OTHER INFORMATION: Aptamer

<400> SEQUENCE: 288
cguccgaucg auacugguau auuggcgccu ucguggaaug                                40

<210> SEQ ID NO 289
<211> LENGTH: 40
<212> TYPE: RNA
<213> ORGANISM: Artificial
<220> FEATURE:
<223> OTHER INFORMATION: Aptamer

<400> SEQUENCE: 289
cgucgggugu auuggcugcu uguuauaucg acggguccag                                40

<210> SEQ ID NO 290
<211> LENGTH: 40
<212> TYPE: RNA
<213> ORGANISM: Artificial
<220> FEATURE:
<223> OTHER INFORMATION: Aptamer

<400> SEQUENCE: 290
cuguuugggg uuauuggcga ccguuacguu cacggugaug                                40

<210> SEQ ID NO 291
<211> LENGTH: 40
<212> TYPE: RNA
<213> ORGANISM: Artificial
<220> FEATURE:
<223> OTHER INFORMATION: Aptamer

<400> SEQUENCE: 291
gacgguugau uggcgguuuc aacgacuucg uuuguacuug                                40

<210> SEQ ID NO 292
<211> LENGTH: 40
<212> TYPE: RNA
<213> ORGANISM: Artificial
<220> FEATURE:
<223> OTHER INFORMATION: Aptamer
```

```
<400> SEQUENCE: 292
uaguuugcgg ggacggucua cuggcgccgu aguuggaaug                              40

<210> SEQ ID NO 293
<211> LENGTH: 40
<212> TYPE: RNA
<213> ORGANISM: Artificial
<220> FEATURE:
<223> OTHER INFORMATION: Aptamer

<400> SEQUENCE: 293
uccggguucc auuggccgaa uucugugucg agucugugug                              40

<210> SEQ ID NO 294
<211> LENGTH: 40
<212> TYPE: RNA
<213> ORGANISM: Artificial
<220> FEATURE:
<223> OTHER INFORMATION: Aptamer

<400> SEQUENCE: 294
ugggccacuu cucguguccg gguauauugg ucaguggeeu                              40

<210> SEQ ID NO 295
<211> LENGTH: 40
<212> TYPE: RNA
<213> ORGANISM: Artificial
<220> FEATURE:
<223> OTHER INFORMATION: Aptamer

<400> SEQUENCE: 295
ugucugguuu auuggcuauc ccacuuccac ggugaugaug                              40

<210> SEQ ID NO 296
<211> LENGTH: 40
<212> TYPE: RNA
<213> ORGANISM: Artificial
<220> FEATURE:
<223> OTHER INFORMATION: Aptamer

<400> SEQUENCE: 296
uuuuacuuuu ccuacgaccg ggugaacugg cucuuggaug                              40

<210> SEQ ID NO 297
<211> LENGTH: 40
<212> TYPE: RNA
<213> ORGANISM: Artificial
<220> FEATURE:
<223> OTHER INFORMATION: Aptamer

<400> SEQUENCE: 297
gguagauugg cuccugcucg gccugguccg uuugggcaug                              40

<210> SEQ ID NO 298
<211> LENGTH: 36
<212> TYPE: RNA
<213> ORGANISM: Artificial
<220> FEATURE:
<223> OTHER INFORMATION: Aptamer

<400> SEQUENCE: 298
agguguacug guuauucggu aauaugcugg auugaa                                  36

<210> SEQ ID NO 299
```

```
<211> LENGTH: 40
<212> TYPE: RNA
<213> ORGANISM: Artificial
<220> FEATURE:
<223> OTHER INFORMATION: Aptamer

<400> SEQUENCE: 299
cacaccgggu ggacuggtaa gauugccuuu acaaucagua                    40

<210> SEQ ID NO 300
<211> LENGTH: 40
<212> TYPE: RNA
<213> ORGANISM: Artificial
<220> FEATURE:
<223> OTHER INFORMATION: Aptamer

<400> SEQUENCE: 300
uccuuuccag guauuggguc cgucacacuu gcgucgggug                    40

<210> SEQ ID NO 301
<211> LENGTH: 40
<212> TYPE: RNA
<213> ORGANISM: Artificial
<220> FEATURE:
<223> OTHER INFORMATION: Aptamer

<400> SEQUENCE: 301
ucggguuauu ggcgaaauuu ugcugugcga aaaucugcug                    40

<210> SEQ ID NO 302
<211> LENGTH: 40
<212> TYPE: RNA
<213> ORGANISM: Artificial
<220> FEATURE:
<223> OTHER INFORMATION: Aptamer

<400> SEQUENCE: 302
ucuguguugu ucagguguac uggcgacacu gugcguaaug                    40

<210> SEQ ID NO 303
<211> LENGTH: 40
<212> TYPE: RNA
<213> ORGANISM: Artificial
<220> FEATURE:
<223> OTHER INFORMATION: Aptamer

<400> SEQUENCE: 303
uguuccaggu guauggugc ucacgaucgu ugggucuaua                     40

<210> SEQ ID NO 304
<211> LENGTH: 40
<212> TYPE: RNA
<213> ORGANISM: Artificial
<220> FEATURE:
<223> OTHER INFORMATION: Aptamer

<400> SEQUENCE: 304
uuacuguaac gucuuacugg guucauuggc gcucggaaug                    40

<210> SEQ ID NO 305
<211> LENGTH: 40
<212> TYPE: RNA
<213> ORGANISM: Artificial
<220> FEATURE:
<223> OTHER INFORMATION: Aptamer

<400> SEQUENCE: 305
```
uuucguccag gugaauuggu gccgggcacu ucuuggagua        40

<210> SEQ ID NO 306
<211> LENGTH: 40
<212> TYPE: RNA
<213> ORGANISM: Artificial
<220> FEATURE:
<223> OTHER INFORMATION: Aptamer

<400> SEQUENCE: 306
ggugaacugg uccgcuaucc gcgaauguca uagaugggug        40

<210> SEQ ID NO 307
<211> LENGTH: 40
<212> TYPE: RNA
<213> ORGANISM: Artificial
<220> FEATURE:
<223> OTHER INFORMATION: Aptamer

<400> SEQUENCE: 307
ggugaacugg uuaccugucg uauucucugc cuugugugua        40

<210> SEQ ID NO 308
<211> LENGTH: 40
<212> TYPE: RNA
<213> ORGANISM: Artificial
<220> FEATURE:
<223> OTHER INFORMATION: Aptamer

<400> SEQUENCE: 308
ggugaauugg ugccucaucc ucucguagga gugaaguuga        40

<210> SEQ ID NO 309
<211> LENGTH: 40
<212> TYPE: RNA
<213> ORGANISM: Artificial
<220> FEATURE:
<223> OTHER INFORMATION: Aptamer

<400> SEQUENCE: 309
gguugauugg uggauuccgu gugacacgc gcagucaaua        40

<210> SEQ ID NO 310
<211> LENGTH: 40
<212> TYPE: RNA
<213> ORGANISM: Artificial
<220> FEATURE:
<223> OTHER INFORMATION: Aptamer

<400> SEQUENCE: 310
gguuuauugg ccuucauuca ucuguaaagg aaugaugaug        40

<210> SEQ ID NO 311
<211> LENGTH: 40
<212> TYPE: RNA
<213> ORGANISM: Artificial
<220> FEATURE:
<223> OTHER INFORMATION: Aptamer

<400> SEQUENCE: 311
gguuugauug gcccucuccu ccauugaggu gguuaggaug        40

<210> SEQ ID NO 312
<211> LENGTH: 40
<212> TYPE: RNA

<213> ORGANISM: Artificial
<220> FEATURE:
<223> OTHER INFORMATION: Aptamer

<400> SEQUENCE: 312
aacuuccggg uggauugguu acugucauug ugauugugga          40

<210> SEQ ID NO 313
<211> LENGTH: 40
<212> TYPE: RNA
<213> ORGANISM: Artificial
<220> FEATURE:
<223> OTHER INFORMATION: Aptamer

<400> SEQUENCE: 313
ccucugcugu gguauauugg cgcucuucgc ugaagucaug          40

<210> SEQ ID NO 314
<211> LENGTH: 39
<212> TYPE: RNA
<213> ORGANISM: Artificial
<220> FEATURE:
<223> OTHER INFORMATION: Aptamer

<400> SEQUENCE: 314
ccuguuuguc uagguucauu ggcgcuuauu ccuggaaug           39

<210> SEQ ID NO 315
<211> LENGTH: 41
<212> TYPE: RNA
<213> ORGANISM: Artificial
<220> FEATURE:
<223> OTHER INFORMATION: Aptamer

<400> SEQUENCE: 315
cggacugcag guguacuggu ucccuuagau caaguggcgu g        41

<210> SEQ ID NO 316
<211> LENGTH: 40
<212> TYPE: RNA
<213> ORGANISM: Artificial
<220> FEATURE:
<223> OTHER INFORMATION: Aptamer

<400> SEQUENCE: 316
ggcguucuuc gcuguaguuc cgguuuauug gucuuuguuu          40

<210> SEQ ID NO 317
<211> LENGTH: 40
<212> TYPE: RNA
<213> ORGANISM: Artificial
<220> FEATURE:
<223> OTHER INFORMATION: Aptamer

<400> SEQUENCE: 317
ggguguauug guuaucugau uauugaaauc augauguaua          40

<210> SEQ ID NO 318
<211> LENGTH: 39
<212> TYPE: RNA
<213> ORGANISM: Artificial
<220> FEATURE:
<223> OTHER INFORMATION: Aptamer

<400> SEQUENCE: 318 uacgcggqug ucuucaggug uacugguuac ucgugugua           39

<210> SEQ ID NO 319
<211> LENGTH: 40
<212> TYPE: RNA
<213> ORGANISM: Artificial
<220> FEATURE:
<223> OTHER INFORMATION: Aptamer

<400> SEQUENCE: 319
uucugcuucg uuaaacggug uacuggcucg agucgaguga                                40

<210> SEQ ID NO 320
<211> LENGTH: 40
<212> TYPE: RNA
<213> ORGANISM: Artificial
<220> FEATURE:
<223> OTHER INFORMATION: Aptamer

<400> SEQUENCE: 320
gguguauugg ugagaacacu cccugaacgg uguucuuuga                                40

<210> SEQ ID NO 321
<211> LENGTH: 40
<212> TYPE: RNA
<213> ORGANISM: Artificial
<220> FEATURE:
<223> OTHER INFORMATION: Aptamer

<400> SEQUENCE: 321
gguguuauug gugcucgcag cguucccgac uucgagaaua                                40

<210> SEQ ID NO 322
<211> LENGTH: 40
<212> TYPE: RNA
<213> ORGANISM: Artificial
<220> FEATURE:
<223> OTHER INFORMATION: Aptamer

<400> SEQUENCE: 322
gguuaacugg cgaaucguug ucauccgauc uugauuaaug                                40

<210> SEQ ID NO 323
<211> LENGTH: 40
<212> TYPE: RNA
<213> ORGANISM: Artificial
<220> FEATURE:
<223> OTHER INFORMATION: Aptamer

<400> SEQUENCE: 323
aauccuccgg cucuugguga auuggcuccc aucgggaaug                                40

<210> SEQ ID NO 324
<211> LENGTH: 40
<212> TYPE: RNA
<213> ORGANISM: Artificial
<220> FEATURE:
<223> OTHER INFORMATION: Aptamer

<400> SEQUENCE: 324
acgacugggu gcacuggcgg aguuuugacu aacuuagcug                                40

<210> SEQ ID NO 325
<211> LENGTH: 40
<212> TYPE: RNA
<213> ORGANISM: Artificial
<220> FEATURE:

```
<223> OTHER INFORMATION: Aptamer

<400> SEQUENCE: 325
cgaccaggug uauuggucuu uccgccuugu ucgcauuaga                              40

<210> SEQ ID NO 326
<211> LENGTH: 40
<212> TYPE: RNA
<213> ORGANISM: Artificial
<220> FEATURE:
<223> OTHER INFORMATION: Aptamer

<400> SEQUENCE: 326
cgcguucuac gguuuuacug gcuuccggcu uuuggacaug                              40

<210> SEQ ID NO 327
<211> LENGTH: 40
<212> TYPE: RNA
<213> ORGANISM: Artificial
<220> FEATURE:
<223> OTHER INFORMATION: Aptamer

<400> SEQUENCE: 327
cucgucuacg uuuuaggugu auuggcccuu ucguuggaug                              40

<210> SEQ ID NO 328
<211> LENGTH: 40
<212> TYPE: RNA
<213> ORGANISM: Artificial
<220> FEATURE:
<223> OTHER INFORMATION: Aptamer

<400> SEQUENCE: 328
cuuucgcgaa aucuggguuc auuggcgauu ccgauggcug                              40

<210> SEQ ID NO 329
<211> LENGTH: 40
<212> TYPE: RNA
<213> ORGANISM: Artificial
<220> FEATURE:
<223> OTHER INFORMATION: Aptamer

<400> SEQUENCE: 329
cgguaacugg cgcugcugcc accgauugcc agcggaacug                              40

<210> SEQ ID NO 330
<211> LENGTH: 40
<212> TYPE: RNA
<213> ORGANISM: Artificial
<220> FEATURE:
<223> OTHER INFORMATION: Aptamer

<400> SEQUENCE: 330
guucugggug gauuggucuu guacaauucu uuuggcugga                              40

<210> SEQ ID NO 331
<211> LENGTH: 40
<212> TYPE: RNA
<213> ORGANISM: Artificial
<220> FEATURE:
<223> OTHER INFORMATION: Aptamer

<400> SEQUENCE: 331
ugcauugcuu agcuuggug uacugguugc auucgcggua                               40
```

```
<210> SEQ ID NO 332
<211> LENGTH: 37
<212> TYPE: RNA
<213> ORGANISM: Artificial
<220> FEATURE:
<223> OTHER INFORMATION: Aptamer

<400> SEQUENCE: 332
gguguauugg uagcuucgga caucguuucg aucucua                               37

<210> SEQ ID NO 333
<211> LENGTH: 40
<212> TYPE: RNA
<213> ORGANISM: Artificial
<220> FEATURE:
<223> OTHER INFORMATION: Aptamer

<400> SEQUENCE: 333
gguugauugg caacuucguc cgcuugggau gaacguaaug                            40

<210> SEQ ID NO 334
<211> LENGTH: 40
<212> TYPE: RNA
<213> ORGANISM: Artificial
<220> FEATURE:
<223> OTHER INFORMATION: Aptamer

<400> SEQUENCE: 334
accgguuccg gguguacugg uuuuacauuc cgauguaauu                            40

<210> SEQ ID NO 335
<211> LENGTH: 40
<212> TYPE: RNA
<213> ORGANISM: Artificial
<220> FEATURE:
<223> OTHER INFORMATION: Aptamer

<400> SEQUENCE: 335
auugcuuccc ugcgcgauag guguacuggu cugugugaua                            40

<210> SEQ ID NO 336
<211> LENGTH: 40
<212> TYPE: RNA
<213> ORGANISM: Artificial
<220> FEATURE:
<223> OTHER INFORMATION: Aptamer

<400> SEQUENCE: 336
caacucuggg uuuacuggcg uuagccucu ggcuuucaug                             40

<210> SEQ ID NO 337
<211> LENGTH: 40
<212> TYPE: RNA
<213> ORGANISM: Artificial
<220> FEATURE:
<223> OTHER INFORMATION: Aptamer

<400> SEQUENCE: 337
cagguuauug gcgcugcgcu ugaguguuga ggcgggacgg                            40

<210> SEQ ID NO 338
<211> LENGTH: 40
<212> TYPE: RNA
<213> ORGANISM: Artificial
<220> FEATURE:
<223> OTHER INFORMATION: Aptamer
```

```
<400> SEQUENCE: 338
ccgacgggug uacuggcgag agucaagcgc ucuaaugcug                           40

<210> SEQ ID NO 339
<211> LENGTH: 40
<212> TYPE: RNA
<213> ORGANISM: Artificial
<220> FEATURE:
<223> OTHER INFORMATION: Aptamer

<400> SEQUENCE: 339
cggaaucuug cauaggugau uggcugugga ggacaugaug                           40

<210> SEQ ID NO 340
<211> LENGTH: 40
<212> TYPE: RNA
<213> ORGANISM: Artificial
<220> FEATURE:
<223> OTHER INFORMATION: Aptamer

<400> SEQUENCE: 340
cggccucugu ccuuuugguu uacuggguggc uuguuguuua                          40

<210> SEQ ID NO 341
<211> LENGTH: 40
<212> TYPE: RNA
<213> ORGANISM: Artificial
<220> FEATURE:
<223> OTHER INFORMATION: Aptamer

<400> SEQUENCE: 341
cucccgguuu auuggcguuc uugacucuag uuuugaauug                           40

<210> SEQ ID NO 342
<211> LENGTH: 40
<212> TYPE: RNA
<213> ORGANISM: Artificial
<220> FEATURE:
<223> OTHER INFORMATION: Aptamer

<400> SEQUENCE: 342
cgguggauug gcgacgauga ccuugauagu ccucguaaug                           40

<210> SEQ ID NO 343
<211> LENGTH: 40
<212> TYPE: RNA
<213> ORGANISM: Artificial
<220> FEATURE:
<223> OTHER INFORMATION: Aptamer

<400> SEQUENCE: 343
uccggguaua uuggucugga cucaucuucu gaguacuuua                           40

<210> SEQ ID NO 344
<211> LENGTH: 40
<212> TYPE: RNA
<213> ORGANISM: Artificial
<220> FEATURE:
<223> OTHER INFORMATION: Aptamer

<400> SEQUENCE: 344
uguaacucgc ccagguauau uggcugcugu cggagugaug                           40

<210> SEQ ID NO 345
<211> LENGTH: 40
```

```
<212> TYPE: RNA
<213> ORGANISM: Artificial
<220> FEATURE:
<223> OTHER INFORMATION: Aptamer

<400> SEQUENCE: 345
uucgacucuu ccagguggac ugguagcggu guccguugug                          40

<210> SEQ ID NO 346
<211> LENGTH: 40
<212> TYPE: RNA
<213> ORGANISM: Artificial
<220> FEATURE:
<223> OTHER INFORMATION: Aptamer

<400> SEQUENCE: 346
uuucugcacu uccaauuggu guauuggcgg ucuucgcuug                          40

<210> SEQ ID NO 347
<211> LENGTH: 40
<212> TYPE: RNA
<213> ORGANISM: Artificial
<220> FEATURE:
<223> OTHER INFORMATION: Aptamer

<400> SEQUENCE: 347
ggucuacugg ccggagucgg cguuaucguu acucugugug                          40

<210> SEQ ID NO 348
<211> LENGTH: 40
<212> TYPE: RNA
<213> ORGANISM: Artificial
<220> FEATURE:
<223> OTHER INFORMATION: Aptamer

<400> SEQUENCE: 348
ggugaacugg cauguauauu ccaaugcggu aggcguguua                          40

<210> SEQ ID NO 349
<211> LENGTH: 40
<212> TYPE: RNA
<213> ORGANISM: Artificial
<220> FEATURE:
<223> OTHER INFORMATION: Aptamer

<400> SEQUENCE: 349
ggugcauugg cucucuuugc uuuaaucagc uggauguaug                          40

<210> SEQ ID NO 350
<211> LENGTH: 38
<212> TYPE: RNA
<213> ORGANISM: Artificial
<220> FEATURE:
<223> OTHER INFORMATION: Aptamer

<400> SEQUENCE: 350
gguguacugg uugcugcuuc uggcguagac uuggcgua                            38

<210> SEQ ID NO 351
<211> LENGTH: 40
<212> TYPE: RNA
<213> ORGANISM: Artificial
<220> FEATURE:
<223> OTHER INFORMATION: Aptamer

<400> SEQUENCE: 351
```

```
gguuuauugg uucuuguugu ugucuugguu uucaagcgug                40

<210> SEQ ID NO 352
<211> LENGTH: 40
<212> TYPE: RNA
<213> ORGANISM: Artificial
<220> FEATURE:
<223> OTHER INFORMATION: Aptamer

<400> SEQUENCE: 352
acauccaggu uaauuggcca cucugccgcu gagugcguug                40

<210> SEQ ID NO 353
<211> LENGTH: 40
<212> TYPE: RNA
<213> ORGANISM: Artificial
<220> FEATURE:
<223> OTHER INFORMATION: Aptamer

<400> SEQUENCE: 353 acccccuga gauccaggug uacuggcugu uccggcgagg                40

<210> SEQ ID NO 354
<211> LENGTH: 40
<212> TYPE: RNA
<213> ORGANISM: Artificial
<220> FEATURE:
<223> OTHER INFORMATION: Aptamer

<400> SEQUENCE: 354
aguuugcugu ucggguguau uggcaaccaa ccgggcuuau                40

<210> SEQ ID NO 355
<211> LENGTH: 40
<212> TYPE: RNA
<213> ORGANISM: Artificial
<220> FEATURE:
<223> OTHER INFORMATION: Aptamer

<400> SEQUENCE: 355
gacuuuuuuu cugguccacg guguauuggc cuuucggagg                40

<210> SEQ ID NO 356
<211> LENGTH: 40
<212> TYPE: RNA
<213> ORGANISM: Artificial
<220> FEATURE:
<223> OTHER INFORMATION: Aptamer

<400> SEQUENCE: 356
gcguacgccc gcuagguuua uuggcugaau uuugucgaug                40

<210> SEQ ID NO 357
<211> LENGTH: 40
<212> TYPE: RNA
<213> ORGANISM: Artificial
<220> FEATURE:
<223> OTHER INFORMATION: Aptamer

<400> SEQUENCE: 357
guucgguuuu acuggcgauu ugcuuacuuc gcaggugcug                40

<210> SEQ ID NO 358
<211> LENGTH: 40
<212> TYPE: RNA
<213> ORGANISM: Artificial
```

```
<220> FEATURE:
<223> OTHER INFORMATION: Aptamer

<400> SEQUENCE: 358
uccaggugua uugguccgag uuacucgggu aauuagucga                            40

<210> SEQ ID NO 359
<211> LENGTH: 40
<212> TYPE: RNA
<213> ORGANISM: Artificial
<220> FEATURE:
<223> OTHER INFORMATION: Aptamer

<400> SEQUENCE: 359
ucugcuuuga cguucaacaa gguuuauugg ucauuuguuu                            40

<210> SEQ ID NO 360
<211> LENGTH: 40
<212> TYPE: RNA
<213> ORGANISM: Artificial
<220> FEATURE:
<223> OTHER INFORMATION: Aptamer

<400> SEQUENCE: 360
uugguucacu ggcgcgucgu aagccucuuc cgacgaucug                            40

<210> SEQ ID NO 361
<211> LENGTH: 40
<212> TYPE: RNA
<213> ORGANISM: Artificial
<220> FEATURE:
<223> OTHER INFORMATION: Aptamer

<400> SEQUENCE: 361
ugguagacug gcgcggaaug aauggaagcu uuucgagug                             40

<210> SEQ ID NO 362
<211> LENGTH: 39
<212> TYPE: RNA
<213> ORGANISM: Artificial
<220> FEATURE:
<223> OTHER INFORMATION: Aptamer

<400> SEQUENCE: 362
uggugauugg cuggguucgg guauacuccu uccuguaug                             39

<210> SEQ ID NO 363
<211> LENGTH: 40
<212> TYPE: RNA
<213> ORGANISM: Artificial
<220> FEATURE:
<223> OTHER INFORMATION: Aptamer

<400> SEQUENCE: 363
gguauuauug gcuaugcccu gguucuccgg uacauguaug                            40

<210> SEQ ID NO 364
<211> LENGTH: 40
<212> TYPE: RNA
<213> ORGANISM: Artificial
<220> FEATURE:
<223> OTHER INFORMATION: Aptamer

<400> SEQUENCE: 364
ggugcauugg cuacucuuuu guucuucuac aauguuugug                            40
```

<210> SEQ ID NO 365
<211> LENGTH: 40
<212> TYPE: RNA
<213> ORGANISM: Artificial
<220> FEATURE:
<223> OTHER INFORMATION: Aptamer

<400> SEQUENCE: 365
gguguacugg cauuugacau uuuucaugcc acauauguga                                  40

<210> SEQ ID NO 366
<211> LENGTH: 40
<212> TYPE: RNA
<213> ORGANISM: Artificial
<220> FEATURE:
<223> OTHER INFORMATION: Aptamer

<400> SEQUENCE: 366
gguguauugg uccgggucuu gccuucuuga gugccgggga                                  40

<210> SEQ ID NO 367
<211> LENGTH: 39
<212> TYPE: RNA
<213> ORGANISM: Artificial
<220> FEATURE:
<223> OTHER INFORMATION: Aptamer

<400> SEQUENCE: 367
gguguauugg ucuucuuccc gacuucuuuc guccguaga                                   39

<210> SEQ ID NO 368
<211> LENGTH: 40
<212> TYPE: RNA
<213> ORGANISM: Artificial
<220> FEATURE:
<223> OTHER INFORMATION: Aptamer

<400> SEQUENCE: 368
gguuauuggu acgcugaguc uugcuugacg gcgcguguuu                                  40

<210> SEQ ID NO 369
<211> LENGTH: 40
<212> TYPE: RNA
<213> ORGANISM: Artificial
<220> FEATURE:
<223> OTHER INFORMATION: Aptamer

<400> SEQUENCE: 369
aagcccaggu guacuggucg uggugauugg cugcuuguca                                  40

<210> SEQ ID NO 370
<211> LENGTH: 40
<212> TYPE: RNA
<213> ORGANISM: Artificial
<220> FEATURE:
<223> OTHER INFORMATION: Aptamer

<400> SEQUENCE: 370
auugcugucc gccggugaac ugguuauucg uugauuggga                                  40

<210> SEQ ID NO 371
<211> LENGTH: 40
<212> TYPE: RNA
<213> ORGANISM: Artificial
<220> FEATURE:
<223> OTHER INFORMATION: Aptamer

```
<400> SEQUENCE: 371
agguguauug gugcaaguuu cguucugcgg aauucgcaaa                    40

<210> SEQ ID NO 372
<211> LENGTH: 40
<212> TYPE: RNA
<213> ORGANISM: Artificial
<220> FEATURE:
<223> OTHER INFORMATION: Aptamer

<400> SEQUENCE: 372
agguuuacug gcggaucacu cuaccuguaa ugaucaccug                    40

<210> SEQ ID NO 373
<211> LENGTH: 40
<212> TYPE: RNA
<213> ORGANISM: Artificial
<220> FEATURE:
<223> OTHER INFORMATION: Aptamer

<400> SEQUENCE: 373
ccgcuugauu cgcuacaccu agguuauugg cguuggcug                     40

<210> SEQ ID NO 374
<211> LENGTH: 40
<212> TYPE: RNA
<213> ORGANISM: Artificial
<220> FEATURE:
<223> OTHER INFORMATION: Aptamer

<400> SEQUENCE: 374
cgucuaacug guguauuggu gguacauuaa ucuguucaca                    40

<210> SEQ ID NO 375
<211> LENGTH: 40
<212> TYPE: RNA
<213> ORGANISM: Artificial
<220> FEATURE:
<223> OTHER INFORMATION: Aptamer

<400> SEQUENCE: 375
cgucuggguu uauugguucg ggucgacguu gucaaaguuu                    40

<210> SEQ ID NO 376
<211> LENGTH: 40
<212> TYPE: RNA
<213> ORGANISM: Artificial
<220> FEATURE:
<223> OTHER INFORMATION: Aptamer

<400> SEQUENCE: 376
cuacacgaac ggguugaauug gccggucgcg gcuccgugug                   40

<210> SEQ ID NO 377
<211> LENGTH: 40
<212> TYPE: RNA
<213> ORGANISM: Artificial
<220> FEATURE:
<223> OTHER INFORMATION: Aptamer

<400> SEQUENCE: 377
cuauucgcca uuucagguau auuggcgcuc gauucgguug                    40

<210> SEQ ID NO 378
```

```
<211> LENGTH: 40
<212> TYPE: RNA
<213> ORGANISM: Artificial
<220> FEATURE:
<223> OTHER INFORMATION: Aptamer

<400> SEQUENCE: 378
cuuguagcgu cuuauuucug gguuuauugg ucgauugugu                    40

<210> SEQ ID NO 379
<211> LENGTH: 40
<212> TYPE: RNA
<213> ORGANISM: Artificial
<220> FEATURE:
<223> OTHER INFORMATION: Aptamer

<400> SEQUENCE: 379
gcacucguuc ggguguacug gcuuucaccu uugauaguua                    40

<210> SEQ ID NO 380
<211> LENGTH: 40
<212> TYPE: RNA
<213> ORGANISM: Artificial
<220> FEATURE:
<223> OTHER INFORMATION: Aptamer

<400> SEQUENCE: 380
gugugacggu gaacuggcug ucucggacuu ccagacgaug                    40

<210> SEQ ID NO 381
<211> LENGTH: 40
<212> TYPE: RNA
<213> ORGANISM: Artificial
<220> FEATURE:
<223> OTHER INFORMATION: Aptamer

<400> SEQUENCE: 381 guguccugc ccggauccgg guguacuggc gcuagugcug                     40

<210> SEQ ID NO 382
<211> LENGTH: 40
<212> TYPE: RNA
<213> ORGANISM: Artificial
<220> FEATURE:
<223> OTHER INFORMATION: Aptamer

<400> SEQUENCE: 382
ggguuauugg cgccauuaca uaauauguua auccggaaug                    40

<210> SEQ ID NO 383
<211> LENGTH: 40
<212> TYPE: RNA
<213> ORGANISM: Artificial
<220> FEATURE:
<223> OTHER INFORMATION: Aptamer

<400> SEQUENCE: 383 uggguuuau uggccucgcc cuuucuaag guucgauaug                      40

<210> SEQ ID NO 384
<211> LENGTH: 40
<212> TYPE: RNA
<213> ORGANISM: Artificial
<220> FEATURE:
<223> OTHER INFORMATION: Aptamer

<400> SEQUENCE: 384
```
ugugcacccu auagguaauu ggugcccuuc cucgggaaua                              40

<210> SEQ ID NO 385
<211> LENGTH: 40
<212> TYPE: RNA
<213> ORGANISM: Artificial
<220> FEATURE:
<223> OTHER INFORMATION: Aptamer

<400> SEQUENCE: 385
uucaugucuu cgguucauug gcgacgcgcc ucgcgaagug                              40

<210> SEQ ID NO 386
<211> LENGTH: 40
<212> TYPE: RNA
<213> ORGANISM: Artificial
<220> FEATURE:
<223> OTHER INFORMATION: Aptamer

<400> SEQUENCE: 386
uuugcuccgg gugcauuggu uuggucuuuu gucuucgaua                              40

<210> SEQ ID NO 387
<211> LENGTH: 40
<212> TYPE: RNA
<213> ORGANISM: Artificial
<220> FEATURE:
<223> OTHER INFORMATION: Aptamer

<400> SEQUENCE: 387
ggugauuggu ugcaucggac ucucuucccu guuugcgaga                              40

<210> SEQ ID NO 388
<211> LENGTH: 40
<212> TYPE: RNA
<213> ORGANISM: Artificial
<220> FEATURE:
<223> OTHER INFORMATION: Aptamer

<400> SEQUENCE: 388 ggugguacugg cccucgugug cgcugcgcuc agaguuucgu                             40

<210> SEQ ID NO 389
<211> LENGTH: 40
<212> TYPE: RNA
<213> ORGANISM: Artificial
<220> FEATURE:
<223> OTHER INFORMATION: Aptamer

<400> SEQUENCE: 389
gguugauugg cacaggguca cucuuuguau uccuugguug                              40

<210> SEQ ID NO 390
<211> LENGTH: 39
<212> TYPE: RNA
<213> ORGANISM: Artificial
<220> FEATURE:
<223> OTHER INFORMATION: Aptamer

<400> SEQUENCE: 390
aacgugugcc ccuccugucu gggugaauug gucuucgga                               39

<210> SEQ ID NO 391
<211> LENGTH: 40
<212> TYPE: RNA

```
<213> ORGANISM: Artificial
<220> FEATURE:
<223> OTHER INFORMATION: Aptamer

<400> SEQUENCE: 391
aacucgcuuc ggguuuauug gcagauaucc gcuuucguug                              40

<210> SEQ ID NO 392
<211> LENGTH: 40
<212> TYPE: RNA
<213> ORGANISM: Artificial
<220> FEATURE:
<223> OTHER INFORMATION: Aptamer

<400> SEQUENCE: 392
aaggguuuau uggcaggucu uugauuagca gagaucgaug                              40

<210> SEQ ID NO 393
<211> LENGTH: 40
<212> TYPE: RNA
<213> ORGANISM: Artificial
<220> FEATURE:
<223> OTHER INFORMATION: Aptamer

<400> SEQUENCE: 393
auugaaacac uaaaggugua cuggucucga auuucgucua                              40

<210> SEQ ID NO 394
<211> LENGTH: 40
<212> TYPE: RNA
<213> ORGANISM: Artificial
<220> FEATURE:
<223> OTHER INFORMATION: Aptamer

<400> SEQUENCE: 394
caacaucgau cgucuagguu gauuggcccg uucccggaug                              40

<210> SEQ ID NO 395
<211> LENGTH: 40
<212> TYPE: RNA
<213> ORGANISM: Artificial
<220> FEATURE:
<223> OTHER INFORMATION: Aptamer

<400> SEQUENCE: 395
caggucuacu ggcugcaccu cucuuuuuga cguguacaug                              40

<210> SEQ ID NO 396
<211> LENGTH: 40
<212> TYPE: RNA
<213> ORGANISM: Artificial
<220> FEATURE:
<223> OTHER INFORMATION: Aptamer

<400> SEQUENCE: 396
cccaucaggu uuauuggcca gcuaguucga augcugugug                              40

<210> SEQ ID NO 397
<211> LENGTH: 40
<212> TYPE: RNA
<213> ORGANISM: Artificial
<220> FEATURE:
<223> OTHER INFORMATION: Aptamer

<400> SEQUENCE: 397
cgauucuugu guaguuccag guuuauuggc uuauaagaug                              40
```

```
<210> SEQ ID NO 398
<211> LENGTH: 40
<212> TYPE: RNA
<213> ORGANISM: Artificial
<220> FEATURE:
<223> OTHER INFORMATION: Aptamer

<400> SEQUENCE: 398
cgguuuauug gcguucuggg gcuucgaacc gccggucuug              40

<210> SEQ ID NO 399
<211> LENGTH: 40
<212> TYPE: RNA
<213> ORGANISM: Artificial
<220> FEATURE:
<223> OTHER INFORMATION: Aptamer

<400> SEQUENCE: 399
gagggugaac uggccaugga cucaugaagu acauacguag              40

<210> SEQ ID NO 400
<211> LENGTH: 40
<212> TYPE: RNA
<213> ORGANISM: Artificial
<220> FEATURE:
<223> OTHER INFORMATION: Aptamer

<400> SEQUENCE: 400
ggcugaugua cuuucggguu auuggcgcuu cuuuggacug              40

<210> SEQ ID NO 401
<211> LENGTH: 40
<212> TYPE: RNA
<213> ORGANISM: Artificial
<220> FEATURE:
<223> OTHER INFORMATION: Aptamer

<400> SEQUENCE: 401
guccgucacg guguacuggc cuuuucguug aauuagucgu              40

<210> SEQ ID NO 402
<211> LENGTH: 40
<212> TYPE: RNA
<213> ORGANISM: Artificial
<220> FEATURE:
<223> OTHER INFORMATION: Aptamer

<400> SEQUENCE: 402
guccuuuugu acguucgccg guguauuggu auuuaggaua              40

<210> SEQ ID NO 403
<211> LENGTH: 40
<212> TYPE: RNA
<213> ORGANISM: Artificial
<220> FEATURE:
<223> OTHER INFORMATION: Aptamer

<400> SEQUENCE: 403
ucaccaaucu acgggugacu ggcgcgauuu cuucgaccug              40

<210> SEQ ID NO 404
<211> LENGTH: 40
<212> TYPE: RNA
<213> ORGANISM: Artificial
<220> FEATURE:
```

<223> OTHER INFORMATION: Aptamer

<400> SEQUENCE: 404
ugccacauug guccggguuu auuggcaccu uaagg guuug                           40

<210> SEQ ID NO 405
<211> LENGTH: 40
<212> TYPE: RNA
<213> ORGANISM: Artificial
<220> FEATURE:
<223> OTHER INFORMATION: Aptamer

<400> SEQUENCE: 405
ugccucuggg uuauuggcgc uuuuaucucg gucaagcaug                           40

<210> SEQ ID NO 406
<211> LENGTH: 40
<212> TYPE: RNA
<213> ORGANISM: Artificial
<220> FEATURE:
<223> OTHER INFORMATION: Aptamer

<400> SEQUENCE: 406
uggccgggug uacugguccc cguguucucu cuuggggua                            40

<210> SEQ ID NO 407
<211> LENGTH: 40
<212> TYPE: RNA
<213> ORGANISM: Artificial
<220> FEATURE:
<223> OTHER INFORMATION: Aptamer

<400> SEQUENCE: 407
ugucuugguu uauuggcggc gucuucgaaa uggcgugug                            40

<210> SEQ ID NO 408
<211> LENGTH: 40
<212> TYPE: RNA
<213> ORGANISM: Artificial
<220> FEATURE:
<223> OTHER INFORMATION: Aptamer

<400> SEQUENCE: 408
uguuccgggu cuacuggcug uuagagaucu cugauguagg                           40

<210> SEQ ID NO 409
<211> LENGTH: 40
<212> TYPE: RNA
<213> ORGANISM: Artificial
<220> FEATURE:
<223> OTHER INFORMATION: Aptamer

<400> SEQUENCE: 409
uuccacgguu uauuggcgac cuuuucuccg aauagucaug                           40

<210> SEQ ID NO 410
<211> LENGTH: 40
<212> TYPE: RNA
<213> ORGANISM: Artificial
<220> FEATURE:
<223> OTHER INFORMATION: Aptamer

<400> SEQUENCE: 410
uucuuguuac gccccggugg auuggcugga cucucccgug                           40

```
<210> SEQ ID NO 411
<211> LENGTH: 40
<212> TYPE: RNA
<213> ORGANISM: Artificial
<220> FEATURE:
<223> OTHER INFORMATION: Aptamer

<400> SEQUENCE: 411
uugugccuca aggucgacug gugcccauau cuugggaaua                              40

<210> SEQ ID NO 412
<211> LENGTH: 40
<212> TYPE: RNA
<213> ORGANISM: Artificial
<220> FEATURE:
<223> OTHER INFORMATION: Aptamer

<400> SEQUENCE: 412
ugguuuauug gccaagucau cuaccccugg aggcuuaaug                              40

<210> SEQ ID NO 413
<211> LENGTH: 40
<212> TYPE: RNA
<213> ORGANISM: Artificial
<220> FEATURE:
<223> OTHER INFORMATION: Aptamer

<400> SEQUENCE: 413
ggucuacugg cucuagguua caaaagugcc gucuggaaug                              40

<210> SEQ ID NO 414
<211> LENGTH: 40
<212> TYPE: RNA
<213> ORGANISM: Artificial
<220> FEATURE:
<223> OTHER INFORMATION: Aptamer

<400> SEQUENCE: 414
ggugaauugg cuggcuacua gugccccugg guagccgaug                              40

<210> SEQ ID NO 415
<211> LENGTH: 40
<212> TYPE: RNA
<213> ORGANISM: Artificial
<220> FEATURE:
<223> OTHER INFORMATION: Aptamer

<400> SEQUENCE: 415
gguguacugg uuauauaugu uccguacguc guguauguua                              40

<210> SEQ ID NO 416
<211> LENGTH: 40
<212> TYPE: RNA
<213> ORGANISM: Artificial
<220> FEATURE:
<223> OTHER INFORMATION: Aptamer

<400> SEQUENCE: 416
gguguauugg caggugcauu uuugaacgau acauuggucg                              40

<210> SEQ ID NO 417
<211> LENGTH: 40
<212> TYPE: RNA
<213> ORGANISM: Artificial
<220> FEATURE:
<223> OTHER INFORMATION: Aptamer
```

<400> SEQUENCE: 417
gguuaauugg ucaccgcacc cguuuacuuc ggucggcuua          40

<210> SEQ ID NO 418
<211> LENGTH: 40
<212> TYPE: RNA
<213> ORGANISM: Artificial
<220> FEATURE:
<223> OTHER INFORMATION: Aptamer

<400> SEQUENCE: 418
gguuuauugg cuucuuaugc guuucuugcg cugggaaaug          40

<210> SEQ ID NO 419
<211> LENGTH: 40
<212> TYPE: RNA
<213> ORGANISM: Artificial
<220> FEATURE:
<223> OTHER INFORMATION: Aptamer

<400> SEQUENCE: 419
aaccgauugu gccucaggug uacugguucu ugucgggcga          40

<210> SEQ ID NO 420
<211> LENGTH: 36
<212> TYPE: RNA
<213> ORGANISM: Artificial
<220> FEATURE:
<223> OTHER INFORMATION: Aptamer

<400> SEQUENCE: 420
aacgguguau uggucuucag auuuuucuga cguuga             36

<210> SEQ ID NO 421
<211> LENGTH: 40
<212> TYPE: RNA
<213> ORGANISM: Artificial
<220> FEATURE:
<223> OTHER INFORMATION: Aptamer

<400> SEQUENCE: 421
acacuucauc gucucggugu acugguucua uauugcguuu          40

<210> SEQ ID NO 422
<211> LENGTH: 39
<212> TYPE: RNA
<213> ORGANISM: Artificial
<220> FEATURE:
<223> OTHER INFORMATION: Aptamer

<400> SEQUENCE: 422
agacucuagg uguauuggca ggauuucgac aguccacug           39

<210> SEQ ID NO 423
<211> LENGTH: 40
<212> TYPE: RNA
<213> ORGANISM: Artificial
<220> FEATURE:
<223> OTHER INFORMATION: Aptamer

<400> SEQUENCE: 423
agguggauug gcgauagcuu caggauugau acuuggcug          40

<210> SEQ ID NO 424
<211> LENGTH: 40

```
<212> TYPE: RNA
<213> ORGANISM: Artificial
<220> FEATURE:
<223> OTHER INFORMATION: Aptamer

<400> SEQUENCE: 424
agguguacug gugagcauac agcaccgguu guucgcugca                                40

<210> SEQ ID NO 425
<211> LENGTH: 40
<212> TYPE: RNA
<213> ORGANISM: Artificial
<220> FEATURE:
<223> OTHER INFORMATION: Aptamer

<400> SEQUENCE: 425
agguuuauug gccuacgacu cuauucuuug guuguagaug                                40

<210> SEQ ID NO 426
<211> LENGTH: 40
<212> TYPE: RNA
<213> ORGANISM: Artificial
<220> FEATURE:
<223> OTHER INFORMATION: Aptamer

<400> SEQUENCE: 426
cagacugcau cggguuuau ugguucuagc uugcucuaua                                 40

<210> SEQ ID NO 427
<211> LENGTH: 40
<212> TYPE: RNA
<213> ORGANISM: Artificial
<220> FEATURE:
<223> OTHER INFORMATION: Aptamer

<400> SEQUENCE: 427
cauccucguu gcgcuucggu ugacuggcgc uuucagaaug                                40

<210> SEQ ID NO 428
<211> LENGTH: 40
<212> TYPE: RNA
<213> ORGANISM: Artificial
<220> FEATURE:
<223> OTHER INFORMATION: Aptamer

<400> SEQUENCE: 428 caucuuccccc uacauccagg ugaauuggug gcuaggcuua                               40

<210> SEQ ID NO 429
<211> LENGTH: 40
<212> TYPE: RNA
<213> ORGANISM: Artificial
<220> FEATURE:
<223> OTHER INFORMATION: Aptamer

<400> SEQUENCE: 429
ccccucacuu ccugguauac uggcggugag uuucgcaaug                                40

<210> SEQ ID NO 430
<211> LENGTH: 40
<212> TYPE: RNA
<213> ORGANISM: Artificial
<220> FEATURE:
<223> OTHER INFORMATION: Aptamer

<400> SEQUENCE: 430
```
ccucccuuac gucaacggug gauugguuga uucgauucuu    40

<210> SEQ ID NO 431
<211> LENGTH: 40
<212> TYPE: RNA
<213> ORGANISM: Artificial
<220> FEATURE:
<223> OTHER INFORMATION: Aptamer

<400> SEQUENCE: 431 ccuguuugu cuagguccau uggcgcuuau uccuggaaug    40

<210> SEQ ID NO 432
<211> LENGTH: 39
<212> TYPE: RNA
<213> ORGANISM: Artificial
<220> FEATURE:
<223> OTHER INFORMATION: Aptamer

<400> SEQUENCE: 432
cgcacucacg uaauaggugu auugucucc ccgggaaua     39

<210> SEQ ID NO 433
<211> LENGTH: 40
<212> TYPE: RNA
<213> ORGANISM: Artificial
<220> FEATURE:
<223> OTHER INFORMATION: Aptamer

<400> SEQUENCE: 433
cgcuucgggu uauuggcgaa accuuugcuu uuguuaaug    40

<210> SEQ ID NO 434
<211> LENGTH: 40
<212> TYPE: RNA
<213> ORGANISM: Artificial
<220> FEATURE:
<223> OTHER INFORMATION: Aptamer

<400> SEQUENCE: 434
cgcuuugcgu gcguggugca gguauauugg cguuggcug    40

<210> SEQ ID NO 435
<211> LENGTH: 40
<212> TYPE: RNA
<213> ORGANISM: Artificial
<220> FEATURE:
<223> OTHER INFORMATION: Aptamer

<400> SEQUENCE: 435
cguucccggu guauuggugc guauagcuug cuauucucua   40

<210> SEQ ID NO 436
<211> LENGTH: 40
<212> TYPE: RNA
<213> ORGANISM: Artificial
<220> FEATURE:
<223> OTHER INFORMATION: Aptamer

<400> SEQUENCE: 436
cuauucgucc gagguguacu ggcucccgug aaggggulua   40

<210> SEQ ID NO 437
<211> LENGTH: 40
<212> TYPE: RNA
<213> ORGANISM: Artificial

```
<220> FEATURE:
<223> OTHER INFORMATION: Aptamer

<400> SEQUENCE: 437
cucaggugua cugguguacu ggucucaacg gcucauacua                              40

<210> SEQ ID NO 438
<211> LENGTH: 40
<212> TYPE: RNA
<213> ORGANISM: Artificial
<220> FEATURE:
<223> OTHER INFORMATION: Aptamer

<400> SEQUENCE: 438
cuggacaucc ggguguauug gugccuuccu acaagguuc                               40

<210> SEQ ID NO 439
<211> LENGTH: 40
<212> TYPE: RNA
<213> ORGANISM: Artificial
<220> FEATURE:
<223> OTHER INFORMATION: Aptamer

<400> SEQUENCE: 439
cuuuugcugu gcucaggugg acuggcuguu cuuuacgaug                              40

<210> SEQ ID NO 440
<211> LENGTH: 40
<212> TYPE: RNA
<213> ORGANISM: Artificial
<220> FEATURE:
<223> OTHER INFORMATION: Aptamer

<400> SEQUENCE: 440
gacauguguc auccuaggug uacuggcgau agauuugcug                              40

<210> SEQ ID NO 441
<211> LENGTH: 40
<212> TYPE: RNA
<213> ORGANISM: Artificial
<220> FEATURE:
<223> OTHER INFORMATION: Aptamer

<400> SEQUENCE: 441
ggagucuuug guuauuggcc guuacauucu cguaucaaug                              40

<210> SEQ ID NO 442
<211> LENGTH: 40
<212> TYPE: RNA
<213> ORGANISM: Artificial
<220> FEATURE:
<223> OTHER INFORMATION: Aptamer

<400> SEQUENCE: 442
gggagaagua uucuacguac ugguaauugg cuuccggaug                              40

<210> SEQ ID NO 443
<211> LENGTH: 40
<212> TYPE: RNA
<213> ORGANISM: Artificial
<220> FEATURE:
<223> OTHER INFORMATION: Aptamer

<400> SEQUENCE: 443 gucuuuuag guuauuggcu uccuaauuuu cuuggagaug                               40
```

```
<210> SEQ ID NO 444
<211> LENGTH: 40
<212> TYPE: RNA
<213> ORGANISM: Artificial
<220> FEATURE:
<223> OTHER INFORMATION: Aptamer

<400> SEQUENCE: 444
ucgcccaagg uggaacuggc gcacuaaccu uuagugagug                            40

<210> SEQ ID NO 445
<211> LENGTH: 38
<212> TYPE: RNA
<213> ORGANISM: Artificial
<220> FEATURE:
<223> OTHER INFORMATION: Aptamer

<400> SEQUENCE: 445
ucgcuccagg uggacuggcu uacuuuuuug guuuguga                             38

<210> SEQ ID NO 446
<211> LENGTH: 40
<212> TYPE: RNA
<213> ORGANISM: Artificial
<220> FEATURE:
<223> OTHER INFORMATION: Aptamer

<400> SEQUENCE: 446
ucgucgguga auugguucuu guucuucucg agcauuuaua                           40

<210> SEQ ID NO 447
<211> LENGTH: 40
<212> TYPE: RNA
<213> ORGANISM: Artificial
<220> FEATURE:
<223> OTHER INFORMATION: Aptamer

<400> SEQUENCE: 447
ucucucuagg uagacuggcg gaauacuuug guguuuaaug                           40

<210> SEQ ID NO 448
<211> LENGTH: 40
<212> TYPE: RNA
<213> ORGANISM: Artificial
<220> FEATURE:
<223> OTHER INFORMATION: Aptamer

<400> SEQUENCE: 448
ucgguucacu ggcgcaguga ucguuuuuga uucuagaaug                           40

<210> SEQ ID NO 449
<211> LENGTH: 40
<212> TYPE: RNA
<213> ORGANISM: Artificial
<220> FEATURE:
<223> OTHER INFORMATION: Aptamer

<400> SEQUENCE: 449
uugaaccucu ggguaauugg ccggcucuca cgcuauguug                           40

<210> SEQ ID NO 450
<211> LENGTH: 40
<212> TYPE: RNA
<213> ORGANISM: Artificial
<220> FEATURE:
<223> OTHER INFORMATION: Aptamer
```

```
<400> SEQUENCE: 450
uuugcuaggu auauuggcga uccguccgga agggaugcug                              40

<210> SEQ ID NO 451
<211> LENGTH: 40
<212> TYPE: RNA
<213> ORGANISM: Artificial
<220> FEATURE:
<223> OTHER INFORMATION: Aptamer

<400> SEQUENCE: 451
uuugguuuua cuggugcuuc gucuuuacgg cguaggcgug                              40

<210> SEQ ID NO 452
<211> LENGTH: 40
<212> TYPE: RNA
<213> ORGANISM: Artificial
<220> FEATURE:
<223> OTHER INFORMATION: Aptamer

<400> SEQUENCE: 452
gguauauugg uccucggcgu ggcuucgguc ugccucguuu                              40

<210> SEQ ID NO 453
<211> LENGTH: 40
<212> TYPE: RNA
<213> ORGANISM: Artificial
<220> FEATURE:
<223> OTHER INFORMATION: Aptamer

<400> SEQUENCE: 453 ggugacugg cccucgugug cgcugcgcuc agagcuucgu                               40

<210> SEQ ID NO 454
<211> LENGTH: 40
<212> TYPE: RNA
<213> ORGANISM: Artificial
<220> FEATURE:
<223> OTHER INFORMATION: Aptamer

<400> SEQUENCE: 454
gguguacugg uuccugucua ucucccgcug acugugaaua                              40

<210> SEQ ID NO 455
<211> LENGTH: 40
<212> TYPE: RNA
<213> ORGANISM: Artificial
<220> FEATURE:
<223> OTHER INFORMATION: Aptamer

<400> SEQUENCE: 455
gguguacugg uuuugcuacc cgguccuucg gcugcauuua                              40

<210> SEQ ID NO 456
<211> LENGTH: 40
<212> TYPE: RNA
<213> ORGANISM: Artificial
<220> FEATURE:
<223> OTHER INFORMATION: Aptamer

<400> SEQUENCE: 456
gguguauugg cagauuugac ucgauuguga caucuugcug                              40

<210> SEQ ID NO 457
```

```
<211> LENGTH: 40
<212> TYPE: RNA
<213> ORGANISM: Artificial
<220> FEATURE:
<223> OTHER INFORMATION: Aptamer

<400> SEQUENCE: 457
gguguauugg uauccuccuc ucuggauuuc ccgggauuua                              40

<210> SEQ ID NO 458
<211> LENGTH: 40
<212> TYPE: RNA
<213> ORGANISM: Artificial
<220> FEATURE:
<223> OTHER INFORMATION: Aptamer

<400> SEQUENCE: 458
gguguauugg uccauugaua gacgcucguu uucaaauaga                              40

<210> SEQ ID NO 459
<211> LENGTH: 40
<212> TYPE: RNA
<213> ORGANISM: Artificial
<220> FEATURE:
<223> OTHER INFORMATION: Aptamer

<400> SEQUENCE: 459
gguucauugg ucucaagaua cgcucucuau cuuguugucu                              40

<210> SEQ ID NO 460
<211> LENGTH: 40
<212> TYPE: RNA
<213> ORGANISM: Artificial
<220> FEATURE:
<223> OTHER INFORMATION: Aptamer

<400> SEQUENCE: 460
gguuuacugg cggagggauc uacuuuugaa uuacuugcug                              40

<210> SEQ ID NO 461
<211> LENGTH: 40
<212> TYPE: RNA
<213> ORGANISM: Artificial
<220> FEATURE:
<223> OTHER INFORMATION: Aptamer

<400> SEQUENCE: 461
gguuuauugg cguggacaca guacuuuugg uguguagcug                              40

<210> SEQ ID NO 462
<211> LENGTH: 40
<212> TYPE: RNA
<213> ORGANISM: Artificial
<220> FEATURE:
<223> OTHER INFORMATION: Aptamer

<400> SEQUENCE: 462
gguuuauugg cuaaucggcc cguuucgggc cuacuugaug                              40

<210> SEQ ID NO 463
<211> LENGTH: 29
<212> TYPE: RNA
<213> ORGANISM: Artificial
<220> FEATURE:
<223> OTHER INFORMATION: Aptamer

<400> SEQUENCE: 463
```

```
gguuuauugg uaccguaggu cgcgguuua                                    29

<210> SEQ ID NO 464
<211> LENGTH: 40
<212> TYPE: RNA
<213> ORGANISM: Artificial
<220> FEATURE:
<223> OTHER INFORMATION: Aptamer

<400> SEQUENCE: 464
acgacccguu cagguugacu gguaucccu ucccgaugug                         40

<210> SEQ ID NO 465
<211> LENGTH: 40
<212> TYPE: RNA
<213> ORGANISM: Artificial
<220> FEATURE:
<223> OTHER INFORMATION: Aptamer

<400> SEQUENCE: 465
aguuugcugu ucugggugua cuggcucagc acucgaaucg                        40

<210> SEQ ID NO 466
<211> LENGTH: 40
<212> TYPE: RNA
<213> ORGANISM: Artificial
<220> FEATURE:
<223> OTHER INFORMATION: Aptamer

<400> SEQUENCE: 466
auacuacguc uaucgguuca uuggcucccg gcgggaaug                         40

<210> SEQ ID NO 467
<211> LENGTH: 40
<212> TYPE: RNA
<213> ORGANISM: Artificial
<220> FEATURE:
<223> OTHER INFORMATION: Aptamer

<400> SEQUENCE: 467
augcgauugg guggauuggc gcagucacuc ugcuggucug                        40

<210> SEQ ID NO 468
<211> LENGTH: 40
<212> TYPE: RNA
<213> ORGANISM: Artificial
<220> FEATURE:
<223> OTHER INFORMATION: Aptamer

<400> SEQUENCE: 468
cauucuaggu ggaugguaa gccuucgcgc uaggcaguua                         40

<210> SEQ ID NO 469
<211> LENGTH: 39
<212> TYPE: RNA
<213> ORGANISM: Artificial
<220> FEATURE:
<223> OTHER INFORMATION: Aptamer

<400> SEQUENCE: 469
ccaugcuuga cccgguuuau ugguuccgu gacggagua                          39

<210> SEQ ID NO 470
<211> LENGTH: 40
<212> TYPE: RNA
```

```
<213> ORGANISM: Artificial
<220> FEATURE:
<223> OTHER INFORMATION: Aptamer

<400> SEQUENCE: 470
cgcaccgccc ggguucauug gcucucgcuu ccaagguaug                             40

<210> SEQ ID NO 471
<211> LENGTH: 40
<212> TYPE: RNA
<213> ORGANISM: Artificial
<220> FEATURE:
<223> OTHER INFORMATION: Aptamer

<400> SEQUENCE: 471
cgcuuguuuc gggugauugg ccaggaaucu ccccugugug                             40

<210> SEQ ID NO 472
<211> LENGTH: 40
<212> TYPE: RNA
<213> ORGANISM: Artificial
<220> FEATURE:
<223> OTHER INFORMATION: Aptamer

<400> SEQUENCE: 472
cgucucuuuc gguuuacugg cgcuucgagg cguaugguug                             40

<210> SEQ ID NO 473
<211> LENGTH: 40
<212> TYPE: RNA
<213> ORGANISM: Artificial
<220> FEATURE:
<223> OTHER INFORMATION: Aptamer

<400> SEQUENCE: 473 cgggguggacu ggcgcgacaa ucuuucuguc gaagucucug                            40

<210> SEQ ID NO 474
<211> LENGTH: 40
<212> TYPE: RNA
<213> ORGANISM: Artificial
<220> FEATURE:
<223> OTHER INFORMATION: Aptamer

<400> SEQUENCE: 474
cuaugcguca aaaugcccgg guguacuggu caauucguuu                             40

<210> SEQ ID NO 475
<211> LENGTH: 40
<212> TYPE: RNA
<213> ORGANISM: Artificial
<220> FEATURE:
<223> OTHER INFORMATION: Aptamer

<400> SEQUENCE: 475
cucguuugca cggucaccgg uuuauugguc caacgcguuu                             40

<210> SEQ ID NO 476
<211> LENGTH: 40
<212> TYPE: RNA
<213> ORGANISM: Artificial
<220> FEATURE:
<223> OTHER INFORMATION: Aptamer

<400> SEQUENCE: 476
cgguguauug gucaucugga ugcggugcau ucggaaggca                             40
```

<210> SEQ ID NO 477
<211> LENGTH: 39
<212> TYPE: RNA
<213> ORGANISM: Artificial
<220> FEATURE:
<223> OTHER INFORMATION: Aptamer

<400> SEQUENCE: 477 gacuuuuuc ugguccacgg uguauuggcc uuucggagg                     39

<210> SEQ ID NO 478
<211> LENGTH: 40
<212> TYPE: RNA
<213> ORGANISM: Artificial
<220> FEATURE:
<223> OTHER INFORMATION: Aptamer

<400> SEQUENCE: 478
gcccccgggu auauuggugg uucuccucuc gagaaacuua                   40

<210> SEQ ID NO 479
<211> LENGTH: 40
<212> TYPE: RNA
<213> ORGANISM: Artificial
<220> FEATURE:
<223> OTHER INFORMATION: Aptamer

<400> SEQUENCE: 479 gcuccccua uacuccaggu gaauuggcgc uuuauguaug                    40

<210> SEQ ID NO 480
<211> LENGTH: 40
<212> TYPE: RNA
<213> ORGANISM: Artificial
<220> FEATURE:
<223> OTHER INFORMATION: Aptamer

<400> SEQUENCE: 480
gucaucgucu gaaaggugaa cugguccguu uuugcgggua                   40

<210> SEQ ID NO 481
<211> LENGTH: 40
<212> TYPE: RNA
<213> ORGANISM: Artificial
<220> FEATURE:
<223> OTHER INFORMATION: Aptamer

<400> SEQUENCE: 481
guccugguaa uuggcugucu acccugaccg gaggugaaug                   40

<210> SEQ ID NO 482
<211> LENGTH: 40
<212> TYPE: RNA
<213> ORGANISM: Artificial
<220> FEATURE:
<223> OTHER INFORMATION: Aptamer

<400> SEQUENCE: 482
guugguaaau ugcgcggga cuugcuuuac auuccgagug                    40

<210> SEQ ID NO 483
<211> LENGTH: 40
<212> TYPE: RNA
<213> ORGANISM: Artificial
<220> FEATURE:

<223> OTHER INFORMATION: Aptamer

<400> SEQUENCE: 483
uccaggugua cuggcucgga uugugcggag uuuuggaaug                    40

<210> SEQ ID NO 484
<211> LENGTH: 40
<212> TYPE: RNA
<213> ORGANISM: Artificial
<220> FEATURE:
<223> OTHER INFORMATION: Aptamer

<400> SEQUENCE: 484
uccggguuac uggcgagcug aguuuuacgc gucgcuagug                    40

<210> SEQ ID NO 485
<211> LENGTH: 41
<212> TYPE: RNA
<213> ORGANISM: Artificial
<220> FEATURE:
<223> OTHER INFORMATION: Aptamer

<400> SEQUENCE: 485
ugucucgguu uauuggcggu cggacuuuuu gcccugcgau g                  41

<210> SEQ ID NO 486
<211> LENGTH: 39
<212> TYPE: RNA
<213> ORGANISM: Artificial
<220> FEATURE:
<223> OTHER INFORMATION: Aptamer

<400> SEQUENCE: 486
uucagguuau uggcccaggc uuuuccaaaa cccggugug                     39

<210> SEQ ID NO 487
<211> LENGTH: 41
<212> TYPE: RNA
<213> ORGANISM: Artificial
<220> FEATURE:
<223> OTHER INFORMATION: Aptamer

<400> SEQUENCE: 487
uuccgcaugu ggguaaacug gcgccugauu uuuuggagu g                   41

<210> SEQ ID NO 488
<211> LENGTH: 40
<212> TYPE: RNA
<213> ORGANISM: Artificial
<220> FEATURE:
<223> OTHER INFORMATION: Aptamer

<400> SEQUENCE: 488
uugcccuccg agguuuauug gucuccagua ucuggucaua                    40

<210> SEQ ID NO 489
<211> LENGTH: 40
<212> TYPE: RNA
<213> ORGANISM: Artificial
<220> FEATURE:
<223> OTHER INFORMATION: Aptamer

<400> SEQUENCE: 489
ugguggauug gcgcagucgg agcuuuggcu cagggucug                     40

```
<210> SEQ ID NO 490
<211> LENGTH: 40
<212> TYPE: RNA
<213> ORGANISM: Artificial
<220> FEATURE:
<223> OTHER INFORMATION: Aptamer

<400> SEQUENCE: 490
ggugaauugg ccgccguucu uuccguggaa ugacgcgaug                              40

<210> SEQ ID NO 491
<211> LENGTH: 40
<212> TYPE: RNA
<213> ORGANISM: Artificial
<220> FEATURE:
<223> OTHER INFORMATION: Aptamer

<400> SEQUENCE: 491
ggugaauugg uacaauggcu uuauucuuag ccaauguuua                              40

<210> SEQ ID NO 492
<211> LENGTH: 40
<212> TYPE: RNA
<213> ORGANISM: Artificial
<220> FEATURE:
<223> OTHER INFORMATION: Aptamer

<400> SEQUENCE: 492
gguggacugg uacccuugac cuagcucuca agcguguuca                              40

<210> SEQ ID NO 493
<211> LENGTH: 40
<212> TYPE: RNA
<213> ORGANISM: Artificial
<220> FEATURE:
<223> OTHER INFORMATION: Aptamer

<400> SEQUENCE: 493
gguguacugg cacccagaga gucuagaagc uaugggacug                              40

<210> SEQ ID NO 494
<211> LENGTH: 40
<212> TYPE: RNA
<213> ORGANISM: Artificial
<220> FEATURE:
<223> OTHER INFORMATION: Aptamer

<400> SEQUENCE: 494
gguguacugg cgugugcccg acaaugucaa aggcgaguug                              40

<210> SEQ ID NO 495
<211> LENGTH: 40
<212> TYPE: RNA
<213> ORGANISM: Artificial
<220> FEATURE:
<223> OTHER INFORMATION: Aptamer

<400> SEQUENCE: 495
gguguacugg uagucgacaa augucuccgu gccggaaaua                              40

<210> SEQ ID NO 496
<211> LENGTH: 40
<212> TYPE: RNA
<213> ORGANISM: Artificial
<220> FEATURE:
<223> OTHER INFORMATION: Aptamer
```

```
<400> SEQUENCE: 496
gguguauugg caguuacucg aucuggccgc uguaauauga                                40

<210> SEQ ID NO 497
<211> LENGTH: 40
<212> TYPE: RNA
<213> ORGANISM: Artificial
<220> FEATURE:
<223> OTHER INFORMATION: Aptamer

<400> SEQUENCE: 497
gguguauugg cgguguuuaa cucucuuggu ugaagcacgg                                40

<210> SEQ ID NO 498
<211> LENGTH: 40
<212> TYPE: RNA
<213> ORGANISM: Artificial
<220> FEATURE:
<223> OTHER INFORMATION: Aptamer

<400> SEQUENCE: 498
gguguauugg cuagguucuu cgauccuuga aucuuggug                                 40

<210> SEQ ID NO 499
<211> LENGTH: 40
<212> TYPE: RNA
<213> ORGANISM: Artificial
<220> FEATURE:
<223> OTHER INFORMATION: Aptamer

<400> SEQUENCE: 499
gguguauugg cuguacucuc cauuuuaugg uccgaucaag                                40

<210> SEQ ID NO 500
<211> LENGTH: 40
<212> TYPE: RNA
<213> ORGANISM: Artificial
<220> FEATURE:
<223> OTHER INFORMATION: Aptamer

<400> SEQUENCE: 500
gguuaacugg cccagcggcu cuggucgggg acgauguaug                                40

<210> SEQ ID NO 501
<211> LENGTH: 40
<212> TYPE: RNA
<213> ORGANISM: Artificial
<220> FEATURE:
<223> OTHER INFORMATION: Aptamer

<400> SEQUENCE: 501
gguugauugg cgccgugacu gaacgcuucc gccaggagug                                40

<210> SEQ ID NO 502
<211> LENGTH: 40
<212> TYPE: RNA
<213> ORGANISM: Artificial
<220> FEATURE:
<223> OTHER INFORMATION: Aptamer

<400> SEQUENCE: 502
gguuuuacug gcgguccaug uugagucucc gugcgcaaug                                40

<210> SEQ ID NO 503
<211> LENGTH: 40
```

```
<212> TYPE: RNA
<213> ORGANISM: Artificial
<220> FEATURE:
<223> OTHER INFORMATION: Aptamer

<400> SEQUENCE: 503
acccugcuuc ucugggugca uugguugcca auuccgcaaa                               40

<210> SEQ ID NO 504
<211> LENGTH: 40
<212> TYPE: RNA
<213> ORGANISM: Artificial
<220> FEATURE:
<223> OTHER INFORMATION: Aptamer

<400> SEQUENCE: 504
acuccgcgcu cccgguguac ugguuccuag cugaggauga                               40

<210> SEQ ID NO 505
<211> LENGTH: 40
<212> TYPE: RNA
<213> ORGANISM: Artificial
<220> FEATURE:
<223> OTHER INFORMATION: Aptamer

<400> SEQUENCE: 505
auaauugucc uuguuccgg guguacuggu cauuuugugg                                40

<210> SEQ ID NO 506
<211> LENGTH: 40
<212> TYPE: RNA
<213> ORGANISM: Artificial
<220> FEATURE:
<223> OTHER INFORMATION: Aptamer

<400> SEQUENCE: 506
aggucgacug gcucgaacug auuucguuca uguccgaaug                               40

<210> SEQ ID NO 507
<211> LENGTH: 40
<212> TYPE: RNA
<213> ORGANISM: Artificial
<220> FEATURE:
<223> OTHER INFORMATION: Aptamer

<400> SEQUENCE: 507
aggugaacug guguacugau cggggaguuu ccaaguauua                               40

<210> SEQ ID NO 508
<211> LENGTH: 40
<212> TYPE: RNA
<213> ORGANISM: Artificial
<220> FEATURE:
<223> OTHER INFORMATION: Aptamer

<400> SEQUENCE: 508
agguguauug gcugugacug cuggauguag uggcaugguc                               40

<210> SEQ ID NO 509
<211> LENGTH: 40
<212> TYPE: RNA
<213> ORGANISM: Artificial
<220> FEATURE:
<223> OTHER INFORMATION: Aptamer

<400> SEQUENCE: 509
```

```
cacgacgccc aauuggguug acuggugccu ugcuggaaua                              40

<210> SEQ ID NO 510
<211> LENGTH: 40
<212> TYPE: RNA
<213> ORGANISM: Artificial
<220> FEATURE:
<223> OTHER INFORMATION: Aptamer

<400> SEQUENCE: 510
cacuccgucu ccgguuauac uggcggcugu ccaagcaaug                              40

<210> SEQ ID NO 511
<211> LENGTH: 40
<212> TYPE: RNA
<213> ORGANISM: Artificial
<220> FEATURE:
<223> OTHER INFORMATION: Aptamer

<400> SEQUENCE: 511
ccccagguuu auggugcgu uauuucugcg acgacguuua                               40

<210> SEQ ID NO 512
<211> LENGTH: 40
<212> TYPE: RNA
<213> ORGANISM: Artificial
<220> FEATURE:
<223> OTHER INFORMATION: Aptamer

<400> SEQUENCE: 512
ccccggguuc cauuggcgcu uugaggauga cucgaacaug                              40

<210> SEQ ID NO 513
<211> LENGTH: 40
<212> TYPE: RNA
<213> ORGANISM: Artificial
<220> FEATURE:
<223> OTHER INFORMATION: Aptamer

<400> SEQUENCE: 513
ccgggugaac uggccuguug cuuuuagcau cugacagaug                              40

<210> SEQ ID NO 514
<211> LENGTH: 40
<212> TYPE: RNA
<213> ORGANISM: Artificial
<220> FEATURE:
<223> OTHER INFORMATION: Aptamer

<400> SEQUENCE: 514
ccucaugucg ggucuauugg cuccggcgua gcacggaaug                              40

<210> SEQ ID NO 515
<211> LENGTH: 40
<212> TYPE: RNA
<213> ORGANISM: Artificial
<220> FEATURE:
<223> OTHER INFORMATION: Aptamer

<400> SEQUENCE: 515
ccuguauugg uuauuggcug cgggaauaac cccgugcaug                              40

<210> SEQ ID NO 516
<211> LENGTH: 34
<212> TYPE: RNA
<213> ORGANISM: Artificial
```

```
<220> FEATURE:
<223> OTHER INFORMATION: Aptamer

<400> SEQUENCE: 516 ccuguuugu cuagguuuac uggcgcuaug aaug                            34

<210> SEQ ID NO 517
<211> LENGTH: 41
<212> TYPE: RNA
<213> ORGANISM: Artificial
<220> FEATURE:
<223> OTHER INFORMATION: Aptamer

<400> SEQUENCE: 517 ccuguuuug ucagguuca uggcgcuua uuccuggaau g                      41

<210> SEQ ID NO 518
<211> LENGTH: 40
<212> TYPE: RNA
<213> ORGANISM: Artificial
<220> FEATURE:
<223> OTHER INFORMATION: Aptamer

<400> SEQUENCE: 518
ccuuccgggu guacugguug cggggcguuu accucgcaua                     40

<210> SEQ ID NO 519
<211> LENGTH: 39
<212> TYPE: RNA
<213> ORGANISM: Artificial
<220> FEATURE:
<223> OTHER INFORMATION: Aptamer

<400> SEQUENCE: 519
cgaugcggua aauuggcggg uacuccuugu aucgaucug                      39

<210> SEQ ID NO 520
<211> LENGTH: 40
<212> TYPE: RNA
<213> ORGANISM: Artificial
<220> FEATURE:
<223> OTHER INFORMATION: Aptamer

<400> SEQUENCE: 520
cggauacuuc ucgucuuagg uguacuggcc uucgcgguua                     40

<210> SEQ ID NO 521
<211> LENGTH: 40
<212> TYPE: RNA
<213> ORGANISM: Artificial
<220> FEATURE:
<223> OTHER INFORMATION: Aptamer

<400> SEQUENCE: 521
cucuaccgua gucuuggurr auuggugccu uccgugguua                     40

<210> SEQ ID NO 522
<211> LENGTH: 40
<212> TYPE: RNA
<213> ORGANISM: Artificial
<220> FEATURE:
<223> OTHER INFORMATION: Aptamer

<400> SEQUENCE: 522 cucuuuggguc auuggcgcau aucgauguug auguuggcug                    40
```

```
<210> SEQ ID NO 523
<211> LENGTH: 40
<212> TYPE: RNA
<213> ORGANISM: Artificial
<220> FEATURE:
<223> OTHER INFORMATION: Aptamer

<400> SEQUENCE: 523
cugggcgacu agguguacug gcuaucacgu ucuggauaag                                40

<210> SEQ ID NO 524
<211> LENGTH: 40
<212> TYPE: RNA
<213> ORGANISM: Artificial
<220> FEATURE:
<223> OTHER INFORMATION: Aptamer

<400> SEQUENCE: 524
cuguuccaua gguuuauugg ucucaccuug uccgugaaug                                40

<210> SEQ ID NO 525
<211> LENGTH: 40
<212> TYPE: RNA
<213> ORGANISM: Artificial
<220> FEATURE:
<223> OTHER INFORMATION: Aptamer

<400> SEQUENCE: 525
cuugguuuac ugguuuugau uucuaccuug aaucacuaua                                40

<210> SEQ ID NO 526
<211> LENGTH: 40
<212> TYPE: RNA
<213> ORGANISM: Artificial
<220> FEATURE:
<223> OTHER INFORMATION: Aptamer

<400> SEQUENCE: 526
gaagucuuug guuauuggcc guuacauucu cguaucaaug                                40

<210> SEQ ID NO 527
<211> LENGTH: 40
<212> TYPE: RNA
<213> ORGANISM: Artificial
<220> FEATURE:
<223> OTHER INFORMATION: Aptamer

<400> SEQUENCE: 527
gacucuuccu guaccaagg gugaacuggc ccgccgcgug                                 40

<210> SEQ ID NO 528
<211> LENGTH: 40
<212> TYPE: RNA
<213> ORGANISM: Artificial
<220> FEATURE:
<223> OTHER INFORMATION: Aptamer

<400> SEQUENCE: 528
gcacgaggga gucuggguuc auugguccau uuuugcguuu                                40

<210> SEQ ID NO 529
<211> LENGTH: 40
<212> TYPE: RNA
<213> ORGANISM: Artificial
<220> FEATURE:
<223> OTHER INFORMATION: Aptamer
```

```
<400> SEQUENCE: 529
gcugucagcc guuugguaa uuggcuccuu acgcggaaug                                40

<210> SEQ ID NO 530
<211> LENGTH: 40
<212> TYPE: RNA
<213> ORGANISM: Artificial
<220> FEATURE:
<223> OTHER INFORMATION: Aptamer

<400> SEQUENCE: 530
guuccaaacg uuccgggugu acugguccag aacgcgguca                                40

<210> SEQ ID NO 531
<211> LENGTH: 40
<212> TYPE: RNA
<213> ORGANISM: Artificial
<220> FEATURE:
<223> OTHER INFORMATION: Aptamer

<400> SEQUENCE: 531
guugauccgg gucuuauugg cucgauuuaa uaucgggaug                                40

<210> SEQ ID NO 532
<211> LENGTH: 40
<212> TYPE: RNA
<213> ORGANISM: Artificial
<220> FEATURE:
<223> OTHER INFORMATION: Aptamer

<400> SEQUENCE: 532
guuucaaggu uuacuggugu uaucacucgu cgauuacgug                                40

<210> SEQ ID NO 533
<211> LENGTH: 40
<212> TYPE: RNA
<213> ORGANISM: Artificial
<220> FEATURE:
<223> OTHER INFORMATION: Aptamer

<400> SEQUENCE: 533
ggguguacug gcuaucgaag caguuucuua cucggucgug                                40

<210> SEQ ID NO 534
<211> LENGTH: 40
<212> TYPE: RNA
<213> ORGANISM: Artificial
<220> FEATURE:
<223> OTHER INFORMATION: Aptamer

<400> SEQUENCE: 534
uacgccuggg uguauugguu ggaggcaauc gcucuuccuu                                40

<210> SEQ ID NO 535
<211> LENGTH: 40
<212> TYPE: RNA
<213> ORGANISM: Artificial
<220> FEATURE:
<223> OTHER INFORMATION: Aptamer

<400> SEQUENCE: 535
uacguaaaug guguacuggu cuuuagaguu ucuauugugu                                40

<210> SEQ ID NO 536
```

```
<211> LENGTH: 40
<212> TYPE: RNA
<213> ORGANISM: Artificial
<220> FEATURE:
<223> OTHER INFORMATION: Aptamer

<400> SEQUENCE: 536
uauacuguac uguucgaugg uuuauuugguc cagcucguua                           40

<210> SEQ ID NO 537
<211> LENGTH: 40
<212> TYPE: RNA
<213> ORGANISM: Artificial
<220> FEATURE:
<223> OTHER INFORMATION: Aptamer

<400> SEQUENCE: 537
ucggcccggg uuuauuggca guccgaugu ggauuguuug                            40

<210> SEQ ID NO 538
<211> LENGTH: 40
<212> TYPE: RNA
<213> ORGANISM: Artificial
<220> FEATURE:
<223> OTHER INFORMATION: Aptamer

<400> SEQUENCE: 538
ucgggcacau ccggguguac uggcgauugg aaaaaugcug                           40

<210> SEQ ID NO 539
<211> LENGTH: 40
<212> TYPE: RNA
<213> ORGANISM: Artificial
<220> FEATURE:
<223> OTHER INFORMATION: Aptamer

<400> SEQUENCE: 539
uuguguguua cagguuguau uggcuucuug cgagagcaug                           40

<210> SEQ ID NO 540
<211> LENGTH: 40
<212> TYPE: RNA
<213> ORGANISM: Artificial
<220> FEATURE:
<223> OTHER INFORMATION: Aptamer

<400> SEQUENCE: 540
uuuucauccg ucgguuacug gcgcuucaaa cgaagaucug                           40

<210> SEQ ID NO 541
<211> LENGTH: 40
<212> TYPE: RNA
<213> ORGANISM: Artificial
<220> FEATURE:
<223> OTHER INFORMATION: Aptamer

<400> SEQUENCE: 541
uggucuuauu ggcggugugu cauguacuuu gaccgcagug                           40

<210> SEQ ID NO 542
<211> LENGTH: 40
<212> TYPE: RNA
<213> ORGANISM: Artificial
<220> FEATURE:
<223> OTHER INFORMATION: Aptamer

<400> SEQUENCE: 542
```
ugguguauug gucugacagu agauuguuac ucgucaagga        40

<210> SEQ ID NO 543
<211> LENGTH: 40
<212> TYPE: RNA
<213> ORGANISM: Artificial
<220> FEATURE:
<223> OTHER INFORMATION: Aptamer

<400> SEQUENCE: 543
gguaaauugg ugcuuacuca ggcagguucg ggguaucuua        40

<210> SEQ ID NO 544
<211> LENGTH: 40
<212> TYPE: RNA
<213> ORGANISM: Artificial
<220> FEATURE:
<223> OTHER INFORMATION: Aptamer

<400> SEQUENCE: 544
gguaauuggc uucuucuuua aauuccuuua gaacuguaug        40

<210> SEQ ID NO 545
<211> LENGTH: 40
<212> TYPE: RNA
<213> ORGANISM: Artificial
<220> FEATURE:
<223> OTHER INFORMATION: Aptamer

<400> SEQUENCE: 545
gguauauugg ccggugugcu ccggggacgc gcacuaugug        40

<210> SEQ ID NO 546
<211> LENGTH: 40
<212> TYPE: RNA
<213> ORGANISM: Artificial
<220> FEATURE:
<223> OTHER INFORMATION: Aptamer

<400> SEQUENCE: 546
gguauauugg cuccaguuua ccuaguuuag gccgugaaug        40

<210> SEQ ID NO 547
<211> LENGTH: 40
<212> TYPE: RNA
<213> ORGANISM: Artificial
<220> FEATURE:
<223> OTHER INFORMATION: Aptamer

<400> SEQUENCE: 547
ggucauauug gcuuuagccc uuugucucgu ggcuaagaug        40

<210> SEQ ID NO 548
<211> LENGTH: 40
<212> TYPE: RNA
<213> ORGANISM: Artificial
<220> FEATURE:
<223> OTHER INFORMATION: Aptamer

<400> SEQUENCE: 548
ggugaacugg uccgcauuua gccuucuuau uugcggguau        40

<210> SEQ ID NO 549
<211> LENGTH: 25
<212> TYPE: RNA

```
<213> ORGANISM: Artificial
<220> FEATURE:
<223> OTHER INFORMATION: Aptamer

<400> SEQUENCE: 549
ggugaacugg uggccgucgg aaaua                                              25

<210> SEQ ID NO 550
<211> LENGTH: 31
<212> TYPE: RNA
<213> ORGANISM: Artificial
<220> FEATURE:
<223> OTHER INFORMATION: Aptamer

<400> SEQUENCE: 550
ggugaauugg cucucaaauu cgcguaggau g                                       31

<210> SEQ ID NO 551
<211> LENGTH: 40
<212> TYPE: RNA
<213> ORGANISM: Artificial
<220> FEATURE:
<223> OTHER INFORMATION: Aptamer

<400> SEQUENCE: 551
ggugauuggc ggugacagaa ccuuugucug ucucacagug                              40

<210> SEQ ID NO 552
<211> LENGTH: 40
<212> TYPE: RNA
<213> ORGANISM: Artificial
<220> FEATURE:
<223> OTHER INFORMATION: Aptamer

<400> SEQUENCE: 552
gguguacugg cauuuguuuu ucucucuccu aacagaacug                              40

<210> SEQ ID NO 553
<211> LENGTH: 40
<212> TYPE: RNA
<213> ORGANISM: Artificial
<220> FEATURE:
<223> OTHER INFORMATION: Aptamer

<400> SEQUENCE: 553
gguguacugg cgccuuggua gcuggcucu agaagaucug                               40

<210> SEQ ID NO 554
<211> LENGTH: 40
<212> TYPE: RNA
<213> ORGANISM: Artificial
<220> FEATURE:
<223> OTHER INFORMATION: Aptamer

<400> SEQUENCE: 554
gguguacugg ucugaguacc uuccguuggc uaucuccgua                              40

<210> SEQ ID NO 555
<211> LENGTH: 40
<212> TYPE: RNA
<213> ORGANISM: Artificial
<220> FEATURE:
<223> OTHER INFORMATION: Aptamer

<400> SEQUENCE: 555
gguguacugg ucugcauuga guuccuuaa ugacagauua                               40
```

```
<210> SEQ ID NO 556
<211> LENGTH: 40
<212> TYPE: RNA
<213> ORGANISM: Artificial
<220> FEATURE:
<223> OTHER INFORMATION: Aptamer

<400> SEQUENCE: 556
gguguacugg ugacuuacua ucuauuuagc aagcaacucu                          40

<210> SEQ ID NO 557
<211> LENGTH: 40
<212> TYPE: RNA
<213> ORGANISM: Artificial
<220> FEATURE:
<223> OTHER INFORMATION: Aptamer

<400> SEQUENCE: 557
gguguacugg uucauucgac ucuagucaug cuaaugaaua                          40

<210> SEQ ID NO 558
<211> LENGTH: 40
<212> TYPE: RNA
<213> ORGANISM: Artificial
<220> FEATURE:
<223> OTHER INFORMATION: Aptamer

<400> SEQUENCE: 558
gguguauugg ccccuugauu cacacauugu ggcggguaug                          40

<210> SEQ ID NO 559
<211> LENGTH: 40
<212> TYPE: RNA
<213> ORGANISM: Artificial
<220> FEATURE:
<223> OTHER INFORMATION: Aptamer

<400> SEQUENCE: 559
gguguauugg uaaauacucu ggacuuuucg uucgguuuua                          40

<210> SEQ ID NO 560
<211> LENGTH: 38
<212> TYPE: RNA
<213> ORGANISM: Artificial
<220> FEATURE:
<223> OTHER INFORMATION: Aptamer

<400> SEQUENCE: 560
gguguauugg ugcuuugcgg uuguaucgca uugucgug                            38

<210> SEQ ID NO 561
<211> LENGTH: 40
<212> TYPE: RNA
<213> ORGANISM: Artificial
<220> FEATURE:
<223> OTHER INFORMATION: Aptamer

<400> SEQUENCE: 561
gguguauugg uuagcagauu uguuccucca uuugcugaga                          40

<210> SEQ ID NO 562
<211> LENGTH: 40
<212> TYPE: RNA
<213> ORGANISM: Artificial
<220> FEATURE:
```

<223> OTHER INFORMATION: Aptamer

<400> SEQUENCE: 562
gguguauugg uuuaucgauc guucucggau cucuuauaua          40

<210> SEQ ID NO 563
<211> LENGTH: 40
<212> TYPE: RNA
<213> ORGANISM: Artificial
<220> FEATURE:
<223> OTHER INFORMATION: Aptamer

<400> SEQUENCE: 563
gguuauuggu cgggacaagg uacucccuag ucugcugucu          40

<210> SEQ ID NO 564
<211> LENGTH: 40
<212> TYPE: RNA
<213> ORGANISM: Artificial
<220> FEATURE:
<223> OTHER INFORMATION: Aptamer

<400> SEQUENCE: 564
gguuauuggu gccgcgcucu cugcugacga cgccggcgug          40

<210> SEQ ID NO 565
<211> LENGTH: 40
<212> TYPE: RNA
<213> ORGANISM: Artificial
<220> FEATURE:
<223> OTHER INFORMATION: Aptamer

<400> SEQUENCE: 565
gguugauugg cgcacuccuc gcuguuuuga ugaucgcaug          40

<210> SEQ ID NO 566
<211> LENGTH: 35
<212> TYPE: RNA
<213> ORGANISM: Artificial
<220> FEATURE:
<223> OTHER INFORMATION: Aptamer

<400> SEQUENCE: 566
gguuuauugg ccaucagucc guuccgccga gaaug          35

<210> SEQ ID NO 567
<211> LENGTH: 40
<212> TYPE: RNA
<213> ORGANISM: Artificial
<220> FEATURE:
<223> OTHER INFORMATION: Aptamer

<400> SEQUENCE: 567
gguuuauugg cucugcuuua cgugauauga gcaugguaug          40

<210> SEQ ID NO 568
<211> LENGTH: 39
<212> TYPE: RNA
<213> ORGANISM: Artificial
<220> FEATURE:
<223> OTHER INFORMATION: Aptamer

<400> SEQUENCE: 568
gguuuauugg uguucgccua ucgauuuuug ggcuuuuua          39

```
<210> SEQ ID NO 569
<211> LENGTH: 40
<212> TYPE: RNA
<213> ORGANISM: Artificial
<220> FEATURE:
<223> OTHER INFORMATION: Aptamer

<400> SEQUENCE: 569
aaaggugaac uggucuaggu ccauccggca uccuuugaua                    40

<210> SEQ ID NO 570
<211> LENGTH: 40
<212> TYPE: RNA
<213> ORGANISM: Artificial
<220> FEATURE:
<223> OTHER INFORMATION: Aptamer

<400> SEQUENCE: 570
aacugcucag guguauuggu uuguccucgg uggacagcaa                    40

<210> SEQ ID NO 571
<211> LENGTH: 40
<212> TYPE: RNA
<213> ORGANISM: Artificial
<220> FEATURE:
<223> OTHER INFORMATION: Aptamer

<400> SEQUENCE: 571
aaugguuuau uggcucgcgc acauggcccu ugcgugcaug                    40

<210> SEQ ID NO 572
<211> LENGTH: 39
<212> TYPE: RNA
<213> ORGANISM: Artificial
<220> FEATURE:
<223> OTHER INFORMATION: Aptamer

<400> SEQUENCE: 572
acacaaaaau gccugccucu cgguucauug gucucguuu                     39

<210> SEQ ID NO 573
<211> LENGTH: 40
<212> TYPE: RNA
<213> ORGANISM: Artificial
<220> FEATURE:
<223> OTHER INFORMATION: Aptamer

<400> SEQUENCE: 573
acgccacuac gguggucucc agguggauug gucgacguuu                    40

<210> SEQ ID NO 574
<211> LENGTH: 40
<212> TYPE: RNA
<213> ORGANISM: Artificial
<220> FEATURE:
<223> OTHER INFORMATION: Aptamer

<400> SEQUENCE: 574
acgucuguug guguauuggu gucuuggaga cccaugagua                    40

<210> SEQ ID NO 575
<211> LENGTH: 40
<212> TYPE: RNA
<213> ORGANISM: Artificial
<220> FEATURE:
<223> OTHER INFORMATION: Aptamer
```

```
<400> SEQUENCE: 575
acucgcgguu uacugggugu acuggugcuu ucgaaguuca                                 40

<210> SEQ ID NO 576
<211> LENGTH: 40
<212> TYPE: RNA
<213> ORGANISM: Artificial
<220> FEATURE:
<223> OTHER INFORMATION: Aptamer

<400> SEQUENCE: 576
acuucauugu uucgguuauu ggcucuucuc uuguugcaug                                 40

<210> SEQ ID NO 577
<211> LENGTH: 40
<212> TYPE: RNA
<213> ORGANISM: Artificial
<220> FEATURE:
<223> OTHER INFORMATION: Aptamer

<400> SEQUENCE: 577
agaaagacgg gugcacuggu ugcuugcuuc cgaguguuuu                                 40

<210> SEQ ID NO 578
<211> LENGTH: 40
<212> TYPE: RNA
<213> ORGANISM: Artificial
<220> FEATURE:
<223> OTHER INFORMATION: Aptamer

<400> SEQUENCE: 578
agcucuucuc cugcauuuaa gguucauugg uucaugugu                                  40

<210> SEQ ID NO 579
<211> LENGTH: 40
<212> TYPE: RNA
<213> ORGANISM: Artificial
<220> FEATURE:
<223> OTHER INFORMATION: Aptamer

<400> SEQUENCE: 579
agucgagucc auucgguaau uggugccucc cccgggaaua                                 40

<210> SEQ ID NO 580
<211> LENGTH: 40
<212> TYPE: RNA
<213> ORGANISM: Artificial
<220> FEATURE:
<223> OTHER INFORMATION: Aptamer

<400> SEQUENCE: 580
aguguugguc uggguuuauu gguuaucguu uccggugcua                                 40

<210> SEQ ID NO 581
<211> LENGTH: 40
<212> TYPE: RNA
<213> ORGANISM: Artificial
<220> FEATURE:
<223> OTHER INFORMATION: Aptamer

<400> SEQUENCE: 581
aggguccacu gguguacugg uguuguugac gaaacuccua                                 40

<210> SEQ ID NO 582
<211> LENGTH: 40
```

```
<212> TYPE: RNA
<213> ORGANISM: Artificial
<220> FEATURE:
<223> OTHER INFORMATION: Aptamer

<400> SEQUENCE: 582
auccguucgg guaucacugg cgucuuauua cuuagaagug                              40

<210> SEQ ID NO 583
<211> LENGTH: 40
<212> TYPE: RNA
<213> ORGANISM: Artificial
<220> FEATURE:
<223> OTHER INFORMATION: Aptamer

<400> SEQUENCE: 583
aucgagucug guuuacuggu gacccguuug gugggagaua                              40

<210> SEQ ID NO 584
<211> LENGTH: 40
<212> TYPE: RNA
<213> ORGANISM: Artificial
<220> FEATURE:
<223> OTHER INFORMATION: Aptamer

<400> SEQUENCE: 584
aucuuucugc ucauuggucu acuggcgcca cccggaacug                              40

<210> SEQ ID NO 585
<211> LENGTH: 40
<212> TYPE: RNA
<213> ORGANISM: Artificial
<220> FEATURE:
<223> OTHER INFORMATION: Aptamer

<400> SEQUENCE: 585
augcgauugg gucgauuggc gcagucacuc ugcuggucug                              40

<210> SEQ ID NO 586
<211> LENGTH: 39
<212> TYPE: RNA
<213> ORGANISM: Artificial
<220> FEATURE:
<223> OTHER INFORMATION: Aptamer

<400> SEQUENCE: 586
augucgccca ucucugcauu cugggucauu ggucucguu                               39

<210> SEQ ID NO 587
<211> LENGTH: 40
<212> TYPE: RNA
<213> ORGANISM: Artificial
<220> FEATURE:
<223> OTHER INFORMATION: Aptamer

<400> SEQUENCE: 587
auugagaguu ggagugcucg gguuuauugg ccuuucggug                              40

<210> SEQ ID NO 588
<211> LENGTH: 40
<212> TYPE: RNA
<213> ORGANISM: Artificial
<220> FEATURE:
<223> OTHER INFORMATION: Aptamer

<400> SEQUENCE: 588
```

```
auuucccuuc gcaccugggu guauuggcuac uacuugguua         40
```

<210> SEQ ID NO 589
<211> LENGTH: 40
<212> TYPE: RNA
<213> ORGANISM: Artificial
<220> FEATURE:
<223> OTHER INFORMATION: Aptamer

<400> SEQUENCE: 589

```
agguaauugg cguuuaaagc ggcguugcua cuggagauug         40
```

<210> SEQ ID NO 590
<211> LENGTH: 40
<212> TYPE: RNA
<213> ORGANISM: Artificial
<220> FEATURE:
<223> OTHER INFORMATION: Aptamer

<400> SEQUENCE: 590

```
agguguacug gcguauggga ucaaugcgau cgcauagugg         40
```

<210> SEQ ID NO 591
<211> LENGTH: 40
<212> TYPE: RNA
<213> ORGANISM: Artificial
<220> FEATURE:
<223> OTHER INFORMATION: Aptamer

<400> SEQUENCE: 591

```
agguuaauug gcccuucacu uuuucgaac gaguuggaug          40
```

<210> SEQ ID NO 592
<211> LENGTH: 40
<212> TYPE: RNA
<213> ORGANISM: Artificial
<220> FEATURE:
<223> OTHER INFORMATION: Aptamer

<400> SEQUENCE: 592

```
caaaacucgu uacaggugua uuggccggcu uuagccaaug         40
```

<210> SEQ ID NO 593
<211> LENGTH: 40
<212> TYPE: RNA
<213> ORGANISM: Artificial
<220> FEATURE:
<223> OTHER INFORMATION: Aptamer

<400> SEQUENCE: 593

```
cacucuccuc uucgucuuua gguguacugg uucuucguuu         40
```

<210> SEQ ID NO 594
<211> LENGTH: 40
<212> TYPE: RNA
<213> ORGANISM: Artificial
<220> FEATURE:
<223> OTHER INFORMATION: Aptamer

<400> SEQUENCE: 594

```
cacugugcgu gcuauguggu uuauuggugc cugucggcua         40
```

<210> SEQ ID NO 595
<211> LENGTH: 40
<212> TYPE: RNA
<213> ORGANISM: Artificial

```
<220> FEATURE:
<223> OTHER INFORMATION: Aptamer

<400> SEQUENCE: 595
cagacagguu aauuggcccu cuggucacuc acggagaaug                              40

<210> SEQ ID NO 596
<211> LENGTH: 40
<212> TYPE: RNA
<213> ORGANISM: Artificial
<220> FEATURE:
<223> OTHER INFORMATION: Aptamer

<400> SEQUENCE: 596
caucuggguu uuacuggugc aauacuucga uuuauuguua                              40

<210> SEQ ID NO 597
<211> LENGTH: 40
<212> TYPE: RNA
<213> ORGANISM: Artificial
<220> FEATURE:
<223> OTHER INFORMATION: Aptamer

<400> SEQUENCE: 597
cauucauccc uguugcgcgg ucggguuauu ggucucgugu                              40

<210> SEQ ID NO 598
<211> LENGTH: 39
<212> TYPE: RNA
<213> ORGANISM: Artificial
<220> FEATURE:
<223> OTHER INFORMATION: Aptamer

<400> SEQUENCE: 598 cauugpccau uccgguaaau uggcgcuuuu aggaggaug                               39

<210> SEQ ID NO 599
<211> LENGTH: 40
<212> TYPE: RNA
<213> ORGANISM: Artificial
<220> FEATURE:
<223> OTHER INFORMATION: Aptamer

<400> SEQUENCE: 599
ccaccuuugu cgcauuuucu ggunguauugg ucgcuuguuu                             40

<210> SEQ ID NO 600
<211> LENGTH: 40
<212> TYPE: RNA
<213> ORGANISM: Artificial
<220> FEATURE:
<223> OTHER INFORMATION: Aptamer

<400> SEQUENCE: 600
ccaucuuucu agguauauug gcgguagguu ucugcggcug                              40

<210> SEQ ID NO 601
<211> LENGTH: 40
<212> TYPE: RNA
<213> ORGANISM: Artificial
<220> FEATURE:
<223> OTHER INFORMATION: Aptamer

<400> SEQUENCE: 601
cccugcgcgc ucucacggug uauuggucca auuugguaua                              40
```

```
<210> SEQ ID NO 602
<211> LENGTH: 40
<212> TYPE: RNA
<213> ORGANISM: Artificial
<220> FEATURE:
<223> OTHER INFORMATION: Aptamer

<400> SEQUENCE: 602
ccgcuugauu cgcuacaccu agguuauugg cguucggcua                           40

<210> SEQ ID NO 603
<211> LENGTH: 40
<212> TYPE: RNA
<213> ORGANISM: Artificial
<220> FEATURE:
<223> OTHER INFORMATION: Aptamer

<400> SEQUENCE: 603
ccguucaggu uuauuggccg aauuaacucu uuuugcguag                           40

<210> SEQ ID NO 604
<211> LENGTH: 40
<212> TYPE: RNA
<213> ORGANISM: Artificial
<220> FEATURE:
<223> OTHER INFORMATION: Aptamer

<400> SEQUENCE: 604
ccucaccguc ucacagguuu auuggcagcc cauggcgaug                           40

<210> SEQ ID NO 605
<211> LENGTH: 40
<212> TYPE: RNA
<213> ORGANISM: Artificial
<220> FEATURE:
<223> OTHER INFORMATION: Aptamer

<400> SEQUENCE: 605
cgcuccauuu cuggucuacu ggcaccauuu cccggauuug                           40

<210> SEQ ID NO 606
<211> LENGTH: 40
<212> TYPE: RNA
<213> ORGANISM: Artificial
<220> FEATURE:
<223> OTHER INFORMATION: Aptamer

<400> SEQUENCE: 606 cgcuccuga cuugguuccg gguuuauugg uucuccguuu                            40

<210> SEQ ID NO 607
<211> LENGTH: 40
<212> TYPE: RNA
<213> ORGANISM: Artificial
<220> FEATURE:
<223> OTHER INFORMATION: Aptamer

<400> SEQUENCE: 607
cgucuguugg gucuacuggc gcaggcuccc acucugagug                           40

<210> SEQ ID NO 608
<211> LENGTH: 40
<212> TYPE: RNA
<213> ORGANISM: Artificial
<220> FEATURE:
<223> OTHER INFORMATION: Aptamer
```

```
<400> SEQUENCE: 608
cgugacaugg uuguacuggc gaaauggucu ucauuugcug                    40

<210> SEQ ID NO 609
<211> LENGTH: 39
<212> TYPE: RNA
<213> ORGANISM: Artificial
<220> FEATURE:
<223> OTHER INFORMATION: Aptamer

<400> SEQUENCE: 609
cguuucgggu guauuggccc uucaaauacu cggggugug                     39

<210> SEQ ID NO 610
<211> LENGTH: 40
<212> TYPE: RNA
<213> ORGANISM: Artificial
<220> FEATURE:
<223> OTHER INFORMATION: Aptamer

<400> SEQUENCE: 610
cuacuuccuu ucuggugaac ugguuuuggc uccucaagua                    40

<210> SEQ ID NO 611
<211> LENGTH: 40
<212> TYPE: RNA
<213> ORGANISM: Artificial
<220> FEATURE:
<223> OTHER INFORMATION: Aptamer

<400> SEQUENCE: 611
cuagucgucc gcgagguuca cuggcgaucc cuguauagug                    40

<210> SEQ ID NO 612
<211> LENGTH: 40
<212> TYPE: RNA
<213> ORGANISM: Artificial
<220> FEATURE:
<223> OTHER INFORMATION: Aptamer

<400> SEQUENCE: 612
cucucucuac gacaagguaa uuggcgcgcu cuuucgaaug                    40

<210> SEQ ID NO 613
<211> LENGTH: 40
<212> TYPE: RNA
<213> ORGANISM: Artificial
<220> FEATURE:
<223> OTHER INFORMATION: Aptamer

<400> SEQUENCE: 613
cucuuuggug aacuggcgau ugauaauuuu gaaaugcuug                    40

<210> SEQ ID NO 614
<211> LENGTH: 40
<212> TYPE: RNA
<213> ORGANISM: Artificial
<220> FEATURE:
<223> OTHER INFORMATION: Aptamer

<400> SEQUENCE: 614
cugcccuggg uaauuggcga augcgcgggu cggauggcug                    40

<210> SEQ ID NO 615
```

```
<211> LENGTH: 40
<212> TYPE: RNA
<213> ORGANISM: Artificial
<220> FEATURE:
<223> OTHER INFORMATION: Aptamer

<400> SEQUENCE: 615
cuguauuuua agguuuauug gucgaccguu aacgggaaug                                40

<210> SEQ ID NO 616
<211> LENGTH: 40
<212> TYPE: RNA
<213> ORGANISM: Artificial
<220> FEATURE:
<223> OTHER INFORMATION: Aptamer

<400> SEQUENCE: 616
cuguccgucc auacgguuau ugguccuuuc caaaucgugu                                40

<210> SEQ ID NO 617
<211> LENGTH: 40
<212> TYPE: RNA
<213> ORGANISM: Artificial
<220> FEATURE:
<223> OTHER INFORMATION: Aptamer

<400> SEQUENCE: 617
cuucaggugg auuggcugcc cgaucgaaaa gauggacgug                                40

<210> SEQ ID NO 618
<211> LENGTH: 40
<212> TYPE: RNA
<213> ORGANISM: Artificial
<220> FEATURE:
<223> OTHER INFORMATION: Aptamer

<400> SEQUENCE: 618
gacguuucau gccccagguu cauuggcgca agcgagaaug                                40

<210> SEQ ID NO 619
<211> LENGTH: 40
<212> TYPE: RNA
<213> ORGANISM: Artificial
<220> FEATURE:
<223> OTHER INFORMATION: Aptamer

<400> SEQUENCE: 619
gcgcucucca cuuuguucag guugauuggu cggaugugu                                 40

<210> SEQ ID NO 620
<211> LENGTH: 38
<212> TYPE: RNA
<213> ORGANISM: Artificial
<220> FEATURE:
<223> OTHER INFORMATION: Aptamer

<400> SEQUENCE: 620
gcguaucuag gugaacuggc gcuacuccgc guggaaug                                  38

<210> SEQ ID NO 621
<211> LENGTH: 40
<212> TYPE: RNA
<213> ORGANISM: Artificial
<220> FEATURE:
<223> OTHER INFORMATION: Aptamer

<400> SEQUENCE: 621
```

```
gcuccuaggg uguauuggcu gcuuccaugu cggauccgug                              40

<210> SEQ ID NO 622
<211> LENGTH: 40
<212> TYPE: RNA
<213> ORGANISM: Artificial
<220> FEATURE:
<223> OTHER INFORMATION: Aptamer

<400> SEQUENCE: 622
gcuucuuuug ccuggggu ga cuggugccag ugauggaaua                             40

<210> SEQ ID NO 623
<211> LENGTH: 39
<212> TYPE: RNA
<213> ORGANISM: Artificial
<220> FEATURE:
<223> OTHER INFORMATION: Aptamer

<400> SEQUENCE: 623
gcuuuguucu gguuuauugg cgacgaauga uuccgcgug                               39

<210> SEQ ID NO 624
<211> LENGTH: 40
<212> TYPE: RNA
<213> ORGANISM: Artificial
<220> FEATURE:
<223> OTHER INFORMATION: Aptamer

<400> SEQUENCE: 624
guccucgucc gugguuuuau uggcggcgua uaucgucaug                              40

<210> SEQ ID NO 625
<211> LENGTH: 40
<212> TYPE: RNA
<213> ORGANISM: Artificial
<220> FEATURE:
<223> OTHER INFORMATION: Aptamer

<400> SEQUENCE: 625
gucgucuuag guuugauugg cgcucccaga uccgagcaug                              40

<210> SEQ ID NO 626
<211> LENGTH: 40
<212> TYPE: RNA
<213> ORGANISM: Artificial
<220> FEATURE:
<223> OTHER INFORMATION: Aptamer

<400> SEQUENCE: 626
uacagccccu gcuuuccag guguauuggu ucaauugucu                               40

<210> SEQ ID NO 627
<211> LENGTH: 39
<212> TYPE: RNA
<213> ORGANISM: Artificial
<220> FEATURE:
<223> OTHER INFORMATION: Aptamer

<400> SEQUENCE: 627
uauaguucgg guguacuggc gcugucac ugcaguaug                                 39

<210> SEQ ID NO 628
<211> LENGTH: 40
<212> TYPE: RNA
```

```
<213> ORGANISM: Artificial
<220> FEATURE:
<223> OTHER INFORMATION: Aptamer

<400> SEQUENCE: 628
ucaauuucug gguuuauugg cggguuugcu caaauccaug                            40

<210> SEQ ID NO 629
<211> LENGTH: 40
<212> TYPE: RNA
<213> ORGANISM: Artificial
<220> FEATURE:
<223> OTHER INFORMATION: Aptamer

<400> SEQUENCE: 629
uccaccccuu cugcgucuug agguuuauug gccgucguuu                            40

<210> SEQ ID NO 630
<211> LENGTH: 39
<212> TYPE: RNA
<213> ORGANISM: Artificial
<220> FEATURE:
<223> OTHER INFORMATION: Aptamer

<400> SEQUENCE: 630
uccagaggug uauuggauauc aagccuagcu cuuggggua                            39

<210> SEQ ID NO 631
<211> LENGTH: 40
<212> TYPE: RNA
<213> ORGANISM: Artificial
<220> FEATURE:
<223> OTHER INFORMATION: Aptamer

<400> SEQUENCE: 631
ucguuuccug gugaacuggu ugugcguuuu cguacgaga                             40

<210> SEQ ID NO 632
<211> LENGTH: 39
<212> TYPE: RNA
<213> ORGANISM: Artificial
<220> FEATURE:
<223> OTHER INFORMATION: Aptamer

<400> SEQUENCE: 632
ucucggugga cugguacuau uucgggguaa augguguuu                             39

<210> SEQ ID NO 633
<211> LENGTH: 40
<212> TYPE: RNA
<213> ORGANISM: Artificial
<220> FEATURE:
<223> OTHER INFORMATION: Aptamer

<400> SEQUENCE: 633
ucugucucug cccccaggug gauuggcccc uucuggaaua                            40

<210> SEQ ID NO 634
<211> LENGTH: 40
<212> TYPE: RNA
<213> ORGANISM: Artificial
<220> FEATURE:
<223> OTHER INFORMATION: Aptamer

<400> SEQUENCE: 634
ucuggugaac uggucuccgc gguuuuacaa ucggguuaua                            40
```

<210> SEQ ID NO 635
<211> LENGTH: 40
<212> TYPE: RNA
<213> ORGANISM: Artificial
<220> FEATURE:
<223> OTHER INFORMATION: Aptamer

<400> SEQUENCE: 635
ugaagccugg guuuacuggu agaaaucuuc cauuucugug                                40

<210> SEQ ID NO 636
<211> LENGTH: 40
<212> TYPE: RNA
<213> ORGANISM: Artificial
<220> FEATURE:
<223> OTHER INFORMATION: Aptamer

<400> SEQUENCE: 636
ugaguaaagc ucacgucaga gggugaauug gucuauguuu                                40

<210> SEQ ID NO 637
<211> LENGTH: 40
<212> TYPE: RNA
<213> ORGANISM: Artificial
<220> FEATURE:
<223> OTHER INFORMATION: Aptamer

<400> SEQUENCE: 637
uguacggcgg guauuauugg cggucgagac aucgaugcug                                40

<210> SEQ ID NO 638
<211> LENGTH: 40
<212> TYPE: RNA
<213> ORGANISM: Artificial
<220> FEATURE:
<223> OTHER INFORMATION: Aptamer

<400> SEQUENCE: 638
uguccaaugg guaaacuggc cccuagcccu gcuucguaug                                40

<210> SEQ ID NO 639
<211> LENGTH: 40
<212> TYPE: RNA
<213> ORGANISM: Artificial
<220> FEATURE:
<223> OTHER INFORMATION: Aptamer

<400> SEQUENCE: 639
ugucucaggu guauuggucg ccauacugua guaaggcuga                                40

<210> SEQ ID NO 640
<211> LENGTH: 40
<212> TYPE: RNA
<213> ORGANISM: Artificial
<220> FEATURE:
<223> OTHER INFORMATION: Aptamer

<400> SEQUENCE: 640
uuacuucggg auuuccguuc uagguuuauu ggucucguuu                                40

<210> SEQ ID NO 641
<211> LENGTH: 40
<212> TYPE: RNA
<213> ORGANISM: Artificial
<220> FEATURE:

<223> OTHER INFORMATION: Aptamer

<400> SEQUENCE: 641
uuaucacuau ugcugggu uu auuggcuuuc uuuugaagug                              40

<210> SEQ ID NO 642
<211> LENGTH: 41
<212> TYPE: RNA
<213> ORGANISM: Artificial
<220> FEATURE:
<223> OTHER INFORMATION: Aptamer

<400> SEQUENCE: 642
uucuggucca gguuuauugg ccacuaucgu cucuuagggu g                             41

<210> SEQ ID NO 643
<211> LENGTH: 39
<212> TYPE: RNA
<213> ORGANISM: Artificial
<220> FEATURE:
<223> OTHER INFORMATION: Aptamer

<400> SEQUENCE: 643 uucuuuuag guuuacuggc cccguguguu gaugguaug                                 39

<210> SEQ ID NO 644
<211> LENGTH: 40
<212> TYPE: RNA
<213> ORGANISM: Artificial
<220> FEATURE:
<223> OTHER INFORMATION: Aptamer

<400> SEQUENCE: 644
uugcacuggu guauggcca uugacuguga guugaugaag                                40

<210> SEQ ID NO 645
<211> LENGTH: 40
<212> TYPE: RNA
<213> ORGANISM: Artificial
<220> FEATURE:
<223> OTHER INFORMATION: Aptamer

<400> SEQUENCE: 645
uuucucguuc ggguguacug gcuuugucag augacauuug                               40

<210> SEQ ID NO 646
<211> LENGTH: 41
<212> TYPE: RNA
<213> ORGANISM: Artificial
<220> FEATURE:
<223> OTHER INFORMATION: Aptamer

<400> SEQUENCE: 646
uuuucuaucc gucgguuacu ggcgcuucaa acgaagaucu g                             41

<210> SEQ ID NO 647
<211> LENGTH: 40
<212> TYPE: RNA
<213> ORGANISM: Artificial
<220> FEATURE:
<223> OTHER INFORMATION: Aptamer

<400> SEQUENCE: 647
ugguaaauug gcccuucccc ugcauaggug aaaugcggug                               40

```
<210> SEQ ID NO 648
<211> LENGTH: 40
<212> TYPE: RNA
<213> ORGANISM: Artificial
<220> FEATURE:
<223> OTHER INFORMATION: Aptamer

<400> SEQUENCE: 648
ugguggauug gcacucuaca augcuuuugg uccgagguug                              40

<210> SEQ ID NO 649
<211> LENGTH: 40
<212> TYPE: RNA
<213> ORGANISM: Artificial
<220> FEATURE:
<223> OTHER INFORMATION: Aptamer

<400> SEQUENCE: 649
ugguggauug gcuguuguuu cgcuuucuga gaccucgaag                              40

<210> SEQ ID NO 650
<211> LENGTH: 40
<212> TYPE: RNA
<213> ORGANISM: Artificial
<220> FEATURE:
<223> OTHER INFORMATION: Aptamer

<400> SEQUENCE: 650
gguauauugg ucuuugccgg ggcucgccuc cgaguggruu                              40

<210> SEQ ID NO 651
<211> LENGTH: 39
<212> TYPE: RNA
<213> ORGANISM: Artificial
<220> FEATURE:
<223> OTHER INFORMATION: Aptamer

<400> SEQUENCE: 651
ggucaauugg cuggcccaau uuuguuuucu gcgucgaug                               39

<210> SEQ ID NO 652
<211> LENGTH: 40
<212> TYPE: RNA
<213> ORGANISM: Artificial
<220> FEATURE:
<223> OTHER INFORMATION: Aptamer

<400> SEQUENCE: 652
ggucuacugg uggugauuca cgauucucau gaauuucuua                              40

<210> SEQ ID NO 653
<211> LENGTH: 40
<212> TYPE: RNA
<213> ORGANISM: Artificial
<220> FEATURE:
<223> OTHER INFORMATION: Aptamer

<400> SEQUENCE: 653
ggugaacugg uccgcauuua acuuucuuau uugcggguau                              40

<210> SEQ ID NO 654
<211> LENGTH: 40
<212> TYPE: RNA
<213> ORGANISM: Artificial
<220> FEATURE:
<223> OTHER INFORMATION: Aptamer
```

```
<400> SEQUENCE: 654
ggugaacugg uuagcgcgcc gguuuguuac ccgugcugua                    40

<210> SEQ ID NO 655
<211> LENGTH: 40
<212> TYPE: RNA
<213> ORGANISM: Artificial
<220> FEATURE:
<223> OTHER INFORMATION: Aptamer

<400> SEQUENCE: 655
ggugaauugg cgcuucuuua ucuacggauc gagucggaug                    40

<210> SEQ ID NO 656
<211> LENGTH: 40
<212> TYPE: RNA
<213> ORGANISM: Artificial
<220> FEATURE:
<223> OTHER INFORMATION: Aptamer

<400> SEQUENCE: 656
ggugaauugg uauucacccu agguuaguug cgugaauuua                    40

<210> SEQ ID NO 657
<211> LENGTH: 40
<212> TYPE: RNA
<213> ORGANISM: Artificial
<220> FEATURE:
<223> OTHER INFORMATION: Aptamer

<400> SEQUENCE: 657
ggugaauugg uccgaagcuu guugcuccca gcuccgugug                    40

<210> SEQ ID NO 658
<211> LENGTH: 39
<212> TYPE: RNA
<213> ORGANISM: Artificial
<220> FEATURE:
<223> OTHER INFORMATION: Aptamer

<400> SEQUENCE: 658
ggugauacug gcccggcaaa ggcuccucuu uccggugug                     39

<210> SEQ ID NO 659
<211> LENGTH: 40
<212> TYPE: RNA
<213> ORGANISM: Artificial
<220> FEATURE:
<223> OTHER INFORMATION: Aptamer

<400> SEQUENCE: 659
gguggacugg cuaucuguac ggaaugucgu agacuuguug                    40

<210> SEQ ID NO 660
<211> LENGTH: 40
<212> TYPE: RNA
<213> ORGANISM: Artificial
<220> FEATURE:
<223> OTHER INFORMATION: Aptamer

<400> SEQUENCE: 660
gguggacugg uccugugcua gaucuuuuag cuucggcaua                    40

<210> SEQ ID NO 661
<211> LENGTH: 40
```

```
<212> TYPE: RNA
<213> ORGANISM: Artificial
<220> FEATURE:
<223> OTHER INFORMATION: Aptamer

<400> SEQUENCE: 661
gguggacugg ugccguugug uuuugccauu auggauucua                           40

<210> SEQ ID NO 662
<211> LENGTH: 40
<212> TYPE: RNA
<213> ORGANISM: Artificial
<220> FEATURE:
<223> OTHER INFORMATION: Aptamer

<400> SEQUENCE: 662
gguguacugg cacuacuaaa auuucauuug aguaggucug                           40

<210> SEQ ID NO 663
<211> LENGTH: 40
<212> TYPE: RNA
<213> ORGANISM: Artificial
<220> FEATURE:
<223> OTHER INFORMATION: Aptamer

<400> SEQUENCE: 663
gguguacugg ccgaaguucc guauaacgga auggauugug                           40

<210> SEQ ID NO 664
<211> LENGTH: 40
<212> TYPE: RNA
<213> ORGANISM: Artificial
<220> FEATURE:
<223> OTHER INFORMATION: Aptamer

<400> SEQUENCE: 664
gguguacugg cguugcuaau ccguuugucg auucaaguug                           40

<210> SEQ ID NO 665
<211> LENGTH: 40
<212> TYPE: RNA
<213> ORGANISM: Artificial
<220> FEATURE:
<223> OTHER INFORMATION: Aptamer

<400> SEQUENCE: 665
gguguacugg uuggucuggu ccuuccacuc agaagcgaga                           40

<210> SEQ ID NO 666
<211> LENGTH: 40
<212> TYPE: RNA
<213> ORGANISM: Artificial
<220> FEATURE:
<223> OTHER INFORMATION: Aptamer

<400> SEQUENCE: 666
gguguacugg uugugcuuga ucauagauca guaccacgua                           40

<210> SEQ ID NO 667
<211> LENGTH: 39
<212> TYPE: RNA
<213> ORGANISM: Artificial
<220> FEATURE:
<223> OTHER INFORMATION: Aptamer

<400> SEQUENCE: 667
```
gguguacugg uuuuugguag acuuuugauu gccgaggug    39

<210> SEQ ID NO 668
<211> LENGTH: 40
<212> TYPE: RNA
<213> ORGANISM: Artificial
<220> FEATURE:
<223> OTHER INFORMATION: Aptamer

<400> SEQUENCE: 668
gguguauugg cacccaggca gaguugucuc ccccggaaug    40

<210> SEQ ID NO 669
<211> LENGTH: 40
<212> TYPE: RNA
<213> ORGANISM: Artificial
<220> FEATURE:
<223> OTHER INFORMATION: Aptamer

<400> SEQUENCE: 669
gguguauugg caggcgugcu cuuuuacgu ucguugcugg    40

<210> SEQ ID NO 670
<211> LENGTH: 40
<212> TYPE: RNA
<213> ORGANISM: Artificial
<220> FEATURE:
<223> OTHER INFORMATION: Aptamer

<400> SEQUENCE: 670
gguguauugg cccucuugcg uuuaaauuuc gcuguugaug    40

<210> SEQ ID NO 671
<211> LENGTH: 40
<212> TYPE: RNA
<213> ORGANISM: Artificial
<220> FEATURE:
<223> OTHER INFORMATION: Aptamer

<400> SEQUENCE: 671
gguguauugg ccuccgguac ucguguacua gacuugguaa    40

<210> SEQ ID NO 672
<211> LENGTH: 40
<212> TYPE: RNA
<213> ORGANISM: Artificial
<220> FEATURE:
<223> OTHER INFORMATION: Aptamer

<400> SEQUENCE: 672
gguguauugg ccucgccugu ccuuucucag uucgauggug    40

<210> SEQ ID NO 673
<211> LENGTH: 40
<212> TYPE: RNA
<213> ORGANISM: Artificial
<220> FEATURE:
<223> OTHER INFORMATION: Aptamer

<400> SEQUENCE: 673
gguguauugg cgaguuugc gcaauucugc cucuguucug    40

<210> SEQ ID NO 674
<211> LENGTH: 40
<212> TYPE: RNA
<213> ORGANISM: Artificial

```
<220> FEATURE:
<223> OTHER INFORMATION: Aptamer

<400> SEQUENCE: 674
gguguauugg cuugcucuac uugcccggua gauugcacug                              40

<210> SEQ ID NO 675
<211> LENGTH: 40
<212> TYPE: RNA
<213> ORGANISM: Artificial
<220> FEATURE:
<223> OTHER INFORMATION: Aptamer

<400> SEQUENCE: 675
gguguauugg uaugccucac cuggcucagg ucuggaugua                              40

<210> SEQ ID NO 676
<211> LENGTH: 40
<212> TYPE: RNA
<213> ORGANISM: Artificial
<220> FEATURE:
<223> OTHER INFORMATION: Aptamer

<400> SEQUENCE: 676
gguguauugg ucucgaucga ccuauggucu gucaaaguuu                              40

<210> SEQ ID NO 677
<211> LENGTH: 40
<212> TYPE: RNA
<213> ORGANISM: Artificial
<220> FEATURE:
<223> OTHER INFORMATION: Aptamer

<400> SEQUENCE: 677
gguguauugg ugcgugucua ccgauuuugg agacucaaua                              40

<210> SEQ ID NO 678
<211> LENGTH: 40
<212> TYPE: RNA
<213> ORGANISM: Artificial
<220> FEATURE:
<223> OTHER INFORMATION: Aptamer

<400> SEQUENCE: 678
gguguauugg uuaggguacc ucugucgcua cuccuuaua                               40

<210> SEQ ID NO 679
<211> LENGTH: 40
<212> TYPE: RNA
<213> ORGANISM: Artificial
<220> FEATURE:
<223> OTHER INFORMATION: Aptamer

<400> SEQUENCE: 679
gguguauugg uuucuucgc aucuuugcuc aacgaucaaa                               40

<210> SEQ ID NO 680
<211> LENGTH: 40
<212> TYPE: RNA
<213> ORGANISM: Artificial
<220> FEATURE:
<223> OTHER INFORMATION: Aptamer

<400> SEQUENCE: 680
gguuuauugg ccuucuuugc cgacuucgcg cuagguuaug                              40
```

<210> SEQ ID NO 681
<211> LENGTH: 40
<212> TYPE: RNA
<213> ORGANISM: Artificial
<220> FEATURE:
<223> OTHER INFORMATION: Aptamer

<400> SEQUENCE: 681
gguuuauugg cgauaaccac guuguugugu guguuauuug                              40

<210> SEQ ID NO 682
<211> LENGTH: 40
<212> TYPE: RNA
<213> ORGANISM: Artificial
<220> FEATURE:
<223> OTHER INFORMATION: Aptamer

<400> SEQUENCE: 682
gguuuauugg cucucuguuc uacaaucgga cucuggaucg                              40

<210> SEQ ID NO 683
<211> LENGTH: 40
<212> TYPE: RNA
<213> ORGANISM: Artificial
<220> FEATURE:
<223> OTHER INFORMATION: Aptamer

<400> SEQUENCE: 683
gguuugauug gcagucaguc gaaauuugac uuacguuucg                              40

<210> SEQ ID NO 684
<211> LENGTH: 40
<212> TYPE: RNA
<213> ORGANISM: Artificial
<220> FEATURE:
<223> OTHER INFORMATION: Aptamer

<400> SEQUENCE: 684
aaacgguucc uucccuuccg gguaaauugg cucaaagaug                              40

<210> SEQ ID NO 685
<211> LENGTH: 41
<212> TYPE: RNA
<213> ORGANISM: Artificial
<220> FEATURE:
<223> OTHER INFORMATION: Aptamer

<400> SEQUENCE: 685
aacguuacuu aagcggugua uuggcacauu ucggugguuu g                            41

<210> SEQ ID NO 686
<211> LENGTH: 40
<212> TYPE: RNA
<213> ORGANISM: Artificial
<220> FEATURE:
<223> OTHER INFORMATION: Aptamer

<400> SEQUENCE: 686
aacugcuucc ggguaauugg ugcaucaagg uucaugcgug                              40

<210> SEQ ID NO 687
<211> LENGTH: 40
<212> TYPE: RNA
<213> ORGANISM: Artificial
<220> FEATURE:
<223> OTHER INFORMATION: Aptamer

```
<400> SEQUENCE: 687
aacgguucac uggugcccaa cgagucuauc cuagggaaua                              40

<210> SEQ ID NO 688
<211> LENGTH: 40
<212> TYPE: RNA
<213> ORGANISM: Artificial
<220> FEATURE:
<223> OTHER INFORMATION: Aptamer

<400> SEQUENCE: 688
aagaugcuua ggguuauugg cgugugccgu cgcacgagug                              40

<210> SEQ ID NO 689
<211> LENGTH: 41
<212> TYPE: RNA
<213> ORGANISM: Artificial
<220> FEATURE:
<223> OTHER INFORMATION: Aptamer

<400> SEQUENCE: 689
aauccuguug ucucaggugg auugguugua auucuuacgg a                            41

<210> SEQ ID NO 690
<211> LENGTH: 40
<212> TYPE: RNA
<213> ORGANISM: Artificial
<220> FEATURE:
<223> OTHER INFORMATION: Aptamer

<400> SEQUENCE: 690
aagguguacu gguugccuua cgucuccugg ucagguguau                              40

<210> SEQ ID NO 691
<211> LENGTH: 40
<212> TYPE: RNA
<213> ORGANISM: Artificial
<220> FEATURE:
<223> OTHER INFORMATION: Aptamer

<400> SEQUENCE: 691
acaaaauucu uacacguuug ggguauugg ucgauugucu                               40

<210> SEQ ID NO 692
<211> LENGTH: 39
<212> TYPE: RNA
<213> ORGANISM: Artificial
<220> FEATURE:
<223> OTHER INFORMATION: Aptamer

<400> SEQUENCE: 692
acacuugcuu uucuuguccg gguuuauugg ucguugugu                               39

<210> SEQ ID NO 693
<211> LENGTH: 39
<212> TYPE: RNA
<213> ORGANISM: Artificial
<220> FEATURE:
<223> OTHER INFORMATION: Aptamer

<400> SEQUENCE: 693
acaugcugcu uucguccugg uuuauugguc aucggguuu                               39

<210> SEQ ID NO 694
```

```
<211> LENGTH: 34
<212> TYPE: RNA
<213> ORGANISM: Artificial
<220> FEATURE:
<223> OTHER INFORMATION: Aptamer

<400> SEQUENCE: 694
acccacguca gguguauugg ugucggucg aaua                              34

<210> SEQ ID NO 695
<211> LENGTH: 40
<212> TYPE: RNA
<213> ORGANISM: Artificial
<220> FEATURE:
<223> OTHER INFORMATION: Aptamer

<400> SEQUENCE: 695
acuaaugucc ugguguauug gucuuugacg cgaucuucga                       40

<210> SEQ ID NO 696
<211> LENGTH: 40
<212> TYPE: RNA
<213> ORGANISM: Artificial
<220> FEATURE:
<223> OTHER INFORMATION: Aptamer

<400> SEQUENCE: 696
acuucacguc uucggugaau uggcgaucuu cugucucaug                       40

<210> SEQ ID NO 697
<211> LENGTH: 40
<212> TYPE: RNA
<213> ORGANISM: Artificial
<220> FEATURE:
<223> OTHER INFORMATION: Aptamer

<400> SEQUENCE: 697
agacaucacg aacggguuau uggcgcgcac ucacgaucug                       40

<210> SEQ ID NO 698
<211> LENGTH: 40
<212> TYPE: RNA
<213> ORGANISM: Artificial
<220> FEATURE:
<223> OTHER INFORMATION: Aptamer

<400> SEQUENCE: 698
agagaacggu uuaacuggcg cgggaguuuc ugaacgaaug                       40

<210> SEQ ID NO 699
<211> LENGTH: 40
<212> TYPE: RNA
<213> ORGANISM: Artificial
<220> FEATURE:
<223> OTHER INFORMATION: Aptamer

<400> SEQUENCE: 699
agcuacgucu ucaaggucua cuggcgcaaa agcuugcaug                       40

<210> SEQ ID NO 700
<211> LENGTH: 40
<212> TYPE: RNA
<213> ORGANISM: Artificial
<220> FEATURE:
<223> OTHER INFORMATION: Aptamer

<400> SEQUENCE: 700
```

```
agcuguuuau auccaggugu acuggcccug cuaugaggug                              40

<210> SEQ ID NO 701
<211> LENGTH: 40
<212> TYPE: RNA
<213> ORGANISM: Artificial
<220> FEATURE:
<223> OTHER INFORMATION: Aptamer

<400> SEQUENCE: 701
aucugugcaa cuuccaaaag gugaauuggu agcgagcuca                              40

<210> SEQ ID NO 702
<211> LENGTH: 40
<212> TYPE: RNA
<213> ORGANISM: Artificial
<220> FEATURE:
<223> OTHER INFORMATION: Aptamer

<400> SEQUENCE: 702
auuccuugcg cacccggggug uacuggucca gaauugaaua                             40

<210> SEQ ID NO 703
<211> LENGTH: 40
<212> TYPE: RNA
<213> ORGANISM: Artificial
<220> FEATURE:
<223> OTHER INFORMATION: Aptamer

<400> SEQUENCE: 703
auggucuauu ggcucucucc aauccgcguu gaagauaaug                              40

<210> SEQ ID NO 704
<211> LENGTH: 40
<212> TYPE: RNA
<213> ORGANISM: Artificial
<220> FEATURE:
<223> OTHER INFORMATION: Aptamer

<400> SEQUENCE: 704
aggugaacug guuccuucu uccuugugaa gugguuuuca                               40

<210> SEQ ID NO 705
<211> LENGTH: 40
<212> TYPE: RNA
<213> ORGANISM: Artificial
<220> FEATURE:
<223> OTHER INFORMATION: Aptamer

<400> SEQUENCE: 705
aggugaauug gcgcaaucuc cuuugccgcg auacugaaug                              40

<210> SEQ ID NO 706
<211> LENGTH: 39
<212> TYPE: RNA
<213> ORGANISM: Artificial
<220> FEATURE:
<223> OTHER INFORMATION: Aptamer

<400> SEQUENCE: 706
aggugaauug gugccauuua cugucuuuua augcguuua                               39

<210> SEQ ID NO 707
<211> LENGTH: 40
<212> TYPE: RNA
```

```
<213> ORGANISM: Artificial
<220> FEATURE:
<223> OTHER INFORMATION: Aptamer

<400> SEQUENCE: 707
agguguacug gugcguagua gccuaaugcg uguuacguua                              40

<210> SEQ ID NO 708
<211> LENGTH: 40
<212> TYPE: RNA
<213> ORGANISM: Artificial
<220> FEATURE:
<223> OTHER INFORMATION: Aptamer

<400> SEQUENCE: 708
agguuacugg cgaauucuuc uuugcccaag acaauugcug                              40

<210> SEQ ID NO 709
<211> LENGTH: 39
<212> TYPE: RNA
<213> ORGANISM: Artificial
<220> FEATURE:
<223> OTHER INFORMATION: Aptamer

<400> SEQUENCE: 709
caacccucuu uccggguguacugguguacu guacgcuua                              39

<210> SEQ ID NO 710
<211> LENGTH: 40
<212> TYPE: RNA
<213> ORGANISM: Artificial
<220> FEATURE:
<223> OTHER INFORMATION: Aptamer

<400> SEQUENCE: 710
cacuuccggg uguauuggua guugccguuu ucucuucaua                             40

<210> SEQ ID NO 711
<211> LENGTH: 39
<212> TYPE: RNA
<213> ORGANISM: Artificial
<220> FEATURE:
<223> OTHER INFORMATION: Aptamer

<400> SEQUENCE: 711
cagcuucauc uccgggucua cugguuaccu ccggucgug                              39

<210> SEQ ID NO 712
<211> LENGTH: 40
<212> TYPE: RNA
<213> ORGANISM: Artificial
<220> FEATURE:
<223> OTHER INFORMATION: Aptamer

<400> SEQUENCE: 712
cagguguauu ggucgagacu uauguucgua aggcugugua                             40

<210> SEQ ID NO 713
<211> LENGTH: 40
<212> TYPE: RNA
<213> ORGANISM: Artificial
<220> FEATURE:
<223> OTHER INFORMATION: Aptamer

<400> SEQUENCE: 713 ccaccccucgu guagguuuac uggccccuc auaagguaug                             40
```

```
<210> SEQ ID NO 714
<211> LENGTH: 39
<212> TYPE: RNA
<213> ORGANISM: Artificial
<220> FEATURE:
<223> OTHER INFORMATION: Aptamer

<400> SEQUENCE: 714
cccuugauac guccucaggu uuauuggcug uucuucgug                              39

<210> SEQ ID NO 715
<211> LENGTH: 40
<212> TYPE: RNA
<213> ORGANISM: Artificial
<220> FEATURE:
<223> OTHER INFORMATION: Aptamer

<400> SEQUENCE: 715
ccgaucguug auagguuacu ggcgucgcau ucacgaaaug                             40

<210> SEQ ID NO 716
<211> LENGTH: 40
<212> TYPE: RNA
<213> ORGANISM: Artificial
<220> FEATURE:
<223> OTHER INFORMATION: Aptamer

<400> SEQUENCE: 716
ccgccucguu cuagguguau uggcucgaca cggcuggag                              40

<210> SEQ ID NO 717
<211> LENGTH: 39
<212> TYPE: RNA
<213> ORGANISM: Artificial
<220> FEATURE:
<223> OTHER INFORMATION: Aptamer

<400> SEQUENCE: 717
ccguccgagg ugaauuggua ccacucuca gauagcuua                               39

<210> SEQ ID NO 718
<211> LENGTH: 40
<212> TYPE: RNA
<213> ORGANISM: Artificial
<220> FEATURE:
<223> OTHER INFORMATION: Aptamer

<400> SEQUENCE: 718
ccuccuuccc uaguccgggu uuauuggccg cauccgaaug                             40

<210> SEQ ID NO 719
<211> LENGTH: 40
<212> TYPE: RNA
<213> ORGANISM: Artificial
<220> FEATURE:
<223> OTHER INFORMATION: Aptamer

<400> SEQUENCE: 719
ccuguuuugu cuagguucau uggcgcuuau uucuggaaug                             40

<210> SEQ ID NO 720
<211> LENGTH: 40
<212> TYPE: RNA
<213> ORGANISM: Artificial
<220> FEATURE:
```

<223> OTHER INFORMATION: Aptamer

<400> SEQUENCE: 720
cgacuccggu uagacuggcg ccucuuucgg aagaguaaug                    40

<210> SEQ ID NO 721
<211> LENGTH: 35
<212> TYPE: RNA
<213> ORGANISM: Artificial
<220> FEATURE:
<223> OTHER INFORMATION: Aptamer

<400> SEQUENCE: 721
cgacugucuc ggguguuacug gcgauugagu uagug                       35

<210> SEQ ID NO 722
<211> LENGTH: 40
<212> TYPE: RNA
<213> ORGANISM: Artificial
<220> FEATURE:
<223> OTHER INFORMATION: Aptamer

<400> SEQUENCE: 722
cgcaaccugg uauauuggcu caucuagucg uaggugcaug                   40

<210> SEQ ID NO 723
<211> LENGTH: 40
<212> TYPE: RNA
<213> ORGANISM: Artificial
<220> FEATURE:
<223> OTHER INFORMATION: Aptamer

<400> SEQUENCE: 723
cgcucaggug aauugguuac guuuucucug acgaugugga                   40

<210> SEQ ID NO 724
<211> LENGTH: 40
<212> TYPE: RNA
<213> ORGANISM: Artificial
<220> FEATURE:
<223> OTHER INFORMATION: Aptamer

<400> SEQUENCE: 724
cgguugggga accacguucg gguucauugg ucuaagguuu                   40

<210> SEQ ID NO 725
<211> LENGTH: 40
<212> TYPE: RNA
<213> ORGANISM: Artificial
<220> FEATURE:
<223> OTHER INFORMATION: Aptamer

<400> SEQUENCE: 725
cgucagcuug guguauuggu auucucaucu cgugaauaaa                   40

<210> SEQ ID NO 726
<211> LENGTH: 40
<212> TYPE: RNA
<213> ORGANISM: Artificial
<220> FEATURE:
<223> OTHER INFORMATION: Aptamer

<400> SEQUENCE: 726
cguccuuguc aggugaacug gcuugauccu uuucuuguaa                   40

```
<210> SEQ ID NO 727
<211> LENGTH: 40
<212> TYPE: RNA
<213> ORGANISM: Artificial
<220> FEATURE:
<223> OTHER INFORMATION: Aptamer

<400> SEQUENCE: 727
cgucgcuucu guugguaauu ggcaguauuu aauacgcuug                   40

<210> SEQ ID NO 728
<211> LENGTH: 39
<212> TYPE: RNA
<213> ORGANISM: Artificial
<220> FEATURE:
<223> OTHER INFORMATION: Aptamer

<400> SEQUENCE: 728
cgucuuaggu guauggcuc caacgucuug cugaauucg                    39

<210> SEQ ID NO 729
<211> LENGTH: 40
<212> TYPE: RNA
<213> ORGANISM: Artificial
<220> FEATURE:
<223> OTHER INFORMATION: Aptamer

<400> SEQUENCE: 729 cguccuguc aggguguauu ggucggcuag uguagugcuu                   40

<210> SEQ ID NO 730
<211> LENGTH: 39
<212> TYPE: RNA
<213> ORGANISM: Artificial
<220> FEATURE:
<223> OTHER INFORMATION: Aptamer

<400> SEQUENCE: 730
cggguacauu ggccccuaua ccucgcggua aaugguaug                   39

<210> SEQ ID NO 731
<211> LENGTH: 40
<212> TYPE: RNA
<213> ORGANISM: Artificial
<220> FEATURE:
<223> OTHER INFORMATION: Aptamer

<400> SEQUENCE: 731
cuaagcgcac auuaaggugu acuggcucag gguuugguuug                 40

<210> SEQ ID NO 732
<211> LENGTH: 40
<212> TYPE: RNA
<213> ORGANISM: Artificial
<220> FEATURE:
<223> OTHER INFORMATION: Aptamer

<400> SEQUENCE: 732
cuagccuggg ugaacuggug augaugauuc guugcauuua                  40

<210> SEQ ID NO 733
<211> LENGTH: 40
<212> TYPE: RNA
<213> ORGANISM: Artificial
<220> FEATURE:
<223> OTHER INFORMATION: Aptamer
```

```
<400> SEQUENCE: 733
cucacuuccc gguguacugg uggaaugucu ccauucgcua                              40

<210> SEQ ID NO 734
<211> LENGTH: 40
<212> TYPE: RNA
<213> ORGANISM: Artificial
<220> FEATURE:
<223> OTHER INFORMATION: Aptamer

<400> SEQUENCE: 734
cuccuacugc ucucccgcgu uggguuaauu ggucucgugu                              40

<210> SEQ ID NO 735
<211> LENGTH: 40
<212> TYPE: RNA
<213> ORGANISM: Artificial
<220> FEATURE:
<223> OTHER INFORMATION: Aptamer

<400> SEQUENCE: 735
cucgaugggu auacuggcga cgguaauuuc uuacguaaug                              40

<210> SEQ ID NO 736
<211> LENGTH: 40
<212> TYPE: RNA
<213> ORGANISM: Artificial
<220> FEATURE:
<223> OTHER INFORMATION: Aptamer

<400> SEQUENCE: 736
cucgguuuuc uucguccauu uggugaacug gccaauguuu                              40

<210> SEQ ID NO 737
<211> LENGTH: 40
<212> TYPE: RNA
<213> ORGANISM: Artificial
<220> FEATURE:
<223> OTHER INFORMATION: Aptamer

<400> SEQUENCE: 737
cucggggugu acuggugucu uggguccuc cccaugacua                               40

<210> SEQ ID NO 738
<211> LENGTH: 40
<212> TYPE: RNA
<213> ORGANISM: Artificial
<220> FEATURE:
<223> OTHER INFORMATION: Aptamer

<400> SEQUENCE: 738
cugccguugg gguguacugg uuugggaau ugccgagugu                               40

<210> SEQ ID NO 739
<211> LENGTH: 40
<212> TYPE: RNA
<213> ORGANISM: Artificial
<220> FEATURE:
<223> OTHER INFORMATION: Aptamer

<400> SEQUENCE: 739
cugcgcccag guuuauuggu cugguacuuc uguaguguuu                              40

<210> SEQ ID NO 740
<211> LENGTH: 40
```

```
<212> TYPE: RNA
<213> ORGANISM: Artificial
<220> FEATURE:
<223> OTHER INFORMATION: Aptamer

<400> SEQUENCE: 740
cugcucugcc uagguguauu gguccgauuu uaaaucauua                              40

<210> SEQ ID NO 741
<211> LENGTH: 40
<212> TYPE: RNA
<213> ORGANISM: Artificial
<220> FEATURE:
<223> OTHER INFORMATION: Aptamer

<400> SEQUENCE: 741
cugcuucucc augguguacu ggcuggaucu uuggccguug                              40

<210> SEQ ID NO 742
<211> LENGTH: 40
<212> TYPE: RNA
<213> ORGANISM: Artificial
<220> FEATURE:
<223> OTHER INFORMATION: Aptamer

<400> SEQUENCE: 742
cuguaucagu cugguuuugg uguauugguc caugugagga                              40

<210> SEQ ID NO 743
<211> LENGTH: 40
<212> TYPE: RNA
<213> ORGANISM: Artificial
<220> FEATURE:
<223> OTHER INFORMATION: Aptamer

<400> SEQUENCE: 743
cuguuccacg cgccgucuau uugguuuauu ggucucguuu                              40

<210> SEQ ID NO 744
<211> LENGTH: 40
<212> TYPE: RNA
<213> ORGANISM: Artificial
<220> FEATURE:
<223> OTHER INFORMATION: Aptamer

<400> SEQUENCE: 744
cuguuccucg guaauuggcu guuucuuccc aguuucaaug                              40

<210> SEQ ID NO 745
<211> LENGTH: 40
<212> TYPE: RNA
<213> ORGANISM: Artificial
<220> FEATURE:
<223> OTHER INFORMATION: Aptamer

<400> SEQUENCE: 745
cuucucggug uauuggcugc gcuaccuuuc guagucucag                              40

<210> SEQ ID NO 746
<211> LENGTH: 40
<212> TYPE: RNA
<213> ORGANISM: Artificial
<220> FEATURE:
<223> OTHER INFORMATION: Aptamer

<400> SEQUENCE: 746
```
cuuuugccgg guuccauugg cucguacacg uugucgaaug                40

<210> SEQ ID NO 747
<211> LENGTH: 40
<212> TYPE: RNA
<213> ORGANISM: Artificial
<220> FEATURE:
<223> OTHER INFORMATION: Aptamer

<400> SEQUENCE: 747
cgguguacug gcggagaggc uuacugguua accuuccuug                40

<210> SEQ ID NO 748
<211> LENGTH: 40
<212> TYPE: RNA
<213> ORGANISM: Artificial
<220> FEATURE:
<223> OTHER INFORMATION: Aptamer

<400> SEQUENCE: 748
cgguguauug guccacaggc uggcucaguc gaccuugcga                40

<210> SEQ ID NO 749
<211> LENGTH: 40
<212> TYPE: RNA
<213> ORGANISM: Artificial
<220> FEATURE:
<223> OTHER INFORMATION: Aptamer

<400> SEQUENCE: 749
gaccgugcgc uucaggucua cuggcuuuca uuugaagaug                40

<210> SEQ ID NO 750
<211> LENGTH: 35
<212> TYPE: RNA
<213> ORGANISM: Artificial
<220> FEATURE:
<223> OTHER INFORMATION: Aptamer

<400> SEQUENCE: 750
gagaucguuc ugguuauugg cgccuucgug gaaug                     35

<210> SEQ ID NO 751
<211> LENGTH: 39
<212> TYPE: RNA
<213> ORGANISM: Artificial
<220> FEATURE:
<223> OTHER INFORMATION: Aptamer

<400> SEQUENCE: 751
gaucgaucug gguacauugg ccaucugaag agacgcgug                 39

<210> SEQ ID NO 752
<211> LENGTH: 40
<212> TYPE: RNA
<213> ORGANISM: Artificial
<220> FEATURE:
<223> OTHER INFORMATION: Aptamer

<400> SEQUENCE: 752
gauuguuugg uaauuggucc uugguccccc acgagguaua                40

<210> SEQ ID NO 753
<211> LENGTH: 40
<212> TYPE: RNA
<213> ORGANISM: Artificial

```
<220> FEATURE:
<223> OTHER INFORMATION: Aptamer

<400> SEQUENCE: 753
gagguguacu ggcagccaau auucccugau auugcuguua                             40

<210> SEQ ID NO 754
<211> LENGTH: 40
<212> TYPE: RNA
<213> ORGANISM: Artificial
<220> FEATURE:
<223> OTHER INFORMATION: Aptamer

<400> SEQUENCE: 754
gcaccauggu aauuggcugc uuucauuuug uguggcgaug                             40

<210> SEQ ID NO 755
<211> LENGTH: 40
<212> TYPE: RNA
<213> ORGANISM: Artificial
<220> FEATURE:
<223> OTHER INFORMATION: Aptamer

<400> SEQUENCE: 755
gcagagguuu acuggcgggc ucauaagucu ugaaccagug                             40

<210> SEQ ID NO 756
<211> LENGTH: 40
<212> TYPE: RNA
<213> ORGANISM: Artificial
<220> FEATURE:
<223> OTHER INFORMATION: Aptamer

<400> SEQUENCE: 756
gcccgagucu ugguauauug gugccgucac uuuucgguua                             40

<210> SEQ ID NO 757
<211> LENGTH: 40
<212> TYPE: RNA
<213> ORGANISM: Artificial
<220> FEATURE:
<223> OTHER INFORMATION: Aptamer

<400> SEQUENCE: 757
gccuuuguuc uacgucuugg uguacuggcg caaucgcuug                             40

<210> SEQ ID NO 758
<211> LENGTH: 40
<212> TYPE: RNA
<213> ORGANISM: Artificial
<220> FEATURE:
<223> OTHER INFORMATION: Aptamer

<400> SEQUENCE: 758
gcucccugaa cggcaggcuc cggguauauu ggucuaguau                             40

<210> SEQ ID NO 759
<211> LENGTH: 40
<212> TYPE: RNA
<213> ORGANISM: Artificial
<220> FEATURE:
<223> OTHER INFORMATION: Aptamer

<400> SEQUENCE: 759 gcuuugagg uuuauuggcu auugcaacuu cgcuuuaaug                              40
```

```
<210> SEQ ID NO 760
<211> LENGTH: 39
<212> TYPE: RNA
<213> ORGANISM: Artificial
<220> FEATURE:
<223> OTHER INFORMATION: Aptamer

<400> SEQUENCE: 760
ggaugagucu ucucaggugu auuggcuggu auucgucag                              39

<210> SEQ ID NO 761
<211> LENGTH: 39
<212> TYPE: RNA
<213> ORGANISM: Artificial
<220> FEATURE:
<223> OTHER INFORMATION: Aptamer

<400> SEQUENCE: 761
gggagaguau ucuacguacu gguaauuggc uuccggaug                              39

<210> SEQ ID NO 762
<211> LENGTH: 40
<212> TYPE: RNA
<213> ORGANISM: Artificial
<220> FEATURE:
<223> OTHER INFORMATION: Aptamer

<400> SEQUENCE: 762
ggguauguau gauggugauu ggcgcugguu guccggagug                             40

<210> SEQ ID NO 763
<211> LENGTH: 40
<212> TYPE: RNA
<213> ORGANISM: Artificial
<220> FEATURE:
<223> OTHER INFORMATION: Aptamer

<400> SEQUENCE: 763
guccgggugu acuggcgaug acuuuuccgu ggguuuugca                             40

<210> SEQ ID NO 764
<211> LENGTH: 40
<212> TYPE: RNA
<213> ORGANISM: Artificial
<220> FEATURE:
<223> OTHER INFORMATION: Aptamer

<400> SEQUENCE: 764
guccggguuu gauuggcugu acuccccucu cguucgaug                              40

<210> SEQ ID NO 765
<211> LENGTH: 40
<212> TYPE: RNA
<213> ORGANISM: Artificial
<220> FEATURE:
<223> OTHER INFORMATION: Aptamer

<400> SEQUENCE: 765
guccuugcuu ucuggguuca cuggugucgu gcccgaugug                             40

<210> SEQ ID NO 766
<211> LENGTH: 40
<212> TYPE: RNA
<213> ORGANISM: Artificial
<220> FEATURE:
<223> OTHER INFORMATION: Aptamer
```

```
<400> SEQUENCE: 766
ggguguauug guuacuagcc cguagaaggu uucuagcgaa                              40

<210> SEQ ID NO 767
<211> LENGTH: 40
<212> TYPE: RNA
<213> ORGANISM: Artificial
<220> FEATURE:
<223> OTHER INFORMATION: Aptamer

<400> SEQUENCE: 767
ggguuaauug gcgcuucacg uagcauggcg aaggagcaug                              40

<210> SEQ ID NO 768
<211> LENGTH: 40
<212> TYPE: RNA
<213> ORGANISM: Artificial
<220> FEATURE:
<223> OTHER INFORMATION: Aptamer

<400> SEQUENCE: 768
uaaguccgac aucauccagg uguauuggcu uccuucggag                              40

<210> SEQ ID NO 769
<211> LENGTH: 40
<212> TYPE: RNA
<213> ORGANISM: Artificial
<220> FEATURE:
<223> OTHER INFORMATION: Aptamer

<400> SEQUENCE: 769
uaagggugua cuggcgauug uugggacgca cuucaauuug                              40

<210> SEQ ID NO 770
<211> LENGTH: 40
<212> TYPE: RNA
<213> ORGANISM: Artificial
<220> FEATURE:
<223> OTHER INFORMATION: Aptamer

<400> SEQUENCE: 770
uaaugacagc uguagaacaa gguuuauugg ccucugggug                              40

<210> SEQ ID NO 771
<211> LENGTH: 40
<212> TYPE: RNA
<213> ORGANISM: Artificial
<220> FEATURE:
<223> OTHER INFORMATION: Aptamer

<400> SEQUENCE: 771
uacgucuugc cuuagguuua uuggucagcc ccggcagcga                              40

<210> SEQ ID NO 772
<211> LENGTH: 40
<212> TYPE: RNA
<213> ORGANISM: Artificial
<220> FEATURE:
<223> OTHER INFORMATION: Aptamer

<400> SEQUENCE: 772
uacugcgucg caugggugua uuggcgaucc acgagauucg                              40

<210> SEQ ID NO 773
```

```
<211> LENGTH: 40
<212> TYPE: RNA
<213> ORGANISM: Artificial
<220> FEATURE:
<223> OTHER INFORMATION: Aptamer

<400> SEQUENCE: 773
uacgguaauu ggccuuggau uucuucgauu uuccucguuu                            40

<210> SEQ ID NO 774
<211> LENGTH: 40
<212> TYPE: RNA
<213> ORGANISM: Artificial
<220> FEATURE:
<223> OTHER INFORMATION: Aptamer

<400> SEQUENCE: 774
uagucucuca uuuccuggug uauuggcggc augcgcgugg                            40

<210> SEQ ID NO 775
<211> LENGTH: 40
<212> TYPE: RNA
<213> ORGANISM: Artificial
<220> FEATURE:
<223> OTHER INFORMATION: Aptamer

<400> SEQUENCE: 775
uaucaggugu acuggucuuc ucaauuuuac cgagacgcga                            40

<210> SEQ ID NO 776
<211> LENGTH: 40
<212> TYPE: RNA
<213> ORGANISM: Artificial
<220> FEATURE:
<223> OTHER INFORMATION: Aptamer

<400> SEQUENCE: 776
uagguuuauu ggcugguacc cggauguugu gguuauugag                            40

<210> SEQ ID NO 777
<211> LENGTH: 40
<212> TYPE: RNA
<213> ORGANISM: Artificial
<220> FEATURE:
<223> OTHER INFORMATION: Aptamer

<400> SEQUENCE: 777
ucacugucuc gguuauuggc ucguuuucau cucgcggaug                            40

<210> SEQ ID NO 778
<211> LENGTH: 40
<212> TYPE: RNA
<213> ORGANISM: Artificial
<220> FEATURE:
<223> OTHER INFORMATION: Aptamer

<400> SEQUENCE: 778
ucccaucgua cuugguuuau uggcucaauu gaauuggaug                            40

<210> SEQ ID NO 779
<211> LENGTH: 40
<212> TYPE: RNA
<213> ORGANISM: Artificial
<220> FEATURE:
<223> OTHER INFORMATION: Aptamer

<400> SEQUENCE: 779
```
ucccgaacau uucugggugg auuggcuagu aucuuccaag        40

<210> SEQ ID NO 780
<211> LENGTH: 40
<212> TYPE: RNA
<213> ORGANISM: Artificial
<220> FEATURE:
<223> OTHER INFORMATION: Aptamer

<400> SEQUENCE: 780
ucccuacacu ccggugaauu uggucaauac cuuguaucga        40

<210> SEQ ID NO 781
<211> LENGTH: 39
<212> TYPE: RNA
<213> ORGANISM: Artificial
<220> FEATURE:
<223> OTHER INFORMATION: Aptamer

<400> SEQUENCE: 781
uccgcccuga uggucaacug gccccuuacg gaagguaug        39

<210> SEQ ID NO 782
<211> LENGTH: 40
<212> TYPE: RNA
<213> ORGANISM: Artificial
<220> FEATURE:
<223> OTHER INFORMATION: Aptamer

<400> SEQUENCE: 782
uccuuuucuu gaugaauuuc cggguguacu ggucauuugg        40

<210> SEQ ID NO 783
<211> LENGTH: 40
<212> TYPE: RNA
<213> ORGANISM: Artificial
<220> FEATURE:
<223> OTHER INFORMATION: Aptamer

<400> SEQUENCE: 783
ucgcacaaga cuucuaccuc cagguuauug gucucgguuu        40

<210> SEQ ID NO 784
<211> LENGTH: 40
<212> TYPE: RNA
<213> ORGANISM: Artificial
<220> FEATURE:
<223> OTHER INFORMATION: Aptamer

<400> SEQUENCE: 784
ucugcuacca ggugacugg ugcucuagug acuagauuua        40

<210> SEQ ID NO 785
<211> LENGTH: 45
<212> TYPE: RNA
<213> ORGANISM: Artificial
<220> FEATURE:
<223> OTHER INFORMATION: Aptamer

<400> SEQUENCE: 785
ucugcuuuga cguucaacaa gguuauugg uuguauucuu acgga        45

<210> SEQ ID NO 786
<211> LENGTH: 40
<212> TYPE: RNA

```
<213> ORGANISM: Artificial
<220> FEATURE:
<223> OTHER INFORMATION: Aptamer

<400> SEQUENCE: 786
ucuucuagca cucuggguau auuggugguu gaagaauuua                              40

<210> SEQ ID NO 787
<211> LENGTH: 40
<212> TYPE: RNA
<213> ORGANISM: Artificial
<220> FEATURE:
<223> OTHER INFORMATION: Aptamer

<400> SEQUENCE: 787
ucuucuuuuu gcuuccggu uauuggcggu gcauaccaug                               40

<210> SEQ ID NO 788
<211> LENGTH: 40
<212> TYPE: RNA
<213> ORGANISM: Artificial
<220> FEATURE:
<223> OTHER INFORMATION: Aptamer

<400> SEQUENCE: 788
ugacugucca uucuagguua uuggcggcug guuuguagug                              40

<210> SEQ ID NO 789
<211> LENGTH: 40
<212> TYPE: RNA
<213> ORGANISM: Artificial
<220> FEATURE:
<223> OTHER INFORMATION: Aptamer

<400> SEQUENCE: 789
ugccugguaa uuggcuccuu aucuccuccg auuccgaaug                              40

<210> SEQ ID NO 790
<211> LENGTH: 40
<212> TYPE: RNA
<213> ORGANISM: Artificial
<220> FEATURE:
<223> OTHER INFORMATION: Aptamer

<400> SEQUENCE: 790
ugcgucuuuc cgguguauug gcugccaguu uuggugauga                              40

<210> SEQ ID NO 791
<211> LENGTH: 40
<212> TYPE: RNA
<213> ORGANISM: Artificial
<220> FEATURE:
<223> OTHER INFORMATION: Aptamer

<400> SEQUENCE: 791
ugcucgcacg acuuugguug acuggccguc ucugacaaug                              40

<210> SEQ ID NO 792
<211> LENGTH: 39
<212> TYPE: RNA
<213> ORGANISM: Artificial
<220> FEATURE:
<223> OTHER INFORMATION: Aptamer

<400> SEQUENCE: 792
ugcuucgggu cuauuggugc cugcuauuca gcaguguua                               39
```

```
<210> SEQ ID NO 793
<211> LENGTH: 40
<212> TYPE: RNA
<213> ORGANISM: Artificial
<220> FEATURE:
<223> OTHER INFORMATION: Aptamer

<400> SEQUENCE: 793
uggguuauug gcgucgugga guuaccacuc uuacgagcug                                40

<210> SEQ ID NO 794
<211> LENGTH: 40
<212> TYPE: RNA
<213> ORGANISM: Artificial
<220> FEATURE:
<223> OTHER INFORMATION: Aptamer

<400> SEQUENCE: 794
uuacacuuac gucauugguu uauuggugcc uuagugguua                                40

<210> SEQ ID NO 795
<211> LENGTH: 40
<212> TYPE: RNA
<213> ORGANISM: Artificial
<220> FEATURE:
<223> OTHER INFORMATION: Aptamer

<400> SEQUENCE: 795
uucagguuau uggcccaggc uuuuccaag acccggugug                                 40

<210> SEQ ID NO 796
<211> LENGTH: 41
<212> TYPE: RNA
<213> ORGANISM: Artificial
<220> FEATURE:
<223> OTHER INFORMATION: Aptamer

<400> SEQUENCE: 796
uucagguuau uggcccaggc uuuuuccaa aacccggugu g                               41

<210> SEQ ID NO 797
<211> LENGTH: 40
<212> TYPE: RNA
<213> ORGANISM: Artificial
<220> FEATURE:
<223> OTHER INFORMATION: Aptamer

<400> SEQUENCE: 797
uucgcggcgc ccggguggac uggcuucauu uacucgagug                                40

<210> SEQ ID NO 798
<211> LENGTH: 40
<212> TYPE: RNA
<213> ORGANISM: Artificial
<220> FEATURE:
<223> OTHER INFORMATION: Aptamer

<400> SEQUENCE: 798
uucgcggucu gguuuauugg uuccccaucc ugcgguaaua                                40

<210> SEQ ID NO 799
<211> LENGTH: 40
<212> TYPE: RNA
<213> ORGANISM: Artificial
<220> FEATURE:
```

<223> OTHER INFORMATION: Aptamer

<400> SEQUENCE: 799
uucgucgggg uguacuggcc gccgcucgcg gauggguuca                                    40

<210> SEQ ID NO 800
<211> LENGTH: 39
<212> TYPE: RNA
<213> ORGANISM: Artificial
<220> FEATURE:
<223> OTHER INFORMATION: Aptamer

<400> SEQUENCE: 800
uucucgucuc gguacauugg cgaccuacuc ugcguaaug                                     39

<210> SEQ ID NO 801
<211> LENGTH: 40
<212> TYPE: RNA
<213> ORGANISM: Artificial
<220> FEATURE:
<223> OTHER INFORMATION: Aptamer

<400> SEQUENCE: 801
uucuuccagg uuuauuggcg uggucuauug caguacauug                                    40

<210> SEQ ID NO 802
<211> LENGTH: 39
<212> TYPE: RNA
<213> ORGANISM: Artificial
<220> FEATURE:
<223> OTHER INFORMATION: Aptamer

<400> SEQUENCE: 802
uugcucaaaa agguguauug guucaacagg ggguuagua                                     39

<210> SEQ ID NO 803
<211> LENGTH: 40
<212> TYPE: RNA
<213> ORGANISM: Artificial
<220> FEATURE:
<223> OTHER INFORMATION: Aptamer

<400> SEQUENCE: 803
uuuaugguua cuggcgcggc auuuuuuguc uuuccgaaug                                    40

<210> SEQ ID NO 804
<211> LENGTH: 40
<212> TYPE: RNA
<213> ORGANISM: Artificial
<220> FEATURE:
<223> OTHER INFORMATION: Aptamer

<400> SEQUENCE: 804
uuucgcuugu ccgcuggugu auuggucucu gucgcgugga                                    40

<210> SEQ ID NO 805
<211> LENGTH: 41
<212> TYPE: RNA
<213> ORGANISM: Artificial
<220> FEATURE:
<223> OTHER INFORMATION: Aptamer

<400> SEQUENCE: 805
uuuucauccg ucgguuacug gcgcuucaaa acgaagaucu g                                  41

```
<210> SEQ ID NO 806
<211> LENGTH: 40
<212> TYPE: RNA
<213> ORGANISM: Artificial
<220> FEATURE:
<223> OTHER INFORMATION: Aptamer

<400> SEQUENCE: 806
uuuggugaac ugguaucauu uuguguuugc auaugaguua                              40

<210> SEQ ID NO 807
<211> LENGTH: 40
<212> TYPE: RNA
<213> ORGANISM: Artificial
<220> FEATURE:
<223> OTHER INFORMATION: Aptamer

<400> SEQUENCE: 807
uggugaacug gccccucgug acuucgucgg gaggauguag                              40

<210> SEQ ID NO 808
<211> LENGTH: 40
<212> TYPE: RNA
<213> ORGANISM: Artificial
<220> FEATURE:
<223> OTHER INFORMATION: Aptamer

<400> SEQUENCE: 808
ugguguauug gucccggaug augguuguuc ucuuccgcga                              40

<210> SEQ ID NO 809
<211> LENGTH: 40
<212> TYPE: RNA
<213> ORGANISM: Artificial
<220> FEATURE:
<223> OTHER INFORMATION: Aptamer

<400> SEQUENCE: 809
gguaaauugg ugccuaucuu ugcgcucgca uuaggguguuc                             40

<210> SEQ ID NO 810
<211> LENGTH: 40
<212> TYPE: RNA
<213> ORGANISM: Artificial
<220> FEATURE:
<223> OTHER INFORMATION: Aptamer

<400> SEQUENCE: 810
gguaauuggu ccguaggucu cgaacgccag aacucuuaua                              40

<210> SEQ ID NO 811
<211> LENGTH: 40
<212> TYPE: RNA
<213> ORGANISM: Artificial
<220> FEATURE:
<223> OTHER INFORMATION: Aptamer

<400> SEQUENCE: 811
gguagauugg ccgucggaua uucuugcgaa gaggugugug                              40

<210> SEQ ID NO 812
<211> LENGTH: 40
<212> TYPE: RNA
<213> ORGANISM: Artificial
<220> FEATURE:
<223> OTHER INFORMATION: Aptamer
```

```
<400> SEQUENCE: 812
gguauauugg cuucggaucc uuuucguucg ggucugagug                                40

<210> SEQ ID NO 813
<211> LENGTH: 40
<212> TYPE: RNA
<213> ORGANISM: Artificial
<220> FEATURE:
<223> OTHER INFORMATION: Aptamer

<400> SEQUENCE: 813
gguauauugg ugcaucgaag cgauucuuug ucgauguuuu                                40

<210> SEQ ID NO 814
<211> LENGTH: 40
<212> TYPE: RNA
<213> ORGANISM: Artificial
<220> FEATURE:
<223> OTHER INFORMATION: Aptamer

<400> SEQUENCE: 814
gguaugauug gcgccgguau uauuccuuuu acaggaucug                                40

<210> SEQ ID NO 815
<211> LENGTH: 40
<212> TYPE: RNA
<213> ORGANISM: Artificial
<220> FEATURE:
<223> OTHER INFORMATION: Aptamer

<400> SEQUENCE: 815
ggucauuggc gaucuugaaa ugaauuuccu cgaguuagug                                40

<210> SEQ ID NO 816
<211> LENGTH: 40
<212> TYPE: RNA
<213> ORGANISM: Artificial
<220> FEATURE:
<223> OTHER INFORMATION: Aptamer

<400> SEQUENCE: 816
ggucuauugg cuccaugggu uucuucagcu aaugcggaug                                40

<210> SEQ ID NO 817
<211> LENGTH: 40
<212> TYPE: RNA
<213> ORGANISM: Artificial
<220> FEATURE:
<223> OTHER INFORMATION: Aptamer

<400> SEQUENCE: 817
ggugaacugg cccuacgcgc ucucgcagug cgaacgguaa                                40

<210> SEQ ID NO 818
<211> LENGTH: 40
<212> TYPE: RNA
<213> ORGANISM: Artificial
<220> FEATURE:
<223> OTHER INFORMATION: Aptamer

<400> SEQUENCE: 818
ggugaauugg ugccucaucc ucucguggga gugaaguuga                                40

<210> SEQ ID NO 819
<211> LENGTH: 40
```

```
<212> TYPE: RNA
<213> ORGANISM: Artificial
<220> FEATURE:
<223> OTHER INFORMATION: Aptamer

<400> SEQUENCE: 819
ggugcacugg cucugcguau cuucugcugc cgcacgaaug                40

<210> SEQ ID NO 820
<211> LENGTH: 40
<212> TYPE: RNA
<213> ORGANISM: Artificial
<220> FEATURE:
<223> OTHER INFORMATION: Aptamer

<400> SEQUENCE: 820
ggugcauugg uucagucgug cgguugcugu gcgcugggua                40

<210> SEQ ID NO 821
<211> LENGTH: 40
<212> TYPE: RNA
<213> ORGANISM: Artificial
<220> FEATURE:
<223> OTHER INFORMATION: Aptamer

<400> SEQUENCE: 821
gguggacugg uggcgaggcu cgcgcuucac uuuccgcuua                40

<210> SEQ ID NO 822
<211> LENGTH: 40
<212> TYPE: RNA
<213> ORGANISM: Artificial
<220> FEATURE:
<223> OTHER INFORMATION: Aptamer

<400> SEQUENCE: 822
gguguacugg cacuacugaa auuucauuug aauaggucug                40

<210> SEQ ID NO 823
<211> LENGTH: 41
<212> TYPE: RNA
<213> ORGANISM: Artificial
<220> FEATURE:
<223> OTHER INFORMATION: Aptamer

<400> SEQUENCE: 823
gguguacugg cacuacugaa auuucauuuu gaguaggucu g              41

<210> SEQ ID NO 824
<211> LENGTH: 41
<212> TYPE: RNA
<213> ORGANISM: Artificial
<220> FEATURE:
<223> OTHER INFORMATION: Aptamer

<400> SEQUENCE: 824
gguguacugg cacuacugaa auuuucauuu gaguaggucu g              41

<210> SEQ ID NO 825
<211> LENGTH: 40
<212> TYPE: RNA
<213> ORGANISM: Artificial
<220> FEATURE:
<223> OTHER INFORMATION: Aptamer

<400> SEQUENCE: 825
```

```
ggguguacugg cgagcacuau cuaauuagau gccguuuug                    40

<210> SEQ ID NO 826
<211> LENGTH: 40
<212> TYPE: RNA
<213> ORGANISM: Artificial
<220> FEATURE:
<223> OTHER INFORMATION: Aptamer

<400> SEQUENCE: 826
gguguacugg cuauaauacg uaauguuuac cuuuuagaug                   40

<210> SEQ ID NO 827
<211> LENGTH: 40
<212> TYPE: RNA
<213> ORGANISM: Artificial
<220> FEATURE:
<223> OTHER INFORMATION: Aptamer

<400> SEQUENCE: 827
gguguacugg cuauuacacu uuuuguaga uuguaaugug                    40

<210> SEQ ID NO 828
<211> LENGTH: 39
<212> TYPE: RNA
<213> ORGANISM: Artificial
<220> FEATURE:
<223> OTHER INFORMATION: Aptamer

<400> SEQUENCE: 828
gguguacugg ucauuacaa uuuaugcugu uggauguca                     39

<210> SEQ ID NO 829
<211> LENGTH: 40
<212> TYPE: RNA
<213> ORGANISM: Artificial
<220> FEATURE:
<223> OTHER INFORMATION: Aptamer

<400> SEQUENCE: 829
gguguacugg ucugcguacu uccuggugc uucgcuuaua                    40

<210> SEQ ID NO 830
<211> LENGTH: 40
<212> TYPE: RNA
<213> ORGANISM: Artificial
<220> FEATURE:
<223> OTHER INFORMATION: Aptamer

<400> SEQUENCE: 830
gguguacugg ugauuuccac uucacaugag guaguuugua                   40

<210> SEQ ID NO 831
<211> LENGTH: 40
<212> TYPE: RNA
<213> ORGANISM: Artificial
<220> FEATURE:
<223> OTHER INFORMATION: Aptamer

<400> SEQUENCE: 831
gguguacugg uguugcggac auugccucgu cggcaucgaa                   40

<210> SEQ ID NO 832
<211> LENGTH: 40
<212> TYPE: RNA
<213> ORGANISM: Artificial
```

```
<220> FEATURE:
<223> OTHER INFORMATION: Aptamer

<400> SEQUENCE: 832
gguguacugg uugccguuuu ggugcccuuc gaucggcuua                              40

<210> SEQ ID NO 833
<211> LENGTH: 40
<212> TYPE: RNA
<213> ORGANISM: Artificial
<220> FEATURE:
<223> OTHER INFORMATION: Aptamer

<400> SEQUENCE: 833
gguguauugg ccaugaaauu uuacuuaguu ugauucacgg                              40

<210> SEQ ID NO 834
<211> LENGTH: 40
<212> TYPE: RNA
<213> ORGANISM: Artificial
<220> FEATURE:
<223> OTHER INFORMATION: Aptamer

<400> SEQUENCE: 834
gguguauugg cgcuuguuca cugcccgcug gacuggucug                              40

<210> SEQ ID NO 835
<211> LENGTH: 40
<212> TYPE: RNA
<213> ORGANISM: Artificial
<220> FEATURE:
<223> OTHER INFORMATION: Aptamer

<400> SEQUENCE: 835
gguguauugg cuuaccgugc uuguuacuuc uugauagaug                              40

<210> SEQ ID NO 836
<211> LENGTH: 40
<212> TYPE: RNA
<213> ORGANISM: Artificial
<220> FEATURE:
<223> OTHER INFORMATION: Aptamer

<400> SEQUENCE: 836
gguguauugg cuuuuguggu augagagccu accuucggag                              40

<210> SEQ ID NO 837
<211> LENGTH: 40
<212> TYPE: RNA
<213> ORGANISM: Artificial
<220> FEATURE:
<223> OTHER INFORMATION: Aptamer

<400> SEQUENCE: 837
gguguauugg uaccucgcaa ccucggaugu uucagaguua                              40

<210> SEQ ID NO 838
<211> LENGTH: 40
<212> TYPE: RNA
<213> ORGANISM: Artificial
<220> FEATURE:
<223> OTHER INFORMATION: Aptamer

<400> SEQUENCE: 838
gguguauugg ugcuaugacc uuuccuuga gucguauaua                               40
```

<210> SEQ ID NO 839
<211> LENGTH: 40
<212> TYPE: RNA
<213> ORGANISM: Artificial
<220> FEATURE:
<223> OTHER INFORMATION: Aptamer

<400> SEQUENCE: 839
gguguauugg uuagcagauu cguuccucua uuugcugaga                              40

<210> SEQ ID NO 840
<211> LENGTH: 40
<212> TYPE: RNA
<213> ORGANISM: Artificial
<220> FEATURE:
<223> OTHER INFORMATION: Aptamer

<400> SEQUENCE: 840
gguguauugg uucgacucgu ucuccuugcg agcucaaaua                              40

<210> SEQ ID NO 841
<211> LENGTH: 40
<212> TYPE: RNA
<213> ORGANISM: Artificial
<220> FEATURE:
<223> OTHER INFORMATION: Aptamer

<400> SEQUENCE: 841
gguuauuggc gcccucgaac caaaauggau gccgggaaug                              40

<210> SEQ ID NO 842
<211> LENGTH: 40
<212> TYPE: RNA
<213> ORGANISM: Artificial
<220> FEATURE:
<223> OTHER INFORMATION: Aptamer

<400> SEQUENCE: 842
gguuauuggc ugggacacgc ucaugcucga ucuuucaaug                              40

<210> SEQ ID NO 843
<211> LENGTH: 40
<212> TYPE: RNA
<213> ORGANISM: Artificial
<220> FEATURE:
<223> OTHER INFORMATION: Aptamer

<400> SEQUENCE: 843
gguuauuggu acguuccgau agacugccuc ggaccgugug                              40

<210> SEQ ID NO 844
<211> LENGTH: 40
<212> TYPE: RNA
<213> ORGANISM: Artificial
<220> FEATURE:
<223> OTHER INFORMATION: Aptamer

<400> SEQUENCE: 844
gguuauuggu cuccgguaaa ugaucuuuau cgugcacaua                              40

<210> SEQ ID NO 845
<211> LENGTH: 40
<212> TYPE: RNA
<213> ORGANISM: Artificial
<220> FEATURE:
<223> OTHER INFORMATION: Aptamer -continued

<400> SEQUENCE: 845
gguuauuggu gccuuuggaa uguauuccc gaucgaucua                    40

<210> SEQ ID NO 846
<211> LENGTH: 40
<212> TYPE: RNA
<213> ORGANISM: Artificial
<220> FEATURE:
<223> OTHER INFORMATION: Aptamer

<400> SEQUENCE: 846
gguugauugg cccccgugcu cuuaaggauc ccuggguaug                   40

<210> SEQ ID NO 847
<211> LENGTH: 40
<212> TYPE: RNA
<213> ORGANISM: Artificial
<220> FEATURE:
<223> OTHER INFORMATION: Aptamer

<400> SEQUENCE: 847
gguugauugg cgcaauccuc gcuguuuga ugaucgcaug                    40

<210> SEQ ID NO 848
<211> LENGTH: 40
<212> TYPE: RNA
<213> ORGANISM: Artificial
<220> FEATURE:
<223> OTHER INFORMATION: Aptamer

<400> SEQUENCE: 848
gguugauugg cucugcuaau ggcucuguac ugggagaaug                   40

<210> SEQ ID NO 849
<211> LENGTH: 40
<212> TYPE: RNA
<213> ORGANISM: Artificial
<220> FEATURE:
<223> OTHER INFORMATION: Aptamer

<400> SEQUENCE: 849
gguuuaauug gcggccuccgg uauacagugu cguggcaaug                  40

<210> SEQ ID NO 850
<211> LENGTH: 40
<212> TYPE: RNA
<213> ORGANISM: Artificial
<220> FEATURE:
<223> OTHER INFORMATION: Aptamer

<400> SEQUENCE: 850
gguuuauugg cucuugagau cccugccugg ucccagaaag                   40

<210> SEQ ID NO 851
<211> LENGTH: 40
<212> TYPE: RNA
<213> ORGANISM: Artificial
<220> FEATURE:
<223> OTHER INFORMATION: Aptamer

<400> SEQUENCE: 851
gguuuauugg uagcucucgu uugccuuugc agagcaugua                   40

<210> SEQ ID NO 852

```
<211> LENGTH: 40
<212> TYPE: RNA
<213> ORGANISM: Artificial
<220> FEATURE:
<223> OTHER INFORMATION: Aptamer

<400> SEQUENCE: 852
gguuuauugg ucaugacuuu cuuucgcgug gucaaaguuu                    40

<210> SEQ ID NO 853
<211> LENGTH: 40
<212> TYPE: RNA
<213> ORGANISM: Artificial
<220> FEATURE:
<223> OTHER INFORMATION: Aptamer

<400> SEQUENCE: 853
gguuuauugg ucggguucca ugcgauuucg uggccugucu                    40

<210> SEQ ID NO 854
<211> LENGTH: 40
<212> TYPE: RNA
<213> ORGANISM: Artificial
<220> FEATURE:
<223> OTHER INFORMATION: Aptamer

<400> SEQUENCE: 854
gguuuauugg ucuacugucc cauuguuugg aaaguaguua                    40

<210> SEQ ID NO 855
<211> LENGTH: 40
<212> TYPE: RNA
<213> ORGANISM: Artificial
<220> FEATURE:
<223> OTHER INFORMATION: Aptamer

<400> SEQUENCE: 855
gguuuauugg uugacuaucu gcguugagca cauauguaua                    40

<210> SEQ ID NO 856
<211> LENGTH: 39
<212> TYPE: RNA
<213> ORGANISM: Artificial
<220> FEATURE:
<223> OTHER INFORMATION: Aptamer

<400> SEQUENCE: 856
gguuuuauug gucggcgggu ucuugccgcc cgaucgcga                     39

<210> SEQ ID NO 857
<211> LENGTH: 40
<212> TYPE: RNA
<213> ORGANISM: Artificial
<220> FEATURE:
<223> OTHER INFORMATION: Aptamer

<400> SEQUENCE: 857
aaaacgucgu ccuagguuua uuggcguucu ucggcuagug                    40

<210> SEQ ID NO 858
<211> LENGTH: 40
<212> TYPE: RNA
<213> ORGANISM: Artificial
<220> FEATURE:
<223> OTHER INFORMATION: Aptamer

<400> SEQUENCE: 858
```

-continued

```
aaagagacug gcucccaggu guauuggucu gcgaucgcaa                              40

<210> SEQ ID NO 859
<211> LENGTH: 40
<212> TYPE: RNA
<213> ORGANISM: Artificial
<220> FEATURE:
<223> OTHER INFORMATION: Aptamer

<400> SEQUENCE: 859
aacaaugggu uuauugguuu uggacucucg guucauuaua                              40

<210> SEQ ID NO 860
<211> LENGTH: 40
<212> TYPE: RNA
<213> ORGANISM: Artificial
<220> FEATURE:
<223> OTHER INFORMATION: Aptamer

<400> SEQUENCE: 860
aaccguagac uccggguuaa uuggcgccug cagagauaug                              40

<210> SEQ ID NO 861
<211> LENGTH: 40
<212> TYPE: RNA
<213> ORGANISM: Artificial
<220> FEATURE:
<223> OTHER INFORMATION: Aptamer

<400> SEQUENCE: 861
aacgacuggu uuacuggcuc cguuauucgc uccgugaaug                              40

<210> SEQ ID NO 862
<211> LENGTH: 40
<212> TYPE: RNA
<213> ORGANISM: Artificial
<220> FEATURE:
<223> OTHER INFORMATION: Aptamer

<400> SEQUENCE: 862
aacguacauu cgcaggugau uggcggcaau gcgggcaaug                              40

<210> SEQ ID NO 863
<211> LENGTH: 40
<212> TYPE: RNA
<213> ORGANISM: Artificial
<220> FEATURE:
<223> OTHER INFORMATION: Aptamer

<400> SEQUENCE: 863
aacuccucgc ugccguguac ugguaauugg cuucuggaug                              40

<210> SEQ ID NO 864
<211> LENGTH: 40
<212> TYPE: RNA
<213> ORGANISM: Artificial
<220> FEATURE:
<223> OTHER INFORMATION: Aptamer

<400> SEQUENCE: 864
aacucugggu guauggguau gcguuuauca cuaaaugcua                              40

<210> SEQ ID NO 865
<211> LENGTH: 38
<212> TYPE: RNA
```

-continued

```
<213> ORGANISM: Artificial
<220> FEATURE:
<223> OTHER INFORMATION: Aptamer

<400> SEQUENCE: 865
aacgguguau uggcuucag auuuuuuucu gacguuga                    38

<210> SEQ ID NO 866
<211> LENGTH: 43
<212> TYPE: RNA
<213> ORGANISM: Artificial
<220> FEATURE:
<223> OTHER INFORMATION: Aptamer

<400> SEQUENCE: 866
aagcucguuc aaacauguca ggguuauugg uccauuagcg uuu              43

<210> SEQ ID NO 867
<211> LENGTH: 38
<212> TYPE: RNA
<213> ORGANISM: Artificial
<220> FEATURE:
<223> OTHER INFORMATION: Aptamer

<400> SEQUENCE: 867
aauccggguc uauugguaau cgcuuuuuaa gggauuua                    38

<210> SEQ ID NO 868
<211> LENGTH: 40
<212> TYPE: RNA
<213> ORGANISM: Artificial
<220> FEATURE:
<223> OTHER INFORMATION: Aptamer

<400> SEQUENCE: 868
aauccuguug ucucaggugg acgguugua uucuuacgga                   40

<210> SEQ ID NO 869
<211> LENGTH: 40
<212> TYPE: RNA
<213> ORGANISM: Artificial
<220> FEATURE:
<223> OTHER INFORMATION: Aptamer

<400> SEQUENCE: 869
aaugacguuu agguuauugg ucuugccuag cgcuaagugu                  40

<210> SEQ ID NO 870
<211> LENGTH: 40
<212> TYPE: RNA
<213> ORGANISM: Artificial
<220> FEATURE:
<223> OTHER INFORMATION: Aptamer

<400> SEQUENCE: 870
aagguucauu ggugcaaaga accgaaauug accuuugcua                  40

<210> SEQ ID NO 871
<211> LENGTH: 39
<212> TYPE: RNA
<213> ORGANISM: Artificial
<220> FEATURE:
<223> OTHER INFORMATION: Aptamer

<400> SEQUENCE: 871
accaggugua uuggucagau aguucucagg gcuauguua                   39
```

<210> SEQ ID NO 872
<211> LENGTH: 40
<212> TYPE: RNA
<213> ORGANISM: Artificial
<220> FEATURE:
<223> OTHER INFORMATION: Aptamer

<400> SEQUENCE: 872
acccuuacau ggcuagguuc auuggugcca ucucugguua                                40

<210> SEQ ID NO 873
<211> LENGTH: 41
<212> TYPE: RNA
<213> ORGANISM: Artificial
<220> FEATURE:
<223> OTHER INFORMATION: Aptamer

<400> SEQUENCE: 873
accuauucuu ccuccgggu u auuggucuug uuuuuuuguu u                              41

<210> SEQ ID NO 874
<211> LENGTH: 40
<212> TYPE: RNA
<213> ORGANISM: Artificial
<220> FEATURE:
<223> OTHER INFORMATION: Aptamer

<400> SEQUENCE: 874
acgcccucca gguaauuggu guuagguuca uaccuauuua                                40

<210> SEQ ID NO 875
<211> LENGTH: 40
<212> TYPE: RNA
<213> ORGANISM: Artificial
<220> FEATURE:
<223> OTHER INFORMATION: Aptamer

<400> SEQUENCE: 875
acuaccgggu guacugguca cguucauuag aacgagcaga                                40

<210> SEQ ID NO 876
<211> LENGTH: 40
<212> TYPE: RNA
<213> ORGANISM: Artificial
<220> FEATURE:
<223> OTHER INFORMATION: Aptamer

<400> SEQUENCE: 876
acucuaugcc cuggguaaau uggugucgaa ucucgucuua                                40

<210> SEQ ID NO 877
<211> LENGTH: 40
<212> TYPE: RNA
<213> ORGANISM: Artificial
<220> FEATURE:
<223> OTHER INFORMATION: Aptamer

<400> SEQUENCE: 877
acuguucgua guagguaauu ggcuggccuc gcgucguuug                                40

<210> SEQ ID NO 878
<211> LENGTH: 40
<212> TYPE: RNA
<213> ORGANISM: Artificial
<220> FEATURE:

```
<223> OTHER INFORMATION: Aptamer

<400> SEQUENCE: 878
acuguugacu cuccaggugu auuggiuguug guucuuugug          40

<210> SEQ ID NO 879
<211> LENGTH: 40
<212> TYPE: RNA
<213> ORGANISM: Artificial
<220> FEATURE:
<223> OTHER INFORMATION: Aptamer

<400> SEQUENCE: 879
acuugaaagg gugaauuggu cuugugucga ucgcaaguaa          40

<210> SEQ ID NO 880
<211> LENGTH: 40
<212> TYPE: RNA
<213> ORGANISM: Artificial
<220> FEATURE:
<223> OTHER INFORMATION: Aptamer

<400> SEQUENCE: 880 acuuguucg uucucguucc uggguguauu gguauuagua           40

<210> SEQ ID NO 881
<211> LENGTH: 40
<212> TYPE: RNA
<213> ORGANISM: Artificial
<220> FEATURE:
<223> OTHER INFORMATION: Aptamer

<400> SEQUENCE: 881
acgguuuuac uggcgauuga ucuggccucg cucuuuagug          40

<210> SEQ ID NO 882
<211> LENGTH: 40
<212> TYPE: RNA
<213> ORGANISM: Artificial
<220> FEATURE:
<223> OTHER INFORMATION: Aptamer

<400> SEQUENCE: 882
agacggugua cuggcacuuu acucauugag uagaaauucg          40

<210> SEQ ID NO 883
<211> LENGTH: 40
<212> TYPE: RNA
<213> ORGANISM: Artificial
<220> FEATURE:
<223> OTHER INFORMATION: Aptamer

<400> SEQUENCE: 883
agcgcauguc gggugaauug guaccgcuuu ugacggacua          40

<210> SEQ ID NO 884
<211> LENGTH: 39
<212> TYPE: RNA
<213> ORGANISM: Artificial
<220> FEATURE:
<223> OTHER INFORMATION: Aptamer

<400> SEQUENCE: 884
aguccucugg guguauuggu cgcacccucg ugugaacga           39
```

```
<210> SEQ ID NO 885
<211> LENGTH: 40
<212> TYPE: RNA
<213> ORGANISM: Artificial
<220> FEATURE:
<223> OTHER INFORMATION: Aptamer

<400> SEQUENCE: 885
aucccacuuu gucugcuuuc ggguguauug gccugugggg                                40

<210> SEQ ID NO 886
<211> LENGTH: 40
<212> TYPE: RNA
<213> ORGANISM: Artificial
<220> FEATURE:
<223> OTHER INFORMATION: Aptamer

<400> SEQUENCE: 886
aucguuucaa cgccccggug uacggucuc uucuuuguuu                                 40

<210> SEQ ID NO 887
<211> LENGTH: 40
<212> TYPE: RNA
<213> ORGANISM: Artificial
<220> FEATURE:
<223> OTHER INFORMATION: Aptamer

<400> SEQUENCE: 887
aucuccuuuc ugguauauug gcuuaucccg ucgauaaaug                                40

<210> SEQ ID NO 888
<211> LENGTH: 40
<212> TYPE: RNA
<213> ORGANISM: Artificial
<220> FEATURE:
<223> OTHER INFORMATION: Aptamer

<400> SEQUENCE: 888
aucugcaguu uggguguauu ggcggacauu ucucucuuug                                40

<210> SEQ ID NO 889
<211> LENGTH: 39
<212> TYPE: RNA
<213> ORGANISM: Artificial
<220> FEATURE:
<223> OTHER INFORMATION: Aptamer

<400> SEQUENCE: 889
aucuugguca acuggcgcgc uuggagacuc ggugaucug                                 39

<210> SEQ ID NO 890
<211> LENGTH: 40
<212> TYPE: RNA
<213> ORGANISM: Artificial
<220> FEATURE:
<223> OTHER INFORMATION: Aptamer

<400> SEQUENCE: 890
augacucguc ucugguauau uggucccguu aaucggugug                                40

<210> SEQ ID NO 891
<211> LENGTH: 40
<212> TYPE: RNA
<213> ORGANISM: Artificial
<220> FEATURE:
<223> OTHER INFORMATION: Aptamer
```

```
<400> SEQUENCE: 891
augcuauugu gcuccuccgg guuuuauugg cccuugggug                              40

<210> SEQ ID NO 892
<211> LENGTH: 40
<212> TYPE: RNA
<213> ORGANISM: Artificial
<220> FEATURE:
<223> OTHER INFORMATION: Aptamer

<400> SEQUENCE: 892
augcugcguc caguagguuu auuggcggcu augcgucuug                              40

<210> SEQ ID NO 893
<211> LENGTH: 40
<212> TYPE: RNA
<213> ORGANISM: Artificial
<220> FEATURE:
<223> OTHER INFORMATION: Aptamer

<400> SEQUENCE: 893
auggguugac uggcuacuug cuggaccgua guaaguaaug                              40

<210> SEQ ID NO 894
<211> LENGTH: 40
<212> TYPE: RNA
<213> ORGANISM: Artificial
<220> FEATURE:
<223> OTHER INFORMATION: Aptamer

<400> SEQUENCE: 894
auuaggucca uuggcgccgu uaaacacguu ucgcgggcug                              40

<210> SEQ ID NO 895
<211> LENGTH: 40
<212> TYPE: RNA
<213> ORGANISM: Artificial
<220> FEATURE:
<223> OTHER INFORMATION: Aptamer

<400> SEQUENCE: 895
auucacuacc gguaauuggc cuccuuugcu gugggaaaug                              40

<210> SEQ ID NO 896
<211> LENGTH: 41
<212> TYPE: RNA
<213> ORGANISM: Artificial
<220> FEATURE:
<223> OTHER INFORMATION: Aptamer

<400> SEQUENCE: 896
auucucaccu gggugauugg cgcauuuucg uuucaugaau g                            41

<210> SEQ ID NO 897
<211> LENGTH: 40
<212> TYPE: RNA
<213> ORGANISM: Artificial
<220> FEATURE:
<223> OTHER INFORMATION: Aptamer

<400> SEQUENCE: 897
auucuguucu gucucuccgg gucuacuggc gcuaugaaug                              40

<210> SEQ ID NO 898
<211> LENGTH: 40
```

```
<212> TYPE: RNA
<213> ORGANISM: Artificial
<220> FEATURE:
<223> OTHER INFORMATION: Aptamer

<400> SEQUENCE: 898
auuucuucaa cuucuguacc agguuuauug gccuuuguuu                              40

<210> SEQ ID NO 899
<211> LENGTH: 40
<212> TYPE: RNA
<213> ORGANISM: Artificial
<220> FEATURE:
<223> OTHER INFORMATION: Aptamer

<400> SEQUENCE: 899
auuugugcug cuaaggugua cuggucuuuc cuuuaaguua                              40

<210> SEQ ID NO 900
<211> LENGTH: 39
<212> TYPE: RNA
<213> ORGANISM: Artificial
<220> FEATURE:
<223> OTHER INFORMATION: Aptamer

<400> SEQUENCE: 900
auuuucgaaa aucuuguauc uggguaauug gucuagugu                               39

<210> SEQ ID NO 901
<211> LENGTH: 40
<212> TYPE: RNA
<213> ORGANISM: Artificial
<220> FEATURE:
<223> OTHER INFORMATION: Aptamer

<400> SEQUENCE: 901
auuuuuggca gcagguuauu ggccccggag accugguaug                              40

<210> SEQ ID NO 902
<211> LENGTH: 40
<212> TYPE: RNA
<213> ORGANISM: Artificial
<220> FEATURE:
<223> OTHER INFORMATION: Aptamer

<400> SEQUENCE: 902
agguaaauug gcuccauucg auuuacucgc gugcugaaug                              40

<210> SEQ ID NO 903
<211> LENGTH: 40
<212> TYPE: RNA
<213> ORGANISM: Artificial
<220> FEATURE:
<223> OTHER INFORMATION: Aptamer

<400> SEQUENCE: 903
agguacuacu ggcgcacagg uuccaccgc gaguugaaug                               40

<210> SEQ ID NO 904
<211> LENGTH: 40
<212> TYPE: RNA
<213> ORGANISM: Artificial
<220> FEATURE:
<223> OTHER INFORMATION: Aptamer

<400> SEQUENCE: 904
```

```
agguauauug gcggcauacg guugucuauc ggugugcuug                              40

<210> SEQ ID NO 905
<211> LENGTH: 40
<212> TYPE: RNA
<213> ORGANISM: Artificial
<220> FEATURE:
<223> OTHER INFORMATION: Aptamer

<400> SEQUENCE: 905
agguauauug guguggacga aaccuagguc gaguuaauua                              40

<210> SEQ ID NO 906
<211> LENGTH: 38
<212> TYPE: RNA
<213> ORGANISM: Artificial
<220> FEATURE:
<223> OTHER INFORMATION: Aptamer

<400> SEQUENCE: 906
aggugaauug gcuuuugcgc uauuuuggu gcuuaggg                                 38

<210> SEQ ID NO 907
<211> LENGTH: 40
<212> TYPE: RNA
<213> ORGANISM: Artificial
<220> FEATURE:
<223> OTHER INFORMATION: Aptamer

<400> SEQUENCE: 907
aggugaauug gcuuuugcgc uauuuuuug gugcuuaggg                               40

<210> SEQ ID NO 908
<211> LENGTH: 40
<212> TYPE: RNA
<213> ORGANISM: Artificial
<220> FEATURE:
<223> OTHER INFORMATION: Aptamer

<400> SEQUENCE: 908
agguguacug gccggugcga ccgacucgac gcacuagaug                              40

<210> SEQ ID NO 909
<211> LENGTH: 40
<212> TYPE: RNA
<213> ORGANISM: Artificial
<220> FEATURE:
<223> OTHER INFORMATION: Aptamer

<400> SEQUENCE: 909
agguguauug gcgcucgaug cggcucuuga ccaccguuug                              40

<210> SEQ ID NO 910
<211> LENGTH: 40
<212> TYPE: RNA
<213> ORGANISM: Artificial
<220> FEATURE:
<223> OTHER INFORMATION: Aptamer

<400> SEQUENCE: 910
agguguauug guccuuugac auugccugug caauucagga                              40

<210> SEQ ID NO 911
<211> LENGTH: 40
<212> TYPE: RNA
<213> ORGANISM: Artificial
```

```
<220> FEATURE:
<223> OTHER INFORMATION: Aptamer

<400> SEQUENCE: 911
agguguauug guuugaaccu uuggucucgc cguaggucua                                40

<210> SEQ ID NO 912
<211> LENGTH: 39
<212> TYPE: RNA
<213> ORGANISM: Artificial
<220> FEATURE:
<223> OTHER INFORMATION: Aptamer

<400> SEQUENCE: 912
agguuaauug gucucucgua uaaagacgua cggcuguua                                 39

<210> SEQ ID NO 913
<211> LENGTH: 40
<212> TYPE: RNA
<213> ORGANISM: Artificial
<220> FEATURE:
<223> OTHER INFORMATION: Aptamer

<400> SEQUENCE: 913
agguuauugg ugguccaacg ugcuuaccau guuuaccgug                                40

<210> SEQ ID NO 914
<211> LENGTH: 40
<212> TYPE: RNA
<213> ORGANISM: Artificial
<220> FEATURE:
<223> OTHER INFORMATION: Aptamer

<400> SEQUENCE: 914
agguucgacu ggcugacuua gcguuaucgc caggccgaug                                40

<210> SEQ ID NO 915
<211> LENGTH: 40
<212> TYPE: RNA
<213> ORGANISM: Artificial
<220> FEATURE:
<223> OTHER INFORMATION: Aptamer

<400> SEQUENCE: 915
agguuuuacu ggcgcauugg acuccacgag accgcgaaug                                40

<210> SEQ ID NO 916
<211> LENGTH: 40
<212> TYPE: RNA
<213> ORGANISM: Artificial
<220> FEATURE:
<223> OTHER INFORMATION: Aptamer

<400> SEQUENCE: 916
agguuuuacu ggguggucg caccuucucg cguacauuua                                 40

<210> SEQ ID NO 917
<211> LENGTH: 40
<212> TYPE: RNA
<213> ORGANISM: Artificial
<220> FEATURE:
<223> OTHER INFORMATION: Aptamer

<400> SEQUENCE: 917
caaggccccg guuuauuggc gcaguuauuu uacugaacug                                40
```

```
<210> SEQ ID NO 918
<211> LENGTH: 40
<212> TYPE: RNA
<213> ORGANISM: Artificial
<220> FEATURE:
<223> OTHER INFORMATION: Aptamer

<400> SEQUENCE: 918
caagucacau ccuucgguua uuggcgauuc accgaacaug                                  40

<210> SEQ ID NO 919
<211> LENGTH: 40
<212> TYPE: RNA
<213> ORGANISM: Artificial
<220> FEATURE:
<223> OTHER INFORMATION: Aptamer

<400> SEQUENCE: 919
cacaugcucg gguuuacugg uccucgcucg gcgaauguuu                                  40

<210> SEQ ID NO 920
<211> LENGTH: 40
<212> TYPE: RNA
<213> ORGANISM: Artificial
<220> FEATURE:
<223> OTHER INFORMATION: Aptamer

<400> SEQUENCE: 920
cacgauggcc uagauccgg guuaauuggc cuagaaggug                                   40

<210> SEQ ID NO 921
<211> LENGTH: 40
<212> TYPE: RNA
<213> ORGANISM: Artificial
<220> FEATURE:
<223> OTHER INFORMATION: Aptamer

<400> SEQUENCE: 921
cacguguuug uugagguuua uuggcucaug cuucggaaug                                  40

<210> SEQ ID NO 922
<211> LENGTH: 40
<212> TYPE: RNA
<213> ORGANISM: Artificial
<220> FEATURE:
<223> OTHER INFORMATION: Aptamer

<400> SEQUENCE: 922
cacuauacgu cccgguuauu ggcugaccuu uggucgcaug                                  40

<210> SEQ ID NO 923
<211> LENGTH: 40
<212> TYPE: RNA
<213> ORGANISM: Artificial
<220> FEATURE:
<223> OTHER INFORMATION: Aptamer

<400> SEQUENCE: 923
cacucuaggu guauuggugu aucuuacucu guacuggaca                                  40

<210> SEQ ID NO 924
<211> LENGTH: 40
<212> TYPE: RNA
<213> ORGANISM: Artificial
<220> FEATURE:
<223> OTHER INFORMATION: Aptamer
```

```
<400> SEQUENCE: 924
cauccuacug guuauuggcc guggacaauu ucuucaggug                                40

<210> SEQ ID NO 925
<211> LENGTH: 40
<212> TYPE: RNA
<213> ORGANISM: Artificial
<220> FEATURE:
<223> OTHER INFORMATION: Aptamer

<400> SEQUENCE: 925
cauugagaag caucgccccg guguuauugg ccucugggug                                40

<210> SEQ ID NO 926
<211> LENGTH: 40
<212> TYPE: RNA
<213> ORGANISM: Artificial
<220> FEATURE:
<223> OTHER INFORMATION: Aptamer

<400> SEQUENCE: 926
caggugaauu ggucaaucug gcccgcuccg gauucggaua                                40

<210> SEQ ID NO 927
<211> LENGTH: 40
<212> TYPE: RNA
<213> ORGANISM: Artificial
<220> FEATURE:
<223> OTHER INFORMATION: Aptamer

<400> SEQUENCE: 927
caggugcaau uggcuggccu ugauuccuu cggacugaug                                 40

<210> SEQ ID NO 928
<211> LENGTH: 40
<212> TYPE: RNA
<213> ORGANISM: Artificial
<220> FEATURE:
<223> OTHER INFORMATION: Aptamer

<400> SEQUENCE: 928
cagguguauu gguuccguau aucgaucuug ggauaugguu                                40

<210> SEQ ID NO 929
<211> LENGTH: 40
<212> TYPE: RNA
<213> ORGANISM: Artificial
<220> FEATURE:
<223> OTHER INFORMATION: Aptamer

<400> SEQUENCE: 929
ccaaauuugu ccgguuuauu ggugccguac uaccugguua                                40

<210> SEQ ID NO 930
<211> LENGTH: 39
<212> TYPE: RNA
<213> ORGANISM: Artificial
<220> FEATURE:
<223> OTHER INFORMATION: Aptamer

<400> SEQUENCE: 930
ccagcccguc gguaacuggc gcaauaugua cauugaaug                                 39

<210> SEQ ID NO 931
```

```
<211> LENGTH: 40
<212> TYPE: RNA
<213> ORGANISM: Artificial
<220> FEATURE:
<223> OTHER INFORMATION: Aptamer

<400> SEQUENCE: 931
ccaugcuagu ccgacgucug gguguauugg ccgguuguuu                              40

<210> SEQ ID NO 932
<211> LENGTH: 40
<212> TYPE: RNA
<213> ORGANISM: Artificial
<220> FEATURE:
<223> OTHER INFORMATION: Aptamer

<400> SEQUENCE: 932
ccagguguau uggucuaggc uucuucguuu aagccauaua                              40

<210> SEQ ID NO 933
<211> LENGTH: 40
<212> TYPE: RNA
<213> ORGANISM: Artificial
<220> FEATURE:
<223> OTHER INFORMATION: Aptamer

<400> SEQUENCE: 933
cccaguuccg augauccggg uucauuggcg cggaugaaug                              40

<210> SEQ ID NO 934
<211> LENGTH: 36
<212> TYPE: RNA
<213> ORGANISM: Artificial
<220> FEATURE:
<223> OTHER INFORMATION: Aptamer

<400> SEQUENCE: 934
cccaggugau uggcgaaguu gcguuuaac uugcug                                   36

<210> SEQ ID NO 935
<211> LENGTH: 40
<212> TYPE: RNA
<213> ORGANISM: Artificial
<220> FEATURE:
<223> OTHER INFORMATION: Aptamer

<400> SEQUENCE: 935
ccccagcauu uuuggguuua cggucuucc gcugguguuu                               40

<210> SEQ ID NO 936
<211> LENGTH: 39
<212> TYPE: RNA
<213> ORGANISM: Artificial
<220> FEATURE:
<223> OTHER INFORMATION: Aptamer

<400> SEQUENCE: 936 cccgguuua uuggcuugcc cuaugcugua uaggaucug                                39

<210> SEQ ID NO 937
<211> LENGTH: 40
<212> TYPE: RNA
<213> ORGANISM: Artificial
<220> FEATURE:
<223> OTHER INFORMATION: Aptamer

<400> SEQUENCE: 937
```

```
cccuucacua cgggutauauu ggcugaaguu cgcuccaaug                              40

<210> SEQ ID NO 938
<211> LENGTH: 40
<212> TYPE: RNA
<213> ORGANISM: Artificial
<220> FEATURE:
<223> OTHER INFORMATION: Aptamer

<400> SEQUENCE: 938
ccgacguucg gguguacugg cuggcgaucu gugcuguagu                               40

<210> SEQ ID NO 939
<211> LENGTH: 40
<212> TYPE: RNA
<213> ORGANISM: Artificial
<220> FEATURE:
<223> OTHER INFORMATION: Aptamer

<400> SEQUENCE: 939
ccgcaucugg guuaauuggc ucuuacguca ggaugguaug                               40

<210> SEQ ID NO 940
<211> LENGTH: 39
<212> TYPE: RNA
<213> ORGANISM: Artificial
<220> FEATURE:
<223> OTHER INFORMATION: Aptamer

<400> SEQUENCE: 940
ccgcucgcuc cgguaauugg cuacuagaca cuagugaug                                39

<210> SEQ ID NO 941
<211> LENGTH: 40
<212> TYPE: RNA
<213> ORGANISM: Artificial
<220> FEATURE:
<223> OTHER INFORMATION: Aptamer

<400> SEQUENCE: 941
ccggaugcaa uccaggugua uggucucua acuccugaga                                40

<210> SEQ ID NO 942
<211> LENGTH: 43
<212> TYPE: RNA
<213> ORGANISM: Artificial
<220> FEATURE:
<223> OTHER INFORMATION: Aptamer

<400> SEQUENCE: 942
ccggguuauu ggcacuagga ucguugacu accccuaggu uug                            43

<210> SEQ ID NO 943
<211> LENGTH: 40
<212> TYPE: RNA
<213> ORGANISM: Artificial
<220> FEATURE:
<223> OTHER INFORMATION: Aptamer

<400> SEQUENCE: 943
ccuccagguu gcguguucgg guuuauuggu cucuugcuca                               40

<210> SEQ ID NO 944
<211> LENGTH: 40
<212> TYPE: RNA
```

```
<213> ORGANISM: Artificial
<220> FEATURE:
<223> OTHER INFORMATION: Aptamer

<400> SEQUENCE: 944
ccuccaggua aauuggcucc gccguagcca gguugggaug                    40

<210> SEQ ID NO 945
<211> LENGTH: 40
<212> TYPE: RNA
<213> ORGANISM: Artificial
<220> FEATURE:
<223> OTHER INFORMATION: Aptamer

<400> SEQUENCE: 945
ccucgcacag guguacuggu ugguuccuuu gguacucgga                    40

<210> SEQ ID NO 946
<211> LENGTH: 40
<212> TYPE: RNA
<213> ORGANISM: Artificial
<220> FEATURE:
<223> OTHER INFORMATION: Aptamer

<400> SEQUENCE: 946
ccucguuuua gcgggcaggu aaauuggcgc ccuaggaaug                    40

<210> SEQ ID NO 947
<211> LENGTH: 40
<212> TYPE: RNA
<213> ORGANISM: Artificial
<220> FEATURE:
<223> OTHER INFORMATION: Aptamer

<400> SEQUENCE: 947
ccucuggguu uauugguucc guccugacgg augcgcuaua                    40

<210> SEQ ID NO 948
<211> LENGTH: 38
<212> TYPE: RNA
<213> ORGANISM: Artificial
<220> FEATURE:
<223> OTHER INFORMATION: Aptamer

<400> SEQUENCE: 948
ccugaaugcu ccaggugaau uggccuuuug acucggug                      38

<210> SEQ ID NO 949
<211> LENGTH: 40
<212> TYPE: RNA
<213> ORGANISM: Artificial
<220> FEATURE:
<223> OTHER INFORMATION: Aptamer

<400> SEQUENCE: 949
ccuguuuugu cuagguucau uggcgcuuau ucuuggaaug                    40

<210> SEQ ID NO 950
<211> LENGTH: 40
<212> TYPE: RNA
<213> ORGANISM: Artificial
<220> FEATURE:
<223> OTHER INFORMATION: Aptamer

<400> SEQUENCE: 950
ccuguuuugu cuagguuuau uggcgcuuuu uccuggaaug                    40
```

<210> SEQ ID NO 951
<211> LENGTH: 40
<212> TYPE: RNA
<213> ORGANISM: Artificial
<220> FEATURE:
<223> OTHER INFORMATION: Aptamer

<400> SEQUENCE: 951
ccgguacauu ggcgcaugag ccgcucaugg ucugugaaug            40

<210> SEQ ID NO 952
<211> LENGTH: 40
<212> TYPE: RNA
<213> ORGANISM: Artificial
<220> FEATURE:
<223> OTHER INFORMATION: Aptamer

<400> SEQUENCE: 952
cgaguuuucu ggguguuacu ggcccuuuua ccggguguug            40

<210> SEQ ID NO 953
<211> LENGTH: 31
<212> TYPE: RNA
<213> ORGANISM: Artificial
<220> FEATURE:
<223> OTHER INFORMATION: Aptamer

<400> SEQUENCE: 953
cgcaaacccg guaaauuggc uccaacgaau g            31

<210> SEQ ID NO 954
<211> LENGTH: 30
<212> TYPE: RNA
<213> ORGANISM: Artificial
<220> FEATURE:
<223> OTHER INFORMATION: Aptamer

<400> SEQUENCE: 954
cgcccaggug uauuggugaac ggccucauua            30

<210> SEQ ID NO 955
<211> LENGTH: 40
<212> TYPE: RNA
<213> ORGANISM: Artificial
<220> FEATURE:
<223> OTHER INFORMATION: Aptamer

<400> SEQUENCE: 955
cgcgcgaucc auuuguggu guacugguuu uuucggaaua            40

<210> SEQ ID NO 956
<211> LENGTH: 40
<212> TYPE: RNA
<213> ORGANISM: Artificial
<220> FEATURE:
<223> OTHER INFORMATION: Aptamer

<400> SEQUENCE: 956
cgcguuucgg guguauuggc ugugaccgcg cggucuccag            40

<210> SEQ ID NO 957
<211> LENGTH: 36
<212> TYPE: RNA
<213> ORGANISM: Artificial
<220> FEATURE:

<223> OTHER INFORMATION: Aptamer

<400> SEQUENCE: 957
cgcucaggug aauugguuac guuuucucug agaaug                36

<210> SEQ ID NO 958
<211> LENGTH: 40
<212> TYPE: RNA
<213> ORGANISM: Artificial
<220> FEATURE:
<223> OTHER INFORMATION: Aptamer

<400> SEQUENCE: 958
cggcacuugu ccaacgguuu acuggcccgg cugcgaagug                40

<210> SEQ ID NO 959
<211> LENGTH: 40
<212> TYPE: RNA
<213> ORGANISM: Artificial
<220> FEATURE:
<223> OTHER INFORMATION: Aptamer

<400> SEQUENCE: 959
cggccggguu uacuggugge agaacuaauu gcucuacuua                40

<210> SEQ ID NO 960
<211> LENGTH: 40
<212> TYPE: RNA
<213> ORGANISM: Artificial
<220> FEATURE:
<223> OTHER INFORMATION: Aptamer

<400> SEQUENCE: 960
cggguuaggu uuauuggugc ccagugcucc ggccggucua                40

<210> SEQ ID NO 961
<211> LENGTH: 40
<212> TYPE: RNA
<213> ORGANISM: Artificial
<220> FEATURE:
<223> OTHER INFORMATION: Aptamer

<400> SEQUENCE: 961
cggugcucgg guggauuggu cgcuuuguca uuaaggcgga                40

<210> SEQ ID NO 962
<211> LENGTH: 40
<212> TYPE: RNA
<213> ORGANISM: Artificial
<220> FEATURE:
<223> OTHER INFORMATION: Aptamer

<400> SEQUENCE: 962
cguaaugcgu cuauggugua uuggcucgu uugggaggua                40

<210> SEQ ID NO 963
<211> LENGTH: 40
<212> TYPE: RNA
<213> ORGANISM: Artificial
<220> FEATURE:
<223> OTHER INFORMATION: Aptamer

<400> SEQUENCE: 963
cguaccaagg guuuuauugg cucucugcga gggggaaug                40

```
<210> SEQ ID NO 964
<211> LENGTH: 40
<212> TYPE: RNA
<213> ORGANISM: Artificial
<220> FEATURE:
<223> OTHER INFORMATION: Aptamer

<400> SEQUENCE: 964
cguaccuguc cucggguuua cuggucuugu uaucagggug                                40

<210> SEQ ID NO 965
<211> LENGTH: 40
<212> TYPE: RNA
<213> ORGANISM: Artificial
<220> FEATURE:
<223> OTHER INFORMATION: Aptamer

<400> SEQUENCE: 965
cguacguccu uauacgguga acuggcucug uuucagguua                                40

<210> SEQ ID NO 966
<211> LENGTH: 40
<212> TYPE: RNA
<213> ORGANISM: Artificial
<220> FEATURE:
<223> OTHER INFORMATION: Aptamer

<400> SEQUENCE: 966
cguccgaucg auacugguau auuggcgccc ucguggaaug                                40

<210> SEQ ID NO 967
<211> LENGTH: 40
<212> TYPE: RNA
<213> ORGANISM: Artificial
<220> FEATURE:
<223> OTHER INFORMATION: Aptamer

<400> SEQUENCE: 967
cguccgaugg guguauuggu uaagaauuua gucucguuua                                40

<210> SEQ ID NO 968
<211> LENGTH: 40
<212> TYPE: RNA
<213> ORGANISM: Artificial
<220> FEATURE:
<223> OTHER INFORMATION: Aptamer

<400> SEQUENCE: 968
cgucucaauu ugguucuggg uguacuggcu gaaaaaaucg                                40

<210> SEQ ID NO 969
<211> LENGTH: 40
<212> TYPE: RNA
<213> ORGANISM: Artificial
<220> FEATURE:
<223> OTHER INFORMATION: Aptamer

<400> SEQUENCE: 969
cgucuucugu ucuaaggucc auuggcuccu uuccggcgug                                40

<210> SEQ ID NO 970
<211> LENGTH: 39
<212> TYPE: RNA
<213> ORGANISM: Artificial
<220> FEATURE:
<223> OTHER INFORMATION: Aptamer
```

<400> SEQUENCE: 970
cgucuugcgg gugaauuggc ucuggcuuag aacaguaug                        39

<210> SEQ ID NO 971
<211> LENGTH: 40
<212> TYPE: RNA
<213> ORGANISM: Artificial
<220> FEATURE:
<223> OTHER INFORMATION: Aptamer

<400> SEQUENCE: 971
cgucuuuacu cggguuuacu ggcacaauuu acuuuggaug                       40

<210> SEQ ID NO 972
<211> LENGTH: 40
<212> TYPE: RNA
<213> ORGANISM: Artificial
<220> FEATURE:
<223> OTHER INFORMATION: Aptamer

<400> SEQUENCE: 972
cgugccugag uuggacuuca gguguauugg cgcgcggcug                       40

<210> SEQ ID NO 973
<211> LENGTH: 40
<212> TYPE: RNA
<213> ORGANISM: Artificial
<220> FEATURE:
<223> OTHER INFORMATION: Aptamer

<400> SEQUENCE: 973
cguuuccggg ugaauuggcu cguuuugaau ugcaucgaug                       40

<210> SEQ ID NO 974
<211> LENGTH: 40
<212> TYPE: RNA
<213> ORGANISM: Artificial
<220> FEATURE:
<223> OTHER INFORMATION: Aptamer

<400> SEQUENCE: 974
cguuugaaag gugaauuggu cuuggacucc gcugaccgga                       40

<210> SEQ ID NO 975
<211> LENGTH: 40
<212> TYPE: RNA
<213> ORGANISM: Artificial
<220> FEATURE:
<223> OTHER INFORMATION: Aptamer

<400> SEQUENCE: 975
cguuuugguu uauuggcucu caauucccgc guugaaaagc                       40

<210> SEQ ID NO 976
<211> LENGTH: 40
<212> TYPE: RNA
<213> ORGANISM: Artificial
<220> FEATURE:
<223> OTHER INFORMATION: Aptamer

<400> SEQUENCE: 976
cggguggacu ggucaccacc ggcucgaucu gguggagaga                       40

<210> SEQ ID NO 977
<211> LENGTH: 40

<212> TYPE: RNA
<213> ORGANISM: Artificial
<220> FEATURE:
<223> OTHER INFORMATION: Aptamer

<400> SEQUENCE: 977
cggguguauu gguuucugg ugcgaguucc ccagauuaaa                40

<210> SEQ ID NO 978
<211> LENGTH: 40
<212> TYPE: RNA
<213> ORGANISM: Artificial
<220> FEATURE:
<223> OTHER INFORMATION: Aptamer

<400> SEQUENCE: 978
cuacagcuag guguauuggu cgcccaaccu uuugugucga                40

<210> SEQ ID NO 979
<211> LENGTH: 40
<212> TYPE: RNA
<213> ORGANISM: Artificial
<220> FEATURE:
<223> OTHER INFORMATION: Aptamer

<400> SEQUENCE: 979
cuacauguuc ccgguguauu ggcucucaua ugcugugcag                40

<210> SEQ ID NO 980
<211> LENGTH: 40
<212> TYPE: RNA
<213> ORGANISM: Artificial
<220> FEATURE:
<223> OTHER INFORMATION: Aptamer

<400> SEQUENCE: 980
cuaguucugc acacgguuau uggcggccua gggguaccug                40

<210> SEQ ID NO 981
<211> LENGTH: 40
<212> TYPE: RNA
<213> ORGANISM: Artificial
<220> FEATURE:
<223> OTHER INFORMATION: Aptamer

<400> SEQUENCE: 981
cuauugcaug uccgaccucg gguuauauug gucaaugucu                40

<210> SEQ ID NO 982
<211> LENGTH: 40
<212> TYPE: RNA
<213> ORGANISM: Artificial
<220> FEATURE:
<223> OTHER INFORMATION: Aptamer

<400> SEQUENCE: 982
cucaccuccu augguuuauu ggugccgagu ucucggacua                40

<210> SEQ ID NO 983
<211> LENGTH: 40
<212> TYPE: RNA
<213> ORGANISM: Artificial
<220> FEATURE:
<223> OTHER INFORMATION: Aptamer

<400> SEQUENCE: 983
cucaccuccu augguuuauu ggugccgagu ucucggauua         40

<210> SEQ ID NO 984
<211> LENGTH: 40
<212> TYPE: RNA
<213> ORGANISM: Artificial
<220> FEATURE:
<223> OTHER INFORMATION: Aptamer

<400> SEQUENCE: 984
cucaggugau uggcgcuauu uaucaaucga uaauugaaug         40

<210> SEQ ID NO 985
<211> LENGTH: 40
<212> TYPE: RNA
<213> ORGANISM: Artificial
<220> FEATURE:
<223> OTHER INFORMATION: Aptamer

<400> SEQUENCE: 985
cucccggugu auuggcuuuc cgguuacgca accgguagug         40

<210> SEQ ID NO 986
<211> LENGTH: 40
<212> TYPE: RNA
<213> ORGANISM: Artificial
<220> FEATURE:
<223> OTHER INFORMATION: Aptamer

<400> SEQUENCE: 986
cuccucccgc ucccgguaaa uuggcuauuc ucgaaugaug         40

<210> SEQ ID NO 987
<211> LENGTH: 40
<212> TYPE: RNA
<213> ORGANISM: Artificial
<220> FEATURE:
<223> OTHER INFORMATION: Aptamer

<400> SEQUENCE: 987
cucucccucg guuuacuggu uucuucuucc cggaguuaua         40

<210> SEQ ID NO 988
<211> LENGTH: 40
<212> TYPE: RNA
<213> ORGANISM: Artificial
<220> FEATURE:
<223> OTHER INFORMATION: Aptamer

<400> SEQUENCE: 988
cucuguucgg guguauuggu uauuggcgcu gcuacauaaa         40

<210> SEQ ID NO 989
<211> LENGTH: 40
<212> TYPE: RNA
<213> ORGANISM: Artificial
<220> FEATURE:
<223> OTHER INFORMATION: Aptamer

<400> SEQUENCE: 989
cugcgauguu agguuuauug gcccuguuaa uggcucgaag         40

<210> SEQ ID NO 990
<211> LENGTH: 40
<212> TYPE: RNA
<213> ORGANISM: Artificial

```
<220> FEATURE:
<223> OTHER INFORMATION: Aptamer

<400> SEQUENCE: 990
cugcuuuucc auucagguua uuggaccuug uuuguuguuu                                40

<210> SEQ ID NO 991
<211> LENGTH: 40
<212> TYPE: RNA
<213> ORGANISM: Artificial
<220> FEATURE:
<223> OTHER INFORMATION: Aptamer

<400> SEQUENCE: 991
cuguacucgc cacggugaac uggucuugcc cugcaacaua                                40

<210> SEQ ID NO 992
<211> LENGTH: 40
<212> TYPE: RNA
<213> ORGANISM: Artificial
<220> FEATURE:
<223> OTHER INFORMATION: Aptamer

<400> SEQUENCE: 992
cuguggaaaa uguaggugaa cuggcgcgga gagacggcug                                40

<210> SEQ ID NO 993
<211> LENGTH: 39
<212> TYPE: RNA
<213> ORGANISM: Artificial
<220> FEATURE:
<223> OTHER INFORMATION: Aptamer

<400> SEQUENCE: 993
cuguucgacg gguguauugg cugcuuguaa uaagcgacg                                 39

<210> SEQ ID NO 994
<211> LENGTH: 40
<212> TYPE: RNA
<213> ORGANISM: Artificial
<220> FEATURE:
<223> OTHER INFORMATION: Aptamer

<400> SEQUENCE: 994
cuggguaauu ggcuuuggac uuuccacgug gcucaagaug                                40

<210> SEQ ID NO 995
<211> LENGTH: 40
<212> TYPE: RNA
<213> ORGANISM: Artificial
<220> FEATURE:
<223> OTHER INFORMATION: Aptamer

<400> SEQUENCE: 995
cuucaggugu auugguugcu acuacuuugu gaagugcaaa                                40

<210> SEQ ID NO 996
<211> LENGTH: 40
<212> TYPE: RNA
<213> ORGANISM: Artificial
<220> FEATURE:
<223> OTHER INFORMATION: Aptamer

<400> SEQUENCE: 996
cuucuguccc ugguuauugg uccguggauu uacccgauua                                40
```

<210> SEQ ID NO 997
<211> LENGTH: 40
<212> TYPE: RNA
<213> ORGANISM: Artificial
<220> FEATURE:
<223> OTHER INFORMATION: Aptamer

<400> SEQUENCE: 997
cuuuugccug uucuggguga auuggucaaa cuucguuucu                                40

<210> SEQ ID NO 998
<211> LENGTH: 40
<212> TYPE: RNA
<213> ORGANISM: Artificial
<220> FEATURE:
<223> OTHER INFORMATION: Aptamer

<400> SEQUENCE: 998
cugguguacu ggucuuacaa cuacgcaugu auuggggua                                 40

<210> SEQ ID NO 999
<211> LENGTH: 40
<212> TYPE: RNA
<213> ORGANISM: Artificial
<220> FEATURE:
<223> OTHER INFORMATION: Aptamer

<400> SEQUENCE: 999
cgguuuacug gcgaucgaag cgcuugugcc uaguuggcgg                                40

<210> SEQ ID NO 1000
<211> LENGTH: 40
<212> TYPE: RNA
<213> ORGANISM: Artificial
<220> FEATURE:
<223> OTHER INFORMATION: Aptamer

<400> SEQUENCE: 1000
cgguuuauug gccuaagugc cuagucuagg ccccuagaug                                40

<210> SEQ ID NO 1001
<211> LENGTH: 40
<212> TYPE: RNA
<213> ORGANISM: Artificial
<220> FEATURE:
<223> OTHER INFORMATION: Aptamer

<400> SEQUENCE: 1001
gaacccguau uggucacagg uggauugguc uauauuguua                                40

<210> SEQ ID NO 1002
<211> LENGTH: 40
<212> TYPE: RNA
<213> ORGANISM: Artificial
<220> FEATURE:
<223> OTHER INFORMATION: Aptamer

<400> SEQUENCE: 1002
gacccuucga gcugcgcccc gagguuauug gucauugugu                                40

<210> SEQ ID NO 1003
<211> LENGTH: 40
<212> TYPE: RNA
<213> ORGANISM: Artificial
<220> FEATURE:
<223> OTHER INFORMATION: Aptamer

```
<400> SEQUENCE: 1003
gacuggcgau uuucgguuau uggcgccuuu cuaggauaug                                40

<210> SEQ ID NO 1004
<211> LENGTH: 40
<212> TYPE: RNA
<213> ORGANISM: Artificial
<220> FEATURE:
<223> OTHER INFORMATION: Aptamer

<400> SEQUENCE: 1004
gacuguugau uuucgguuau uggcgccuuu cuaggauaug                                40

<210> SEQ ID NO 1005
<211> LENGTH: 40
<212> TYPE: RNA
<213> ORGANISM: Artificial
<220> FEATURE:
<223> OTHER INFORMATION: Aptamer

<400> SEQUENCE: 1005
gagaaccgaa ucguccgggu guauuggucg uaguuuacua                                40

<210> SEQ ID NO 1006
<211> LENGTH: 41
<212> TYPE: RNA
<213> ORGANISM: Artificial
<220> FEATURE:
<223> OTHER INFORMATION: Aptamer

<400> SEQUENCE: 1006
gaggguaauu gguuuugcca accugaaagu gggguaauau a                              41

<210> SEQ ID NO 1007
<211> LENGTH: 40
<212> TYPE: RNA
<213> ORGANISM: Artificial
<220> FEATURE:
<223> OTHER INFORMATION: Aptamer

<400> SEQUENCE: 1007
gauacauccg gguucacugg uacuagauuc uuuaguguuu                                40

<210> SEQ ID NO 1008
<211> LENGTH: 41
<212> TYPE: RNA
<213> ORGANISM: Artificial
<220> FEATURE:
<223> OTHER INFORMATION: Aptamer

<400> SEQUENCE: 1008
gauuuuuggu uuauuggcuu ugccguuuga agugcaaaau g                              41

<210> SEQ ID NO 1009
<211> LENGTH: 40
<212> TYPE: RNA
<213> ORGANISM: Artificial
<220> FEATURE:
<223> OTHER INFORMATION: Aptamer

<400> SEQUENCE: 1009
gcacauccuu ucggguguau uggcuuagua uaaugcuucg                                40

<210> SEQ ID NO 1010
```

```
<211> LENGTH: 40
<212> TYPE: RNA
<213> ORGANISM: Artificial
<220> FEATURE:
<223> OTHER INFORMATION: Aptamer

<400> SEQUENCE: 1010
gcccgaccuu cguccgggu ggauuggugc uuuuugaua                              40

<210> SEQ ID NO 1011
<211> LENGTH: 40
<212> TYPE: RNA
<213> ORGANISM: Artificial
<220> FEATURE:
<223> OTHER INFORMATION: Aptamer

<400> SEQUENCE: 1011
gcccgucguc guccugguga acugguccug aaucggguag                            40

<210> SEQ ID NO 1012
<211> LENGTH: 40
<212> TYPE: RNA
<213> ORGANISM: Artificial
<220> FEATURE:
<223> OTHER INFORMATION: Aptamer

<400> SEQUENCE: 1012
gccggguuua uuggcuaccg agauucauca ucuccuuaag                            40

<210> SEQ ID NO 1013
<211> LENGTH: 40
<212> TYPE: RNA
<213> ORGANISM: Artificial
<220> FEATURE:
<223> OTHER INFORMATION: Aptamer

<400> SEQUENCE: 1013
gccggugaau uggcccguac augcggugcu uggcggugug                            40

<210> SEQ ID NO 1014
<211> LENGTH: 39
<212> TYPE: RNA
<213> ORGANISM: Artificial
<220> FEATURE:
<223> OTHER INFORMATION: Aptamer

<400> SEQUENCE: 1014
gcgcuucucg uuugcuuucc ggguuuauug gucucgugu                             39

<210> SEQ ID NO 1015
<211> LENGTH: 40
<212> TYPE: RNA
<213> ORGANISM: Artificial
<220> FEATURE:
<223> OTHER INFORMATION: Aptamer

<400> SEQUENCE: 1015
gcguucugca cacauggugu auuggcuggu uauacuguug                            40

<210> SEQ ID NO 1016
<211> LENGTH: 40
<212> TYPE: RNA
<213> ORGANISM: Artificial
<220> FEATURE:
<223> OTHER INFORMATION: Aptamer

<400> SEQUENCE: 1016
```

```
gcuaaauucc cccuaccucg uccgguaauu ggucucguuu                              40

<210> SEQ ID NO 1017
<211> LENGTH: 40
<212> TYPE: RNA
<213> ORGANISM: Artificial
<220> FEATURE:
<223> OTHER INFORMATION: Aptamer

<400> SEQUENCE: 1017
gcuccgggua uacuggcgac gaccguuauu gugucgcaua                              40

<210> SEQ ID NO 1018
<211> LENGTH: 40
<212> TYPE: RNA
<213> ORGANISM: Artificial
<220> FEATURE:
<223> OTHER INFORMATION: Aptamer

<400> SEQUENCE: 1018
gcucguccgg guguauuggu agcucuuucu ccggagaauu                              40

<210> SEQ ID NO 1019
<211> LENGTH: 40
<212> TYPE: RNA
<213> ORGANISM: Artificial
<220> FEATURE:
<223> OTHER INFORMATION: Aptamer

<400> SEQUENCE: 1019
gcucuucccu gguguacugg uccugucgac gacagagugu                              40

<210> SEQ ID NO 1020
<211> LENGTH: 39
<212> TYPE: RNA
<213> ORGANISM: Artificial
<220> FEATURE:
<223> OTHER INFORMATION: Aptamer

<400> SEQUENCE: 1020
gcugauugug cgaggucuag guguauuggc uggaucgag                               39

<210> SEQ ID NO 1021
<211> LENGTH: 40
<212> TYPE: RNA
<213> ORGANISM: Artificial
<220> FEATURE:
<223> OTHER INFORMATION: Aptamer

<400> SEQUENCE: 1021
gcuuuguguu uacauccguc ucagguuauu ggucucguuu                              40

<210> SEQ ID NO 1022
<211> LENGTH: 40
<212> TYPE: RNA
<213> ORGANISM: Artificial
<220> FEATURE:
<223> OTHER INFORMATION: Aptamer

<400> SEQUENCE: 1022 ggaguccag guggacuggu ugcucccuu ggccgcguua                                40

<210> SEQ ID NO 1023
<211> LENGTH: 40
<212> TYPE: RNA
```

```
<213> ORGANISM: Artificial
<220> FEATURE:
<223> OTHER INFORMATION: Aptamer

<400> SEQUENCE: 1023
ggcuucacuc uagguucgac uggcuccuuc ccacggcgug                                40

<210> SEQ ID NO 1024
<211> LENGTH: 40
<212> TYPE: RNA
<213> ORGANISM: Artificial
<220> FEATURE:
<223> OTHER INFORMATION: Aptamer

<400> SEQUENCE: 1024
gggcuaucgu cgguuauugg cuccuugcuu uacaggaaug                                40

<210> SEQ ID NO 1025
<211> LENGTH: 40
<212> TYPE: RNA
<213> ORGANISM: Artificial
<220> FEATURE:
<223> OTHER INFORMATION: Aptamer

<400> SEQUENCE: 1025
ggggaagggu uuuacuggug ucuaagccau cuuagaagug                                40

<210> SEQ ID NO 1026
<211> LENGTH: 40
<212> TYPE: RNA
<213> ORGANISM: Artificial
<220> FEATURE:
<223> OTHER INFORMATION: Aptamer

<400> SEQUENCE: 1026
ggggucuccg gguuuauugg ugcgcacuuu uugucgcua                                 40

<210> SEQ ID NO 1027
<211> LENGTH: 40
<212> TYPE: RNA
<213> ORGANISM: Artificial
<220> FEATURE:
<223> OTHER INFORMATION: Aptamer

<400> SEQUENCE: 1027
ggguccuugg guguacuggu uuacguaauu ucguacuaua                                40

<210> SEQ ID NO 1028
<211> LENGTH: 40
<212> TYPE: RNA
<213> ORGANISM: Artificial
<220> FEATURE:
<223> OTHER INFORMATION: Aptamer

<400> SEQUENCE: 1028
ggugcaccgu ggugguugac uggcgccuuu cagcggaaug                                40

<210> SEQ ID NO 1029
<211> LENGTH: 40
<212> TYPE: RNA
<213> ORGANISM: Artificial
<220> FEATURE:
<223> OTHER INFORMATION: Aptamer

<400> SEQUENCE: 1029
gggguuauug guuugucgaa agccuccguc ucgacauaua                                40
```

```
<210> SEQ ID NO 1030
<211> LENGTH: 40
<212> TYPE: RNA
<213> ORGANISM: Artificial
<220> FEATURE:
<223> OTHER INFORMATION: Aptamer

<400> SEQUENCE: 1030
guccacagca uauaggugua uuggcuuuuc ugggaaagug                             40

<210> SEQ ID NO 1031
<211> LENGTH: 40
<212> TYPE: RNA
<213> ORGANISM: Artificial
<220> FEATURE:
<223> OTHER INFORMATION: Aptamer

<400> SEQUENCE: 1031
guccuugagu ucagguguau uggcgaucag gcuuguuaug                             40

<210> SEQ ID NO 1032
<211> LENGTH: 40
<212> TYPE: RNA
<213> ORGANISM: Artificial
<220> FEATURE:
<223> OTHER INFORMATION: Aptamer

<400> SEQUENCE: 1032
gucugccuuu guucaaggug uauuggcuuu guuuacuaag                             40

<210> SEQ ID NO 1033
<211> LENGTH: 40
<212> TYPE: RNA
<213> ORGANISM: Artificial
<220> FEATURE:
<223> OTHER INFORMATION: Aptamer

<400> SEQUENCE: 1033
gugauuucgg cccaggugua cugguguaca uccuguauua                             40

<210> SEQ ID NO 1034
<211> LENGTH: 40
<212> TYPE: RNA
<213> ORGANISM: Artificial
<220> FEATURE:
<223> OTHER INFORMATION: Aptamer

<400> SEQUENCE: 1034
gugguuuacu agcugcuucc agguguauug gucuucgaga                             40

<210> SEQ ID NO 1035
<211> LENGTH: 40
<212> TYPE: RNA
<213> ORGANISM: Artificial
<220> FEATURE:
<223> OTHER INFORMATION: Aptamer

<400> SEQUENCE: 1035
guuauguccu gguguauugg ugguucuacg agaauuguuu                             40

<210> SEQ ID NO 1036
<211> LENGTH: 40
<212> TYPE: RNA
<213> ORGANISM: Artificial
<220> FEATURE:
```

```
<223> OTHER INFORMATION: Aptamer

<400> SEQUENCE: 1036
guuccagguc auuggcgccg uucugccgag aaucugaaug                    40

<210> SEQ ID NO 1037
<211> LENGTH: 40
<212> TYPE: RNA
<213> ORGANISM: Artificial
<220> FEATURE:
<223> OTHER INFORMATION: Aptamer

<400> SEQUENCE: 1037
guuccaggug gauuggcccc uuugcuucgc uggcuggaug                    40

<210> SEQ ID NO 1038
<211> LENGTH: 41
<212> TYPE: RNA
<213> ORGANISM: Artificial
<220> FEATURE:
<223> OTHER INFORMATION: Aptamer

<400> SEQUENCE: 1038
guucugggug gauuggucuu guacaauucu uuuuggcugg a                  41

<210> SEQ ID NO 1039
<211> LENGTH: 40
<212> TYPE: RNA
<213> ORGANISM: Artificial
<220> FEATURE:
<223> OTHER INFORMATION: Aptamer

<400> SEQUENCE: 1039
guuguuacac ugaugccccg gguguacugg uuuucgagag                    40

<210> SEQ ID NO 1040
<211> LENGTH: 40
<212> TYPE: RNA
<213> ORGANISM: Artificial
<220> FEATURE:
<223> OTHER INFORMATION: Aptamer

<400> SEQUENCE: 1040
guuguuccuu accagguuua uuggccgaac uguucgcgug                    40

<210> SEQ ID NO 1041
<211> LENGTH: 40
<212> TYPE: RNA
<213> ORGANISM: Artificial
<220> FEATURE:
<223> OTHER INFORMATION: Aptamer

<400> SEQUENCE: 1041
guuuucacgg acauggugua uuggucgucu uuccgaaaga                    40

<210> SEQ ID NO 1042
<211> LENGTH: 40
<212> TYPE: RNA
<213> ORGANISM: Artificial
<220> FEATURE:
<223> OTHER INFORMATION: Aptamer

<400> SEQUENCE: 1042
guugguggau uggucgcuuc guuuuccuga acgaugguuu                    40
```

```
<210> SEQ ID NO 1043
<211> LENGTH: 40
<212> TYPE: RNA
<213> ORGANISM: Artificial
<220> FEATURE:
<223> OTHER INFORMATION: Aptamer

<400> SEQUENCE: 1043
uaaugguaau uggcuacagu cuccggacgg aaacugggug                              40

<210> SEQ ID NO 1044
<211> LENGTH: 40
<212> TYPE: RNA
<213> ORGANISM: Artificial
<220> FEATURE:
<223> OTHER INFORMATION: Aptamer

<400> SEQUENCE: 1044
uacccaauga uacgagucua gguuuauugg ccuucggguG                              40

<210> SEQ ID NO 1045
<211> LENGTH: 40
<212> TYPE: RNA
<213> ORGANISM: Artificial
<220> FEATURE:
<223> OTHER INFORMATION: Aptamer

<400> SEQUENCE: 1045
uaccucgggu guacuggugc uuuagcuuag cucuugccca                              40

<210> SEQ ID NO 1046
<211> LENGTH: 40
<212> TYPE: RNA
<213> ORGANISM: Artificial
<220> FEATURE:
<223> OTHER INFORMATION: Aptamer

<400> SEQUENCE: 1046
uacgaccuug ucuggguuca uuggugguuc cugagacuua                              40

<210> SEQ ID NO 1047
<211> LENGTH: 40
<212> TYPE: RNA
<213> ORGANISM: Artificial
<220> FEATURE:
<223> OTHER INFORMATION: Aptamer

<400> SEQUENCE: 1047
uacgugaacu accuccuggu auauggugg cuacgguuua                               40

<210> SEQ ID NO 1048
<211> LENGTH: 40
<212> TYPE: RNA
<213> ORGANISM: Artificial
<220> FEATURE:
<223> OTHER INFORMATION: Aptamer

<400> SEQUENCE: 1048
uacuuaucac aagccuguua gguuuauugg ccucgaggug                              40

<210> SEQ ID NO 1049
<211> LENGTH: 40
<212> TYPE: RNA
<213> ORGANISM: Artificial
<220> FEATURE:
<223> OTHER INFORMATION: Aptamer
```

```
<400> SEQUENCE: 1049
uaucccggua gauugguauu cguaacuuuu acgucuauuu                          40

<210> SEQ ID NO 1050
<211> LENGTH: 40
<212> TYPE: RNA
<213> ORGANISM: Artificial
<220> FEATURE:
<223> OTHER INFORMATION: Aptamer

<400> SEQUENCE: 1050
uaucgcuggu uuauuggcgg gcuccgaguu cagccgacug                          40

<210> SEQ ID NO 1051
<211> LENGTH: 40
<212> TYPE: RNA
<213> ORGANISM: Artificial
<220> FEATURE:
<223> OTHER INFORMATION: Aptamer

<400> SEQUENCE: 1051
ucacacgcuc gcacagcagg uggauuggcu ggaucucgug                          40

<210> SEQ ID NO 1052
<211> LENGTH: 41
<212> TYPE: RNA
<213> ORGANISM: Artificial
<220> FEATURE:
<223> OTHER INFORMATION: Aptamer

<400> SEQUENCE: 1052
ucacguccac uccugguuau uggcgucauu uuucgagcu g                         41

<210> SEQ ID NO 1053
<211> LENGTH: 40
<212> TYPE: RNA
<213> ORGANISM: Artificial
<220> FEATURE:
<223> OTHER INFORMATION: Aptamer

<400> SEQUENCE: 1053
ucauuuucgg guguauuggu cuggaacuuu guucucguuu                          40

<210> SEQ ID NO 1054
<211> LENGTH: 40
<212> TYPE: RNA
<213> ORGANISM: Artificial
<220> FEATURE:
<223> OTHER INFORMATION: Aptamer

<400> SEQUENCE: 1054
ucauggugaa cuggcgccau uaacuccugu ccgaugguug                          40

<210> SEQ ID NO 1055
<211> LENGTH: 40
<212> TYPE: RNA
<213> ORGANISM: Artificial
<220> FEATURE:
<223> OTHER INFORMATION: Aptamer

<400> SEQUENCE: 1055
ucauggugaa cuggcuaacu uauucuauga uuucgucaag                          40

<210> SEQ ID NO 1056
<211> LENGTH: 42
```

-continued

<212> TYPE: RNA
<213> ORGANISM: Artificial
<220> FEATURE:
<223> OTHER INFORMATION: Aptamer

<400> SEQUENCE: 1056
uccacuguau cucucgggug uacuggcucu uagcagagga ug                42

<210> SEQ ID NO 1057
<211> LENGTH: 40
<212> TYPE: RNA
<213> ORGANISM: Artificial
<220> FEATURE:
<223> OTHER INFORMATION: Aptamer

<400> SEQUENCE: 1057
uccagguugu auuggcgcuc uaguccaauu gcuagucaug                  40

<210> SEQ ID NO 1058
<211> LENGTH: 42
<212> TYPE: RNA
<213> ORGANISM: Artificial
<220> FEATURE:
<223> OTHER INFORMATION: Aptamer

<400> SEQUENCE: 1058 uccccccggaa aaaacaugc ccagguugau uggcauugu gu                42

<210> SEQ ID NO 1059
<211> LENGTH: 39
<212> TYPE: RNA
<213> ORGANISM: Artificial
<220> FEATURE:
<223> OTHER INFORMATION: Aptamer

<400> SEQUENCE: 1059
uccccuucgu cccacugcau ucggguguau uggcuccug                   39

<210> SEQ ID NO 1060
<211> LENGTH: 40
<212> TYPE: RNA
<213> ORGANISM: Artificial
<220> FEATURE:
<223> OTHER INFORMATION: Aptamer

<400> SEQUENCE: 1060
ucccuuacgc uguccgguaa uuggcucuuu ccggguauug                  40

<210> SEQ ID NO 1061
<211> LENGTH: 40
<212> TYPE: RNA
<213> ORGANISM: Artificial
<220> FEATURE:
<223> OTHER INFORMATION: Aptamer

<400> SEQUENCE: 1061
ucccuuccag guaauugguc cgucacacuu gcgucgggug                  40

<210> SEQ ID NO 1062
<211> LENGTH: 40
<212> TYPE: RNA
<213> ORGANISM: Artificial
<220> FEATURE:
<223> OTHER INFORMATION: Aptamer

<400> SEQUENCE: 1062
uccgccgcaa ucagguguac uggccagucg ggauugguaa                    40

<210> SEQ ID NO 1063
<211> LENGTH: 40
<212> TYPE: RNA
<213> ORGANISM: Artificial
<220> FEATURE:
<223> OTHER INFORMATION: Aptamer

<400> SEQUENCE: 1063
uccgggugga uugguuauug guugcagggg caucggugaa                    40

<210> SEQ ID NO 1064
<211> LENGTH: 40
<212> TYPE: RNA
<213> ORGANISM: Artificial
<220> FEATURE:
<223> OTHER INFORMATION: Aptamer

<400> SEQUENCE: 1064
uccuuguucu gcacgcuucg auagguuauu ggucgcguuu                    40

<210> SEQ ID NO 1065
<211> LENGTH: 40
<212> TYPE: RNA
<213> ORGANISM: Artificial
<220> FEATURE:
<223> OTHER INFORMATION: Aptamer

<400> SEQUENCE: 1065
uccuuuagac gaaccccgg guuacuggcg cacuggaaug                     40

<210> SEQ ID NO 1066
<211> LENGTH: 39
<212> TYPE: RNA
<213> ORGANISM: Artificial
<220> FEATURE:
<223> OTHER INFORMATION: Aptamer

<400> SEQUENCE: 1066
ucgcuccagg uggacuggcu uacuuuuuuu gguuguga                      39

<210> SEQ ID NO 1067
<211> LENGTH: 40
<212> TYPE: RNA
<213> ORGANISM: Artificial
<220> FEATURE:
<223> OTHER INFORMATION: Aptamer

<400> SEQUENCE: 1067
ucguccuggu ggauuggcgc cgcguucauu cguaugcaug                    40

<210> SEQ ID NO 1068
<211> LENGTH: 40
<212> TYPE: RNA
<213> ORGANISM: Artificial
<220> FEATURE:
<223> OTHER INFORMATION: Aptamer

<400> SEQUENCE: 1068
ucguucgggu guauuggucc uucgacuuuu aucgaccgga                    40

<210> SEQ ID NO 1069
<211> LENGTH: 39
<212> TYPE: RNA
<213> ORGANISM: Artificial

```
<220> FEATURE:
<223> OTHER INFORMATION: Aptamer

<400> SEQUENCE: 1069
ucuaggugug acuggcacgc agaagacucu ugcgauuug                           39

<210> SEQ ID NO 1070
<211> LENGTH: 40
<212> TYPE: RNA
<213> ORGANISM: Artificial
<220> FEATURE:
<223> OTHER INFORMATION: Aptamer

<400> SEQUENCE: 1070
ucucuaucua cgguguacug gcccgcuuug cgugugaaug                          40

<210> SEQ ID NO 1071
<211> LENGTH: 40
<212> TYPE: RNA
<213> ORGANISM: Artificial
<220> FEATURE:
<223> OTHER INFORMATION: Aptamer

<400> SEQUENCE: 1071
ucucugucua cgguguacug gcccgcuuug cgugugaaug                          40

<210> SEQ ID NO 1072
<211> LENGTH: 38
<212> TYPE: RNA
<213> ORGANISM: Artificial
<220> FEATURE:
<223> OTHER INFORMATION: Aptamer

<400> SEQUENCE: 1072
ucuguugggu aauuggcugg guuaacggga cccguaug                            38

<210> SEQ ID NO 1073
<211> LENGTH: 40
<212> TYPE: RNA
<213> ORGANISM: Artificial
<220> FEATURE:
<223> OTHER INFORMATION: Aptamer

<400> SEQUENCE: 1073
ucuggguuua uggucugua ccucgugggg augcuggaua                           40

<210> SEQ ID NO 1074
<211> LENGTH: 40
<212> TYPE: RNA
<213> ORGANISM: Artificial
<220> FEATURE:
<223> OTHER INFORMATION: Aptamer

<400> SEQUENCE: 1074
ucuuacguuc uagguauacu ggcucguuuu gcaucgaaug                          40

<210> SEQ ID NO 1075
<211> LENGTH: 40
<212> TYPE: RNA
<213> ORGANISM: Artificial
<220> FEATURE:
<223> OTHER INFORMATION: Aptamer

<400> SEQUENCE: 1075
ucuugucacu ccggguguac ugguccgaac uuugagugua                          40
```

```
<210> SEQ ID NO 1076
<211> LENGTH: 39
<212> TYPE: RNA
<213> ORGANISM: Artificial
<220> FEATURE:
<223> OTHER INFORMATION: Aptamer

<400> SEQUENCE: 1076
ucuuucuauc cgggugaauu gguggucuuu cuuucucca                    39

<210> SEQ ID NO 1077
<211> LENGTH: 40
<212> TYPE: RNA
<213> ORGANISM: Artificial
<220> FEATURE:
<223> OTHER INFORMATION: Aptamer

<400> SEQUENCE: 1077
ugacagguga acuggcucaa ucgcucgggc cauugaaaug                   40

<210> SEQ ID NO 1078
<211> LENGTH: 40
<212> TYPE: RNA
<213> ORGANISM: Artificial
<220> FEATURE:
<223> OTHER INFORMATION: Aptamer

<400> SEQUENCE: 1078
ugacucucgu cucucugaug guguauuggc ggauggcuug                   40

<210> SEQ ID NO 1079
<211> LENGTH: 40
<212> TYPE: RNA
<213> ORGANISM: Artificial
<220> FEATURE:
<223> OTHER INFORMATION: Aptamer

<400> SEQUENCE: 1079
ugaguuucca gguguauugg uauuucguuu uccccgguua                   40

<210> SEQ ID NO 1080
<211> LENGTH: 41
<212> TYPE: RNA
<213> ORGANISM: Artificial
<220> FEATURE:
<223> OTHER INFORMATION: Aptamer

<400> SEQUENCE: 1080
ugauacgucu gcgguuuacu ggcuuuccgu gggaagaaau g                 41

<210> SEQ ID NO 1081
<211> LENGTH: 40
<212> TYPE: RNA
<213> ORGANISM: Artificial
<220> FEATURE:
<223> OTHER INFORMATION: Aptamer

<400> SEQUENCE: 1081
ugccccggug uauuggcccc caggacacug cgccugcuua                   40

<210> SEQ ID NO 1082
<211> LENGTH: 40
<212> TYPE: RNA
<213> ORGANISM: Artificial
<220> FEATURE:
<223> OTHER INFORMATION: Aptamer
```

```
<400> SEQUENCE: 1082
ugcuccaggu ucauuggucg uuguccuugu acuucugaua                                  40

<210> SEQ ID NO 1083
<211> LENGTH: 40
<212> TYPE: RNA
<213> ORGANISM: Artificial
<220> FEATURE:
<223> OTHER INFORMATION: Aptamer

<400> SEQUENCE: 1083
uggccggguu uauuggucgg uggugcugag ccacucguua                                  40

<210> SEQ ID NO 1084
<211> LENGTH: 40
<212> TYPE: RNA
<213> ORGANISM: Artificial
<220> FEATURE:
<223> OTHER INFORMATION: Aptamer

<400> SEQUENCE: 1084
uggcucucau cuccucuggg ugaacuggcu uaaccagaug                                  40

<210> SEQ ID NO 1085
<211> LENGTH: 40
<212> TYPE: RNA
<213> ORGANISM: Artificial
<220> FEATURE:
<223> OTHER INFORMATION: Aptamer

<400> SEQUENCE: 1085
uguccaacua auggugacug gcgggacucc gcuccgucug                                  40

<210> SEQ ID NO 1086
<211> LENGTH: 40
<212> TYPE: RNA
<213> ORGANISM: Artificial
<220> FEATURE:
<223> OTHER INFORMATION: Aptamer

<400> SEQUENCE: 1086
ugucggguaa uuggcggucu uugcacuuau ugacgucuug                                  40

<210> SEQ ID NO 1087
<211> LENGTH: 40
<212> TYPE: RNA
<213> ORGANISM: Artificial
<220> FEATURE:
<223> OTHER INFORMATION: Aptamer

<400> SEQUENCE: 1087
ugucucgguu uauuggcggu cggacuuuug cccugcgaag                                  40

<210> SEQ ID NO 1088
<211> LENGTH: 40
<212> TYPE: RNA
<213> ORGANISM: Artificial
<220> FEATURE:
<223> OTHER INFORMATION: Aptamer

<400> SEQUENCE: 1088
uguucaggug uauuggucuc gguguuuucc uuaccuguua                                  40

<210> SEQ ID NO 1089
```

```
<211> LENGTH: 40
<212> TYPE: RNA
<213> ORGANISM: Artificial
<220> FEATURE:
<223> OTHER INFORMATION: Aptamer

<400> SEQUENCE: 1089
uguuccggug uauuggcgac cagcucuacc ggcaguagug                           40

<210> SEQ ID NO 1090
<211> LENGTH: 40
<212> TYPE: RNA
<213> ORGANISM: Artificial
<220> FEATURE:
<223> OTHER INFORMATION: Aptamer

<400> SEQUENCE: 1090
uguucgggug uauuggcaac ugcuuguuug caguaauugg                           40

<210> SEQ ID NO 1091
<211> LENGTH: 40
<212> TYPE: RNA
<213> ORGANISM: Artificial
<220> FEATURE:
<223> OTHER INFORMATION: Aptamer

<400> SEQUENCE: 1091
uguugugucc aagguuuauu ggcgugucgc uugaccuaug                           40

<210> SEQ ID NO 1092
<211> LENGTH: 40
<212> TYPE: RNA
<213> ORGANISM: Artificial
<220> FEATURE:
<223> OTHER INFORMATION: Aptamer

<400> SEQUENCE: 1092
uuacccucgu cgucggugaa uugguagugc cuucacuuua                           40

<210> SEQ ID NO 1093
<211> LENGTH: 40
<212> TYPE: RNA
<213> ORGANISM: Artificial
<220> FEATURE:
<223> OTHER INFORMATION: Aptamer

<400> SEQUENCE: 1093
uucauguguc ugccggguuu auugguccac uguccgguua                           40

<210> SEQ ID NO 1094
<211> LENGTH: 38
<212> TYPE: RNA
<213> ORGANISM: Artificial
<220> FEATURE:
<223> OTHER INFORMATION: Aptamer

<400> SEQUENCE: 1094
uucagguuau uggcccagcu uuccaaaac ccggugug                              38

<210> SEQ ID NO 1095
<211> LENGTH: 40
<212> TYPE: RNA
<213> ORGANISM: Artificial
<220> FEATURE:
<223> OTHER INFORMATION: Aptamer

<400> SEQUENCE: 1095
```
uucagguuau uggcgcuuau gauucaacau cucgggcaug          40

<210> SEQ ID NO 1096
<211> LENGTH: 40
<212> TYPE: RNA
<213> ORGANISM: Artificial
<220> FEATURE:
<223> OTHER INFORMATION: Aptamer

<400> SEQUENCE: 1096
uuccccaggu aaauggugc aagcgauuaa gcgaugaaua          40

<210> SEQ ID NO 1097
<211> LENGTH: 40
<212> TYPE: RNA
<213> ORGANISM: Artificial
<220> FEATURE:
<223> OTHER INFORMATION: Aptamer

<400> SEQUENCE: 1097
uucgcugucu gguuuauugg uuccccaucc ugcgguaaua          40

<210> SEQ ID NO 1098
<211> LENGTH: 40
<212> TYPE: RNA
<213> ORGANISM: Artificial
<220> FEATURE:
<223> OTHER INFORMATION: Aptamer

<400> SEQUENCE: 1098
uucgcuucug ccccucgguc uacuggcccc uaacgguaug          40

<210> SEQ ID NO 1099
<211> LENGTH: 40
<212> TYPE: RNA
<213> ORGANISM: Artificial
<220> FEATURE:
<223> OTHER INFORMATION: Aptamer

<400> SEQUENCE: 1099
uucgucucgu ccagguggau ugguucguag uguugcgguu          40

<210> SEQ ID NO 1100
<211> LENGTH: 40
<212> TYPE: RNA
<213> ORGANISM: Artificial
<220> FEATURE:
<223> OTHER INFORMATION: Aptamer

<400> SEQUENCE: 1100
uucgggugua cuggcucauu gucuggcuuc gacaugauac          40

<210> SEQ ID NO 1101
<211> LENGTH: 40
<212> TYPE: RNA
<213> ORGANISM: Artificial
<220> FEATURE:
<223> OTHER INFORMATION: Aptamer

<400> SEQUENCE: 1101
uucugcgggu uuauggugu cgguuuucug uaaccuuuua          40

<210> SEQ ID NO 1102
<211> LENGTH: 40
<212> TYPE: RNA

```
<213> ORGANISM: Artificial
<220> FEATURE:
<223> OTHER INFORMATION: Aptamer

<400> SEQUENCE: 1102
uugcccgaca guucgcgguu uacuggcucu guauagcaug                          40

<210> SEQ ID NO 1103
<211> LENGTH: 40
<212> TYPE: RNA
<213> ORGANISM: Artificial
<220> FEATURE:
<223> OTHER INFORMATION: Aptamer

<400> SEQUENCE: 1103
uugucugggu guauugguug auaucgaaug aacgaaucuu                          40

<210> SEQ ID NO 1104
<211> LENGTH: 41
<212> TYPE: RNA
<213> ORGANISM: Artificial
<220> FEATURE:
<223> OTHER INFORMATION: Aptamer

<400> SEQUENCE: 1104
uuguuggccg ccugguuuua cuggcucuca uuccgagcau g                        41

<210> SEQ ID NO 1105
<211> LENGTH: 40
<212> TYPE: RNA
<213> ORGANISM: Artificial
<220> FEATURE:
<223> OTHER INFORMATION: Aptamer

<400> SEQUENCE: 1105
uuggguguau uggucccucu ggguauuugc ccucggagga                          40

<210> SEQ ID NO 1106
<211> LENGTH: 39
<212> TYPE: RNA
<213> ORGANISM: Artificial
<220> FEATURE:
<223> OTHER INFORMATION: Aptamer

<400> SEQUENCE: 1106
uuucauucgc cagguuuauu gguuagcagu aagcuuaua                           39

<210> SEQ ID NO 1107
<211> LENGTH: 40
<212> TYPE: RNA
<213> ORGANISM: Artificial
<220> FEATURE:
<223> OTHER INFORMATION: Aptamer

<400> SEQUENCE: 1107
uuucgguuua uggcguggc cucuaccuug gggucagcug                           40

<210> SEQ ID NO 1108
<211> LENGTH: 40
<212> TYPE: RNA
<213> ORGANISM: Artificial
<220> FEATURE:
<223> OTHER INFORMATION: Aptamer

<400> SEQUENCE: 1108
uuugccuaac gucuucggug uauuggucuu cuuguuguuu                          40
```

```
<210> SEQ ID NO 1109
<211> LENGTH: 40
<212> TYPE: RNA
<213> ORGANISM: Artificial
<220> FEATURE:
<223> OTHER INFORMATION: Aptamer

<400> SEQUENCE: 1109
uuugguacca ugcaugccgg gugcacuggc ucuuggauug                             40

<210> SEQ ID NO 1110
<211> LENGTH: 40
<212> TYPE: RNA
<213> ORGANISM: Artificial
<220> FEATURE:
<223> OTHER INFORMATION: Aptamer

<400> SEQUENCE: 1110
uuuucucggu auacugguuu cgauacucug uguugauaua                             40

<210> SEQ ID NO 1111
<211> LENGTH: 40
<212> TYPE: RNA
<213> ORGANISM: Artificial
<220> FEATURE:
<223> OTHER INFORMATION: Aptamer

<400> SEQUENCE: 1111
uuuucucggu cgauuggcgg cgcuggauuc ugcguaucug                             40

<210> SEQ ID NO 1112
<211> LENGTH: 40
<212> TYPE: RNA
<213> ORGANISM: Artificial
<220> FEATURE:
<223> OTHER INFORMATION: Aptamer

<400> SEQUENCE: 1112
uuuugggguu acuggcgcuu gugauuagug cacucgaaug                             40

<210> SEQ ID NO 1113
<211> LENGTH: 40
<212> TYPE: RNA
<213> ORGANISM: Artificial
<220> FEATURE:
<223> OTHER INFORMATION: Aptamer

<400> SEQUENCE: 1113
ugguguauug guguauuuuc acucugccgg uguuuagcca                             40

<210> SEQ ID NO 1114
<211> LENGTH: 40
<212> TYPE: RNA
<213> ORGANISM: Artificial
<220> FEATURE:
<223> OTHER INFORMATION: Aptamer

<400> SEQUENCE: 1114
ugguuauugg cuacuguccu cguccuucgg ugcaggaaug                             40

<210> SEQ ID NO 1115
<211> LENGTH: 40
<212> TYPE: RNA
<213> ORGANISM: Artificial
<220> FEATURE:
```

<223> OTHER INFORMATION: Aptamer

<400> SEQUENCE: 1115
ugguucauug gcuacuuugg uacccucugu ucagagcaag                              40

<210> SEQ ID NO 1116
<211> LENGTH: 40
<212> TYPE: RNA
<213> ORGANISM: Artificial
<220> FEATURE:
<223> OTHER INFORMATION: Aptamer

<400> SEQUENCE: 1116
ugguuuauug gcggggccuc auuuuguuga augaccuuug                              40

<210> SEQ ID NO 1117
<211> LENGTH: 35
<212> TYPE: RNA
<213> ORGANISM: Artificial
<220> FEATURE:
<223> OTHER INFORMATION: Aptamer

<400> SEQUENCE: 1117
gguaaacugg cgcggcgucc uuauggcgua gaaug                                   35

<210> SEQ ID NO 1118
<211> LENGTH: 40
<212> TYPE: RNA
<213> ORGANISM: Artificial
<220> FEATURE:
<223> OTHER INFORMATION: Aptamer

<400> SEQUENCE: 1118
gguaaauugg cacuugcgua guuuucgguu cgcacuuaug                              40

<210> SEQ ID NO 1119
<211> LENGTH: 40
<212> TYPE: RNA
<213> ORGANISM: Artificial
<220> FEATURE:
<223> OTHER INFORMATION: Aptamer

<400> SEQUENCE: 1119
gguaaauugg cggcguuauc ucucauccuu gaacgcagug                              40

<210> SEQ ID NO 1120
<211> LENGTH: 40
<212> TYPE: RNA
<213> ORGANISM: Artificial
<220> FEATURE:
<223> OTHER INFORMATION: Aptamer

<400> SEQUENCE: 1120
gguaaauugg uggccuaacg uuccaaacgg ucgggcuuua                              40

<210> SEQ ID NO 1121
<211> LENGTH: 40
<212> TYPE: RNA
<213> ORGANISM: Artificial
<220> FEATURE:
<223> OTHER INFORMATION: Aptamer

<400> SEQUENCE: 1121
gguaauuggc gcuaggauau uuugacuaua cuugggfuugg                             40

```
<210> SEQ ID NO 1122
<211> LENGTH: 40
<212> TYPE: RNA
<213> ORGANISM: Artificial
<220> FEATURE:
<223> OTHER INFORMATION: Aptamer

<400> SEQUENCE: 1122
gguaauuggu ucuacucaug cuccguauga cguagauua                                 40

<210> SEQ ID NO 1123
<211> LENGTH: 39
<212> TYPE: RNA
<213> ORGANISM: Artificial
<220> FEATURE:
<223> OTHER INFORMATION: Aptamer

<400> SEQUENCE: 1123
gguauauugg cgccacuucc ccgcgacuag uggaacuug                                 39

<210> SEQ ID NO 1124
<211> LENGTH: 38
<212> TYPE: RNA
<213> ORGANISM: Artificial
<220> FEATURE:
<223> OTHER INFORMATION: Aptamer

<400> SEQUENCE: 1124
gguauauugg cgccucauug ccuauugcug aggaucug                                  38

<210> SEQ ID NO 1125
<211> LENGTH: 39
<212> TYPE: RNA
<213> ORGANISM: Artificial
<220> FEATURE:
<223> OTHER INFORMATION: Aptamer

<400> SEQUENCE: 1125
gguauauugg ugccucucga cuuccggucg uuauaguua                                 39

<210> SEQ ID NO 1126
<211> LENGTH: 40
<212> TYPE: RNA
<213> ORGANISM: Artificial
<220> FEATURE:
<223> OTHER INFORMATION: Aptamer

<400> SEQUENCE: 1126
gguauauugg uucaaccuac accuucgugu acguaguaua                                40

<210> SEQ ID NO 1127
<211> LENGTH: 40
<212> TYPE: RNA
<213> ORGANISM: Artificial
<220> FEATURE:
<223> OTHER INFORMATION: Aptamer

<400> SEQUENCE: 1127
gguauauugg uucccggcuc uugaauccgc cgucagagug                                40

<210> SEQ ID NO 1128
<211> LENGTH: 40
<212> TYPE: RNA
<213> ORGANISM: Artificial
<220> FEATURE:
<223> OTHER INFORMATION: Aptamer
```

```
<400> SEQUENCE: 1128
gguauauugg uuguuggccu gguucuacua cccagcagug                          40

<210> SEQ ID NO 1129
<211> LENGTH: 39
<212> TYPE: RNA
<213> ORGANISM: Artificial
<220> FEATURE:
<223> OTHER INFORMATION: Aptamer

<400> SEQUENCE: 1129
ggucuacugg ugccuacgcg uauuacguau cauggaaua                           39

<210> SEQ ID NO 1130
<211> LENGTH: 39
<212> TYPE: RNA
<213> ORGANISM: Artificial
<220> FEATURE:
<223> OTHER INFORMATION: Aptamer

<400> SEQUENCE: 1130
ggucuauugg ugugggagaa cucuuugucu aaccgagug                           39

<210> SEQ ID NO 1131
<211> LENGTH: 40
<212> TYPE: RNA
<213> ORGANISM: Artificial
<220> FEATURE:
<223> OTHER INFORMATION: Aptamer

<400> SEQUENCE: 1131
ggugaacugg caaacagagg cucuugagcu aguguggaug                          40

<210> SEQ ID NO 1132
<211> LENGTH: 41
<212> TYPE: RNA
<213> ORGANISM: Artificial
<220> FEATURE:
<223> OTHER INFORMATION: Aptamer

<400> SEQUENCE: 1132
ggugaacugg cucgagauuu ugucgcuugu ugaucgguau g                        41

<210> SEQ ID NO 1133
<211> LENGTH: 41
<212> TYPE: RNA
<213> ORGANISM: Artificial
<220> FEATURE:
<223> OTHER INFORMATION: Aptamer

<400> SEQUENCE: 1133
ggugaacugg uccgcauuua gcuuucuuau uuugcgggua u                        41

<210> SEQ ID NO 1134
<211> LENGTH: 40
<212> TYPE: RNA
<213> ORGANISM: Artificial
<220> FEATURE:
<223> OTHER INFORMATION: Aptamer

<400> SEQUENCE: 1134
ggugaacugg uccgcauuug gcuuucuuau uugcggguau                          40

<210> SEQ ID NO 1135
<211> LENGTH: 40
```

```
<212> TYPE: RNA
<213> ORGANISM: Artificial
<220> FEATURE:
<223> OTHER INFORMATION: Aptamer

<400> SEQUENCE: 1135
ggugaacugg uccgcguuua gcuuucuuau uugcggguau                    40

<210> SEQ ID NO 1136
<211> LENGTH: 40
<212> TYPE: RNA
<213> ORGANISM: Artificial
<220> FEATURE:
<223> OTHER INFORMATION: Aptamer

<400> SEQUENCE: 1136
ggugaacugg ugaacuaacc cucucgaccg gcguguuuua                    40

<210> SEQ ID NO 1137
<211> LENGTH: 40
<212> TYPE: RNA
<213> ORGANISM: Artificial
<220> FEATURE:
<223> OTHER INFORMATION: Aptamer

<400> SEQUENCE: 1137
ggugaacugg ugguggguug gaauauuuca uauccauuua                    40

<210> SEQ ID NO 1138
<211> LENGTH: 41
<212> TYPE: RNA
<213> ORGANISM: Artificial
<220> FEATURE:
<223> OTHER INFORMATION: Aptamer

<400> SEQUENCE: 1138
ggugaacugg uuacguguag uugaaaaauu gcugcugugu a                  41

<210> SEQ ID NO 1139
<211> LENGTH: 34
<212> TYPE: RNA
<213> ORGANISM: Artificial
<220> FEATURE:
<223> OTHER INFORMATION: Aptamer

<400> SEQUENCE: 1139
ggugaauugg uuacguuuuc ucugacaaug ugga                          34

<210> SEQ ID NO 1140
<211> LENGTH: 34
<212> TYPE: RNA
<213> ORGANISM: Artificial
<220> FEATURE:
<223> OTHER INFORMATION: Aptamer

<400> SEQUENCE: 1140
ggugauuggc uguugcucug ucggggugac aaug                          34

<210> SEQ ID NO 1141
<211> LENGTH: 40
<212> TYPE: RNA
<213> ORGANISM: Artificial
<220> FEATURE:
<223> OTHER INFORMATION: Aptamer

<400> SEQUENCE: 1141
```
ggugcauugg ucggugugca agcuuuuugg gauacuuaua       40

<210> SEQ ID NO 1142
<211> LENGTH: 40
<212> TYPE: RNA
<213> ORGANISM: Artificial
<220> FEATURE:
<223> OTHER INFORMATION: Aptamer

<400> SEQUENCE: 1142 ggugggacugg cgccuucuag ucuucuggua uugcggcuug       40

<210> SEQ ID NO 1143
<211> LENGTH: 40
<212> TYPE: RNA
<213> ORGANISM: Artificial
<220> FEATURE:
<223> OTHER INFORMATION: Aptamer

<400> SEQUENCE: 1143 ggugggacugg cuaccgagau gcgcuguauu gaaggugaag       40

<210> SEQ ID NO 1144
<211> LENGTH: 40
<212> TYPE: RNA
<213> ORGANISM: Artificial
<220> FEATURE:
<223> OTHER INFORMATION: Aptamer

<400> SEQUENCE: 1144 ggugggacugg cugccaauug cccuacguca ugcagcaaug       40

<210> SEQ ID NO 1145
<211> LENGTH: 40
<212> TYPE: RNA
<213> ORGANISM: Artificial
<220> FEATURE:
<223> OTHER INFORMATION: Aptamer

<400> SEQUENCE: 1145 ggugggacugg ugucaacaga cgugucggcu guuuucguau       40

<210> SEQ ID NO 1146
<211> LENGTH: 35
<212> TYPE: RNA
<213> ORGANISM: Artificial
<220> FEATURE:
<223> OTHER INFORMATION: Aptamer

<400> SEQUENCE: 1146 ggugggacugg uuauaaccuu uaucugcgug augua       35

<210> SEQ ID NO 1147
<211> LENGTH: 40
<212> TYPE: RNA
<213> ORGANISM: Artificial
<220> FEATURE:
<223> OTHER INFORMATION: Aptamer

<400> SEQUENCE: 1147 ggugggauugg ucaggauaga acuuuuuggg ucucgucgua       40

<210> SEQ ID NO 1148
<211> LENGTH: 40
<212> TYPE: RNA
<213> ORGANISM: Artificial

```
<220> FEATURE:
<223> OTHER INFORMATION: Aptamer

<400> SEQUENCE: 1148
gguguacugg cacccagaga gucuagaggc uaugggacug                    40

<210> SEQ ID NO 1149
<211> LENGTH: 39
<212> TYPE: RNA
<213> ORGANISM: Artificial
<220> FEATURE:
<223> OTHER INFORMATION: Aptamer

<400> SEQUENCE: 1149
gguguacugg cacuacugaa auucauuuga guaggucug                     39

<210> SEQ ID NO 1150
<211> LENGTH: 40
<212> TYPE: RNA
<213> ORGANISM: Artificial
<220> FEATURE:
<223> OTHER INFORMATION: Aptamer

<400> SEQUENCE: 1150
gguguacugg cacuacugga auucauuug aguaggucug                     40

<210> SEQ ID NO 1151
<211> LENGTH: 40
<212> TYPE: RNA
<213> ORGANISM: Artificial
<220> FEATURE:
<223> OTHER INFORMATION: Aptamer

<400> SEQUENCE: 1151
gguguacugg caguuuaaag gugaaaagcu uuuuaugaug                    40

<210> SEQ ID NO 1152
<211> LENGTH: 41
<212> TYPE: RNA
<213> ORGANISM: Artificial
<220> FEATURE:
<223> OTHER INFORMATION: Aptamer

<400> SEQUENCE: 1152
gguguacugg cauuugacau uuuuucaugc cacauaugug a                  41

<210> SEQ ID NO 1153
<211> LENGTH: 40
<212> TYPE: RNA
<213> ORGANISM: Artificial
<220> FEATURE:
<223> OTHER INFORMATION: Aptamer

<400> SEQUENCE: 1153
gguguacugg ccacuugaau ccuuccuuca uaaguaggug                    40

<210> SEQ ID NO 1154
<211> LENGTH: 41
<212> TYPE: RNA
<213> ORGANISM: Artificial
<220> FEATURE:
<223> OTHER INFORMATION: Aptamer

<400> SEQUENCE: 1154
gguguacugg ccagugacga cuaugagaug gcguauggug a                  41
```

```
<210> SEQ ID NO 1155
<211> LENGTH: 40
<212> TYPE: RNA
<213> ORGANISM: Artificial
<220> FEATURE:
<223> OTHER INFORMATION: Aptamer

<400> SEQUENCE: 1155
gguguacugg cccugucguu uuauauaacu cugcaggaug                                40

<210> SEQ ID NO 1156
<211> LENGTH: 39
<212> TYPE: RNA
<213> ORGANISM: Artificial
<220> FEATURE:
<223> OTHER INFORMATION: Aptamer

<400> SEQUENCE: 1156
gguguacugg ccgcgaaugu ugcaucccau uaacgguga                                 39

<210> SEQ ID NO 1157
<211> LENGTH: 40
<212> TYPE: RNA
<213> ORGANISM: Artificial
<220> FEATURE:
<223> OTHER INFORMATION: Aptamer

<400> SEQUENCE: 1157
gguguacugg ccggcugccg cguucaaaug gggucaaugu                                40

<210> SEQ ID NO 1158
<211> LENGTH: 38
<212> TYPE: RNA
<213> ORGANISM: Artificial
<220> FEATURE:
<223> OTHER INFORMATION: Aptamer

<400> SEQUENCE: 1158
gguguacugg ccuucacuug cuaacagucu ccuuggug                                  38

<210> SEQ ID NO 1159
<211> LENGTH: 40
<212> TYPE: RNA
<213> ORGANISM: Artificial
<220> FEATURE:
<223> OTHER INFORMATION: Aptamer

<400> SEQUENCE: 1159
gguguacugg cgcuacugaa auuucauuug aguaggucug                                40

<210> SEQ ID NO 1160
<211> LENGTH: 40
<212> TYPE: RNA
<213> ORGANISM: Artificial
<220> FEATURE:
<223> OTHER INFORMATION: Aptamer

<400> SEQUENCE: 1160
gguguacugg cggcucgcgc uuacugaugu gggaccguua                                40

<210> SEQ ID NO 1161
<211> LENGTH: 40
<212> TYPE: RNA
<213> ORGANISM: Artificial
<220> FEATURE:
<223> OTHER INFORMATION: Aptamer
```

```
<400> SEQUENCE: 1161
gguguacugg cuauuacaca uuuuuguaga uuguaaugug                    40

<210> SEQ ID NO 1162
<211> LENGTH: 40
<212> TYPE: RNA
<213> ORGANISM: Artificial
<220> FEATURE:
<223> OTHER INFORMATION: Aptamer

<400> SEQUENCE: 1162
gguguacugg ucugugaauu ugucggcaua acucaccgua                    40

<210> SEQ ID NO 1163
<211> LENGTH: 40
<212> TYPE: RNA
<213> ORGANISM: Artificial
<220> FEATURE:
<223> OTHER INFORMATION: Aptamer

<400> SEQUENCE: 1163
gguguacugg uguuacucga uuuccuccg cccguaucua                     40

<210> SEQ ID NO 1164
<211> LENGTH: 40
<212> TYPE: RNA
<213> ORGANISM: Artificial
<220> FEATURE:
<223> OTHER INFORMATION: Aptamer

<400> SEQUENCE: 1164
gguguacugg uguuuggug uuauucccgc aucagccgug                     40

<210> SEQ ID NO 1165
<211> LENGTH: 40
<212> TYPE: RNA
<213> ORGANISM: Artificial
<220> FEATURE:
<223> OTHER INFORMATION: Aptamer

<400> SEQUENCE: 1165
gguguacugg uuaguugaca cggcuuugag ugaauuugga                    40

<210> SEQ ID NO 1166
<211> LENGTH: 38
<212> TYPE: RNA
<213> ORGANISM: Artificial
<220> FEATURE:
<223> OTHER INFORMATION: Aptamer

<400> SEQUENCE: 1166
gguguacugg uuuugguaga cuuuugauug ccgaggug                      38

<210> SEQ ID NO 1167
<211> LENGTH: 40
<212> TYPE: RNA
<213> ORGANISM: Artificial
<220> FEATURE:
<223> OTHER INFORMATION: Aptamer

<400> SEQUENCE: 1167
gguguauugg caauccuacg guuuaaccaa gaaagguucg                    40

<210> SEQ ID NO 1168
```

```
<211> LENGTH: 40
<212> TYPE: RNA
<213> ORGANISM: Artificial
<220> FEATURE:
<223> OTHER INFORMATION: Aptamer

<400> SEQUENCE: 1168
gguguauugg cacccgucua acuacgguaa cgcgguaaug                    40

<210> SEQ ID NO 1169
<211> LENGTH: 39
<212> TYPE: RNA
<213> ORGANISM: Artificial
<220> FEATURE:
<223> OTHER INFORMATION: Aptamer

<400> SEQUENCE: 1169
gguguauugg caggugcauu uugaacgaua cauuggucg                     39

<210> SEQ ID NO 1170
<211> LENGTH: 40
<212> TYPE: RNA
<213> ORGANISM: Artificial
<220> FEATURE:
<223> OTHER INFORMATION: Aptamer

<400> SEQUENCE: 1170
gguguauugg cccauuaugg ggauugacug ugauugagug                    40

<210> SEQ ID NO 1171
<211> LENGTH: 40
<212> TYPE: RNA
<213> ORGANISM: Artificial
<220> FEATURE:
<223> OTHER INFORMATION: Aptamer

<400> SEQUENCE: 1171
gguguauugg ccugugacag ucugcucugc ugugcucugg                    40

<210> SEQ ID NO 1172
<211> LENGTH: 40
<212> TYPE: RNA
<213> ORGANISM: Artificial
<220> FEATURE:
<223> OTHER INFORMATION: Aptamer

<400> SEQUENCE: 1172
gguguauugg ccuucaucgu gccuccgcag gugcuuguua                    40

<210> SEQ ID NO 1173
<211> LENGTH: 40
<212> TYPE: RNA
<213> ORGANISM: Artificial
<220> FEATURE:
<223> OTHER INFORMATION: Aptamer

<400> SEQUENCE: 1173
gguguauugg cgaucaucga ugaucgaccg guggcugcug                    40

<210> SEQ ID NO 1174
<211> LENGTH: 40
<212> TYPE: RNA
<213> ORGANISM: Artificial
<220> FEATURE:
<223> OTHER INFORMATION: Aptamer

<400> SEQUENCE: 1174
```

```
gguguauugg cggauuguau uuuguuugau cucucaccug                    40

<210> SEQ ID NO 1175
<211> LENGTH: 34
<212> TYPE: RNA
<213> ORGANISM: Artificial
<220> FEATURE:
<223> OTHER INFORMATION: Aptamer

<400> SEQUENCE: 1175
gguguauugg cuugucuucg ugauggagac uaug                          34

<210> SEQ ID NO 1176
<211> LENGTH: 40
<212> TYPE: RNA
<213> ORGANISM: Artificial
<220> FEATURE:
<223> OTHER INFORMATION: Aptamer

<400> SEQUENCE: 1176
gguguauugg uaccuuacgc ucuggaaagu gaguuuguua                    40

<210> SEQ ID NO 1177
<211> LENGTH: 39
<212> TYPE: RNA
<213> ORGANISM: Artificial
<220> FEATURE:
<223> OTHER INFORMATION: Aptamer

<400> SEQUENCE: 1177
gguguauugg ucaacgauac cucguuuugg guccaacga                     39

<210> SEQ ID NO 1178
<211> LENGTH: 40
<212> TYPE: RNA
<213> ORGANISM: Artificial
<220> FEATURE:
<223> OTHER INFORMATION: Aptamer

<400> SEQUENCE: 1178
gguguauugg ucagcuggaa agugauuccg uguguucgaa                    40

<210> SEQ ID NO 1179
<211> LENGTH: 40
<212> TYPE: RNA
<213> ORGANISM: Artificial
<220> FEATURE:
<223> OTHER INFORMATION: Aptamer

<400> SEQUENCE: 1179
gguguauugg ucauucggcu cgugaaucuc gauucaagga                    40

<210> SEQ ID NO 1180
<211> LENGTH: 40
<212> TYPE: RNA
<213> ORGANISM: Artificial
<220> FEATURE:
<223> OTHER INFORMATION: Aptamer

<400> SEQUENCE: 1180
gguguauugg ucggccgggu gacauugccu ugguaaucga                    40

<210> SEQ ID NO 1181
<211> LENGTH: 40
<212> TYPE: RNA
```

```
<213> ORGANISM: Artificial
<220> FEATURE:
<223> OTHER INFORMATION: Aptamer

<400> SEQUENCE: 1181
gguguauugg ucguuaacag gcuucuucca guuuuaucuu                           40

<210> SEQ ID NO 1182
<211> LENGTH: 40
<212> TYPE: RNA
<213> ORGANISM: Artificial
<220> FEATURE:
<223> OTHER INFORMATION: Aptamer

<400> SEQUENCE: 1182
gguguauugg ucguuagcuu aguucuugau ucuaauucga                           40

<210> SEQ ID NO 1183
<211> LENGTH: 40
<212> TYPE: RNA
<213> ORGANISM: Artificial
<220> FEATURE:
<223> OTHER INFORMATION: Aptamer

<400> SEQUENCE: 1183
gguguauugg ucuaccucuc gcgauacucg cguuguuuga                           40

<210> SEQ ID NO 1184
<211> LENGTH: 38
<212> TYPE: RNA
<213> ORGANISM: Artificial
<220> FEATURE:
<223> OTHER INFORMATION: Aptamer

<400> SEQUENCE: 1184
gguguauugg ucuauuaacu acggacguga agguuaga                             38

<210> SEQ ID NO 1185
<211> LENGTH: 40
<212> TYPE: RNA
<213> ORGANISM: Artificial
<220> FEATURE:
<223> OTHER INFORMATION: Aptamer

<400> SEQUENCE: 1185
gguguauugg ugcaucuuca gcugcuuuga acgacaaaca                           40

<210> SEQ ID NO 1186
<211> LENGTH: 40
<212> TYPE: RNA
<213> ORGANISM: Artificial
<220> FEATURE:
<223> OTHER INFORMATION: Aptamer

<400> SEQUENCE: 1186
gguguauugg ugcauucggc uauuaauuga accgacuacu                           40

<210> SEQ ID NO 1187
<211> LENGTH: 28
<212> TYPE: RNA
<213> ORGANISM: Artificial
<220> FEATURE:
<223> OTHER INFORMATION: Aptamer

<400> SEQUENCE: 1187
gguguauugg uggccuucuu uguccgug                                        28
```

```
<210> SEQ ID NO 1188
<211> LENGTH: 40
<212> TYPE: RNA
<213> ORGANISM: Artificial
<220> FEATURE:
<223> OTHER INFORMATION: Aptamer

<400> SEQUENCE: 1188
gguguauugg uuccucuguu acuucugguu ucaaguugaa                              40

<210> SEQ ID NO 1189
<211> LENGTH: 40
<212> TYPE: RNA
<213> ORGANISM: Artificial
<220> FEATURE:
<223> OTHER INFORMATION: Aptamer

<400> SEQUENCE: 1189
gguguauugg uuucaaaugc uucccggaag uugacgaguc                              40

<210> SEQ ID NO 1190
<211> LENGTH: 40
<212> TYPE: RNA
<213> ORGANISM: Artificial
<220> FEATURE:
<223> OTHER INFORMATION: Aptamer

<400> SEQUENCE: 1190
gguguauugg uuuuucuuuc cgaucaguuc guuagaaaua                              40

<210> SEQ ID NO 1191
<211> LENGTH: 40
<212> TYPE: RNA
<213> ORGANISM: Artificial
<220> FEATURE:
<223> OTHER INFORMATION: Aptamer

<400> SEQUENCE: 1191
gguuaacugg cccccguugc ccuaugcauc uugguggaug                              40

<210> SEQ ID NO 1192
<211> LENGTH: 40
<212> TYPE: RNA
<213> ORGANISM: Artificial
<220> FEATURE:
<223> OTHER INFORMATION: Aptamer

<400> SEQUENCE: 1192
gguuaacugg cgaaucguug ucauccgacc uugauuaaug                              40

<210> SEQ ID NO 1193
<211> LENGTH: 40
<212> TYPE: RNA
<213> ORGANISM: Artificial
<220> FEATURE:
<223> OTHER INFORMATION: Aptamer

<400> SEQUENCE: 1193
gguuaauugg ucuauagugu uuuaaucgau gccauaguua                              40

<210> SEQ ID NO 1194
<211> LENGTH: 40
<212> TYPE: RNA
<213> ORGANISM: Artificial
<220> FEATURE:
```

```
<223> OTHER INFORMATION: Aptamer

<400> SEQUENCE: 1194
gguuauauug gcuaugcgua ccuucugacg uagcacgaug                            40

<210> SEQ ID NO 1195
<211> LENGTH: 40
<212> TYPE: RNA
<213> ORGANISM: Artificial
<220> FEATURE:
<223> OTHER INFORMATION: Aptamer

<400> SEQUENCE: 1195
gguuauuggc gaccguucuu ucuaccuuga acuuggcuua                            40

<210> SEQ ID NO 1196
<211> LENGTH: 40
<212> TYPE: RNA
<213> ORGANISM: Artificial
<220> FEATURE:
<223> OTHER INFORMATION: Aptamer

<400> SEQUENCE: 1196
gguuauuggc uguucccga ugucuuggca ugauucgaug                             40

<210> SEQ ID NO 1197
<211> LENGTH: 40
<212> TYPE: RNA
<213> ORGANISM: Artificial
<220> FEATURE:
<223> OTHER INFORMATION: Aptamer

<400> SEQUENCE: 1197
gguuauuggu aggacuucuc uuccuuuag agguucguua                             40

<210> SEQ ID NO 1198
<211> LENGTH: 40
<212> TYPE: RNA
<213> ORGANISM: Artificial
<220> FEATURE:
<223> OTHER INFORMATION: Aptamer

<400> SEQUENCE: 1198
gguuauuggu cuaugcgauc acacuguugu cgcauauaua                            40

<210> SEQ ID NO 1199
<211> LENGTH: 40
<212> TYPE: RNA
<213> ORGANISM: Artificial
<220> FEATURE:
<223> OTHER INFORMATION: Aptamer

<400> SEQUENCE: 1199
gguugaauug gcuccgugcu cugaggggag agacgaaagu                            40

<210> SEQ ID NO 1200
<211> LENGTH: 40
<212> TYPE: RNA
<213> ORGANISM: Artificial
<220> FEATURE:
<223> OTHER INFORMATION: Aptamer

<400> SEQUENCE: 1200
gguugaauug gcucuggcau auuccuugga gugcagaaug                            40
```

```
<210> SEQ ID NO 1201
<211> LENGTH: 31
<212> TYPE: RNA
<213> ORGANISM: Artificial
<220> FEATURE:
<223> OTHER INFORMATION: Aptamer

<400> SEQUENCE: 1201
gguuuacugg cgauuucgcu uguauuuagu g                                    31

<210> SEQ ID NO 1202
<211> LENGTH: 40
<212> TYPE: RNA
<213> ORGANISM: Artificial
<220> FEATURE:
<223> OTHER INFORMATION: Aptamer

<400> SEQUENCE: 1202
gguuuacugg cgcuagcggc uguuggaccg cuugaucug                            40

<210> SEQ ID NO 1203
<211> LENGTH: 40
<212> TYPE: RNA
<213> ORGANISM: Artificial
<220> FEATURE:
<223> OTHER INFORMATION: Aptamer

<400> SEQUENCE: 1203
gguuuacugg cgcuaguggc uguuggaccg cuugaacug                            40

<210> SEQ ID NO 1204
<211> LENGTH: 40
<212> TYPE: RNA
<213> ORGANISM: Artificial
<220> FEATURE:
<223> OTHER INFORMATION: Aptamer

<400> SEQUENCE: 1204
gguuuacugg uccugcagcc gcuuuccggg ucgacgguua                           40

<210> SEQ ID NO 1205
<211> LENGTH: 40
<212> TYPE: RNA
<213> ORGANISM: Artificial
<220> FEATURE:
<223> OTHER INFORMATION: Aptamer

<400> SEQUENCE: 1205
gguuuauugg ccgaauucua aagcucucag uuuccgcgug                           40

<210> SEQ ID NO 1206
<211> LENGTH: 40
<212> TYPE: RNA
<213> ORGANISM: Artificial
<220> FEATURE:
<223> OTHER INFORMATION: Aptamer

<400> SEQUENCE: 1206
gguuuauugg cgauaaccac guuguugugu auguuauuug                           40

<210> SEQ ID NO 1207
<211> LENGTH: 40
<212> TYPE: RNA
<213> ORGANISM: Artificial
<220> FEATURE:
<223> OTHER INFORMATION: Aptamer
```

-continued

<400> SEQUENCE: 1207
gguuuauugg cgucaggauc gccaccgauc ugacgagcug                          40

<210> SEQ ID NO 1208
<211> LENGTH: 40
<212> TYPE: RNA
<213> ORGANISM: Artificial
<220> FEATURE:
<223> OTHER INFORMATION: Aptamer

<400> SEQUENCE: 1208
gguuuauugg cuagccaugu aaaugacuac uaugcucaug                          40

<210> SEQ ID NO 1209
<211> LENGTH: 40
<212> TYPE: RNA
<213> ORGANISM: Artificial
<220> FEATURE:
<223> OTHER INFORMATION: Aptamer

<400> SEQUENCE: 1209
gguuuauugg cuagccgugu aaaugacuac uaugcucaug                          40

<210> SEQ ID NO 1210
<211> LENGTH: 40
<212> TYPE: RNA
<213> ORGANISM: Artificial
<220> FEATURE:
<223> OTHER INFORMATION: Aptamer

<400> SEQUENCE: 1210
gguuuauugg ucgugacuuu cuuucgcgug gucaaaguuu                          40

<210> SEQ ID NO 1211
<211> LENGTH: 38
<212> TYPE: RNA
<213> ORGANISM: Artificial
<220> FEATURE:
<223> OTHER INFORMATION: Aptamer

<400> SEQUENCE: 1211
gguuuauugg uguucgccua ucgauuuuug ggcuuuua                            38

<210> SEQ ID NO 1212
<211> LENGTH: 41
<212> TYPE: RNA
<213> ORGANISM: Artificial
<220> FEATURE:
<223> OTHER INFORMATION: Aptamer

<400> SEQUENCE: 1212
gguuuauugg uguucgccua ucgauuuuuu gggcuuuuua u                        41

<210> SEQ ID NO 1213
<211> LENGTH: 40
<212> TYPE: RNA
<213> ORGANISM: Artificial
<220> FEATURE:
<223> OTHER INFORMATION: Aptamer

<400> SEQUENCE: 1213
gguuuauugg uguuugcuca guccgccccg aacauccgug                          40

<210> SEQ ID NO 1214
<211> LENGTH: 40

```
<212> TYPE: RNA
<213> ORGANISM: Artificial
<220> FEATURE:
<223> OTHER INFORMATION: Aptamer

<400> SEQUENCE: 1214
gguuuauugg uuugccuuga augggucccgc cauggcagug                              40

<210> SEQ ID NO 1215
<211> LENGTH: 40
<212> TYPE: RNA
<213> ORGANISM: Artificial
<220> FEATURE:
<223> OTHER INFORMATION: Aptamer

<400> SEQUENCE: 1215
gguuuuacug gcgcuggacc uuugucaccc ugacugaaug                              40

<210> SEQ ID NO 1216
<211> LENGTH: 40
<212> TYPE: RNA
<213> ORGANISM: Artificial
<220> FEATURE:
<223> OTHER INFORMATION: Aptamer

<400> SEQUENCE: 1216
gguuuuauug guuucagcgc cagucugagg ucguuggaua                              40

<210> SEQ ID NO 1217
<211> LENGTH: 40
<212> TYPE: RNA
<213> ORGANISM: Artificial
<220> FEATURE:
<223> OTHER INFORMATION: Aptamer

<400> SEQUENCE: 1217
aaauugcuug uccacaucgg uuuacugguc uccccuguuu                              40

<210> SEQ ID NO 1218
<211> LENGTH: 40
<212> TYPE: RNA
<213> ORGANISM: Artificial
<220> FEATURE:
<223> OTHER INFORMATION: Aptamer

<400> SEQUENCE: 1218
aaagguguau uggucucgcu acaguuacuu gcauacuuga                              40

<210> SEQ ID NO 1219
<211> LENGTH: 40
<212> TYPE: RNA
<213> ORGANISM: Artificial
<220> FEATURE:
<223> OTHER INFORMATION: Aptamer

<400> SEQUENCE: 1219
aacacguuau gguguauugg cgagagcauu gcuuugaagu                              40

<210> SEQ ID NO 1220
<211> LENGTH: 41
<212> TYPE: RNA
<213> ORGANISM: Artificial
<220> FEATURE:
<223> OTHER INFORMATION: Aptamer

<400> SEQUENCE: 1220
```
aacacguuau ggnguauugg cgaggagcau ugcuuugaag u        41

<210> SEQ ID NO 1221
<211> LENGTH: 40
<212> TYPE: RNA
<213> ORGANISM: Artificial
<220> FEATURE:
<223> OTHER INFORMATION: Aptamer

<400> SEQUENCE: 1221
aacacuccac gagucugggu uuacuggucg uucuuugucu          40

<210> SEQ ID NO 1222
<211> LENGTH: 40
<212> TYPE: RNA
<213> ORGANISM: Artificial
<220> FEATURE:
<223> OTHER INFORMATION: Aptamer

<400> SEQUENCE: 1222
aaccaugacu cuacaaccgg guauauuggu cuucuugucu          40

<210> SEQ ID NO 1223
<211> LENGTH: 41
<212> TYPE: RNA
<213> ORGANISM: Artificial
<220> FEATURE:
<223> OTHER INFORMATION: Aptamer

<400> SEQUENCE: 1223
aaccgauugu ggccucaggu guacugguuc uugucgggcg a        41

<210> SEQ ID NO 1224
<211> LENGTH: 40
<212> TYPE: RNA
<213> ORGANISM: Artificial
<220> FEATURE:
<223> OTHER INFORMATION: Aptamer

<400> SEQUENCE: 1224
aaccgccggu uggguguauu ggucuuguau ccuacgauga          40

<210> SEQ ID NO 1225
<211> LENGTH: 39
<212> TYPE: RNA
<213> ORGANISM: Artificial
<220> FEATURE:
<223> OTHER INFORMATION: Aptamer

<400> SEQUENCE: 1225
aaccucaguc uagguguauu ggcuuguguc gcuacguag           39

<210> SEQ ID NO 1226
<211> LENGTH: 41
<212> TYPE: RNA
<213> ORGANISM: Artificial
<220> FEATURE:
<223> OTHER INFORMATION: Aptamer

<400> SEQUENCE: 1226
aacguagaug cuaugucggu gccacuggug auucggccgc g        41

<210> SEQ ID NO 1227
<211> LENGTH: 40
<212> TYPE: RNA
<213> ORGANISM: Artificial

```
<220> FEATURE:
<223> OTHER INFORMATION: Aptamer

<400> SEQUENCE: 1227
aacgucgacg guguauuggc caaucauacu gagauucugg                               40

<210> SEQ ID NO 1228
<211> LENGTH: 40
<212> TYPE: RNA
<213> ORGANISM: Artificial
<220> FEATURE:
<223> OTHER INFORMATION: Aptamer

<400> SEQUENCE: 1228
aacgugaugc uaugucggug ccacugguga uucggccgca                               40

<210> SEQ ID NO 1229
<211> LENGTH: 40
<212> TYPE: RNA
<213> ORGANISM: Artificial
<220> FEATURE:
<223> OTHER INFORMATION: Aptamer

<400> SEQUENCE: 1229
aacgugugcc cccuccuguc ugggugaauu ggcuucgga                                40

<210> SEQ ID NO 1230
<211> LENGTH: 40
<212> TYPE: RNA
<213> ORGANISM: Artificial
<220> FEATURE:
<223> OTHER INFORMATION: Aptamer

<400> SEQUENCE: 1230
aacucgcgca aaccaggugu auuggccacg accgcggaua                               40

<210> SEQ ID NO 1231
<211> LENGTH: 42
<212> TYPE: RNA
<213> ORGANISM: Artificial
<220> FEATURE:
<223> OTHER INFORMATION: Aptamer

<400> SEQUENCE: 1231
aacucgcuuc ggguuuauug gcaggauuuc gacaguccac ug                            42

<210> SEQ ID NO 1232
<211> LENGTH: 34
<212> TYPE: RNA
<213> ORGANISM: Artificial
<220> FEATURE:
<223> OTHER INFORMATION: Aptamer

<400> SEQUENCE: 1232
aacucugggu guauggguau gcguuuaaau gcua                                     34

<210> SEQ ID NO 1233
<211> LENGTH: 40
<212> TYPE: RNA
<213> ORGANISM: Artificial
<220> FEATURE:
<223> OTHER INFORMATION: Aptamer

<400> SEQUENCE: 1233
aacucgguua cuggcugcau cagacucgcu ggugcgcaug                               40
```

<210> SEQ ID NO 1234
<211> LENGTH: 40
<212> TYPE: RNA
<213> ORGANISM: Artificial
<220> FEATURE:
<223> OTHER INFORMATION: Aptamer

<400> SEQUENCE: 1234
aacugcagaa accgggugga uuggcuccuu cauugguacg                                40

<210> SEQ ID NO 1235
<211> LENGTH: 40
<212> TYPE: RNA
<213> ORGANISM: Artificial
<220> FEATURE:
<223> OTHER INFORMATION: Aptamer

<400> SEQUENCE: 1235
aacugccugu cuagguguau ugguuggaua ggaacgcgua                                40

<210> SEQ ID NO 1236
<211> LENGTH: 40
<212> TYPE: RNA
<213> ORGANISM: Artificial
<220> FEATURE:
<223> OTHER INFORMATION: Aptamer

<400> SEQUENCE: 1236
aacugcuucc ggguaauugg ugcaucgagg uucaugcgug                                40

<210> SEQ ID NO 1237
<211> LENGTH: 40
<212> TYPE: RNA
<213> ORGANISM: Artificial
<220> FEATURE:
<223> OTHER INFORMATION: Aptamer

<400> SEQUENCE: 1237
aacuguacaa ccccggugua ugguuaccc aucucguaaa                                 40

<210> SEQ ID NO 1238
<211> LENGTH: 40
<212> TYPE: RNA
<213> ORGANISM: Artificial
<220> FEATURE:
<223> OTHER INFORMATION: Aptamer

<400> SEQUENCE: 1238
aacuucggug uauugguugu gaccguuaag gcuucgcgua                                40

<210> SEQ ID NO 1239
<211> LENGTH: 40
<212> TYPE: RNA
<213> ORGANISM: Artificial
<220> FEATURE:
<223> OTHER INFORMATION: Aptamer

<400> SEQUENCE: 1239
aacuuuccag guguacuggu augugccuuc ugcccuguuc                                40

<210> SEQ ID NO 1240
<211> LENGTH: 40
<212> TYPE: RNA
<213> ORGANISM: Artificial
<220> FEATURE:
<223> OTHER INFORMATION: Aptamer

<400> SEQUENCE: 1240
aacgguguac uggcuucuuu gguuucuuc uggagguaug                                   40

<210> SEQ ID NO 1241
<211> LENGTH: 35
<212> TYPE: RNA
<213> ORGANISM: Artificial
<220> FEATURE:
<223> OTHER INFORMATION: Aptamer

<400> SEQUENCE: 1241
aacgguguau uggcuucag auuucugac guuga                                        35

<210> SEQ ID NO 1242
<211> LENGTH: 39
<212> TYPE: RNA
<213> ORGANISM: Artificial
<220> FEATURE:
<223> OTHER INFORMATION: Aptamer

<400> SEQUENCE: 1242
aagacgacuc cucaaggugu acugguucaa accucgaua                                   39

<210> SEQ ID NO 1243
<211> LENGTH: 40
<212> TYPE: RNA
<213> ORGANISM: Artificial
<220> FEATURE:
<223> OTHER INFORMATION: Aptamer

<400> SEQUENCE: 1243
aagcugacug ccuuuagguu uacuggugga cuccuccgug                                  40

<210> SEQ ID NO 1244
<211> LENGTH: 37
<212> TYPE: RNA
<213> ORGANISM: Artificial
<220> FEATURE:
<223> OTHER INFORMATION: Aptamer

<400> SEQUENCE: 1244
aagucccuaa gccccggugu acuggucuuc cgauuua                                     37

<210> SEQ ID NO 1245
<211> LENGTH: 40
<212> TYPE: RNA
<213> ORGANISM: Artificial
<220> FEATURE:
<223> OTHER INFORMATION: Aptamer

<400> SEQUENCE: 1245
aauccuccgg cucuugguaa auuggcuccc aucgggaaug                                  40

<210> SEQ ID NO 1246
<211> LENGTH: 40
<212> TYPE: RNA
<213> ORGANISM: Artificial
<220> FEATURE:
<223> OTHER INFORMATION: Aptamer

<400> SEQUENCE: 1246
aaucuugacu uguccgggu auauuggugg aaaaucuaua                                   40

<210> SEQ ID NO 1247

```
<211> LENGTH: 40
<212> TYPE: RNA
<213> ORGANISM: Artificial
<220> FEATURE:
<223> OTHER INFORMATION: Aptamer

<400> SEQUENCE: 1247
aaugcuaucc auacgguuua cuggcggacc uccugucgug                              40

<210> SEQ ID NO 1248
<211> LENGTH: 40
<212> TYPE: RNA
<213> ORGANISM: Artificial
<220> FEATURE:
<223> OTHER INFORMATION: Aptamer

<400> SEQUENCE: 1248
aaugucugau augucugggu guacuggugc auccauguua                              40

<210> SEQ ID NO 1249
<211> LENGTH: 40
<212> TYPE: RNA
<213> ORGANISM: Artificial
<220> FEATURE:
<223> OTHER INFORMATION: Aptamer

<400> SEQUENCE: 1249
aauucgcuuc cuuucuuggu agacuggcgg gcagguauuu                              40

<210> SEQ ID NO 1250
<211> LENGTH: 40
<212> TYPE: RNA
<213> ORGANISM: Artificial
<220> FEATURE:
<223> OTHER INFORMATION: Aptamer

<400> SEQUENCE: 1250
aauuuggucu acuggucgca ugggucucgu cucggcggug                              40

<210> SEQ ID NO 1251
<211> LENGTH: 41
<212> TYPE: RNA
<213> ORGANISM: Artificial
<220> FEATURE:
<223> OTHER INFORMATION: Aptamer

<400> SEQUENCE: 1251
aauuuggucu acuggucgca ugggucucgu cucggucggu g                            41

<210> SEQ ID NO 1252
<211> LENGTH: 40
<212> TYPE: RNA
<213> ORGANISM: Artificial
<220> FEATURE:
<223> OTHER INFORMATION: Aptamer

<400> SEQUENCE: 1252
aaugguguac uggcgcacac cccuuuacug uggugcugug                              40

<210> SEQ ID NO 1253
<211> LENGTH: 40
<212> TYPE: RNA
<213> ORGANISM: Artificial
<220> FEATURE:
<223> OTHER INFORMATION: Aptamer

<400> SEQUENCE: 1253
```

-continued aagguaaacu gguggaugu cguuugacga ucguucgug        40

<210> SEQ ID NO 1254
<211> LENGTH: 40
<212> TYPE: RNA
<213> ORGANISM: Artificial
<220> FEATURE:
<223> OTHER INFORMATION: Aptamer

<400> SEQUENCE: 1254
aagguguauu ggcauaguuu guucgaguuc gcaacauuug        40

<210> SEQ ID NO 1255
<211> LENGTH: 40
<212> TYPE: RNA
<213> ORGANISM: Artificial
<220> FEATURE:
<223> OTHER INFORMATION: Aptamer

<400> SEQUENCE: 1255
aagguguauu ggcucggccg uucccaggac ggugucaggu        40

<210> SEQ ID NO 1256
<211> LENGTH: 40
<212> TYPE: RNA
<213> ORGANISM: Artificial
<220> FEATURE:
<223> OTHER INFORMATION: Aptamer

<400> SEQUENCE: 1256
aagguuaauu ggugcacaca cucguugucu cuugugaaua        40

<210> SEQ ID NO 1257
<211> LENGTH: 40
<212> TYPE: RNA
<213> ORGANISM: Artificial
<220> FEATURE:
<223> OTHER INFORMATION: Aptamer

<400> SEQUENCE: 1257
aagguugauu ggugaagggc aaucucucgc accuuaucua        40

<210> SEQ ID NO 1258
<211> LENGTH: 40
<212> TYPE: RNA
<213> ORGANISM: Artificial
<220> FEATURE:
<223> OTHER INFORMATION: Aptamer

<400> SEQUENCE: 1258
aagguugauu ggugcuucga guccucauac uccuggcgug        40

<210> SEQ ID NO 1259
<211> LENGTH: 40
<212> TYPE: RNA
<213> ORGANISM: Artificial
<220> FEATURE:
<223> OTHER INFORMATION: Aptamer

<400> SEQUENCE: 1259
acacuugccu uuucuugucc ggguuuauug gucguugugu        40

<210> SEQ ID NO 1260
<211> LENGTH: 38
<212> TYPE: RNA

```
<213> ORGANISM: Artificial
<220> FEATURE:
<223> OTHER INFORMATION: Aptamer

<400> SEQUENCE: 1260
acacuugcuu uucuuguccg gguuuauugg ucguugug                                   38

<210> SEQ ID NO 1261
<211> LENGTH: 41
<212> TYPE: RNA
<213> ORGANISM: Artificial
<220> FEATURE:
<223> OTHER INFORMATION: Aptamer

<400> SEQUENCE: 1261
acacuugcuu uuucuuguc cggguuuauu ggucguugug u                                41

<210> SEQ ID NO 1262
<211> LENGTH: 41
<212> TYPE: RNA
<213> ORGANISM: Artificial
<220> FEATURE:
<223> OTHER INFORMATION: Aptamer

<400> SEQUENCE: 1262
acacuugucu uuucuuguc cggguuuauu ggucguugug u                                41

<210> SEQ ID NO 1263
<211> LENGTH: 40
<212> TYPE: RNA
<213> ORGANISM: Artificial
<220> FEATURE:
<223> OTHER INFORMATION: Aptamer

<400> SEQUENCE: 1263
acacgguuau ugguccaugc uucgaucugu ugcaggaaua                                 40

<210> SEQ ID NO 1264
<211> LENGTH: 40
<212> TYPE: RNA
<213> ORGANISM: Artificial
<220> FEATURE:
<223> OTHER INFORMATION: Aptamer

<400> SEQUENCE: 1264
acagcaccga cuacgcguau ccgguuuauu gguccaguuu                                 40

<210> SEQ ID NO 1265
<211> LENGTH: 40
<212> TYPE: RNA
<213> ORGANISM: Artificial
<220> FEATURE:
<223> OTHER INFORMATION: Aptamer

<400> SEQUENCE: 1265
accaauugcg uguuucggg uuauuggcuc acuuugcaug                                  40

<210> SEQ ID NO 1266
<211> LENGTH: 39
<212> TYPE: RNA
<213> ORGANISM: Artificial
<220> FEATURE:
<223> OTHER INFORMATION: Aptamer

<400> SEQUENCE: 1266 accccccugag auccaggugu acuggcuguu ccggcgagg                                 39
```

<210> SEQ ID NO 1267
<211> LENGTH: 38
<212> TYPE: RNA
<213> ORGANISM: Artificial
<220> FEATURE:
<223> OTHER INFORMATION: Aptamer

<400> SEQUENCE: 1267 acccgucua gguuauuggc ucucuaaggu cgggaaug                    38

<210> SEQ ID NO 1268
<211> LENGTH: 40
<212> TYPE: RNA
<213> ORGANISM: Artificial
<220> FEATURE:
<223> OTHER INFORMATION: Aptamer

<400> SEQUENCE: 1268
acccgggugu acuggcgcug ggcaucaugc aucucggcug                 40

<210> SEQ ID NO 1269
<211> LENGTH: 40
<212> TYPE: RNA
<213> ORGANISM: Artificial
<220> FEATURE:
<223> OTHER INFORMATION: Aptamer

<400> SEQUENCE: 1269
acccucacuc cgggucaaau uggcgccaau guaugaaaug                 40

<210> SEQ ID NO 1270
<211> LENGTH: 40
<212> TYPE: RNA
<213> ORGANISM: Artificial
<220> FEATURE:
<223> OTHER INFORMATION: Aptamer

<400> SEQUENCE: 1270
acccugauuc cgguuuauug gcuggaugcg uguauccaag                 40

<210> SEQ ID NO 1271
<211> LENGTH: 40
<212> TYPE: RNA
<213> ORGANISM: Artificial
<220> FEATURE:
<223> OTHER INFORMATION: Aptamer

<400> SEQUENCE: 1271
acccugcuuc gcugggugca uugguugcca auuccgcaaa                 40

<210> SEQ ID NO 1272
<211> LENGTH: 40
<212> TYPE: RNA
<213> ORGANISM: Artificial
<220> FEATURE:
<223> OTHER INFORMATION: Aptamer

<400> SEQUENCE: 1272
acccuucuuc ugccaggua uauugguuuc uccgagagua                  40

<210> SEQ ID NO 1273
<211> LENGTH: 40
<212> TYPE: RNA
<213> ORGANISM: Artificial
<220> FEATURE:

<223> OTHER INFORMATION: Aptamer

<400> SEQUENCE: 1273
accggguuac uggcgucauu acgauuaccg ugucgaagug                                40

<210> SEQ ID NO 1274
<211> LENGTH: 40
<212> TYPE: RNA
<213> ORGANISM: Artificial
<220> FEATURE:
<223> OTHER INFORMATION: Aptamer

<400> SEQUENCE: 1274
accggguuac uggcgucguu acaauuaccg ugucgaagug                                40

<210> SEQ ID NO 1275
<211> LENGTH: 40
<212> TYPE: RNA
<213> ORGANISM: Artificial
<220> FEATURE:
<223> OTHER INFORMATION: Aptamer

<400> SEQUENCE: 1275
accggguuac uggcgucguu acgguuaccg ugucgaagug                                40

<210> SEQ ID NO 1276
<211> LENGTH: 40
<212> TYPE: RNA
<213> ORGANISM: Artificial
<220> FEATURE:
<223> OTHER INFORMATION: Aptamer

<400> SEQUENCE: 1276
accuucacgu ucggguguga uugguguau cuuugaguaa                                 40

<210> SEQ ID NO 1277
<211> LENGTH: 39
<212> TYPE: RNA
<213> ORGANISM: Artificial
<220> FEATURE:
<223> OTHER INFORMATION: Aptamer

<400> SEQUENCE: 1277
accgguuacu ggcgucguua cgauuaccgu gucgaagug                                 39

<210> SEQ ID NO 1278
<211> LENGTH: 39
<212> TYPE: RNA
<213> ORGANISM: Artificial
<220> FEATURE:
<223> OTHER INFORMATION: Aptamer

<400> SEQUENCE: 1278
acgacugggu gcacuggcgg aguuugacua acuuagcug                                 39

<210> SEQ ID NO 1279
<211> LENGTH: 40
<212> TYPE: RNA
<213> ORGANISM: Artificial
<220> FEATURE:
<223> OTHER INFORMATION: Aptamer

<400> SEQUENCE: 1279
acgauccuuu gacgguguau uggcuuucgu cuugcgcaga                                40

```
<210> SEQ ID NO 1280
<211> LENGTH: 40
<212> TYPE: RNA
<213> ORGANISM: Artificial
<220> FEATURE:
<223> OTHER INFORMATION: Aptamer

<400> SEQUENCE: 1280
acgcagaucu uccacgugcc uagguguauu gguaguauua                                40

<210> SEQ ID NO 1281
<211> LENGTH: 40
<212> TYPE: RNA
<213> ORGANISM: Artificial
<220> FEATURE:
<223> OTHER INFORMATION: Aptamer

<400> SEQUENCE: 1281
acgcggucau uggcuucguc cuaccuuuca ggacgugaug                                40

<210> SEQ ID NO 1282
<211> LENGTH: 40
<212> TYPE: RNA
<213> ORGANISM: Artificial
<220> FEATURE:
<223> OTHER INFORMATION: Aptamer

<400> SEQUENCE: 1282
acgcggucua cuggcgcauc uuuucccag aguauggcug                                 40

<210> SEQ ID NO 1283
<211> LENGTH: 40
<212> TYPE: RNA
<213> ORGANISM: Artificial
<220> FEATURE:
<223> OTHER INFORMATION: Aptamer

<400> SEQUENCE: 1283
acguaugucg ucgagagguc auuggcggcu agaagcaaug                                40

<210> SEQ ID NO 1284
<211> LENGTH: 37
<212> TYPE: RNA
<213> ORGANISM: Artificial
<220> FEATURE:
<223> OTHER INFORMATION: Aptamer

<400> SEQUENCE: 1284
acguccgggu uuauuggcgc ucuuucaccu uugaaug                                   37

<210> SEQ ID NO 1285
<211> LENGTH: 39
<212> TYPE: RNA
<213> ORGANISM: Artificial
<220> FEATURE:
<223> OTHER INFORMATION: Aptamer

<400> SEQUENCE: 1285
acgucugcgg uuuauugguu ggcccacuug gugccuaua                                 39

<210> SEQ ID NO 1286
<211> LENGTH: 39
<212> TYPE: RNA
<213> ORGANISM: Artificial
<220> FEATURE:
<223> OTHER INFORMATION: Aptamer
```

```
<400> SEQUENCE: 1286
acgucuuagg uuuauuggug cuauuauuuu acuggcgug                              39

<210> SEQ ID NO 1287
<211> LENGTH: 40
<212> TYPE: RNA
<213> ORGANISM: Artificial
<220> FEATURE:
<223> OTHER INFORMATION: Aptamer

<400> SEQUENCE: 1287 acguccaca cuguccuccu gcgguguauu ggucuuucua                              40

<210> SEQ ID NO 1288
<211> LENGTH: 40
<212> TYPE: RNA
<213> ORGANISM: Artificial
<220> FEATURE:
<223> OTHER INFORMATION: Aptamer

<400> SEQUENCE: 1288
acgggugaau ugguaguggu gcuccuuggc gucauacuua                             40

<210> SEQ ID NO 1289
<211> LENGTH: 40
<212> TYPE: RNA
<213> ORGANISM: Artificial
<220> FEATURE:
<223> OTHER INFORMATION: Aptamer

<400> SEQUENCE: 1289
acuauuggug gauugguaau ucgguuuugc uugaaacaua                             40

<210> SEQ ID NO 1290
<211> LENGTH: 40
<212> TYPE: RNA
<213> ORGANISM: Artificial
<220> FEATURE:
<223> OTHER INFORMATION: Aptamer

<400> SEQUENCE: 1290
acuaugguca uuggcugccc uccuuaaucg ccgggcgaug                             40

<210> SEQ ID NO 1291
<211> LENGTH: 40
<212> TYPE: RNA
<213> ORGANISM: Artificial
<220> FEATURE:
<223> OTHER INFORMATION: Aptamer

<400> SEQUENCE: 1291
acucggcguu uacgguguac uggguucucu cggaauugua                             40

<210> SEQ ID NO 1292
<211> LENGTH: 40
<212> TYPE: RNA
<213> ORGANISM: Artificial
<220> FEATURE:
<223> OTHER INFORMATION: Aptamer

<400> SEQUENCE: 1292
acucucgggu guauuggucg ccgaucuuuu ucaggugaga                             40

<210> SEQ ID NO 1293
<211> LENGTH: 40
```

```
<212> TYPE: RNA
<213> ORGANISM: Artificial
<220> FEATURE:
<223> OTHER INFORMATION: Aptamer

<400> SEQUENCE: 1293
acucugcuuu ucggcucggu gaacuggccu gucugggug                              40

<210> SEQ ID NO 1294
<211> LENGTH: 40
<212> TYPE: RNA
<213> ORGANISM: Artificial
<220> FEATURE:
<223> OTHER INFORMATION: Aptamer

<400> SEQUENCE: 1294
acugggcuua ccguccaaac gguguauugg ccaccuggug                             40

<210> SEQ ID NO 1295
<211> LENGTH: 40
<212> TYPE: RNA
<213> ORGANISM: Artificial
<220> FEATURE:
<223> OTHER INFORMATION: Aptamer

<400> SEQUENCE: 1295
acugguuccg gguguacugg uuuuacauuc cgauguaauu                             40

<210> SEQ ID NO 1296
<211> LENGTH: 40
<212> TYPE: RNA
<213> ORGANISM: Artificial
<220> FEATURE:
<223> OTHER INFORMATION: Aptamer

<400> SEQUENCE: 1296
acugucuguu ggguaauugg cuugucuccu cugauagaug                             40

<210> SEQ ID NO 1297
<211> LENGTH: 40
<212> TYPE: RNA
<213> ORGANISM: Artificial
<220> FEATURE:
<223> OTHER INFORMATION: Aptamer

<400> SEQUENCE: 1297
acuguuuugu cuagguucau uggcgcuuau uccuggaaug                             40

<210> SEQ ID NO 1298
<211> LENGTH: 40
<212> TYPE: RNA
<213> ORGANISM: Artificial
<220> FEATURE:
<223> OTHER INFORMATION: Aptamer

<400> SEQUENCE: 1298
acuuccgcuu gucuuggugg acugguuauu uguuaaugua                             40

<210> SEQ ID NO 1299
<211> LENGTH: 40
<212> TYPE: RNA
<213> ORGANISM: Artificial
<220> FEATURE:
<223> OTHER INFORMATION: Aptamer

<400> SEQUENCE: 1299
```

```
acuugccguu ucggguacu ggcgacguuu agacgaugug                    40

<210> SEQ ID NO 1300
<211> LENGTH: 41
<212> TYPE: RNA
<213> ORGANISM: Artificial
<220> FEATURE:
<223> OTHER INFORMATION: Aptamer

<400> SEQUENCE: 1300
acuuucucga uuucaggugu auuggccauc uuccgaucua g                 41

<210> SEQ ID NO 1301
<211> LENGTH: 40
<212> TYPE: RNA
<213> ORGANISM: Artificial
<220> FEATURE:
<223> OTHER INFORMATION: Aptamer

<400> SEQUENCE: 1301
acgguagacu ggcugcuaac cggcgucugu cuuggcgaug                   40

<210> SEQ ID NO 1302
<211> LENGTH: 40
<212> TYPE: RNA
<213> ORGANISM: Artificial
<220> FEATURE:
<223> OTHER INFORMATION: Aptamer

<400> SEQUENCE: 1302
acggugaauu ggcugaacca guuugcagcu uggcucaaug                   40

<210> SEQ ID NO 1303
<211> LENGTH: 41
<212> TYPE: RNA
<213> ORGANISM: Artificial
<220> FEATURE:
<223> OTHER INFORMATION: Aptamer

<400> SEQUENCE: 1303
acgguuuuac uggcgauuga ucuggccucg cucuuuuagu g                 41

<210> SEQ ID NO 1304
<211> LENGTH: 41
<212> TYPE: RNA
<213> ORGANISM: Artificial
<220> FEATURE:
<223> OTHER INFORMATION: Aptamer

<400> SEQUENCE: 1304
agaaagacgg gugcacuggu ugcuugcuuc cgaguguuuu u                 41

<210> SEQ ID NO 1305
<211> LENGTH: 40
<212> TYPE: RNA
<213> ORGANISM: Artificial
<220> FEATURE:
<223> OTHER INFORMATION: Aptamer

<400> SEQUENCE: 1305
agaaucuuuc guucacgcug gguguacugg ucuaccgcga                   40

<210> SEQ ID NO 1306
<211> LENGTH: 40
<212> TYPE: RNA
<213> ORGANISM: Artificial
```

```
<220> FEATURE:
<223> OTHER INFORMATION: Aptamer

<400> SEQUENCE: 1306
agacaucacg aacgguuau uggcgcguac ucacgaucug                              40

<210> SEQ ID NO 1307
<211> LENGTH: 39
<212> TYPE: RNA
<213> ORGANISM: Artificial
<220> FEATURE:
<223> OTHER INFORMATION: Aptamer

<400> SEQUENCE: 1307
agacuucgug cacaacaggu uuauuggucu uauuugaua                              39

<210> SEQ ID NO 1308
<211> LENGTH: 42
<212> TYPE: RNA
<213> ORGANISM: Artificial
<220> FEATURE:
<223> OTHER INFORMATION: Aptamer

<400> SEQUENCE: 1308
agacggugua cuggcacuuu uacuucauug aguagaaauu cg                          42

<210> SEQ ID NO 1309
<211> LENGTH: 40
<212> TYPE: RNA
<213> ORGANISM: Artificial
<220> FEATURE:
<223> OTHER INFORMATION: Aptamer

<400> SEQUENCE: 1309
agagcucgcc accucucgcc cgdguucauu gguccguuu                              40

<210> SEQ ID NO 1310
<211> LENGTH: 40
<212> TYPE: RNA
<213> ORGANISM: Artificial
<220> FEATURE:
<223> OTHER INFORMATION: Aptamer

<400> SEQUENCE: 1310
agaugcgccc cagguguauu gguccaucuu uugcugguga                             40

<210> SEQ ID NO 1311
<211> LENGTH: 40
<212> TYPE: RNA
<213> ORGANISM: Artificial
<220> FEATURE:
<223> OTHER INFORMATION: Aptamer

<400> SEQUENCE: 1311
agcaggugua cuggcucuag agucccuga uuugagaaug                              40

<210> SEQ ID NO 1312
<211> LENGTH: 40
<212> TYPE: RNA
<213> ORGANISM: Artificial
<220> FEATURE:
<223> OTHER INFORMATION: Aptamer

<400> SEQUENCE: 1312
agccucgucu ucuuggugua uuggucauua ugcuauguaa                             40
```

<210> SEQ ID NO 1313
<211> LENGTH: 40
<212> TYPE: RNA
<213> ORGANISM: Artificial
<220> FEATURE:
<223> OTHER INFORMATION: Aptamer

<400> SEQUENCE: 1313
agccuugggu guacuggcga aguugcguuu uaacuugcug                                40

<210> SEQ ID NO 1314
<211> LENGTH: 41
<212> TYPE: RNA
<213> ORGANISM: Artificial
<220> FEATURE:
<223> OTHER INFORMATION: Aptamer

<400> SEQUENCE: 1314
agccuuuuug ccuccccgau gguguauugg ucacgaaucg a                             41

<210> SEQ ID NO 1315
<211> LENGTH: 40
<212> TYPE: RNA
<213> ORGANISM: Artificial
<220> FEATURE:
<223> OTHER INFORMATION: Aptamer

<400> SEQUENCE: 1315
agcgccucga uaucgucucu agguguauug gcucuucuug                               40

<210> SEQ ID NO 1316
<211> LENGTH: 41
<212> TYPE: RNA
<213> ORGANISM: Artificial
<220> FEATURE:
<223> OTHER INFORMATION: Aptamer

<400> SEQUENCE: 1316
agcguuacuu aagcggugua uuggcacauu ucggugguuu g                             41

<210> SEQ ID NO 1317
<211> LENGTH: 40
<212> TYPE: RNA
<213> ORGANISM: Artificial
<220> FEATURE:
<223> OTHER INFORMATION: Aptamer

<400> SEQUENCE: 1317
agcuauguca ucgguguacu ggucgccuau cuaggcaaga                               40

<210> SEQ ID NO 1318
<211> LENGTH: 41
<212> TYPE: RNA
<213> ORGANISM: Artificial
<220> FEATURE:
<223> OTHER INFORMATION: Aptamer

<400> SEQUENCE: 1318
agcugcaguc ccccuuggug aacuggcugc uuccauguaa g                             41

<210> SEQ ID NO 1319
<211> LENGTH: 40
<212> TYPE: RNA
<213> ORGANISM: Artificial
<220> FEATURE:
<223> OTHER INFORMATION: Aptamer

```
<400> SEQUENCE: 1319
agcuggugaa uugguucuuu acuaauugug guguauugaa                          40

<210> SEQ ID NO 1320
<211> LENGTH: 40
<212> TYPE: RNA
<213> ORGANISM: Artificial
<220> FEATURE:
<223> OTHER INFORMATION: Aptamer

<400> SEQUENCE: 1320
aggaaaugca auggcucggu auacggugu cgcgcgauua                           40

<210> SEQ ID NO 1321
<211> LENGTH: 40
<212> TYPE: RNA
<213> ORGANISM: Artificial
<220> FEATURE:
<223> OTHER INFORMATION: Aptamer

<400> SEQUENCE: 1321
aggagcgaug uacucgccag guuaauuggu cauuucguuu                          40

<210> SEQ ID NO 1322
<211> LENGTH: 40
<212> TYPE: RNA
<213> ORGANISM: Artificial
<220> FEATURE:
<223> OTHER INFORMATION: Aptamer

<400> SEQUENCE: 1322
aggcacuucu cagguuuacu ggcacaaauu ugcuggaugg                          40

<210> SEQ ID NO 1323
<211> LENGTH: 37
<212> TYPE: RNA
<213> ORGANISM: Artificial
<220> FEATURE:
<223> OTHER INFORMATION: Aptamer

<400> SEQUENCE: 1323
aggucugggu guauuggcga aaucucgguu uguuug                              37

<210> SEQ ID NO 1324
<211> LENGTH: 40
<212> TYPE: RNA
<213> ORGANISM: Artificial
<220> FEATURE:
<223> OTHER INFORMATION: Aptamer

<400> SEQUENCE: 1324 aggggguguau uggcgguaga uagcucaaug uuuaccaugu                         40

<210> SEQ ID NO 1325
<211> LENGTH: 40
<212> TYPE: RNA
<213> ORGANISM: Artificial
<220> FEATURE:
<223> OTHER INFORMATION: Aptamer

<400> SEQUENCE: 1325
aguacugcuu caagguguau ugguagccuu caauugguca                          40

<210> SEQ ID NO 1326
```

```
<211> LENGTH: 40
<212> TYPE: RNA
<213> ORGANISM: Artificial
<220> FEATURE:
<223> OTHER INFORMATION: Aptamer

<400> SEQUENCE: 1326
agucacacag guccacuggu acuggauucu guccagugug                          40

<210> SEQ ID NO 1327
<211> LENGTH: 40
<212> TYPE: RNA
<213> ORGANISM: Artificial
<220> FEATURE:
<223> OTHER INFORMATION: Aptamer

<400> SEQUENCE: 1327
aguccauuug gguuacuggc aguugcuccg ucuacguugg                          40

<210> SEQ ID NO 1328
<211> LENGTH: 40
<212> TYPE: RNA
<213> ORGANISM: Artificial
<220> FEATURE:
<223> OTHER INFORMATION: Aptamer

<400> SEQUENCE: 1328
agucccggug uauuggccuc uuuucacuuc gauugguaug                          40

<210> SEQ ID NO 1329
<211> LENGTH: 40
<212> TYPE: RNA
<213> ORGANISM: Artificial
<220> FEATURE:
<223> OTHER INFORMATION: Aptamer

<400> SEQUENCE: 1329
agucguucgg guuuauuggu guccaugauc aacguucua                           40

<210> SEQ ID NO 1330
<211> LENGTH: 40
<212> TYPE: RNA
<213> ORGANISM: Artificial
<220> FEATURE:
<223> OTHER INFORMATION: Aptamer

<400> SEQUENCE: 1330
agucugcauc aaggugaacu ggcgaugccc cccaugucug                          40

<210> SEQ ID NO 1331
<211> LENGTH: 40
<212> TYPE: RNA
<213> ORGANISM: Artificial
<220> FEATURE:
<223> OTHER INFORMATION: Aptamer

<400> SEQUENCE: 1331
agucugcauc aaggugaauu ggcgaucgcc cccaugucug                          40

<210> SEQ ID NO 1332
<211> LENGTH: 39
<212> TYPE: RNA
<213> ORGANISM: Artificial
<220> FEATURE:
<223> OTHER INFORMATION: Aptamer

<400> SEQUENCE: 1332
```

```
agucugcauc aaggugaauu ggcgaugccc ccaugucug                                39

<210> SEQ ID NO 1333
<211> LENGTH: 41
<212> TYPE: RNA
<213> ORGANISM: Artificial
<220> FEATURE:
<223> OTHER INFORMATION: Aptamer

<400> SEQUENCE: 1333
agucugcauc aaggugaauu ggcgaugccc ccccaugucu g                             41

<210> SEQ ID NO 1334
<211> LENGTH: 40
<212> TYPE: RNA
<213> ORGANISM: Artificial
<220> FEATURE:
<223> OTHER INFORMATION: Aptamer

<400> SEQUENCE: 1334
agucuugggu guacuggcga aguugcguuu caacuugcug                              40

<210> SEQ ID NO 1335
<211> LENGTH: 40
<212> TYPE: RNA
<213> ORGANISM: Artificial
<220> FEATURE:
<223> OTHER INFORMATION: Aptamer

<400> SEQUENCE: 1335
agugcucguc uacuuggugg uuacuggugu cgcuggauua                              40

<210> SEQ ID NO 1336
<211> LENGTH: 39
<212> TYPE: RNA
<213> ORGANISM: Artificial
<220> FEATURE:
<223> OTHER INFORMATION: Aptamer

<400> SEQUENCE: 1336
aguuuucgca acguucgggu guauuggcgu aaaaacgag                               39

<210> SEQ ID NO 1337
<211> LENGTH: 40
<212> TYPE: RNA
<213> ORGANISM: Artificial
<220> FEATURE:
<223> OTHER INFORMATION: Aptamer

<400> SEQUENCE: 1337 augguuauu ggcgcauagc uuuucguagg uuuuugcaug                               40

<210> SEQ ID NO 1338
<211> LENGTH: 41
<212> TYPE: RNA
<213> ORGANISM: Artificial
<220> FEATURE:
<223> OTHER INFORMATION: Aptamer

<400> SEQUENCE: 1338
aggguaauug gcgcugucug guuuugaauc ugggcuggcu g                            41

<210> SEQ ID NO 1339
<211> LENGTH: 39
<212> TYPE: RNA
```

```
<213> ORGANISM: Artificial
<220> FEATURE:
<223> OTHER INFORMATION: Aptamer

<400> SEQUENCE: 1339
aggguaauug gcgcugucug uuugaaucug ggcuggcug                                39

<210> SEQ ID NO 1340
<211> LENGTH: 40
<212> TYPE: RNA
<213> ORGANISM: Artificial
<220> FEATURE:
<223> OTHER INFORMATION: Aptamer

<400> SEQUENCE: 1340
aggguaauug gcgcugucug uuuugaaucu gggcugacug                               40

<210> SEQ ID NO 1341
<211> LENGTH: 40
<212> TYPE: RNA
<213> ORGANISM: Artificial
<220> FEATURE:
<223> OTHER INFORMATION: Aptamer

<400> SEQUENCE: 1341 ggguggauu ggcgcuaagg aaguuaaucu acuuagaucg                                40

<210> SEQ ID NO 1342
<211> LENGTH: 40
<212> TYPE: RNA
<213> ORGANISM: Artificial
<220> FEATURE:
<223> OTHER INFORMATION: Aptamer

<400> SEQUENCE: 1342
aggguguauu ggcacaguuu ugccuacggc uaauugguug                               40

<210> SEQ ID NO 1343
<211> LENGTH: 40
<212> TYPE: RNA
<213> ORGANISM: Artificial
<220> FEATURE:
<223> OTHER INFORMATION: Aptamer

<400> SEQUENCE: 1343
aggguguauu ggcacaguuu ugcuuacgac uaauugguug                               40

<210> SEQ ID NO 1344
<211> LENGTH: 41
<212> TYPE: RNA
<213> ORGANISM: Artificial
<220> FEATURE:
<223> OTHER INFORMATION: Aptamer

<400> SEQUENCE: 1344
aggguguauu ggcacaguuu uugcuuacgg cuaauugguu g                             41

<210> SEQ ID NO 1345
<211> LENGTH: 40
<212> TYPE: RNA
<213> ORGANISM: Artificial
<220> FEATURE:
<223> OTHER INFORMATION: Aptamer

<400> SEQUENCE: 1345
aggguugauu ggugccacug uuguacugac aucggaguuu                               40
```

<210> SEQ ID NO 1346
<211> LENGTH: 40
<212> TYPE: RNA
<213> ORGANISM: Artificial
<220> FEATURE:
<223> OTHER INFORMATION: Aptamer

<400> SEQUENCE: 1346
auaacggugu auuggcuacu cagcuuuuga gcauguuguu                              40

<210> SEQ ID NO 1347
<211> LENGTH: 40
<212> TYPE: RNA
<213> ORGANISM: Artificial
<220> FEATURE:
<223> OTHER INFORMATION: Aptamer

<400> SEQUENCE: 1347
auacgacagu cuucagguua uuggcuucuu cuuagaaaug                              40

<210> SEQ ID NO 1348
<211> LENGTH: 40
<212> TYPE: RNA
<213> ORGANISM: Artificial
<220> FEATURE:
<223> OTHER INFORMATION: Aptamer

<400> SEQUENCE: 1348
auacugcauc augguagauu ggcagacuuc ccggucagug                              40

<210> SEQ ID NO 1349
<211> LENGTH: 40
<212> TYPE: RNA
<213> ORGANISM: Artificial
<220> FEATURE:
<223> OTHER INFORMATION: Aptamer

<400> SEQUENCE: 1349
auacugccuc guccgggug uacugguuaa ggauauugua                               40

<210> SEQ ID NO 1350
<211> LENGTH: 40
<212> TYPE: RNA
<213> ORGANISM: Artificial
<220> FEATURE:
<223> OTHER INFORMATION: Aptamer

<400> SEQUENCE: 1350
aucagguggu ucaacugguc cuuucgcaau ucaucgccca                              40

<210> SEQ ID NO 1351
<211> LENGTH: 40
<212> TYPE: RNA
<213> ORGANISM: Artificial
<220> FEATURE:
<223> OTHER INFORMATION: Aptamer

<400> SEQUENCE: 1351
auccgucuug guguauuggc ugugcccuug gcuuguauug                              40

<210> SEQ ID NO 1352
<211> LENGTH: 40
<212> TYPE: RNA
<213> ORGANISM: Artificial
<220> FEATURE:

```
<223> OTHER INFORMATION: Aptamer

<400> SEQUENCE: 1352
auccuaccgg cuccuuucca gguuaauugg ccucgcggug                          40

<210> SEQ ID NO 1353
<211> LENGTH: 40
<212> TYPE: RNA
<213> ORGANISM: Artificial
<220> FEATURE:
<223> OTHER INFORMATION: Aptamer

<400> SEQUENCE: 1353
aucgagaucu gcccaagggu gauuggcagc gaaauacuug                          40

<210> SEQ ID NO 1354
<211> LENGTH: 40
<212> TYPE: RNA
<213> ORGANISM: Artificial
<220> FEATURE:
<223> OTHER INFORMATION: Aptamer

<400> SEQUENCE: 1354
aucgccuggu gaauugguua gaugcgguga acucaucuuu                          40

<210> SEQ ID NO 1355
<211> LENGTH: 40
<212> TYPE: RNA
<213> ORGANISM: Artificial
<220> FEATURE:
<223> OTHER INFORMATION: Aptamer

<400> SEQUENCE: 1355
aucggugaau ugguacuaua cagcucacgu uguagaguua                          40

<210> SEQ ID NO 1356
<211> LENGTH: 40
<212> TYPE: RNA
<213> ORGANISM: Artificial
<220> FEATURE:
<223> OTHER INFORMATION: Aptamer

<400> SEQUENCE: 1356
aucgguuuac uggugguaau ucuuuccgag caauugcaua                          40

<210> SEQ ID NO 1357
<211> LENGTH: 40
<212> TYPE: RNA
<213> ORGANISM: Artificial
<220> FEATURE:
<223> OTHER INFORMATION: Aptamer

<400> SEQUENCE: 1357
augacguaca auggugaauu ggcuaucauu guugaaugug                          40

<210> SEQ ID NO 1358
<211> LENGTH: 40
<212> TYPE: RNA
<213> ORGANISM: Artificial
<220> FEATURE:
<223> OTHER INFORMATION: Aptamer

<400> SEQUENCE: 1358
augacucguc uucugguaua uuggccgguu aaucggugug                          40
```

```
<210> SEQ ID NO 1359
<211> LENGTH: 40
<212> TYPE: RNA
<213> ORGANISM: Artificial
<220> FEATURE:
<223> OTHER INFORMATION: Aptamer

<400> SEQUENCE: 1359
augacgguaa auuggcgaag auauuuauuc caucuucaug                            40

<210> SEQ ID NO 1360
<211> LENGTH: 40
<212> TYPE: RNA
<213> ORGANISM: Artificial
<220> FEATURE:
<223> OTHER INFORMATION: Aptamer

<400> SEQUENCE: 1360
augcuaguuc cucgguguau uggcgggucu uuccuguaaa                            40

<210> SEQ ID NO 1361
<211> LENGTH: 52
<212> TYPE: RNA
<213> ORGANISM: Artificial
<220> FEATURE:
<223> OTHER INFORMATION: Aptamer

<400> SEQUENCE: 1361
augcuaguuc cucgguguau ugguuugucg aaagccuccg ucucgacaua ua              52

<210> SEQ ID NO 1362
<211> LENGTH: 40
<212> TYPE: RNA
<213> ORGANISM: Artificial
<220> FEATURE:
<223> OTHER INFORMATION: Aptamer

<400> SEQUENCE: 1362
augcuauuuu uggguggacu ggcagcucuu gacgcgguaa                            40

<210> SEQ ID NO 1363
<211> LENGTH: 40
<212> TYPE: RNA
<213> ORGANISM: Artificial
<220> FEATURE:
<223> OTHER INFORMATION: Aptamer

<400> SEQUENCE: 1363
augguucaag guguauuggu agagucgcuu gcgcccgcua                            40

<210> SEQ ID NO 1364
<211> LENGTH: 40
<212> TYPE: RNA
<213> ORGANISM: Artificial
<220> FEATURE:
<223> OTHER INFORMATION: Aptamer

<400> SEQUENCE: 1364
auguccaggu guacugguag cucuuggccc uugaacuuca                            40

<210> SEQ ID NO 1365
<211> LENGTH: 40
<212> TYPE: RNA
<213> ORGANISM: Artificial
<220> FEATURE:
<223> OTHER INFORMATION: Aptamer
```

```
<400> SEQUENCE: 1365
auuauggugu auugguuggc cuuucuuucu cgcgugccga                              40

<210> SEQ ID NO 1366
<211> LENGTH: 40
<212> TYPE: RNA
<213> ORGANISM: Artificial
<220> FEATURE:
<223> OTHER INFORMATION: Aptamer

<400> SEQUENCE: 1366
auuccucucg guugauuggc uuugucguuc gcgacugaug                              40

<210> SEQ ID NO 1367
<211> LENGTH: 40
<212> TYPE: RNA
<213> ORGANISM: Artificial
<220> FEATURE:
<223> OTHER INFORMATION: Aptamer

<400> SEQUENCE: 1367
auuccuuguu cgaucccggu guauugguaa uacguuuuua                              40

<210> SEQ ID NO 1368
<211> LENGTH: 40
<212> TYPE: RNA
<213> ORGANISM: Artificial
<220> FEATURE:
<223> OTHER INFORMATION: Aptamer

<400> SEQUENCE: 1368
auucuccuuc agguguauug guuuuucaug guccauguua                              40

<210> SEQ ID NO 1369
<211> LENGTH: 42
<212> TYPE: RNA
<213> ORGANISM: Artificial
<220> FEATURE:
<223> OTHER INFORMATION: Aptamer

<400> SEQUENCE: 1369
auucuguucg ugucucuccg gguuuuacug gcgcuaugaa ug                           42

<210> SEQ ID NO 1370
<211> LENGTH: 40
<212> TYPE: RNA
<213> ORGANISM: Artificial
<220> FEATURE:
<223> OTHER INFORMATION: Aptamer

<400> SEQUENCE: 1370
auucuguucu gucccuccgg guuuacuggc gcuaugaaug                              40

<210> SEQ ID NO 1371
<211> LENGTH: 39
<212> TYPE: RNA
<213> ORGANISM: Artificial
<220> FEATURE:
<223> OTHER INFORMATION: Aptamer

<400> SEQUENCE: 1371
auucuguucu gucucuccgg guuacuggcg cuaugaaug                               39

<210> SEQ ID NO 1372
<211> LENGTH: 41
```

```
<212> TYPE: RNA
<213> ORGANISM: Artificial
<220> FEATURE:
<223> OTHER INFORMATION: Aptamer

<400> SEQUENCE: 1372
auucuguucu gucucuccgg guuuacuggc gacuaugaau g                          41

<210> SEQ ID NO 1373
<211> LENGTH: 40
<212> TYPE: RNA
<213> ORGANISM: Artificial
<220> FEATURE:
<223> OTHER INFORMATION: Aptamer

<400> SEQUENCE: 1373
auucuguucu gucucuccgg guuuacuggc gcaaugaaug                            40

<210> SEQ ID NO 1374
<211> LENGTH: 40
<212> TYPE: RNA
<213> ORGANISM: Artificial
<220> FEATURE:
<223> OTHER INFORMATION: Aptamer

<400> SEQUENCE: 1374
auucuguucu gucucuccgg guuuacuggc gcucugaaug                            40

<210> SEQ ID NO 1375
<211> LENGTH: 39
<212> TYPE: RNA
<213> ORGANISM: Artificial
<220> FEATURE:
<223> OTHER INFORMATION: Aptamer

<400> SEQUENCE: 1375
auucuguucu gucucuccgg guuuacuggc gcuuggcug                             39

<210> SEQ ID NO 1376
<211> LENGTH: 40
<212> TYPE: RNA
<213> ORGANISM: Artificial
<220> FEATURE:
<223> OTHER INFORMATION: Aptamer

<400> SEQUENCE: 1376
auucgguuua uugguagaac uguauuacuu accgcccaua                            40

<210> SEQ ID NO 1377
<211> LENGTH: 39
<212> TYPE: RNA
<213> ORGANISM: Artificial
<220> FEATURE:
<223> OTHER INFORMATION: Aptamer

<400> SEQUENCE: 1377
auuguccuca accguccuuu uugguaauug gucucgugu                             39

<210> SEQ ID NO 1378
<211> LENGTH: 39
<212> TYPE: RNA
<213> ORGANISM: Artificial
<220> FEATURE:
<223> OTHER INFORMATION: Aptamer

<400> SEQUENCE: 1378
```
auuuucccag guguacuggc aggaucguug auuucggcg                    39

<210> SEQ ID NO 1379
<211> LENGTH: 40
<212> TYPE: RNA
<213> ORGANISM: Artificial
<220> FEATURE:
<223> OTHER INFORMATION: Aptamer

<400> SEQUENCE: 1379
auuuucccag guguacuggc aggaucguug auuuucggcg                   40

<210> SEQ ID NO 1380
<211> LENGTH: 40
<212> TYPE: RNA
<213> ORGANISM: Artificial
<220> FEATURE:
<223> OTHER INFORMATION: Aptamer

<400> SEQUENCE: 1380
auuuucgacc auggugaauu ggcagucuuu guuacuauag                   40

<210> SEQ ID NO 1381
<211> LENGTH: 40
<212> TYPE: RNA
<213> ORGANISM: Artificial
<220> FEATURE:
<223> OTHER INFORMATION: Aptamer

<400> SEQUENCE: 1381
augguguauu ggucuccuaa ucucucgugg acuaauuuga                   40

<210> SEQ ID NO 1382
<211> LENGTH: 40
<212> TYPE: RNA
<213> ORGANISM: Artificial
<220> FEATURE:
<223> OTHER INFORMATION: Aptamer

<400> SEQUENCE: 1382
augguucauu ggcggguacg auuuacguuc augcuaucug                   40

<210> SEQ ID NO 1383
<211> LENGTH: 40
<212> TYPE: RNA
<213> ORGANISM: Artificial
<220> FEATURE:
<223> OTHER INFORMATION: Aptamer

<400> SEQUENCE: 1383
augguucauu ggcggguaug auuuacguuc augcuaccug                   40

<210> SEQ ID NO 1384
<211> LENGTH: 40
<212> TYPE: RNA
<213> ORGANISM: Artificial
<220> FEATURE:
<223> OTHER INFORMATION: Aptamer

<400> SEQUENCE: 1384
augguucauu ggcggguaug auuuacguuc augcuaucug                   40

<210> SEQ ID NO 1385
<211> LENGTH: 39
<212> TYPE: RNA
<213> ORGANISM: Artificial

```
-continued

<220> FEATURE:
<223> OTHER INFORMATION: Aptamer

<400> SEQUENCE: 1385
agguaaacug gcccugucgc gacuccuucc ccgggugug                              39

<210> SEQ ID NO 1386
<211> LENGTH: 40
<212> TYPE: RNA
<213> ORGANISM: Artificial
<220> FEATURE:
<223> OTHER INFORMATION: Aptamer

<400> SEQUENCE: 1386
agguaauugg ccgguuccuu cgcgugcugg aaaauggug                              40

<210> SEQ ID NO 1387
<211> LENGTH: 40
<212> TYPE: RNA
<213> ORGANISM: Artificial
<220> FEATURE:
<223> OTHER INFORMATION: Aptamer

<400> SEQUENCE: 1387
agguaauugg uauucuguag aucaaggucc uccgguugug                             40

<210> SEQ ID NO 1388
<211> LENGTH: 40
<212> TYPE: RNA
<213> ORGANISM: Artificial
<220> FEATURE:
<223> OTHER INFORMATION: Aptamer

<400> SEQUENCE: 1388
agguagaauu ggucuugucc ucgucaucuc gaggcuguuu                             40

<210> SEQ ID NO 1389
<211> LENGTH: 38
<212> TYPE: RNA
<213> ORGANISM: Artificial
<220> FEATURE:
<223> OTHER INFORMATION: Aptamer

<400> SEQUENCE: 1389
agguauaacu ggcgucguaa cuuugguuac cgggucug                               38

<210> SEQ ID NO 1390
<211> LENGTH: 40
<212> TYPE: RNA
<213> ORGANISM: Artificial
<220> FEATURE:
<223> OTHER INFORMATION: Aptamer

<400> SEQUENCE: 1390
agguauauug guuucuguug guuuagaucc accgguuaua                             40

<210> SEQ ID NO 1391
<211> LENGTH: 40
<212> TYPE: RNA
<213> ORGANISM: Artificial
<220> FEATURE:
<223> OTHER INFORMATION: Aptamer

<400> SEQUENCE: 1391
aggucuauug gcucccgagg cugcguuccu cugaggaaug                             40
```

<210> SEQ ID NO 1392
<211> LENGTH: 40
<212> TYPE: RNA
<213> ORGANISM: Artificial
<220> FEATURE:
<223> OTHER INFORMATION: Aptamer

<400> SEQUENCE: 1392
aggugaauug guugcccaau gguucuguga ccgggauuua					40

<210> SEQ ID NO 1393
<211> LENGTH: 40
<212> TYPE: RNA
<213> ORGANISM: Artificial
<220> FEATURE:
<223> OTHER INFORMATION: Aptamer

<400> SEQUENCE: 1393
aggugacugg uucacuuagc cugauuaggc cuagcgagug					40

<210> SEQ ID NO 1394
<211> LENGTH: 40
<212> TYPE: RNA
<213> ORGANISM: Artificial
<220> FEATURE:
<223> OTHER INFORMATION: Aptamer

<400> SEQUENCE: 1394
aggugauugg cgcagaugga guucgggacu gcgcuggcug					40

<210> SEQ ID NO 1395
<211> LENGTH: 40
<212> TYPE: RNA
<213> ORGANISM: Artificial
<220> FEATURE:
<223> OTHER INFORMATION: Aptamer

<400> SEQUENCE: 1395
aggugcauug guuucggugc uacucguuau gcccggcgua					40

<210> SEQ ID NO 1396
<211> LENGTH: 40
<212> TYPE: RNA
<213> ORGANISM: Artificial
<220> FEATURE:
<223> OTHER INFORMATION: Aptamer

<400> SEQUENCE: 1396
agguggauug guugcucauc cguucuucuc ucgagcaaua					40

<210> SEQ ID NO 1397
<211> LENGTH: 40
<212> TYPE: RNA
<213> ORGANISM: Artificial
<220> FEATURE:
<223> OTHER INFORMATION: Aptamer

<400> SEQUENCE: 1397
agguguacug guaauccuuu ugucggauga cuaggcgaua					40

<210> SEQ ID NO 1398
<211> LENGTH: 41
<212> TYPE: RNA
<213> ORGANISM: Artificial
<220> FEATURE:
<223> OTHER INFORMATION: Aptamer -continued

<400> SEQUENCE: 1398
agguguacug gucgguaauu gucugaaaau uugcuucguu a       41

<210> SEQ ID NO 1399
<211> LENGTH: 40
<212> TYPE: RNA
<213> ORGANISM: Artificial
<220> FEATURE:
<223> OTHER INFORMATION: Aptamer

<400> SEQUENCE: 1399
agguguauug gccgugcuuu ggaucucggg gugcauugcg       40

<210> SEQ ID NO 1400
<211> LENGTH: 40
<212> TYPE: RNA
<213> ORGANISM: Artificial
<220> FEATURE:
<223> OTHER INFORMATION: Aptamer

<400> SEQUENCE: 1400
agguguauug gcggguggc ccaaacgguc cgcgucauag       40

<210> SEQ ID NO 1401
<211> LENGTH: 40
<212> TYPE: RNA
<213> ORGANISM: Artificial
<220> FEATURE:
<223> OTHER INFORMATION: Aptamer

<400> SEQUENCE: 1401
agguguauug guuagccguu uuuacuuugu uaccguugaa       40

<210> SEQ ID NO 1402
<211> LENGTH: 40
<212> TYPE: RNA
<213> ORGANISM: Artificial
<220> FEATURE:
<223> OTHER INFORMATION: Aptamer

<400> SEQUENCE: 1402
agguguauug guucucccga augauccugu cucgagacaa       40

<210> SEQ ID NO 1403
<211> LENGTH: 40
<212> TYPE: RNA
<213> ORGANISM: Artificial
<220> FEATURE:
<223> OTHER INFORMATION: Aptamer

<400> SEQUENCE: 1403
agguuaauug gcugaaucug cgcuugucgc cggcuugaug       40

<210> SEQ ID NO 1404
<211> LENGTH: 39
<212> TYPE: RNA
<213> ORGANISM: Artificial
<220> FEATURE:
<223> OTHER INFORMATION: Aptamer

<400> SEQUENCE: 1404
agguuauugg cucuauuuuc cuaucuggcg ccuagcaug       39

<210> SEQ ID NO 1405

```
<211> LENGTH: 40
<212> TYPE: RNA
<213> ORGANISM: Artificial
<220> FEATURE:
<223> OTHER INFORMATION: Aptamer

<400> SEQUENCE: 1405
agguuauugg ugcugugcgc ccggaauugg augccggcua                           40

<210> SEQ ID NO 1406
<211> LENGTH: 39
<212> TYPE: RNA
<213> ORGANISM: Artificial
<220> FEATURE:
<223> OTHER INFORMATION: Aptamer

<400> SEQUENCE: 1406
agguuauugg uguuucuuuu cccucgcuu gaaaaguuu                             39

<210> SEQ ID NO 1407
<211> LENGTH: 40
<212> TYPE: RNA
<213> ORGANISM: Artificial
<220> FEATURE:
<223> OTHER INFORMATION: Aptamer

<400> SEQUENCE: 1407
agguuauugg uuacggaugu cuguuccuc aucuguggug                            40

<210> SEQ ID NO 1408
<211> LENGTH: 39
<212> TYPE: RNA
<213> ORGANISM: Artificial
<220> FEATURE:
<223> OTHER INFORMATION: Aptamer

<400> SEQUENCE: 1408
agguuuacug gcucugccuu caguuggaaa ugcagcgug                            39

<210> SEQ ID NO 1409
<211> LENGTH: 40
<212> TYPE: RNA
<213> ORGANISM: Artificial
<220> FEATURE:
<223> OTHER INFORMATION: Aptamer

<400> SEQUENCE: 1409
agguuuacug gucggaacua ggggcgcauc uacaccggug                           40

<210> SEQ ID NO 1410
<211> LENGTH: 40
<212> TYPE: RNA
<213> ORGANISM: Artificial
<220> FEATURE:
<223> OTHER INFORMATION: Aptamer

<400> SEQUENCE: 1410
agguuuauug gcauuugugc acuuuucgg ucgaucacug                            40

<210> SEQ ID NO 1411
<211> LENGTH: 40
<212> TYPE: RNA
<213> ORGANISM: Artificial
<220> FEATURE:
<223> OTHER INFORMATION: Aptamer

<400> SEQUENCE: 1411
```

-continued

```
agguuuauug guagcccucu agaggcugua gaagggugua                    40

<210> SEQ ID NO 1412
<211> LENGTH: 39
<212> TYPE: RNA
<213> ORGANISM: Artificial
<220> FEATURE:
<223> OTHER INFORMATION: Aptamer

<400> SEQUENCE: 1412
agguuuauug guucgcggag cccuuuggug cccguggua                     39

<210> SEQ ID NO 1413
<211> LENGTH: 39
<212> TYPE: RNA
<213> ORGANISM: Artificial
<220> FEATURE:
<223> OTHER INFORMATION: Aptamer

<400> SEQUENCE: 1413
agguuuauug guucgcggag cccuuuggug cccguggua                     39

<210> SEQ ID NO 1414
<211> LENGTH: 40
<212> TYPE: RNA
<213> ORGANISM: Artificial
<220> FEATURE:
<223> OTHER INFORMATION: Aptamer

<400> SEQUENCE: 1414
agguuuuacu ggcgcauugg acuccacgag accgcgagug                    40

<210> SEQ ID NO 1415
<211> LENGTH: 40
<212> TYPE: RNA
<213> ORGANISM: Artificial
<220> FEATURE:
<223> OTHER INFORMATION: Aptamer

<400> SEQUENCE: 1415
caaaacucca gguaaauugg ugaucuccau ccagauagug                    40

<210> SEQ ID NO 1416
<211> LENGTH: 40
<212> TYPE: RNA
<213> ORGANISM: Artificial
<220> FEATURE:
<223> OTHER INFORMATION: Aptamer

<400> SEQUENCE: 1416
caaaauucca augccgucau ggugaacugg cucacggaug                    40

<210> SEQ ID NO 1417
<211> LENGTH: 40
<212> TYPE: RNA
<213> ORGANISM: Artificial
<220> FEATURE:
<223> OTHER INFORMATION: Aptamer

<400> SEQUENCE: 1417
caaagucugg guuauuggua cuuugcucgu uucauucuua                    40

<210> SEQ ID NO 1418
<211> LENGTH: 40
<212> TYPE: RNA
```

```
<213> ORGANISM: Artificial
<220> FEATURE:
<223> OTHER INFORMATION: Aptamer

<400> SEQUENCE: 1418
caaccaaugg uguacugguc uucucuuccu gagucguuua                              40

<210> SEQ ID NO 1419
<211> LENGTH: 40
<212> TYPE: RNA
<213> ORGANISM: Artificial
<220> FEATURE:
<223> OTHER INFORMATION: Aptamer

<400> SEQUENCE: 1419
caaccagguu uauuggucuu cuugcccuug ggcauuguua                              40

<210> SEQ ID NO 1420
<211> LENGTH: 26
<212> TYPE: RNA
<213> ORGANISM: Artificial
<220> FEATURE:
<223> OTHER INFORMATION: Aptamer

<400> SEQUENCE: 1420
caacucuggg uuuacuggcg uugugu                                             26

<210> SEQ ID NO 1421
<211> LENGTH: 40
<212> TYPE: RNA
<213> ORGANISM: Artificial
<220> FEATURE:
<223> OTHER INFORMATION: Aptamer

<400> SEQUENCE: 1421
caaggucuca gcgcgcacac agguauauug gucaacgugu                              40

<210> SEQ ID NO 1422
<211> LENGTH: 40
<212> TYPE: RNA
<213> ORGANISM: Artificial
<220> FEATURE:
<223> OTHER INFORMATION: Aptamer

<400> SEQUENCE: 1422
caagguguac uggccauuug acgcucgucg uuaaauagug                              40

<210> SEQ ID NO 1423
<211> LENGTH: 40
<212> TYPE: RNA
<213> ORGANISM: Artificial
<220> FEATURE:
<223> OTHER INFORMATION: Aptamer

<400> SEQUENCE: 1423
caccauacuc cggguguauu gguguuucau uuccgcuaua                              40

<210> SEQ ID NO 1424
<211> LENGTH: 40
<212> TYPE: RNA
<213> ORGANISM: Artificial
<220> FEATURE:
<223> OTHER INFORMATION: Aptamer

<400> SEQUENCE: 1424
caccccgucc guugaagucc ggguguauug gucucgucuu                              40
```

<210> SEQ ID NO 1425
<211> LENGTH: 39
<212> TYPE: RNA
<213> ORGANISM: Artificial
<220> FEATURE:
<223> OTHER INFORMATION: Aptamer

<400> SEQUENCE: 1425
caccugguug acuggcgcac uuacuacgga uuguggcug                              39

<210> SEQ ID NO 1426
<211> LENGTH: 39
<212> TYPE: RNA
<213> ORGANISM: Artificial
<220> FEATURE:
<223> OTHER INFORMATION: Aptamer

<400> SEQUENCE: 1426
caccugguug acuggcgcac uuacuacgga uuguggcug                              39

<210> SEQ ID NO 1427
<211> LENGTH: 40
<212> TYPE: RNA
<213> ORGANISM: Artificial
<220> FEATURE:
<223> OTHER INFORMATION: Aptamer

<400> SEQUENCE: 1427
cacucacgcc accgggugua uuggucgauc ccccgauuga                             40

<210> SEQ ID NO 1428
<211> LENGTH: 40
<212> TYPE: RNA
<213> ORGANISM: Artificial
<220> FEATURE:
<223> OTHER INFORMATION: Aptamer

<400> SEQUENCE: 1428
cacucgcugg guaauuggug ccagguuuug gaucugaaua                             40

<210> SEQ ID NO 1429
<211> LENGTH: 42
<212> TYPE: RNA
<213> ORGANISM: Artificial
<220> FEATURE:
<223> OTHER INFORMATION: Aptamer

<400> SEQUENCE: 1429
cacucuccuc uucguucguu uagguguacu gguucuucgu uu                          42

<210> SEQ ID NO 1430
<211> LENGTH: 40
<212> TYPE: RNA
<213> ORGANISM: Artificial
<220> FEATURE:
<223> OTHER INFORMATION: Aptamer

<400> SEQUENCE: 1430
cacugguccg agguguacug guuccgcguc uccuggauua                             40

<210> SEQ ID NO 1431
<211> LENGTH: 40
<212> TYPE: RNA
<213> ORGANISM: Artificial
<220> FEATURE:

```
<223> OTHER INFORMATION: Aptamer

<400> SEQUENCE: 1431
cacuguccga acuuggugga uuggucuacg ucucguguca                    40

<210> SEQ ID NO 1432
<211> LENGTH: 40
<212> TYPE: RNA
<213> ORGANISM: Artificial
<220> FEATURE:
<223> OTHER INFORMATION: Aptamer

<400> SEQUENCE: 1432
cacugugaau cccuggguga auugguugcu aaccgcuaua                    40

<210> SEQ ID NO 1433
<211> LENGTH: 40
<212> TYPE: RNA
<213> ORGANISM: Artificial
<220> FEATURE:
<223> OTHER INFORMATION: Aptamer

<400> SEQUENCE: 1433
cacuuccagg uguauuggua guugccguuu ucucuucaua                    40

<210> SEQ ID NO 1434
<211> LENGTH: 40
<212> TYPE: RNA
<213> ORGANISM: Artificial
<220> FEATURE:
<223> OTHER INFORMATION: Aptamer

<400> SEQUENCE: 1434
cacuuccggg uuuauuggcg gguuccggcc uuucaccuug                    40

<210> SEQ ID NO 1435
<211> LENGTH: 39
<212> TYPE: RNA
<213> ORGANISM: Artificial
<220> FEATURE:
<223> OTHER INFORMATION: Aptamer

<400> SEQUENCE: 1435
cacuugcuuu uucuuguccg gguuuauugg ucguugugu                     39

<210> SEQ ID NO 1436
<211> LENGTH: 40
<212> TYPE: RNA
<213> ORGANISM: Artificial
<220> FEATURE:
<223> OTHER INFORMATION: Aptamer

<400> SEQUENCE: 1436
cagaaauccg ggugaauugg ccccgucuag acgacguaug                    40

<210> SEQ ID NO 1437
<211> LENGTH: 39
<212> TYPE: RNA
<213> ORGANISM: Artificial
<220> FEATURE:
<223> OTHER INFORMATION: Aptamer

<400> SEQUENCE: 1437
cagacagguu aauuggccuc uggucacuca cggagaaug                     39
```

```
<210> SEQ ID NO 1438
<211> LENGTH: 40
<212> TYPE: RNA
<213> ORGANISM: Artificial
<220> FEATURE:
<223> OTHER INFORMATION: Aptamer

<400> SEQUENCE: 1438
cagcuucugg uagcuguugc gguucauugg ccuuagggug                              40

<210> SEQ ID NO 1439
<211> LENGTH: 40
<212> TYPE: RNA
<213> ORGANISM: Artificial
<220> FEATURE:
<223> OTHER INFORMATION: Aptamer

<400> SEQUENCE: 1439
cauauguccg gguggacugg ucuuuucuug acgaacguuu                              40

<210> SEQ ID NO 1440
<211> LENGTH: 40
<212> TYPE: RNA
<213> ORGANISM: Artificial
<220> FEATURE:
<223> OTHER INFORMATION: Aptamer

<400> SEQUENCE: 1440
cauauguccg gguggacugg ucuuuucuug acgaauguuu                              40

<210> SEQ ID NO 1441
<211> LENGTH: 40
<212> TYPE: RNA
<213> ORGANISM: Artificial
<220> FEATURE:
<223> OTHER INFORMATION: Aptamer

<400> SEQUENCE: 1441
cauccacggu gaacuggccg cgucgagccg cgaagugaug                              40

<210> SEQ ID NO 1442
<211> LENGTH: 40
<212> TYPE: RNA
<213> ORGANISM: Artificial
<220> FEATURE:
<223> OTHER INFORMATION: Aptamer

<400> SEQUENCE: 1442
cauccagguu gauuggcggc augccuauga guagcgacug                              40

<210> SEQ ID NO 1443
<211> LENGTH: 40
<212> TYPE: RNA
<213> ORGANISM: Artificial
<220> FEATURE:
<223> OTHER INFORMATION: Aptamer

<400> SEQUENCE: 1443
cauccagguu gauuggcggc augccuaugg gcagcgacug                              40

<210> SEQ ID NO 1444
<211> LENGTH: 40
<212> TYPE: RNA
<213> ORGANISM: Artificial
<220> FEATURE:
<223> OTHER INFORMATION: Aptamer
```

```
<400> SEQUENCE: 1444
cauccagguu gauuggcggc augccuaugg guagcgucug                                40

<210> SEQ ID NO 1445
<211> LENGTH: 40
<212> TYPE: RNA
<213> ORGANISM: Artificial
<220> FEATURE:
<223> OTHER INFORMATION: Aptamer

<400> SEQUENCE: 1445
cauccgguga auuggucugc cgacucgcug ccgcuuauaa                                40

<210> SEQ ID NO 1446
<211> LENGTH: 40
<212> TYPE: RNA
<213> ORGANISM: Artificial
<220> FEATURE:
<223> OTHER INFORMATION: Aptamer

<400> SEQUENCE: 1446
cauccgguua uuggucucgu ggauuccccu ccagaguaua                                40

<210> SEQ ID NO 1447
<211> LENGTH: 40
<212> TYPE: RNA
<213> ORGANISM: Artificial
<220> FEATURE:
<223> OTHER INFORMATION: Aptamer

<400> SEQUENCE: 1447
caugaaauau ccagguuauu gguaccuuuu cuacggaaua                                40

<210> SEQ ID NO 1448
<211> LENGTH: 40
<212> TYPE: RNA
<213> ORGANISM: Artificial
<220> FEATURE:
<223> OTHER INFORMATION: Aptamer

<400> SEQUENCE: 1448
caugucuggg ugcauugguc cgcgagcuua cgcuuacgcu                                40

<210> SEQ ID NO 1449
<211> LENGTH: 41
<212> TYPE: RNA
<213> ORGANISM: Artificial
<220> FEATURE:
<223> OTHER INFORMATION: Aptamer

<400> SEQUENCE: 1449
caggucuaac uggcugcacc ucucuuuuug acguguacau g                              41

<210> SEQ ID NO 1450
<211> LENGTH: 41
<212> TYPE: RNA
<213> ORGANISM: Artificial
<220> FEATURE:
<223> OTHER INFORMATION: Aptamer

<400> SEQUENCE: 1450
caggucuacu ggcugcaccu cucuuuuug acguguacau g                               41

<210> SEQ ID NO 1451
<211> LENGTH: 40
```

```
<212> TYPE: RNA
<213> ORGANISM: Artificial
<220> FEATURE:
<223> OTHER INFORMATION: Aptamer

<400> SEQUENCE: 1451
cagguguauu ggucauacuc ucuuuaagc ugguuagga                                40

<210> SEQ ID NO 1452
<211> LENGTH: 40
<212> TYPE: RNA
<213> ORGANISM: Artificial
<220> FEATURE:
<223> OTHER INFORMATION: Aptamer

<400> SEQUENCE: 1452
cagguguauu gguccaccug ucacauuuug acucggucga                              40

<210> SEQ ID NO 1453
<211> LENGTH: 40
<212> TYPE: RNA
<213> ORGANISM: Artificial
<220> FEATURE:
<223> OTHER INFORMATION: Aptamer

<400> SEQUENCE: 1453
cagguguauu gguuacucac cuaguuucag ucguagcaaa                              40

<210> SEQ ID NO 1454
<211> LENGTH: 40
<212> TYPE: RNA
<213> ORGANISM: Artificial
<220> FEATURE:
<223> OTHER INFORMATION: Aptamer

<400> SEQUENCE: 1454
cagguuuauu ggugcauuug gguccuuga ugccuuguua                               40

<210> SEQ ID NO 1455
<211> LENGTH: 40
<212> TYPE: RNA
<213> ORGANISM: Artificial
<220> FEATURE:
<223> OTHER INFORMATION: Aptamer

<400> SEQUENCE: 1455
cagguuuuau uggcuacacu ccgccuuguc gaaugcaagu                              40

<210> SEQ ID NO 1456
<211> LENGTH: 40
<212> TYPE: RNA
<213> ORGANISM: Artificial
<220> FEATURE:
<223> OTHER INFORMATION: Aptamer

<400> SEQUENCE: 1456
ccaauuccug ccgaucgggu ggauuggguag acuugucuua                             40

<210> SEQ ID NO 1457
<211> LENGTH: 40
<212> TYPE: RNA
<213> ORGANISM: Artificial
<220> FEATURE:
<223> OTHER INFORMATION: Aptamer

<400> SEQUENCE: 1457
```
ccacccucuc ccgugcccgg gugcgacugg cuccuggaug                              40

<210> SEQ ID NO 1458
<211> LENGTH: 39
<212> TYPE: RNA
<213> ORGANISM: Artificial
<220> FEATURE:
<223> OTHER INFORMATION: Aptamer

<400> SEQUENCE: 1458
ccaccuuugu cgcauuucug guguauuggu cgcuuguuu                               39

<210> SEQ ID NO 1459
<211> LENGTH: 40
<212> TYPE: RNA
<213> ORGANISM: Artificial
<220> FEATURE:
<223> OTHER INFORMATION: Aptamer

<400> SEQUENCE: 1459
ccacucgcgu cgaaaaguuu uggguauug guuacuuuga                               40

<210> SEQ ID NO 1460
<211> LENGTH: 40
<212> TYPE: RNA
<213> ORGANISM: Artificial
<220> FEATURE:
<223> OTHER INFORMATION: Aptamer

<400> SEQUENCE: 1460
ccagcccgca cccaggucca uuggcggagg acucucaaug                              40

<210> SEQ ID NO 1461
<211> LENGTH: 40
<212> TYPE: RNA
<213> ORGANISM: Artificial
<220> FEATURE:
<223> OTHER INFORMATION: Aptamer

<400> SEQUENCE: 1461
ccagcugacg ggucuacugg cucgcuguau uuagcggaug                              40

<210> SEQ ID NO 1462
<211> LENGTH: 39
<212> TYPE: RNA
<213> ORGANISM: Artificial
<220> FEATURE:
<223> OTHER INFORMATION: Aptamer

<400> SEQUENCE: 1462
ccagguguau uggcuuuccu auuuucgaau uugcgacag                               39

<210> SEQ ID NO 1463
<211> LENGTH: 40
<212> TYPE: RNA
<213> ORGANISM: Artificial
<220> FEATURE:
<223> OTHER INFORMATION: Aptamer

<400> SEQUENCE: 1463
cccaaaggug aauugguccu ucuuuguguc agauguguga                              40

<210> SEQ ID NO 1464
<211> LENGTH: 39
<212> TYPE: RNA
<213> ORGANISM: Artificial

```
<220> FEATURE:
<223> OTHER INFORMATION: Aptamer

<400> SEQUENCE: 1464
cccacucccg guaauugguc ugauuccucg agucaaaua                    39

<210> SEQ ID NO 1465
<211> LENGTH: 41
<212> TYPE: RNA
<213> ORGANISM: Artificial
<220> FEATURE:
<223> OTHER INFORMATION: Aptamer

<400> SEQUENCE: 1465
cccaguuccg augauccggg uucauuggcg cggaugaaug u                 41

<210> SEQ ID NO 1466
<211> LENGTH: 40
<212> TYPE: RNA
<213> ORGANISM: Artificial
<220> FEATURE:
<223> OTHER INFORMATION: Aptamer

<400> SEQUENCE: 1466
ccccacccga ucccugucca cgguauauug gucucgguuu                   40

<210> SEQ ID NO 1467
<211> LENGTH: 40
<212> TYPE: RNA
<213> ORGANISM: Artificial
<220> FEATURE:
<223> OTHER INFORMATION: Aptamer

<400> SEQUENCE: 1467
ccccacgucc uuucuuuugg uguacuggcc agaugcgaug                   40

<210> SEQ ID NO 1468
<211> LENGTH: 41
<212> TYPE: RNA
<213> ORGANISM: Artificial
<220> FEATURE:
<223> OTHER INFORMATION: Aptamer

<400> SEQUENCE: 1468
ccccgguguc ugcgcuucuu cugagguuau uggucgcguu u                 41

<210> SEQ ID NO 1469
<211> LENGTH: 40
<212> TYPE: RNA
<213> ORGANISM: Artificial
<220> FEATURE:
<223> OTHER INFORMATION: Aptamer

<400> SEQUENCE: 1469
ccccuuuguu cugguguauu ggcggauuga cuuguucuug                   40

<210> SEQ ID NO 1470
<211> LENGTH: 40
<212> TYPE: RNA
<213> ORGANISM: Artificial
<220> FEATURE:
<223> OTHER INFORMATION: Aptamer

<400> SEQUENCE: 1470
cccucuagug gccguuggu guacuggugc uuuucgcuua                    40
```

```
<210> SEQ ID NO 1471
<211> LENGTH: 39
<212> TYPE: RNA
<213> ORGANISM: Artificial
<220> FEATURE:
<223> OTHER INFORMATION: Aptamer

<400> SEQUENCE: 1471
cccucugggu auacuggcga auucauucuc guuugucug                              39

<210> SEQ ID NO 1472
<211> LENGTH: 40
<212> TYPE: RNA
<213> ORGANISM: Artificial
<220> FEATURE:
<223> OTHER INFORMATION: Aptamer

<400> SEQUENCE: 1472
cccugcacuc ggcguggugu acuggcugac uuugucuaug                             40

<210> SEQ ID NO 1473
<211> LENGTH: 40
<212> TYPE: RNA
<213> ORGANISM: Artificial
<220> FEATURE:
<223> OTHER INFORMATION: Aptamer

<400> SEQUENCE: 1473
cccugcgcgc ucuuacggug uauuggucca auuugguaua                             40

<210> SEQ ID NO 1474
<211> LENGTH: 30
<212> TYPE: RNA
<213> ORGANISM: Artificial
<220> FEATURE:
<223> OTHER INFORMATION: Aptamer

<400> SEQUENCE: 1474 ccgacggguyg uacuggcgau agauuugcug                                       30

<210> SEQ ID NO 1475
<211> LENGTH: 40
<212> TYPE: RNA
<213> ORGANISM: Artificial
<220> FEATURE:
<223> OTHER INFORMATION: Aptamer

<400> SEQUENCE: 1475
ccgaucuguc gcggguucug gguguauugg uacgcacgua                             40

<210> SEQ ID NO 1476
<211> LENGTH: 40
<212> TYPE: RNA
<213> ORGANISM: Artificial
<220> FEATURE:
<223> OTHER INFORMATION: Aptamer

<400> SEQUENCE: 1476
ccgcacacuu ccgguaauug gcgcaagcuu cucuugcaug                             40

<210> SEQ ID NO 1477
<211> LENGTH: 40
<212> TYPE: RNA
<213> ORGANISM: Artificial
<220> FEATURE:
<223> OTHER INFORMATION: Aptamer
```

```
<400> SEQUENCE: 1477
ccgcacuccc acugugucau ccggguguac uggucaagua                     40

<210> SEQ ID NO 1478
<211> LENGTH: 40
<212> TYPE: RNA
<213> ORGANISM: Artificial
<220> FEATURE:
<223> OTHER INFORMATION: Aptamer

<400> SEQUENCE: 1478
ccgcgucugg guuaauuggc ucuuacguca ggaugguaug                     40

<210> SEQ ID NO 1479
<211> LENGTH: 40
<212> TYPE: RNA
<213> ORGANISM: Artificial
<220> FEATURE:
<223> OTHER INFORMATION: Aptamer

<400> SEQUENCE: 1479
ccgcuugcug gucugggugu acugguuucc gcggguguau                     40

<210> SEQ ID NO 1480
<211> LENGTH: 40
<212> TYPE: RNA
<213> ORGANISM: Artificial
<220> FEATURE:
<223> OTHER INFORMATION: Aptamer

<400> SEQUENCE: 1480
ccgucguucc ugguucauug gcuauugacu uucaauaaug                     40

<210> SEQ ID NO 1481
<211> LENGTH: 40
<212> TYPE: RNA
<213> ORGANISM: Artificial
<220> FEATURE:
<223> OTHER INFORMATION: Aptamer

<400> SEQUENCE: 1481
ccgucuuggu guauggcug uauugcuucg guguaucgug                      40

<210> SEQ ID NO 1482
<211> LENGTH: 40
<212> TYPE: RNA
<213> ORGANISM: Artificial
<220> FEATURE:
<223> OTHER INFORMATION: Aptamer

<400> SEQUENCE: 1482
ccggguguac uggcucuagu gauuaacauc cuaggauuug                     40

<210> SEQ ID NO 1483
<211> LENGTH: 40
<212> TYPE: RNA
<213> ORGANISM: Artificial
<220> FEATURE:
<223> OTHER INFORMATION: Aptamer

<400> SEQUENCE: 1483
ccggguuauu ggcgcaauau ugguauucug uauuggucug                     40

<210> SEQ ID NO 1484
```

```
<211> LENGTH: 40
<212> TYPE: RNA
<213> ORGANISM: Artificial
<220> FEATURE:
<223> OTHER INFORMATION: Aptamer
<220> FEATURE:
<221> NAME/KEY: misc_feauure
<222> LOCATION: (25)..(25)
<223> OTHER INFORMATION: n suands for any base.

<400> SEQUENCE: 1484
ccggguuauu ggcgcaauau ggunuccug uauuggucug                    40

<210> SEQ ID NO 1485
<211> LENGTH: 33
<212> TYPE: RNA
<213> ORGANISM: Artificial
<220> FEATURE:
<223> OTHER INFORMATION: Aptamer

<400> SEQUENCE: 1485
ccggguuauu ggcuccuugu ugaccagggg aug                          33

<210> SEQ ID NO 1486
<211> LENGTH: 40
<212> TYPE: RNA
<213> ORGANISM: Artificial
<220> FEATURE:
<223> OTHER INFORMATION: Aptamer

<400> SEQUENCE: 1486
ccggguugac uggcgcccac ucauucacuu guugguaaug                   40

<210> SEQ ID NO 1487
<211> LENGTH: 40
<212> TYPE: RNA
<213> ORGANISM: Artificial
<220> FEATURE:
<223> OTHER INFORMATION: Aptamer

<400> SEQUENCE: 1487
ccucacagau ccuagguuca uugguugcug aguucgcgga                   40

<210> SEQ ID NO 1488
<211> LENGTH: 40
<212> TYPE: RNA
<213> ORGANISM: Artificial
<220> FEATURE:
<223> OTHER INFORMATION: Aptamer

<400> SEQUENCE: 1488
ccucaccguc ucacagguuc auuggcagcc cauggcgaug                   40

<210> SEQ ID NO 1489
<211> LENGTH: 40
<212> TYPE: RNA
<213> ORGANISM: Artificial
<220> FEATURE:
<223> OTHER INFORMATION: Aptamer

<400> SEQUENCE: 1489
ccuccggguu uauugguauu gucucaagug guacaacuua                   40

<210> SEQ ID NO 1490
<211> LENGTH: 40
<212> TYPE: RNA
<213> ORGANISM: Artificial
```

```
<220> FEATURE:
<223> OTHER INFORMATION: Aptamer

<400> SEQUENCE: 1490
ccucgagcau ugggugaacu ggccauuauu acagugguua                                40

<210> SEQ ID NO 1491
<211> LENGTH: 40
<212> TYPE: RNA
<213> ORGANISM: Artificial
<220> FEATURE:
<223> OTHER INFORMATION: Aptamer

<400> SEQUENCE: 1491
ccucgauguc caggugcauu gguuuccacg uauuggagga                                40

<210> SEQ ID NO 1492
<211> LENGTH: 40
<212> TYPE: RNA
<213> ORGANISM: Artificial
<220> FEATURE:
<223> OTHER INFORMATION: Aptamer

<400> SEQUENCE: 1492
ccucucacuc uggguguauu gguaccauuu uccggaauau                                40

<210> SEQ ID NO 1493
<211> LENGTH: 40
<212> TYPE: RNA
<213> ORGANISM: Artificial
<220> FEATURE:
<223> OTHER INFORMATION: Aptamer

<400> SEQUENCE: 1493
ccucuuguug uuccgguuac uggcccagac ugcugacgug                                40

<210> SEQ ID NO 1494
<211> LENGTH: 40
<212> TYPE: RNA
<213> ORGANISM: Artificial
<220> FEATURE:
<223> OTHER INFORMATION: Aptamer

<400> SEQUENCE: 1494
ccucgguuua uuggcguaua cuuuucgaga guuuagucug                                40

<210> SEQ ID NO 1495
<211> LENGTH: 40
<212> TYPE: RNA
<213> ORGANISM: Artificial
<220> FEATURE:
<223> OTHER INFORMATION: Aptamer

<400> SEQUENCE: 1495
ccugacuaca aucuagguua uugguccuug cccggggKuu                                40

<210> SEQ ID NO 1496
<211> LENGTH: 40
<212> TYPE: RNA
<213> ORGANISM: Artificial
<220> FEATURE:
<223> OTHER INFORMATION: Aptamer

<400> SEQUENCE: 1496
ccuguuaugu ucuugaggug uauuggucuu uuccguuga                                 40
```

```
<210> SEQ ID NO 1497
<211> LENGTH: 40
<212> TYPE: RNA
<213> ORGANISM: Artificial
<220> FEATURE:
<223> OTHER INFORMATION: Aptamer

<400> SEQUENCE: 1497 ccguuggac uggguggacu ggcugguacu guuuccgcug                              40

<210> SEQ ID NO 1498
<211> LENGTH: 40
<212> TYPE: RNA
<213> ORGANISM: Artificial
<220> FEATURE:
<223> OTHER INFORMATION: Aptamer

<400> SEQUENCE: 1498 ccuguuugu cagguucau uggcgauuau uccuggaaug                              40

<210> SEQ ID NO 1499
<211> LENGTH: 40
<212> TYPE: RNA
<213> ORGANISM: Artificial
<220> FEATURE:
<223> OTHER INFORMATION: Aptamer

<400> SEQUENCE: 1499
ccuguuuugu cagguucau uggcgcuuau uacuggaaug                             40

<210> SEQ ID NO 1500
<211> LENGTH: 41
<212> TYPE: RNA
<213> ORGANISM: Artificial
<220> FEATURE:
<223> OTHER INFORMATION: Aptamer

<400> SEQUENCE: 1500
ccuguuuugu cagguucau uggcgcuuau uccguggaau g                           41

<210> SEQ ID NO 1501
<211> LENGTH: 40
<212> TYPE: RNA
<213> ORGANISM: Artificial
<220> FEATURE:
<223> OTHER INFORMATION: Aptamer

<400> SEQUENCE: 1501
ccuguuuugu cagguucau uggcgcuuau uccuagaaug                             40

<210> SEQ ID NO 1502
<211> LENGTH: 40
<212> TYPE: RNA
<213> ORGANISM: Artificial
<220> FEATURE:
<223> OTHER INFORMATION: Aptamer

<400> SEQUENCE: 1502
ccuguuuugu cuggguucau uggcgcuuau uccuggaaug                            40

<210> SEQ ID NO 1503
<211> LENGTH: 40
<212> TYPE: RNA
<213> ORGANISM: Artificial
<220> FEATURE:
<223> OTHER INFORMATION: Aptamer
```

```
<220> FEATURE:
<221> NAME/KEY: misc_feauure
<222> LOCATION: (9)..(9)
<223> OTHER INFORMATION: n suands for any base.

<400> SEQUENCE: 1503
ccuguuuunu cuagguucau uggcgcuuau uccuggaaug                              40

<210> SEQ ID NO 1504
<211> LENGTH: 40
<212> TYPE: RNA
<213> ORGANISM: Artificial
<220> FEATURE:
<223> OTHER INFORMATION: Aptamer

<400> SEQUENCE: 1504
ccuuccaggu guauugguca cuuggcucuc uuacuuguga                             40

<210> SEQ ID NO 1505
<211> LENGTH: 40
<212> TYPE: RNA
<213> ORGANISM: Artificial
<220> FEATURE:
<223> OTHER INFORMATION: Aptamer

<400> SEQUENCE: 1505
ccuuccgauu cgaugccuag guguauuggu auuacucaua                             40

<210> SEQ ID NO 1506
<211> LENGTH: 39
<212> TYPE: RNA
<213> ORGANISM: Artificial
<220> FEATURE:
<223> OTHER INFORMATION: Aptamer

<400> SEQUENCE: 1506
ccuucguccc gguguauugg ugccuuuucu uuguggua                               39

<210> SEQ ID NO 1507
<211> LENGTH: 40
<212> TYPE: RNA
<213> ORGANISM: Artificial
<220> FEATURE:
<223> OTHER INFORMATION: Aptamer

<400> SEQUENCE: 1507
ccuuuccggu aauuggcgau ucucuuuguc ugaacagcug                             40

<210> SEQ ID NO 1508
<211> LENGTH: 40
<212> TYPE: RNA
<213> ORGANISM: Artificial
<220> FEATURE:
<223> OTHER INFORMATION: Aptamer

<400> SEQUENCE: 1508
ccuugguaac uggcgcuacu acgggccgcc gcagggaaug                             40

<210> SEQ ID NO 1509
<211> LENGTH: 39
<212> TYPE: RNA
<213> ORGANISM: Artificial
<220> FEATURE:
<223> OTHER INFORMATION: Aptamer

<400> SEQUENCE: 1509
```

```
ccugguucau uggcagcuag aggccucucg uagugauug                                    39

<210> SEQ ID NO 1510
<211> LENGTH: 39
<212> TYPE: RNA
<213> ORGANISM: Artificial
<220> FEATURE:
<223> OTHER INFORMATION: Aptamer

<400> SEQUENCE: 1510
ccgguuauug gcgcaauauu gguauccugu auuggucug                                    39

<210> SEQ ID NO 1511
<211> LENGTH: 33
<212> TYPE: RNA
<213> ORGANISM: Artificial
<220> FEATURE:
<223> OTHER INFORMATION: Aptamer

<400> SEQUENCE: 1511
ccgguuuauu ggcgcaguua uuuuacugaa cug                                          33

<210> SEQ ID NO 1512
<211> LENGTH: 40
<212> TYPE: RNA
<213> ORGANISM: Artificial
<220> FEATURE:
<223> OTHER INFORMATION: Aptamer

<400> SEQUENCE: 1512 cgaacggguUg gacugguacu ccuagUccuc auggagacua                                  40
```

```
cgaacggguUg gacugguacu ccuagUccuc auggagacua                                  40

<210> SEQ ID NO 1513
<211> LENGTH: 40
<212> TYPE: RNA
<213> ORGANISM: Artificial
<220> FEATURE:
<223> OTHER INFORMATION: Aptamer

<400> SEQUENCE: 1513
cgaaguccag guuugauugg cguggcaccc uugccaagug                                   40

<210> SEQ ID NO 1514
<211> LENGTH: 40
<212> TYPE: RNA
<213> ORGANISM: Artificial
<220> FEATURE:
<223> OTHER INFORMATION: Aptamer

<400> SEQUENCE: 1514
cgaaggugua uggguuaaca cacuuuucuc gcguguucaa                                   40

<210> SEQ ID NO 1515
<211> LENGTH: 40
<212> TYPE: RNA
<213> ORGANISM: Artificial
<220> FEATURE:
<223> OTHER INFORMATION: Aptamer

<400> SEQUENCE: 1515
cgacuaggug uauuggcugg cgcaugcucc ugccguucag                                   40

<210> SEQ ID NO 1516
<211> LENGTH: 40
<212> TYPE: RNA
<213> ORGANISM: Artificial
```

-continued

```
<220> FEATURE:
<223> OTHER INFORMATION: Aptamer

<400> SEQUENCE: 1516
cgaggcccaa gacacuuguu cggguaaauu ggucuuguuu                              40

<210> SEQ ID NO 1517
<211> LENGTH: 40
<212> TYPE: RNA
<213> ORGANISM: Artificial
<220> FEATURE:
<223> OTHER INFORMATION: Aptamer

<400> SEQUENCE: 1517
cgagggugga uuggcucguu gucucgguug ugacacaaag                              40

<210> SEQ ID NO 1518
<211> LENGTH: 40
<212> TYPE: RNA
<213> ORGANISM: Artificial
<220> FEATURE:
<223> OTHER INFORMATION: Aptamer

<400> SEQUENCE: 1518
cgaucguccg gguuuauugg ugaguugcaa ucgcccuuua                              40

<210> SEQ ID NO 1519
<211> LENGTH: 40
<212> TYPE: RNA
<213> ORGANISM: Artificial
<220> FEATURE:
<223> OTHER INFORMATION: Aptamer

<400> SEQUENCE: 1519
cgauuccucg guguacuggu aaagcguuuu cacgcccuug                              40

<210> SEQ ID NO 1520
<211> LENGTH: 40
<212> TYPE: RNA
<213> ORGANISM: Artificial
<220> FEATURE:
<223> OTHER INFORMATION: Aptamer

<400> SEQUENCE: 1520
cgauuggggu aauuggcucc augauugcuc auuggaaug                               40

<210> SEQ ID NO 1521
<211> LENGTH: 40
<212> TYPE: RNA
<213> ORGANISM: Artificial
<220> FEATURE:
<223> OTHER INFORMATION: Aptamer

<400> SEQUENCE: 1521
cgcgccuaag guguauuggu cugcgugguu cuacgaaaga                              40

<210> SEQ ID NO 1522
<211> LENGTH: 40
<212> TYPE: RNA
<213> ORGANISM: Artificial
<220> FEATURE:
<223> OTHER INFORMATION: Aptamer

<400> SEQUENCE: 1522
cgcguucuac gguuuuacug gcuuccggcc uuuggacaug                              40
```

<210> SEQ ID NO 1523
<211> LENGTH: 40
<212> TYPE: RNA
<213> ORGANISM: Artificial
<220> FEATURE:
<223> OTHER INFORMATION: Aptamer

<400> SEQUENCE: 1523
cgcuaaaggu aaauugguca cgcaguuuug ugcguuguuu                    40

<210> SEQ ID NO 1524
<211> LENGTH: 41
<212> TYPE: RNA
<213> ORGANISM: Artificial
<220> FEATURE:
<223> OTHER INFORMATION: Aptamer

<400> SEQUENCE: 1524
cgcucaggug aauugguuac guuuuucucu gacaaugugg a                  41

<210> SEQ ID NO 1525
<211> LENGTH: 40
<212> TYPE: RNA
<213> ORGANISM: Artificial
<220> FEATURE:
<223> OTHER INFORMATION: Aptamer

<400> SEQUENCE: 1525
cgcuccaucu cuggucuacu ggcaccauuu cccggauuug                    40

<210> SEQ ID NO 1526
<211> LENGTH: 40
<212> TYPE: RNA
<213> ORGANISM: Artificial
<220> FEATURE:
<223> OTHER INFORMATION: Aptamer

<400> SEQUENCE: 1526
cgcuccccgg uucuacuggc gcuuacgauu gucugaccug                    40

<210> SEQ ID NO 1527
<211> LENGTH: 39
<212> TYPE: RNA
<213> ORGANISM: Artificial
<220> FEATURE:
<223> OTHER INFORMATION: Aptamer

<400> SEQUENCE: 1527
cgcuuguuuc gggugauugg ccaggaaucu cccugugug                     39

<210> SEQ ID NO 1528
<211> LENGTH: 40
<212> TYPE: RNA
<213> ORGANISM: Artificial
<220> FEATURE:
<223> OTHER INFORMATION: Aptamer

<400> SEQUENCE: 1528
cggaaucuug cauaggugau ugguugugga ggacaugaug                    40

<210> SEQ ID NO 1529
<211> LENGTH: 43
<212> TYPE: RNA
<213> ORGANISM: Artificial
<220> FEATURE:
<223> OTHER INFORMATION: Aptamer

<400> SEQUENCE: 1529
cggacugcag guguacuggu uucccuuaag aucaaguggc gug        43

<210> SEQ ID NO 1530
<211> LENGTH: 40
<212> TYPE: RNA
<213> ORGANISM: Artificial
<220> FEATURE:
<223> OTHER INFORMATION: Aptamer

<400> SEQUENCE: 1530
cggagccgac agguugaauu ggcgaucggu uaccgacaug        40

<210> SEQ ID NO 1531
<211> LENGTH: 40
<212> TYPE: RNA
<213> ORGANISM: Artificial
<220> FEATURE:
<223> OTHER INFORMATION: Aptamer

<400> SEQUENCE: 1531
cggucccagg uguacugguu guuccguuuc ggucgcguua        40

<210> SEQ ID NO 1532
<211> LENGTH: 40
<212> TYPE: RNA
<213> ORGANISM: Artificial
<220> FEATURE:
<223> OTHER INFORMATION: Aptamer
<220> FEATURE:
<221> NAME/KEY: misc_feauure
<222> LOCATION: (40)..(40)
<223> OTHER INFORMATION: n suands for any base.

<400> SEQUENCE: 1532
cggucccagg uguacugguu guuccguuuc gguugcguun        40

<210> SEQ ID NO 1533
<211> LENGTH: 40
<212> TYPE: RNA
<213> ORGANISM: Artificial
<220> FEATURE:
<223> OTHER INFORMATION: Aptamer

<400> SEQUENCE: 1533
cggucccagg uguauugguu guuccguuuc gguugcguua        40

<210> SEQ ID NO 1534
<211> LENGTH: 40
<212> TYPE: RNA
<213> ORGANISM: Artificial
<220> FEATURE:
<223> OTHER INFORMATION: Aptamer

<400> SEQUENCE: 1534
cguacuguuu cccuaggugu acuggcucug auacagcaug        40

<210> SEQ ID NO 1535
<211> LENGTH: 40
<212> TYPE: RNA
<213> ORGANISM: Artificial
<220> FEATURE:
<223> OTHER INFORMATION: Aptamer

<400> SEQUENCE: 1535

```
cguaguuggu ucuauuggcc cucgcuucuc agcguugaug                40
```

<210> SEQ ID NO 1536
<211> LENGTH: 40
<212> TYPE: RNA
<213> ORGANISM: Artificial
<220> FEATURE:
<223> OTHER INFORMATION: Aptamer

<400> SEQUENCE: 1536

```
cgucacggug uauuggcgau uauucccaag ggugauuaug                40
```

<210> SEQ ID NO 1537
<211> LENGTH: 39
<212> TYPE: RNA
<213> ORGANISM: Artificial
<220> FEATURE:
<223> OTHER INFORMATION: Aptamer

<400> SEQUENCE: 1537

```
cgucaugggu guauugguua ccuucgagcc gaaugcaaa                 39
```

<210> SEQ ID NO 1538
<211> LENGTH: 42
<212> TYPE: RNA
<213> ORGANISM: Artificial
<220> FEATURE:
<223> OTHER INFORMATION: Aptamer

<400> SEQUENCE: 1538

```
cgucagguga uuggcgcuau uuuaucgauc gauaauugaa ug             42
```

<210> SEQ ID NO 1539
<211> LENGTH: 42
<212> TYPE: RNA
<213> ORGANISM: Artificial
<220> FEATURE:
<223> OTHER INFORMATION: Aptamer

<400> SEQUENCE: 1539

```
cguccgauuc gauacuggua uauuggcguc cuucguggaa ug             42
```

<210> SEQ ID NO 1540
<211> LENGTH: 40
<212> TYPE: RNA
<213> ORGANISM: Artificial
<220> FEATURE:
<223> OTHER INFORMATION: Aptamer

<400> SEQUENCE: 1540

```
cgucuccgau gguuuauugg uucuacauuu cucuagauua                40
```

<210> SEQ ID NO 1541
<211> LENGTH: 40
<212> TYPE: RNA
<213> ORGANISM: Artificial
<220> FEATURE:
<223> OTHER INFORMATION: Aptamer

<400> SEQUENCE: 1541

```
cgucucuuuc gguuuacugg cgcuucaagg cguaugguug                40
```

<210> SEQ ID NO 1542
<211> LENGTH: 37
<212> TYPE: RNA
<213> ORGANISM: Artificial

```
<220> FEATURE:
<223> OTHER INFORMATION: Aptamer

<400> SEQUENCE: 1542
cgucucggug uacuggucuu uagaguuucu auugugu                              37

<210> SEQ ID NO 1543
<211> LENGTH: 40
<212> TYPE: RNA
<213> ORGANISM: Artificial
<220> FEATURE:
<223> OTHER INFORMATION: Aptamer

<400> SEQUENCE: 1543
cgucugaucg auacugguau auuggcgccu ucguggaaug                           40

<210> SEQ ID NO 1544
<211> LENGTH: 40
<212> TYPE: RNA
<213> ORGANISM: Artificial
<220> FEATURE:
<223> OTHER INFORMATION: Aptamer

<400> SEQUENCE: 1544
cgugaucacu cgguuaauug gcgagagaua ucuccgucug                           40

<210> SEQ ID NO 1545
<211> LENGTH: 40
<212> TYPE: RNA
<213> ORGANISM: Artificial
<220> FEATURE:
<223> OTHER INFORMATION: Aptamer

<400> SEQUENCE: 1545
cgugcuacgg guauacuggu uccugcgacg uuaaggagug                           40

<210> SEQ ID NO 1546
<211> LENGTH: 40
<212> TYPE: RNA
<213> ORGANISM: Artificial
<220> FEATURE:
<223> OTHER INFORMATION: Aptamer

<400> SEQUENCE: 1546
cgugcuuucu gguguauugg uaaaguucga cggcuuucua                           40

<210> SEQ ID NO 1547
<211> LENGTH: 40
<212> TYPE: RNA
<213> ORGANISM: Artificial
<220> FEATURE:
<223> OTHER INFORMATION: Aptamer

<400> SEQUENCE: 1547
cguguggucu cggguauauu ggugaucggc ugugaucuua                           40

<210> SEQ ID NO 1548
<211> LENGTH: 40
<212> TYPE: RNA
<213> ORGANISM: Artificial
<220> FEATURE:
<223> OTHER INFORMATION: Aptamer

<400> SEQUENCE: 1548
cguuguguac ggguacugg uaccguugau ugauggugug                            40
```

```
<210> SEQ ID NO 1549
<211> LENGTH: 39
<212> TYPE: RNA
<213> ORGANISM: Artificial
<220> FEATURE:
<223> OTHER INFORMATION: Aptamer

<400> SEQUENCE: 1549
cguuuagggu guacuggcgu agcgaaugcu aaucuugau                              39

<210> SEQ ID NO 1550
<211> LENGTH: 39
<212> TYPE: RNA
<213> ORGANISM: Artificial
<220> FEATURE:
<223> OTHER INFORMATION: Aptamer

<400> SEQUENCE: 1550
cguuuagguc uacuggcuuc uaucacgcga auaggaaug                              39

<210> SEQ ID NO 1551
<211> LENGTH: 40
<212> TYPE: RNA
<213> ORGANISM: Artificial
<220> FEATURE:
<223> OTHER INFORMATION: Aptamer

<400> SEQUENCE: 1551
cguuuaggug uauugguaca cagucguagu acugaguaua                             40

<210> SEQ ID NO 1552
<211> LENGTH: 40
<212> TYPE: RNA
<213> ORGANISM: Artificial
<220> FEATURE:
<223> OTHER INFORMATION: Aptamer

<400> SEQUENCE: 1552 cguuuccgg guguauuggc cuuucgguuu ucguuagaau                              40

<210> SEQ ID NO 1553
<211> LENGTH: 40
<212> TYPE: RNA
<213> ORGANISM: Artificial
<220> FEATURE:
<223> OTHER INFORMATION: Aptamer

<400> SEQUENCE: 1553
cgugguucua uuggccgggu uugaugaacg agcuugugug                             40

<210> SEQ ID NO 1554
<211> LENGTH: 39
<212> TYPE: RNA
<213> ORGANISM: Artificial
<220> FEATURE:
<223> OTHER INFORMATION: Aptamer

<400> SEQUENCE: 1554
cggguacauu ggccccuaua ccucacggua aaugguaug                              39

<210> SEQ ID NO 1555
<211> LENGTH: 40
<212> TYPE: RNA
<213> ORGANISM: Artificial
<220> FEATURE:
<223> OTHER INFORMATION: Aptamer
```

```
<400> SEQUENCE: 1555
cggguacauu ggccccuaua ccucgcggua aaaugguaug                                40

<210> SEQ ID NO 1556
<211> LENGTH: 39
<212> TYPE: RNA
<213> ORGANISM: Artificial
<220> FEATURE:
<223> OTHER INFORMATION: Aptamer

<400> SEQUENCE: 1556
cggguguacu ggugacgcua cuucuccugu cguagcucg                                 39

<210> SEQ ID NO 1557
<211> LENGTH: 40
<212> TYPE: RNA
<213> ORGANISM: Artificial
<220> FEATURE:
<223> OTHER INFORMATION: Aptamer

<400> SEQUENCE: 1557
cggguguacu gguuccggu cuauuaaucc ugauucgaga                                 40

<210> SEQ ID NO 1558
<211> LENGTH: 39
<212> TYPE: RNA
<213> ORGANISM: Artificial
<220> FEATURE:
<223> OTHER INFORMATION: Aptamer

<400> SEQUENCE: 1558
cggguguauu gguuucuggu gcgaguuccc cagauuaaa                                 39

<210> SEQ ID NO 1559
<211> LENGTH: 40
<212> TYPE: RNA
<213> ORGANISM: Artificial
<220> FEATURE:
<223> OTHER INFORMATION: Aptamer

<400> SEQUENCE: 1559
cggguguagu uggcuugccg ucuuaggugu cggcaguaug                                40

<210> SEQ ID NO 1560
<211> LENGTH: 40
<212> TYPE: RNA
<213> ORGANISM: Artificial
<220> FEATURE:
<223> OTHER INFORMATION: Aptamer

<400> SEQUENCE: 1560
cggguucuac uggucggcuc uguccuucuu cgcguuugau                                40

<210> SEQ ID NO 1561
<211> LENGTH: 40
<212> TYPE: RNA
<213> ORGANISM: Artificial
<220> FEATURE:
<223> OTHER INFORMATION: Aptamer

<400> SEQUENCE: 1561
cggguuuauu ggcgacaagu ggauaagucu acgcguguac                                40

<210> SEQ ID NO 1562
```

```
<211> LENGTH: 40
<212> TYPE: RNA
<213> ORGANISM: Artificial
<220> FEATURE:
<223> OTHER INFORMATION: Aptamer

<400> SEQUENCE: 1562
cuaacccccc ucgguuuacu ggguuugcau uugcagugug                               40

<210> SEQ ID NO 1563
<211> LENGTH: 40
<212> TYPE: RNA
<213> ORGANISM: Artificial
<220> FEATURE:
<223> OTHER INFORMATION: Aptamer

<400> SEQUENCE: 1563
cuaaccgccu ucguaugucc ggguggauug gccuccguuu                               40

<210> SEQ ID NO 1564
<211> LENGTH: 40
<212> TYPE: RNA
<213> ORGANISM: Artificial
<220> FEATURE:
<223> OTHER INFORMATION: Aptamer

<400> SEQUENCE: 1564
cuaaugugcc caucucggug uauuggguucc uucaaggaaa                              40

<210> SEQ ID NO 1565
<211> LENGTH: 40
<212> TYPE: RNA
<213> ORGANISM: Artificial
<220> FEATURE:
<223> OTHER INFORMATION: Aptamer

<400> SEQUENCE: 1565
cuacacacuc gguguauugg ucgucgguua uucgaauuga                               40

<210> SEQ ID NO 1566
<211> LENGTH: 40
<212> TYPE: RNA
<213> ORGANISM: Artificial
<220> FEATURE:
<223> OTHER INFORMATION: Aptamer

<400> SEQUENCE: 1566
cuacacguuu ccuaggugua uuggcugucu acacgaccag                               40

<210> SEQ ID NO 1567
<211> LENGTH: 40
<212> TYPE: RNA
<213> ORGANISM: Artificial
<220> FEATURE:
<223> OTHER INFORMATION: Aptamer

<400> SEQUENCE: 1567
cuaccucuca cuccgguaua uuggcgcacc cucucgaaug                               40

<210> SEQ ID NO 1568
<211> LENGTH: 40
<212> TYPE: RNA
<213> ORGANISM: Artificial
<220> FEATURE:
<223> OTHER INFORMATION: Aptamer

<400> SEQUENCE: 1568
```
cuacuacuac guuaggguau auuggcuccu cacggacaug                              40

<210> SEQ ID NO 1569
<211> LENGTH: 40
<212> TYPE: RNA
<213> ORGANISM: Artificial
<220> FEATURE:
<223> OTHER INFORMATION: Aptamer

<400> SEQUENCE: 1569
cuacuaggug uacuggcauu cauucuucuc cugaauguua                              40

<210> SEQ ID NO 1570
<211> LENGTH: 40
<212> TYPE: RNA
<213> ORGANISM: Artificial
<220> FEATURE:
<223> OTHER INFORMATION: Aptamer

<400> SEQUENCE: 1570
cuacuuugau accguccggu uuauuggcuu ccuuggagug                              40

<210> SEQ ID NO 1571
<211> LENGTH: 38
<212> TYPE: RNA
<213> ORGANISM: Artificial
<220> FEATURE:
<223> OTHER INFORMATION: Aptamer

<400> SEQUENCE: 1571
cuagcucugg guuuauuggu cuugcuuaau gcguagua                                38

<210> SEQ ID NO 1572
<211> LENGTH: 40
<212> TYPE: RNA
<213> ORGANISM: Artificial
<220> FEATURE:
<223> OTHER INFORMATION: Aptamer

<400> SEQUENCE: 1572
cuagcugcau ucgggugaau ugguuacuuu guuagcacaa                              40

<210> SEQ ID NO 1573
<211> LENGTH: 40
<212> TYPE: RNA
<213> ORGANISM: Artificial
<220> FEATURE:
<223> OTHER INFORMATION: Aptamer

<400> SEQUENCE: 1573
cuauacggug cggaggggug acuggcgguu gaugacaaug                              40

<210> SEQ ID NO 1574
<211> LENGTH: 37
<212> TYPE: RNA
<213> ORGANISM: Artificial
<220> FEATURE:
<223> OTHER INFORMATION: Aptamer

<400> SEQUENCE: 1574
cuauccgggu uuauuggucc uguacgcuaa cagaaua                                 37

<210> SEQ ID NO 1575
<211> LENGTH: 40
<212> TYPE: RNA

<213> ORGANISM: Artificial
<220> FEATURE:
<223> OTHER INFORMATION: Aptamer

<400> SEQUENCE: 1575
cuaucuugca cucgguucau uggugcccgc guuggguuc         40

<210> SEQ ID NO 1576
<211> LENGTH: 40
<212> TYPE: RNA
<213> ORGANISM: Artificial
<220> FEATURE:
<223> OTHER INFORMATION: Aptamer

<400> SEQUENCE: 1576
cuagguccau uggcggccuu acaucggaug uuuggcgcgg         40

<210> SEQ ID NO 1577
<211> LENGTH: 40
<212> TYPE: RNA
<213> ORGANISM: Artificial
<220> FEATURE:
<223> OTHER INFORMATION: Aptamer

<400> SEQUENCE: 1577
cucaccgugu ucccagguu uauuggggu auuuacuuuu         40

<210> SEQ ID NO 1578
<211> LENGTH: 40
<212> TYPE: RNA
<213> ORGANISM: Artificial
<220> FEATURE:
<223> OTHER INFORMATION: Aptamer

<400> SEQUENCE: 1578
cucacuccau accagguuua uuggccccgg auccaggaug         40

<210> SEQ ID NO 1579
<211> LENGTH: 41
<212> TYPE: RNA
<213> ORGANISM: Artificial
<220> FEATURE:
<223> OTHER INFORMATION: Aptamer

<400> SEQUENCE: 1579
cucacugcag ucucucggug gauuggnuugg uaaccccuau a         41

<210> SEQ ID NO 1580
<211> LENGTH: 40
<212> TYPE: RNA
<213> ORGANISM: Artificial
<220> FEATURE:
<223> OTHER INFORMATION: Aptamer

<400> SEQUENCE: 1580
cucaugaucc gugguaauug guucgccuuc ggacgcauuu         40

<210> SEQ ID NO 1581
<211> LENGTH: 41
<212> TYPE: RNA
<213> ORGANISM: Artificial
<220> FEATURE:
<223> OTHER INFORMATION: Aptamer

<400> SEQUENCE: 1581
cucaggugau uggcgcuauu uaucgcuucg auuuaagaau g         41

<210> SEQ ID NO 1582
<211> LENGTH: 40
<212> TYPE: RNA
<213> ORGANISM: Artificial
<220> FEATURE:
<223> OTHER INFORMATION: Aptamer

<400> SEQUENCE: 1582
cuccagguuu auuggcuacu cugcuaucug gcugguuaug        40

<210> SEQ ID NO 1583
<211> LENGTH: 40
<212> TYPE: RNA
<213> ORGANISM: Artificial
<220> FEATURE:
<223> OTHER INFORMATION: Aptamer

<400> SEQUENCE: 1583
cucccgcccg ggugcacugg ucucuccuga cgugcuguuc        40

<210> SEQ ID NO 1584
<211> LENGTH: 40
<212> TYPE: RNA
<213> ORGANISM: Artificial
<220> FEATURE:
<223> OTHER INFORMATION: Aptamer

<400> SEQUENCE: 1584
cucccuacug cuucucucag guggacuggu guuguucgug        40

<210> SEQ ID NO 1585
<211> LENGTH: 40
<212> TYPE: RNA
<213> ORGANISM: Artificial
<220> FEATURE:
<223> OTHER INFORMATION: Aptamer

<400> SEQUENCE: 1585
cucccggugg auugguacca gcuaguuucu gagcucuuua        40

<210> SEQ ID NO 1586
<211> LENGTH: 40
<212> TYPE: RNA
<213> ORGANISM: Artificial
<220> FEATURE:
<223> OTHER INFORMATION: Aptamer

<400> SEQUENCE: 1586
cucccggugu auggccuuc cgguuacgca accgguagug        40

<210> SEQ ID NO 1587
<211> LENGTH: 39
<212> TYPE: RNA
<213> ORGANISM: Artificial
<220> FEATURE:
<223> OTHER INFORMATION: Aptamer

<400> SEQUENCE: 1587
cucccggugu auggcuucc gguuacgcaa ccgguagug        39

<210> SEQ ID NO 1588
<211> LENGTH: 40
<212> TYPE: RNA
<213> ORGANISM: Artificial
<220> FEATURE:

```
<223> OTHER INFORMATION: Aptamer

<400> SEQUENCE: 1588
cuccucgucu ugguuguauu ggcacacucg ccguggcuug                    40

<210> SEQ ID NO 1589
<211> LENGTH: 40
<212> TYPE: RNA
<213> ORGANISM: Artificial
<220> FEATURE:
<223> OTHER INFORMATION: Aptamer

<400> SEQUENCE: 1589
cuccuguccu ggucggugua cuggcuauuu ccgaauguug                    40

<210> SEQ ID NO 1590
<211> LENGTH: 40
<212> TYPE: RNA
<213> ORGANISM: Artificial
<220> FEATURE:
<223> OTHER INFORMATION: Aptamer

<400> SEQUENCE: 1590
cuccugguca auuggcgcgc auuauccugg guguugaaug                    40

<210> SEQ ID NO 1591
<211> LENGTH: 40
<212> TYPE: RNA
<213> ORGANISM: Artificial
<220> FEATURE:
<223> OTHER INFORMATION: Aptamer

<400> SEQUENCE: 1591
cucgcacgcc uugguaauug gcgccgcggg cuggggcaug                    40

<210> SEQ ID NO 1592
<211> LENGTH: 40
<212> TYPE: RNA
<213> ORGANISM: Artificial
<220> FEATURE:
<223> OTHER INFORMATION: Aptamer

<400> SEQUENCE: 1592
cucgcucugc uaaauuccug ugguaauugg cucauggaug                    40

<210> SEQ ID NO 1593
<211> LENGTH: 40
<212> TYPE: RNA
<213> ORGANISM: Artificial
<220> FEATURE:
<223> OTHER INFORMATION: Aptamer

<400> SEQUENCE: 1593
cucuacaccg gguguacugg uugagcuagu uuguucguaa                    40

<210> SEQ ID NO 1594
<211> LENGTH: 40
<212> TYPE: RNA
<213> ORGANISM: Artificial
<220> FEATURE:
<223> OTHER INFORMATION: Aptamer

<400> SEQUENCE: 1594
cucucucuac gaccagguaa uuggcgcgcu cuuucgaaug                    40
```

```
<210> SEQ ID NO 1595
<211> LENGTH: 40
<212> TYPE: RNA
<213> ORGANISM: Artificial
<220> FEATURE:
<223> OTHER INFORMATION: Aptamer

<400> SEQUENCE: 1595
cucuugccua uugguauauu ggcgcuucug cggaaauaug                                40

<210> SEQ ID NO 1596
<211> LENGTH: 40
<212> TYPE: RNA
<213> ORGANISM: Artificial
<220> FEATURE:
<223> OTHER INFORMATION: Aptamer

<400> SEQUENCE: 1596
cucuuugcug uaacaaaagc gguauauugg cucacggaug                                40

<210> SEQ ID NO 1597
<211> LENGTH: 42
<212> TYPE: RNA
<213> ORGANISM: Artificial
<220> FEATURE:
<223> OTHER INFORMATION: Aptamer

<400> SEQUENCE: 1597
cugaaggggu ugauuggcgg cuuccagggg gacgaagcgc ug                             42

<210> SEQ ID NO 1598
<211> LENGTH: 40
<212> TYPE: RNA
<213> ORGANISM: Artificial
<220> FEATURE:
<223> OTHER INFORMATION: Aptamer

<400> SEQUENCE: 1598
cugaaggguc gauuggcggc uuccagggga cgaagcgcug                                40

<210> SEQ ID NO 1599
<211> LENGTH: 40
<212> TYPE: RNA
<213> ORGANISM: Artificial
<220> FEATURE:
<223> OTHER INFORMATION: Aptamer

<400> SEQUENCE: 1599
cugaauggca ggugaacugg uagggcuuuu gugcuuugug                                40

<210> SEQ ID NO 1600
<211> LENGTH: 39
<212> TYPE: RNA
<213> ORGANISM: Artificial
<220> FEATURE:
<223> OTHER INFORMATION: Aptamer

<400> SEQUENCE: 1600
cugaagguug auuggcggcu uccagggac gaagcgcug                                  39

<210> SEQ ID NO 1601
<211> LENGTH: 40
<212> TYPE: RNA
<213> ORGANISM: Artificial
<220> FEATURE:
<223> OTHER INFORMATION: Aptamer
```

```
<400> SEQUENCE: 1601
cugauuuaac guccauuuug gguuuauugg ucauucguau                              40

<210> SEQ ID NO 1602
<211> LENGTH: 53
<212> TYPE: RNA
<213> ORGANISM: Artificial
<220> FEATURE:
<223> OTHER INFORMATION: Aptamer

<400> SEQUENCE: 1602
cugccgucca ucugcggguga acugguuguc agagcuuuua gcccugggcu gaa             53

<210> SEQ ID NO 1603
<211> LENGTH: 40
<212> TYPE: RNA
<213> ORGANISM: Artificial
<220> FEATURE:
<223> OTHER INFORMATION: Aptamer

<400> SEQUENCE: 1603
cugccguugg gguguacugg uucggggaau ugccgagugu                              40

<210> SEQ ID NO 1604
<211> LENGTH: 40
<212> TYPE: RNA
<213> ORGANISM: Artificial
<220> FEATURE:
<223> OTHER INFORMATION: Aptamer

<400> SEQUENCE: 1604
cugcgauuac ggguguauug gcauuaucaa gaauaaaacg                              40

<210> SEQ ID NO 1605
<211> LENGTH: 40
<212> TYPE: RNA
<213> ORGANISM: Artificial
<220> FEATURE:
<223> OTHER INFORMATION: Aptamer

<400> SEQUENCE: 1605
cugcuaacag guucaauugg cccgaaguug auucuggaug                              40

<210> SEQ ID NO 1606
<211> LENGTH: 40
<212> TYPE: RNA
<213> ORGANISM: Artificial
<220> FEATURE:
<223> OTHER INFORMATION: Aptamer

<400> SEQUENCE: 1606
cugcuagucu cucagguuua uuggcgucau uuuucgauug                              40

<210> SEQ ID NO 1607
<211> LENGTH: 40
<212> TYPE: RNA
<213> ORGANISM: Artificial
<220> FEATURE:
<223> OTHER INFORMATION: Aptamer

<400> SEQUENCE: 1607
cugcuuaucu cucagguuua uuggcgucau uuuucgauug                              40

<210> SEQ ID NO 1608
<211> LENGTH: 39
```

<212> TYPE: RNA
<213> ORGANISM: Artificial
<220> FEATURE:
<223> OTHER INFORMATION: Aptamer

<400> SEQUENCE: 1608
cugcuugucu cucagguuua uuggcgucau uuucgauug                      39

<210> SEQ ID NO 1609
<211> LENGTH: 41
<212> TYPE: RNA
<213> ORGANISM: Artificial
<220> FEATURE:
<223> OTHER INFORMATION: Aptamer

<400> SEQUENCE: 1609
cugcuugucu cucagguuua uuggcgucua uuuuucgauu g                   41

<210> SEQ ID NO 1610
<211> LENGTH: 41
<212> TYPE: RNA
<213> ORGANISM: Artificial
<220> FEATURE:
<223> OTHER INFORMATION: Aptamer

<400> SEQUENCE: 1610
cugcuuuuuc cauucagguu auugguccuu guuguuguu u                    41

<210> SEQ ID NO 1611
<211> LENGTH: 40
<212> TYPE: RNA
<213> ORGANISM: Artificial
<220> FEATURE:
<223> OTHER INFORMATION: Aptamer

<400> SEQUENCE: 1611
cuguacgcac guuuugggug uauugguucg acgaccccga                     40

<210> SEQ ID NO 1612
<211> LENGTH: 40
<212> TYPE: RNA
<213> ORGANISM: Artificial
<220> FEATURE:
<223> OTHER INFORMATION: Aptamer

<400> SEQUENCE: 1612
cuguagacgc uagguguacu ggcugcuacu gccaugcaag                     40

<210> SEQ ID NO 1613
<211> LENGTH: 40
<212> TYPE: RNA
<213> ORGANISM: Artificial
<220> FEATURE:
<223> OTHER INFORMATION: Aptamer

<400> SEQUENCE: 1613
cuguaugugc cgguuuauug guuucugucg aggcaguuua                     40

<210> SEQ ID NO 1614
<211> LENGTH: 39
<212> TYPE: RNA
<213> ORGANISM: Artificial
<220> FEATURE:
<223> OTHER INFORMATION: Aptamer

<400> SEQUENCE: 1614
cugugccccc agguguauug gucagccgcg uugaaucga        39

<210> SEQ ID NO 1615
<211> LENGTH: 40
<212> TYPE: RNA
<213> ORGANISM: Artificial
<220> FEATURE:
<223> OTHER INFORMATION: Aptamer

<400> SEQUENCE: 1615
cuguucgcag uaugauccgg guauauuggc cuuaugggug        40

<210> SEQ ID NO 1616
<211> LENGTH: 40
<212> TYPE: RNA
<213> ORGANISM: Artificial
<220> FEATURE:
<223> OTHER INFORMATION: Aptamer

<400> SEQUENCE: 1616 cugguuaau uguccguau ccauaaacca ugguucggua        40

<210> SEQ ID NO 1617
<211> LENGTH: 40
<212> TYPE: RNA
<213> ORGANISM: Artificial
<220> FEATURE:
<223> OTHER INFORMATION: Aptamer

<400> SEQUENCE: 1617
cuuacucuuu cuuuacucgu uugguuuaau uggucuaaua        40

<210> SEQ ID NO 1618
<211> LENGTH: 40
<212> TYPE: RNA
<213> ORGANISM: Artificial
<220> FEATURE:
<223> OTHER INFORMATION: Aptamer

<400> SEQUENCE: 1618
cuuacucuuu cuuuacucgu uugguuuaau uggucuaaua        40

<210> SEQ ID NO 1619
<211> LENGTH: 38
<212> TYPE: RNA
<213> ORGANISM: Artificial
<220> FEATURE:
<223> OTHER INFORMATION: Aptamer

<400> SEQUENCE: 1619
cuuccacggu guacuggugc gcaaacaugc ugcgugug        38

<210> SEQ ID NO 1620
<211> LENGTH: 40
<212> TYPE: RNA
<213> ORGANISM: Artificial
<220> FEATURE:
<223> OTHER INFORMATION: Aptamer

<400> SEQUENCE: 1620
cuuccugcgg ucuucggugg auugguaaca cucuggauua        40

<210> SEQ ID NO 1621
<211> LENGTH: 40
<212> TYPE: RNA
<213> ORGANISM: Artificial

```
<220> FEATURE:
<223> OTHER INFORMATION: Aptamer

<400> SEQUENCE: 1621
cuucgcccag guaauuggcu cguagucuau ccauggaaug                              40

<210> SEQ ID NO 1622
<211> LENGTH: 40
<212> TYPE: RNA
<213> ORGANISM: Artificial
<220> FEATURE:
<223> OTHER INFORMATION: Aptamer

<400> SEQUENCE: 1622
cuucguccuu uaggguguac uggucccuuc caccgggua                               40

<210> SEQ ID NO 1623
<211> LENGTH: 40
<212> TYPE: RNA
<213> ORGANISM: Artificial
<220> FEATURE:
<223> OTHER INFORMATION: Aptamer

<400> SEQUENCE: 1623
cuucugcugu gcucaggugg acuggcuguu cuuuacgaug                              40

<210> SEQ ID NO 1624
<211> LENGTH: 40
<212> TYPE: RNA
<213> ORGANISM: Artificial
<220> FEATURE:
<223> OTHER INFORMATION: Aptamer

<400> SEQUENCE: 1624
cuucuguccg acggguuuau ugguugcuau cugugucgua                              40

<210> SEQ ID NO 1625
<211> LENGTH: 40
<212> TYPE: RNA
<213> ORGANISM: Artificial
<220> FEATURE:
<223> OTHER INFORMATION: Aptamer

<400> SEQUENCE: 1625
cuucuggguu uauugguacc gaaacuccgu auucucuaua                              40

<210> SEQ ID NO 1626
<211> LENGTH: 41
<212> TYPE: RNA
<213> ORGANISM: Artificial
<220> FEATURE:
<223> OTHER INFORMATION: Aptamer

<400> SEQUENCE: 1626
cuucuuuccc acucacgucu cgguuuuauu gguccaguuu u                            41

<210> SEQ ID NO 1627
<211> LENGTH: 40
<212> TYPE: RNA
<213> ORGANISM: Artificial
<220> FEATURE:
<223> OTHER INFORMATION: Aptamer

<400> SEQUENCE: 1627
cuugacagcu cuuucgggug uauugguuuc gcuagcgaaa                              40
```

```
<210> SEQ ID NO 1628
<211> LENGTH: 40
<212> TYPE: RNA
<213> ORGANISM: Artificial
<220> FEATURE:
<223> OTHER INFORMATION: Aptamer

<400> SEQUENCE: 1628
cuugugcacu agguggauug gucuuucugu cguagaguua                              40

<210> SEQ ID NO 1629
<211> LENGTH: 40
<212> TYPE: RNA
<213> ORGANISM: Artificial
<220> FEATURE:
<223> OTHER INFORMATION: Aptamer

<400> SEQUENCE: 1629
cuuuccacug cuuccgguau auuggcgaca ggagguaaug                              40

<210> SEQ ID NO 1630
<211> LENGTH: 40
<212> TYPE: RNA
<213> ORGANISM: Artificial
<220> FEATURE:
<223> OTHER INFORMATION: Aptamer

<400> SEQUENCE: 1630
cuuuugcugu gcucaggugg acuggcugcu cuuuacgaug                              40

<210> SEQ ID NO 1631
<211> LENGTH: 44
<212> TYPE: RNA
<213> ORGANISM: Artificial
<220> FEATURE:
<223> OTHER INFORMATION: Aptamer

<400> SEQUENCE: 1631
cuuuugcugu gcucaggugg acuggcuguu cuuuacgaug ucag                         44

<210> SEQ ID NO 1632
<211> LENGTH: 40
<212> TYPE: RNA
<213> ORGANISM: Artificial
<220> FEATURE:
<223> OTHER INFORMATION: Aptamer

<400> SEQUENCE: 1632
cuuuuuggcc gucgguaua auggucgcc gaauggaaug                               40

<210> SEQ ID NO 1633
<211> LENGTH: 40
<212> TYPE: RNA
<213> ORGANISM: Artificial
<220> FEATURE:
<223> OTHER INFORMATION: Aptamer

<400> SEQUENCE: 1633 cuuggugaa uuggucggcu ccacuuucug gaagacuaga                               40

<210> SEQ ID NO 1634
<211> LENGTH: 40
<212> TYPE: RNA
<213> ORGANISM: Artificial
<220> FEATURE:
<223> OTHER INFORMATION: Aptamer
```

```
<400> SEQUENCE: 1634
cugguaauug gcggauguuu ugaauugaac gauggucuug                                40

<210> SEQ ID NO 1635
<211> LENGTH: 40
<212> TYPE: RNA
<213> ORGANISM: Artificial
<220> FEATURE:
<223> OTHER INFORMATION: Aptamer

<400> SEQUENCE: 1635
cgguaaaacu gguuauugca agaauauucu ggugaugaga                                40

<210> SEQ ID NO 1636
<211> LENGTH: 40
<212> TYPE: RNA
<213> ORGANISM: Artificial
<220> FEATURE:
<223> OTHER INFORMATION: Aptamer

<400> SEQUENCE: 1636
cgguauacug gcgccaaacc ugggcaugag ccuuggagug                                40

<210> SEQ ID NO 1637
<211> LENGTH: 40
<212> TYPE: RNA
<213> ORGANISM: Artificial
<220> FEATURE:
<223> OTHER INFORMATION: Aptamer

<400> SEQUENCE: 1637
cggucgauug gcaaguaagu cugaauagau cgcgcuguug                                40

<210> SEQ ID NO 1638
<211> LENGTH: 40
<212> TYPE: RNA
<213> ORGANISM: Artificial
<220> FEATURE:
<223> OTHER INFORMATION: Aptamer

<400> SEQUENCE: 1638
cggugaacug gcaguuuucg gugcugacug uaaaacuuua                                40

<210> SEQ ID NO 1639
<211> LENGTH: 31
<212> TYPE: RNA
<213> ORGANISM: Artificial
<220> FEATURE:
<223> OTHER INFORMATION: Aptamer

<400> SEQUENCE: 1639
cgguguacug guauuugaua cuucgaagcu a                                         31

<210> SEQ ID NO 1640
<211> LENGTH: 40
<212> TYPE: RNA
<213> ORGANISM: Artificial
<220> FEATURE:
<223> OTHER INFORMATION: Aptamer

<400> SEQUENCE: 1640
cgguguacug gugcucgcca ccuugagagg caaagugcua                                40

<210> SEQ ID NO 1641
```

```
<211> LENGTH: 40
<212> TYPE: RNA
<213> ORGANISM: Artificial
<220> FEATURE:
<223> OTHER INFORMATION: Aptamer

<400> SEQUENCE: 1641
cgguguauug gcccuccuug cguugauuc aaggucugug                              40

<210> SEQ ID NO 1642
<211> LENGTH: 40
<212> TYPE: RNA
<213> ORGANISM: Artificial
<220> FEATURE:
<223> OTHER INFORMATION: Aptamer

<400> SEQUENCE: 1642
cgguguauug gucggacugu ugguauuuac uaaugcccuu                             40

<210> SEQ ID NO 1643
<211> LENGTH: 40
<212> TYPE: RNA
<213> ORGANISM: Artificial
<220> FEATURE:
<223> OTHER INFORMATION: Aptamer

<400> SEQUENCE: 1643
cgguguauug gucuacgauu gcaguaucgc ucggcguuga                             40

<210> SEQ ID NO 1644
<211> LENGTH: 40
<212> TYPE: RNA
<213> ORGANISM: Artificial
<220> FEATURE:
<223> OTHER INFORMATION: Aptamer

<400> SEQUENCE: 1644
cgguguauug gugugccgcu acagguguuu gaaacgguca                             40

<210> SEQ ID NO 1645
<211> LENGTH: 40
<212> TYPE: RNA
<213> ORGANISM: Artificial
<220> FEATURE:
<223> OTHER INFORMATION: Aptamer

<400> SEQUENCE: 1645
cgguguauug guuugcacgu cguacucuuu gcggcuuaaa                             40

<210> SEQ ID NO 1646
<211> LENGTH: 40
<212> TYPE: RNA
<213> ORGANISM: Artificial
<220> FEATURE:
<223> OTHER INFORMATION: Aptamer

<400> SEQUENCE: 1646
cgguuauugg cggaggaucu gucacggcau gccucgacug                             40

<210> SEQ ID NO 1647
<211> LENGTH: 40
<212> TYPE: RNA
<213> ORGANISM: Artificial
<220> FEATURE:
<223> OTHER INFORMATION: Aptamer

<400> SEQUENCE: 1647
```

-continued

```
cgguuauugg cggaggauuu gucauggcau gccucgacug          40
```

<210> SEQ ID NO 1648
<211> LENGTH: 40
<212> TYPE: RNA
<213> ORGANISM: Artificial
<220> FEATURE:
<223> OTHER INFORMATION: Aptamer

<400> SEQUENCE: 1648

```
cgguuauugg cggggccgcu agcuuaaugu agucugacug          40
```

<210> SEQ ID NO 1649
<211> LENGTH: 40
<212> TYPE: RNA
<213> ORGANISM: Artificial
<220> FEATURE:
<223> OTHER INFORMATION: Aptamer

<400> SEQUENCE: 1649

```
cgguuauugg cuugucgccc guuucuacg ucgccaaaug           40
```

<210> SEQ ID NO 1650
<211> LENGTH: 40
<212> TYPE: RNA
<213> ORGANISM: Artificial
<220> FEATURE:
<223> OTHER INFORMATION: Aptamer

<400> SEQUENCE: 1650

```
cgguuggacu ggcgcuccua ccuuucugug gcgcagaaug          40
```

<210> SEQ ID NO 1651
<211> LENGTH: 40
<212> TYPE: RNA
<213> ORGANISM: Artificial
<220> FEATURE:
<223> OTHER INFORMATION: Aptamer

<400> SEQUENCE: 1651

```
cgguuuacug gcgaagccag ugucaccacc cgcuuaacug          40
```

<210> SEQ ID NO 1652
<211> LENGTH: 40
<212> TYPE: RNA
<213> ORGANISM: Artificial
<220> FEATURE:
<223> OTHER INFORMATION: Aptamer

<400> SEQUENCE: 1652

```
cgguuuacug gucuuugguu uuuacugaac accgaacaua          40
```

<210> SEQ ID NO 1653
<211> LENGTH: 40
<212> TYPE: RNA
<213> ORGANISM: Artificial
<220> FEATURE:
<223> OTHER INFORMATION: Aptamer

<400> SEQUENCE: 1653

```
cgguuuauug gcugauuuac uggcuccuug uauuugaug           40
```

<210> SEQ ID NO 1654
<211> LENGTH: 40
<212> TYPE: RNA

```
<213> ORGANISM: Artificial
<220> FEATURE:
<223> OTHER INFORMATION: Aptamer

<400> SEQUENCE: 1654
cgguuuuauu ggcguguugg ucaaaaguug gacuacauug                               40

<210> SEQ ID NO 1655
<211> LENGTH: 40
<212> TYPE: RNA
<213> ORGANISM: Artificial
<220> FEATURE:
<223> OTHER INFORMATION: Aptamer

<400> SEQUENCE: 1655
gaaccacggg uuuacuggcg cuaaacaaau guuuaguaug                               40

<210> SEQ ID NO 1656
<211> LENGTH: 40
<212> TYPE: RNA
<213> ORGANISM: Artificial
<220> FEATURE:
<223> OTHER INFORMATION: Aptamer

<400> SEQUENCE: 1656
gaaugcauug ucgucgguu auacuggucc uucuuggua                                 40

<210> SEQ ID NO 1657
<211> LENGTH: 40
<212> TYPE: RNA
<213> ORGANISM: Artificial
<220> FEATURE:
<223> OTHER INFORMATION: Aptamer

<400> SEQUENCE: 1657
gaaggugaau uggcucuaua ucguuuuuug uguagcaugc                               40

<210> SEQ ID NO 1658
<211> LENGTH: 40
<212> TYPE: RNA
<213> ORGANISM: Artificial
<220> FEATURE:
<223> OTHER INFORMATION: Aptamer

<400> SEQUENCE: 1658
gaagguguau uggcuguacg accgcuggcc ggucgcauag                               40

<210> SEQ ID NO 1659
<211> LENGTH: 40
<212> TYPE: RNA
<213> ORGANISM: Artificial
<220> FEATURE:
<223> OTHER INFORMATION: Aptamer

<400> SEQUENCE: 1659
gacaugcguc auccuaggug uacuggcgau agauuugcug                               40

<210> SEQ ID NO 1660
<211> LENGTH: 40
<212> TYPE: RNA
<213> ORGANISM: Artificial
<220> FEATURE:
<223> OTHER INFORMATION: Aptamer

<400> SEQUENCE: 1660
gacccuucga gcugcgcccc gagguuauug gucacugugu                               40
```

<210> SEQ ID NO 1661
<211> LENGTH: 40
<212> TYPE: RNA
<213> ORGANISM: Artificial
<220> FEATURE:
<223> OTHER INFORMATION: Aptamer

<400> SEQUENCE: 1661
gaccgugcgc uucaggucua cuggccuuca uuugaagaug                               40

<210> SEQ ID NO 1662
<211> LENGTH: 40
<212> TYPE: RNA
<213> ORGANISM: Artificial
<220> FEATURE:
<223> OTHER INFORMATION: Aptamer

<400> SEQUENCE: 1662
gacgccgauu uccaggugua uugguaacag uaaugcgcua                               40

<210> SEQ ID NO 1663
<211> LENGTH: 40
<212> TYPE: RNA
<213> ORGANISM: Artificial
<220> FEATURE:
<223> OTHER INFORMATION: Aptamer

<400> SEQUENCE: 1663
gacuccaggu uauugguuuu gugcuccuac gcaugacgug                               40

<210> SEQ ID NO 1664
<211> LENGTH: 40
<212> TYPE: RNA
<213> ORGANISM: Artificial
<220> FEATURE:
<223> OTHER INFORMATION: Aptamer

<400> SEQUENCE: 1664
gacugcacuu gcgguuuauu ggucccucug cucuggaaua                               40

<210> SEQ ID NO 1665
<211> LENGTH: 40
<212> TYPE: RNA
<213> ORGANISM: Artificial
<220> FEATURE:
<223> OTHER INFORMATION: Aptamer

<400> SEQUENCE: 1665
gacugucgau uuucgguuau uggcgccuuu cuaggauaug                               40

<210> SEQ ID NO 1666
<211> LENGTH: 39
<212> TYPE: RNA
<213> ORGANISM: Artificial
<220> FEATURE:
<223> OTHER INFORMATION: Aptamer

<400> SEQUENCE: 1666
gacuguugau uucgguuauu ggcgccuuuc uaggauaug                                39

<210> SEQ ID NO 1667
<211> LENGTH: 40
<212> TYPE: RNA
<213> ORGANISM: Artificial
<220> FEATURE:

-continued

```
<223> OTHER INFORMATION: Aptamer

<400> SEQUENCE: 1667
gacuuguucu ggaggugaac uggcggacau cagugccaug                    40

<210> SEQ ID NO 1668
<211> LENGTH: 40
<212> TYPE: RNA
<213> ORGANISM: Artificial
<220> FEATURE:
<223> OTHER INFORMATION: Aptamer

<400> SEQUENCE: 1668
gagcuucgcu guaccgcuug guugaauugg cgcuuggcug                    40

<210> SEQ ID NO 1669
<211> LENGTH: 40
<212> TYPE: RNA
<213> ORGANISM: Artificial
<220> FEATURE:
<223> OTHER INFORMATION: Aptamer

<400> SEQUENCE: 1669
gaguuugaca gguuuauugg uagcgcaacu uugcguugug                    40

<210> SEQ ID NO 1670
<211> LENGTH: 40
<212> TYPE: RNA
<213> ORGANISM: Artificial
<220> FEATURE:
<223> OTHER INFORMATION: Aptamer

<400> SEQUENCE: 1670
gaucacguua aggguucauu ggcggccgcg cacggcuaug                    40

<210> SEQ ID NO 1671
<211> LENGTH: 40
<212> TYPE: RNA
<213> ORGANISM: Artificial
<220> FEATURE:
<223> OTHER INFORMATION: Aptamer

<400> SEQUENCE: 1671
gaucccggua cauuggcuac cguucucgag uacggcaagu                    40

<210> SEQ ID NO 1672
<211> LENGTH: 40
<212> TYPE: RNA
<213> ORGANISM: Artificial
<220> FEATURE:
<223> OTHER INFORMATION: Aptamer

<400> SEQUENCE: 1672
gaugacacgg uuauggucuu auuggcucgu ucgucgaaug                    40

<210> SEQ ID NO 1673
<211> LENGTH: 40
<212> TYPE: RNA
<213> ORGANISM: Artificial
<220> FEATURE:
<223> OTHER INFORMATION: Aptamer

<400> SEQUENCE: 1673
gauguguuag uugguuacu ggcgcacuac ucgaugaaug                     40
```

<210> SEQ ID NO 1674
<211> LENGTH: 40
<212> TYPE: RNA
<213> ORGANISM: Artificial
<220> FEATURE:
<223> OTHER INFORMATION: Aptamer

<400> SEQUENCE: 1674
gauguuagcu ggugaccccg cccgggugua cgguuccua                    40

<210> SEQ ID NO 1675
<211> LENGTH: 40
<212> TYPE: RNA
<213> ORGANISM: Artificial
<220> FEATURE:
<223> OTHER INFORMATION: Aptamer

<400> SEQUENCE: 1675
gauucgaaca ugcccuacca ggugaauugg cuuucagaug                    40

<210> SEQ ID NO 1676
<211> LENGTH: 40
<212> TYPE: RNA
<213> ORGANISM: Artificial
<220> FEATURE:
<223> OTHER INFORMATION: Aptamer

<400> SEQUENCE: 1676
gauugcacuu gcgguuuauu ggucccucug cucuggaaua                    40

<210> SEQ ID NO 1677
<211> LENGTH: 40
<212> TYPE: RNA
<213> ORGANISM: Artificial
<220> FEATURE:
<223> OTHER INFORMATION: Aptamer

<400> SEQUENCE: 1677
gauuguuugg uaauuggucc uuggucccu acgagguaua                     40

<210> SEQ ID NO 1678
<211> LENGTH: 40
<212> TYPE: RNA
<213> ORGANISM: Artificial
<220> FEATURE:
<223> OTHER INFORMATION: Aptamer

<400> SEQUENCE: 1678
gauuucuucg ucgcgggugu auuggcuuuc caugaagggu                    40

<210> SEQ ID NO 1679
<211> LENGTH: 42
<212> TYPE: RNA
<213> ORGANISM: Artificial
<220> FEATURE:
<223> OTHER INFORMATION: Aptamer

<400> SEQUENCE: 1679 gauuuuggu uuauuggcu uugccguuug aagugcaaaa ug                   42

<210> SEQ ID NO 1680
<211> LENGTH: 41
<212> TYPE: RNA
<213> ORGANISM: Artificial
<220> FEATURE:
<223> OTHER INFORMATION: Aptamer

```
<400> SEQUENCE: 1680
gauuuugguu uauuggcuuu gccguuugaa gugcaaaaau g            41

<210> SEQ ID NO 1681
<211> LENGTH: 40
<212> TYPE: RNA
<213> ORGANISM: Artificial
<220> FEATURE:
<223> OTHER INFORMATION: Aptamer

<400> SEQUENCE: 1681
gauuuugguu uauuggcuuu gccguuugaa uugcaaaaug             40

<210> SEQ ID NO 1682
<211> LENGTH: 40
<212> TYPE: RNA
<213> ORGANISM: Artificial
<220> FEATURE:
<223> OTHER INFORMATION: Aptamer

<400> SEQUENCE: 1682
gauuggugua uuggcgauag caguuuuuua cgcuaauuug             40

<210> SEQ ID NO 1683
<211> LENGTH: 41
<212> TYPE: RNA
<213> ORGANISM: Artificial
<220> FEATURE:
<223> OTHER INFORMATION: Aptamer

<400> SEQUENCE: 1683
gagguuauug gccgcuaaug cuccgcgaua uuaguuguuu u            41

<210> SEQ ID NO 1684
<211> LENGTH: 40
<212> TYPE: RNA
<213> ORGANISM: Artificial
<220> FEATURE:
<223> OTHER INFORMATION: Aptamer

<400> SEQUENCE: 1684
gagguuuauu ggcgacgggc agauuucuug gauugugcug             40

<210> SEQ ID NO 1685
<211> LENGTH: 40
<212> TYPE: RNA
<213> ORGANISM: Artificial
<220> FEATURE:
<223> OTHER INFORMATION: Aptamer

<400> SEQUENCE: 1685
gcaccugggg uguauuggcu gaucgcgguc cucggguuag             40

<210> SEQ ID NO 1686
<211> LENGTH: 40
<212> TYPE: RNA
<213> ORGANISM: Artificial
<220> FEATURE:
<223> OTHER INFORMATION: Aptamer

<400> SEQUENCE: 1686
gcacucguuc ggguauacug gcuuucaccu uugauaguua             40

<210> SEQ ID NO 1687
<211> LENGTH: 41
```

```
<212> TYPE: RNA
<213> ORGANISM: Artificial
<220> FEATURE:
<223> OTHER INFORMATION: Aptamer

<400> SEQUENCE: 1687
gcacucguuu cggguguacu ggcuuucacc uuugauaguu a                    41

<210> SEQ ID NO 1688
<211> LENGTH: 42
<212> TYPE: RNA
<213> ORGANISM: Artificial
<220> FEATURE:
<223> OTHER INFORMATION: Aptamer

<400> SEQUENCE: 1688
gcagagguuu acuggcguua ucucucaucc uugaacgcag ug                   42

<210> SEQ ID NO 1689
<211> LENGTH: 39
<212> TYPE: RNA
<213> ORGANISM: Artificial
<220> FEATURE:
<223> OTHER INFORMATION: Aptamer

<400> SEQUENCE: 1689
gccccgggua uauugguggu ucuccucucg agaaacuua                       39

<210> SEQ ID NO 1690
<211> LENGTH: 41
<212> TYPE: RNA
<213> ORGANISM: Artificial
<220> FEATURE:
<223> OTHER INFORMATION: Aptamer

<400> SEQUENCE: 1690
gcccgagucu ugguauauug gugccgucac uuuuucgguu a                    41

<210> SEQ ID NO 1691
<211> LENGTH: 41
<212> TYPE: RNA
<213> ORGANISM: Artificial
<220> FEATURE:
<223> OTHER INFORMATION: Aptamer

<400> SEQUENCE: 1691
gcccuuuuuc ggcagguuca uuggcgcauu uuuguugcau g                    41

<210> SEQ ID NO 1692
<211> LENGTH: 40
<212> TYPE: RNA
<213> ORGANISM: Artificial
<220> FEATURE:
<223> OTHER INFORMATION: Aptamer

<400> SEQUENCE: 1692
gccuguaugc uucguccgag guuuauuggu cuauuugucu                      40

<210> SEQ ID NO 1693
<211> LENGTH: 40
<212> TYPE: RNA
<213> ORGANISM: Artificial
<220> FEATURE:
<223> OTHER INFORMATION: Aptamer

<400> SEQUENCE: 1693
```
gcgacguuug agguuuauug guuguuaauu auuuaccgua           40

<210> SEQ ID NO 1694
<211> LENGTH: 40
<212> TYPE: RNA
<213> ORGANISM: Artificial
<220> FEATURE:
<223> OTHER INFORMATION: Aptamer

<400> SEQUENCE: 1694
gcgcucucca ccuguucag guugauuggu cggaugugu           40

<210> SEQ ID NO 1695
<211> LENGTH: 39
<212> TYPE: RNA
<213> ORGANISM: Artificial
<220> FEATURE:
<223> OTHER INFORMATION: Aptamer

<400> SEQUENCE: 1695
gcgcucucca cuuguucagg uugauugguc ggauugugu           39

<210> SEQ ID NO 1696
<211> LENGTH: 40
<212> TYPE: RNA
<213> ORGANISM: Artificial
<220> FEATURE:
<223> OTHER INFORMATION: Aptamer

<400> SEQUENCE: 1696
gcgcucucca cuuuguucag guuaauuggu cggaugugu           40

<210> SEQ ID NO 1697
<211> LENGTH: 40
<212> TYPE: RNA
<213> ORGANISM: Artificial
<220> FEATURE:
<223> OTHER INFORMATION: Aptamer

<400> SEQUENCE: 1697
gcgcuucucg uucgcuuucc ggguucauug guccauguuu           40

<210> SEQ ID NO 1698
<211> LENGTH: 40
<212> TYPE: RNA
<213> ORGANISM: Artificial
<220> FEATURE:
<223> OTHER INFORMATION: Aptamer

<400> SEQUENCE: 1698
gcgugcaggu guauuggcuu uguuuucucc gggaaccgag           40

<210> SEQ ID NO 1699
<211> LENGTH: 39
<212> TYPE: RNA
<213> ORGANISM: Artificial
<220> FEATURE:
<223> OTHER INFORMATION: Aptamer

<400> SEQUENCE: 1699
gcuaaauucc ccuaccucgu ccgguaauug gucucguuu           39

<210> SEQ ID NO 1700
<211> LENGTH: 41
<212> TYPE: RNA
<213> ORGANISM: Artificial

```
<220> FEATURE:
<223> OTHER INFORMATION: Aptamer

<400> SEQUENCE: 1700
gcuccccccu auacuccagg ugaauuggcg cuuuauguau g                    41

<210> SEQ ID NO 1701
<211> LENGTH: 39
<212> TYPE: RNA
<213> ORGANISM: Artificial
<220> FEATURE:
<223> OTHER INFORMATION: Aptamer

<400> SEQUENCE: 1701
gcucccuucg acucuaggug uauuggucag cccggucua                       39

<210> SEQ ID NO 1702
<211> LENGTH: 40
<212> TYPE: RNA
<213> ORGANISM: Artificial
<220> FEATURE:
<223> OTHER INFORMATION: Aptamer

<400> SEQUENCE: 1702
gcuccuccag guuauuggcu caacuccucg uagcuggaug                      40

<210> SEQ ID NO 1703
<211> LENGTH: 39
<212> TYPE: RNA
<213> ORGANISM: Artificial
<220> FEATURE:
<223> OTHER INFORMATION: Aptamer

<400> SEQUENCE: 1703
gcuccgguau acuggcgacg accguuauug ugucgcaug                       39

<210> SEQ ID NO 1704
<211> LENGTH: 40
<212> TYPE: RNA
<213> ORGANISM: Artificial
<220> FEATURE:
<223> OTHER INFORMATION: Aptamer

<400> SEQUENCE: 1704
gcucguucau aagcgguuaa cuggcucggu aauacgcaug                      40

<210> SEQ ID NO 1705
<211> LENGTH: 38
<212> TYPE: RNA
<213> ORGANISM: Artificial
<220> FEATURE:
<223> OTHER INFORMATION: Aptamer

<400> SEQUENCE: 1705
gcucucuuac uuccugggug acuggcucuu cgguaug                         38

<210> SEQ ID NO 1706
<211> LENGTH: 39
<212> TYPE: RNA
<213> ORGANISM: Artificial
<220> FEATURE:
<223> OTHER INFORMATION: Aptamer

<400> SEQUENCE: 1706
gcuggaaauu gggcaucucg gguguauugg uaccagua                        39
```

<210> SEQ ID NO 1707
<211> LENGTH: 40
<212> TYPE: RNA
<213> ORGANISM: Artificial
<220> FEATURE:
<223> OTHER INFORMATION: Aptamer

<400> SEQUENCE: 1707
gcuuaucgcu uccacgguga acuggcuauu uuccuugaug                    40

<210> SEQ ID NO 1708
<211> LENGTH: 40
<212> TYPE: RNA
<213> ORGANISM: Artificial
<220> FEATURE:
<223> OTHER INFORMATION: Aptamer

<400> SEQUENCE: 1708
gcuuccccgg uauauuggcg cauuuaaaug cuagauguug                    40

<210> SEQ ID NO 1709
<211> LENGTH: 40
<212> TYPE: RNA
<213> ORGANISM: Artificial
<220> FEATURE:
<223> OTHER INFORMATION: Aptamer

<400> SEQUENCE: 1709
gcuuggggug caugguauac uggcgccgau ugaggaccug                    40

<210> SEQ ID NO 1710
<211> LENGTH: 40
<212> TYPE: RNA
<213> ORGANISM: Artificial
<220> FEATURE:
<223> OTHER INFORMATION: Aptamer

<400> SEQUENCE: 1710
gcuuucgucc ggguggauug guucccgcuu ucguguuaua                    40

<210> SEQ ID NO 1711
<211> LENGTH: 40
<212> TYPE: RNA
<213> ORGANISM: Artificial
<220> FEATURE:
<223> OTHER INFORMATION: Aptamer

<400> SEQUENCE: 1711
gcuuucuuug auuggvguga cugguuaucu agccgaugua                    40

<210> SEQ ID NO 1712
<211> LENGTH: 40
<212> TYPE: RNA
<213> ORGANISM: Artificial
<220> FEATURE:
<223> OTHER INFORMATION: Aptamer

<400> SEQUENCE: 1712
ggaugagucu ucucaggugu auuggcuggu auucgucaag                    40

<210> SEQ ID NO 1713
<211> LENGTH: 40
<212> TYPE: RNA
<213> ORGANISM: Artificial
<220> FEATURE:
<223> OTHER INFORMATION: Aptamer

```
<400> SEQUENCE: 1713
ggcgucuaaa ugguucuauu ggcuugcucg uuagcaaaug                              40

<210> SEQ ID NO 1714
<211> LENGTH: 40
<212> TYPE: RNA
<213> ORGANISM: Artificial
<220> FEATURE:
<223> OTHER INFORMATION: Aptamer

<400> SEQUENCE: 1714
ggcguucuuc gcuguaguuc cgguuuauug guccuuguuu                              40

<210> SEQ ID NO 1715
<211> LENGTH: 41
<212> TYPE: RNA
<213> ORGANISM: Artificial
<220> FEATURE:
<223> OTHER INFORMATION: Aptamer

<400> SEQUENCE: 1715
ggcguucuuc gcuguaguuc cgguuuauug gucuuuguuu u                            41

<210> SEQ ID NO 1716
<211> LENGTH: 40
<212> TYPE: RNA
<213> ORGANISM: Artificial
<220> FEATURE:
<223> OTHER INFORMATION: Aptamer

<400> SEQUENCE: 1716
ggcucauagu ccgguuuacu ggcgggcggu ccugucaaug                              40

<210> SEQ ID NO 1717
<211> LENGTH: 40
<212> TYPE: RNA
<213> ORGANISM: Artificial
<220> FEATURE:
<223> OTHER INFORMATION: Aptamer

<400> SEQUENCE: 1717
ggcuccacuc uagguucgac uggcuccuuc ccacggcaug                              40

<210> SEQ ID NO 1718
<211> LENGTH: 40
<212> TYPE: RNA
<213> ORGANISM: Artificial
<220> FEATURE:
<223> OTHER INFORMATION: Aptamer

<400> SEQUENCE: 1718
ggcugcgagu ugucuucccg guguauuggu cuguuugcga                              40

<210> SEQ ID NO 1719
<211> LENGTH: 40
<212> TYPE: RNA
<213> ORGANISM: Artificial
<220> FEATURE:
<223> OTHER INFORMATION: Aptamer

<400> SEQUENCE: 1719
ggcuucacuc uagguucgau uggcuccuuc ccacggcaug                              40

<210> SEQ ID NO 1720
```

```
<211> LENGTH: 40
<212> TYPE: RNA
<213> ORGANISM: Artificial
<220> FEATURE:
<223> OTHER INFORMATION: Aptamer

<400> SEQUENCE: 1720
gggaaagccg gguggacugg cugauauucu cauaucauag                              40

<210> SEQ ID NO 1721
<211> LENGTH: 40
<212> TYPE: RNA
<213> ORGANISM: Artificial
<220> FEATURE:
<223> OTHER INFORMATION: Aptamer

<400> SEQUENCE: 1721
gggcacuugu uggugacugg uuguuuuuga uaaagcgaga                              40

<210> SEQ ID NO 1722
<211> LENGTH: 40
<212> TYPE: RNA
<213> ORGANISM: Artificial
<220> FEATURE:
<223> OTHER INFORMATION: Aptamer

<400> SEQUENCE: 1722
gggucauaau uccuucgucu agguuuauug gucgcgguuu                              40

<210> SEQ ID NO 1723
<211> LENGTH: 40
<212> TYPE: RNA
<213> ORGANISM: Artificial
<220> FEATURE:
<223> OTHER INFORMATION: Aptamer

<400> SEQUENCE: 1723
gguguacgac agguuaauug gccuucuaau cuggaagaug                              40

<210> SEQ ID NO 1724
<211> LENGTH: 40
<212> TYPE: RNA
<213> ORGANISM: Artificial
<220> FEATURE:
<223> OTHER INFORMATION: Aptamer

<400> SEQUENCE: 1724
gguguucggg uucauuggcu gcaacugucg auuugccaug                              40

<210> SEQ ID NO 1725
<211> LENGTH: 40
<212> TYPE: RNA
<213> ORGANISM: Artificial
<220> FEATURE:
<223> OTHER INFORMATION: Aptamer

<400> SEQUENCE: 1725 gguccggug uauuggugcg caauaacugu cuugcguuua                               40

<210> SEQ ID NO 1726
<211> LENGTH: 40
<212> TYPE: RNA
<213> ORGANISM: Artificial
<220> FEATURE:
<223> OTHER INFORMATION: Aptamer

<400> SEQUENCE: 1726
```
guacuccagc gccucagccc cgguguauug gccccucugg         40

<210> SEQ ID NO 1727
<211> LENGTH: 40
<212> TYPE: RNA
<213> ORGANISM: Artificial
<220> FEATURE:
<223> OTHER INFORMATION: Aptamer

<400> SEQUENCE: 1727
guacugugcg cugguuaauu ggcugccaau uuuuggaaug         40

<210> SEQ ID NO 1728
<211> LENGTH: 40
<212> TYPE: RNA
<213> ORGANISM: Artificial
<220> FEATURE:
<223> OTHER INFORMATION: Aptamer

<400> SEQUENCE: 1728
guaguuguuc gggugcauug gugcuucggg uguaaguuca         40

<210> SEQ ID NO 1729
<211> LENGTH: 40
<212> TYPE: RNA
<213> ORGANISM: Artificial
<220> FEATURE:
<223> OTHER INFORMATION: Aptamer

<400> SEQUENCE: 1729
guaucccauu gucccuggug uauuggcggg uauaucuaug         40

<210> SEQ ID NO 1730
<211> LENGTH: 40
<212> TYPE: RNA
<213> ORGANISM: Artificial
<220> FEATURE:
<223> OTHER INFORMATION: Aptamer

<400> SEQUENCE: 1730
guaucuuucc aggucgauug gcucuugugu ccuaagaaug         40

<210> SEQ ID NO 1731
<211> LENGTH: 40
<212> TYPE: RNA
<213> ORGANISM: Artificial
<220> FEATURE:
<223> OTHER INFORMATION: Aptamer

<400> SEQUENCE: 1731
guauuccggc ugcguugcgg ugaacuggcu cuuggggaug         40

<210> SEQ ID NO 1732
<211> LENGTH: 40
<212> TYPE: RNA
<213> ORGANISM: Artificial
<220> FEATURE:
<223> OTHER INFORMATION: Aptamer

<400> SEQUENCE: 1732
guauuuggug gauugguaua gauguuaguc guugucuuua         40

<210> SEQ ID NO 1733
<211> LENGTH: 40
<212> TYPE: RNA

```
<213> ORGANISM: Artificial
<220> FEATURE:
<223> OTHER INFORMATION: Aptamer

<400> SEQUENCE: 1733
guagguguau uggucuaccg uugacucugu cuucuccaga                    40

<210> SEQ ID NO 1734
<211> LENGTH: 40
<212> TYPE: RNA
<213> ORGANISM: Artificial
<220> FEATURE:
<223> OTHER INFORMATION: Aptamer

<400> SEQUENCE: 1734
gucauuuaaa cgcguuugua gguguauugg cuuuucuuag                    40

<210> SEQ ID NO 1735
<211> LENGTH: 40
<212> TYPE: RNA
<213> ORGANISM: Artificial
<220> FEATURE:
<223> OTHER INFORMATION: Aptamer

<400> SEQUENCE: 1735
guccaagguu aauuggcugu auacgacacg uuuauguaug                    40

<210> SEQ ID NO 1736
<211> LENGTH: 40
<212> TYPE: RNA
<213> ORGANISM: Artificial
<220> FEATURE:
<223> OTHER INFORMATION: Aptamer

<400> SEQUENCE: 1736
guccauaggu uuauuggccu uccuuugccg gggcagugug                    40

<210> SEQ ID NO 1737
<211> LENGTH: 40
<212> TYPE: RNA
<213> ORGANISM: Artificial
<220> FEATURE:
<223> OTHER INFORMATION: Aptamer

<400> SEQUENCE: 1737
gucccugaau uguucaucca cgguguaauu ggucaguuu                     40

<210> SEQ ID NO 1738
<211> LENGTH: 44
<212> TYPE: RNA
<213> ORGANISM: Artificial
<220> FEATURE:
<223> OTHER INFORMATION: Aptamer

<400> SEQUENCE: 1738
gucccuuuuu ucggcagguu cauuggcgcu auuuuguug caug                44

<210> SEQ ID NO 1739
<211> LENGTH: 40
<212> TYPE: RNA
<213> ORGANISM: Artificial
<220> FEATURE:
<223> OTHER INFORMATION: Aptamer

<400> SEQUENCE: 1739
guccgccggg uuuauugguc uccguguccc cgcgguuaaa                    40
```

<210> SEQ ID NO 1740
<211> LENGTH: 40
<212> TYPE: RNA
<213> ORGANISM: Artificial
<220> FEATURE:
<223> OTHER INFORMATION: Aptamer

<400> SEQUENCE: 1740
guccgugggu guauuggcaa accaucgagu cuuggugcug            40

<210> SEQ ID NO 1741
<211> LENGTH: 40
<212> TYPE: RNA
<213> ORGANISM: Artificial
<220> FEATURE:
<223> OTHER INFORMATION: Aptamer

<400> SEQUENCE: 1741
guccucuugu acguucgccg guguauuggu auuuaggaua            40

<210> SEQ ID NO 1742
<211> LENGTH: 40
<212> TYPE: RNA
<213> ORGANISM: Artificial
<220> FEATURE:
<223> OTHER INFORMATION: Aptamer

<400> SEQUENCE: 1742
guccuguccg gguguacugg ucacaaaugg caguuguua            40

<210> SEQ ID NO 1743
<211> LENGTH: 38
<212> TYPE: RNA
<213> ORGANISM: Artificial
<220> FEATURE:
<223> OTHER INFORMATION: Aptamer

<400> SEQUENCE: 1743
guccuugagu ucagguguau uggcgacuaa uugucaug            38

<210> SEQ ID NO 1744
<211> LENGTH: 41
<212> TYPE: RNA
<213> ORGANISM: Artificial
<220> FEATURE:
<223> OTHER INFORMATION: Aptamer

<400> SEQUENCE: 1744
guccuugagu ucagguguau uggcgaucua ggcuuguuau g            41

<210> SEQ ID NO 1745
<211> LENGTH: 40
<212> TYPE: RNA
<213> ORGANISM: Artificial
<220> FEATURE:
<223> OTHER INFORMATION: Aptamer

<400> SEQUENCE: 1745
guccgguuaa uuggcguaca uauaucccuu guuguaaaug            40

<210> SEQ ID NO 1746
<211> LENGTH: 40
<212> TYPE: RNA
<213> ORGANISM: Artificial
<220> FEATURE:

```
<223> OTHER INFORMATION: Aptamer

<400> SEQUENCE: 1746
gucgcacauc gcguuugggu uuauuggucg ggaaaccaua                    40

<210> SEQ ID NO 1747
<211> LENGTH: 40
<212> TYPE: RNA
<213> ORGANISM: Artificial
<220> FEATURE:
<223> OTHER INFORMATION: Aptamer

<400> SEQUENCE: 1747
gucggguuua uugguaucgc cuccacgugg cuggagucua                    40

<210> SEQ ID NO 1748
<211> LENGTH: 40
<212> TYPE: RNA
<213> ORGANISM: Artificial
<220> FEATURE:
<223> OTHER INFORMATION: Aptamer

<400> SEQUENCE: 1748
gucuacucag ucuaggucau uggugauccg gaggaucgug                    40

<210> SEQ ID NO 1749
<211> LENGTH: 40
<212> TYPE: RNA
<213> ORGANISM: Artificial
<220> FEATURE:
<223> OTHER INFORMATION: Aptamer

<400> SEQUENCE: 1749
gucucguccu uugcggugua cuggccacuc aggugcgucg                    40

<210> SEQ ID NO 1750
<211> LENGTH: 40
<212> TYPE: RNA
<213> ORGANISM: Artificial
<220> FEATURE:
<223> OTHER INFORMATION: Aptamer

<400> SEQUENCE: 1750
gucuuacuuc acgcccaugg uguacuggcg cgguuguuug                    40

<210> SEQ ID NO 1751
<211> LENGTH: 40
<212> TYPE: RNA
<213> ORGANISM: Artificial
<220> FEATURE:
<223> OTHER INFORMATION: Aptamer

<400> SEQUENCE: 1751
gucuuggcug cccgggugua cuggcucuau ugcagcguua                    40

<210> SEQ ID NO 1752
<211> LENGTH: 39
<212> TYPE: RNA
<213> ORGANISM: Artificial
<220> FEATURE:
<223> OTHER INFORMATION: Aptamer

<400> SEQUENCE: 1752
gucuuuuagg uuauuggcuu ccuaauuuuc uuggagaug                     39
```

```
<210> SEQ ID NO 1753
<211> LENGTH: 40
<212> TYPE: RNA
<213> ORGANISM: Artificial
<220> FEATURE:
<223> OTHER INFORMATION: Aptamer

<400> SEQUENCE: 1753
gucgguucau uggcucaauc auccuuaucu guuugguaug                              40

<210> SEQ ID NO 1754
<211> LENGTH: 40
<212> TYPE: RNA
<213> ORGANISM: Artificial
<220> FEATURE:
<223> OTHER INFORMATION: Aptamer

<400> SEQUENCE: 1754
gugcaaaagg ugaauuggcg cucuaccuac ucggggaaug                              40

<210> SEQ ID NO 1755
<211> LENGTH: 39
<212> TYPE: RNA
<213> ORGANISM: Artificial
<220> FEATURE:
<223> OTHER INFORMATION: Aptamer

<400> SEQUENCE: 1755
gugcauuucu gggguggacug guauaguauc gacuaugug                              39

<210> SEQ ID NO 1756
<211> LENGTH: 41
<212> TYPE: RNA
<213> ORGANISM: Artificial
<220> FEATURE:
<223> OTHER INFORMATION: Aptamer

<400> SEQUENCE: 1756
gugcauuucu gggguggacug guauaguauc guacuaugug u                           41

<210> SEQ ID NO 1757
<211> LENGTH: 40
<212> TYPE: RNA
<213> ORGANISM: Artificial
<220> FEATURE:
<223> OTHER INFORMATION: Aptamer

<400> SEQUENCE: 1757
guguuccugc ccagauccgg guguacuggc gcuagugcug                              40

<210> SEQ ID NO 1758
<211> LENGTH: 46
<212> TYPE: RNA
<213> ORGANISM: Artificial
<220> FEATURE:
<223> OTHER INFORMATION: Aptamer

<400> SEQUENCE: 1758
guguuccugc ccggauccgg guguacuggc gcuuauuccu ggaaug                       46

<210> SEQ ID NO 1759
<211> LENGTH: 40
<212> TYPE: RNA
<213> ORGANISM: Artificial
<220> FEATURE:
<223> OTHER INFORMATION: Aptamer
```

<400> SEQUENCE: 1759
guguucugug guguauuggc ggguuuacuu guacacucug 40

<210> SEQ ID NO 1760
<211> LENGTH: 40
<212> TYPE: RNA
<213> ORGANISM: Artificial
<220> FEATURE:
<223> OTHER INFORMATION: Aptamer

<400> SEQUENCE: 1760
guucaauggu uauugguacu agcgcgaguu cgguagugug 40

<210> SEQ ID NO 1761
<211> LENGTH: 40
<212> TYPE: RNA
<213> ORGANISM: Artificial
<220> FEATURE:
<223> OTHER INFORMATION: Aptamer

<400> SEQUENCE: 1761
guucagguua cuggcgacgu uccccaccgg gaguguaaug 40

<210> SEQ ID NO 1762
<211> LENGTH: 40
<212> TYPE: RNA
<213> ORGANISM: Artificial
<220> FEATURE:
<223> OTHER INFORMATION: Aptamer

<400> SEQUENCE: 1762
guucccuagu uccgggucua uuggcccaau uugccggaug 40

<210> SEQ ID NO 1763
<211> LENGTH: 40
<212> TYPE: RNA
<213> ORGANISM: Artificial
<220> FEATURE:
<223> OTHER INFORMATION: Aptamer

<400> SEQUENCE: 1763
guucuauguu aguccgdguc gauuggcggu uucgaccaug 40

<210> SEQ ID NO 1764
<211> LENGTH: 39
<212> TYPE: RNA
<213> ORGANISM: Artificial
<220> FEATURE:
<223> OTHER INFORMATION: Aptamer
<220> FEATURE:
<221> NAME/KEY: misc_feauure
<222> LOCATION: (38)..(38)
<223> OTHER INFORMATION: n suands for any base.

<400> SEQUENCE: 1764
guuguucagg ugauuggcgc uggucugugg gcccgaang 39

<210> SEQ ID NO 1765
<211> LENGTH: 40
<212> TYPE: RNA
<213> ORGANISM: Artificial
<220> FEATURE:
<223> OTHER INFORMATION: Aptamer

<400> SEQUENCE: 1765
guuggguuua cugguaucgg gacgucaccg uccgauguuu 40

```
<210> SEQ ID NO 1766
<211> LENGTH: 40
<212> TYPE: RNA
<213> ORGANISM: Artificial
<220> FEATURE:
<223> OTHER INFORMATION: Aptamer

<400> SEQUENCE: 1766
guuucgcguc ucgaggugua cuggcucuua caaaguguca                            40

<210> SEQ ID NO 1767
<211> LENGTH: 40
<212> TYPE: RNA
<213> ORGANISM: Artificial
<220> FEATURE:
<223> OTHER INFORMATION: Aptamer

<400> SEQUENCE: 1767 guuucacgg acauggugua uuggucgucu uuccgaaagc                             40

<210> SEQ ID NO 1768
<211> LENGTH: 38
<212> TYPE: RNA
<213> ORGANISM: Artificial
<220> FEATURE:
<223> OTHER INFORMATION: Aptamer

<400> SEQUENCE: 1768
guugguuauu ggcgcuucau ggucuuccgu auaguaug                              38

<210> SEQ ID NO 1769
<211> LENGTH: 40
<212> TYPE: RNA
<213> ORGANISM: Artificial
<220> FEATURE:
<223> OTHER INFORMATION: Aptamer

<400> SEQUENCE: 1769
gggugauugg ugccacgucu uuggucucga acguagguua                            40

<210> SEQ ID NO 1770
<211> LENGTH: 39
<212> TYPE: RNA
<213> ORGANISM: Artificial
<220> FEATURE:
<223> OTHER INFORMATION: Aptamer

<400> SEQUENCE: 1770
gggugauugg uuaucugauu auugaaauca ugauguaua                             39

<210> SEQ ID NO 1771
<211> LENGTH: 35
<212> TYPE: RNA
<213> ORGANISM: Artificial
<220> FEATURE:
<223> OTHER INFORMATION: Aptamer

<400> SEQUENCE: 1771
ggguguauug gcaacugcau guuugcagua auugg                                 35

<210> SEQ ID NO 1772
<211> LENGTH: 40
<212> TYPE: RNA
<213> ORGANISM: Artificial
<220> FEATURE:
```

```
<223> OTHER INFORMATION: Aptamer

<400> SEQUENCE: 1772
ggguguauug gucuaugaug ucuucugcuu aggcacuaga                              40

<210> SEQ ID NO 1773
<211> LENGTH: 26
<212> TYPE: RNA
<213> ORGANISM: Artificial
<220> FEATURE:
<223> OTHER INFORMATION: Aptamer

<400> SEQUENCE: 1773
ggguuauugg uccaguuuuu ugggug                                             26

<210> SEQ ID NO 1774
<211> LENGTH: 40
<212> TYPE: RNA
<213> ORGANISM: Artificial
<220> FEATURE:
<223> OTHER INFORMATION: Aptamer

<400> SEQUENCE: 1774
ggguuuacug gcgauaauug agcguuugcu cguuacgcug                              40

<210> SEQ ID NO 1775
<211> LENGTH: 39
<212> TYPE: RNA
<213> ORGANISM: Artificial
<220> FEATURE:
<223> OTHER INFORMATION: Aptamer
<220> FEATURE:
<221> NAME/KEY: misc_feauure
<222> LOCATION: (1)..(1)
<223> OTHER INFORMATION: n suands for any base.

<400> SEQUENCE: 1775
ngucugguuu auuggcgguc ggacuuuugc ccugcgaug                               39

<210> SEQ ID NO 1776
<211> LENGTH: 40
<212> TYPE: RNA
<213> ORGANISM: Artificial
<220> FEATURE:
<223> OTHER INFORMATION: Aptamer

<400> SEQUENCE: 1776
uaaacucacu ucaagggugu auuggcaaag uugucugaug                              40

<210> SEQ ID NO 1777
<211> LENGTH: 40
<212> TYPE: RNA
<213> ORGANISM: Artificial
<220> FEATURE:
<223> OTHER INFORMATION: Aptamer

<400> SEQUENCE: 1777
uaaaguguuc agguguauug guuuugccug cucuuggcga                              40

<210> SEQ ID NO 1778
<211> LENGTH: 40
<212> TYPE: RNA
<213> ORGANISM: Artificial
<220> FEATURE:
<223> OTHER INFORMATION: Aptamer

<400> SEQUENCE: 1778
```

-continued uaacauccag guguauuggu agucgccgua agggacgcua                    40

<210> SEQ ID NO 1779
<211> LENGTH: 40
<212> TYPE: RNA
<213> ORGANISM: Artificial
<220> FEATURE:
<223> OTHER INFORMATION: Aptamer

<400> SEQUENCE: 1779
uaacggugaa cuggcugccg guauaguccc ugcuagcaag                    40

<210> SEQ ID NO 1780
<211> LENGTH: 40
<212> TYPE: RNA
<213> ORGANISM: Artificial
<220> FEATURE:
<223> OTHER INFORMATION: Aptamer

<400> SEQUENCE: 1780
uaagguuguc caugguaauu ggcggcuuag cucggcagug                    40

<210> SEQ ID NO 1781
<211> LENGTH: 40
<212> TYPE: RNA
<213> ORGANISM: Artificial
<220> FEATURE:
<223> OTHER INFORMATION: Aptamer

<400> SEQUENCE: 1781
uaaucuugcg gugcugucug gguuggauug gucgauguuu                    40

<210> SEQ ID NO 1782
<211> LENGTH: 39
<212> TYPE: RNA
<213> ORGANISM: Artificial
<220> FEATURE:
<223> OTHER INFORMATION: Aptamer

<400> SEQUENCE: 1782
uacagccccu gcuuccagg uguauugguu caauugucu                      39

<210> SEQ ID NO 1783
<211> LENGTH: 38
<212> TYPE: RNA
<213> ORGANISM: Artificial
<220> FEATURE:
<223> OTHER INFORMATION: Aptamer

<400> SEQUENCE: 1783
uacccaauga uacgagucua gguuuauugg ccucggug                      38

<210> SEQ ID NO 1784
<211> LENGTH: 57
<212> TYPE: RNA
<213> ORGANISM: Artificial
<220> FEATURE:
<223> OTHER INFORMATION: Aptamer

<400> SEQUENCE: 1784
uacccaauga uacgagucua gguuuauugg cgcuauuuau cgaucgauaa uugaaug  57

<210> SEQ ID NO 1785
<211> LENGTH: 40
<212> TYPE: RNA

```
<213> ORGANISM: Artificial
<220> FEATURE:
<223> OTHER INFORMATION: Aptamer

<400> SEQUENCE: 1785
uacccuaauu cguuuccag guguauuggu auugccgaua                    40

<210> SEQ ID NO 1786
<211> LENGTH: 41
<212> TYPE: RNA
<213> ORGANISM: Artificial
<220> FEATURE:
<223> OTHER INFORMATION: Aptamer

<400> SEQUENCE: 1786
uaccgaccuc caagguuuac uggugugu au gauuuacauu a                 41

<210> SEQ ID NO 1787
<211> LENGTH: 38
<212> TYPE: RNA
<213> ORGANISM: Artificial
<220> FEATURE:
<223> OTHER INFORMATION: Aptamer

<400> SEQUENCE: 1787
uaccgggugu acuggcuguu agacccuuuu uaacuaug                     38

<210> SEQ ID NO 1788
<211> LENGTH: 40
<212> TYPE: RNA
<213> ORGANISM: Artificial
<220> FEATURE:
<223> OTHER INFORMATION: Aptamer

<400> SEQUENCE: 1788
uaccuagguc aauuggcggg ccucucuguu uggucaucug                   40

<210> SEQ ID NO 1789
<211> LENGTH: 40
<212> TYPE: RNA
<213> ORGANISM: Artificial
<220> FEATURE:
<223> OTHER INFORMATION: Aptamer

<400> SEQUENCE: 1789
uacgcugggu uuauugguca auguguaauc guuugcugua                   40

<210> SEQ ID NO 1790
<211> LENGTH: 41
<212> TYPE: RNA
<213> ORGANISM: Artificial
<220> FEATURE:
<223> OTHER INFORMATION: Aptamer

<400> SEQUENCE: 1790
uacguuaacg uucucugaug guuauuggcg guuuuucgau g                 41

<210> SEQ ID NO 1791
<211> LENGTH: 39
<212> TYPE: RNA
<213> ORGANISM: Artificial
<220> FEATURE:
<223> OTHER INFORMATION: Aptamer

<400> SEQUENCE: 1791
uacugcguuu aaucagguuu auugguucuu aacugugua                    39
```

<210> SEQ ID NO 1792
<211> LENGTH: 40
<212> TYPE: RNA
<213> ORGANISM: Artificial
<220> FEATURE:
<223> OTHER INFORMATION: Aptamer

<400> SEQUENCE: 1792
uacugggucc ugcuacgcuc cgguuuaauu ggucucguuu                              40

<210> SEQ ID NO 1793
<211> LENGTH: 40
<212> TYPE: RNA
<213> ORGANISM: Artificial
<220> FEATURE:
<223> OTHER INFORMATION: Aptamer

<400> SEQUENCE: 1793
uagaaucucg gcucgguaca cuggcgcgcu ccgcgaucug                              40

<210> SEQ ID NO 1794
<211> LENGTH: 39
<212> TYPE: RNA
<213> ORGANISM: Artificial
<220> FEATURE:
<223> OTHER INFORMATION: Aptamer

<400> SEQUENCE: 1794
uagaguguau uguaccaggu auacuggcgc gaacgaaug                               39

<210> SEQ ID NO 1795
<211> LENGTH: 40
<212> TYPE: RNA
<213> ORGANISM: Artificial
<220> FEATURE:
<223> OTHER INFORMATION: Aptamer

<400> SEQUENCE: 1795
uagaguguau uuguaccagg uauacuggcg cgcacgaaug                              40

<210> SEQ ID NO 1796
<211> LENGTH: 40
<212> TYPE: RNA
<213> ORGANISM: Artificial
<220> FEATURE:
<223> OTHER INFORMATION: Aptamer

<400> SEQUENCE: 1796
uagcucguuc ggguguacug gcuggcgguu uacgccgugu                              40

<210> SEQ ID NO 1797
<211> LENGTH: 40
<212> TYPE: RNA
<213> ORGANISM: Artificial
<220> FEATURE:
<223> OTHER INFORMATION: Aptamer

<400> SEQUENCE: 1797
uagcugccca acgagguuua uuggcucccu caccgguaug                              40

<210> SEQ ID NO 1798
<211> LENGTH: 40
<212> TYPE: RNA
<213> ORGANISM: Artificial
<220> FEATURE:

```
<223> OTHER INFORMATION: Aptamer

<400> SEQUENCE: 1798
uaggccggaa cggugaauug gcuaacuguc uuugguugug                              40

<210> SEQ ID NO 1799
<211> LENGTH: 40
<212> TYPE: RNA
<213> ORGANISM: Artificial
<220> FEATURE:
<223> OTHER INFORMATION: Aptamer

<400> SEQUENCE: 1799
uaguucguac agguguauug guaaccaauu guggaucgua                              40

<210> SEQ ID NO 1800
<211> LENGTH: 38
<212> TYPE: RNA
<213> ORGANISM: Artificial
<220> FEATURE:
<223> OTHER INFORMATION: Aptamer

<400> SEQUENCE: 1800
uauacgcaaa cugguccggu gaauuggccu ucgqquug                                38

<210> SEQ ID NO 1801
<211> LENGTH: 40
<212> TYPE: RNA
<213> ORGANISM: Artificial
<220> FEATURE:
<223> OTHER INFORMATION: Aptamer

<400> SEQUENCE: 1801
uauccaggug uauuggcgau uggaugggau auucuuggcg                              40

<210> SEQ ID NO 1802
<211> LENGTH: 41
<212> TYPE: RNA
<213> ORGANISM: Artificial
<220> FEATURE:
<223> OTHER INFORMATION: Aptamer

<400> SEQUENCE: 1802
uaucccggua gauugguauu cguaaacuuu uacgucuauu u                            41

<210> SEQ ID NO 1803
<211> LENGTH: 42
<212> TYPE: RNA
<213> ORGANISM: Artificial
<220> FEATURE:
<223> OTHER INFORMATION: Aptamer

<400> SEQUENCE: 1803
uaucccggua gauugguauu cguaacuuuu acguccaugu uu                           42

<210> SEQ ID NO 1804
<211> LENGTH: 40
<212> TYPE: RNA
<213> ORGANISM: Artificial
<220> FEATURE:
<223> OTHER INFORMATION: Aptamer

<400> SEQUENCE: 1804
uaucugucuu gcauugcuua gggguguacu ggcucgucuc                              40
```

```
<210> SEQ ID NO 1805
<211> LENGTH: 39
<212> TYPE: RNA
<213> ORGANISM: Artificial
<220> FEATURE:
<223> OTHER INFORMATION: Aptamer

<400> SEQUENCE: 1805
uaugccgacu agguguauug guaccucuca cgagucuaa                              39

<210> SEQ ID NO 1806
<211> LENGTH: 40
<212> TYPE: RNA
<213> ORGANISM: Artificial
<220> FEATURE:
<223> OTHER INFORMATION: Aptamer

<400> SEQUENCE: 1806
uagguguacu ggcucacggc ugcagaucug guauccugag                             40

<210> SEQ ID NO 1807
<211> LENGTH: 40
<212> TYPE: RNA
<213> ORGANISM: Artificial
<220> FEATURE:
<223> OTHER INFORMATION: Aptamer

<400> SEQUENCE: 1807
uagguguauu ggcucugaac caggucuuug auucguaaug                             40

<210> SEQ ID NO 1808
<211> LENGTH: 40
<212> TYPE: RNA
<213> ORGANISM: Artificial
<220> FEATURE:
<223> OTHER INFORMATION: Aptamer

<400> SEQUENCE: 1808
ucacaguugc gauuccgggu guauuggcuc ugaaagcgag                             40

<210> SEQ ID NO 1809
<211> LENGTH: 40
<212> TYPE: RNA
<213> ORGANISM: Artificial
<220> FEATURE:
<223> OTHER INFORMATION: Aptamer

<400> SEQUENCE: 1809
ucacgucuua cggugaacug gugcaaaugg cugguuguua                             40

<210> SEQ ID NO 1810
<211> LENGTH: 40
<212> TYPE: RNA
<213> ORGANISM: Artificial
<220> FEATURE:
<223> OTHER INFORMATION: Aptamer

<400> SEQUENCE: 1810
ucacuacuca cacaucuugg uguauugguc cuccugguaa                             40

<210> SEQ ID NO 1811
<211> LENGTH: 40
<212> TYPE: RNA
<213> ORGANISM: Artificial
<220> FEATURE:
<223> OTHER INFORMATION: Aptamer
```

```
<400> SEQUENCE: 1811
ucaccccuuc ugguaaauug gcucuguuug gaucagcgug                              40

<210> SEQ ID NO 1812
<211> LENGTH: 40
<212> TYPE: RNA
<213> ORGANISM: Artificial
<220> FEATURE:
<223> OTHER INFORMATION: Aptamer

<400> SEQUENCE: 1812
ucacugucuc ggguuauugg cucguuucau cucgcggaug                              40

<210> SEQ ID NO 1813
<211> LENGTH: 40
<212> TYPE: RNA
<213> ORGANISM: Artificial
<220> FEATURE:
<223> OTHER INFORMATION: Aptamer

<400> SEQUENCE: 1813
ucacggugga cuggcuuuau gaacucaggc uuguaagaug                              40

<210> SEQ ID NO 1814
<211> LENGTH: 40
<212> TYPE: RNA
<213> ORGANISM: Artificial
<220> FEATURE:
<223> OTHER INFORMATION: Aptamer

<400> SEQUENCE: 1814
ucaguccuag guucuacugg cgccgucuga aaacgagaug                              40

<210> SEQ ID NO 1815
<211> LENGTH: 40
<212> TYPE: RNA
<213> ORGANISM: Artificial
<220> FEATURE:
<223> OTHER INFORMATION: Aptamer

<400> SEQUENCE: 1815
ucagcuaauu guucgccguu cagguuuauu ggucucguuu                              40

<210> SEQ ID NO 1816
<211> LENGTH: 40
<212> TYPE: RNA
<213> ORGANISM: Artificial
<220> FEATURE:
<223> OTHER INFORMATION: Aptamer

<400> SEQUENCE: 1816
ucaugucucg guguacuggu ugucaagcuu cgcuucagua                              40

<210> SEQ ID NO 1817
<211> LENGTH: 40
<212> TYPE: RNA
<213> ORGANISM: Artificial
<220> FEATURE:
<223> OTHER INFORMATION: Aptamer

<400> SEQUENCE: 1817
uccaacuuca ugcugcgggu guauuggguag cuuugcuuua                             40

<210> SEQ ID NO 1818
<211> LENGTH: 39
```

```
<212> TYPE: RNA
<213> ORGANISM: Artificial
<220> FEATURE:
<223> OTHER INFORMATION: Aptamer

<400> SEQUENCE: 1818
uccaauucuc ggguuuacug gcucuuuaau uauugaaug                    39

<210> SEQ ID NO 1819
<211> LENGTH: 41
<212> TYPE: RNA
<213> ORGANISM: Artificial
<220> FEATURE:
<223> OTHER INFORMATION: Aptamer

<400> SEQUENCE: 1819
uccaccccuu cugcgucuug agguuuauug gccgucguuu u                 41

<210> SEQ ID NO 1820
<211> LENGTH: 40
<212> TYPE: RNA
<213> ORGANISM: Artificial
<220> FEATURE:
<223> OTHER INFORMATION: Aptamer

<400> SEQUENCE: 1820
uccacuguau cccucgggug uacuggcgcg auacugaaug                   40

<210> SEQ ID NO 1821
<211> LENGTH: 40
<212> TYPE: RNA
<213> ORGANISM: Artificial
<220> FEATURE:
<223> OTHER INFORMATION: Aptamer

<400> SEQUENCE: 1821
uccaggucau auuggcgggc uccuucuggg uuguuguuug                   40

<210> SEQ ID NO 1822
<211> LENGTH: 40
<212> TYPE: RNA
<213> ORGANISM: Artificial
<220> FEATURE:
<223> OTHER INFORMATION: Aptamer

<400> SEQUENCE: 1822
ucccacucgg uuaauuggcu acagaaaucc ucuguguaug                   40

<210> SEQ ID NO 1823
<211> LENGTH: 40
<212> TYPE: RNA
<213> ORGANISM: Artificial
<220> FEATURE:
<223> OTHER INFORMATION: Aptamer

<400> SEQUENCE: 1823
ucccauacgu ucgggugaac ugguuuccuc ggugaucgua                   40

<210> SEQ ID NO 1824
<211> LENGTH: 41
<212> TYPE: RNA
<213> ORGANISM: Artificial
<220> FEATURE:
<223> OTHER INFORMATION: Aptamer

<400> SEQUENCE: 1824
```

```
uccccccggaa aaaacaugcc cagguugauu ggucauugug u         41
```

<210> SEQ ID NO 1825
<211> LENGTH: 45
<212> TYPE: RNA
<213> ORGANISM: Artificial
<220> FEATURE:
<223> OTHER INFORMATION: Aptamer

<400> SEQUENCE: 1825

```
uccccggaaa aaaaaaacaa ugcccagguu gauuggucau ugugu      45
```

<210> SEQ ID NO 1826
<211> LENGTH: 38
<212> TYPE: RNA
<213> ORGANISM: Artificial
<220> FEATURE:
<223> OTHER INFORMATION: Aptamer

<400> SEQUENCE: 1826

```
uccccggaaa acaugcccag guugauuggu caugugu              38
```

<210> SEQ ID NO 1827
<211> LENGTH: 40
<212> TYPE: RNA
<213> ORGANISM: Artificial
<220> FEATURE:
<223> OTHER INFORMATION: Aptamer

<400> SEQUENCE: 1827

```
ucccucugcg cgguuccuuu ugccggugaa uuggccugug            40
```

<210> SEQ ID NO 1828
<211> LENGTH: 40
<212> TYPE: RNA
<213> ORGANISM: Artificial
<220> FEATURE:
<223> OTHER INFORMATION: Aptamer

<400> SEQUENCE: 1828

```
ucccgguuua cuggugugac agucaucuga cuauugcgug            40
```

<210> SEQ ID NO 1829
<211> LENGTH: 34
<212> TYPE: RNA
<213> ORGANISM: Artificial
<220> FEATURE:
<223> OTHER INFORMATION: Aptamer

<400> SEQUENCE: 1829

```
uccgaguacg guauauuggu gcuuucggaa guua                  34
```

<210> SEQ ID NO 1830
<211> LENGTH: 38
<212> TYPE: RNA
<213> ORGANISM: Artificial
<220> FEATURE:
<223> OTHER INFORMATION: Aptamer

<400> SEQUENCE: 1830

```
uccgcaugug gguaaacugg cgccugauuu uuggagug              38
```

<210> SEQ ID NO 1831
<211> LENGTH: 40
<212> TYPE: RNA
<213> ORGANISM: Artificial
<220> FEATURE:
<223> OTHER INFORMATION: Aptamer

<400> SEQUENCE: 1831
uccgcuucgu ccacugguca acuggccccg gccggacgug                              40

<210> SEQ ID NO 1832
<211> LENGTH: 40
<212> TYPE: RNA
<213> ORGANISM: Artificial
<220> FEATURE:
<223> OTHER INFORMATION: Aptamer

<400> SEQUENCE: 1832
uccgucuagg uauauuggug uccuguacau gguuuucuuu                              40

<210> SEQ ID NO 1833
<211> LENGTH: 40
<212> TYPE: RNA
<213> ORGANISM: Artificial
<220> FEATURE:
<223> OTHER INFORMATION: Aptamer

<400> SEQUENCE: 1833
uccguucggg uguacuggcu ugucucuuua gggcaugaug                              40

<210> SEQ ID NO 1834
<211> LENGTH: 41
<212> TYPE: RNA
<213> ORGANISM: Artificial
<220> FEATURE:
<223> OTHER INFORMATION: Aptamer

<400> SEQUENCE: 1834
uccguuugcu gugauuaucu ggguguacug gucuuucucc a                            41

<210> SEQ ID NO 1835
<211> LENGTH: 40
<212> TYPE: RNA
<213> ORGANISM: Artificial
<220> FEATURE:
<223> OTHER INFORMATION: Aptamer

<400> SEQUENCE: 1835
uccgggugca cuggcgguuc cuaccaaccu ucggaucuug                              40

<210> SEQ ID NO 1836
<211> LENGTH: 40
<212> TYPE: RNA
<213> ORGANISM: Artificial
<220> FEATURE:
<223> OTHER INFORMATION: Aptamer

<400> SEQUENCE: 1836
uccgggugga uugguuauac cucugcugac gugucaugua                              40

<210> SEQ ID NO 1837
<211> LENGTH: 42
<212> TYPE: RNA
<213> ORGANISM: Artificial
<220> FEATURE:
<223> OTHER INFORMATION: Aptamer

<400> SEQUENCE: 1837
uccgggugga uugguuauug guugcagggg gcaucggguc aa                           42

<210> SEQ ID NO 1838
<211> LENGTH: 40
<212> TYPE: RNA
<213> ORGANISM: Artificial
<220> FEATURE:
<223> OTHER INFORMATION: Aptamer

<400> SEQUENCE: 1838
uccggguuca uuggugagag uguaagacca cauuucuuua          40

<210> SEQ ID NO 1839
<211> LENGTH: 40
<212> TYPE: RNA
<213> ORGANISM: Artificial
<220> FEATURE:
<223> OTHER INFORMATION: Aptamer

<400> SEQUENCE: 1839
uccggguucc auuggccgaa uucugugucg agccugugug          40

<210> SEQ ID NO 1840
<211> LENGTH: 40
<212> TYPE: RNA
<213> ORGANISM: Artificial
<220> FEATURE:
<223> OTHER INFORMATION: Aptamer

<400> SEQUENCE: 1840
uccuacucca gguguauugg uuucucucuu cgaaugguua          40

<210> SEQ ID NO 1841
<211> LENGTH: 40
<212> TYPE: RNA
<213> ORGANISM: Artificial
<220> FEATURE:
<223> OTHER INFORMATION: Aptamer

<400> SEQUENCE: 1841
uccuuuccag guaauugguc cgucacaccu gcgucgggug          40

<210> SEQ ID NO 1842
<211> LENGTH: 40
<212> TYPE: RNA
<213> ORGANISM: Artificial
<220> FEATURE:
<223> OTHER INFORMATION: Aptamer

<400> SEQUENCE: 1842
uccuuuccag guaauugguc cgucacuacu ugcgucggug          40

<210> SEQ ID NO 1843
<211> LENGTH: 40
<212> TYPE: RNA
<213> ORGANISM: Artificial
<220> FEATURE:
<223> OTHER INFORMATION: Aptamer

<400> SEQUENCE: 1843
ucgaucguuc cagguuauug gcgacacauu cgugggacug          40

<210> SEQ ID NO 1844
<211> LENGTH: 40
<212> TYPE: RNA
<213> ORGANISM: Artificial
<220> FEATURE:
<223> OTHER INFORMATION: Aptamer

```
<400> SEQUENCE: 1844
ucgaucguuu cagguuauug gcgacacauu cguaggacug                            40

<210> SEQ ID NO 1845
<211> LENGTH: 39
<212> TYPE: RNA
<213> ORGANISM: Artificial
<220> FEATURE:
<223> OTHER INFORMATION: Aptamer

<400> SEQUENCE: 1845
ucgauuguau aguuugggua auggugugu uuucucuuu                              39

<210> SEQ ID NO 1846
<211> LENGTH: 40
<212> TYPE: RNA
<213> ORGANISM: Artificial
<220> FEATURE:
<223> OTHER INFORMATION: Aptamer

<400> SEQUENCE: 1846
ucgcacuccu uuuacggugu acuggugccg ugcugugcua                            40

<210> SEQ ID NO 1847
<211> LENGTH: 41
<212> TYPE: RNA
<213> ORGANISM: Artificial
<220> FEATURE:
<223> OTHER INFORMATION: Aptamer

<400> SEQUENCE: 1847
ucgccguucu gguuuacugg cuucagguuu ucuuugaaau g                          41

<210> SEQ ID NO 1848
<211> LENGTH: 40
<212> TYPE: RNA
<213> ORGANISM: Artificial
<220> FEATURE:
<223> OTHER INFORMATION: Aptamer

<400> SEQUENCE: 1848
ucgcggcauu uggugacugg cgggucuuau uguccaacug                            40

<210> SEQ ID NO 1849
<211> LENGTH: 40
<212> TYPE: RNA
<213> ORGANISM: Artificial
<220> FEATURE:
<223> OTHER INFORMATION: Aptamer

<400> SEQUENCE: 1849
ucgcucagug auuggugga cuggcucugu uuucugaaug                             40

<210> SEQ ID NO 1850
<211> LENGTH: 40
<212> TYPE: RNA
<213> ORGANISM: Artificial
<220> FEATURE:
<223> OTHER INFORMATION: Aptamer

<400> SEQUENCE: 1850
ucgcuccagg uggacuggcu uacuuuuuuu ugguuuguga                            40

<210> SEQ ID NO 1851
```

```
<211> LENGTH: 41
<212> TYPE: RNA
<213> ORGANISM: Artificial
<220> FEATURE:
<223> OTHER INFORMATION: Aptamer

<400> SEQUENCE: 1851
ucgcuccagg uggacuggcu uuacuuuuuu uugguuugug a              41

<210> SEQ ID NO 1852
<211> LENGTH: 40
<212> TYPE: RNA
<213> ORGANISM: Artificial
<220> FEATURE:
<223> OTHER INFORMATION: Aptamer

<400> SEQUENCE: 1852
ucgcucgugg guucacuggc gcacgcacuu ugauugaaug               40

<210> SEQ ID NO 1853
<211> LENGTH: 40
<212> TYPE: RNA
<213> ORGANISM: Artificial
<220> FEATURE:
<223> OTHER INFORMATION: Aptamer

<400> SEQUENCE: 1853
ucggccuaau guucgccguu cagguuuauu ggucucguuu               40

<210> SEQ ID NO 1854
<211> LENGTH: 39
<212> TYPE: RNA
<213> ORGANISM: Artificial
<220> FEATURE:
<223> OTHER INFORMATION: Aptamer

<400> SEQUENCE: 1854
ucgggcacau ccggguguac uggcgauugg aaaaugcug                39

<210> SEQ ID NO 1855
<211> LENGTH: 40
<212> TYPE: RNA
<213> ORGANISM: Artificial
<220> FEATURE:
<223> OTHER INFORMATION: Aptamer

<400> SEQUENCE: 1855
ucggucugcg aucaagguuu auuggcccau uucccggaag               40

<210> SEQ ID NO 1856
<211> LENGTH: 40
<212> TYPE: RNA
<213> ORGANISM: Artificial
<220> FEATURE:
<223> OTHER INFORMATION: Aptamer

<400> SEQUENCE: 1856
ucguaucguc gcguucacgg uguacuggua cggaaguuaa               40

<210> SEQ ID NO 1857
<211> LENGTH: 40
<212> TYPE: RNA
<213> ORGANISM: Artificial
<220> FEATURE:
<223> OTHER INFORMATION: Aptamer

<400> SEQUENCE: 1857
```

-continued ucguccucaa gguguacugg ucucuguucu gucucgaaua    40

<210> SEQ ID NO 1858
<211> LENGTH: 40
<212> TYPE: RNA
<213> ORGANISM: Artificial
<220> FEATURE:
<223> OTHER INFORMATION: Aptamer

<400> SEQUENCE: 1858
ucgucucagg uguauuggcu ggcgcugcga agagucgagg    40

<210> SEQ ID NO 1859
<211> LENGTH: 41
<212> TYPE: RNA
<213> ORGANISM: Artificial
<220> FEATURE:
<223> OTHER INFORMATION: Aptamer

<400> SEQUENCE: 1859
ucgucuccag guguauuggc uggcgcugcg aggagucgag g    41

<210> SEQ ID NO 1860
<211> LENGTH: 40
<212> TYPE: RNA
<213> ORGANISM: Artificial
<220> FEATURE:
<223> OTHER INFORMATION: Aptamer

<400> SEQUENCE: 1860
ucgucugcgg uguauuggcu ucccuuuucc aagggcgggg    40

<210> SEQ ID NO 1861
<211> LENGTH: 40
<212> TYPE: RNA
<213> ORGANISM: Artificial
<220> FEATURE:
<223> OTHER INFORMATION: Aptamer

<400> SEQUENCE: 1861
ucguuggucc guucagguuu auuggucuuu uccuuaguua    40

<210> SEQ ID NO 1862
<211> LENGTH: 41
<212> TYPE: RNA
<213> ORGANISM: Artificial
<220> FEATURE:
<223> OTHER INFORMATION: Aptamer

<400> SEQUENCE: 1862
ucggguuauu ggcgaaauuu uugcugugcg aaaaucugcu g    41

<210> SEQ ID NO 1863
<211> LENGTH: 40
<212> TYPE: RNA
<213> ORGANISM: Artificial
<220> FEATURE:
<223> OTHER INFORMATION: Aptamer

<400> SEQUENCE: 1863
ucggguuauu ggcgcaauau ugguauccug uauuggucug    40

<210> SEQ ID NO 1864
<211> LENGTH: 40
<212> TYPE: RNA

-continued

```
<213> ORGANISM: Artificial
<220> FEATURE:
<223> OTHER INFORMATION: Aptamer

<400> SEQUENCE: 1864
ucggguuuua cuggcgcuuc ggaccuuugg acgcaguaug                         40

<210> SEQ ID NO 1865
<211> LENGTH: 40
<212> TYPE: RNA
<213> ORGANISM: Artificial
<220> FEATURE:
<223> OTHER INFORMATION: Aptamer

<400> SEQUENCE: 1865
ucuacguuau ggucuauugg cgcuaguuuc agacuggcug                         40

<210> SEQ ID NO 1866
<211> LENGTH: 38
<212> TYPE: RNA
<213> ORGANISM: Artificial
<220> FEATURE:
<223> OTHER INFORMATION: Aptamer

<400> SEQUENCE: 1866
ucuaguccgg guuucauugg cuuucagaua ugaacaug                           38

<210> SEQ ID NO 1867
<211> LENGTH: 39
<212> TYPE: RNA
<213> ORGANISM: Artificial
<220> FEATURE:
<223> OTHER INFORMATION: Aptamer

<400> SEQUENCE: 1867
ucuaucgugc cgguuuacug gcgccuccgc uugcgaaug                          39

<210> SEQ ID NO 1868
<211> LENGTH: 40
<212> TYPE: RNA
<213> ORGANISM: Artificial
<220> FEATURE:
<223> OTHER INFORMATION: Aptamer

<400> SEQUENCE: 1868
ucuaggugua uuggucuguu gaacgguguu caucuuguuu                         40

<210> SEQ ID NO 1869
<211> LENGTH: 40
<212> TYPE: RNA
<213> ORGANISM: Artificial
<220> FEATURE:
<223> OTHER INFORMATION: Aptamer

<400> SEQUENCE: 1869
ucucagucgu ucguacaggu guauggcgg uucuucuuug                          40

<210> SEQ ID NO 1870
<211> LENGTH: 40
<212> TYPE: RNA
<213> ORGANISM: Artificial
<220> FEATURE:
<223> OTHER INFORMATION: Aptamer

<400> SEQUENCE: 1870
ucucgagguu uauugguegu ggugaucuuu accaucggug                         40
```

<210> SEQ ID NO 1871
<211> LENGTH: 40
<212> TYPE: RNA
<213> ORGANISM: Artificial
<220> FEATURE:
<223> OTHER INFORMATION: Aptamer

<400> SEQUENCE: 1871
ucucgccguc gguuuacugg ugauucuuuu gauauucgug                      40

<210> SEQ ID NO 1872
<211> LENGTH: 40
<212> TYPE: RNA
<213> ORGANISM: Artificial
<220> FEATURE:
<223> OTHER INFORMATION: Aptamer

<400> SEQUENCE: 1872
ucucggguuu auuggcucac gggcaaugcu cucguauuug                      40

<210> SEQ ID NO 1873
<211> LENGTH: 43
<212> TYPE: RNA
<213> ORGANISM: Artificial
<220> FEATURE:
<223> OTHER INFORMATION: Aptamer

<400> SEQUENCE: 1873
ucucuguugc uuauucuagg uguuauuggc uagcccucuu gug                  43

<210> SEQ ID NO 1874
<211> LENGTH: 38
<212> TYPE: RNA
<213> ORGANISM: Artificial
<220> FEATURE:
<223> OTHER INFORMATION: Aptamer

<400> SEQUENCE: 1874
ucucggugga cugguacuau uucgggguaa augguguu                        38

<210> SEQ ID NO 1875
<211> LENGTH: 40
<212> TYPE: RNA
<213> ORGANISM: Artificial
<220> FEATURE:
<223> OTHER INFORMATION: Aptamer

<400> SEQUENCE: 1875
ucugaagggu uugauuggcu cacucgcugg cgagaguaug                      40

<210> SEQ ID NO 1876
<211> LENGTH: 40
<212> TYPE: RNA
<213> ORGANISM: Artificial
<220> FEATURE:
<223> OTHER INFORMATION: Aptamer

<400> SEQUENCE: 1876
ucugaccugu gcggugguga auuggcuagc agucguuaag                      40

<210> SEQ ID NO 1877
<211> LENGTH: 40
<212> TYPE: RNA
<213> ORGANISM: Artificial
<220> FEATURE:

<223> OTHER INFORMATION: Aptamer

<400> SEQUENCE: 1877
ucugcgggug gaacuggcgg gggauuuauu uccucaucug         40

<210> SEQ ID NO 1878
<211> LENGTH: 45
<212> TYPE: RNA
<213> ORGANISM: Artificial
<220> FEATURE:
<223> OTHER INFORMATION: Aptamer

<400> SEQUENCE: 1878
ucugcuuuga cguucaacaa gguuuauugg uccacugucc gguua         45

<210> SEQ ID NO 1879
<211> LENGTH: 40
<212> TYPE: RNA
<213> ORGANISM: Artificial
<220> FEATURE:
<223> OTHER INFORMATION: Aptamer

<400> SEQUENCE: 1879
ucuggacggu guauuggcgc cugaggcugu caggaccuug         40

<210> SEQ ID NO 1880
<211> LENGTH: 39
<212> TYPE: RNA
<213> ORGANISM: Artificial
<220> FEATURE:
<223> OTHER INFORMATION: Aptamer
<220> FEATURE:
<221> NAME/KEY: misc_feauure
<222> LOCATION: (9)..(9)
<223> OTHER INFORMATION: n suands for any base.

<400> SEQUENCE: 1880
ucugucucng ccccaggugg auuggucccu ucuggaaua         39

<210> SEQ ID NO 1881
<211> LENGTH: 39
<212> TYPE: RNA
<213> ORGANISM: Artificial
<220> FEATURE:
<223> OTHER INFORMATION: Aptamer

<400> SEQUENCE: 1881
ucugggugua uuggucgaua aagaaauugu ucuuucgga         39

<210> SEQ ID NO 1882
<211> LENGTH: 40
<212> TYPE: RNA
<213> ORGANISM: Artificial
<220> FEATURE:
<223> OTHER INFORMATION: Aptamer

<400> SEQUENCE: 1882
ucugggugua uuggucgaua aagaaauugu ucuuuucgga         40

<210> SEQ ID NO 1883
<211> LENGTH: 41
<212> TYPE: RNA
<213> ORGANISM: Artificial
<220> FEATURE:
<223> OTHER INFORMATION: Aptamer

<400> SEQUENCE: 1883
ucugggugua uuggucgaua aagaaguugu ucuuuucgg a        41

<210> SEQ ID NO 1884
<211> LENGTH: 40
<212> TYPE: RNA
<213> ORGANISM: Artificial
<220> FEATURE:
<223> OTHER INFORMATION: Aptamer

<400> SEQUENCE: 1884
ucuggguucu auuggugccu caccuuaauc agugaucuua        40

<210> SEQ ID NO 1885
<211> LENGTH: 40
<212> TYPE: RNA
<213> ORGANISM: Artificial
<220> FEATURE:
<223> OTHER INFORMATION: Aptamer

<400> SEQUENCE: 1885
ucuucgcaac gcuugguuau uggcggaucc ucgaucguug        40

<210> SEQ ID NO 1886
<211> LENGTH: 40
<212> TYPE: RNA
<213> ORGANISM: Artificial
<220> FEATURE:
<223> OTHER INFORMATION: Aptamer

<400> SEQUENCE: 1886
ucuucgcgug ccgcaggugu auggcugggg gauccuugag        40

<210> SEQ ID NO 1887
<211> LENGTH: 39
<212> TYPE: RNA
<213> ORGANISM: Artificial
<220> FEATURE:
<223> OTHER INFORMATION: Aptamer

<400> SEQUENCE: 1887
ucuucuaggu uauuggcgcg uugaucacau cuaccgcug        39

<210> SEQ ID NO 1888
<211> LENGTH: 40
<212> TYPE: RNA
<213> ORGANISM: Artificial
<220> FEATURE:
<223> OTHER INFORMATION: Aptamer

<400> SEQUENCE: 1888
ucuucucguc uugguguacu ggcuaacuac uuaguaaagu        40

<210> SEQ ID NO 1889
<211> LENGTH: 40
<212> TYPE: RNA
<213> ORGANISM: Artificial
<220> FEATURE:
<223> OTHER INFORMATION: Aptamer

<400> SEQUENCE: 1889
ucuuucuacg uucuggucau acuggcgcgu uuacugaaug        40

<210> SEQ ID NO 1890
<211> LENGTH: 40
<212> TYPE: RNA

```
<213> ORGANISM: Artificial
<220> FEATURE:
<223> OTHER INFORMATION: Aptamer

<400> SEQUENCE: 1890
ucuuucuguu ugggucuauu ggcggucacu uuuccacuug                              40

<210> SEQ ID NO 1891
<211> LENGTH: 40
<212> TYPE: RNA
<213> ORGANISM: Artificial
<220> FEATURE:
<223> OTHER INFORMATION: Aptamer

<400> SEQUENCE: 1891
ucuuuggugu auuggucggc uccucgugcg aagccgguaa                              40

<210> SEQ ID NO 1892
<211> LENGTH: 40
<212> TYPE: RNA
<213> ORGANISM: Artificial
<220> FEATURE:
<223> OTHER INFORMATION: Aptamer

<400> SEQUENCE: 1892
ucggucggau uggcaguacu cgguuuugu uuguauaaug                               40

<210> SEQ ID NO 1893
<211> LENGTH: 40
<212> TYPE: RNA
<213> ORGANISM: Artificial
<220> FEATURE:
<223> OTHER INFORMATION: Aptamer

<400> SEQUENCE: 1893
ucggugccau uggcuggcgg uaauucgcuc ccgcugauug                              40

<210> SEQ ID NO 1894
<211> LENGTH: 39
<212> TYPE: RNA
<213> ORGANISM: Artificial
<220> FEATURE:
<223> OTHER INFORMATION: Aptamer

<400> SEQUENCE: 1894
ucggugguau uggcggucuc agaccggcgg agauggcug                               39

<210> SEQ ID NO 1895
<211> LENGTH: 40
<212> TYPE: RNA
<213> ORGANISM: Artificial
<220> FEATURE:
<223> OTHER INFORMATION: Aptamer

<400> SEQUENCE: 1895
ugaacugcuc cuagguguca cuggcuucuu ccagaguaug                              40

<210> SEQ ID NO 1896
<211> LENGTH: 41
<212> TYPE: RNA
<213> ORGANISM: Artificial
<220> FEATURE:
<223> OTHER INFORMATION: Aptamer

<400> SEQUENCE: 1896
ugacccuugu acagucuagg ugaauuggcc caaucgaguu u                            41
```

```
<210> SEQ ID NO 1897
<211> LENGTH: 41
<212> TYPE: RNA
<213> ORGANISM: Artificial
<220> FEATURE:
<223> OTHER INFORMATION: Aptamer

<400> SEQUENCE: 1897
ugaguaaagc ucacgucaga gggugaauug gucuauguuu u                              41

<210> SEQ ID NO 1898
<211> LENGTH: 40
<212> TYPE: RNA
<213> ORGANISM: Artificial
<220> FEATURE:
<223> OTHER INFORMATION: Aptamer

<400> SEQUENCE: 1898
ugaguccggg uucauugguc cgcuaguuau ucucgguuu                                40

<210> SEQ ID NO 1899
<211> LENGTH: 40
<212> TYPE: RNA
<213> ORGANISM: Artificial
<220> FEATURE:
<223> OTHER INFORMATION: Aptamer

<400> SEQUENCE: 1899
ugauacgucu gcgguuuacu ggcuuccgug ggaagaaaug                                40

<210> SEQ ID NO 1900
<211> LENGTH: 40
<212> TYPE: RNA
<213> ORGANISM: Artificial
<220> FEATURE:
<223> OTHER INFORMATION: Aptamer

<400> SEQUENCE: 1900
ugauacuucu ccguuccggg uuuauugguc cgaauuguuu                                40

<210> SEQ ID NO 1901
<211> LENGTH: 39
<212> TYPE: RNA
<213> ORGANISM: Artificial
<220> FEATURE:
<223> OTHER INFORMATION: Aptamer

<400> SEQUENCE: 1901
ugcaacacuc uaugguguac ugguucuucu uguuggaua                                 39

<210> SEQ ID NO 1902
<211> LENGTH: 40
<212> TYPE: RNA
<213> ORGANISM: Artificial
<220> FEATURE:
<223> OTHER INFORMATION: Aptamer

<400> SEQUENCE: 1902
ugcacgccgu cuccgguaua uuggcgguau ccguuacuug                                40

<210> SEQ ID NO 1903
<211> LENGTH: 40
<212> TYPE: RNA
<213> ORGANISM: Artificial
<220> FEATURE:
```

<223> OTHER INFORMATION: Aptamer

<400> SEQUENCE: 1903
ugcaucucac uucuugguuu cagguaaauu ggucucgucu                             40

<210> SEQ ID NO 1904
<211> LENGTH: 40
<212> TYPE: RNA
<213> ORGANISM: Artificial
<220> FEATURE:
<223> OTHER INFORMATION: Aptamer

<400> SEQUENCE: 1904
ugcauucgua aauucauucc agguguauug gucuccgcga                             40

<210> SEQ ID NO 1905
<211> LENGTH: 40
<212> TYPE: RNA
<213> ORGANISM: Artificial
<220> FEATURE:
<223> OTHER INFORMATION: Aptamer

<400> SEQUENCE: 1905
ugcauuuacu gcuccgggug uacgguacc uuaccgauga                              40

<210> SEQ ID NO 1906
<211> LENGTH: 39
<212> TYPE: RNA
<213> ORGANISM: Artificial
<220> FEATURE:
<223> OTHER INFORMATION: Aptamer

<400> SEQUENCE: 1906
ugcauuuacu gcuccgggug uacgguacu uaccgauga                               39

<210> SEQ ID NO 1907
<211> LENGTH: 40
<212> TYPE: RNA
<213> ORGANISM: Artificial
<220> FEATURE:
<223> OTHER INFORMATION: Aptamer

<400> SEQUENCE: 1907
ugccaaaagu ccgguuuacu ggcucaaguu ucgugguaug                             40

<210> SEQ ID NO 1908
<211> LENGTH: 40
<212> TYPE: RNA
<213> ORGANISM: Artificial
<220> FEATURE:
<223> OTHER INFORMATION: Aptamer

<400> SEQUENCE: 1908
ugccaccuug cgaccacggu guacuggccu gucuguuugg                             40

<210> SEQ ID NO 1909
<211> LENGTH: 40
<212> TYPE: RNA
<213> ORGANISM: Artificial
<220> FEATURE:
<223> OTHER INFORMATION: Aptamer

<400> SEQUENCE: 1909
ugcgcuccag guguauuggu ggguuccug agaucccgua                              40

```
<210> SEQ ID NO 1910
<211> LENGTH: 40
<212> TYPE: RNA
<213> ORGANISM: Artificial
<220> FEATURE:
<223> OTHER INFORMATION: Aptamer

<400> SEQUENCE: 1910
ugcuccgaug uacgccgggu gaacuggucc auuugcgucu                              40

<210> SEQ ID NO 1911
<211> LENGTH: 40
<212> TYPE: RNA
<213> ORGANISM: Artificial
<220> FEATURE:
<223> OTHER INFORMATION: Aptamer

<400> SEQUENCE: 1911
ugcugggugu acggucuuc ccaagucugc uggguucuua                               40

<210> SEQ ID NO 1912
<211> LENGTH: 43
<212> TYPE: RNA
<213> ORGANISM: Artificial
<220> FEATURE:
<223> OTHER INFORMATION: Aptamer

<400> SEQUENCE: 1912
ugcuucgggu cuauuggugc cuggcgggac uccgcuccgu cug                          43

<210> SEQ ID NO 1913
<211> LENGTH: 40
<212> TYPE: RNA
<213> ORGANISM: Artificial
<220> FEATURE:
<223> OTHER INFORMATION: Aptamer

<400> SEQUENCE: 1913
ugcuucgggu guauugguca ugucuacgu cuagcuucga                               40

<210> SEQ ID NO 1914
<211> LENGTH: 40
<212> TYPE: RNA
<213> ORGANISM: Artificial
<220> FEATURE:
<223> OTHER INFORMATION: Aptamer

<400> SEQUENCE: 1914
ugcuucuauu guuuagguuu auugguuccu acgagggcuua                             40

<210> SEQ ID NO 1915
<211> LENGTH: 40
<212> TYPE: RNA
<213> ORGANISM: Artificial
<220> FEATURE:
<223> OTHER INFORMATION: Aptamer

<400> SEQUENCE: 1915
ugcuugccag guguauuggc uuacguaccc cgugaguuua                              40

<210> SEQ ID NO 1916
<211> LENGTH: 40
<212> TYPE: RNA
<213> ORGANISM: Artificial
<220> FEATURE:
<223> OTHER INFORMATION: Aptamer
```

```
<400> SEQUENCE: 1916
ugggagcacc ugauggugga cugguaccgu gucugguuga                            40

<210> SEQ ID NO 1917
<211> LENGTH: 39
<212> TYPE: RNA
<213> ORGANISM: Artificial
<220> FEATURE:
<223> OTHER INFORMATION: Aptamer

<400> SEQUENCE: 1917
ugggccacuu cucguguccg gguauauugg ucagugguu                             39

<210> SEQ ID NO 1918
<211> LENGTH: 40
<212> TYPE: RNA
<213> ORGANISM: Artificial
<220> FEATURE:
<223> OTHER INFORMATION: Aptamer

<400> SEQUENCE: 1918
uggggucggu gacuggcgau acaugauuug uguauaucug                            40

<210> SEQ ID NO 1919
<211> LENGTH: 40
<212> TYPE: RNA
<213> ORGANISM: Artificial
<220> FEATURE:
<223> OTHER INFORMATION: Aptamer

<400> SEQUENCE: 1919
ugggucucaa ugucggucuu gguaaauugg ucuaucgucu                            40

<210> SEQ ID NO 1920
<211> LENGTH: 40
<212> TYPE: RNA
<213> ORGANISM: Artificial
<220> FEATURE:
<223> OTHER INFORMATION: Aptamer

<400> SEQUENCE: 1920
ugguccacuc caggugaaauu ggccggagcu uccucgggug                           40

<210> SEQ ID NO 1921
<211> LENGTH: 40
<212> TYPE: RNA
<213> ORGANISM: Artificial
<220> FEATURE:
<223> OTHER INFORMATION: Aptamer

<400> SEQUENCE: 1921
uggucggcgc uuccacucca cgguguauug guccaguga                             40

<210> SEQ ID NO 1922
<211> LENGTH: 40
<212> TYPE: RNA
<213> ORGANISM: Artificial
<220> FEATURE:
<223> OTHER INFORMATION: Aptamer

<400> SEQUENCE: 1922
ugguucuuag ccugccaucc gagguguacu gguucgagua                            40

<210> SEQ ID NO 1923
<211> LENGTH: 40
```

```
<212> TYPE: RNA
<213> ORGANISM: Artificial
<220> FEATURE:
<223> OTHER INFORMATION: Aptamer

<400> SEQUENCE: 1923
uguaacucgc ccggguauau uggcugcugu cggagugaug                    40

<210> SEQ ID NO 1924
<211> LENGTH: 40
<212> TYPE: RNA
<213> ORGANISM: Artificial
<220> FEATURE:
<223> OTHER INFORMATION: Aptamer

<400> SEQUENCE: 1924
uguagugcuc uuuagguuca uuggcgcauu uuuugaccug                    40

<210> SEQ ID NO 1925
<211> LENGTH: 40
<212> TYPE: RNA
<213> ORGANISM: Artificial
<220> FEATURE:
<223> OTHER INFORMATION: Aptamer

<400> SEQUENCE: 1925
uguaugucua ggoguuauug guuaccggac gacuggcgga                    40

<210> SEQ ID NO 1926
<211> LENGTH: 40
<212> TYPE: RNA
<213> ORGANISM: Artificial
<220> FEATURE:
<223> OTHER INFORMATION: Aptamer

<400> SEQUENCE: 1926
ugucaggugu auuggcgcgg uuguuauuua caucccuaug                    40

<210> SEQ ID NO 1927
<211> LENGTH: 42
<212> TYPE: RNA
<213> ORGANISM: Artificial
<220> FEATURE:
<223> OTHER INFORMATION: Aptamer

<400> SEQUENCE: 1927
uguccacuga aaaaacuggu cggguugaacu ggcgguugcu ug                42

<210> SEQ ID NO 1928
<211> LENGTH: 41
<212> TYPE: RNA
<213> ORGANISM: Artificial
<220> FEATURE:
<223> OTHER INFORMATION: Aptamer

<400> SEQUENCE: 1928
uguccacuga aaaacuggguc gggugaacug gcgguugcuu g                 41

<210> SEQ ID NO 1929
<211> LENGTH: 40
<212> TYPE: RNA
<213> ORGANISM: Artificial
<220> FEATURE:
<223> OTHER INFORMATION: Aptamer

<400> SEQUENCE: 1929
``` ugucccccaau gcauccgggu gaacuggcuu cuggaaguaa                     40

<210> SEQ ID NO 1930
<211> LENGTH: 40
<212> TYPE: RNA
<213> ORGANISM: Artificial
<220> FEATURE:
<223> OTHER INFORMATION: Aptamer

<400> SEQUENCE: 1930
uguccgcuac ggguguauugg uaaacgccaa cuggugcaua                     40

<210> SEQ ID NO 1931
<211> LENGTH: 40
<212> TYPE: RNA
<213> ORGANISM: Artificial
<220> FEATURE:
<223> OTHER INFORMATION: Aptamer

<400> SEQUENCE: 1931
ugucucgguu uauuggcggu cggacuuuug ccuugcgaug                     40

<210> SEQ ID NO 1932
<211> LENGTH: 40
<212> TYPE: RNA
<213> ORGANISM: Artificial
<220> FEATURE:
<223> OTHER INFORMATION: Aptamer

<400> SEQUENCE: 1932
ugucucgguu uauuggcggu cggacuuuug cucugcgaug                     40

<210> SEQ ID NO 1933
<211> LENGTH: 41
<212> TYPE: RNA
<213> ORGANISM: Artificial
<220> FEATURE:
<223> OTHER INFORMATION: Aptamer

<400> SEQUENCE: 1933
ugucucgguu uauuggcggu cgguacuuuu gcccugcgau g                   41

<210> SEQ ID NO 1934
<211> LENGTH: 40
<212> TYPE: RNA
<213> ORGANISM: Artificial
<220> FEATURE:
<223> OTHER INFORMATION: Aptamer

<400> SEQUENCE: 1934
ugucuucaaa ccagguucga cuggcccggc gcgccgaaug                     40

<210> SEQ ID NO 1935
<211> LENGTH: 40
<212> TYPE: RNA
<213> ORGANISM: Artificial
<220> FEATURE:
<223> OTHER INFORMATION: Aptamer

<400> SEQUENCE: 1935
ugucuugggu gaacuggucu ggauaccucu gcgaaagaua                     40

<210> SEQ ID NO 1936
<211> LENGTH: 40
<212> TYPE: RNA
<213> ORGANISM: Artificial

```
<220> FEATURE:
<223> OTHER INFORMATION: Aptamer

<400> SEQUENCE: 1936
ugucugguuu auuggcuauc ccacuuccac gguaaugaug                              40

<210> SEQ ID NO 1937
<211> LENGTH: 40
<212> TYPE: RNA
<213> ORGANISM: Artificial
<220> FEATURE:
<223> OTHER INFORMATION: Aptamer

<400> SEQUENCE: 1937
ugucugguuu auuggcuauc ccacuuccac ggugauaaug                              40

<210> SEQ ID NO 1938
<211> LENGTH: 52
<212> TYPE: RNA
<213> ORGANISM: Artificial
<220> FEATURE:
<223> OTHER INFORMATION: Aptamer

<400> SEQUENCE: 1938
ugugcacccu auagguaauu ggugccuguu cccguccguu ggaaucggaa ua                52

<210> SEQ ID NO 1939
<211> LENGTH: 40
<212> TYPE: RNA
<213> ORGANISM: Artificial
<220> FEATURE:
<223> OTHER INFORMATION: Aptamer

<400> SEQUENCE: 1939
uguuauaaau ucgguguacu ggugcauaau ggaugcguau                              40

<210> SEQ ID NO 1940
<211> LENGTH: 40
<212> TYPE: RNA
<213> ORGANISM: Artificial
<220> FEATURE:
<223> OTHER INFORMATION: Aptamer

<400> SEQUENCE: 1940
uguucaggug uauuggugca ucgacgucuc gucugucaua                              40

<210> SEQ ID NO 1941
<211> LENGTH: 40
<212> TYPE: RNA
<213> ORGANISM: Artificial
<220> FEATURE:
<223> OTHER INFORMATION: Aptamer

<400> SEQUENCE: 1941
uguuccgggu agacuggcug uuagagaucu cugauguagg                              40

<210> SEQ ID NO 1942
<211> LENGTH: 40
<212> TYPE: RNA
<213> ORGANISM: Artificial
<220> FEATURE:
<223> OTHER INFORMATION: Aptamer

<400> SEQUENCE: 1942
uguuccgggu cgauuggcug uuagagaucu cugauguagg                              40
```

<210> SEQ ID NO 1943
<211> LENGTH: 41
<212> TYPE: RNA
<213> ORGANISM: Artificial
<220> FEATURE:
<223> OTHER INFORMATION: Aptamer

<400> SEQUENCE: 1943
uguuccuuuu ggguuauugg cuccuuguug accaggggau g                 41

<210> SEQ ID NO 1944
<211> LENGTH: 39
<212> TYPE: RNA
<213> ORGANISM: Artificial
<220> FEATURE:
<223> OTHER INFORMATION: Aptamer

<400> SEQUENCE: 1944
uguuccgguc gacuggcugu uagagaucuc ugauguagg                    39

<210> SEQ ID NO 1945
<211> LENGTH: 40
<212> TYPE: RNA
<213> ORGANISM: Artificial
<220> FEATURE:
<223> OTHER INFORMATION: Aptamer

<400> SEQUENCE: 1945
uguucgcugg guuuauuggu cgcuacugga uuuagcagua                   40

<210> SEQ ID NO 1946
<211> LENGTH: 40
<212> TYPE: RNA
<213> ORGANISM: Artificial
<220> FEATURE:
<223> OTHER INFORMATION: Aptamer

<400> SEQUENCE: 1946
uguugcuagu guagguguau ugguugacuu uguacgucga                   40

<210> SEQ ID NO 1947
<211> LENGTH: 40
<212> TYPE: RNA
<213> ORGANISM: Artificial
<220> FEATURE:
<223> OTHER INFORMATION: Aptamer

<400> SEQUENCE: 1947 uguggguguau ugguuuaaaa gcgauguuug ucuucuuaaa                  40

<210> SEQ ID NO 1948
<211> LENGTH: 40
<212> TYPE: RNA
<213> ORGANISM: Artificial
<220> FEATURE:
<223> OTHER INFORMATION: Aptamer

<400> SEQUENCE: 1948
ugggucugac uggcgcuccc ugggauccca gugcugaaug                   40

<210> SEQ ID NO 1949
<211> LENGTH: 40
<212> TYPE: RNA
<213> ORGANISM: Artificial
<220> FEATURE:
<223> OTHER INFORMATION: Aptamer

```
<400> SEQUENCE: 1949
ugggugacug gcgcuacgau uuacagucua ucguagaaug                              40

<210> SEQ ID NO 1950
<211> LENGTH: 38
<212> TYPE: RNA
<213> ORGANISM: Artificial
<220> FEATURE:
<223> OTHER INFORMATION: Aptamer

<400> SEQUENCE: 1950
ugggugacug gcgcuacgau uuagucuauc guagaaug                                38

<210> SEQ ID NO 1951
<211> LENGTH: 40
<212> TYPE: RNA
<213> ORGANISM: Artificial
<220> FEATURE:
<223> OTHER INFORMATION: Aptamer

<400> SEQUENCE: 1951
uggguguacu ggccuccaaa ucgucguauu ugguuuguga                              40

<210> SEQ ID NO 1952
<211> LENGTH: 40
<212> TYPE: RNA
<213> ORGANISM: Artificial
<220> FEATURE:
<223> OTHER INFORMATION: Aptamer

<400> SEQUENCE: 1952
uuaccggauu gucuaggugu auugguaacc accgggugug                              40

<210> SEQ ID NO 1953
<211> LENGTH: 39
<212> TYPE: RNA
<213> ORGANISM: Artificial
<220> FEATURE:
<223> OTHER INFORMATION: Aptamer

<400> SEQUENCE: 1953
uuacucuuuu cggcgucacg guugauuggc cuuugggug                               39

<210> SEQ ID NO 1954
<211> LENGTH: 40
<212> TYPE: RNA
<213> ORGANISM: Artificial
<220> FEATURE:
<223> OTHER INFORMATION: Aptamer

<400> SEQUENCE: 1954
uuacuugguc cccuaaagcu ccgggutuauu ggucuuguuu                             40

<210> SEQ ID NO 1955
<211> LENGTH: 40
<212> TYPE: RNA
<213> ORGANISM: Artificial
<220> FEATURE:
<223> OTHER INFORMATION: Aptamer

<400> SEQUENCE: 1955 uuacuuggu gauggacucg cggguuauug gucgugguuu                               40

<210> SEQ ID NO 1956
```

```
<211> LENGTH: 40
<212> TYPE: RNA
<213> ORGANISM: Artificial
<220> FEATURE:
<223> OTHER INFORMATION: Aptamer

<400> SEQUENCE: 1956
uuagaccguc ucgguguauu ggucagucgu aguaccgcga                              40

<210> SEQ ID NO 1957
<211> LENGTH: 40
<212> TYPE: RNA
<213> ORGANISM: Artificial
<220> FEATURE:
<223> OTHER INFORMATION: Aptamer

<400> SEQUENCE: 1957
uuauauauug acuauacugu cuggguuauu ggucucgucu                              40

<210> SEQ ID NO 1958
<211> LENGTH: 40
<212> TYPE: RNA
<213> ORGANISM: Artificial
<220> FEATURE:
<223> OTHER INFORMATION: Aptamer

<400> SEQUENCE: 1958
uuauccucuu ugguaauugg uaccuaugau guuaggugug                              40

<210> SEQ ID NO 1959
<211> LENGTH: 40
<212> TYPE: RNA
<213> ORGANISM: Artificial
<220> FEATURE:
<223> OTHER INFORMATION: Aptamer

<400> SEQUENCE: 1959
uuaugaucug uucgcaucgc cgggugaauu gguaauucua                              40

<210> SEQ ID NO 1960
<211> LENGTH: 39
<212> TYPE: RNA
<213> ORGANISM: Artificial
<220> FEATURE:
<223> OTHER INFORMATION: Aptamer

<400> SEQUENCE: 1960
uuagguuauu ggccgguuug cucuuucuuu uuccuggug                               39

<210> SEQ ID NO 1961
<211> LENGTH: 40
<212> TYPE: RNA
<213> ORGANISM: Artificial
<220> FEATURE:
<223> OTHER INFORMATION: Aptamer

<400> SEQUENCE: 1961
uucaccugca ugaugggguag auuggcucca aaaggguuug                             40

<210> SEQ ID NO 1962
<211> LENGTH: 40
<212> TYPE: RNA
<213> ORGANISM: Artificial
<220> FEATURE:
<223> OTHER INFORMATION: Aptamer

<400> SEQUENCE: 1962
```

```
uucaggugua uuggaccuug uuagaggucu gcuaccgcga              40
```

<210> SEQ ID NO 1963
<211> LENGTH: 42
<212> TYPE: RNA
<213> ORGANISM: Artificial
<220> FEATURE:
<223> OTHER INFORMATION: Aptamer

<400> SEQUENCE: 1963

```
uucagguuau uggcccaggc uuuuuuccaa aaacccggug ug           42
```

<210> SEQ ID NO 1964
<211> LENGTH: 41
<212> TYPE: RNA
<213> ORGANISM: Artificial
<220> FEATURE:
<223> OTHER INFORMATION: Aptamer

<400> SEQUENCE: 1964

```
uuccacguuu acgguguauu ggucggucgg uuaacguuug a            41
```

<210> SEQ ID NO 1965
<211> LENGTH: 40
<212> TYPE: RNA
<213> ORGANISM: Artificial
<220> FEATURE:
<223> OTHER INFORMATION: Aptamer

<400> SEQUENCE: 1965

```
uuccagguaa uuggcggcug uauuuuucac acagcaaugu              40
```

<210> SEQ ID NO 1966
<211> LENGTH: 43
<212> TYPE: RNA
<213> ORGANISM: Artificial
<220> FEATURE:
<223> OTHER INFORMATION: Aptamer

<400> SEQUENCE: 1966

```
uuccgcaugu ggguaaaacu ggcgccugua uuuuuugga gug           43
```

<210> SEQ ID NO 1967
<211> LENGTH: 40
<212> TYPE: RNA
<213> ORGANISM: Artificial
<220> FEATURE:
<223> OTHER INFORMATION: Aptamer

<400> SEQUENCE: 1967

```
uuccgcaugu ggguaaacug gcgccugauu uucuggagug              40
```

<210> SEQ ID NO 1968
<211> LENGTH: 39
<212> TYPE: RNA
<213> ORGANISM: Artificial
<220> FEATURE:
<223> OTHER INFORMATION: Aptamer

<400> SEQUENCE: 1968

```
uuccgcaugu ggguaaacug gcgccugauu uuuggagug               39
```

<210> SEQ ID NO 1969
<211> LENGTH: 41
<212> TYPE: RNA

```
<213> ORGANISM: Artificial
<220> FEATURE:
<223> OTHER INFORMATION: Aptamer

<400> SEQUENCE: 1969
uuccgcaugu ggguaaacug gcgccugauu uuuugguagu g                41

<210> SEQ ID NO 1970
<211> LENGTH: 41
<212> TYPE: RNA
<213> ORGANISM: Artificial
<220> FEATURE:
<223> OTHER INFORMATION: Aptamer

<400> SEQUENCE: 1970
uuccgcaugu ggguaaacug gcgccugauu uuuugaagu g                 41

<210> SEQ ID NO 1971
<211> LENGTH: 42
<212> TYPE: RNA
<213> ORGANISM: Artificial
<220> FEATURE:
<223> OTHER INFORMATION: Aptamer

<400> SEQUENCE: 1971
uuccgcaugu ggguaaacug gcgccugauu uuuugggca ug                42

<210> SEQ ID NO 1972
<211> LENGTH: 41
<212> TYPE: RNA
<213> ORGANISM: Artificial
<220> FEATURE:
<223> OTHER INFORMATION: Aptamer

<400> SEQUENCE: 1972
uuccgcaugu ggguaaacug gcgccuguau uuuuggagu g                 41

<210> SEQ ID NO 1973
<211> LENGTH: 40
<212> TYPE: RNA
<213> ORGANISM: Artificial
<220> FEATURE:
<223> OTHER INFORMATION: Aptamer

<400> SEQUENCE: 1973
uuccuacagu uucggguuca uuggcgucgu caugaaguug                  40

<210> SEQ ID NO 1974
<211> LENGTH: 40
<212> TYPE: RNA
<213> ORGANISM: Artificial
<220> FEATURE:
<223> OTHER INFORMATION: Aptamer

<400> SEQUENCE: 1974
uuccucuuga gcucgggugu acuggcuauc uuugugugug                  40

<210> SEQ ID NO 1975
<211> LENGTH: 40
<212> TYPE: RNA
<213> ORGANISM: Artificial
<220> FEATURE:
<223> OTHER INFORMATION: Aptamer

<400> SEQUENCE: 1975
uuccugcacu uccaauuggu guauuggcgg ucuucgcuug                  40
```

<210> SEQ ID NO 1976
<211> LENGTH: 41
<212> TYPE: RNA
<213> ORGANISM: Artificial
<220> FEATURE:
<223> OTHER INFORMATION: Aptamer

<400> SEQUENCE: 1976
uucgaccggg uuauuggcua gcucuccucu gguuugugau g          41

<210> SEQ ID NO 1977
<211> LENGTH: 40
<212> TYPE: RNA
<213> ORGANISM: Artificial
<220> FEATURE:
<223> OTHER INFORMATION: Aptamer

<400> SEQUENCE: 1977
uucgacucuu ccagguggac ugguagcagu guccguugug            40

<210> SEQ ID NO 1978
<211> LENGTH: 40
<212> TYPE: RNA
<213> ORGANISM: Artificial
<220> FEATURE:
<223> OTHER INFORMATION: Aptamer

<400> SEQUENCE: 1978
uucgcuucga ccgguaaauu ggcgccuucc cugggaaug             40

<210> SEQ ID NO 1979
<211> LENGTH: 40
<212> TYPE: RNA
<213> ORGANISM: Artificial
<220> FEATURE:
<223> OTHER INFORMATION: Aptamer

<400> SEQUENCE: 1979
uucgcuuggu cuugguaauu gguucgugac uacgaguuga            40

<210> SEQ ID NO 1980
<211> LENGTH: 40
<212> TYPE: RNA
<213> ORGANISM: Artificial
<220> FEATURE:
<223> OTHER INFORMATION: Aptamer

<400> SEQUENCE: 1980
uucguccggg uuauuggcug cucuccucug guuugugaug            40

<210> SEQ ID NO 1981
<211> LENGTH: 40
<212> TYPE: RNA
<213> ORGANISM: Artificial
<220> FEATURE:
<223> OTHER INFORMATION: Aptamer

<400> SEQUENCE: 1981
uucuucucuc uuugcucuuc uggguguacu ggcugcaugg            40

<210> SEQ ID NO 1982
<211> LENGTH: 40
<212> TYPE: RNA
<213> ORGANISM: Artificial
<220> FEATURE:

```
<223> OTHER INFORMATION: Aptamer

<400> SEQUENCE: 1982
uucuuugguc auuggcgcau aucgauguug auguuggcug                      40

<210> SEQ ID NO 1983
<211> LENGTH: 40
<212> TYPE: RNA
<213> ORGANISM: Artificial
<220> FEATURE:
<223> OTHER INFORMATION: Aptamer

<400> SEQUENCE: 1983
uucggugauu ggcugcucag cgcggggcgc uuaguugaug                      40

<210> SEQ ID NO 1984
<211> LENGTH: 40
<212> TYPE: RNA
<213> ORGANISM: Artificial
<220> FEATURE:
<223> OTHER INFORMATION: Aptamer

<400> SEQUENCE: 1984
uugacccggu cgauggugc caguuuacga acugugaaua                       40

<210> SEQ ID NO 1985
<211> LENGTH: 40
<212> TYPE: RNA
<213> ORGANISM: Artificial
<220> FEATURE:
<223> OTHER INFORMATION: Aptamer

<400> SEQUENCE: 1985
uugaccgggu ugauuggucu ugcucgaaac gagugggug                       40

<210> SEQ ID NO 1986
<211> LENGTH: 40
<212> TYPE: RNA
<213> ORGANISM: Artificial
<220> FEATURE:
<223> OTHER INFORMATION: Aptamer

<400> SEQUENCE: 1986 uugccccgc ugagucuggg uguauuggu ugucgauaaa                        40

<210> SEQ ID NO 1987
<211> LENGTH: 40
<212> TYPE: RNA
<213> ORGANISM: Artificial
<220> FEATURE:
<223> OTHER INFORMATION: Aptamer

<400> SEQUENCE: 1987
uugcccgggu gcauugguac uggggccggc uccucucuua                      40

<210> SEQ ID NO 1988
<211> LENGTH: 40
<212> TYPE: RNA
<213> ORGANISM: Artificial
<220> FEATURE:
<223> OTHER INFORMATION: Aptamer

<400> SEQUENCE: 1988
uuggguacgg uuccacgcc uggguguauu gguauucgua                       40
```

<210> SEQ ID NO 1989
<211> LENGTH: 40
<212> TYPE: RNA
<213> ORGANISM: Artificial
<220> FEATURE:
<223> OTHER INFORMATION: Aptamer

<400> SEQUENCE: 1989
uuguccgucu cgguuuacug guuugccauu cgcgcuuaua                40

<210> SEQ ID NO 1990
<211> LENGTH: 40
<212> TYPE: RNA
<213> ORGANISM: Artificial
<220> FEATURE:
<223> OTHER INFORMATION: Aptamer

<400> SEQUENCE: 1990
uuguucuggu ugauugguua uuggggcuuu ccacuuugua                40

<210> SEQ ID NO 1991
<211> LENGTH: 40
<212> TYPE: RNA
<213> ORGANISM: Artificial
<220> FEATURE:
<223> OTHER INFORMATION: Aptamer

<400> SEQUENCE: 1991
uuuccguacc agguuuauug guccgcccuu aagucgguua                40

<210> SEQ ID NO 1992
<211> LENGTH: 40
<212> TYPE: RNA
<213> ORGANISM: Artificial
<220> FEATURE:
<223> OTHER INFORMATION: Aptamer

<400> SEQUENCE: 1992 uuccucagc gguuccgggu guacuggcca aauucgguua                40

<210> SEQ ID NO 1993
<211> LENGTH: 40
<212> TYPE: RNA
<213> ORGANISM: Artificial
<220> FEATURE:
<223> OTHER INFORMATION: Aptamer

<400> SEQUENCE: 1993
uuucgggucu acuggugaua cggugacucc cgugugccua                40

<210> SEQ ID NO 1994
<211> LENGTH: 40
<212> TYPE: RNA
<213> ORGANISM: Artificial
<220> FEATURE:
<223> OTHER INFORMATION: Aptamer

<400> SEQUENCE: 1994
uuucugcacu uccaauuggu guauuggcgg ucuucacuug                40

<210> SEQ ID NO 1995
<211> LENGTH: 40
<212> TYPE: RNA
<213> ORGANISM: Artificial
<220> FEATURE:
<223> OTHER INFORMATION: Aptamer

```
<400> SEQUENCE: 1995
uuugaagguc uacuggcgga uuggcccugg ugauuccaug                                40

<210> SEQ ID NO 1996
<211> LENGTH: 40
<212> TYPE: RNA
<213> ORGANISM: Artificial
<220> FEATURE:
<223> OTHER INFORMATION: Aptamer

<400> SEQUENCE: 1996
uuuucauccg ucgguuacug gcgcuucaaa cgaaaaucug                                40

<210> SEQ ID NO 1997
<211> LENGTH: 40
<212> TYPE: RNA
<213> ORGANISM: Artificial
<220> FEATURE:
<223> OTHER INFORMATION: Aptamer

<400> SEQUENCE: 1997
uuuucggguu uacggguguu acugcgcugc uuguaauaua                                40

<210> SEQ ID NO 1998
<211> LENGTH: 41
<212> TYPE: RNA
<213> ORGANISM: Artificial
<220> FEATURE:
<223> OTHER INFORMATION: Aptamer

<400> SEQUENCE: 1998
uuuucucggu cgaauuggcg gcgcuggauu cugcguaucu g                              41

<210> SEQ ID NO 1999
<211> LENGTH: 40
<212> TYPE: RNA
<213> ORGANISM: Artificial
<220> FEATURE:
<223> OTHER INFORMATION: Aptamer

<400> SEQUENCE: 1999
uuuucuugcc aaccgggugc auuggcuguu gcucuucaag                                40

<210> SEQ ID NO 2000
<211> LENGTH: 40
<212> TYPE: RNA
<213> ORGANISM: Artificial
<220> FEATURE:
<223> OTHER INFORMATION: Aptamer

<400> SEQUENCE: 2000
uuuugcuugu ccgcuggugu auggucucu gucgcgugga                                 40

<210> SEQ ID NO 2001
<211> LENGTH: 40
<212> TYPE: RNA
<213> ORGANISM: Artificial
<220> FEATURE:
<223> OTHER INFORMATION: Aptamer

<400> SEQUENCE: 2001 uuuggguguac uggcaccgaa ggcuuaauuc ccuuguuuug                               40

<210> SEQ ID NO 2002
<211> LENGTH: 40
```

```
<212> TYPE: RNA
<213> ORGANISM: Artificial
<220> FEATURE:
<223> OTHER INFORMATION: Aptamer

<400> SEQUENCE: 2002
uuugguguau uggucaaacc agcuuuaaac ccggaaguga                              40

<210> SEQ ID NO 2003
<211> LENGTH: 41
<212> TYPE: RNA
<213> ORGANISM: Artificial
<220> FEATURE:
<223> OTHER INFORMATION: Aptamer

<400> SEQUENCE: 2003
ugguaaauug gcccuucccc cugcauaggu gaaaugcggu g                            41

<210> SEQ ID NO 2004
<211> LENGTH: 40
<212> TYPE: RNA
<213> ORGANISM: Artificial
<220> FEATURE:
<223> OTHER INFORMATION: Aptamer

<400> SEQUENCE: 2004
ugguaauugg ugucgcucau cgaaaucgau ucggccuuua                              40

<210> SEQ ID NO 2005
<211> LENGTH: 40
<212> TYPE: RNA
<213> ORGANISM: Artificial
<220> FEATURE:
<223> OTHER INFORMATION: Aptamer

<400> SEQUENCE: 2005
uggugaacug gcggccgauu ucgcggaucu ccgggaugug                              40

<210> SEQ ID NO 2006
<211> LENGTH: 35
<212> TYPE: RNA
<213> ORGANISM: Artificial
<220> FEATURE:
<223> OTHER INFORMATION: Aptamer

<400> SEQUENCE: 2006
uggugaacug gcuugguuau uagaauaauc ggaug                                   35

<210> SEQ ID NO 2007
<211> LENGTH: 40
<212> TYPE: RNA
<213> ORGANISM: Artificial
<220> FEATURE:
<223> OTHER INFORMATION: Aptamer

<400> SEQUENCE: 2007
uggugaacug guuacuuuug cucuccgcag caucagugaa                              40

<210> SEQ ID NO 2008
<211> LENGTH: 40
<212> TYPE: RNA
<213> ORGANISM: Artificial
<220> FEATURE:
<223> OTHER INFORMATION: Aptamer

<400> SEQUENCE: 2008
```

```
uggugaauug guuacuuuug cucuccgcag caucagugaa                              40

<210> SEQ ID NO 2009
<211> LENGTH: 40
<212> TYPE: RNA
<213> ORGANISM: Artificial
<220> FEATURE:
<223> OTHER INFORMATION: Aptamer

<400> SEQUENCE: 2009
uggugcaacu ggcgaccacu aucuuuggua gacgguagug                              40

<210> SEQ ID NO 2010
<211> LENGTH: 40
<212> TYPE: RNA
<213> ORGANISM: Artificial
<220> FEATURE:
<223> OTHER INFORMATION: Aptamer

<400> SEQUENCE: 2010
ugguggacug guuggcuaga cuccgaacuc ucugcucgua                              40

<210> SEQ ID NO 2011
<211> LENGTH: 36
<212> TYPE: RNA
<213> ORGANISM: Artificial
<220> FEATURE:
<223> OTHER INFORMATION: Aptamer

<400> SEQUENCE: 2011
ugguggauug gugcaucuau gucuucuuac uuguua                                  36

<210> SEQ ID NO 2012
<211> LENGTH: 40
<212> TYPE: RNA
<213> ORGANISM: Artificial
<220> FEATURE:
<223> OTHER INFORMATION: Aptamer

<400> SEQUENCE: 2012 uguguauug gcuacguguu gguugaugcg acacgcaggg                               40

<210> SEQ ID NO 2013
<211> LENGTH: 40
<212> TYPE: RNA
<213> ORGANISM: Artificial
<220> FEATURE:
<223> OTHER INFORMATION: Aptamer

<400> SEQUENCE: 2013 uguguauug guccgucgga gacaccgaaa gauuccgaaa                               40

<210> SEQ ID NO 2014
<211> LENGTH: 40
<212> TYPE: RNA
<213> ORGANISM: Artificial
<220> FEATURE:
<223> OTHER INFORMATION: Aptamer

<400> SEQUENCE: 2014 uguguauug gugcuuuacu uaaccugguu auuuucguua                               40

<210> SEQ ID NO 2015
<211> LENGTH: 40
<212> TYPE: RNA
<213> ORGANISM: Artificial
```

```
<220> FEATURE:
<223> OTHER INFORMATION: Aptamer

<400> SEQUENCE: 2015
ugguuaacug gcagugagaa auuuugucuu ccagcguugg                        40

<210> SEQ ID NO 2016
<211> LENGTH: 39
<212> TYPE: RNA
<213> ORGANISM: Artificial
<220> FEATURE:
<223> OTHER INFORMATION: Aptamer

<400> SEQUENCE: 2016
ugguuacugg uccggggugu uuuugcucuc ugucugaua                         39

<210> SEQ ID NO 2017
<211> LENGTH: 40
<212> TYPE: RNA
<213> ORGANISM: Artificial
<220> FEATURE:
<223> OTHER INFORMATION: Aptamer

<400> SEQUENCE: 2017
ugguuauugg ucgaccucac cgcaugcggu guguguagug                        40

<210> SEQ ID NO 2018
<211> LENGTH: 33
<212> TYPE: RNA
<213> ORGANISM: Artificial
<220> FEATURE:
<223> OTHER INFORMATION: Aptamer

<400> SEQUENCE: 2018
ugguucuacu ggcguagcgg guuucgguaa gug                               33

<210> SEQ ID NO 2019
<211> LENGTH: 40
<212> TYPE: RNA
<213> ORGANISM: Artificial
<220> FEATURE:
<223> OTHER INFORMATION: Aptamer

<400> SEQUENCE: 2019
ugguuuacug gcgcauccuc uuucugauug ucuugaccug                        40

<210> SEQ ID NO 2020
<211> LENGTH: 40
<212> TYPE: RNA
<213> ORGANISM: Artificial
<220> FEATURE:
<223> OTHER INFORMATION: Aptamer

<400> SEQUENCE: 2020
ugguuuacug guagcuuucu uaacaugugu uggggcugug                        40

<210> SEQ ID NO 2021
<211> LENGTH: 40
<212> TYPE: RNA
<213> ORGANISM: Artificial
<220> FEATURE:
<223> OTHER INFORMATION: Aptamer

<400> SEQUENCE: 2021
ugguuuacug guagcuuucu ugacaugugu uggggcugug                        40
```

```
<210> SEQ ID NO 2022
<211> LENGTH: 41
<212> TYPE: RNA
<213> ORGANISM: Artificial
<220> FEATURE:
<223> OTHER INFORMATION: Aptamer

<400> SEQUENCE: 2022
ugguuuauug gccaagucau cuaccccugg agggcuuaau g                    41

<210> SEQ ID NO 2023
<211> LENGTH: 41
<212> TYPE: RNA
<213> ORGANISM: Artificial
<220> FEATURE:
<223> OTHER INFORMATION: Aptamer

<400> SEQUENCE: 2023
ugguuuauug gcggggccuc auuuuuguug aaugaccuuu g                    41

<210> SEQ ID NO 2024
<211> LENGTH: 38
<212> TYPE: RNA
<213> ORGANISM: Artificial
<220> FEATURE:
<223> OTHER INFORMATION: Aptamer

<400> SEQUENCE: 2024
ugguuuuauu ggugucgagu uguucaauug cuggauua                        38

<210> SEQ ID NO 2025
<211> LENGTH: 40
<212> TYPE: RNA
<213> ORGANISM: Artificial
<220> FEATURE:
<223> OTHER INFORMATION: Aptamer

<400> SEQUENCE: 2025
gguaaacugg uuuagacaga guguuucucu ucccuaagug                      40

<210> SEQ ID NO 2026
<211> LENGTH: 40
<212> TYPE: RNA
<213> ORGANISM: Artificial
<220> FEATURE:
<223> OTHER INFORMATION: Aptamer

<400> SEQUENCE: 2026
gguaaauugg caccguuugg auucgcuuuc cacggauuug                      40

<210> SEQ ID NO 2027
<211> LENGTH: 40
<212> TYPE: RNA
<213> ORGANISM: Artificial
<220> FEATURE:
<223> OTHER INFORMATION: Aptamer

<400> SEQUENCE: 2027
gguaaauugg ccccuuaggc uuacgaaccu cugcugaaug                      40

<210> SEQ ID NO 2028
<211> LENGTH: 34
<212> TYPE: RNA
<213> ORGANISM: Artificial
<220> FEATURE:
<223> OTHER INFORMATION: Aptamer
```

<400> SEQUENCE: 2028
gguaaauugg uagcagcagu gaccuucugu uuca                           34

<210> SEQ ID NO 2029
<211> LENGTH: 40
<212> TYPE: RNA
<213> ORGANISM: Artificial
<220> FEATURE:
<223> OTHER INFORMATION: Aptamer

<400> SEQUENCE: 2029
gguaacuggc uccuuccgga aauucucucu guacggcaug                     40

<210> SEQ ID NO 2030
<211> LENGTH: 40
<212> TYPE: RNA
<213> ORGANISM: Artificial
<220> FEATURE:
<223> OTHER INFORMATION: Aptamer

<400> SEQUENCE: 2030
gguaauuggc gaucuauuuu cuuauagucu cggaugccug                     40

<210> SEQ ID NO 2031
<211> LENGTH: 40
<212> TYPE: RNA
<213> ORGANISM: Artificial
<220> FEATURE:
<223> OTHER INFORMATION: Aptamer

<400> SEQUENCE: 2031
gguaauuggc gcacucucau uauugauggu aguggcucug                     40

<210> SEQ ID NO 2032
<211> LENGTH: 40
<212> TYPE: RNA
<213> ORGANISM: Artificial
<220> FEATURE:
<223> OTHER INFORMATION: Aptamer

<400> SEQUENCE: 2032
gguaauuggc gcuaggaucu guugacuacc ccuagguuug                     40

<210> SEQ ID NO 2033
<211> LENGTH: 40
<212> TYPE: RNA
<213> ORGANISM: Artificial
<220> FEATURE:
<223> OTHER INFORMATION: Aptamer

<400> SEQUENCE: 2033
gguaauuggc uuauauuacu agaguuuuug uauauaaaug                     40

<210> SEQ ID NO 2034
<211> LENGTH: 39
<212> TYPE: RNA
<213> ORGANISM: Artificial
<220> FEATURE:
<223> OTHER INFORMATION: Aptamer

<400> SEQUENCE: 2034
gguaauuggu acuuacagcg auuucguugu uuguguugu                      39

<210> SEQ ID NO 2035

```
<211> LENGTH: 40
<212> TYPE: RNA
<213> ORGANISM: Artificial
<220> FEATURE:
<223> OTHER INFORMATION: Aptamer

<400> SEQUENCE: 2035
gguaauuggu ccugcucugu cuccuucagc agcggggaaa                            40

<210> SEQ ID NO 2036
<211> LENGTH: 38
<212> TYPE: RNA
<213> ORGANISM: Artificial
<220> FEATURE:
<223> OTHER INFORMATION: Aptamer

<400> SEQUENCE: 2036
gguaauuggu ggccauuacc uuucguuuug gugucuga                              38

<210> SEQ ID NO 2037
<211> LENGTH: 39
<212> TYPE: RNA
<213> ORGANISM: Artificial
<220> FEATURE:
<223> OTHER INFORMATION: Aptamer

<400> SEQUENCE: 2037
gguaauuggu ggccauuacc uuucguuuu ggugucuga                              39

<210> SEQ ID NO 2038
<211> LENGTH: 40
<212> TYPE: RNA
<213> ORGANISM: Artificial
<220> FEATURE:
<223> OTHER INFORMATION: Aptamer

<400> SEQUENCE: 2038
gguaauuggu ggccauuacc uuucguuuu uggugucuga                             40

<210> SEQ ID NO 2039
<211> LENGTH: 39
<212> TYPE: RNA
<213> ORGANISM: Artificial
<220> FEATURE:
<223> OTHER INFORMATION: Aptamer

<400> SEQUENCE: 2039
gguagaauug gcucaucuug acucccgucu gcucgaaua                             39

<210> SEQ ID NO 2040
<211> LENGTH: 39
<212> TYPE: RNA
<213> ORGANISM: Artificial
<220> FEATURE:
<223> OTHER INFORMATION: Aptamer

<400> SEQUENCE: 2040
gguagaauug gcucaucuug acuccugucu gcucgaaug                             39

<210> SEQ ID NO 2041
<211> LENGTH: 40
<212> TYPE: RNA
<213> ORGANISM: Artificial
<220> FEATURE:
<223> OTHER INFORMATION: Aptamer

<400> SEQUENCE: 2041
```

```
gguaguauug gcuagucuaa ggagauccua agacgaauga                              40

<210> SEQ ID NO 2042
<211> LENGTH: 40
<212> TYPE: RNA
<213> ORGANISM: Artificial
<220> FEATURE:
<223> OTHER INFORMATION: Aptamer

<400> SEQUENCE: 2042
gguauauugg cgcaccguca cguagcuguc ugugggaaug                              40

<210> SEQ ID NO 2043
<211> LENGTH: 41
<212> TYPE: RNA
<213> ORGANISM: Artificial
<220> FEATURE:
<223> OTHER INFORMATION: Aptamer

<400> SEQUENCE: 2043
gguauauugg cgccacuucc cccgccgacu aguggaacuu g                            41

<210> SEQ ID NO 2044
<211> LENGTH: 40
<212> TYPE: RNA
<213> ORGANISM: Artificial
<220> FEATURE:
<223> OTHER INFORMATION: Aptamer

<400> SEQUENCE: 2044
gguauauugg cgccacuuuu cccgcgacua guggaacuug                              40

<210> SEQ ID NO 2045
<211> LENGTH: 41
<212> TYPE: RNA
<213> ORGANISM: Artificial
<220> FEATURE:
<223> OTHER INFORMATION: Aptamer

<400> SEQUENCE: 2045
gguauauugg cggaguucuc gugaccggua gguucucgcu g                            41

<210> SEQ ID NO 2046
<211> LENGTH: 39
<212> TYPE: RNA
<213> ORGANISM: Artificial
<220> FEATURE:
<223> OTHER INFORMATION: Aptamer

<400> SEQUENCE: 2046
gguauauugg cugguauuuu uucacucaau cuaccgaug                               39

<210> SEQ ID NO 2047
<211> LENGTH: 39
<212> TYPE: RNA
<213> ORGANISM: Artificial
<220> FEATURE:
<223> OTHER INFORMATION: Aptamer

<400> SEQUENCE: 2047
gguauauugg cuucggaucc uuucguucgg gucugagug                               39

<210> SEQ ID NO 2048
<211> LENGTH: 40
<212> TYPE: RNA
```

```
<213> ORGANISM: Artificial
<220> FEATURE:
<223> OTHER INFORMATION: Aptamer

<400> SEQUENCE: 2048
gguauauugg cuucggaucc uuuucguucg ggucuaagug                                    40

<210> SEQ ID NO 2049
<211> LENGTH: 40
<212> TYPE: RNA
<213> ORGANISM: Artificial
<220> FEATURE:
<223> OTHER INFORMATION: Aptamer

<400> SEQUENCE: 2049
gguauauugg ucguuguccg cagugucuga gaugaaggau                                    40

<210> SEQ ID NO 2050
<211> LENGTH: 40
<212> TYPE: RNA
<213> ORGANISM: Artificial
<220> FEATURE:
<223> OTHER INFORMATION: Aptamer

<400> SEQUENCE: 2050
gguauauugg ugaccugaau guauuaucgu ucgcggagua                                    40

<210> SEQ ID NO 2051
<211> LENGTH: 39
<212> TYPE: RNA
<213> ORGANISM: Artificial
<220> FEATURE:
<223> OTHER INFORMATION: Aptamer

<400> SEQUENCE: 2051
gguauauugg ugcaucgaag cgauucuuug ucgauguuu                                     39

<210> SEQ ID NO 2052
<211> LENGTH: 40
<212> TYPE: RNA
<213> ORGANISM: Artificial
<220> FEATURE:
<223> OTHER INFORMATION: Aptamer

<400> SEQUENCE: 2052
gguaugauug gcgccgauau uauuccuuuu acaggaucug                                    40

<210> SEQ ID NO 2053
<211> LENGTH: 41
<212> TYPE: RNA
<213> ORGANISM: Artificial
<220> FEATURE:
<223> OTHER INFORMATION: Aptamer

<400> SEQUENCE: 2053
ggucaauugg cuggcccaau uuuuguuuuu cugcgucgau g                                  41

<210> SEQ ID NO 2054
<211> LENGTH: 40
<212> TYPE: RNA
<213> ORGANISM: Artificial
<220> FEATURE:
<223> OTHER INFORMATION: Aptamer

<400> SEQUENCE: 2054
ggucgauugg uaucuauuca cucguucggu gccggauaua                                    40
```

<210> SEQ ID NO 2055
<211> LENGTH: 39
<212> TYPE: RNA
<213> ORGANISM: Artificial
<220> FEATURE:
<223> OTHER INFORMATION: Aptamer

<400> SEQUENCE: 2055
ggucuacugg ugccuacgcg uauuacguau cacggaaua                              39

<210> SEQ ID NO 2056
<211> LENGTH: 40
<212> TYPE: RNA
<213> ORGANISM: Artificial
<220> FEATURE:
<223> OTHER INFORMATION: Aptamer

<400> SEQUENCE: 2056
ggucuauugg cggagugaau uugcaccuuu uuccccuug                              40

<210> SEQ ID NO 2057
<211> LENGTH: 40
<212> TYPE: RNA
<213> ORGANISM: Artificial
<220> FEATURE:
<223> OTHER INFORMATION: Aptamer

<400> SEQUENCE: 2057
ggucuauugg uguuugcaaa ugagagguga cguaaacgug                             40

<210> SEQ ID NO 2058
<211> LENGTH: 40
<212> TYPE: RNA
<213> ORGANISM: Artificial
<220> FEATURE:
<223> OTHER INFORMATION: Aptamer

<400> SEQUENCE: 2058
ggucuuauug gugucgugcu gacuuuguuu aguccgagua                             40

<210> SEQ ID NO 2059
<211> LENGTH: 40
<212> TYPE: RNA
<213> ORGANISM: Artificial
<220> FEATURE:
<223> OTHER INFORMATION: Aptamer

<400> SEQUENCE: 2059
ggugaacugg caacgacacu ccuuuuccgc cgacgugaug                             40

<210> SEQ ID NO 2060
<211> LENGTH: 40
<212> TYPE: RNA
<213> ORGANISM: Artificial
<220> FEATURE:
<223> OTHER INFORMATION: Aptamer

<400> SEQUENCE: 2060
ggugaacugg cgauuaugga aaaguuuguu ucacaaugug                             40

<210> SEQ ID NO 2061
<211> LENGTH: 40
<212> TYPE: RNA
<213> ORGANISM: Artificial
<220> FEATURE:

```
<223> OTHER INFORMATION: Aptamer

<400> SEQUENCE: 2061
ggugaacugg cucugcuugu aauaauuguc ugcagguuug                                40

<210> SEQ ID NO 2062
<211> LENGTH: 40
<212> TYPE: RNA
<213> ORGANISM: Artificial
<220> FEATURE:
<223> OTHER INFORMATION: Aptamer

<400> SEQUENCE: 2062
ggugaacugg uaauggguua gcuuucccgc ucaaauugug                                40

<210> SEQ ID NO 2063
<211> LENGTH: 40
<212> TYPE: RNA
<213> ORGANISM: Artificial
<220> FEATURE:
<223> OTHER INFORMATION: Aptamer

<400> SEQUENCE: 2063
ggugaacugg uacuuggugc cuggcggguc gacuugucua                                40

<210> SEQ ID NO 2064
<211> LENGTH: 40
<212> TYPE: RNA
<213> ORGANISM: Artificial
<220> FEATURE:
<223> OTHER INFORMATION: Aptamer

<400> SEQUENCE: 2064
ggugaacugg uccacauuua gcuuucuuau uugcggguau                                40

<210> SEQ ID NO 2065
<211> LENGTH: 42
<212> TYPE: RNA
<213> ORGANISM: Artificial
<220> FEATURE:
<223> OTHER INFORMATION: Aptamer

<400> SEQUENCE: 2065
ggugaacugg uccgacaauu uagcuuucuu auuugcgggu au                             42

<210> SEQ ID NO 2066
<211> LENGTH: 41
<212> TYPE: RNA
<213> ORGANISM: Artificial
<220> FEATURE:
<223> OTHER INFORMATION: Aptamer

<400> SEQUENCE: 2066
ggugaacugg uccgacauuu agccuucuua uuugcgggua u                              41

<210> SEQ ID NO 2067
<211> LENGTH: 41
<212> TYPE: RNA
<213> ORGANISM: Artificial
<220> FEATURE:
<223> OTHER INFORMATION: Aptamer

<400> SEQUENCE: 2067
ggugaacugg uccgcauuua gccuucuua uuugcgggua u                               41
```

```
<210> SEQ ID NO 2068
<211> LENGTH: 41
<212> TYPE: RNA
<213> ORGANISM: Artificial
<220> FEATURE:
<223> OTHER INFORMATION: Aptamer

<400> SEQUENCE: 2068
ggugaacugg uccgcauuua gcuuucuua uuugcgggua u          41

<210> SEQ ID NO 2069
<211> LENGTH: 40
<212> TYPE: RNA
<213> ORGANISM: Artificial
<220> FEATURE:
<223> OTHER INFORMATION: Aptamer

<400> SEQUENCE: 2069
ggugaacugg uggugggpuug gaguauuuca uauccauuua            40

<210> SEQ ID NO 2070
<211> LENGTH: 42
<212> TYPE: RNA
<213> ORGANISM: Artificial
<220> FEATURE:
<223> OTHER INFORMATION: Aptamer

<400> SEQUENCE: 2070
ggugaacugg uuacguguag uugaaaaaau ugcugcugug ua          42

<210> SEQ ID NO 2071
<211> LENGTH: 42
<212> TYPE: RNA
<213> ORGANISM: Artificial
<220> FEATURE:
<223> OTHER INFORMATION: Aptamer

<400> SEQUENCE: 2071
ggugaacugg uuacguguag uugaaaaauu agcugcugug ua          42

<210> SEQ ID NO 2072
<211> LENGTH: 40
<212> TYPE: RNA
<213> ORGANISM: Artificial
<220> FEATURE:
<223> OTHER INFORMATION: Aptamer

<400> SEQUENCE: 2072
ggugaacugg uuacguguag uugaaaauug cugccgugua            40

<210> SEQ ID NO 2073
<211> LENGTH: 39
<212> TYPE: RNA
<213> ORGANISM: Artificial
<220> FEATURE:
<223> OTHER INFORMATION: Aptamer

<400> SEQUENCE: 2073
ggugaacugg uuacguguag uugaaauugc ugcugugua             39

<210> SEQ ID NO 2074
<211> LENGTH: 40
<212> TYPE: RNA
<213> ORGANISM: Artificial
<220> FEATURE:
<223> OTHER INFORMATION: Aptamer
```

```
<400> SEQUENCE: 2074
ggugaacugg uuacguguag uugaagauug cugcugugua                          40

<210> SEQ ID NO 2075
<211> LENGTH: 40
<212> TYPE: RNA
<213> ORGANISM: Artificial
<220> FEATURE:
<223> OTHER INFORMATION: Aptamer

<400> SEQUENCE: 2075
ggugaauugg cacuuccuua ucuacggauc gagucggaug                          40

<210> SEQ ID NO 2076
<211> LENGTH: 39
<212> TYPE: RNA
<213> ORGANISM: Artificial
<220> FEATURE:
<223> OTHER INFORMATION: Aptamer

<400> SEQUENCE: 2076
ggugaauugg cacuucuuau cuacggaucg agucggaug                           39

<210> SEQ ID NO 2077
<211> LENGTH: 40
<212> TYPE: RNA
<213> ORGANISM: Artificial
<220> FEATURE:
<223> OTHER INFORMATION: Aptamer

<400> SEQUENCE: 2077
ggugaauugg cacuucuuca ucuacggauc gagucggaug                          40

<210> SEQ ID NO 2078
<211> LENGTH: 40
<212> TYPE: RNA
<213> ORGANISM: Artificial
<220> FEATURE:
<223> OTHER INFORMATION: Aptamer

<400> SEQUENCE: 2078
ggugaauugg cacuucuuua ucuacggauc gaaucggaug                          40

<210> SEQ ID NO 2079
<211> LENGTH: 40
<212> TYPE: RNA
<213> ORGANISM: Artificial
<220> FEATURE:
<223> OTHER INFORMATION: Aptamer

<400> SEQUENCE: 2079
ggugaauugg cacuucuuua ucuacggauc gagucggacg                          40

<210> SEQ ID NO 2080
<211> LENGTH: 40
<212> TYPE: RNA
<213> ORGANISM: Artificial
<220> FEATURE:
<223> OTHER INFORMATION: Aptamer

<400> SEQUENCE: 2080
ggugaauugg cacuucuuua ucuacggauc gagucggcug                          40

<210> SEQ ID NO 2081
<211> LENGTH: 40
```

```
<212> TYPE: RNA
<213> ORGANISM: Artificial
<220> FEATURE:
<223> OTHER INFORMATION: Aptamer

<400> SEQUENCE: 2081
ggugaauugg cacuucuuua ucuacggauc gaguuggaug                           40

<210> SEQ ID NO 2082
<211> LENGTH: 41
<212> TYPE: RNA
<213> ORGANISM: Artificial
<220> FEATURE:
<223> OTHER INFORMATION: Aptamer

<400> SEQUENCE: 2082
ggugaauugg cacuucuuug cuuuaaucag cuggauguau g                         41

<210> SEQ ID NO 2083
<211> LENGTH: 41
<212> TYPE: RNA
<213> ORGANISM: Artificial
<220> FEATURE:
<223> OTHER INFORMATION: Aptamer

<400> SEQUENCE: 2083
ggugaauugg ccgccguucu uuccguggga augacgcgau g                         41

<210> SEQ ID NO 2084
<211> LENGTH: 40
<212> TYPE: RNA
<213> ORGANISM: Artificial
<220> FEATURE:
<223> OTHER INFORMATION: Aptamer

<400> SEQUENCE: 2084
ggugaauugg cgccaguucu caguagcucc uucucgaaug                           40

<210> SEQ ID NO 2085
<211> LENGTH: 40
<212> TYPE: RNA
<213> ORGANISM: Artificial
<220> FEATURE:
<223> OTHER INFORMATION: Aptamer

<400> SEQUENCE: 2085
ggugaauugg cugcggguaa cuggauuacg gcgacguuug                           40

<210> SEQ ID NO 2086
<211> LENGTH: 40
<212> TYPE: RNA
<213> ORGANISM: Artificial
<220> FEATURE:
<223> OTHER INFORMATION: Aptamer

<400> SEQUENCE: 2086
ggugaauugg cuggcgauuu cuauccuggg accucucgug                           40

<210> SEQ ID NO 2087
<211> LENGTH: 40
<212> TYPE: RNA
<213> ORGANISM: Artificial
<220> FEATURE:
<223> OTHER INFORMATION: Aptamer

<400> SEQUENCE: 2087
```
ggugaauugg cuguaugcaa cgcccgacuu gccacgauug        40

<210> SEQ ID NO 2088
<211> LENGTH: 40
<212> TYPE: RNA
<213> ORGANISM: Artificial
<220> FEATURE:
<223> OTHER INFORMATION: Aptamer

<400> SEQUENCE: 2088
ggugaauugg uaaaauaagg uuccuauuac cccguuuaua        40

<210> SEQ ID NO 2089
<211> LENGTH: 40
<212> TYPE: RNA
<213> ORGANISM: Artificial
<220> FEATURE:
<223> OTHER INFORMATION: Aptamer

<400> SEQUENCE: 2089
ggugaauugg uacuucuuua ucuacggauc gagucggaug        40

<210> SEQ ID NO 2090
<211> LENGTH: 40
<212> TYPE: RNA
<213> ORGANISM: Artificial
<220> FEATURE:
<223> OTHER INFORMATION: Aptamer

<400> SEQUENCE: 2090
ggugaauugg uagaauucug cucaaguuga ccggauucua        40

<210> SEQ ID NO 2091
<211> LENGTH: 40
<212> TYPE: RNA
<213> ORGANISM: Artificial
<220> FEATURE:
<223> OTHER INFORMATION: Aptamer

<400> SEQUENCE: 2091
ggugaauugg uagccaugac agaauccugu ugucgguaca        40

<210> SEQ ID NO 2092
<211> LENGTH: 40
<212> TYPE: RNA
<213> ORGANISM: Artificial
<220> FEATURE:
<223> OTHER INFORMATION: Aptamer

<400> SEQUENCE: 2092
ggugaauugg uauuaccauc ugcucggcaa gaacguaaua        40

<210> SEQ ID NO 2093
<211> LENGTH: 41
<212> TYPE: RNA
<213> ORGANISM: Artificial
<220> FEATURE:
<223> OTHER INFORMATION: Aptamer

<400> SEQUENCE: 2093
ggugaauugg ucacuucuuu aucuacggau cgagucggau g        41

<210> SEQ ID NO 2094
<211> LENGTH: 40
<212> TYPE: RNA
<213> ORGANISM: Artificial

```
<220> FEATURE:
<223> OTHER INFORMATION: Aptamer

<400> SEQUENCE: 2094
ggugaauugg uccauguccu ucuauugaag uaccucgaua                              40

<210> SEQ ID NO 2095
<211> LENGTH: 40
<212> TYPE: RNA
<213> ORGANISM: Artificial
<220> FEATURE:
<223> OTHER INFORMATION: Aptamer

<400> SEQUENCE: 2095
ggugaauugg ucugcucuaa gcagugucgc uuuucagaua                              40

<210> SEQ ID NO 2096
<211> LENGTH: 40
<212> TYPE: RNA
<213> ORGANISM: Artificial
<220> FEATURE:
<223> OTHER INFORMATION: Aptamer

<400> SEQUENCE: 2096
ggugaauugg ugguuggugc cccuuccucg uaccuuaccu                              40

<210> SEQ ID NO 2097
<211> LENGTH: 40
<212> TYPE: RNA
<213> ORGANISM: Artificial
<220> FEATURE:
<223> OTHER INFORMATION: Aptamer

<400> SEQUENCE: 2097
ggugaauugg uguucucggu guuauuuuuu cacguggauc                              40

<210> SEQ ID NO 2098
<211> LENGTH: 40
<212> TYPE: RNA
<213> ORGANISM: Artificial
<220> FEATURE:
<223> OTHER INFORMATION: Aptamer

<400> SEQUENCE: 2098
ggugaauugg uuaaucuggg uuucucguac ccgugaacga                              40

<210> SEQ ID NO 2099
<211> LENGTH: 27
<212> TYPE: RNA
<213> ORGANISM: Artificial
<220> FEATURE:
<223> OTHER INFORMATION: Aptamer

<400> SEQUENCE: 2099
ggugaauugg uuaccuaaac uggugua                                            27

<210> SEQ ID NO 2100
<211> LENGTH: 40
<212> TYPE: RNA
<213> ORGANISM: Artificial
<220> FEATURE:
<223> OTHER INFORMATION: Aptamer

<400> SEQUENCE: 2100
ggugaauugg uuugcaagau auuuugaauc ugauguguua                              40
```

<210> SEQ ID NO 2101
<211> LENGTH: 40
<212> TYPE: RNA
<213> ORGANISM: Artificial
<220> FEATURE:
<223> OTHER INFORMATION: Aptamer

<400> SEQUENCE: 2101
ggugaauugg uuuucgugua gggauuuucg cacguauuua         40

<210> SEQ ID NO 2102
<211> LENGTH: 39
<212> TYPE: RNA
<213> ORGANISM: Artificial
<220> FEATURE:
<223> OTHER INFORMATION: Aptamer

<400> SEQUENCE: 2102
ggugauuggc cuuuccacu aauucuucag uggcuguuu         39

<210> SEQ ID NO 2103
<211> LENGTH: 41
<212> TYPE: RNA
<213> ORGANISM: Artificial
<220> FEATURE:
<223> OTHER INFORMATION: Aptamer

<400> SEQUENCE: 2103
ggugauuggc gccaaacaaa auuauuguug cccagggaau g         41

<210> SEQ ID NO 2104
<211> LENGTH: 25
<212> TYPE: RNA
<213> ORGANISM: Artificial
<220> FEATURE:
<223> OTHER INFORMATION: Aptamer

<400> SEQUENCE: 2104
ggugauuggc gccaaacagg gaaug         25

<210> SEQ ID NO 2105
<211> LENGTH: 39
<212> TYPE: RNA
<213> ORGANISM: Artificial
<220> FEATURE:
<223> OTHER INFORMATION: Aptamer

<400> SEQUENCE: 2105
ggugauuggc gggaagaguu ucaaaaugca caccgucug         39

<210> SEQ ID NO 2106
<211> LENGTH: 39
<212> TYPE: RNA
<213> ORGANISM: Artificial
<220> FEATURE:
<223> OTHER INFORMATION: Aptamer
<220> FEATURE:
<221> NAME/KEY: misc_feauure
<222> LOCATION: (11)..(11)
<223> OTHER INFORMATION: n suands for any base.

<400> SEQUENCE: 2106
ggugauuggc ncuucuuuau cuacggaucg agucggaug         39

<210> SEQ ID NO 2107
<211> LENGTH: 40

```
<212> TYPE: RNA
<213> ORGANISM: Artificial
<220> FEATURE:
<223> OTHER INFORMATION: Aptamer

<400> SEQUENCE: 2107
ggugauuggu gcauugcggc ugaugccuac cacgugauua                          40

<210> SEQ ID NO 2108
<211> LENGTH: 41
<212> TYPE: RNA
<213> ORGANISM: Artificial
<220> FEATURE:
<223> OTHER INFORMATION: Aptamer

<400> SEQUENCE: 2108
ggugauuggu ucuuuccuaa augauuuuua aggaaucuau a                        41

<210> SEQ ID NO 2109
<211> LENGTH: 40
<212> TYPE: RNA
<213> ORGANISM: Artificial
<220> FEATURE:
<223> OTHER INFORMATION: Aptamer

<400> SEQUENCE: 2109
ggugcacugg ccuguucguu guccuuccu gguucuggug                           40

<210> SEQ ID NO 2110
<211> LENGTH: 40
<212> TYPE: RNA
<213> ORGANISM: Artificial
<220> FEATURE:
<223> OTHER INFORMATION: Aptamer

<400> SEQUENCE: 2110
ggugcacugg cguacuuuca uguugcugaa augugggcug                          40

<210> SEQ ID NO 2111
<211> LENGTH: 40
<212> TYPE: RNA
<213> ORGANISM: Artificial
<220> FEATURE:
<223> OTHER INFORMATION: Aptamer

<400> SEQUENCE: 2111
ggugcacugg ucacauguuu ggcuugcuaa cguuugugga                          40

<210> SEQ ID NO 2112
<211> LENGTH: 40
<212> TYPE: RNA
<213> ORGANISM: Artificial
<220> FEATURE:
<223> OTHER INFORMATION: Aptamer

<400> SEQUENCE: 2112
ggugcauugg cucucuuugc uuuaaucagc uggauguaua                          40

<210> SEQ ID NO 2113
<211> LENGTH: 40
<212> TYPE: RNA
<213> ORGANISM: Artificial
<220> FEATURE:
<223> OTHER INFORMATION: Aptamer

<400> SEQUENCE: 2113
```

```
ggugcauugg uaaccggccu cugcgcuguc cucguguuua                    40
```

<210> SEQ ID NO 2114
<211> LENGTH: 40
<212> TYPE: RNA
<213> ORGANISM: Artificial
<220> FEATURE:
<223> OTHER INFORMATION: Aptamer

<400> SEQUENCE: 2114

```
ggugccacug guggauacuu ggauuugauc uguaucggca                    40
```

<210> SEQ ID NO 2115
<211> LENGTH: 41
<212> TYPE: RNA
<213> ORGANISM: Artificial
<220> FEATURE:
<223> OTHER INFORMATION: Aptamer

<400> SEQUENCE: 2115

```
ggugqacugg cccucgugug cgcugacgcu cagaguuucg u                  41
```

<210> SEQ ID NO 2116
<211> LENGTH: 40
<212> TYPE: RNA
<213> ORGANISM: Artificial
<220> FEATURE:
<223> OTHER INFORMATION: Aptamer

<400> SEQUENCE: 2116

```
gguggacugg ccgggcuuuu cgauuuccuu uuccuacgug                    40
```

<210> SEQ ID NO 2117
<211> LENGTH: 40
<212> TYPE: RNA
<213> ORGANISM: Artificial
<220> FEATURE:
<223> OTHER INFORMATION: Aptamer

<400> SEQUENCE: 2117

```
gguggacugg ccgggcuuuu cgauuucuuu uuccuacgug                    40
```

<210> SEQ ID NO 2118
<211> LENGTH: 40
<212> TYPE: RNA
<213> ORGANISM: Artificial
<220> FEATURE:
<223> OTHER INFORMATION: Aptamer

<400> SEQUENCE: 2118

```
gguggacugg uagccccuuu ugauuuaggg auccuguuaa                    40
```

<210> SEQ ID NO 2119
<211> LENGTH: 40
<212> TYPE: RNA
<213> ORGANISM: Artificial
<220> FEATURE:
<223> OTHER INFORMATION: Aptamer

<400> SEQUENCE: 2119

```
gguggacugg ugccuaaaga cuuaaucgcu cccuggcuga                    40
```

<210> SEQ ID NO 2120
<211> LENGTH: 40
<212> TYPE: RNA
<213> ORGANISM: Artificial

```
<220> FEATURE:
<223> OTHER INFORMATION: Aptamer

<400> SEQUENCE: 2120
gguggacugg ugucaacaga cgugucgguu guuuucguau                40

<210> SEQ ID NO 2121
<211> LENGTH: 39
<212> TYPE: RNA
<213> ORGANISM: Artificial
<220> FEATURE:
<223> OTHER INFORMATION: Aptamer

<400> SEQUENCE: 2121
gguggacugg uguuucuuua uauucguuua uaaagcuua                 39

<210> SEQ ID NO 2122
<211> LENGTH: 40
<212> TYPE: RNA
<213> ORGANISM: Artificial
<220> FEATURE:
<223> OTHER INFORMATION: Aptamer

<400> SEQUENCE: 2122
gguggacugg uugauauuga ugucguauga cauaacucuu                40

<210> SEQ ID NO 2123
<211> LENGTH: 37
<212> TYPE: RNA
<213> ORGANISM: Artificial
<220> FEATURE:
<223> OTHER INFORMATION: Aptamer

<400> SEQUENCE: 2123
gguggacugg uuucuaagug cuuuggcugc uggagga                   37

<210> SEQ ID NO 2124
<211> LENGTH: 35
<212> TYPE: RNA
<213> ORGANISM: Artificial
<220> FEATURE:
<223> OTHER INFORMATION: Aptamer

<400> SEQUENCE: 2124
gguggauugg cagucuaaug uuaagagaau guuug                     35

<210> SEQ ID NO 2125
<211> LENGTH: 40
<212> TYPE: RNA
<213> ORGANISM: Artificial
<220> FEATURE:
<223> OTHER INFORMATION: Aptamer

<400> SEQUENCE: 2125
gguggauugg cggcgcaucc ucuucuuaga augccguacg                40

<210> SEQ ID NO 2126
<211> LENGTH: 40
<212> TYPE: RNA
<213> ORGANISM: Artificial
<220> FEATURE:
<223> OTHER INFORMATION: Aptamer

<400> SEQUENCE: 2126
gguggauugg cggcgcaucc uuucuuaga augccguacg                 40
```

<210> SEQ ID NO 2127
<211> LENGTH: 40
<212> TYPE: RNA
<213> ORGANISM: Artificial
<220> FEATURE:
<223> OTHER INFORMATION: Aptamer

<400> SEQUENCE: 2127
gguggauugg cuauucguga uucucaguau cauuaaucgg                                40

<210> SEQ ID NO 2128
<211> LENGTH: 40
<212> TYPE: RNA
<213> ORGANISM: Artificial
<220> FEATURE:
<223> OTHER INFORMATION: Aptamer

<400> SEQUENCE: 2128
gguggauugg cuguaguaca caacauggug uauccacaag                                40

<210> SEQ ID NO 2129
<211> LENGTH: 40
<212> TYPE: RNA
<213> ORGANISM: Artificial
<220> FEATURE:
<223> OTHER INFORMATION: Aptamer

<400> SEQUENCE: 2129
gguggauugg uaccuauucu gcuguuugcc ggaccaguua                                40

<210> SEQ ID NO 2130
<211> LENGTH: 40
<212> TYPE: RNA
<213> ORGANISM: Artificial
<220> FEATURE:
<223> OTHER INFORMATION: Aptamer

<400> SEQUENCE: 2130
gguggauugg uauggcgauc uccuaccgug aucgguaaua                                40

<210> SEQ ID NO 2131
<211> LENGTH: 40
<212> TYPE: RNA
<213> ORGANISM: Artificial
<220> FEATURE:
<223> OTHER INFORMATION: Aptamer

<400> SEQUENCE: 2131
gguggauugg uuuaaggagu cuaacucuag augucuucua                                40

<210> SEQ ID NO 2132
<211> LENGTH: 41
<212> TYPE: RNA
<213> ORGANISM: Artificial
<220> FEATURE:
<223> OTHER INFORMATION: Aptamer

<400> SEQUENCE: 2132
gguguacugg cacuacugaa aauuucauuu gaguaggucu g                              41

<210> SEQ ID NO 2133
<211> LENGTH: 40
<212> TYPE: RNA
<213> ORGANISM: Artificial
<220> FEATURE:
<223> OTHER INFORMATION: Aptamer

```
<400> SEQUENCE: 2133
gguguacugg cacuacugaa auuucauuug aguagaucug                    40

<210> SEQ ID NO 2134
<211> LENGTH: 41
<212> TYPE: RNA
<213> ORGANISM: Artificial
<220> FEATURE:
<223> OTHER INFORMATION: Aptamer

<400> SEQUENCE: 2134
gguguacugg cacuacugaa auuucauuug aguuaggucu g                  41

<210> SEQ ID NO 2135
<211> LENGTH: 40
<212> TYPE: RNA
<213> ORGANISM: Artificial
<220> FEATURE:
<223> OTHER INFORMATION: Aptamer

<400> SEQUENCE: 2135
gguguacugg cacuacugaa auuucauuug gguaggucug                    40

<210> SEQ ID NO 2136
<211> LENGTH: 41
<212> TYPE: RNA
<213> ORGANISM: Artificial
<220> FEATURE:
<223> OTHER INFORMATION: Aptamer

<400> SEQUENCE: 2136
gguguacugg cacuacugaa auuucuauuu gaguaggucu g                  41

<210> SEQ ID NO 2137
<211> LENGTH: 40
<212> TYPE: RNA
<213> ORGANISM: Artificial
<220> FEATURE:
<223> OTHER INFORMATION: Aptamer

<400> SEQUENCE: 2137
gguguacugg cacuacugaa guuucauuug aguaggucug                    40

<210> SEQ ID NO 2138
<211> LENGTH: 40
<212> TYPE: RNA
<213> ORGANISM: Artificial
<220> FEATURE:
<223> OTHER INFORMATION: Aptamer

<400> SEQUENCE: 2138
gguguacugg cauagccgug cucuaucgua ugcgauguaa                    40

<210> SEQ ID NO 2139
<211> LENGTH: 40
<212> TYPE: RNA
<213> ORGANISM: Artificial
<220> FEATURE:
<223> OTHER INFORMATION: Aptamer

<400> SEQUENCE: 2139
gguguacugg cauuggcuau acuucgcggc caugauguua                    40

<210> SEQ ID NO 2140
```

```
<211> LENGTH: 42
<212> TYPE: RNA
<213> ORGANISM: Artificial
<220> FEATURE:
<223> OTHER INFORMATION: Aptamer

<400> SEQUENCE: 2140
gguguacugg ccagugacga cuaugagaug ggcguauggu ga                               42

<210> SEQ ID NO 2141
<211> LENGTH: 40
<212> TYPE: RNA
<213> ORGANISM: Artificial
<220> FEATURE:
<223> OTHER INFORMATION: Aptamer

<400> SEQUENCE: 2141
gguguacugg ccaugacgac uaugagaugg cguaugguga                                  40

<210> SEQ ID NO 2142
<211> LENGTH: 40
<212> TYPE: RNA
<213> ORGANISM: Artificial
<220> FEATURE:
<223> OTHER INFORMATION: Aptamer

<400> SEQUENCE: 2142
gguguacugg cccaccgugg gauuuccgu ugagugcgug                                   40

<210> SEQ ID NO 2143
<211> LENGTH: 38
<212> TYPE: RNA
<213> ORGANISM: Artificial
<220> FEATURE:
<223> OTHER INFORMATION: Aptamer

<400> SEQUENCE: 2143
gguguacugg cccugucguu uuauaacucu gcaggaug                                    38

<210> SEQ ID NO 2144
<211> LENGTH: 40
<212> TYPE: RNA
<213> ORGANISM: Artificial
<220> FEATURE:
<223> OTHER INFORMATION: Aptamer

<400> SEQUENCE: 2144
gguguacugg ccgccgguuc uucaagauca cucgaaggug                                  40

<210> SEQ ID NO 2145
<211> LENGTH: 40
<212> TYPE: RNA
<213> ORGANISM: Artificial
<220> FEATURE:
<223> OTHER INFORMATION: Aptamer

<400> SEQUENCE: 2145
gguguacugg ccuaagguug auuugagucg cgaucuuacg                                  40

<210> SEQ ID NO 2146
<211> LENGTH: 40
<212> TYPE: RNA
<213> ORGANISM: Artificial
<220> FEATURE:
<223> OTHER INFORMATION: Aptamer

<400> SEQUENCE: 2146
```

```
gguguacugg cgcguuggua cguuucgucc aauaucguaa                    40
```

<210> SEQ ID NO 2147
<211> LENGTH: 40
<212> TYPE: RNA
<213> ORGANISM: Artificial
<220> FEATURE:
<223> OTHER INFORMATION: Aptamer

<400> SEQUENCE: 2147

```
gguguacugg cggaguccuu ugacgaguug cagacuuuug                    40
```

<210> SEQ ID NO 2148
<211> LENGTH: 40
<212> TYPE: RNA
<213> ORGANISM: Artificial
<220> FEATURE:
<223> OTHER INFORMATION: Aptamer

<400> SEQUENCE: 2148

```
gguguacugg cggagugcca cgagaggaac auugcguuua                    40
```

<210> SEQ ID NO 2149
<211> LENGTH: 39
<212> TYPE: RNA
<213> ORGANISM: Artificial
<220> FEATURE:
<223> OTHER INFORMATION: Aptamer

<400> SEQUENCE: 2149

```
gguguacugg cgugagaaug agccaucuau cgcguaaaa                     39
```

<210> SEQ ID NO 2150
<211> LENGTH: 40
<212> TYPE: RNA
<213> ORGANISM: Artificial
<220> FEATURE:
<223> OTHER INFORMATION: Aptamer

<400> SEQUENCE: 2150

```
gguguacugg cgugugcccg acaaugucaa gggcgaguug                    40
```

<210> SEQ ID NO 2151
<211> LENGTH: 42
<212> TYPE: RNA
<213> ORGANISM: Artificial
<220> FEATURE:
<223> OTHER INFORMATION: Aptamer

<400> SEQUENCE: 2151

```
gguguacugg cuauaauacg uaauguuuua ccuuuuaga ug                  42
```

<210> SEQ ID NO 2152
<211> LENGTH: 39
<212> TYPE: RNA
<213> ORGANISM: Artificial
<220> FEATURE:
<223> OTHER INFORMATION: Aptamer

<400> SEQUENCE: 2152

```
gguguacugg cuuauauugu uucuuucucg agugaguaa                     39
```

<210> SEQ ID NO 2153
<211> LENGTH: 40
<212> TYPE: RNA

```
<213> ORGANISM: Artificial
<220> FEATURE:
<223> OTHER INFORMATION: Aptamer

<400> SEQUENCE: 2153
gguguacugg cuucgcacgu acauaaaauc gucggaguaa                                40

<210> SEQ ID NO 2154
<211> LENGTH: 40
<212> TYPE: RNA
<213> ORGANISM: Artificial
<220> FEATURE:
<223> OTHER INFORMATION: Aptamer

<400> SEQUENCE: 2154
gguguacugg uaagacuccu cgacaagucg ucgguccaua                                40

<210> SEQ ID NO 2155
<211> LENGTH: 40
<212> TYPE: RNA
<213> ORGANISM: Artificial
<220> FEATURE:
<223> OTHER INFORMATION: Aptamer

<400> SEQUENCE: 2155
gguguacugg uaccagugau cgaacgcuga acggguugau                                40

<210> SEQ ID NO 2156
<211> LENGTH: 40
<212> TYPE: RNA
<213> ORGANISM: Artificial
<220> FEATURE:
<223> OTHER INFORMATION: Aptamer

<400> SEQUENCE: 2156
gguguacugg uacgggucgg agucgaguuc cuauuucuua                                40

<210> SEQ ID NO 2157
<211> LENGTH: 40
<212> TYPE: RNA
<213> ORGANISM: Artificial
<220> FEATURE:
<223> OTHER INFORMATION: Aptamer

<400> SEQUENCE: 2157
gguguacugg uaugcagacg aaccuucccc gugcaugaug                                40

<210> SEQ ID NO 2158
<211> LENGTH: 40
<212> TYPE: RNA
<213> ORGANISM: Artificial
<220> FEATURE:
<223> OTHER INFORMATION: Aptamer

<400> SEQUENCE: 2158
gguguacugg ucacgcgaga uuuuccgccc augcgagcga                                40

<210> SEQ ID NO 2159
<211> LENGTH: 39
<212> TYPE: RNA
<213> ORGANISM: Artificial
<220> FEATURE:
<223> OTHER INFORMATION: Aptamer

<400> SEQUENCE: 2159
gguguacugg ucucuugucg uugucgcagg aaguuuuca                                 39
```

<210> SEQ ID NO 2160
<211> LENGTH: 42
<212> TYPE: RNA
<213> ORGANISM: Artificial
<220> FEATURE:
<223> OTHER INFORMATION: Aptamer

<400> SEQUENCE: 2160
gguguacugg ugacaaguuc guucgugccc uuauucugcu ua                        42

<210> SEQ ID NO 2161
<211> LENGTH: 40
<212> TYPE: RNA
<213> ORGANISM: Artificial
<220> FEATURE:
<223> OTHER INFORMATION: Aptamer

<400> SEQUENCE: 2161
gguguacugg ugacaaguuc guucgugccu auucugcuua                           40

<210> SEQ ID NO 2162
<211> LENGTH: 39
<212> TYPE: RNA
<213> ORGANISM: Artificial
<220> FEATURE:
<223> OTHER INFORMATION: Aptamer

<400> SEQUENCE: 2162
gguguacugg ugacuuacua ucuauuagca agcaacucu                            39

<210> SEQ ID NO 2163
<211> LENGTH: 41
<212> TYPE: RNA
<213> ORGANISM: Artificial
<220> FEATURE:
<223> OTHER INFORMATION: Aptamer

<400> SEQUENCE: 2163
gguguacugg ugauguugag uuucugcuu cugaaaaagc a                          41

<210> SEQ ID NO 2164
<211> LENGTH: 40
<212> TYPE: RNA
<213> ORGANISM: Artificial
<220> FEATURE:
<223> OTHER INFORMATION: Aptamer

<400> SEQUENCE: 2164
gguguacugg ugauguugag uuucugcuu cugaaaagca                            40

<210> SEQ ID NO 2165
<211> LENGTH: 40
<212> TYPE: RNA
<213> ORGANISM: Artificial
<220> FEATURE:
<223> OTHER INFORMATION: Aptamer

<400> SEQUENCE: 2165
gguguacugg uggcauucgg uagauuaccu gauggcggua                           40

<210> SEQ ID NO 2166
<211> LENGTH: 40
<212> TYPE: RNA
<213> ORGANISM: Artificial
<220> FEATURE:

```
<223> OTHER INFORMATION: Aptamer

<400> SEQUENCE: 2166
gguguacugg uuaacuuuga cuugcgguag uuuuggauuu                              40

<210> SEQ ID NO 2167
<211> LENGTH: 40
<212> TYPE: RNA
<213> ORGANISM: Artificial
<220> FEATURE:
<223> OTHER INFORMATION: Aptamer

<400> SEQUENCE: 2167
gguguacugg uuacucucca uucgcuuugg uauuguucaa                              40

<210> SEQ ID NO 2168
<211> LENGTH: 40
<212> TYPE: RNA
<213> ORGANISM: Artificial
<220> FEATURE:
<223> OTHER INFORMATION: Aptamer

<400> SEQUENCE: 2168
gguguacugg uuccgauuug ccaaugugcu augcgagucu                              40

<210> SEQ ID NO 2169
<211> LENGTH: 40
<212> TYPE: RNA
<213> ORGANISM: Artificial
<220> FEATURE:
<223> OTHER INFORMATION: Aptamer

<400> SEQUENCE: 2169
gguguacugg uucgucagau cuuuaccucu guucgaauaa                              40

<210> SEQ ID NO 2170
<211> LENGTH: 39
<212> TYPE: RNA
<213> ORGANISM: Artificial
<220> FEATURE:
<223> OTHER INFORMATION: Aptamer

<400> SEQUENCE: 2170
gguguacugg uugcugacuu cuggcguaga cuuggcgua                               39

<210> SEQ ID NO 2171
<211> LENGTH: 40
<212> TYPE: RNA
<213> ORGANISM: Artificial
<220> FEATURE:
<223> OTHER INFORMATION: Aptamer

<400> SEQUENCE: 2171
gguguacugg uugcuucauu ccuucuacag auugacugga                              40

<210> SEQ ID NO 2172
<211> LENGTH: 40
<212> TYPE: RNA
<213> ORGANISM: Artificial
<220> FEATURE:
<223> OTHER INFORMATION: Aptamer

<400> SEQUENCE: 2172
gguguacugg uuuacgucgu aauuagcuac ggcguuauuu                              40
```

```
<210> SEQ ID NO 2173
<211> LENGTH: 40
<212> TYPE: RNA
<213> ORGANISM: Artificial
<220> FEATURE:
<223> OTHER INFORMATION: Aptamer

<400> SEQUENCE: 2173
gguguacugg uuucgccuuu cuccuccuug aggcccaaua                          40

<210> SEQ ID NO 2174
<211> LENGTH: 40
<212> TYPE: RNA
<213> ORGANISM: Artificial
<220> FEATURE:
<223> OTHER INFORMATION: Aptamer

<400> SEQUENCE: 2174
gguguacugg uuucugauuc cggcucuccu gguaaucaca                          40

<210> SEQ ID NO 2175
<211> LENGTH: 40
<212> TYPE: RNA
<213> ORGANISM: Artificial
<220> FEATURE:
<223> OTHER INFORMATION: Aptamer

<400> SEQUENCE: 2175
gguguauugg cacaggguca cucuuuguau uccuugguug                          40

<210> SEQ ID NO 2176
<211> LENGTH: 32
<212> TYPE: RNA
<213> ORGANISM: Artificial
<220> FEATURE:
<223> OTHER INFORMATION: Aptamer

<400> SEQUENCE: 2176
gguguauugg cacgcuuuca uuagcgaauu ug                                  32

<210> SEQ ID NO 2177
<211> LENGTH: 40
<212> TYPE: RNA
<213> ORGANISM: Artificial
<220> FEATURE:
<223> OTHER INFORMATION: Aptamer

<400> SEQUENCE: 2177
gguguauugg ccacucgguc gguuuucaau cagcgcucgg                          40

<210> SEQ ID NO 2178
<211> LENGTH: 40
<212> TYPE: RNA
<213> ORGANISM: Artificial
<220> FEATURE:
<223> OTHER INFORMATION: Aptamer

<400> SEQUENCE: 2178
gguguauugg ccaguuuaga ugugacaacc uacuccaggg                          40

<210> SEQ ID NO 2179
<211> LENGTH: 39
<212> TYPE: RNA
<213> ORGANISM: Artificial
<220> FEATURE:
<223> OTHER INFORMATION: Aptamer
```

<400> SEQUENCE: 2179
gguguauugg cccggacuug auaucccucu ccggcagug          39

<210> SEQ ID NO 2180
<211> LENGTH: 39
<212> TYPE: RNA
<213> ORGANISM: Artificial
<220> FEATURE:
<223> OTHER INFORMATION: Aptamer

<400> SEQUENCE: 2180
gguguauugg cccuagaccg gccaucugcg agucuaaag          39

<210> SEQ ID NO 2181
<211> LENGTH: 40
<212> TYPE: RNA
<213> ORGANISM: Artificial
<220> FEATURE:
<223> OTHER INFORMATION: Aptamer

<400> SEQUENCE: 2181
gguguauugg cccucuuacg cucaaugcuc agguggugug          40

<210> SEQ ID NO 2182
<211> LENGTH: 41
<212> TYPE: RNA
<213> ORGANISM: Artificial
<220> FEATURE:
<223> OTHER INFORMATION: Aptamer

<400> SEQUENCE: 2182
gguguauugg ccgagcaugu cuuucgccuc augucuccuc g          41

<210> SEQ ID NO 2183
<211> LENGTH: 40
<212> TYPE: RNA
<213> ORGANISM: Artificial
<220> FEATURE:
<223> OTHER INFORMATION: Aptamer

<400> SEQUENCE: 2183
gguguauugg ccgggcccuu ggacggacgg guugcaggac          40

<210> SEQ ID NO 2184
<211> LENGTH: 40
<212> TYPE: RNA
<213> ORGANISM: Artificial
<220> FEATURE:
<223> OTHER INFORMATION: Aptamer

<400> SEQUENCE: 2184
gguguauugg cgaguuuugc gcaauucugc uucuguucug          40

<210> SEQ ID NO 2185
<211> LENGTH: 40
<212> TYPE: RNA
<213> ORGANISM: Artificial
<220> FEATURE:
<223> OTHER INFORMATION: Aptamer

<400> SEQUENCE: 2185
gguguauugg cggaguucuc ugaccgguag guucucgcug          40

<210> SEQ ID NO 2186
<211> LENGTH: 32

<212> TYPE: RNA
<213> ORGANISM: Artificial
<220> FEATURE:
<223> OTHER INFORMATION: Aptamer

<400> SEQUENCE: 2186
gguguauugg cggcaauagc aauggagcca ug         32

<210> SEQ ID NO 2187
<211> LENGTH: 40
<212> TYPE: RNA
<213> ORGANISM: Artificial
<220> FEATURE:
<223> OTHER INFORMATION: Aptamer

<400> SEQUENCE: 2187
gguguauugg cggggacucc uuguugaauc ucccugucug         40

<210> SEQ ID NO 2188
<211> LENGTH: 40
<212> TYPE: RNA
<213> ORGANISM: Artificial
<220> FEATURE:
<223> OTHER INFORMATION: Aptamer

<400> SEQUENCE: 2188
gguguauugg cuagguucuu cgguccuuga aucuuggug         40

<210> SEQ ID NO 2189
<211> LENGTH: 39
<212> TYPE: RNA
<213> ORGANISM: Artificial
<220> FEATURE:
<223> OTHER INFORMATION: Aptamer

<400> SEQUENCE: 2189
gguguauugg cuauugugcg cucgccugug ccaacggug         39

<210> SEQ ID NO 2190
<211> LENGTH: 40
<212> TYPE: RNA
<213> ORGANISM: Artificial
<220> FEATURE:
<223> OTHER INFORMATION: Aptamer

<400> SEQUENCE: 2190
gguguauugg cucauugcgc uccccugugg acgugacugg         40

<210> SEQ ID NO 2191
<211> LENGTH: 40
<212> TYPE: RNA
<213> ORGANISM: Artificial
<220> FEATURE:
<223> OTHER INFORMATION: Aptamer

<400> SEQUENCE: 2191
gguguauugg cucgauuacc aguguguugc uucucgauug         40

<210> SEQ ID NO 2192
<211> LENGTH: 39
<212> TYPE: RNA
<213> ORGANISM: Artificial
<220> FEATURE:
<223> OTHER INFORMATION: Aptamer

<400> SEQUENCE: 2192

```
gguguauugg cucgcagacu ucucggaaag acugcaguu           39
```

<210> SEQ ID NO 2193
<211> LENGTH: 40
<212> TYPE: RNA
<213> ORGANISM: Artificial
<220> FEATURE:
<223> OTHER INFORMATION: Aptamer

<400> SEQUENCE: 2193

```
gguguauugg cucgcagacu ucucggaaag acugcaguuu          40
```

<210> SEQ ID NO 2194
<211> LENGTH: 40
<212> TYPE: RNA
<213> ORGANISM: Artificial
<220> FEATURE:
<223> OTHER INFORMATION: Aptamer

<400> SEQUENCE: 2194

```
gguguauugg cucgcagacu ucucggaaag acugcuguuu          40
```

<210> SEQ ID NO 2195
<211> LENGTH: 40
<212> TYPE: RNA
<213> ORGANISM: Artificial
<220> FEATURE:
<223> OTHER INFORMATION: Aptamer

<400> SEQUENCE: 2195

```
gguguauugg cucuguugaa caguuaccug gccgcaguag          40
```

<210> SEQ ID NO 2196
<211> LENGTH: 34
<212> TYPE: RNA
<213> ORGANISM: Artificial
<220> FEATURE:
<223> OTHER INFORMATION: Aptamer

<400> SEQUENCE: 2196

```
gguguauugg cuggaucuuc cugguuucuc uaag                34
```

<210> SEQ ID NO 2197
<211> LENGTH: 40
<212> TYPE: RNA
<213> ORGANISM: Artificial
<220> FEATURE:
<223> OTHER INFORMATION: Aptamer

<400> SEQUENCE: 2197

```
gguguauugg cuguggaagc gcgaaucggu ccauccuaag          40
```

<210> SEQ ID NO 2198
<211> LENGTH: 36
<212> TYPE: RNA
<213> ORGANISM: Artificial
<220> FEATURE:
<223> OTHER INFORMATION: Aptamer

<400> SEQUENCE: 2198

```
gguguauugg cuuccuucuc gccgcagccu agguag              36
```

<210> SEQ ID NO 2199
<211> LENGTH: 39
<212> TYPE: RNA
<213> ORGANISM: Artificial

```
<220> FEATURE:
<223> OTHER INFORMATION: Aptamer

<400> SEQUENCE: 2199
gguguauugg cuucuaaaca uaauuucugg ugggucaag                              39

<210> SEQ ID NO 2200
<211> LENGTH: 41
<212> TYPE: RNA
<213> ORGANISM: Artificial
<220> FEATURE:
<223> OTHER INFORMATION: Aptamer

<400> SEQUENCE: 2200
gguguauugg uaaauacucu ggacuuuucg uuucgguuuu a                           41

<210> SEQ ID NO 2201
<211> LENGTH: 40
<212> TYPE: RNA
<213> ORGANISM: Artificial
<220> FEATURE:
<223> OTHER INFORMATION: Aptamer

<400> SEQUENCE: 2201
gguguauugg uacgguggua gccucggguc ucauuguuua                             40

<210> SEQ ID NO 2202
<211> LENGTH: 40
<212> TYPE: RNA
<213> ORGANISM: Artificial
<220> FEATURE:
<223> OTHER INFORMATION: Aptamer

<400> SEQUENCE: 2202
gguguauugg uacuuacguu aagaaucgcg gaagauguuu                             40

<210> SEQ ID NO 2203
<211> LENGTH: 40
<212> TYPE: RNA
<213> ORGANISM: Artificial
<220> FEATURE:
<223> OTHER INFORMATION: Aptamer

<400> SEQUENCE: 2203
gguguauugg uagcuguaua agacucgauc uggcuccgua                             40

<210> SEQ ID NO 2204
<211> LENGTH: 37
<212> TYPE: RNA
<213> ORGANISM: Artificial
<220> FEATURE:
<223> OTHER INFORMATION: Aptamer

<400> SEQUENCE: 2204
gguguauugg uagcuucggg caucguuucg aucucua                                37

<210> SEQ ID NO 2205
<211> LENGTH: 40
<212> TYPE: RNA
<213> ORGANISM: Artificial
<220> FEATURE:
<223> OTHER INFORMATION: Aptamer

<400> SEQUENCE: 2205
gguguauugg uagggucuua uucuccgggu guugauucua                             40
```

```
<210> SEQ ID NO 2206
<211> LENGTH: 40
<212> TYPE: RNA
<213> ORGANISM: Artificial
<220> FEATURE:
<223> OTHER INFORMATION: Aptamer

<400> SEQUENCE: 2206
gguguauugg ucgcgggaga ucuuauaaug auguucucga                          40

<210> SEQ ID NO 2207
<211> LENGTH: 40
<212> TYPE: RNA
<213> ORGANISM: Artificial
<220> FEATURE:
<223> OTHER INFORMATION: Aptamer

<400> SEQUENCE: 2207
gguguauugg ucuaaugccc gccccuuugu gagcuaguuu                          40

<210> SEQ ID NO 2208
<211> LENGTH: 40
<212> TYPE: RNA
<213> ORGANISM: Artificial
<220> FEATURE:
<223> OTHER INFORMATION: Aptamer

<400> SEQUENCE: 2208
gguguauugg ucuuaacccc ugggaaaaca ucgauugaaa                          40

<210> SEQ ID NO 2209
<211> LENGTH: 40
<212> TYPE: RNA
<213> ORGANISM: Artificial
<220> FEATURE:
<223> OTHER INFORMATION: Aptamer

<400> SEQUENCE: 2209
gguguauugg ucuuucggcu cgugaaucuc gauucaagga                          40

<210> SEQ ID NO 2210
<211> LENGTH: 40
<212> TYPE: RNA
<213> ORGANISM: Artificial
<220> FEATURE:
<223> OTHER INFORMATION: Aptamer

<400> SEQUENCE: 2210
gguguauugg ugaucuagcc ggacugaauc ggacgacuua                          40

<210> SEQ ID NO 2211
<211> LENGTH: 40
<212> TYPE: RNA
<213> ORGANISM: Artificial
<220> FEATURE:
<223> OTHER INFORMATION: Aptamer

<400> SEQUENCE: 2211
gguguauugg ugcaucgaag cgauucuuug ucgauguuuu                          40

<210> SEQ ID NO 2212
<211> LENGTH: 38
<212> TYPE: RNA
<213> ORGANISM: Artificial
<220> FEATURE:
<223> OTHER INFORMATION: Aptamer
```

-continued

```
<400> SEQUENCE: 2212
gguguauugg ugcuuugcgg uuguaucgcu uugucgug                              38

<210> SEQ ID NO 2213
<211> LENGTH: 40
<212> TYPE: RNA
<213> ORGANISM: Artificial
<220> FEATURE:
<223> OTHER INFORMATION: Aptamer

<400> SEQUENCE: 2213
gguguauugg uggcguuacc uguacuuagg cuaucgcuua                            40

<210> SEQ ID NO 2214
<211> LENGTH: 41
<212> TYPE: RNA
<213> ORGANISM: Artificial
<220> FEATURE:
<223> OTHER INFORMATION: Aptamer

<400> SEQUENCE: 2214
gguguauugg uggucuagcc gguacugaau cggacgacuu a                          41

<210> SEQ ID NO 2215
<211> LENGTH: 26
<212> TYPE: RNA
<213> ORGANISM: Artificial
<220> FEATURE:
<223> OTHER INFORMATION: Aptamer

<400> SEQUENCE: 2215
gguguauugg uuaccuuagu gcaaaa                                           26

<210> SEQ ID NO 2216
<211> LENGTH: 28
<212> TYPE: RNA
<213> ORGANISM: Artificial
<220> FEATURE:
<223> OTHER INFORMATION: Aptamer

<400> SEQUENCE: 2216
gguguauugg uuaccuuagu gcaaaaaa                                         28

<210> SEQ ID NO 2217
<211> LENGTH: 40
<212> TYPE: RNA
<213> ORGANISM: Artificial
<220> FEATURE:
<223> OTHER INFORMATION: Aptamer

<400> SEQUENCE: 2217
gguguauugg uuacgaaugc agacuagaca ucugcguaaa                            40

<210> SEQ ID NO 2218
<211> LENGTH: 40
<212> TYPE: RNA
<213> ORGANISM: Artificial
<220> FEATURE:
<223> OTHER INFORMATION: Aptamer

<400> SEQUENCE: 2218
gguguauugg uuagcagauu cguuccucca cuugcugaga                            40

<210> SEQ ID NO 2219
```

```
<211> LENGTH: 40
<212> TYPE: RNA
<213> ORGANISM: Artificial
<220> FEATURE:
<223> OTHER INFORMATION: Aptamer

<400> SEQUENCE: 2219
gguguauugg uuagcagauu cguuccucca uuugcuggga                                40

<210> SEQ ID NO 2220
<211> LENGTH: 40
<212> TYPE: RNA
<213> ORGANISM: Artificial
<220> FEATURE:
<223> OTHER INFORMATION: Aptamer

<400> SEQUENCE: 2220
gguguauugg uuagggugcc ucugucgcua cucccuuaua                                40

<210> SEQ ID NO 2221
<211> LENGTH: 40
<212> TYPE: RNA
<213> ORGANISM: Artificial
<220> FEATURE:
<223> OTHER INFORMATION: Aptamer

<400> SEQUENCE: 2221
gguguauugg uugacauauu auugagauug ccucguugaa                                40

<210> SEQ ID NO 2222
<211> LENGTH: 40
<212> TYPE: RNA
<213> ORGANISM: Artificial
<220> FEATURE:
<223> OTHER INFORMATION: Aptamer

<400> SEQUENCE: 2222
gguguauugg uugcgugauu uuucugaaca gauuuugcau                                40

<210> SEQ ID NO 2223
<211> LENGTH: 41
<212> TYPE: RNA
<213> ORGANISM: Artificial
<220> FEATURE:
<223> OTHER INFORMATION: Aptamer

<400> SEQUENCE: 2223
gguguauugg uuuuucuugg cucgucagcu gcuagauguu a                              41

<210> SEQ ID NO 2224
<211> LENGTH: 41
<212> TYPE: RNA
<213> ORGANISM: Artificial
<220> FEATURE:
<223> OTHER INFORMATION: Aptamer

<400> SEQUENCE: 2224
gguguuacug gcacuacuga aauuucauuu gaguaggucu g                              41

<210> SEQ ID NO 2225
<211> LENGTH: 36
<212> TYPE: RNA
<213> ORGANISM: Artificial
<220> FEATURE:
<223> OTHER INFORMATION: Aptamer

<400> SEQUENCE: 2225
```

```
gguguuauug gccggaggcu guuggccgcc auguug                                36
```

<210> SEQ ID NO 2226
<211> LENGTH: 40
<212> TYPE: RNA
<213> ORGANISM: Artificial
<220> FEATURE:
<223> OTHER INFORMATION: Aptamer

<400> SEQUENCE: 2226

```
gguuaacugg cgaaccuugu uucccucacu ccuguugcug                            40
```

<210> SEQ ID NO 2227
<211> LENGTH: 40
<212> TYPE: RNA
<213> ORGANISM: Artificial
<220> FEATURE:
<223> OTHER INFORMATION: Aptamer

<400> SEQUENCE: 2227

```
gguuaacugg cgaauuguug ucauccgauc uugauuaaug                            40
```

<210> SEQ ID NO 2228
<211> LENGTH: 40
<212> TYPE: RNA
<213> ORGANISM: Artificial
<220> FEATURE:
<223> OTHER INFORMATION: Aptamer

<400> SEQUENCE: 2228

```
gguuaauugg cacuucuuua ucuacggauc gagucggaug                            40
```

<210> SEQ ID NO 2229
<211> LENGTH: 40
<212> TYPE: RNA
<213> ORGANISM: Artificial
<220> FEATURE:
<223> OTHER INFORMATION: Aptamer

<400> SEQUENCE: 2229

```
gguuaauugg cuaaggccgc ggauuugacg uguccuugug                            40
```

<210> SEQ ID NO 2230
<211> LENGTH: 40
<212> TYPE: RNA
<213> ORGANISM: Artificial
<220> FEATURE:
<223> OTHER INFORMATION: Aptamer

<400> SEQUENCE: 2230

```
gguuaauugg cuuccgccgu gguacuucca gccgagcaug                            40
```

<210> SEQ ID NO 2231
<211> LENGTH: 39
<212> TYPE: RNA
<213> ORGANISM: Artificial
<220> FEATURE:
<223> OTHER INFORMATION: Aptamer

<400> SEQUENCE: 2231

```
gguuaauugg uggaauuuga ucgcuuucuu uuuccguuc                             39
```

<210> SEQ ID NO 2232
<211> LENGTH: 39
<212> TYPE: RNA

```
<213> ORGANISM: Artificial
<220> FEATURE:
<223> OTHER INFORMATION: Aptamer

<400> SEQUENCE: 2232
gguuacuggc uggcgacuaa auucuuuugu aacuguaug                              39

<210> SEQ ID NO 2233
<211> LENGTH: 40
<212> TYPE: RNA
<213> ORGANISM: Artificial
<220> FEATURE:
<223> OTHER INFORMATION: Aptamer

<400> SEQUENCE: 2233
gguuagacug guccuaggag ucccaugucu cguagaugug                             40

<210> SEQ ID NO 2234
<211> LENGTH: 40
<212> TYPE: RNA
<213> ORGANISM: Artificial
<220> FEATURE:
<223> OTHER INFORMATION: Aptamer

<400> SEQUENCE: 2234
gguuauacug gcccaaucua guggaaagau agacuguaug                             40

<210> SEQ ID NO 2235
<211> LENGTH: 40
<212> TYPE: RNA
<213> ORGANISM: Artificial
<220> FEATURE:
<223> OTHER INFORMATION: Aptamer

<400> SEQUENCE: 2235
gguuauuggc acccucgaac caaaauggau gccgggaaug                             40

<210> SEQ ID NO 2236
<211> LENGTH: 40
<212> TYPE: RNA
<213> ORGANISM: Artificial
<220> FEATURE:
<223> OTHER INFORMATION: Aptamer

<400> SEQUENCE: 2236
gguuauuggc cggaucuggc uagccaucuu uauccacgug                             40

<210> SEQ ID NO 2237
<211> LENGTH: 40
<212> TYPE: RNA
<213> ORGANISM: Artificial
<220> FEATURE:
<223> OTHER INFORMATION: Aptamer

<400> SEQUENCE: 2237
gguuauuggc gaccguucuu ucuaccuuga acuuggcuug                             40

<210> SEQ ID NO 2238
<211> LENGTH: 39
<212> TYPE: RNA
<213> ORGANISM: Artificial
<220> FEATURE:
<223> OTHER INFORMATION: Aptamer

<400> SEQUENCE: 2238
gguuauuggc gauuggucag cuugcccuaa ccauugaug                              39
```

<210> SEQ ID NO 2239
<211> LENGTH: 40
<212> TYPE: RNA
<213> ORGANISM: Artificial
<220> FEATURE:
<223> OTHER INFORMATION: Aptamer

<400> SEQUENCE: 2239
gguuauuggc gccacugucu cuucuacuag aguacgaaug        40

<210> SEQ ID NO 2240
<211> LENGTH: 24
<212> TYPE: RNA
<213> ORGANISM: Artificial
<220> FEATURE:
<223> OTHER INFORMATION: Aptamer

<400> SEQUENCE: 2240
gguuauuggc ggcagauagc aaug        24

<210> SEQ ID NO 2241
<211> LENGTH: 40
<212> TYPE: RNA
<213> ORGANISM: Artificial
<220> FEATURE:
<223> OTHER INFORMATION: Aptamer

<400> SEQUENCE: 2241
gguuauuggc ggcuuucugu guuuucucgu ucgagcggug        40

<210> SEQ ID NO 2242
<211> LENGTH: 40
<212> TYPE: RNA
<213> ORGANISM: Artificial
<220> FEATURE:
<223> OTHER INFORMATION: Aptamer

<400> SEQUENCE: 2242
gguuauuggc gugguuccag cuugcuagc uuacugagug        40

<210> SEQ ID NO 2243
<211> LENGTH: 40
<212> TYPE: RNA
<213> ORGANISM: Artificial
<220> FEATURE:
<223> OTHER INFORMATION: Aptamer

<400> SEQUENCE: 2243
gguuauuggc ucaucuuguc uguugcaaca ugucugaaug        40

<210> SEQ ID NO 2244
<211> LENGTH: 39
<212> TYPE: RNA
<213> ORGANISM: Artificial
<220> FEATURE:
<223> OTHER INFORMATION: Aptamer

<400> SEQUENCE: 2244
gguuauuggu acgcugaguc uugcuugacg gcgcguguu        39

<210> SEQ ID NO 2245
<211> LENGTH: 40
<212> TYPE: RNA
<213> ORGANISM: Artificial
<220> FEATURE:

<223> OTHER INFORMATION: Aptamer

<400> SEQUENCE: 2245
gguuauuggu ccucuuugua cuuuuuguca cgcaguccua                    40

<210> SEQ ID NO 2246
<211> LENGTH: 39
<212> TYPE: RNA
<213> ORGANISM: Artificial
<220> FEATURE:
<223> OTHER INFORMATION: Aptamer

<400> SEQUENCE: 2246
gguuauuggu cgccaucggg uuucgacucg augacauua                     39

<210> SEQ ID NO 2247
<211> LENGTH: 32
<212> TYPE: RNA
<213> ORGANISM: Artificial
<220> FEATURE:
<223> OTHER INFORMATION: Aptamer

<400> SEQUENCE: 2247
gguuauuggu gccguguuau gagcucgugu ua                            32

<210> SEQ ID NO 2248
<211> LENGTH: 40
<212> TYPE: RNA
<213> ORGANISM: Artificial
<220> FEATURE:
<223> OTHER INFORMATION: Aptamer

<400> SEQUENCE: 2248
gguuauuggu gucuggccug cuugcuuuug gcuuguucua                    40

<210> SEQ ID NO 2249
<211> LENGTH: 39
<212> TYPE: RNA
<213> ORGANISM: Artificial
<220> FEATURE:
<223> OTHER INFORMATION: Aptamer

<400> SEQUENCE: 2249
gguuauuggu gucuggccug cuugcuuuug gcuuguuua                     39

<210> SEQ ID NO 2250
<211> LENGTH: 40
<212> TYPE: RNA
<213> ORGANISM: Artificial
<220> FEATURE:
<223> OTHER INFORMATION: Aptamer

<400> SEQUENCE: 2250
gguuauuggu gucuggccug cuugcuuuug gcuuguuuua                    40

<210> SEQ ID NO 2251
<211> LENGTH: 40
<212> TYPE: RNA
<213> ORGANISM: Artificial
<220> FEATURE:
<223> OTHER INFORMATION: Aptamer

<400> SEQUENCE: 2251
gguuauuggu ucuuguaugc ucgccucagc uuacgaaaaa                    40

```
<210> SEQ ID NO 2252
<211> LENGTH: 33
<212> TYPE: RNA
<213> ORGANISM: Artificial
<220> FEATURE:
<223> OTHER INFORMATION: Aptamer

<400> SEQUENCE: 2252
gguucacugg ucuugacccc ucuggucucg uuu                                    33

<210> SEQ ID NO 2253
<211> LENGTH: 27
<212> TYPE: RNA
<213> ORGANISM: Artificial
<220> FEATURE:
<223> OTHER INFORMATION: Aptamer

<400> SEQUENCE: 2253
gguucauugg cgaggguuau ccggcug                                           27

<210> SEQ ID NO 2254
<211> LENGTH: 40
<212> TYPE: RNA
<213> ORGANISM: Artificial
<220> FEATURE:
<223> OTHER INFORMATION: Aptamer

<400> SEQUENCE: 2254
gguucauugg cguugcuaau cucaugauca agcaagucug                             40

<210> SEQ ID NO 2255
<211> LENGTH: 41
<212> TYPE: RNA
<213> ORGANISM: Artificial
<220> FEATURE:
<223> OTHER INFORMATION: Aptamer

<400> SEQUENCE: 2255
gguucauugg cguugcuagu cucuaugauc aagcaagucu g                           41

<210> SEQ ID NO 2256
<211> LENGTH: 40
<212> TYPE: RNA
<213> ORGANISM: Artificial
<220> FEATURE:
<223> OTHER INFORMATION: Aptamer

<400> SEQUENCE: 2256
gguucauugg cguugcuggu cucaugauca agcaagucug                             40

<210> SEQ ID NO 2257
<211> LENGTH: 35
<212> TYPE: RNA
<213> ORGANISM: Artificial
<220> FEATURE:
<223> OTHER INFORMATION: Aptamer

<400> SEQUENCE: 2257
gguugacugg cgcagguuuu uauuuacccg aacug                                  35

<210> SEQ ID NO 2258
<211> LENGTH: 40
<212> TYPE: RNA
<213> ORGANISM: Artificial
<220> FEATURE:
<223> OTHER INFORMATION: Aptamer
```

```
<400> SEQUENCE: 2258
gguugacugg ugcuucuccc ucuuuugggc gacgaguuua                              40

<210> SEQ ID NO 2259
<211> LENGTH: 40
<212> TYPE: RNA
<213> ORGANISM: Artificial
<220> FEATURE:
<223> OTHER INFORMATION: Aptamer

<400> SEQUENCE: 2259
gguugauugg cccuguuacc ccucggggag cagugggggug                             40

<210> SEQ ID NO 2260
<211> LENGTH: 39
<212> TYPE: RNA
<213> ORGANISM: Artificial
<220> FEATURE:
<223> OTHER INFORMATION: Aptamer

<400> SEQUENCE: 2260
gguugauugg cgcacuccuc gcuguuugau gaucgcaug                               39

<210> SEQ ID NO 2261
<211> LENGTH: 40
<212> TYPE: RNA
<213> ORGANISM: Artificial
<220> FEATURE:
<223> OTHER INFORMATION: Aptamer

<400> SEQUENCE: 2261
gguugauugg cgccaugacu gaacgcuucc gccaggagug                              40

<210> SEQ ID NO 2262
<211> LENGTH: 40
<212> TYPE: RNA
<213> ORGANISM: Artificial
<220> FEATURE:
<223> OTHER INFORMATION: Aptamer

<400> SEQUENCE: 2262
gguugauugg cgccgugacu gaacgcuucc gccaggggug                              40

<210> SEQ ID NO 2263
<211> LENGTH: 40
<212> TYPE: RNA
<213> ORGANISM: Artificial
<220> FEATURE:
<223> OTHER INFORMATION: Aptamer

<400> SEQUENCE: 2263
gguugauugg cuacgauauc uaauccagaa accgcguaug                              40

<210> SEQ ID NO 2264
<211> LENGTH: 29
<212> TYPE: RNA
<213> ORGANISM: Artificial
<220> FEATURE:
<223> OTHER INFORMATION: Aptamer

<400> SEQUENCE: 2264
gguugauugg cuuucgggau ccgaaaaug                                          29

<210> SEQ ID NO 2265
<211> LENGTH: 40
```

```
<212> TYPE: RNA
<213> ORGANISM: Artificial
<220> FEATURE:
<223> OTHER INFORMATION: Aptamer

<400> SEQUENCE: 2265
gguugauugg uaguuaauca aguuucccg uauuaacgug                    40

<210> SEQ ID NO 2266
<211> LENGTH: 40
<212> TYPE: RNA
<213> ORGANISM: Artificial
<220> FEATURE:
<223> OTHER INFORMATION: Aptamer

<400> SEQUENCE: 2266
gguugauugg uccaccugcc cucugugccu ccgcugguua                   40

<210> SEQ ID NO 2267
<211> LENGTH: 40
<212> TYPE: RNA
<213> ORGANISM: Artificial
<220> FEATURE:
<223> OTHER INFORMATION: Aptamer

<400> SEQUENCE: 2267
gguugauugg uggaucccgu ugugacacgc gcagucaaua                   40

<210> SEQ ID NO 2268
<211> LENGTH: 40
<212> TYPE: RNA
<213> ORGANISM: Artificial
<220> FEATURE:
<223> OTHER INFORMATION: Aptamer

<400> SEQUENCE: 2268
gguuuaauug gcuugacguc uucccuggag gacgcagaug                   40

<210> SEQ ID NO 2269
<211> LENGTH: 40
<212> TYPE: RNA
<213> ORGANISM: Artificial
<220> FEATURE:
<223> OTHER INFORMATION: Aptamer

<400> SEQUENCE: 2269
gguuuacugg cagccagaau gcuuugcuga augguggugg                   40

<210> SEQ ID NO 2270
<211> LENGTH: 40
<212> TYPE: RNA
<213> ORGANISM: Artificial
<220> FEATURE:
<223> OTHER INFORMATION: Aptamer

<400> SEQUENCE: 2270
gguuuacugg ucacuuaugu cucgcucgag caagguaaua                   40

<210> SEQ ID NO 2271
<211> LENGTH: 39
<212> TYPE: RNA
<213> ORGANISM: Artificial
<220> FEATURE:
<223> OTHER INFORMATION: Aptamer

<400> SEQUENCE: 2271
```

```
gguuuacugg uggcucauau accucccugc aguggcuua           39

<210> SEQ ID NO 2272
<211> LENGTH: 40
<212> TYPE: RNA
<213> ORGANISM: Artificial
<220> FEATURE:
<223> OTHER INFORMATION: Aptamer

<400> SEQUENCE: 2272
gguuuacugg uguuaauagg augaauccgu auuaccguuu          40

<210> SEQ ID NO 2273
<211> LENGTH: 40
<212> TYPE: RNA
<213> ORGANISM: Artificial
<220> FEATURE:
<223> OTHER INFORMATION: Aptamer

<400> SEQUENCE: 2273
gguuuauugg caaccgaccu uacucaaaag cccggguuug          40

<210> SEQ ID NO 2274
<211> LENGTH: 40
<212> TYPE: RNA
<213> ORGANISM: Artificial
<220> FEATURE:
<223> OTHER INFORMATION: Aptamer

<400> SEQUENCE: 2274
gguuuauugg cacuuggaau aacguuauuc cauggcuuug          40

<210> SEQ ID NO 2275
<211> LENGTH: 40
<212> TYPE: RNA
<213> ORGANISM: Artificial
<220> FEATURE:
<223> OTHER INFORMATION: Aptamer

<400> SEQUENCE: 2275
gguuuauugg cccucucuua ucuccccguc ugagagcgug          40

<210> SEQ ID NO 2276
<211> LENGTH: 40
<212> TYPE: RNA
<213> ORGANISM: Artificial
<220> FEATURE:
<223> OTHER INFORMATION: Aptamer

<400> SEQUENCE: 2276
gguuuauugg ccuccagcu ccuuuccccu gcgaagucgu           40

<210> SEQ ID NO 2277
<211> LENGTH: 40
<212> TYPE: RNA
<213> ORGANISM: Artificial
<220> FEATURE:
<223> OTHER INFORMATION: Aptamer

<400> SEQUENCE: 2277
gguuuauugg cgacauucuc cgaccuggag gcaugaugug          40

<210> SEQ ID NO 2278
<211> LENGTH: 40
<212> TYPE: RNA
<213> ORGANISM: Artificial
```

```
<220> FEATURE:
<223> OTHER INFORMATION: Aptamer

<400> SEQUENCE: 2278
gguuuauugg cgauaaccac guugcugugu auguuauuug                                40

<210> SEQ ID NO 2279
<211> LENGTH: 40
<212> TYPE: RNA
<213> ORGANISM: Artificial
<220> FEATURE:
<223> OTHER INFORMATION: Aptamer

<400> SEQUENCE: 2279
gguuuauugg cgcuuggaac acguuuaucu acccauuuug                                40

<210> SEQ ID NO 2280
<211> LENGTH: 37
<212> TYPE: RNA
<213> ORGANISM: Artificial
<220> FEATURE:
<223> OTHER INFORMATION: Aptamer

<400> SEQUENCE: 2280
gguuuauugg cguagcuaac gaaaaggucg cuacaug                                   37

<210> SEQ ID NO 2281
<211> LENGTH: 40
<212> TYPE: RNA
<213> ORGANISM: Artificial
<220> FEATURE:
<223> OTHER INFORMATION: Aptamer

<400> SEQUENCE: 2281
gguuuauugg cucucucuua ccuccccguc ugagagcgug                                40

<210> SEQ ID NO 2282
<211> LENGTH: 38
<212> TYPE: RNA
<213> ORGANISM: Artificial
<220> FEATURE:
<223> OTHER INFORMATION: Aptamer

<400> SEQUENCE: 2282
gguuuauugg cucucuguuc uaaucggacu cuggaucg                                  38

<210> SEQ ID NO 2283
<211> LENGTH: 39
<212> TYPE: RNA
<213> ORGANISM: Artificial
<220> FEATURE:
<223> OTHER INFORMATION: Aptamer

<400> SEQUENCE: 2283
gguuuauugg cucuuaugcg uuucuugcgc ugggaaaug                                 39

<210> SEQ ID NO 2284
<211> LENGTH: 40
<212> TYPE: RNA
<213> ORGANISM: Artificial
<220> FEATURE:
<223> OTHER INFORMATION: Aptamer

<400> SEQUENCE: 2284
gguuuauugg cucuucgguu ggaucuuuuc aacuuuguuu                                40
```

<210> SEQ ID NO 2285
<211> LENGTH: 40
<212> TYPE: RNA
<213> ORGANISM: Artificial
<220> FEATURE:
<223> OTHER INFORMATION: Aptamer

<400> SEQUENCE: 2285
gguuuauugg cuggcccugc acuuuaucgc cggucugaug					40

<210> SEQ ID NO 2286
<211> LENGTH: 40
<212> TYPE: RNA
<213> ORGANISM: Artificial
<220> FEATURE:
<223> OTHER INFORMATION: Aptamer

<400> SEQUENCE: 2286
gguuuauugg ucucuucgcc uucgcuggcu cgaacgguaa					40

<210> SEQ ID NO 2287
<211> LENGTH: 40
<212> TYPE: RNA
<213> ORGANISM: Artificial
<220> FEATURE:
<223> OTHER INFORMATION: Aptamer

<400> SEQUENCE: 2287
gguuuauugg ucuuggaauu uccuccgauu ugugccguga					40

<210> SEQ ID NO 2288
<211> LENGTH: 40
<212> TYPE: RNA
<213> ORGANISM: Artificial
<220> FEATURE:
<223> OTHER INFORMATION: Aptamer

<400> SEQUENCE: 2288
gguuuauugg ugccguguga uuccauuau caguggaaua					40

<210> SEQ ID NO 2289
<211> LENGTH: 40
<212> TYPE: RNA
<213> ORGANISM: Artificial
<220> FEATURE:
<223> OTHER INFORMATION: Aptamer

<400> SEQUENCE: 2289
gguuuauugg ugcucuguuu gugucacgaa uucuugaaua					40

<210> SEQ ID NO 2290
<211> LENGTH: 41
<212> TYPE: RNA
<213> ORGANISM: Artificial
<220> FEATURE:
<223> OTHER INFORMATION: Aptamer

<400> SEQUENCE: 2290
gguuuauugg uguucgccua ucgauuuuuu ugggcuuuuu a					41

<210> SEQ ID NO 2291
<211> LENGTH: 36
<212> TYPE: RNA
<213> ORGANISM: Artificial
<220> FEATURE:
<223> OTHER INFORMATION: Aptamer

```
<400> SEQUENCE: 2291
gguuuauugg uuacgauagg uuaugccagu cgccaa                               36

<210> SEQ ID NO 2292
<211> LENGTH: 40
<212> TYPE: RNA
<213> ORGANISM: Artificial
<220> FEATURE:
<223> OTHER INFORMATION: Aptamer

<400> SEQUENCE: 2292
gguuuauugg uucccgccu agugaagccu guggucuaua                            40

<210> SEQ ID NO 2293
<211> LENGTH: 40
<212> TYPE: RNA
<213> ORGANISM: Artificial
<220> FEATURE:
<223> OTHER INFORMATION: Aptamer

<400> SEQUENCE: 2293
gguuuauugg uucugucauc gccugccgau uauacaaaaa                           40

<210> SEQ ID NO 2294
<211> LENGTH: 40
<212> TYPE: RNA
<213> ORGANISM: Artificial
<220> FEATURE:
<223> OTHER INFORMATION: Aptamer

<400> SEQUENCE: 2294
gguuuauugg uugauccuau ccuugugaga cagcucuuaa                           40

<210> SEQ ID NO 2295
<211> LENGTH: 40
<212> TYPE: RNA
<213> ORGANISM: Artificial
<220> FEATURE:
<223> OTHER INFORMATION: Aptamer

<400> SEQUENCE: 2295
gguuuauugg uuggcccggg ggugccccgc cggcucguua                           40

<210> SEQ ID NO 2296
<211> LENGTH: 40
<212> TYPE: RNA
<213> ORGANISM: Artificial
<220> FEATURE:
<223> OTHER INFORMATION: Aptamer

<400> SEQUENCE: 2296
gguuucacug gcgcucugga cguuccuaau uccgagaaug                           40

<210> SEQ ID NO 2297
<211> LENGTH: 40
<212> TYPE: RNA
<213> ORGANISM: Artificial
<220> FEATURE:
<223> OTHER INFORMATION: Aptamer

<400> SEQUENCE: 2297
gguuucauug gugaccgauc cgguccuggg ggucggcaua                           40

<210> SEQ ID NO 2298
```

```
<211> LENGTH: 40
<212> TYPE: RNA
<213> ORGANISM: Artificial
<220> FEATURE:
<223> OTHER INFORMATION: Aptamer

<400> SEQUENCE: 2298
gguuuuacug gcgguccaug uugagucucc gcgcgcaaug                            40

<210> SEQ ID NO 2299
<211> LENGTH: 40
<212> TYPE: RNA
<213> ORGANISM: Artificial
<220> FEATURE:
<223> OTHER INFORMATION: Aptamer

<400> SEQUENCE: 2299
gguuuuacug gucccaucuc uuugcgcuga gauguguaua                            40

<210> SEQ ID NO 2300
<211> LENGTH: 42
<212> TYPE: RNA
<213> ORGANISM: Artificial
<220> FEATURE:
<223> OTHER INFORMATION: Aptamer

<400> SEQUENCE: 2300
gguuuuauug gcacuuggaa ugacguuauu ccauggcuuu ug                         42

<210> SEQ ID NO 2301
<211> LENGTH: 43
<212> TYPE: RNA
<213> ORGANISM: Artificial
<220> FEATURE:
<223> OTHER INFORMATION: Aptamer

<400> SEQUENCE: 2301
gguuuuauug gcucucucuu uaucucccccc gucugagagc gug                       43

<210> SEQ ID NO 2302
<211> LENGTH: 41
<212> TYPE: RNA
<213> ORGANISM: Artificial
<220> FEATURE:
<223> OTHER INFORMATION: Aptamer

<400> SEQUENCE: 2302
gguuuuauug gcuucuuaug cguuucuugc gcugggaaau g                          41

<210> SEQ ID NO 2303
<211> LENGTH: 40
<212> TYPE: RNA
<213> ORGANISM: Artificial
<220> FEATURE:
<223> OTHER INFORMATION: Aptamer

<400> SEQUENCE: 2303
ggugaacugg uccgcauuua gcuuucuuau uugcggguau                            40

<210> SEQ ID NO 2304
<211> LENGTH: 40
<212> TYPE: RNA
<213> ORGANISM: Artificial
<220> FEATURE:
<223> OTHER INFORMATION: Aptamer

<400> SEQUENCE: 2304
```

-continued ggugaauugg ccgccguucu uuccguggaa ugacgcgaug        40

<210> SEQ ID NO 2305
<211> LENGTH: 40
<212> TYPE: RNA
<213> ORGANISM: Artificial
<220> FEATURE:
<223> OTHER INFORMATION: Aptamer

<400> SEQUENCE: 2305
gguguacugg cacuacugaa auuucauuug aguaggucug        40

<210> SEQ ID NO 2306
<211> LENGTH: 40
<212> TYPE: RNA
<213> ORGANISM: Artificial
<220> FEATURE:
<223> OTHER INFORMATION: Aptamer

<400> SEQUENCE: 2306
uaagggugua cuggcgauug uugggacgca cuucaauuug        40

<210> SEQ ID NO 2307
<211> LENGTH: 40
<212> TYPE: RNA
<213> ORGANISM: Artificial
<220> FEATURE:
<223> OTHER INFORMATION: Aptamer

<400> SEQUENCE: 2307
gaacccguau uggucacagg uggauugguc uauauuguua        40

<210> SEQ ID NO 2308
<211> LENGTH: 40
<212> TYPE: RNA
<213> ORGANISM: Artificial
<220> FEATURE:
<223> OTHER INFORMATION: Aptamer

<400> SEQUENCE: 2308
gguguauugg auuugcuccg aggguguaga ccccacagau        40

<210> SEQ ID NO 2309
<211> LENGTH: 40
<212> TYPE: RNA
<213> ORGANISM: Artificial
<220> FEATURE:
<223> OTHER INFORMATION: Aptamer

<400> SEQUENCE: 2309
cugggcgacu agguguacug gcuaucacgu ucuggauaag        40

<210> SEQ ID NO 2310
<211> LENGTH: 36
<212> TYPE: RNA
<213> ORGANISM: Artificial
<220> FEATURE:
<223> OTHER INFORMATION: Aptamer

<400> SEQUENCE: 2310
ugguggauug gugcaucuau gucuucuuac uuguua        36

<210> SEQ ID NO 2311
<211> LENGTH: 42
<212> TYPE: RNA

<213> ORGANISM: Artificial
<220> FEATURE:
<223> OTHER INFORMATION: Aptamer

<400> SEQUENCE: 2311
agacggugua cuggcacuuu uacuucauug aguagaaauu cg                           42

<210> SEQ ID NO 2312
<211> LENGTH: 40
<212> TYPE: RNA
<213> ORGANISM: Artificial
<220> FEATURE:
<223> OTHER INFORMATION: Aptamer

<400> SEQUENCE: 2312
uuagcuuagc uucaugcccg gguguacugg agaucucuua                              40

<210> SEQ ID NO 2313
<211> LENGTH: 40
<212> TYPE: RNA
<213> ORGANISM: Artificial
<220> FEATURE:
<223> OTHER INFORMATION: Aptamer

<400> SEQUENCE: 2313
gguguacugu aaccugccug ccaccugcgg cuucgcggac                              40

<210> SEQ ID NO 2314
<211> LENGTH: 40
<212> TYPE: RNA
<213> ORGANISM: Artificial
<220> FEATURE:
<223> OTHER INFORMATION: Aptamer

<400> SEQUENCE: 2314
aacuugaucc ugguuuccag caguaugccg cgugauuucg                              40

<210> SEQ ID NO 2315
<211> LENGTH: 38
<212> TYPE: RNA
<213> ORGANISM: Artificial
<220> FEATURE:
<223> OTHER INFORMATION: Aptamer

<400> SEQUENCE: 2315
acccgcgacu agguuuuccu ggcgaccguc cgguagug                                38

<210> SEQ ID NO 2316
<211> LENGTH: 40
<212> TYPE: RNA
<213> ORGANISM: Artificial
<220> FEATURE:
<223> OTHER INFORMATION: Aptamer

<400> SEQUENCE: 2316
caacuuguau uguccgggug uacuguaccg aaacucguga                              40

<210> SEQ ID NO 2317
<211> LENGTH: 40
<212> TYPE: RNA
<213> ORGANISM: Artificial
<220> FEATURE:
<223> OTHER INFORMATION: Aptamer

<400> SEQUENCE: 2317
gguugauccc guucuucuug acuggcgccu ucauggagug                              40

<210> SEQ ID NO 2318
<211> LENGTH: 40
<212> TYPE: RNA
<213> ORGANISM: Artificial
<220> FEATURE:
<223> OTHER INFORMATION: Aptamer

<400> SEQUENCE: 2318
acucccucuu ucgcgggcuc cuuuccgcaa cacgacuggc                                40

<210> SEQ ID NO 2319
<211> LENGTH: 40
<212> TYPE: RNA
<213> ORGANISM: Artificial
<220> FEATURE:
<223> OTHER INFORMATION: Aptamer

<400> SEQUENCE: 2319
aaaguuuugc acguucuccc gguguccugg cgcuuggcug                                40

<210> SEQ ID NO 2320
<211> LENGTH: 40
<212> TYPE: RNA
<213> ORGANISM: Artificial
<220> FEATURE:
<223> OTHER INFORMATION: Aptamer

<400> SEQUENCE: 2320
gacguucaag uaaauuggcc cuauauuucg uuauaguaug                                40

<210> SEQ ID NO 2321
<211> LENGTH: 40
<212> TYPE: RNA
<213> ORGANISM: Artificial
<220> FEATURE:
<223> OTHER INFORMATION: Aptamer

<400> SEQUENCE: 2321
gcacugcuua cggggucucc ggcaguaugc ccugguguau                                40

<210> SEQ ID NO 2322
<211> LENGTH: 40
<212> TYPE: RNA
<213> ORGANISM: Artificial
<220> FEATURE:
<223> OTHER INFORMATION: Aptamer

<400> SEQUENCE: 2322
guugguugcu gugcagucug ggugucuugg cuuucggaug                                40

<210> SEQ ID NO 2323
<211> LENGTH: 40
<212> TYPE: RNA
<213> ORGANISM: Artificial
<220> FEATURE:
<223> OTHER INFORMATION: Aptamer

<400> SEQUENCE: 2323
cuacaauaau auuaccccuu guuuucguuu aguccggguu                                40

<210> SEQ ID NO 2324
<211> LENGTH: 40
<212> TYPE: RNA
<213> ORGANISM: Artificial
<220> FEATURE:

```
<223> OTHER INFORMATION: Aptamer

<400> SEQUENCE: 2324
ugguguacug uaccuauucg acacuucugu ugauuaguga                                40

<210> SEQ ID NO 2325
<211> LENGTH: 40
<212> TYPE: RNA
<213> ORGANISM: Artificial
<220> FEATURE:
<223> OTHER INFORMATION: Aptamer

<400> SEQUENCE: 2325
uacuuccggg uguacuguaa gcccuacgcu ggaggggcuc                                40

<210> SEQ ID NO 2326
<211> LENGTH: 40
<212> TYPE: RNA
<213> ORGANISM: Artificial
<220> FEATURE:
<223> OTHER INFORMATION: Aptamer

<400> SEQUENCE: 2326
ggcuacuggu cagagguuuc cagcagauuu ccugccuaaa                                40

<210> SEQ ID NO 2327
<211> LENGTH: 40
<212> TYPE: RNA
<213> ORGANISM: Artificial
<220> FEATURE:
<223> OTHER INFORMATION: Aptamer

<400> SEQUENCE: 2327
agacuccugu guuucgggug uacugucacg auucguuguc                                40

<210> SEQ ID NO 2328
<211> LENGTH: 40
<212> TYPE: RNA
<213> ORGANISM: Artificial
<220> FEATURE:
<223> OTHER INFORMATION: Aptamer

<400> SEQUENCE: 2328
aauugucuuc gcguugucuu gaauggguaa uaguagacga                                40

<210> SEQ ID NO 2329
<211> LENGTH: 40
<212> TYPE: RNA
<213> ORGANISM: Artificial
<220> FEATURE:
<223> OTHER INFORMATION: Aptamer

<400> SEQUENCE: 2329
aaaccugugc ugaucgcugu uggacaguuc uacaugcgca                                40

<210> SEQ ID NO 2330
<211> LENGTH: 40
<212> TYPE: RNA
<213> ORGANISM: Artificial
<220> FEATURE:
<223> OTHER INFORMATION: Aptamer

<400> SEQUENCE: 2330
cgcuuuaaug aucugaucgu gcuucgcugc guaguauugg                                40
```

```
<210> SEQ ID NO 2331
<211> LENGTH: 40
<212> TYPE: RNA
<213> ORGANISM: Artificial
<220> FEATURE:
<223> OTHER INFORMATION: Aptamer

<400> SEQUENCE: 2331
gagucguuau cuccuguacu aaucaccuac ugaucgagca                           40

<210> SEQ ID NO 2332
<211> LENGTH: 40
<212> TYPE: RNA
<213> ORGANISM: Artificial
<220> FEATURE:
<223> OTHER INFORMATION: Aptamer

<400> SEQUENCE: 2332
uuagacguuc ucuacguccg ugccgcccug aucgagcgac                           40

<210> SEQ ID NO 2333
<211> LENGTH: 40
<212> TYPE: RNA
<213> ORGANISM: Artificial
<220> FEATURE:
<223> OTHER INFORMATION: Aptamer

<400> SEQUENCE: 2333
aaugaccccg auuccccuuu cguguugucu gaucgcaggc                           40

<210> SEQ ID NO 2334
<211> LENGTH: 40
<212> TYPE: RNA
<213> ORGANISM: Artificial
<220> FEATURE:
<223> OTHER INFORMATION: Aptamer

<400> SEQUENCE: 2334
caccuagagc cugaacugcc uaagcgcuga ucggcauuua                           40

<210> SEQ ID NO 2335
<211> LENGTH: 40
<212> TYPE: RNA
<213> ORGANISM: Artificial
<220> FEATURE:
<223> OTHER INFORMATION: Aptamer

<400> SEQUENCE: 2335
caggcugauc gcuucuuuac gucuaaguau ugacuuuagc                           40

<210> SEQ ID NO 2336
<211> LENGTH: 39
<212> TYPE: RNA
<213> ORGANISM: Artificial
<220> FEATURE:
<223> OTHER INFORMATION: Aptamer

<400> SEQUENCE: 2336
ucgauuagaa uacucuuugu gcgccgucgg ccugaucgu                            39

<210> SEQ ID NO 2337
<211> LENGTH: 40
<212> TYPE: RNA
<213> ORGANISM: Artificial
<220> FEATURE:
<223> OTHER INFORMATION: Aptamer
```

<400> SEQUENCE: 2337
ucgucguagg cguacugauc gaaucguacu uacuauugcg                          40

<210> SEQ ID NO 2338
<211> LENGTH: 40
<212> TYPE: RNA
<213> ORGANISM: Artificial
<220> FEATURE:
<223> OTHER INFORMATION: Aptamer

<400> SEQUENCE: 2338
ugagacugau cgugacaacu ccuguauguu cgaucucauc                          40

<210> SEQ ID NO 2339
<211> LENGTH: 40
<212> TYPE: RNA
<213> ORGANISM: Artificial
<220> FEATURE:
<223> OTHER INFORMATION: Aptamer

<400> SEQUENCE: 2339
ugcugaucgu ucggugaauc auuccuuac cuaccuacgu                           40

<210> SEQ ID NO 2340
<211> LENGTH: 40
<212> TYPE: RNA
<213> ORGANISM: Artificial
<220> FEATURE:
<223> OTHER INFORMATION: Aptamer

<400> SEQUENCE: 2340
uguauuucug uuagugcucg guccugcuga ucgguuagac                          40

<210> SEQ ID NO 2341
<211> LENGTH: 40
<212> TYPE: RNA
<213> ORGANISM: Artificial
<220> FEATURE:
<223> OTHER INFORMATION: Aptamer

<400> SEQUENCE: 2341
uguccgcugu uaaagaucgc gacucugggc ccugaucgau                          40

<210> SEQ ID NO 2342
<211> LENGTH: 40
<212> TYPE: RNA
<213> ORGANISM: Artificial
<220> FEATURE:
<223> OTHER INFORMATION: Aptamer

<400> SEQUENCE: 2342
ugacaucuga ggcuuuuuuc uuggggaauu uuccgagacc                          40

<210> SEQ ID NO 2343
<211> LENGTH: 40
<212> TYPE: RNA
<213> ORGANISM: Artificial
<220> FEATURE:
<223> OTHER INFORMATION: Aptamer

<400> SEQUENCE: 2343
cugugcucgg auuucauccg gguccuauac uucuacuaua                          40

<210> SEQ ID NO 2344
<211> LENGTH: 40

```
<212> TYPE: RNA
<213> ORGANISM: Artificial
<220> FEATURE:
<223> OTHER INFORMATION: Aptamer

<400> SEQUENCE: 2344
guccauuuuc gucguguaau uucggcaacg guuccgggga                           40

<210> SEQ ID NO 2345
<211> LENGTH: 40
<212> TYPE: RNA
<213> ORGANISM: Artificial
<220> FEATURE:
<223> OTHER INFORMATION: Aptamer

<400> SEQUENCE: 2345
uauguucgac uuaauuugau cugcauguuu gucuccgggc                           40

<210> SEQ ID NO 2346
<211> LENGTH: 40
<212> TYPE: RNA
<213> ORGANISM: Artificial
<220> FEATURE:
<223> OTHER INFORMATION: Aptamer

<400> SEQUENCE: 2346 uguccgggc cgacuggcug uuagagaucu cugauguagg                            40

<210> SEQ ID NO 2347
<211> LENGTH: 40
<212> TYPE: RNA
<213> ORGANISM: Artificial
<220> FEATURE:
<223> OTHER INFORMATION: Aptamer

<400> SEQUENCE: 2347
uuuuuccucu uugcccuaug uuugggcgac gcauccgggu                           40
```

APTAMER THAT RECOGNIZES PEPTIDE

CROSS REFERENCE TO RELATED APPLICATIONS

This application is a National Stage of International Application No. PCT/JP2010/058221 filed May 14, 2010, claiming priority based on Japanese Patent Application No. 2009-119269 filed May 15, 2009, the contents of all of which are incorporated herein by reference in their entirety.

TECHNICAL FIELD

The present invention relates to an aptamer that recognizes a peptide, specifically an aptamer that recognizes a histidine peptide.

BACKGROUND ART

Antibodies such as monoclonal antibodies are widely studied as binding molecules that recognize and specifically bind to a target. Antibodies are generally produced by immunization to animals. However, it is difficult to produce antibodies against low molecular weight compounds such as ion atoms and peptides or antigens highly conserved in biological species, for example. Therefore, it is not always possible that an antibody that specifically binds to a target can be obtained. Thus, in recent years, a nucleic acid molecule such as an RNA oligonucleotide or a DNA oligonucleotide, being capable of specifically binding to a target have received attention as a substitute for an antibody. The nucleic acid molecule is generally called an aptamer. It has been reported that an aptamer that specifically binds to a target such as a low molecular weight compound from which it is difficult to obtain an antibody, can be obtained (Non-Patent Document 1).

As described above, it is possible to obtain an aptamer that specifically binds to a target from which it is difficult to produce an antibody. Therefore, for example, using the aptamer as an important tool in the biochemical field and the medical field are attempted as described below.

For example, it is possible to chemically synthesize a large quantity of aptamer. Some aptamers have low immunogenicity and show a strong binding ability to a target as compared with antibodies. Therefore, aptamers can be candidates of superior molecular target drugs (Non-Patent Document 2). Specifically, Pegaptanib (generic name: Pegaptanib, product name: Macugen) is known as an aptamer that binds to a vascular endothelial growth factor (VEGF). This aptamer has been approved as a therapeutic drug for age-related macular degeneration in the United States, Europe, and Japan (Non-Patent Document 3). In addition, currently, clinical trials of at least five kinds of aptamers are conducted in the United States.

Moreover, studies to utilize aptamers as novel molecular sensors are conducted actively. For example, an aptamer against a target such as a serum protein (Non-Patent Document 4), cocaine (Non-Patent Document 5), or an ion (Non-Patent Document 6) changes its conformation by binding to a target. A method for measuring such a target, utilizing the above-described characteristics, has been developed (Non-Patent Document 7).

Using aptamers for affinity purification of, for example, a protein or the like is also attempted. According to this method, contaminations by substances derived from a protein such as a peptide can be extremely reduced as compared with a conventional method using antibodies. Therefore, according to this method, a purified product having a really high medical value and biochemical value can be obtained, for example (Non-Patent Document 8).

On the other hand, conventionally, a method for expressing a fusion protein obtained by fusing a peptide, as a tag, having several to dozens of consecutive amino acids with the N-terminal or the C-terminal of an intended protein in order to synthesize a large quantity of the intended protein has been known. According to this method, it is possible to check an expression of the intended protein and purify the intended protein, using the tag of the fusion protein as a clue. As the tag, a histidine peptide including several histidines, being called a histidine tag, is widely used, for example. A fusion protein to which the histidine tag has been added can be purified using a nickel ion column or an anti-histidine tag antibody, for example. However, there are problems in that the nickel ion column involves high nonspecific adsorption, and the anti-histidine antibody is expensive, and the like. Therefore, in the purification of an intended protein using the histidine tag, a development of a novel anti-histidine tag antibody or a binding molecule as an alternative of the anti-histidine tag antibody has been advanced.

PRIOR ART DOCUMENTS

Non-Patent Documents

Non-Patent Document 1: Mairal T. et al., "Anal. Bioanal. Chem.", 2008, Vol. 390, pp. 989-1007
Non-Patent Document 2: Bunka D. H. and Stockley P. G., "Nat. Rev. Microbiol.", 2006, Vol. 4, pp. 588-596
Non-Patent Document 3: Nimjee S. M. et al., "Trends Cardiovasc. Med.", 2005, Vol. 15, pp. 41-45
Non-Patent Document 4: Nimjee S. M. et al., "Annu Rev. Med.", 2005, Vol. 56, pp. 555-583
Non-Patent Document 5: Ng E. W. et al., "Nat. Rev. Drug Discov.", 2006, Vol. 5, pp. 123-132
Non-Patent Document 6: Huang Y. C. et al., J. Am. Chem. Soc.", 2008, Vol. 130, pp. 8023-8029
Non-Patent Document 7: Deng C. et al., "Anal. Chem.", 2009, Vol. 81, pp. 739-745
Non-Patent Document 8: Xu H et al., "Anal. Chem.", 2009, Vol. 81, pp. 669-675

DISCLOSURE OF THE INVENTION

Problem to be Solved by the Invention

Hence, the present invention is intended to provide an aptamer capable of binding to a histidine peptide.

Means for Solving Problem

An aptamer of the present invention is an aptamer capable of binding to a histidine peptide, being any of the following nucleic acids (a) to (d):

(a) a nucleic acid having a base sequence represented by SEQ ID NO: 17:

$$GGUN_nAYU_mGGH, \quad (SEQ\ ID\ NO:\ 17)$$

where in the nucleic acid (a),
N represents A, G, C, U, or T,
n of Nn represents the number of Ns and is an integer from 1 to 3,
Y represents U, T, or C, m of Um represents the number of Us and is an integer from 1 to 3, and H represents U, T, C, or A;

(b) a nucleic acid having a base sequence obtained by substitution, deletion, addition, or insertion of one or more bases in a base sequence of the nucleic acid (a) and being capable of binding to the histidine peptide;

(c) a nucleic acid having a base sequence represented by SEQ ID NO:18:

GGCGCCUUCGUGGAAUGUC; (SEQ ID NO: 18)

and (d) a nucleic acid having a base sequence obtained by substitution, deletion, addition, or insertion of one or more bases in a base sequence of the nucleic acid (c) and being capable of binding to the histidine peptide.

A reagent of the present invention contains the aptamer of the present invention. A kit of the prevent invention contains the aptamer of the present invention.

A nucleic acid for producing the aptamer of the present invention is for producing the aptamer of the present invention and has a base sequence complementary to the aptamer of the present invention.

An antisense nucleic acid of the present invention has a base sequence complementary to the aptamer of the present invention.

An identification method of the present invention is a method for identifying an aptamer being capable of binding to a target, the method having the following steps (i) to (iv):

(i) mixing an RNA pool and the target;

(ii) separating RNA binding to the target from the RNA pool;

(iii) synthesizing cDNA using the separated RNA as a template and a DNA polymerase; and (iv) synthesizing RNA using the cDNA as a template and an RNA polymerase.

Effects of the Invention

The aptamer of the present invention has superior binding force to a histidine peptide as compared with a general anti-histidine peptide antibody that binds to a histidine peptide. Therefore, for example, the aptamer can be used in detection of a histidine peptide as a substitute for the anti-histidine peptide antibody, and it becomes possible to detect a histidine peptide with superior accuracy. As described above, the aptamer of the present invention is a very useful tool in the detection of a histidine peptide of biological means.

DESCRIPTION OF EMBODIMENTS

Figure 1:
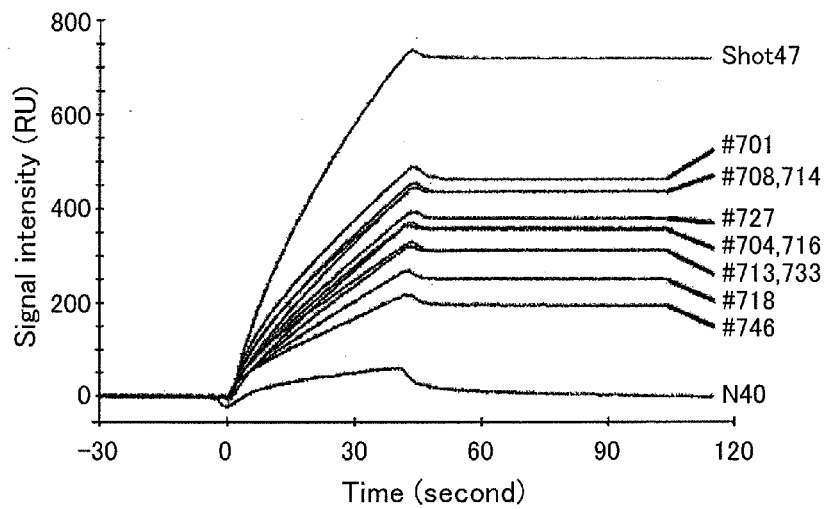
FIG. 1 shows sensorgrams of various aptamers in the examples of the present invention.

In the present invention, hereinafter, histidine is referred to as "His", and a histidine peptide is referred to as a "His peptide". The His peptide can be used as a histidine tag as mentioned above. Hereinafter, the histidine tag is referred to as a "His-tag". The His peptide can be read as the His-tag. Hereinafter, an aptamer capable of binding to the His peptide is referred to as a "His peptide aptamer", a "His-tag aptamer", or an "aptamer".

In the present invention, the His peptide means a peptide containing a plurality of histidines. The His peptide may be, for example, a peptide composed of only a plurality of consecutive histidines, i.e., a poly His peptide (hereinafter referred to as a "poly His") or a peptide containing the poly His peptide, i.e., a peptide containing the poly His that has an additional sequence on at least one of the N-terminal side and the C-terminal side thereof. The additional sequence may be, for example, one amino-acid residue or a peptide composed of two or more amino-acid residues. The His peptide may also be, for example, a peptide containing a plurality of nonconsecutive histidines, i.e., a peptide containing a plurality of histidines and the other amino acids. In the present invention, the length of the His peptide is not particularly limited, and the number of amino-acid residues is, for example, from 6 to 30, preferably from 6 to 15, and more preferably from 8 to 15. The number of histidines in the poly His of the His peptide is, for example, preferably from 6 to 10 and more preferably from 6 to 8.

<Aptamer>

The aptamer of the present invention is, as mentioned above, an aptamer capable of binding to a His peptide, being any of the following nucleic acids (a) to (d):

(a) a nucleic acid having a base sequence represented by SEQ ID NO: 17:

GGUN$_n$AYU$_m$GGH, (SEQ ID NO: 17)

where in the nucleic acid (a),

N represents A, G, C, U, or T, n of Nn represents the number of Ns and is an integer from 1 to 3, Y represents U, T, or C, m of Um represents the number of Us and is an integer from 1 to 3, and H represents U, T, C, or A;

(b) a nucleic acid having a base sequence obtained by substitution, deletion, addition, or insertion of one or more bases in a base sequence of the nucleic acid (a) and being capable of binding to the His peptide;

(c) a nucleic acid having a base sequence represented by SEQ ID NO:18:

GGCGCCUUCGUGGAAUGUC;  (SEQ ID NO: 18)

and (d) a nucleic acid having a base sequence obtained by substitution, deletion, addition, or insertion of one or more bases in a base sequence of the nucleic acid (c) and being capable of binding to the His peptide.

It is only necessary that the aptamer of the item (a) is a nucleic acid having a base sequence represented by SEQ ID NO: 17. Hereinafter, the base sequence represented by SEQ ID NO: 17 is also referred to as a "binding motif sequence". In the binding motif sequence represented by SEQ ID NO: 17, N represents A, G, C, U, or T and is preferably A, G, C, or U, n of Nn represents the number of Ns and is an integer from 1 to 3, Y represents U, T, or C and is preferably U or C, m of Um represents the number of Us and is an integer from 1 to 3, and H represents U, T, C, or A and is preferably U, C, or A. The binding motif sequence is a consensus sequence in common with base sequences represented by SEQ ID NOs: 1 to 16 described below. In the binding motif sequence, the number (n) of Ns of Nn is not particularly limited and may be, for example, any of one (N), two (NN), and three (NNN). The Ns may be identical to or different from each other. In the binding motif sequence, the number (m) of Um is not particularly limited and may be, for example, any of one (U), two (UU), and three (UUU).

The aptamer of the item (a) can be, for example, the following nucleic acid (a1):

(a1) a nucleic acid having a base sequence represented by any of SEQ ID NOs: 89 to 104.

Each of the base sequences represented by SEQ ID NOs: 89 to 104 has the binding motif sequence represented by SEQ ID NO: 17. The aptamer of the item (a1) may be, for example, a nucleic acid composed of a base sequence represented by any of SEQ ID NOs: 89 to 104 or a nucleic acid having the base sequence. The base sequences represented by SEQ ID NOs: 89 to 104 are shown in Table 1 below. In Table 1, each underlined part indicates the binding motif sequence represented by SEQ ID NO: 17. In the present invention, each of aptamers in Table 1 is hereinafter also referred to as each name shown on the left side of each sequence (the same applies hereinafter).

TABLE 1

| Name | Sequence | No. |
|---|---|---|
| #701 | CCG<u>GGUUAUU GGC</u>GCAAUAU UGGUAUCCUG UAUUGGUCUG | SEQ ID NO: 89 |
| shot47 | CGUCCGAUCG AUACU<u>GGUAU AUUGGCGCCU</u> UCGUGGAAUG | SEQ ID NO: 90 |
| #716 | CCUGUUUUGU CUA<u>GGUUUAU UGGCGCUUAU</u> UCCUGGAAUG | SEQ ID NO: 91 |
| #727 | CUCA<u>GGUGAU UGGCGCUAUU</u> UAUCGAUCGA UAAUUGAAUG | SEQ ID NO: 92 |
| #704 | UGUUCCUUUG <u>GGUUAUUGGC</u> UCCUUGUUGA CCAGGGGAUG | SEQ ID NO: 93 |
| #713 | CAACACUCGA A<u>GGGUUUAUU GGC</u>CCCACCA UGGUGGAAUG | SEQ ID NO: 94 |
| #708 | C<u>GGUUAUUGG C</u>GGAGGAUCU GUCAUGGCAU GCCUCGACUG | SEQ ID NO: 95 |
| #718 | CUUCUUUCCC ACUCACGUCU C<u>GGUUUUAUU GGU</u>CCAGUUU | SEQ ID NO: 96 |
| #746 | GGUGAAUUGG CACUUCUUUA UCUACGGAUC GAGUCGGAUG | SEQ ID NO: 97 |
| #714 | ---------- ---<u>GGUUUAU UGGU</u>GCCGUG UAGUGGAAUA | SEQ ID NO: 98 |
| #733 | CUUCCCUAGA CCCUCCA<u>GGU UACAGGCGCC</u> GCCCGGAAUG | SEQ ID NO: 99 |
| #47s | ---------- -----<u>GGUAU AUUGGCGCCU</u> UCGUGGAAUG | SEQ ID NO: 100 |
| #47sT | ---------- -----<u>GGUAU AUUGGCGCC</u>- UCG-GGAAUG | SEQ ID NO: 101 |
| shot47sss | ---------- -----<u>GGUAU AUUGGCGCCU</u> UCGUGGAAUG | SEQ ID NO: 102 |
| #47M1 | ---------- -UACU<u>GGUAU AUUGGCGCCU</u> UCGUGGAAUG | SEQ ID NO: 103 |
| #47sssT | ---------- -----<u>GGUAU AUUGGCGCC</u>- UCG GGAAUG | SEQ ID NO: 104 |

A specific example of the aptamer of the item (a1) can be, for example, the following nucleic acid (a1-1):

(a1-1) a nucleic acid having a base sequence represented by any of SEQ ID NOs: 1 to 16.

The base sequences represented by SEQ ID NOs: 1 to 16 have the base sequences represented by SEQ ID NOs: 89 to 104, respectively. The aptamer of the item (a1-1) may be, for example, a nucleic acid composed of a base sequence represented by any of SEQ ID NOs: 1 to 16 or a nucleic acid having the base sequence. The base sequences represented by SEQ ID NOs: 1 to 16 are shown in Table 2 below. In Table 2, each underlined part indicates the binding motif sequence represented by SEQ ID NO: 17. In the present invention, each of aptamers in Table 2 is hereinafter also referred to as each name shown on the left side of each sequence (the same applies hereinafter).

TABLE 2

| Name | Sequence | No. |
|---|---|---|
| #701 | gggacgcuca cguacgcuca CCGGGUUAUU GGCGCAAUAU UGGUAUCCUG UAUUGGUCUG ucagugccug gacgugcagu | SEQ ID NO: 1 |
| shot47 | gggacgcuca cguacgcuca CGUCCGAUCG AUACUGGUAU AUUGGCGCCU UCGUGGAAUG ucagugccug gacgugcagu | SEQ ID NO: 2 |
| #716 | gggacgcuca cguacgcuca CCUGUUUUGU CUAGGUUUAU UGGCGCUUAU UCCUGGAAUG ucagugccug gacgugcagu | SEQ ID NO: 3 |
| #727 | gggacgcuca cguacgcuca CUCAGGUGAU UGGCGCUAUU UAUCGAUCGA UAAUUGAAUG ucagugccug gacgugcagu | SEQ ID NO: 4 |
| #704 | gggacgcuca cguacgcuca UGUUCCUUUG GGUUAUUGGC UCCUUGUUGA CCAGGGGAUG ucagugccug gacgugcagu | SEQ ID NO: 5 |
| #713 | gggacgcuca cguacgcuca CAACACUCGA AGGGUUUAUU GGCCCCACCA UGGUGGAAUG ucagugccug gacgugcagu | SEQ ID NO: 6 |
| #708 | gggacgcuca cguacgcuca CGGUUAUUGG CGGAGGAUCU GUCAUGGCAU GCCUCGACUG ucagugccug gacgugcagu | SEQ ID NO: 7 |
| #718 | gggacgcuca cguacgcuca CUUCUUUCCC ACUCACGUCU CGGUUUUAUU GGUCCAGUUU ucagugccug gacgugcagu | SEQ ID NO: 8 |
| #746 | gggacgcuca cguacgcuca GGUGAAUUGG CACUUCUUUA UCUACGGAUC GAGUCGGAUG ucagugccug gacgugcagu | SEQ ID NO: 9 |
| #714 | gggacgcuca cguacgcuca ---------- ---GGUUUAU UGGUGCCGUG UAGUGGAAUA ucagugccug gacgugcagu | SEQ ID NO: 10 |
| #733 | gggacgcuca cguacgcuca CUUCCCUAGA CCCUCCAGGU UACAGGCGCC GCCCGGAAUG ucagugccug gacgugcagu | SEQ ID NO: 11 |
| #47s | ---------g gguacgcuca ---------- -----GGUAU AUUGGCGCCU UCGUGGAAUG ucagugccug gacgugcagu | SEQ ID NO: 12 |
| #47sT | ---------g gguacgcuca ---------- -----GGUAU AUUGGCGCC- UCG-GGAAUG ucagugccug gacgugcagu | SEQ ID NO: 13 |
| shot47sss | ---------- ---------g ---------- -----GGUAU AUUGGCGCCU UCGUGGAAUG ucagugccug g | SEQ ID NO: 14 |
| #47M1 | ---------- -------ggg ---------- -UACUGGUAU AUUGGCGCCU UCGUGGAAUG ucagug | SEQ ID NO: 15 |
| #47sssT | ---------- ---------g ---------- -----GGUAU AUUGGCGCC- UCG GGAAUG ucagugccug g | SEQ ID NO: 16 |

A specific example of the aptamer of the item (a) can also be, for example, the following nucleic acid (a2):

(a2) a nucleic acid having a base sequence represented by any of SEQ ID NOs: 105 to 114, 116 to 124, and 127 to 146.

Each of the base sequences represented by SEQ ID NOs: 105 to 114, 116 to 124, and 127 to 146 has the binding motif sequence represented by SEQ ID NO: 17. The aptamer of the item (a2) may be, for example, a nucleic acid composed of a base sequence represented by any of SEQ ID NOs: 105 to 114, 116 to 124, and 127 to 146 or a nucleic acid having the base sequence. The base sequences represented by SEQ ID NOs: 105 to 114, 116 to 124, and 127 to 146 are shown in Tables 3 and 4 below. In Tables 3 and 4, each underlined part indicates the binding motif sequence represented by SEQ ID NO: 17. In the present invention, each of aptamers in Tables 3 and 4 is hereinafter also referred to as each name shown on the left side of each sequence (the same applies hereinafter).

TABLE 3

| Name | Sequence | No. |
|---|---|---|
| #730 | UUCGACCGGG UUAUUGGCUG CUCUCCUCUG GUUUGUGAUG | SEQ ID NO: 105 |
| #743 | ACACUUGCUU UUUCUUGUCC GGGUUUAUUG GUCGUUGUAU | SEQ ID NO: 106 |
| #7007 | GAGAUCGUUC UGGUUAUUGG CGCCUUCUGA UAAAGGAAUG | SEQ ID NO: 107 |
| #7008 | UUGUCUUGGU GAUUGGUUA CUGUCCAAUG GGCGGUGUAU | SEQ ID NO: 108 |
| #7034 | AAAUGCUGUU GCAGGUUAUU UGGCUCUCGG UCUGAGAAUG | SEQ ID NO: 109 |
| #707 | CGGUGGAUUG GCGACGAUGA CCUUGAUAGU CCUCGUAAUG | SEQ ID NO: 110 |

TABLE 3-continued

| Name | Sequence | No. |
|---|---|---|
| #715 | UAGAGUGUAU UUGUACCAGG UAUACUGGCG CGAACGAAUG | SEQ ID NO: 111 |
| #719 | GCUCUCUUAC UUCCUGGGUG ACUGGCUCUU UCGGGGUAUG | SEQ ID NO: 112 |
| #723 | GGUUAUUGGC GCCCUCGAAC CAAAAUGGAU GCCGGGAAUG | SEQ ID NO: 113 |
| #725 | CAUGUCCGGG UGGAUUGGAU CGAUUACUUG UUUUCGUUUA | SEQ ID NO: 114 |
| #736 | CCUCAAGUCG GGUCUAUUGU CUCCGGCGAA GCAUGGACUG | SEQ ID NO: 115 |
| #745 | GAGCCACGGG UUUACUGGCG CUAAACAAAU GUUUAGGAUG | SEQ ID NO: 116 |
| #748 | GCGCUUCUCG UUUGCUUUCC GGGUUCAUUG GUCCAUGUUU | SEQ ID NO: 117 |
| #7004 | GGCGUUCUUC GCUGUAGUUC CGGUUUAUUG GUCUUUGUUU | SEQ ID NO: 118 |
| #7015 | UGUCUCGGUU UAUUGGCGGU CGGACUUUUG CCCUGCGAUG | SEQ ID NO: 119 |
| #7029 | CGAAAUCCAG GUUUGAUUGG CGUGGCACCC UUGCCAAGUG | SEQ ID NO: 120 |
| #7030 | AUGAGCUCAC CUGGGUAAUU GGCGCCAAUU CAAGGGUCUG | SEQ ID NO: 121 |
| #7049 | CGCUCAGGUG AAUUGGUUAC GUUUUCUCUG ACAAUGUGGA | SEQ ID NO: 122 |
| #7052 | AUUCUGUUCU GUCUCUCCGG GUUUACUGGC GCUAUGAAUG | SEQ ID NO: 123 |
| #7054 | AAGUGUCUGC AAGUCUACCG GUUUACUGGC CACUCCGUUU | SEQ ID NO: 124 |
| #7009 | UGAUUGAAUG GGCGAAUCGA CCUUACCGGU UUUCUGCAAC | SEQ ID NO: 125 |
| #7062 | UCUCGCCGCA UUUCCAGGUU UUUUGGCGCU UAUGAAUGA- | SEQ ID NO: 126 |
| #47sC3 | ---------- -----GGUAU AUUGGCGCC- CCG-GGAAUG | SEQ ID NO: 127 |
| #47sA1 | ---------- -----GGUAU AUUGGCGCCU UCGUGGA-UG | SEQ ID NO: 128 |
| #47sA | ---------- -----GGUAU AUUGGCGCCU UCGUGG--UG | SEQ ID NO: 129 |
| #47sTA | ---------- -----GGUAU AUUGGCGCC- UCG-GG--UG | SEQ ID NO: 130 |

TABLE 4

| Name | Sequence | No. |
|---|---|---|
| #627 | UUUUACUUUU CCUACGACCG GGUGAACUGG CUCUUGGAUG | SEQ ID NO: 131 |
| #629 | AAAUGCUGUU GCAGGUUAUU UGGCUCUCGG UCUGAGAAUG | SEQ ID NO: 132 |
| #504 | UGUUCCGGGU CGACUGGCUG UUAGAGAUCU CUGAUGUAGG | SEQ ID NO: 133 |
| #505 | GCUCCGGGUA UACUGGCGAC GACCGUUAUU GUGUCGCAUG | SEQ ID NO: 134 |
| #402 | GGUGUACUGG CACUACUGAA AUUUCAUUUG AGUAGGUCUG | SEQ ID NO: 135 |
| #403 | GGUGAACUGG UCCGCAUUUA GCUUUCUUAU UUGCGGGUAU | SEQ ID NO: 136 |
| #404 | GGUGUAUUGG AUGCUUUAAG CAGGUCUCUG CUUCAGCAAU | SEQ ID NO: 137 |
| #405 | AUUCUGUUCU GUCUCUCCGG GUUUACUGGC GCUAUGAAUG | SEQ ID NO: 138 |
| #303 | ---GGUGGAC UGGUUUCUAA GUGCUUUGAC UGCUGGAGGA | SEQ ID NO: 139 |
| #304 | ---------- ----GGUUAU UGGCUUUCCG AGCGAAGAUG | SEQ ID NO: 140 |
| #305 | GGUGUAUUGG AUAACAGCUG CUUCUUGGAA CGUUGUCGUU | SEQ ID NO: 141 |
| #306 | GGUUUAUUGG AUGUUGUCU CCCGUUCGGG ACAUUCGUUU | SEQ ID NO: 142 |
| #AT5-5 | GGUUGAUCCC GUUCUUCUUG ACUGGCGCCU UCAUGGAGUG | SEQ ID NO: 143 |

TABLE 4-continued

| Name | Sequence | No. |
|---|---|---|
| #14sTT | ---------- ---GGUUUAU UGGUGCCGUG UAGUGGAAUG | SEQ ID NO: 144 |
| #47ss | ---------- -----GGUAU AUUGGCGCCU UCGUGGAAUG | SEQ ID NO: 145 |
| #47ssT | ---------- -----GGUAU AUUGGCGCC- UCG-GGAAUG | SEQ ID NO: 146 |

A specific example of the aptamer of the item (a2) can be, for example, the following nucleic acid (a2-1):

(a2-1) a nucleic acid having a base sequence represented by any of SEQ ID NOs: 26 to 35, 37 to 45, 65 to 68, 19 to 25, and 48 to 56.

The base sequences represented by SEQ ID NOs: 26 to 35, 37 to 45, 65 to 68, 19 to 25, and 48 to 56 have the base sequences represented by SEQ ID NOs: 105 to 114, 116 to 124, and 127 to 146, respectively. The aptamer of the item (a2-1) may be, for example, a nucleic acid composed of a base sequence represented by any of SEQ ID NOs: 26 to 35, 37 to 45, 65 to 68, 19 to 25, and 48 to 56 or a nucleic acid having the base sequence. The base sequences represented by SEQ ID NOs: 26 to 35, 37 to 45, 65 to 68, 19 to 25, and 48 to 56 are shown in Tables 5 and 6 below. In Tables 5 and 6, each underlined part indicates the binding motif sequence represented by SEQ ID NO: 17. In the present invention, each of aptamers in Tables 5 and 6 is also referred to as each name shown on the left side of each sequence (the same applies hereinafter).

TABLE 5

| Name | Sequence | No. |
|---|---|---|
| #730 | gggacgcuca cguacgcuca UUCGACCGGG UUAUUGGCUG CUCUCCUCUG GUUUGUGAUG ucagugccug gacgugcagu | SEQ ID NO: 26 |
| #743 | gggacgcuca cguacgcuca ACACUUGCUU UUUCUUGUCC GGGUUUAUUG GUCGUUGUAU ucagugccug gacgugcagu | SEQ ID NO: 27 |
| #7007 | gggacgcuca cguacgcuca GAGAUCGUUC UGGUUAUUGG CGCCUUCUGA UAAAGGAAUG ucagugccug gacgugcagu | SEQ ID NO: 28 |
| #7008 | gggacgcuca cguacgcuca UUGUCUUGGU GUAUGGUUA CUGUCCAAUG GGCGGUGUAU ucagugccug gacgugcagu | SEQ ID NO: 29 |
| #7034 | gggacgcuca cguacgcuca AAAUGCUGUU GCAGGUUAUU UGGCUCUCGG UCUGAGAAUG ucagugccug gacgugcagu | SEQ ID NO: 30 |
| #707 | gggacgcuca cguacgcuca CGGUGGAUUG GCGACGAUGA CCUUGAUAGU CCUCGUAAUG ucagugccug gacgugcagu | SEQ ID NO: 31 |
| #715 | gggacgcuca cguacgcuca UAGAGUGUAU UUGUACCAGG UAUACUGGCG CGAACGAAUG ucagugccug gacgugcagu | SEQ ID NO: 32 |
| #719 | gggacgcuca cguacgcuca GCUCUCUUAC UUCCUGGGUG ACUGGCUCUU UCGGGUAUG ucagugccug gacgugcagu | SEQ ID NO: 33 |
| #723 | gggacgcuca cguacgcuca GGUUAUUGGC GCCCUCGAAC CAAAAUGGAU GCCGGGAAUG ucagugccug gacgugcagu | SEQ ID NO: 34 |
| #725 | gggacgcuca cguacgcuca CAUGUCCGGG UGGAUUGGAU CGAUUACUUG UUUUCGUUUA ucagugccug gacgugcagu | SEQ ID NO: 35 |
| #736 | gggacgcuca cguacgcuca CCUCAAGUCG GGUCUAUUGU CUCCGGCGAA GCAUGGACUG ucagugccug gacgugcagu | SEQ ID NO: 36 |
| #745 | gggacgcuca cguacgcuca GAGCCACGGG UUUACUGGCG CUAAACAAAU GUUUAGGAUG ucagugccug gacgugcagu | SEQ ID NO: 37 |
| #748 | gggacgcuca cguacgcuca GCGCUUCUCG UUUGCUUUCC GGGUUCAUUG GUCCAUGUUU ucagugccug gacgugcagu | SEQ ID NO: 38 |
| #7004 | gggacgcuca cguacgcuca GGCGUUCUUC GCUGUAGUUC CGGUUUAUUG GUCUUUGUUU ucagugccug gacgugcagu | SEQ ID NO: 39 |
| #7015 | gggacgcuca cguacgcuca UGUCUCGGUU UAUUGGCGGU CGGACUUUUG CCCUGCGAUG ucagugccug gacgugcagu | SEQ ID NO: 40 |
| #7029 | gggacgcuca cguacgcuca CGAAAUCCAG GUUUGAUUGG CGUGGCACCC UUGCCAAGUG ucagugccug gacgugcagu | SEQ ID NO: 41 |
| #7030 | gggacgcuca cguacgcuca AUGAGCUCAC CUGGGUAAUU GGCGCCAAUU CAAGGGUCUG ucagugccug gacgugcagu | SEQ ID NO: 42 |

TABLE 5-continued

| Name | Sequence | No. |
|---|---|---|
| #7049 | gggacgcuca cguacgcuca CGCUCAGGUG AAUUGGUUAC GUUUUCUCUG ACAAUGUGGA ucagugccug gacgugcagu | SEQ ID NO: 43 |
| #7052 | gggacgcuca cguacgcuca AUUCUGUUCU GUCUCUCCGG GUUUACUGGC GCUAUGAAUG ucagugccug gacgugcagu | SEQ ID NO: 44 |
| #7054 | gggacgcuca cguacgcuca AAGUGUCUGC AAGUCUACCG GUUUACUGGC CACUCCGUUU ucagugccug gacgugcagu | SEQ ID NO: 45 |
| #7009 | gggacgcuca cguacgcuca UGAUUGAAUG GGCGAAUCGA CCUUACCGGU UUUCUGCAAC ucagugccug gacgugcagu | SEQ ID NO: 46 |
| #7062 | gggacgcuca cguacgcuca UCUCGCCGCA UUUCCAGGUU UUUUGGCGCU UAUGAAUGA- ucagugccug gacgugcagu | SEQ ID NO: 47 |
| #47sT | ---------g gguacgcuca ---------- -----GGUAU AUUGGCGCC- CCG-GGAAUG ucagugccug gacgug cagu | SEQ ID NO: 65 |
| #47sA1 | ---------g gguacgcuca ---------- -----GGUAU AUUGGCGCCU UCGUGGA-UG ucagugccug gacgu gcagu | SEQ ID NO: 66 |
| #47sA | ---------g gguacgcuca ---------- -----GGUAU AUUGGCGCCU UCGUGG--UG ucagugccug gacgug cagu | SEQ ID NO: 67 |
| #47sTA | ---------g gguacgcuca ---------- -----GGUAU AUUGGCGCCU UCG-GG--UG ucagugccug gacgugca gu | SEQ ID NO: 68 |

TABLE 6

| Name | Sequence | No. |
|---|---|---|
| #627 | gggacgcuca cguacgcuca UUUUACUUUU CCUACGACCG GGUGAACUGG CUCUUGGAUG ucagugccug gacgugcagu | SEQ ID NO: 19 |
| #629 | gggacgcuca cguacgcuca AAAUGCUGUU GCAGGUUAUU UGGCUCUCGG UCUGAGAAUG ucagugccug gacgugcagu | SEQ ID NO: 20 |
| #504 | gggacgcuca cguacgcuca UGUUCCGGGU CGACUGGCUG UUAGAGAUCU CUGAUGUAGG ucagugccug gacgugcagu | SEQ ID NO: 21 |
| #505 | gggacgcuca cguacgcuca GCUCCGGGUA UACUGGCGAC GACCGUUAUU GUGUCGCAUG ucagugccug gacgugcagu | SEQ ID NO: 22 |
| #402 | gggacgcuca cguacgcuca GGUGUACUGG CACUACUGAA AUUUCAUUUG AGUAGGUCUG ucagugccug gacgugcagu | SEQ ID NO: 23 |
| #403 | gggacgcuca cguacgcuca GGUGAACUGG UCCGCAUUUA GCUUUCUUAU UUGCGGGUAU ucagugccug gacgugcagu | SEQ ID NO: 24 |
| #404 | gggacgcuca cguacgcuca GGUGUAUUGG AUGCUUUAAG CAGGUCUCUG CUUCAGCAAU ucagugccug gacgugcagu | SEQ ID NO: 25 |
| #405 | gggacgcuca cguacgcuca AUUCUGUUCU GUCUCUCCGG GUUUACUGGC GCUAUGAAUG ucagugccug gacgugcagu | SEQ ID NO: 48 |
| #303 | gggacgcuca cguacgcuca ---GGUGGAC UGGUUUCUAA GUGCUUUGAC UGCUGGAGGA ucagugccug gacgugcagu | SEQ ID NO: 49 |
| #304 | gggacgcuca cguacgcuca ---------- ----GGUUAU UGGCUUUCCG AGCGAAGAUG ucagugccug gacgugcagu | SEQ ID NO: 50 |
| #305 | gggacgcuca cguacgcuca GGUGUAUUGG AUAACAGCUG CUUCUUGGAA CGUUGUCGUU ucagugccug gacgugcagu | SEQ ID NO: 51 |
| #306 | gggacgcuca cguacgcuca GGUUUAUUGG AUGUUUGUCU CCCGUUCGGG ACAUUCGUUU ucagugccug gacgugcagu | SEQ ID NO: 52 |
| #AT5-5 | gggacgcuca cguacgcuca GGUUGAUCCC GUUCUUCUUG ACUGGCGCCU UCAUGGAGUG ucagugccug gacgugcagu | SEQ ID NO: 53 |
| #14sTT | ---------g gguacgcuca ---------- ---GGUUUAU UGGUGCCGUG UAGUGGAAUG ucagugccug gacgugcagu | SEQ ID NO: 54 |

TABLE 6-continued

| Name | Sequence | No. |
|------|----------|-----|
| #47ss | ---------- ----ggguca ---------- -----GGUAU AUUGGCGCCU UCGUGGAAUG ucagugccug g--------- | SEQ ID NO: 55 |
| #47ssT | ---------- ----ggguca ---------- -----GGUAU AUUGGCGCC- UCG-GGAAUG ucagugccug g--------- | SEQ ID NO: 56 |

A specific example of the aptamer of the item (a) can also be, for example, the following nucleic acid (a3): (a3) a nucleic acid having a base sequence represented by SEQ ID NO: 147:

(SEQ ID NO: 147)
GGUN$_n$AYU$_m$GGHGCCUUCGUGGAAUGUC.

In the base sequence represented by SEQ ID NO: 147, "GGUN$_n$AYU$_m$GGH" is the above-mentioned binding motif sequence represented by SEQ ID NO: 17. In the base sequence represented by SEQ ID NO: 147, "GGHGCCU-UCGUGGAAUGUC" is a base sequence represented by SEQ ID NO: 18 (where H is C) described below. The base sequence represented by SEQ ID NO: 18 is, for example, a base sequence in a region of forming a stem-loop structure of an aptamer and is hereinafter also referred to as a stem loop motif sequence". In the base sequence represented by SEQ ID NO: 147, three bases from the 3'-end of the binding motif sequence overlaps with those from the 5'-end of the stem loop motif sequence.

The base sequence represented by SEQ ID NO: 147 can be, for example, the base sequence represented by SEQ ID NO: 148:

(SEQ ID NO: 148)
GGUAUAUUGGCGCCUUCGUGGAAUGUC.

A specific example of the aptamer of the item (a3) can be, for example, the following nucleic acid (a3-1):

(a3-1) a nucleic acid having a base sequence represented by any of SEQ ID NOs: 2, 12, 14, 15, and 55.

Each of the base sequences represented by SEQ ID NOs: 2, 12, 14, 15, and 55 has the above-mentioned base sequence represented by SEQ ID NO: 147, specifically, SEQ ID NO: 148. The aptamer of the item (a3-1) may be, for example, a nucleic acid composed of a base sequence represented by any of SEQ ID NOs: 2, 12, 14, 15, and 55 or a nucleic acid having the base sequence. The base sequences represented by SEQ ID NOs: 2, 12, 14, 15, and 55 are shown in Table 7 below. In Table 7, each underlined part indicates the binding motif sequence represented by SEQ ID NO: 17, and each region enclosed in a rectangle indicates the base sequence represented by SEQ ID NO: 18.

TABLE 7

| Name | Sequence | No. |
|------|----------|-----|
| shot47 | gggacgcuca cguacgcuca CGUCCGAUCG AUACUGGUAU AUUGGCGCCU UCGUGGAAUG ucagugccug gacgugcagu | SEQ ID NO: 2 |
| #47s | ---------g gguacgcuca ---------- -----GGUAU AUUGGCGCCU UCGUGGAAUG ucagugccug gacgugcagu | SEQ ID NO: 12 |
| #47sT | ---------g gguacgcuca ---------- -----GGUAU AUUGGCGCC- UCG-GGAAUG ucagugccug gacgugcagu | SEQ ID NO: 13 |
| #47sT | ---------g gguacgcuca ---------- -----GGUAU AUUGGCGCC- CCG-GGAAUG ucagugccug gacgug cagu | SEQ ID NO: 65 |
| #47sA1 | ---------g gguacgcuca ---------- -----GGUAU AUUGGCGCCU UCGUGGA-UG ucagugccug gacgu gcagu | SEQ ID NO: 66 |
| #47sA | ---------g gguacgcuca ---------- -----GGUAU AUUGGCGCCU UCGUGG--UG ucagugccug gacgug cagu | SEQ ID NO: 67 |
| #47sTA | ---------g gguacgcuca ---------- -----GGUAU AUUGGCGCC- UCG-GG--UG ucagugccug gacgugca gu | SEQ ID NO: 68 |
| shot47sss | ---------- ---------g ---------- -----GGUAU AUUGGCGCCU UCGUGGAAUG ucagugccug g | SEQ ID NO: 14 |
| #47M1 | ---------- -------ggg ---------- -UACUGGUAU AUUGGCGCCU UCGUGGAAUG ucagug | SEQ ID NO: 15 |
| #47sssT | ---------- ---------g ---------- -----GGUAU AUUGGCGCC- UCG-GGAAUG ucagugccug g | SEQ ID NO: 16 |
| #14sTT | ---------g gguacgcuca ---------- ---GGUUUAU UGGUGCCGUG UAGUGGAAUG ucagugccug gacgugcagu | SEQ ID NO: 54 |

TABLE 7-continued

| Name | Sequence | No. |
|------|----------|-----|
| #47ss | ---------- ----ggguca ---------- -----<u>GGUAU AUU</u>|GGCGCCU UCGUGGAAUG| u<u>c</u>agugccug g--------- | SEQ ID NO: 55 |
| #47ssT | ---------- ----ggguca ---------- -----<u>GGUAU AUU</u>|GGCGCC- UCG-GGAAUG| u<u>c</u>agugccug g--------- | SEQ ID NO: 56 |

A specific example of the aptamer of the item (a) can also be, for example, the following nucleic acid (a4). The aptamer of the item (a4) may be, for example, a nucleic acid composed of a base sequence represented by any of SEQ ID NOs: 158 to 2302 and 2303 to 2312 or a nucleic acid having the base sequence:

(a4) a nucleic acid having a base sequence represented by any of SEQ ID NOs: 158 to 2302 and 2303 to 2312.

A specific example of the aptamer of the item (a) can also be, for example, the following nucleic acid (a5). The aptamer of the item (a5) may be, for example, a nucleic acid composed of a base sequence represented by any of SEQ ID NOs: 2313 to 2347 or a nucleic acid having the base sequence.

(a5) a nucleic acid having a base sequence represented by any of SEQ ID NOs: 2313 to 2347

The aptamer of the item (b) is, as mentioned above, a nucleic acid having a base sequence obtained by substitution, deletion, addition, or insertion of one or more bases in a base sequence of the nucleic acid (a) and being capable of binding to the His peptide. The expression "one or more" is not particularly limited and is, for example, from 1 to 5, preferably from 1 to 4, more preferably from 1 to 3, yet more preferably from 1 or 2, and particularly preferably 1, in the base sequence represented by SEQ ID NO: 17. The aptamer of the item (b) may also be, for example, a nucleic acid having a base sequence obtained by substitution, deletion, addition, or insertion of one or more bases in any of the base sequences represented by the respective sequence numbers listed for the aptamer of the item (a) and being capable of binding to the His peptide. In this case, the expression "one or more" is not particularly limited and is, for example, from 1 to 10, preferably from 1 to 5, more preferably from 1 to 4, yet more preferably from 1 to 3, particularly preferably 1 or 2, and most preferably 1, in the base sequence. The aptamer of the nucleic acid (b) may also be, for example, a nucleic acid having a base sequence obtained by substitution, deletion, addition, or insertion of one or more bases in a full-length base sequence of the aptamer of the item (a) and being capable of binding to the His peptide. In this case, the expression "one or more" is not particularly limited and is, for example, from 1 to 10, preferably from 1 to 5, more preferably from 1 to 4, yet more preferably from 1 to 3, particularly preferably 1 or 2, and most preferably 1, in the full-length base sequence.

A base(s) used for the substitution, the addition, or the insertion is not particularly limited and examples thereof include A, C, G, U, and T and further include a modified base and an artificial base. Examples of the modified base include 2'-fluoropyrimidine and 2'-O-methylpyrimidine. A nucleoside, a nucleotide, a deoxynucleoside, or a deoxynucleotide may also be used for the substitution, the addition, or the insertion of the base(s), for example. Furthermore, a PNA (Peptide Nucleic Acid), a LNA (Locked Nucleic Acid), or the like may also be used, for example.

Examples of the aptamer of the item (b) include nucleic acids each having any of the base sequences shown in Tables 3 and 5. A specific example thereof can be, for example, a nucleic acid having a base sequence represented by SEQ ID NO: 115 (#736) or SEQ ID NO: 36 (#736) or a nucleic acid composed of the base sequence. The base sequence represented by SEQ ID NO: 36 has a base sequence represented by SEQ ID NO: 115. The specific example can also be, for example, a nucleic acid having base sequences represented by SEQ ID NO: 125 (#7009) and SEQ ID NO: 46 (#7009) or a nucleic acid composed of the base sequences. The base sequence represented by SEQ ID NO: 46 has a base sequence represented by SEQ ID NO: 125. In these base sequences in Tables 3 and 5, each double-underlined part corresponds to the binding motif sequence represented by SEQ ID NO: 17, and each base enclosed in a rectangle is a substituted base that is different in the base sequence represented by SEQ ID NO: 17. The specific example can also be, for example, a nucleic acid composed of base sequences represented by SEQ ID NO: 126 (#7062) and SEQ ID NO: 47 (#7062) or a nucleic acid having the base sequences. In these base sequences in Tables 3 and 5, each double-underlined part corresponds to the binding motif sequence represented by SEQ ID NO: 17, any of bases (UU) enclosed in a rectangle is a substituted base that is different from A in the binding motif sequence represented by SEQ ID NO: 17. The specific example can also be, for example, a nucleic acid composed of base sequences represented by SEQ ID NO: 143 (#AT5-5) and SEQ ID NO: 53 (#AT5-5) or a nucleic acid having the base sequences.

The aptamer of the present invention may also be, for example, a nucleic acid (e) or (f):

(e) a nucleic acid having a base sequence with 60% or more homology (identity) to the base sequence of the nucleic acid (a) and being capable of binding to the His peptide; and (f) a nucleic acid having a base sequence that hybridizes to the base sequence of the nucleic acid (a) under stringent conditions and being capable of biding to the His peptide.

In the nucleic acid (e), the homology is, for example, 70% or more, more preferably 80% or more, yet more preferably 90% or more, still yet more preferably 95% or more, and particularly preferably 99% or more. The homology can be determined by calculating under default conditions using BLAST or the like, for example. The aptamer of the item (e) may also be, for example, a nucleic acid having a base sequence with the homology to the base sequence represented by SEQ ID NO: 17 in the aptamer of the item (a) and being capable of binding to the His peptide. The aptamer of the item (e) may also be, for example, a nucleic acid having a base sequence with homology to any of the base sequences represented by the respective sequence numbers listed for the aptamer of the item (a) and being capable of binding to the His peptide. The aptamer of the item (e) may also be, for example, a nucleic acid having a base sequence with homology to a full-length base sequence of the aptamer of the item (a) and being capable of binding to the His peptide.

In the nucleic acid (f), "hybridization under stringent conditions" means hybridization under experimental conditions well known to those skilled in the art, for example. Specifically, the term "stringent conditions" refers to, for example, conditions under which a hybrid formed is identified after performing hybridization at 60° C. to 68° C. in the presence of 0.7 to 1 mol/L NaCl and then washing at 65° C. to 68° C. using a 0.1- to 2-fold SSC solution. Note here that 1×SSC is composed of 150 mmol/L NaCl and 15 mmol/L sodium citrate. The aptamer of the item (f) may be, for example, a nucleic acid having a base sequence that hybridizes to the base sequence represented by SEQ ID NO: 17 under stringent conditions and being capable of binding to the His peptide. The aptamer of the item (f) may also be, for example, a nucleic acid having a base sequence that hybridizes to any of the base sequences represented by the respective sequence numbers listed for the aptamer of the item (a) under stringent conditions and being capable of binding to the His peptide. The aptamer of the item (f) may also be, for example, a nucleic acid having a base sequence that hybridizes to a full-length base sequence of the aptamer of the item (a) under stringent conditions and being capable of binding to the His peptide.

The aptamer of the present invention may also be, for example, a nucleic acid having a partial sequence of any of the base sequences listed for the aptamer of the item (a) and being capable of binding to the His peptide. The partial sequence is, for example, a sequence composed of a plurality of consecutive bases, preferably from 5 to 40 consecutive bases, more preferably from 8 to 30 consecutive bases, and particularly preferably from 10 to 12 consecutive bases.

The aptamer of the item (c) is, as mentioned above, a nucleic acid having a base sequence represented by SEQ ID NO: 18. In the aptamer, the base sequence represented by SEQ ID NO: 18 is, for example, as mentioned above, a base sequence in a region of forming a stem-loop structure of an aptamer.

```
                                           (SEQ ID NO: 18)
        GGCGCCUUCGUGGAAUGUC
```

Examples of the aptamer of the item (c) include nucleic acids each having any of the base sequences represented by SEQ ID NOs: 2, 12, 14, 15, and 55. The aptamer of the item (c) may be, for example, a nucleic acid composed of a base sequence represented by any of SEQ ID NOs: 2, 12, 14, 15, and 55 or a nucleic acid having the base sequence. These base sequences are as shown in Table 7.

The aptamer of the item (d) is, as mentioned above, a nucleic acid having a base sequence obtained by substitution, deletion, addition, or insertion of one or more bases in a base sequence of the nucleic acid (c) and being capable of binding to the His peptide. The expression "one or more" is not particularly limited and is, for example, from 1 to 5, preferably from 1 to 4, more preferably from 1 to 3, yet more preferably 1 or 2, and particularly preferably 1, in the base sequence represented by SEQ ID NO: 18. The aptamer of the item (d) may also be, for example, the above-mentioned nucleic acid having a base sequence obtained by substitution, deletion, addition, or insertion of one or more bases in a base sequence represented by any of SEQ ID NO: 2, 12, 14, or 15 and being capable of binding to the His peptide. In this case, the expression "one or more" is not particularly limited and is, for example, from 1 to 10, preferably from 1 to 5, more preferably from 1 to 4, yet more preferably from 1 to 3, particularly preferably 1 or 2, and most preferably 1, in the base sequence. The aptamer of the item (d) may also be a nucleic acid having a base sequence obtained by substitution, deletion, addition, or insertion of one or more bases in a full-length base sequence of the aptamer of the item (c) and being capable of binding to the His peptide. In this case, the expression "one or more" is not particularly limited and is, for example, from 1 to 10, preferably from 1 to 5, more preferably from 1 to 4, yet more preferably from 1 to 3, particularly preferably 1 or 2, and most preferably 1, in the full-length base sequence. It is preferred that the aptamer of the item (d) has a stem-loop structure that is substantially the same as a stem-loop structure formed of a base sequence represented by SEQ ID NO: 18, for example.

A base(s) used for the substitution, the addition, or the insertion is not particularly limited and examples thereof include A, C, G, U, and T and further include a modified base and an artificial base. Examples of the modified base include 2'-fluoropyrimidine and 2'-O-methylpyrimidine. A nucleoside, a nucleotide, a deoxynucleoside, or a deoxynucleotide may also be used for the substitution, the addition, or the insertion of the base(s), for example. Furthermore, a PNA (Peptide Nucleic Acid), a LNA (Locked Nucleic Acid), or the like may also be used, for example.

Examples of the aptamer of the item (d) include nucleic acids each composed of any of the base sequences represented by SEQ ID NOs: 13, 65 to 68, 16, 54, and 56 or nucleic acids each having any of the base sequences. These base sequences are shown in Table 7. In each of the base sequences each represented by any of SEQ ID NOs: 13, 65 to 68, 16, 54, and 56, shown in Table 7, bases enclosed in a rectangle are at the same site compared with the stem loop motif sequence represented by SEQ ID NO: 18, and an outlined base(s) is at a site deleted or substituted with respect to the stem loop motif sequence. In Table 7, the deleted site is indicated by "–". It is preferred that Us at bases 7 and 11 and A at base 15 are maintained in the stem loop motif sequence represented by SEQ ID NO: 18 of the aptamer of the nucleic acid (a), for example.

The aptamer of the present invention may also be, for example, the following nucleic acid (g) or (h):

(g) a nucleic acid having a base sequence with 60% or more homology to the base sequence of the nucleic acid (c) and being capable of binding to the His peptide; and (h) a nucleic acid having a base sequence that hybridizes to the base sequence of the nucleic acid (c) under stringent conditions and being capable of binding to the His peptide.

In the nucleic acid (g), the homology is, for example, 70% or more, more preferably 80% or more, yet more preferably 90% or more, still yet more preferably 95% or more, and particularly preferably 99% or more. The aptamer of the item (g) may also be, for example, a nucleic acid having a base sequence with the homology to any of the base sequences represented by SEQ ID NOs: 2, 12, 14, 15, and 55 in the aptamer of the item (c) and being capable of binding to the His peptide. The aptamer of the item (g) may also be, for example, a nucleic acid having a base sequence with homology to any of the base sequences represented by the respective sequence numbers listed for the aptamer of the item (c) and being capable of binding to the His peptide. The aptamer of the item (g) may also be, for example, a nucleic acid having a base sequence with homology to a full-length base sequence of the aptamer of the item (c) and 20 being capable of binding to the His peptide. It is preferred that the aptamer of the item (g) has a stem-loop structure that is substantially the same as a stem-loop structure formed of a base sequence represented by SEQ ID NO: 18, for example.

In the nucleic acid (h), "hybridization under stringent conditions" means the same as mentioned above. The aptamer of the item (h) may be, for example, a nucleic acid having a base sequence that hybridizes to the base sequence represented by any of SEQ ID NOs: 2, 12, 14, 15, and 55 under stringent conditions and being capable of binding to the His peptide. The aptamer of the item (h) may also be, for example, a nucleic acid having a base sequence that hybridizes to any of the base sequences represented by the respective sequence numbers listed for the aptamer of the item (c) under stringent conditions and being capable of binding to the His peptide. The aptamer of the item (h) may also be, for example, a nucleic acid having a base sequence that hybridize to a full-length base sequence of the aptamer of the item (c) under stringent conditions and being capable of binding to the His peptide.

The aptamer of the present invention may also be, for example, a nucleic acid having a partial sequence of any of the base sequences listed for the aptamer of the item (c) and being capable of binding to the His peptide. The partial sequence is, for example, a sequence composed of a plurality of consecutive bases, preferably from 5 to 40 consecutive bases, more preferably from 8 to 30 consecutive bases, and particularly preferably from 10 to 12 consecutive bases.

Figure 3:
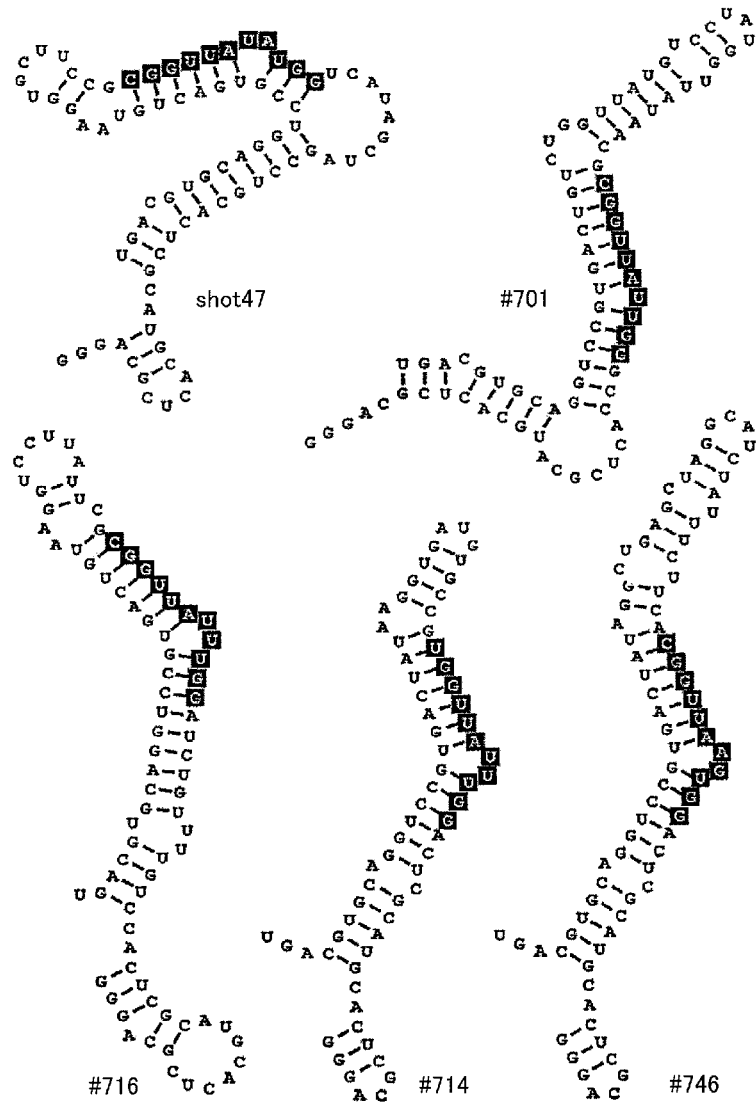
FIG. 3 shows schematic views of predictable secondary structures of various aptamers in the examples of the present invention.

As examples of the aptamer of the present invention, schematic views of predictable secondary structures of the respective aptamers, namely, shot47 (SEQ ID NO: 2); #701 (SEQ ID NO: 1); #716 (SEQ ID NO: 3); #714 (SEQ ID NO: 10); and #746 (SEQ ID NO: 9) are shown in FIG. 3. In FIG. 3, each outlined sequence is a consensus sequence among these aptamers, i.e., the binding motif sequence represented by SEQ ID NO: 17. The binding motif sequence is positioned in a part of bending a stem. The present invention is not limited to this.

Figure 4:
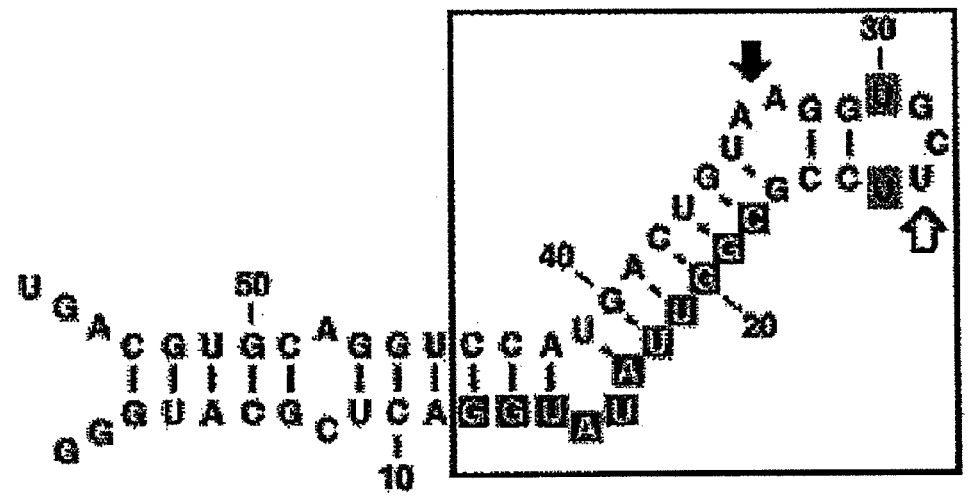
FIG. 4 shows schematic view of a secondary structure of #47s as an aptamer in the examples of the present invention.

As another example of the aptamer of the present invention, as schematic view of a predictable secondary structure of #47s (SEQ ID NO: 12) as an aptamer is shown in FIG. 4. In FIG. 4, an outlined sequence from bases 12 to 22 is the consensus sequence, i.e., the binding motif sequence represented by SEQ ID NO: 17. In FIG. 4, a sequence from bases 20 to 38 in the 3' region of the binding motif sequence is the stem loop motif sequence represented by SEQ ID NO: 18. In FIG. 4, the stem loop motif sequence in #47s as an aptamer forms a stem loop structure by intermolecular annealing. Moreover, in FIG. 4, the binding motif sequence is positioned in a part of bending a stem. The present invention is not limited to this.

The form of the aptamer of the present invention is not particularly limited and can be, as an example, for example, an aptamer including a Y region, an X region, and a Y' region, being linked from the 5'-end thereof. In the aptamer having this form, it is preferred that the X region includes a base sequence of any of the nucleic acids (a) to (h), for example. Specifically, it is preferred that the X region includes a base sequence represented by any of the sequence numbers listed in Tables 1, 3, and 4 or a base sequence represented by any of SEQ ID NOs: 158 to 2302, 2303 to 2312, and 2313 to 2347, for example.

In the aptamer having this form, it is preferred that at least one of the 5' side (upstream) of the X region, i.e., the Y region and the 3' side (downstream) of the X region, i.e., the Y' region has a primer sequence to which a primer can anneal and a polymerase recognition sequence that can be recognized by a polymerase, for example. For example, when the aptamer of the present invention has the primer sequence and the polymerase recognition sequence as described above, the aptamer can be amplified by, for example, a reverse transcription reaction and/or a nucleic acid amplification reaction using a primer, a polymerase, and the like. The polymerase recognition sequence can be decided as appropriate according to the type of the polymerase used in nucleic acid amplification, for example. The polymerase recognition sequence is, for example, preferably a DNA-dependent RNA polymerase recognition sequence (hereinafter, also referred to as an "RNA polymerase recognition sequence"), and a specific example thereof can be a T7 promoter that is a T7 RNA polymerase recognition sequence, for example. When the aptamer having this from is RNA, it is preferred that the Y region on the 5'-end side includes the RNA polymerase recognition sequence and the primer sequence (hereinafter, also referred to as a "5'-end side primer sequence") in this order, for example. It is more preferred that the 3'-end side of the Y region is linked to the X region. It is yet more preferred that the Y' region is linked to the 3'-end side of the X region and includes the primer sequence (hereinafter, also referred to as a "3'-end side primer sequence"). It is preferred that the 5'-end side primer sequence in the RNA is, for example, a sequence complementary to the 3'-end of a DNA antisense strand synthesized using the RNA as a template, i.e., a sequence that is the same as a sequence of a primer that can bind to the 3'-end of the antisense strand. In the aptamer having this form, the Y region and the X region may be directly adjacent to the X region and the Y' region, respectively or may be indirectly adjacent to the same via intervening sequences, respectively, for example. The Y region and the Y' region are not particularly limited and can be decided as appropriate by those skilled in the art according to the types of a primer to be used and a polymerase to be used, for example.

The respective base sequences of the Y region and the Y region are not particularly limited and can be decided as appropriate. An example of the Y region can be, for example, a region composed of a base sequence represented by SEQ ID NO: 149 or a region having the base sequence. An example of the Y' region can be, for example, a region composed of a base sequence represented by SEQ ID NO: 150 or a region having the base sequence. These examples are merely illustrative and do not limit the present invention.

```
                                    (SEQ ID NO: 149)
           GGGACGCUCA CGUACGCUCA (SEQ ID NO: 150)
           UCAGUGCCUG GACGUGCAGU
```

A specific example of the aptamer including a Y region, an X region, and a Y' region can be, for example, a nucleic acid composed of a base sequence represented by any of the sequence numbers listed in Tables 2, 5, and 6 or a nucleic acid having the base sequence. In each of Tables 2, 5, and 6, for example, each sequence on the 5'-end side, indicated by lower-case characters is a Y region composed of the base sequence represented by SEQ ID NO: 149, each sequence indicated by upper-case characters is an X region, and each sequence on the 3'-end side, indicated by lower-case characters is a Y' region composed of the base sequence represented by SEQ ID NO: 150. A specific example of the aptamer including a Y region, an X region, and a Y' region can also be, for example, a nucleic acid including a Y region composed of the base sequence represented by SEQ ID NO: 149, an X region being a base sequence represented by any of SEQ ID NOs: 158 to 2302, 2303 to 2312, and 2313 to 2347, and a Y region composed of the base sequence represented by SEQ ID NO: 150, in which the Y region is at the 5'-end of the X region, and the Y' region is at the 3'-end of the X region.

The number of bases in the X region is not particularly limited and is, for example, from 10 to 60 bases, preferably from 15 to 50 bases, and more preferably from 20 to 40 bases. The number of bases in each of the Y region and the Y' region is not particularly limited and is, for example, from 10 to 50 bases, preferably from 15 to 40 bases, and more preferably from 20 to 30 bases. The number of total bases in the aptamer of the present invention is not particularly limited and is, for example from 20 to 160 bases, preferably from 30 to 120 bases, and more preferably from 40 to 100 bases.

In the present invention, "being capable of binding to a His peptide" can also be referred to as having a binding ability to a His peptide or having a binding activity to the same (His peptide binding activity), for example. A bond between the aptamer and the His peptide can be determined by, for example, surface plasmon resonance molecular interaction analysis using, for example, Biacore X ((product name), GE Healthcare UK Ltd.).

The binding activity of the aptamer of the present invention to the His peptide is, for example, represented by a dissociation constant of the aptamer with the His peptide. The dissociation constant of the aptamer of the present invention is, for example, $1.0 \times 10^{-9}$ mol/L or less. Generally, the dissociation constant (Kd) of an antibody to the His peptide is in excess of $1.0 \times 10^{-9}$ mol/L. Therefore, the aptamer of the present invention has superior binding properties as compared with an antibody. The dissociation constant of the aptamer of the present invention is preferably $5.0 \times 10^{-10}$ mol/L or less and more preferably $1.0 \times 10^{-10}$ mol/L or less. The aptamer of the present invention is, for example, an aptamer with a dissociation constant with the His peptide of $1.0 \times 10^{-9}$ or less.

The aptamer of the present invention binds to an independent His peptide and is capable of binding to a fusion peptide including a His peptide via the His peptide, for example. Examples of the fusion peptide include a fusion peptide including a His peptide on the N-terminal side thereof, a fusion peptide including a His peptide on the C-terminal side thereof, and a fusion peptide including a His peptide inside thereof. The fusion peptide may include a His peptide and the other peptide, for example. The other peptide may be, for example, a protein. The fusion peptide encompasses a fusion protein, for example. The fusion peptide may include a fusion tag peptide including a His-tag as a His peptide and the other tag, for example. Examples of the other tag include amino acid sequences such as a T7 gene 10 leader sequence and an Xpress™ Epitope (hereinafter, also referred to as an "Xpress tag"). The fusion tag peptide may include, from the N-terminal thereof, a His-tag, a T7 gene 10 leader sequence, and an Xpress tag or may include, from the same, a His-tag and a T7 gene 10 leader sequence, for example.

The aptamer of the present invention may be, for example, a single-stranded nucleic acid or a double-stranded nucleic acid. Examples of the single-stranded nucleic acid include a single-stranded RNA and a single-stranded DNA. Examples of the double-stranded nucleic acid include a double-stranded RNA, a double-stranded DNA, and a double strand between RNA and DNA (RNA-DNA hybrid). When the aptamer of the present invention is the double-stranded nucleic acid, the one single-stranded nucleic acid is the above-mentioned nucleic acid, and the other one is a nucleic acid complementary to a part or a whole of the one single-stranded nucleic acid, for example. It is preferred that the double-stranded nucleic acid is caused to be single-stranded nucleic acids by denaturation or the like prior to the use thereof, for example. The single-stranded nucleic acid may be, for example, DNA or RNA as mentioned above and may include, in a sequence thereof, both of a deoxyribonucleic acid as a component of DNA and ribonucleotide as a component of RNA. The aptamer of the present Invention is, for example, preferably RNA and specifically preferably a single-stranded RNA.

In the aptamer of the present invention, bases are not limited to natural bases (non-artificial bases) such as adenine (A), cytosine (C), guanine (G), thymine (T), and uracil (U) and may be, for example, non-natural bases (artificial bases) having the same functions as the natural bases, such as modified bases and altered bases. Examples of the artificial bases having the same functions as the natural bases include an artificial base capable of binding to cytosine (C) substituted for guanine (G), an artificial base capable of binding to guanine (G) substituted for cytosine (C), an artificial base capable of binding to thymine (T) or uracil (U) substituted for adenine (A), an artificial base capable of binding to adenine (A) substituted for thymine (T), and an artificial base capable of binding to adenine (A) substituted for uracil (U). Examples of the modified bases include 2'-fluorouracil, 2'-aminouracil, 2'-O-methyluracil, and 2-thiouracil. The components of the aptamer of the present invention may include, for example, a PNA (Peptide Nucleic Acid) and a LNA (Locked Nucleic Acid) besides nucleotides such as a deoxyribonucleotide and a ribonucleotide.

The aptamer of the present invention can be used as an anti-His peptide antibody used for detection of a His peptide. A method for detecting the His peptide is not particularly limited, and examples thereof include various biochemical analysis methods including fluorescence analyses such as flow cytometry and ELISA. In these analysis methods, the aptamer of the present invention can be used as a substitute for the anti-His antibody, for example. In the aptamer of the present invention, a necessary reagent can be added to the nucleic acid as appropriate according to the analysis method, for example. In the aptamer of the present invention, the reagent to be added to the nucleic acid is not particularly limited, and examples thereof include a fluorescent material, a radioactive substance, and an enzyme.

The aptamer of the present invention can be used for detection, collection, purification, and the like of the fusion protein including a His peptide, for example. Specifically, for example, the aptamer of the present invention is immobilized on a solid phase, which is then brought into contact with a sample containing a fusion protein to which a His peptide has been added. Thus, the fusion protein in the sample binds, via the His peptide, to the aptamer of the present invention being immobilized on the solid phase. Thereafter, the solid phase is washed, so that components in the sample, not binding to the aptamer of the present invention are removed. Subsequently, the fusion protein is dissociated from the aptamer of the present invention being immobilized on the solid phase, to which the fusion protein has been bound. Therefore, it is possible to collect the fusion protein. A method for detecting the fusion protein is not particularly limited, and examples thereof include Northwestern blotting, a pull-down assay, ELISA, and flow cytometry, and in the method, the aptamer of the present invention may be used as a substitute for an anti-His antibody, for example.

The aptamer of the present invention can be produced by a conventionally known method based on information of base sequences, for example. The conventionally known method is not particularly limited, and examples thereof include a chemical synthesis method using an automatic synthesis device, a synthesis method by an enzyme reaction using various polymerases, and a synthesis by an in vitro transcription from a DNA template.

The aptamer of the present invention can be prepared by a conventionally known SELEX method, for example. The aptamer of the present invention can also be produced by the following method for identifying an aptamer (hereinafter, also referred to as an aptamer identification method) established by the inventors of the present invention, for example. The present invention is not at all limited by the following method.

<Aptamer Identification Method>

The aptamer identification method of the present invention includes, for example, the following steps (i) to (iv):
(i) mixing an RNA pool and the target;
(ii) separating RNA binding to the target from the RNA pool;
(iii) synthesizing cDNA using the separated RNA as a template and a DNA polymerase; and
(iv) synthesizing RNA using the cDNA as a template and an RNA polymerase.

According to the aptamer identification method of the present invention, RNA capable of binding to the target can be selected efficiently as an aptamer, for example. Therefore, it can be said that the aptamer identification method of the present invention is an aptamer selection method, for example. Hereinafter, the aptamer identification method of the present invention is referred to as an improved SELEX method (SELEX-T method).

It is desired for the conventional SELEX method to improve to a method capable of obtaining an aptamer with a lower dissociation constant to a target, for example. The SELEX-T method of the present invention is, as mentioned above, capable of obtaining an aptamer with a lower dissociation constant such as mentioned above by synthesizing RNA in the step (iv) using an RNA polymerase. It is considered because it became possible for a SELEX method to suppress a bias due to a PCR, i.e., a sequence deviation in an RNA pool, for example.

The RNA pool is, for example, a group of RNAs, including a random sequence. The random sequence is, for example, a sequence composed of 10 to 60 Ns (A, C, G, U, or T) and preferably 30 to 50 Ns.

The target is not particularly limited, and examples thereof include: ion atoms, low molecular weight compounds such as an amino acid and a peptide, virus, proteins, and cells. In the case where an aptamer capable of binding to a His peptide is identified as mentioned above, the target may be, for example, a His peptide or a substance to which a His peptide has been added. The latter target can be, for example, a fusion polypeptide obtained by adding a His peptide to other peptide.

In the step (iii), the cDNA can be synthesized by a reverse transcription, for example. A method for synthesizing cDNA by a reverse transcription can be, for example, a method using a primer and a polymerase such as a RNA-dependent DNA polymerase. The cDNA may be amplified by synthesizing cDNA using RNA as a template and then performing nucleic acid amplification using the synthesized cDNA as a template, for example. In this case, it is preferred that cDNA is synthesized by a reverse transcription (RT)-polymerase chain reaction (PCR) in the step (iii), for example. The cDNA obtained in the step (iii) can also be referred to as a DNA product, for example. In the present invention, it is preferred that the number of cycles of an amplification reaction is reduced in nucleic acid amplification using a synthesized cDNA as a template.

In the step (iv), the RNA can be synthesized by a reaction using a primer and a polymerase such as a DNA-dependent RNA polymerase, for example.

When the primer is used in the steps (iii) and (iv) as mentioned above, it is preferred that an RNA pool is, for example, the one obtained by functionally linking a predetermined primer sequence to each of the both ends of the random sequence. It is more preferred that the RNA pool is, for example, the one obtained by functionally linking a promoter sequence or a sequence complementary thereto to each of the both ends of the random sequence. With respect to the RNA pool, the primer sequence and the promoter sequence can be set according to the conventionally known SELEX method, for example.

An example of the SELEX-T method is described below.

First, an RNA pool and a target are prepared. The RNA pool can be chemically synthesized using an automated nucleic acid synthesizer or can be synthesized from a DNA template by an in vitro transcription, for example. Examples of the target include commercially available products, chemically synthesized substances, and substances isolated from biological samples. When the target is, for example, a peptide or a protein, it may be, for example, a substance isolated from a biological sample or a substance synthesized by an in vitro transcription and a translation, for example.

Then, the RNA pool and the target are mixed. In this case, for example, the target may be immobilized on a solid phase such as a carrier or a support. The immobilization may be performed before or after mixing the RNA pool and the target, for example. In the immobilization of the target, for example, a biotin-avidin bond, a $Ni^{2+}$-[His-tag] bond or a $Co^{2+}$-[His-tag] bond, a covalent bond by a chemical cross-linking agent, nucleic acid hybridization, and the like can be utilized. Examples of the solid phase include beads, chips, and resins. Conditions of mixing the RNA pool and the target are not particularly limited as long as the RNA and the target are specifically bound to each other, for example. As a specific example of the conditions, a temperature is, for example, from 4° C. to 40° C., preferably from 20° C. to 37° C., a pH is, for example, from 5.0 to 9.0, preferably from 6.5 to 7.5, a salt concentration is, for example, from 50 to 500 mmol/L, preferably from 100 to 150 mmol/L, and a treating time is, for example, from 10 minutes to 18 hours, preferably from 30 minutes to 2 hours.

After mixing the both, a formed complex between the RNA and the target is washed, eluted, purified, and the like. Thus, RNA binding to the target is separated. It is preferred that the washing is performed under mild conditions compared with washing in a general SELEX method, for example. By the washing, for example, a bias due to a PCR, i.e., a sequence deviation in an RNA pool can be suppressed, and it becomes possible to obtain an aptamer with a lower dissociation constant. Examples of a washing method include a method in which a supernatant is removed through causing a solid phase on which the complex has been immobilized to precipitate and a method in which a solid phase on which the complex has been immobilized is washed with a buffer for washing after removing the supernatant. The amount of the buffer for washing is not particularly limited and can be, for example, 100 times the volume of the solid phase. The number of times of the washing with the buffer for washing is not particularly limited and is, for example, one. As the buffer for washing, 20 mmol/L HEPES (pH 7. 2) containing 100 mmol/L sodium chloride, 0.1 mmol/L magnesium acetate, and 0.01% Tween 20 can be used, for example. The elution can be performed using imidazole with a predetermined concentration, for example. Specifically, as an elution solvent, 100 to 300 mmol/L imidazole can be used, for example. Examples of the purification means include a phenol chloroform extraction and ethanol precipitation.

Thereafter, a purified RNA is subjected to an RT-PCR, so that cDNA is synthesized. Specifically, for example, the RNA is added to a reaction solution containing dNTP Mix, a predetermined primer, a reverse transcriptase, a DNA polymerase, and the like, which is then subjected to an one-step RT-PCR. For the RT-PCR, a QIAGEN (registered trademark) OneStep RT-PCR Kit can be used, for example. Conditions of RT-PCR can be, for example, after treating at 50° C. for 30 minutes and at 95° C. for 10 minutes, one cycle of treatment at 94° C. for 1 minute, 56° C. for 1 minute, and 72° C. for 1 minute was repeated a total of 5 cycles, and further treatment at 72° C. for 5 minutes is conducted, for example. It is preferred that the number of cycles of RT-PCR in the SELEX-T method is smaller than that in a general SELEX method in order to suppress a bias due to a PCR, i.e., a sequence deviation in an RNA pool, for example. Specifically, compared with the number of cycles in a general SELEX method of 15 to 30, for example, the number of cycles in the SELEX-T method is, for example, from 1 to 10, preferably from 4 to 8, more preferably from 4 to 6, and yet more preferably from 4 to 5. In the present invention, it is preferred that the number of cycles of PCR is extremely reduced throughout all steps thereof, and amplifications of clones are performed mainly by an RNA transcription, for example. It is considered that by this, amplification efficiency of each of clones can be maintained virtually constant, and it becomes possible to conduct a screening reflecting a binding force to a target, for example.

Then, RNA, i.e., an RNA aptamer is synthesized using the synthesized cDNA as a template and an RNA polymerase. The RNA polymerase is not particularly limited and can be decided as appropriate, and a conventionally known polymerase can be used, for example. A specific example of the RNA polymerase can be, for example, a thermostable T7 RNA polymerase (ScriptMAX Thermo T7 Transcription Kit, produced by TOYOBO CO., LTD.). When the thermostable T7 RNA polymerase is used, it is preferred that a T7 promoter is linked to one end of the random sequence in production of an RNA pool, for example. By the linkage, RNA can be synthesized using the thermostable T7 RNA polymerase, for example. Conditions of synthesizing RNA by an RNA polymerase are not particularly limited and can be, for example, at 37° C. to 50° C. for 2 to 6 hours.

After the synthesis of RNA, an obtained RNA is separated and purified. A method for purifying RNA is not particularly limited, and examples thereof include a DNase I treatment, gel filtration, a phenol chloroform extraction, and ethanol precipitation. The aptamer capable of binding to a His peptide can be obtained in the above-described manner.

The obtained RNA may be iteratively further subjected to the step (i) of mixing with the target to the step (iv) of synthesizing RNA. The number of iterations, i.e., the number of rounds is not particularly limited and is, for example, from 5 to 10 and preferably from 6 to 8. A binding ability of the obtained RNA aptamer with the target can be determined by surface plasmon resonance molecular interaction analysis using BiacoreX (GE Healthcare UK Ltd.), for example.

Further, a base sequence of the obtained RNA aptamer is determined. The RNA aptamer can be produced by a conventionally known method on the basis of information of this base sequence, for example.

The SELEX-T method does not require any special device, and by the SELEX-T method, an RNA aptamer can be obtained at low cost, for example.

<Reagent and Kit>

The reagent of the present invention contains the aptamer of the present invention. The kit of the present invention includes the aptamer of the present invention.

According to the reagent or the kit of the present invention, the His peptide can be detected, and further, a fusion peptide to which the His peptide has been added can be detected or purified easily, for example. Therefore, it can be said that the reagent or the kit of the present invention is a reagent or a kit for detecting a His peptide, for example.

The kit of the present invention may further includes, for example, buffers such as a buffer for a reaction and a buffer for washing, a carrier such as a magnetic bead, and an instruction, if necessary.

<Aptamer for Producing Nucleic Acid>

The nucleic acid of the present invention is a nucleic acid having a base sequence complementary to the aptamer of the present invention. The nucleic acid of the present invention is a nucleic acid for producing the aptamer of the present invention. Therefore, it can be said that the nucleic acid is a nucleic acid for aptamer production of the present invention. When the aptamer of the present invention is RNA, it is preferred that the nucleic acid for aptamer production of the present invention is, for example, DNA having a base sequence complementary to the aptamer of the present invention.

The aptamer of the present invention can be easily produced with convenience by synthesizing a base sequence complementary to the nucleic acid for aptamer production of the present invention using it as a template, for example. Specifically, the aptamer of the present invention can be produced by, for example, nucleic acid amplification such as a PCR using the nucleic acid for aptamer production of the present invention.

The nucleic acid for aptamer production of the present invention may be, for example, a single strand or a double strand. In the present invention, term of sense strand or antisense strand is used. This does not limit the nucleic acid for aptamer production of the present invention to a double strand and is, for example, for clarifying whether a sequence is described as an antisense strand being a template of transcription or as a strand complementary thereto.

When the aptamer of the present invention is an RNA aptamer, DNA complementary to the RNA aptamer is used as the nucleic acid for aptamer production, being a template, for example. Hereinafter, DNA as a template of an RNA aptamer is also referred to as an antisense strand, and DNA having a sequence obtained by substituting thymine (T) for uracil (U) of the RNA aptamer is also referred to as a sense strand. It is preferred that the DNA as a template includes, as an antisense strand, any one of DNA having a sequence obtained by substituting thymine (T) for uracil (U) of a strand complementary to the RNA aptamer or DNA composed of the sequence and, as a sense strand, DNA having a sequence obtained by substituting thymine (T) for uracil (U) of the RNA aptamer or DNA composed of the sequence, for example. An RNA aptamer can be amplified by performing a nucleic acid amplification using any of these DNAs as a template and a DNA-dependent DNA polymerase and thereafter transcribing RNA using an obtained DNA amplification product as a template and a DNA-dependent RNA polymerase. Further, an RNA aptamer may be amplified by, for example, preparing cDNA by a reverse transcription using the RNA aptamer as a template and an RNA-dependent DNA polymerase, then performing a nucleic acid amplification of DNA using the cDNA as a template, and transcribing the RNA aptamer using a DNA-dependent RNA polymerase. When the aptamer of the present invention is, for example, a DNA aptamer, the DNA aptamer can be amplified by, for example, a polymerase chain reaction (PCR) or the like.

It is preferred that the nucleic acid for aptamer production of the present invention further includes a vector, and the base sequence complementary to the aptamer of the present invention has been inserted into the vector. In this case, the nucleic acid for aptamer production of the present invention can also be referred to as an aptamer expression vector of the present invention.

The vector is not particularly limited, and a conventionally known vector can be used. Examples thereof include a plasmid vector and a virus vector. Examples of the plasmid vector include: plasmid vectors derived from *Escherichia coli* such as pBR322, pBR325, pUC118, pUC119, a pCold series (trademark, Takara Bio Inc.), a pET series (Merck & Co., Inc., Invitrogen Corporation, and the like), a pRSET series (Invitrogen Corporation), a pBAD series (Invitrogen Corporation), a pcDNA series (Invitrogen Corporation), and a pEF series (Invitrogen Corporation); plasmid vectors derived from *Bacillus subtilis* such as pUB110 and pTP5; and plasmid vectors derived from yeast such as YEp13, YEp24, and YCp50. Examples of the virus vector include: λ phage vectors such as Charon4A, Charon21A, EMBL3, EMBL4, λgt10, λgt11, and λZAP; filamentous phage vectors such as M13KE and pCANTAB5E; aT7 phage vector such as a T7Select series; animal DNA virus vectors or RNA virus vectors such as retrovirus, vaccinia virus, and adenovirus; an insect virus vector such as baculovirus; and plant virus vectors.

The aptamer expression vector can be used for producing the aptamer of the present invention as follows, for example. Specifically, for example, the aptamer of the present invention can be obtained by incubating a host into which the aptamer expression vector has been introduced and thereafter collecting a nucleic acid from an obtained transformant.

The type of the host is not particularly limited and can be decided as appropriate according to the type of the vector, for example. Examples of the host include: bacteria belonging to genus *Escherichia* such as *Escherichia coli*, genus *Bacillus* such as *Bacillus subtilis*, genus *Pseudomonas* such as *Pseudomonas putida*, and genus *Rhizobium* such as *Rhizobium meliloti*; and yeast such as *Saccharomyces cerevisiae* and *Schizosaccharomyces pombe*. As the host, an animal cell such as a COS cell or CHO cell or an insect cell such as Sf9 or Sf21 can also be used. The conditions of the incubation can be decided as appropriate according to the type of the host, for example. A method for collecting an RNA aptamer from an incubated transformant is not particularly limited and can be performed by homogenizing the transformant, for example.

It is also possible that the aptamer expression vector is transcribed in vitro, and an obtained nucleic acid is collected as the aptamer of the present invention, for example.

<Antisense Nucleic Acid>

An antisense nucleic acid of the present invention is a nucleic acid having a base sequence complementary to the aptamer of the present invention. When the aptamer of the present invention is, for example, RNA, the antisense nucleic acid of the present invention is preferably DNA having a base sequence complementary to the aptamer of the present invention. According to the antisense nucleic acid of the present invention, binding of the aptamer of the present invention to a His peptide can be suppressed as required, for example. The antisense nucleic acid of the present invention can also be referred to as a nucleic acid for inhibiting binding of the aptamer of the present invention to a His peptide, for example.

EXAMPLES

The examples of the present invention are described below. Note here that the present invention is not limited by the following examples. Commercially available reagents were used in accordance with protocols thereof unless otherwise shown.

Example 1

An aptamer was produced, and a binding ability thereof was checked.

1. Material and Method (1) Reagent

As monoclonal antibodies, an anti-GFP antibody (JL-8) was purchased from Takara Bio Inc., an anti His-tag antibody was purchased from QIAGEN GmbH, and an anti-MIF antibody (MAB289) was purchased from R&D Systems Inc. An HRP-anti MIF antibody was purchased from R&D systems Inc.

(2) RNA Aptamer

RNA aptamers composed of the respective sequences represented by SEQ ID NOs: 1 to 12 and 26 to 47 shown in Tables 2 and 5 were synthesized. Hereinafter, each sequence indicated by lower-case characters in the same is referred to as a common sequence, and each sequence indicated by upper-case characters in Tables 2 and 5 is referred to as a random sequence.

Schematic views of predictable secondary structures of the respective RNA aptamers are shown in FIGS. 3 and 4. FIG. 3 shows views of shot47 (SEQ ID NO: 2), #701 (SEQ ID NO: 1), #714 (SEQ ID NO: 10), #716 (SEQ ID NO: 3), and #746 (SEQ ID NO: 9) as the RNA aptamers. FIG. 4 shows a view of #47s (SEQ ID NO: 12) as a downsized aptamer. These secondary structures were predicted using GENETYX-MAX software. In FIGS. 3 and 4, each consensus sequence represented by SEQ ID NO: 17 is indicated by outlined characters in a black rectangle. As shown in FIGS. 3 and 4, it can be assumed that each of these RNA aptamers has the consensus sequence in a part of bending a stem.

Further, on the basis of information of secondary structures of the aptamers, specifically information of shot47 and #714 shown in FIG. 3, the respective downsized RNA aptamers represented by SEQ ID NOs: 12 to 16, 54 to 56, and 65 to 68 shown in Tables 2, 5, and 6 were synthesized.

(3) Target Protein

Figure 6:
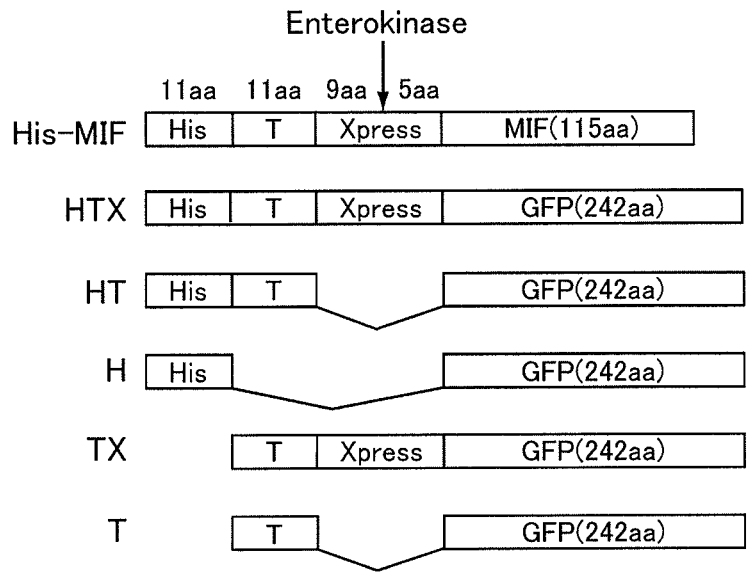
FIG. 6 shows schematic views of the respective structures of various fusion proteins in the examples of the present invention.

As target proteins, a fusion protein including a tag region and a macrophage migration inhibitory factor (MIF) and fusion proteins each including a tag region and GFP shown in FIG. 6 were prepared. FIG. 6 shows schematic views of the structures of the respective six fusion proteins, namely, His-MIF, HTX, HT, H, TX, and T. In FIG. 6, "His" is a His-tag (11 amino-acid residues) including a poly His in which six histidines have been linked, "T" is a peptide tag (11 amino-acid residues) including a T7 gene 10 leader that includes 10 amino-acid residues, "Xpress" is Xpress™ Epitope (hereinafter, also referred to as an "Xpress tag") including 14 amino-acid residues, and the entire region of them are called a tag region. Further, in FIG. 6, "MIF" is MIF including 115 amino-acid residues, and "GFP" is GFP including 242 amino-acid residues. In a sequence of "Xpress", a linkage between 9th amino acid and 10th amino acid starting from the N-terminal thereof is cleavable by enterokinase. Amino acid sequences in the respective N-terminal regions of the fusion proteins shown in Table 6 and base sequences corresponding to the respective amino acid sequences, specifically a base sequence and an amino acid sequence of the fusion protein including a tag region and MIF and base sequences and amino acid sequences of the respective fusion proteins each including a tag region and GFP are shown in Table 8 below. In Table 8, as a base sequence of MIF or GFP, only bases with a base length of 9 starting from the 5'-end thereof are shown, and as an amino acid sequence of MIF or GFP, only 3 amino-acid residues starting from the N-terminal thereof are shown.

TABLE 8

| Fusion Protein | His-tag | T7 gene 10 leader |
|---|---|---|
| His-MIF | ATGCGGGGTTCTCATCATCATCATCATCATGGT<br>M R G S H H H H H H G | ATGGCTAGCATGACTGGTGGACAGCAAATGGGT<br>M A S M T G G Q Q M G |
| HTX | ATGCGGGGTTCTCATCATCATCATCATCATGGT<br>M R G S H H H H H H G | ATGGCTAGCATGACTGGTGGACAGCAAATGGGT<br>M A S M T G G Q Q M G |
| HT | ATGCGGGGTTCTCATCATCATCATCATCATGGT<br>M R G S H H H H H H G | ATGGCTAGCATGACTGGTGGACAGCAAATGGGT<br>M A S M T G G Q Q M G |
| H | ATGCGGGGTTCTCATCATCATCATCATCATGGT<br>M R G S H H H H H H G | ---------------------------------- |
| TX | ---------------------------------- | ATGGCTAGCATGACTGGTGGACAGCAAATGGGT<br>M A S M T G G Q Q M G |
| T | ---------------------------------- | ATGGCTAGCATGACTGGTGGACAGCAAATGGGT<br>M A S M T G G Q Q M G |

←──────────────── Tag Region ────────────────→

| Fusion Protein | Xpress Epitope | | MIF/GFP | No. |
|---|---|---|---|---|
| His-MIF | CGGGATCTGTACGACGATGACGATAAGGATCGATGGGGATCC<br>R D L Y D D D D K D R W G S | | (MIF)<br>atgccgatg<br>M P M | 69<br>70 |
| HTX | CGGGATCTGTACGACGATGACGATAAGGATCGATGGGGATCC<br>R D L Y D D D D K D R W G S | | (GFP)<br>atcgccacc<br>I A T | 71<br>72 |
| HT | ----------------------------------GGATCC<br>G S | | (GFP)<br>atcgccacc<br>I A T | 73<br>74 |
| H | ----------------------------------GGATCC<br>G S | | (GFP)<br>atcgccacc<br>I A T | 75<br>76 |
| TX | CGGGATCTGTACGACGATGACGATAAGGATCGATGGGGATCC<br>R D L Y D D D D K D R W G S | | (GFP)<br>atcgccacc<br>I A T | 77<br>78 |
| T | ----------------------------------GGATCC<br>G S | | (GFP)<br>atcgccacc<br>I A T | 79<br>80 |

←──────────────── Tag Region ────────────────→

His-MIF that is a fusion polypeptide including a His-tag and MIF was purchased from ATGen Co., Ltd. (Gyeonggi-do, South Korea). MIF having no His-tag was produced by cleaving the His-tag by a treatment with enterokinase (Novagen, EMD Chemicals, Inc., USA).

The fusion proteins (HTX, HT, H, TX, and T) each including GFP were prepared by the following method. First, a DNA segment of each of the tag regions of the respective fusion proteins shown in Table 8 was amplified by PCR with a primer set using each of the respective pRSET expression vectors (Invitrogen Corporation, USA) including DNA coding a His-tag, DNA coding a T7 gene 10 leader, and DNA coding an Xpress tag as a template. Then, the obtained DNA segment and a GFP gene (Takara Bio Inc., Japan) were integrated into a pCold IV expression vector (Takara Bio Inc., Japan). Thereafter, this recombinant vector thus obtained was transformed by introducing it into *Escherichia coli* BL21 Star (DE3) (Invitrogen Corporation). Subsequently, the transformant of *Escherichia coli* was cultivated in a culture medium containing 1 mmol/L isopropyl β-D-1-thiogalactopyranoside at 15° C. for 18 hours according to a standard method for using a pCold IV expression vector so as to express a fusion protein. After the cultivation, bacterial cells were collected by centrifugation (5,000×g, 10 minutes), which were then suspended in 20 mmol/L HEPES (pH 7.2) containing 1% Triton (registered trademark)-X100. This suspension thus obtained was freeze-thawed two times. Thereafter, an equivalent amount of 20 mmol/L HEPES (pH 7.2) containing 300 mmol/L sodium chloride and 0.2 mmol/L magnesium acetate with the suspension was added thereto, which was then subjected to centrifugation (14,000×g, 10 minutes). Thus, a supernatant as the fusion protein solution was obtained. The concentration of the fusion protein in the fusion protein solution was estimated from a result of Western blot using a serially diluted samples and an anti-GFP antibody.

(4) Molecular Interaction Analysis

A molecular interaction between each of the RNA aptamers and each of fusion proteins, i.e., a binding ability of each of the RNA aptamers to each of the fusion proteins was analyzed using surface plasmon resonance. The analysis of the binding ability was performed using BiacoreX (GE Healthcare UK Ltd.) according to the instruction thereof. Specifically, first, polyadenine having 20 bases was added to the 3'-end of the RNA aptamer. Thus, polyadenine-added RNA aptamer was prepared. This was then heated at 95° C. for 5 minutes and rapidly cooled on ice. Biotinylated polythymine having 20 bases obtained by biotinylating the 5'-end of polythymine had been bound to a streptavidin chip (Sensor chip SA, GE Healthcare UK Ltd.). The polyadenine-added RNA aptamer was introduced into a flow cell on the streptavidin chip using a running buffer. At this stage, the polyadenine-added RNA aptamer was immobilized on the chip via the biotinylated polythymine by complementary binding between poly A of the polyadenine-added RNA aptamer and the biotinylated polythymine. The polyadenine-added RNA aptamer was caused to bind to the biotinylated polythymine until a resonance unit (RU) (resonance unit; $1 RU=1 pg/mm^2$) reaches 700 RU. Subsequently, HBS (Hepes Buffered Saline) containing the fusion protein with a predetermined concentration was introduced into the chip using a running buffer, and a signal (RU) was measured. The composition of the running buffer includes 10 mmol/L HEPES (4-(2-hydroxyethyl)-1-piperazine ethanesulfonic acid), 150 mmol/L sodium chloride, 0.1 mmol/L magnesium acetate, and 0.01% Tween (registered trademark) 20 (pH 7.2). As a control, an introduction of the fusion protein and a measurement of a signal were performed in the same manner as described above using a chip to which biotinylated polythymine had been bound, on which no polyadenine-added RNA aptamer had been immobilized.

(5) Improved ELISA Method Using RNA Aptamer

Various antibodies (an anti-GFP antibody, an anti-His-tag antibody, and an anti-MIF antibody) were adsorbed in a 96-well plate (Iwaki, AGC TECHNO GLASS CO., LTD., Japan), which was then blocked with 1% bovine serum albumin. Thereafter, 50 μL of a fusion protein (1 μg/mL), 20 mmol/L HEPES, 150 mmol/L sodium chloride, 0.1 mmol/L magnesium acetate, and 0.5% Triton (registered trademark)-X100 were added to the plate, which was then incubated at room temperature for 3 hours. Thus, the fusion protein was bound to the plate. After the incubation, the plate was washed with HBS-T three times. As a control, 50 μL of the HBS-T was added as a substitute for 50 μL of the fusion protein, and incubation and wash were performed in the same manner as described above.

Then, polyadenine (poly A) having 20 bases was added to the 3'-end of an RNA aptamer. Thus, polyadenine-added RNA aptamer was prepared. Subsequently, the polyadenine-added RNA aptamer was denatured, which was then mixed with biotinylated polythymine (740 nmol/L) having 20 bases obtained by biotinylating the 5'-end of polythymine, tRNA (100 μg/mL), and an RNase inhibitor (0.16 units/mL), so that the poly A of the polyadenine-added RNA aptamer and the polythymine of the biotinylated polythymine are complementary bound to each other. Thus, a biotin-labeled RNA aptamer was produced. This biotin-labeled RNA aptamer was added to the plate, which was then incubated at 4° C. for 30 minutes. Subsequently, the plate was washed, and 0.1 μg/mL HRP-streptavidin (Thermo Fisher Scientific Inc., USA) was added thereto. After washing the plate, 1—Step Ultra TMB substrate (Thermo Fisher Scientific Inc., USA) was added to the plate so as to cause the biotin-labeled RNA aptamer to develop color. Then, absorbance at 450 nm was measured.

(6) Pull-Down Assay

A biotin-labeled RNA aptamer was produced in the same manner as in the item (5). Equal parts of the biotin-labeled RNA aptamer (50 μL) and a solution containing a fusion protein were mixed, which was then incubated at 4° C. for 15 minutes. Thus, the biotin-labeled RNA aptamer and each of samples containing a fusion protein were bound to each other. As the samples containing a fusion protein, HBS-T (containing 200 μg/mL tRNA) to which His-MIF had been added so that the final concentration thereof became 10 μg/mL, a culture supernatant (containing a 5% fetal bovine serum) of a cell strain (RK-13 cell strain) derived from a rabbit kidney, to which His-MIF had been added so that the final concentration thereof became 10 μg/mL, an extract of *Escherichia coli*, in which His-GFP (HT) had been expressed were used. Thereafter, 5 μL of streptavidin-sepharose (GE Healthcare) was added to an obtained mixed solution, which was then incubated at 40° C. for 1 hour. Thus, the biotin-labeled RNA aptamer was bound to the sepharose. After the incubation, the sepharose was washed with HBS-T three times, and thereafter a sample buffer for SDS-polyacrylamide electrophoresis was added thereto, which was then subjected to a heat treatment at 95° C. for 5 minutes. Thus, the fusion protein binding to the sepharose via a bond between the streptavidin and the biotin was eluted. The eluted protein was subjected to 15% SDS-polyacrylamide electrophoresis, so that the protein was transcribed to a PVDF film (Immobilon-P, Millipore). The PVDF film after the transcription was blocked with 5% skim milk, and thereafter, a 1 μg/mL antibody was added thereto, which was then treated at room temperature for 3 hours so as to bind to the PVDF film, As the antibody, an anti-MIF antibody or an anti His-tag antibody was used. The PVDF film was further washed, and thereafter, a HRP-anti-mouse IgG antibody (GE Healthcare) was bound thereto. Then, the PVDF film was yet further washed, and thereafter the presence of the fusion protein was checked using an ECL chemiluminescence reagent (GE Healthcare).

(7) Northwestern Blotting

Each of serially diluted fusion proteins was subjected to nonreducing SDS-polyacrylamide electrophoresis. The fusion protein was then blotted to a PVDF film in the same manner as in the item (6), and thereafter, the PVDF film was blocked. Subsequently, a biotin-labeled RNA aptamer prepared in the same manner as in the item (6) was added to the PVDF film as a substitute for the antibody (an anti-MIF antibody or an anti-His-tag antibody), and further, HRP-streptavidin was added thereto. Thereafter, the presence of the fusion protein was checked in the same manner as in the item (6) using an ECL chemiluminescence reagent (GE Healthcare).

2. Result (i) Molecular Interaction Analysis (1-1) Bindings of Various RNA Aptamers to His-MIF A binding ability of each of RNA aptamers to His-MIF as a fusion protein was analyzed by the same molecular interaction analysis as described above except that the concentration of His-MIF in the HBS-T introduced into the chip was 600 nmol/L. As the RNA aptamers, SEQ ID NOs: 1 to 11 and 26 to 47 each having the common sequences with a base length of 20 at the 5'-side thereof and the 3'-side thereof were used. Results obtained using RNA aptamers, namely, #701 (SEQ ID NO: 1), shot47 (SEQ ID NO: 2), #716 (SEQ ID NO: 3), #727 (SEQ ID NO: 4), #704 (SEQ ID NO: 5), #713 (SEQ ID NO: 6), #708 (SEQ ID NO: 7), #718 (SEQ ID NO: 8), #746 (SEQ ID NO: 9), #714 (SEQ ID NO: 10), and #733 (SEQ ID NO: 11) among the above-described RNA aptamers were shown in FIG. 1. FIG. 1 shows sensorgrams of signals detected using Biacore. In FIG. 1, the vertical axis indicates the signal intensity (RU) measured by BIACORE X, and the horizontal axis indicates the analysis time (second). On the horizontal axis, the time from 0 to 45 seconds is time of introducing the fusion protein. FIG. 1 also shows, as a comparative example, a result obtained by using an RNA pool (hereinafter, referred to as "N40") in Round 0 prepared in Example 3 described below as a substitute for each of the RNA aptamers. The N40 was an RNA pool having the same common sequences each with a base length of 20 as in each of the above-described RNA aptamers at the 5'-side thereof and the 3'-side thereof and having a random sequence with a base length of 40 between the common sequences.

As shown in FIG. 1, all of the RNA aptamers exerted a binding ability to His-MIF. Among them, shot47 exerted an excellent binding ability. Although not shown in FIG. 1, the other RNA aptamers represented by SEQ ID NOs: 26 to 47 also exerted a binding ability to His-MIF.

(1-2) Binding Ability of Shot47

Figure 2:
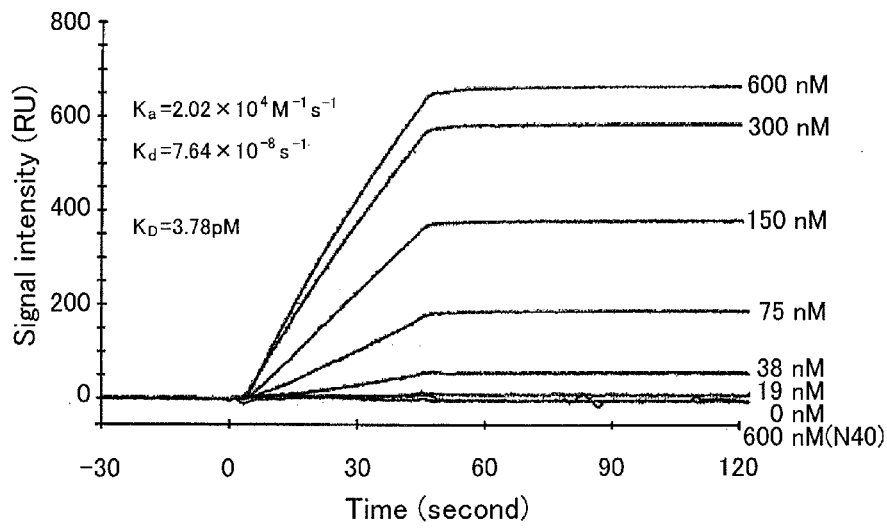
FIG. 2 shows sensorgrams of shot47 as an aptamer in the examples of the present invention.

The shot47 (SEQ ID NO: 2) as an RNA aptamer was subjected to molecular interaction analysis in the same manner as mentioned above except that the concentrations of His-MIF in the HBS-T introduced into the chip were 0, 19, 38, 75, 150, 300, and 600 nmol/L. Further, as a comparative example, molecular interaction analysis was performed in the same manner as mentioned above except that N40 was used as a substitute for the RNA aptamer. Then, an association rate constant (Ka), a dissociation rate constant (Kd), and a dissociation constant ($K_D$=Kd/Ka) of shot47 as the RNA aptamer were determined from these results. These results are shown in FIG. 2. FIG. 2 shows sensorgrams of signals detected using Biacore, and the vertical axis and the horizontal axis in FIG. 2 indicate the same as those in FIG. 1.

As shown in FIG. 2, it was found by the molecular interaction analysis, that shot47 has the association rate constant (Ka) of $2.02 \times 10^4$ mol/L$^{-1}$ s$^{-1}$, the dissociation rate constant (Kd) of $7.64 \times 10^{-8}$ s$^{-1}$, and the dissociation constant ($K_D$) of $3.78 \times 10^{-12}$ mol/L. A dissociation constant of an antibody to a commercially available His-tag is $1 \times 10^{-9}$ mol/L (QIAexpress Detection and Assay Handbook, QIAGEN GmbH, Hilden, Germany, October, 2002, p. 15.), and it was found that shot47 as the RNA aptamer has an excellent binding force.

(1-3) Bindings of Downsized RNA Aptamers to His-MIF

Figure 5:
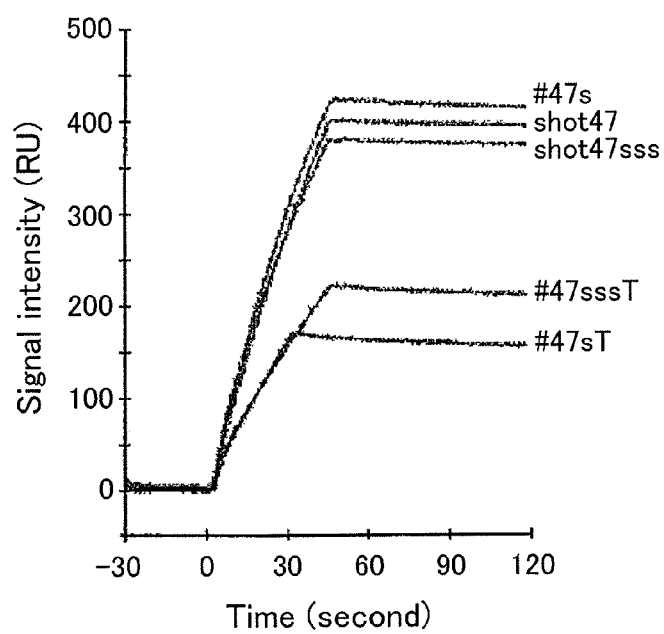
FIG. 5 shows other sensorgrams of various aptamers in the examples of the present invention.

A binding ability of each of downsized RNA aptamers to His-MIF as a fusion protein was analyzed by the molecular interaction analysis. As the downsized RNA aptamers, #47S (SEQ ID NO: 12), #47sT (SEQ ID NO: 13), shot47sss (SEQ ID NO:14), and #47sssT (SEQ ID NO: 16), obtained by downsizing shot47 (SEQ ID NO: 2) as the RNA aptamer, were used. These results are shown in FIG. 5. FIG. 5 shows sensorgrams of signals detected using Biacore, and the vertical axis and the horizontal axis indicate the same as those in FIG. 1. FIG. 5 also shows a result obtained by using shot47 as the RNA aptamer which was not downsized.

As shown in FIG. 5, all of the downsized RNA aptamers exerted a binding ability to His-MIF. Among them, #47s and shot47sss are downsized aptamers designed so as not to destroy a stem-loop structure of shot47 shown in FIG. 3 and exerted the same effect as shot47. Therefore, it is presumed that the stem-loop structure is an important structure for aptamers. Moreover, #47s and shot47sss exerted a superior binding ability as compared with the other downsized RNA aptamers. As shown in Table 7, any of U at base 7, U at base 11, and A at base 15 had been deleted or substituted in a sequence represented by SEQ ID NO: 18 enclosed in a rectangle of the base sequence of #47s of each of the other downsized RNA aptamers, namely, #47sT (SEQ ID NO: 13) and #47sssT (SEQ ID NO: 16). Therefore, it is presumed that it is important that U at base 7 and U at base H in a loop structure and A at base 15 in a parts of bending a stem structure shown in FIG. 4 are conserved in SEQ ID NO: 18.

(2) Improved ELISA Method (2-1) Binding Site of Shot47 in His-GFP

A site in each of the fusion proteins, to which shot47 as the RNA aptamer was bound was checked by the above-mentioned improved ELISA method. As the fusion proteins, five types of fusion proteins, namely, HTX, HT, H, TX, and T containing GFP shown in FIG. 6 were used among the fusion proteins. In the improved ELISA method, an anti-GFP antibody was immobilized on a plate. As a comparative example, a binding was checked in the same manner as mentioned above except that N40 was used as a substitute for shot47.

Figure 7:
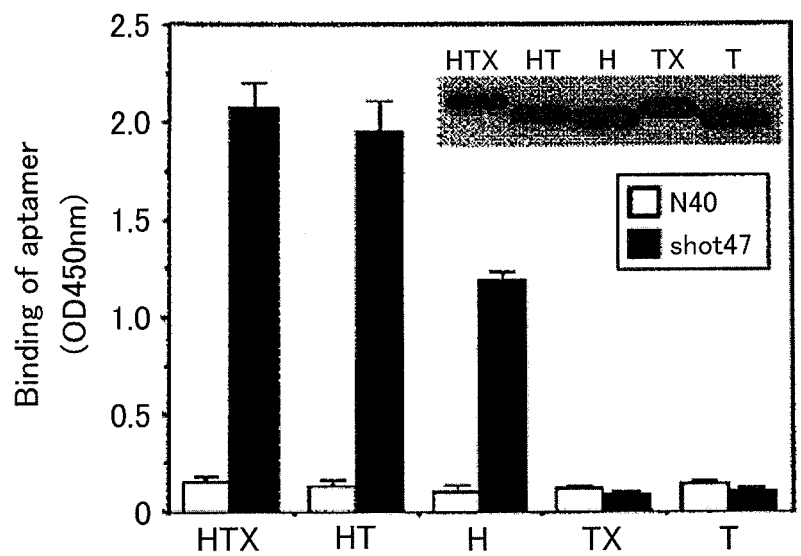
FIG. 7 is a graph showing bindings of shot47 as an aptamer to various fusion proteins in the examples of the present invention.

These results are shown in FIG. 7. FIG. 7 is a graph showing binding abilities of shot47 as the RNA aptamer to fusion proteins. In FIG. 7, the vertical axis indicates the absorbance at 450 nm showing each of the binding abilities (binding of the RNA aptamer) and shows an average value based on three time measurements±variation (SD). The horizontal axis indicates the type of fusion protein. Each white bar indicates the result of N40, and each black bar indicates the result of shot47. A photograph shown in the upper right of FIG. 7 shows the results of Western blot of the used fusion proteins, and it had been confirmed that various proteins are obtained by preparation using the above-mentioned transformant.

As shown in the graph of FIG. 7, shot47 exerted binding abilities to the fusion proteins (HTX, HT, and H) having a His-tag, whereas it did not bind to the fusion proteins (TX and T) having no His-tag. Since all of the fusion proteins have GFP, it was revealed that shot47 does not bind to GFP. Since Xpress (Xpress™ Epitope) was missing in HT, and T (T7 gene 10 leader) was missing in H among the fusion proteins, it was revealed that shot47 binds to the His-tag. Moreover, since the binding ability of shot47 shows HTX≈HT>H, it was found that the binding ability is higher as the fusion protein has a tag such as Xpress (Xpress™ Epitope) or T (T7 gene 10 leader) besides the His-tag.

(2-2) Binding of Shot47 to His-MIF

A binding ability of shot47 as the RNA aptamer to each of His-MIF and MIF having no His-tag as the fusion proteins were checked by the above-mentioned improved ELISA method. In the improved ELISA method, an anti-MIF antibody and an anti-His-tag antibody were immobilized on a plate. As a comparative example, a binding was checked in the same manner as mentioned above except that N40 was used as a substitute for shot47. As a control for checking a binding of His-MIF to the plate, HRP-labeled anti-MIF polyclonal antibody (anti-MIFpAb) was added as a substitute for the RNA aptamer, a substrate was added in the same manner as mentioned above, and an absorbance at 450 nm was measured.

Figure 8:
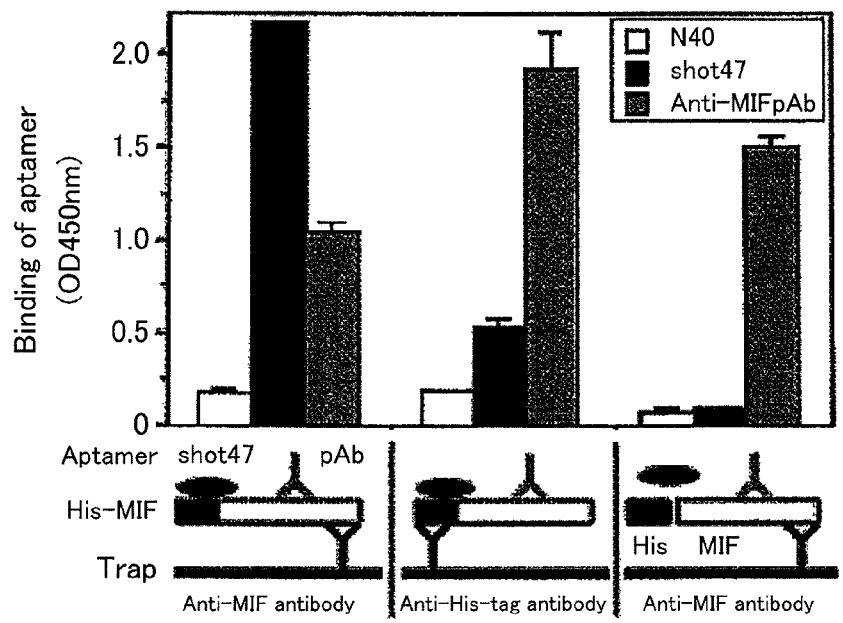
FIG. 8 is a graph showing bindings of shot47 as an aptamer to a fusion protein in the examples of the present invention.

These results are shown in FIG. 8. FIG. 8 is a graph showing a binding ability of shot47 as the RNA aptamer to His-MIF as the fusion protein. In FIG. 8, the vertical axis indicates the absorbance at 450 nm showing the binding ability of the RNA aptamer and shows an average value based on three time measurements±variation (SD). In FIG. 8, each white bar indicates the result of N40, each black bar indicates the result of shot47, and each gray bar indicates the result obtained using the HRP-labeled anti-MIF polyclonal antibody. Further, the result on the left side is a result of His-MIF in the plate on which an anti-MIF antibody had been immobilized, the result on the middle is a result of His-MIF in the plate on which an anti-His-tag antibody had been immobilized, and the result on the right side is a result of MIF in the plate on which an anti-MIF antibody had been immobilized. FIG. 8 also shows schematic views of the respective binding forms on the bottom side thereof.

As shown in FIG. 8, since MIF having no His-tag was detected by the anti-MIF 15 polyclonal antibody when the immobilized anti-MIF antibody and MIF having no His-tag were caused to bind to each other, it was confirmed that MIF was bound to the immobilized MIF antibody, and a bond of shot47 to MIF was not confirmed. In contrast, when the immobilized anti-MIF antibody and His-MIF as the fusion protein were caused to bind to each other, a bond of shot47 to His-MIF was confirmed. It was found from this result that, shot47 recognizes a His-tag, and thus, the fusion protein having the His-tag can be detected by shot47. When the immobilized anti-His-tag antibody and His-MIF as the fusion protein were caused to bind to each other, a bond of shot47 to His-MIF was weakened as compared with the case using the immobilized anti-MIF antibody. This was considered that since the immobilized anti-MIF antibody was bound to the His-tag that is a target of shot47, it became difficult for shot47 to bind to the His-MIF.

(2-3) Bindings of Shot47 and Shot47sss to HT

A binding ability of each of shot47 and shot47sss as the RNA aptamers to HT composed of His (His-tag), T (T7 gene 10 leader), and GFP, as the fusion protein was checked by the above-mentioned improved ELISA method. In the improved ELISA method, an anti-GFP antibody was immobilized on a plate. As a comparative example, a binding was checked in the same manner as mentioned above except that N40 was used as a substitute for shot47.

Figure 9:
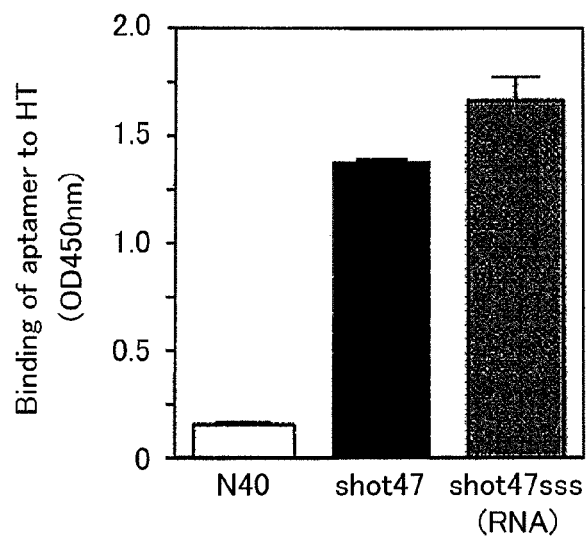
FIG. 9 is a graph showing bindings of various RNA aptamers to a fusion protein of the examples of the present invention.

These results are shown in FIG. 9. FIG. 9 is a graph showing binding abilities of shot47 and shot47sss as the RNA aptamers to HT as the fusion protein. In FIG. 9, the vertical axis indicates the absorbance at 450 nm showing each of the binding abilities (binding of the RNA aptamer) and shows an average value based on three time measurements±variation (SD). The horizontal axis indicates the type of RNA aptamer. Each white bar indicates the result of N40, each black bar indicates the result of shot47, and each gray bar indicates the result of shot47sss.

As shown in the graph of FIG. 9, both of shot47 and shot47sss exerted a binding ability to HT as the fusion protein having a His-tag.

(3) Pull-Down Assay (3-1) Binding of Shot47 to Fusion Protein

A binding of shot47 as the RNA aptamer to each of His-MIF and His-GFP as the fusion proteins was checked by the above-mentioned pull-down assay and the above-mentioned Northwestern blotting. As a comparative example, a binding was checked in the same manner as mentioned above except that N40 was used as a substitute for the shot47.

Figure 10:
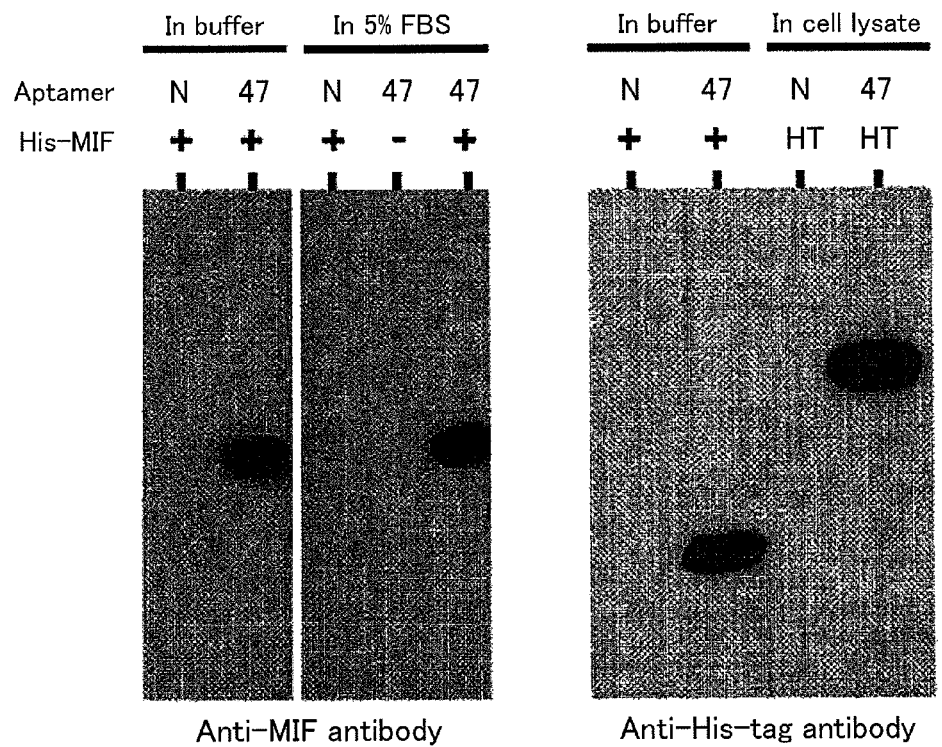
FIG. 10 shows blotting photographs of bindings of shot47 as an aptamer to various fusion proteins in the examples of the present invention.

The results obtained by the pull-down assay were shown in FIG. 10. FIG. 10 shows photographs showing the respective bindings of shot47 to His-MIF and HT as the fusion proteins, obtained by the pull-down assay. In FIG. 10, the result indicated by "In buffer" is a result obtained by using HBS-T containing His-MIF, the result indicated by "In 5% FBS" is a result obtained using a culture supernatant containing His-MIF, and the result indicated by "In cell lysate" is a result obtained using an extract of Escherichia coli, in which HT had been expressed. In the "Aptamer" section of FIG. 10, "N" indicates a result obtained using N40 as the RNA aptamer, and "47" indicates a result obtained using shot47 as the RNA aptamer. In the "His-MIF" section, "+" indicates that the fusion protein in the sample is His-MIF, "HT" indicates that the fusion protein in the sample is HT, and "−" indicates that the sample does not contain any fusion protein. As shown in FIG. 10, His-MIF and HT as the fusion proteins were pulled down by shot47 as the RNA aptamer. As shown in the result indicated by "In cell lysate" of FIG. 10, HT could be pulled down from a homogenate of Escherichia coli by shot47 as the RNA aptamer.

Figure 11:
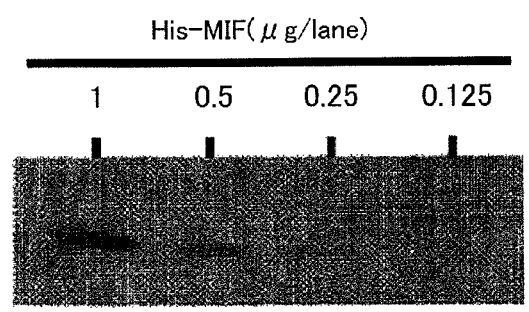
FIG. 11 shows a blotting photograph of a binding of shot47 as an aptamer to His-MIF in the examples of the present invention.

The result obtained by the Northwestern blotting are shown in FIG. 11. In FIG. 11, a numerical value in each of lanes indicates the concentration (µg/lane) of His-MIF per a lane.

As shown in FIG. 11, the fusion protein subjected to blotting could be detected by Northwestern blotting using Shot47 as the RNA aptamer.

Example 2

His_1, His_2, His_3, His_4, His_5, His_6, and His_10 as RNA aptamers were synthesized. Each of these aptamers had a sequence (Y region-X region-Y' region) continuously including a Y region, an X region, and a Y' region from the 5'-side thereof. In each of the aptamers, the Y region and the Y' region have a common part. These sequences are shown below. The X regions in the respective aptamers are random sequences different from each other. Sequences of the respective X regions of the aptamers, i.e., random sequences (His_1, His_2, His_3, His_4, His_5, His_6, and His_10) are shown below.

```
Y regions
                                     (SEQ ID NO: 149)
GGGACGCUCA CGUACGCUCA Y' region
                                     (SEQ ID NO: 150)
UCAGUGCCUG GACGUGCAGU Random sequence
His_1
                                     (SEQ ID NO: 2303)
GGUGAACUGGUCCGCAUUUAGCUUUCUUAUUUGCGGGUAU His_2
                                     (SEQ ID NO: 2304)
GGUGAAUUGGCCGCCGUUCUUUCCGUGGAAUGACGCGAUG His_3
                                     (SEQ ID NO: 2305)
GGUGUACUGGCACUACUGAAAUUUCAUUUGAGUAGGUCUG His_4
                                     (SEQ ID NO: 2306)
UAAGGGUGUACUGGCGAUUGUUGGGACGCACUUCAAUUUG His_5
                                     (SEQ ID NO: 2307)
GAACCCGUAUUGGUCACAGGUGGAUUGGUCUAUAUUGUUA His_6
                                     (SEQ ID NO: 2308)
GGUGUAUUGGAUUUGCUCCGAGGGUGUAGACCCCACAGAU His_10
                                     (SEQ ID NO: 2312)
UUAGCUUAGCUUCAUGCCCGGGUGUACUGGAGAUCUCUUA
```

Figure 12:
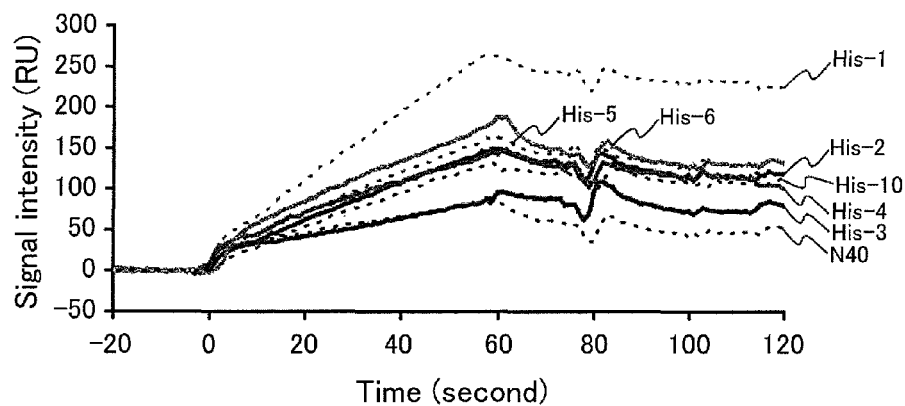
FIG. 12 shows yet other sensorgrams of various aptamers in the examples of the present invention.

A binding ability of each of these RNA aptamers to His-MIF was analyzed by surface plasmon resonance in the same manner as in "1. (4) Molecular interaction analysis" of Example 1. The concentration of His-MIF in the HBS-T introduced into a chip was 600 nmol/L. These results are shown in FIG. 12. FIG. 12 shows sensorgrams of signals detected using Biacore. In FIG. 12, the vertical axis indicates the signal intensity (RU) measured by BIACORE X, and the horizontal axis indicates the analysis time (second). On the horizontal axis, the time from 0 to 40 seconds is time of introducing the fusion protein. As a comparative example, FIG. 12 also shows a result obtained using N40 substituted for each of the RNA aptamers.

As shown in FIG. 12, all of the RNA aptamers exerted a binding ability to His-MIF. Among them, His_1 as the aptamer exerted an excellent binding ability. Although not shown in FIG. 12, it was confirmed that the RNA aptamers represented by Y region (SEQ ID NO: 149)-X region-Y' region (SEQ ID NO: 150), in each of which the X region is a random sequence represented by any of SEQ ID NOs: 2309 to 2312 and 2313 to 2347, also exerted a binding ability to His-MIF.

Example 3

It was presumed that, in the conventional SELEX method, a bias caused at the time of amplification by a PCR is a cause of reducing efficiency of obtaining an intended aptamer. That is, it was considered that when the number of cycles of PCR are big, an increase in sequence that is easily amplified by a PCR are progressed more rapidly as compared with concentrating RNA that binds to a target. Therefore, an aptamer to His-MIF was produced by the SELEX-T method in which amplification of RNA molecules performed in each round is performed not by a PCR but mainly by using a T7 RNA polymerase.

Material and Method (1) RNA Library

A library of single-stranded DNA represented by SEQ ID NO: 151, including, from the 5'-side thereof, a fixed sequence with a base length of 20, a random sequence with a base length of 40, a fixed sequence with a base length of 20, and a sequence complementary to a T7 promoter in this order was synthesized.

```
DNA library
                                          (SEQ ID NO: 151)
ACTGCACGTCCAGGCACTGAN₄₀TGAGCGTACGTGAGCGTCCCTATAGTGA
GTCGTATTA
```

The single-stranded DNA (50 pmol, $3 \times 10^{13}$ molecules) and a T7 promoter sequence (250 pmol) represented by SEQ ID NO: 152 were mixed with each other, which was then heated at 95° C. for 5 minutes and rapidly cooled. Then, a double-stranded DNA obtained by hybridization of the T7 promoter sequence to the sequence complementary to a T7 promoter in the single-stranded DNA was used as a template for RNA synthesis.

```
T7 promoter sequence
                                          (SEQ ID NO: 152)
TAATACGACTCACTATAGGG
```

RNA was transcribed from the template using a thermostable T7 RNA polymerase, and then the template was degraded using DNase I. Thereafter, the RNA was purified by a purification treatment. Thus, a purified RNA was obtained. As the purification treatment, gel filtration, a phenol chloroform extraction, and ethanol precipitation were performed. For the gel filtration, Micro Bio-spin Columns ((product name), Bio-Rad Laboratories, Inc., Hercules, Calif.) was used.

The purified RNA was denatured, and then HB-T, an RNase inhibitor (Toyobo Co., Ltd.) with a final concentration of 0.4 units/mL, and tRNA with a final concentration of 0.5 mg/mL were added thereto so that a total amount became 50 µL. This was used as an RNA pool. The composition of the HB-T includes 20 mmol/L HEPES, 100 mmol/L sodium chloride, 0.1 mmol/L magnesium acetate, and 0.01% Tween 20 (pH 7.2).

The RNA pool was subjected to a pretreatment prior to being subjected to the following SELEX-T method. First, the RNA pool was mixed with 20 µL of resin (TALON Metal Affinity Resin (product name), Takara Bio Inc., hereinafter the same) at room temperature for 30 minutes. This mixture thus obtained was filtered with a filter (Ultrafree-MC (product name), 5 µm, Millipore), so that the resin and RNA binding thereto were removed. The RNA pool obtained after this pretreatment as an RNA pool in Round 0 was subjected to the following SELEX-T method.

(2) SELEX-T Method

His-MIF and the RNA pool were mixed at room temperature for 15 minutes. Thus, they were bound to each other. The His-MIF is a fusion polypeptide of His-tag and MIF and was purchased from ATGen Co., Ltd. (Gyeonggi-do, South Korea). Then, 2.5 µL of resin (TALON Metal Affinity Resin (product name)) was added to the mixture thus obtained. Thus, a complex of the fusion protein and RNA was immobilized on the resin. Thereafter, the resin was washed with HB-T and was then eluted using 150 mmol/L imidazole. The number of times of washing with HB-T is shown in Table 9 below. The eluate thus obtained was subjected to a phenol chloroform extraction and ethanol precipitation by adding a coprecipitating agent (ethachinmate (product name), Wako Pure Chemical Industries, Ltd.). Thus, the RNA was purified. The purified RNA was subjected to an RT-PCR. Thus, a DNA template including a T7 promoter was produced. In the RT-PCR, 20 µL of a reaction solution of QIAGEN (registered trademark) OneStep RT-PCR Kit (QIAGEN) was used. Sequences of a forward primer for SELEX and a reverse primer for SELEX, contained in the reaction solution, are shown below. The concentration of each of the primers in the reaction solution was 10 µmol/L. Conditions of RT-PCR was after treating at 50° C. for 30 minutes and at 95° C. for 15 minutes, one cycle of treatment at 94° C. for 1 minute, 53° C. for 1 minute, and 72° C. for 1 minute was repeated for the predetermined number of cycles. The number of cycles in each round is shown in Table 9 below.

```
Reverse primer for SELEX
                                          (SEQ ID NO: 153)
TAATACGACTCACTATAGGGACGCTCACGTACGCTCA Reverse primer for SELEX
                                          (SEQ ID NO: 154)
ACTGCACGTCCAGGCACTGA
```

RNA was synthesized using the obtained PCR product as a template and a thermostable T7 RNA polymerase and a primer for T promoter, then the template was degraded by DNase I, and thereafter, the RNA was subjected to a purification treatment. Thus, purified RNA was obtained. A sequence of the primer for T7 promoter is shown below. As the purification treatment, gel filtration, a phenol chloroform extraction, and ethanol precipitation were performed. In the gel filtration, Micro Bio-spin 30 Columns ((product name), Bio-Rad Laboratories, Inc., Hercules, Calif.) was used. The purified RNA thus obtained was used as an RNA pool in a next round. The above-described step was repeated a total of 7 rounds. The conditions of each round are shown in Table 9 below.

Primer for T7 Promoter

```
        Primer for T7 promoter
                         (SEQ ID NO: 155)
        TAATACGACTCACTATA
```

(3) Determination of Base Sequence

An RNA pool (0.1 μg) in 6th Round and an RNA pool (0.1 μg) in 7th Round, obtained by the SELEX-T method were subjected to an RT-PCR, so that cDNAs each including a restriction enzyme site were produced. In the RT-PCR, QIAGEN (registered trademark) OneStep RT-PCR Kit (QIAGEN) was used. As primers, a forward primer for sequence and a reverse primer for sequence shown below were used. The concentration of the primers in the reaction solution for the RT-PCR was 10 μmol/L.

```
Forward primer for sequence
                             (SEQ ID NO: 156)
TCGACCTCGAGAAAAAAAAAAGGGACGCTCACGTACGCTCA Reverse primer for sequence
                             (SEQ ID NO: 157)
GAGTCGCGGCCGCTTTTTTTTTTACTGCACGTCCAGGCACTGA
```

The PCR product thus obtained was purified using MiniElute PCR Purification kit (QIAGEN GmbH) and was thereafter digested with restriction enzymes of Xho I and Not I, which was then integrated into a plasmid vector for determining a base sequence. The plasmid was introduced into *Escherichia coli* (DH5α competent cell, Toyobo Co. Ltd.). As a result, 113 clones were obtained from the cDNA derived from the RNA in 6th Round, and 105 clones were obtained from the cDNA derived from the RNA in 7th Round. The clones thus obtained were amplified using Templiphi DNA amplification kit (GE Healthcare), and thereafter base sequences thereof were determined. With respect to each of the RNA pools in 2nd to 5th Rounds obtained by the SELEX-T method, cDNA was produced using the PCR primers for sequence, and thereafter a base sequence thereof was determined by a Roche Genome Sequencer FLX system.

(4) Molecular Interaction Analysis

A binding ability of each of the RNA pools in the respective rounds to His-MIF was analyzed by surface plasmon resonance in the same manner as in "1. (4) Molecular interaction analysis" of Example 1. The concentration of His-MIF in the HBS-T introduced into the chip was 600 nmol/L. RNA aptamers, each sequence of which was determined among 105 clones obtained from the RNA pool in 7th Round were analyzed. N40 (control RNA) also was analyzed in the same manner as mentioned above.

2. Result

With respect to each of the rounds, the amount of the RNA pool (initial RNA), the amount of His-MIF mixed with the RNA pool, the number of times of washing the complex, the number of cycles of PCR, the amount of RNA (amplified RNA) obtained by synthesis using a T7 RNA polymerase, the number of bonds of the RNA pool to His-MIF, and a proportion of RNA having a conserved sequence represented by SEQ ID NO: 17 that is common in aptamers binding to His-MIF are shown in Table 9 below.

TABLE 9

| Round | Initial RNA pmol (μg) | His-MIF pmol (μg) | The number of times of washing | The number of cycles of PCR | Amplified RNA μg | The number of bonds*[1] His-MIF/RNA | Conserved sequence*[2] (SEQ ID NO: 17) % |
|---|---|---|---|---|---|---|---|
| 1 | 2500 (65.0) | 300 (5.0) | 1 | 8 | 44.1 | 0.05 | Nonmeasured |
| 2 | 700 (18.0) | 270 (4.5) | 2 | 6 | 32.4 | 0.09 | 0.84 |
| 3 | 350 (9.0) | 140 (2.3) | 3 | 4 | 8.1 | 0.35 | 50.3 |
| 4 | 175 (4.5) | 140 (2.3) | 3 | 5 | 12.3 | 0.68 | 68.8 |
| 5 | 175 (4.5) | 140 (2.3) | 3 | 5 | 17.0 | 1.01 | 82.5 |
| 6 | 175 (4.5) | 140 (2.3) | 3 | 5 | 47.0 | 1.23 | 97.0 |
| 7 | 175 (4.5) | 70 (1.2) | 4 | 4 | 43.3 | 1.64 | 96.2 |

*[1]An evaluation was performed based on a calculation result obtained by calculating a molecular weight on the sensor chip from a signal of surface plasmon resonance, according to a reference (Rusconi C. P. et al., "Nature", 2002, Vol. 419, pp. 90-94) (1 pg/mm$^2$ per a resonance unit). The number of bonds of control RNA (N40): 0.10

*[2]An RNA pool in Round 0 theoretically contains 0.14% of clones each having the conserved sequence.

According to the SELEX-T method, an increase in the number of bonds and an increase in proportion of clones having the conserved sequence were confirmed from a relatively early round (4th Round).

Further, as shown in Table 9, a binding ability of the RNA pool was increased by performing RT-PCR to 7th Round. The RNA aptamers obtained in 7th Round, whose sequences were determined, are shown in Table 10 below. All of the RNA aptamers obtained in 7th Round and shown in Table 10 below include a conserved sequence represented by SEQ ID NO: 17 or a sequence that is nearly identical thereto.

TABLE 10

| Name | Frequency*[1] | SEQ ID NO: |
|---|---|---|
| #701 | 31 | 1 |
| shot47 | 11 | 2 |

TABLE 10-continued

| Name | Frequency*[1] | SEQ ID NO: |
|---|---|---|
| #716 | 11 | 3 |
| #727 | 8 | 4 |
| #704 | 6 | 5 |
| #713 | 3 | 6 |
| #708 | 2 | 7 |
| #718 | 2 | 8 |
| #746 | 2 | 9 |
| #730 | 2 | 26 |
| #743 | 2 | 27 |
| #7007 | 2 | 28 |
| #7008 | 2 | 29 |

TABLE 10-continued

| Name | Frequency*[1] | SEQ ID NO: |
|---|---|---|
| #7034 | 2 | 30 |
| #714 | 1 | 10 |
| #733 | 1 | 11 |
| #707 | 1 | 31 |
| #715 | 1 | 32 |
| #719 | 1 | 33 |
| #723 | 1 | 34 |
| #725 | 1 | 35 |
| #736 | 1 | 36 |
| #745 | 1 | 37 |
| #748 | 1 | 38 |
| #7004 | 1 | 39 |
| #7015 | 1 | 40 |
| #7029 | 1 | 41 |
| #7030 | 1 | 42 |
| #7049 | 1 | 43 |
| #7052 | 1 | 44 |
| #7054 | 1 | 45 |
| #7009 | 1 | 46 |
| #7062 | 1 | 47 |

*[1]Frequency (the number of clones) per 105 clones

Figure 13:
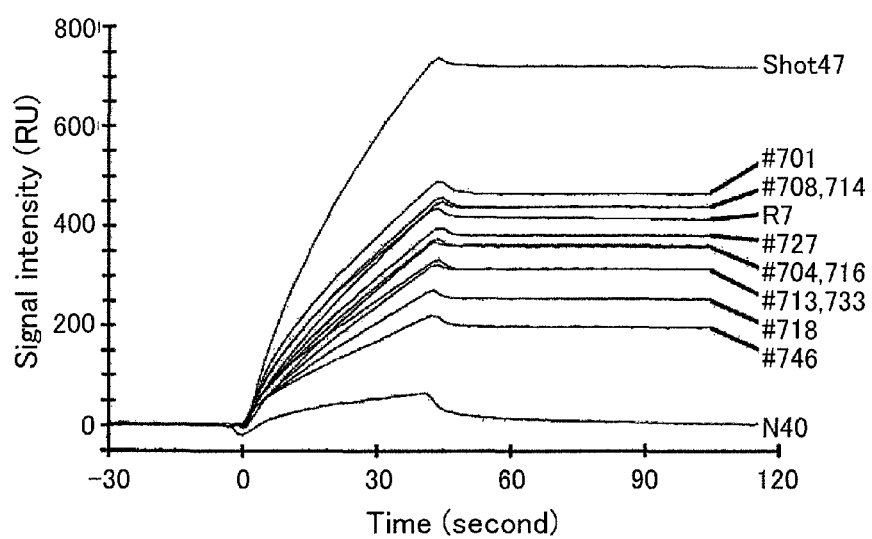
FIG. 13 shows yet other sensorgrams of various aptamers in the examples of the present invention.

The results obtained by subjecting the RNA pool in 7th Round and #701 (SEQ ID NO: 1), shot47 (SEQ ID NO: 2), #716 (SEQ ID NO: 3), #727 (SEQ ID NO: 4), #704 (SEQ ID NO: 5), #713 (SEQ ID NO: 6), #708 (SEQ ID NO: 7), #718 (SEQ ID NO: 8), #746 (SEQ ID NO: 9), #714 (SEQ ID NO: 10), and #733 (SEQ ID NO: 11) among the RNA aptamers shown in Table 10 to molecular interaction analysis are shown in Table 13. FIG. 13 shows sensorgrams of signals detected using Biacore. In FIG. 13, the vertical axis indicates the signal intensity (RU) measured by BIACORE X, and the horizontal axis indicates the analysis time (second). On the horizontal axis, the time from 0 to 45 seconds is time of introducing the fusion protein. FIG. 13 also shows a result obtained by using N40 substituted for each of the RNA aptamers. As shown in FIG. 13, a binding ability of the RNA pool in 7th Round was significantly improved. Further, it was shown that all of the RNA aptamers contained in the RNA pool in 7th Round have the binding ability. From this result, it is considered that the SELEX-T method exhibits high practical utility.

The proportions (%) of typical clones in each of the rounds are shown in Table 11 below.

TABLE 11

| Name | The number of bonds (His-MIF/RNA) | R7 (105) | R6 (113) | R5 (6016) | R4 (8431) | R3 (3077) | R2 (8211) |
|---|---|---|---|---|---|---|---|
| shot47 | 1.88 | 10.5 | 0.9 | 0.25 | — | — | — |
| #701 | 1.32 | *29.5 | *20.4 | *4.69 | 0.42 | 0.16 | — |
| #708 | 1.16 | 1.9 | 0.9 | 0.38 | 0.09 | — | — |
| #727 | 1.05 | 7.6 | 5.3 | 3.32 | 0.52 | 0.19 | — |
| #714 | 1.01 | 1.0 | — | — | — | — | — |
| #716 | 0.99 | 10.5 | 6.2 | 4.02 | 1.57 | 0.10 | — |
| #704 | 0.96 | 5.7 | 1.8 | 0.75 | 0.18 | 0.03 | — |
| #713 | 0.88 | 2.9 | | 0.37 | 0.11 | — | — |
| #733 | 0.86 | 1.0 | 2.7 | 0.35 | 0.04 | — | — |
| #718 | 0.75 | 1.9 | 2.7 | 0.62 | 0.14 | — | — |
| #746 | 0.50 | 1.9 | 4.4 | 2.43 | *4.47 | *1.40 | 0.01 |

The number of total clones obtained in each round, each sequence of which was determined was shown in parentheses below the round number.
"—" indicates that a clone was "undetected".
*indicates dominant clones in each round.

It is considered that an RNA pool in round 0 at starting time theoretically includes about 0.14% of clones each having the conserved sequence. In 3rd Round, the proportion of clones each having the conserved sequence was increased up to 50.3%, and an increase in binding ability was also found as shown in Table 9. As shown in Table 11, in 3rd Round, there was no specifically predominant clone. In contrast, in 6th Round, the amount of synthesized amplified RNA was increased as shown in Table 9, and the proportion of clones in #701 as a specific sequence was in excess of about 20% as shown in Table 11. Moreover, in 7th Round, #701, shot47, and #716 as specific clones were dominant, and among them, shot47 accounting for 20% and being secondly dominant had the strongest bond to His-MIF.

INDUSTRIAL APPLICABILITY

The aptamer of the present invention has a superior binding force to the histidine peptide as compared with a general anti-His peptide antibody that binds to a His peptide, for example. Therefore, for example, the aptamer can be used in detection of a His peptide as a substitute for the anti-His peptide antibody, and it becomes possible to detect a His peptide with superior accuracy. As described above, the aptamer of the preset invention is a very useful tool in the detection of a His peptide by biological means, for example.

While the present invention is described with reference to the illustrative embodiments and the examples, it is to be understood that changes and modifications that may become apparent to those skilled in the art may be made without departing from the scope of the present invention.

This application claims priority from Japanese Patent Application No. 2009-119269 filed on May 15, 2009. The entire subject matter of the Japanese Patent Applications is incorporated herein by reference.

The invention claimed is:

1. An aptamer which comprises a nucleotide sequence selected from the group consisting of SEQ ID NOs: 1-16.

2. A reagent comprising the aptamer according to claim 1.

3. A kit comprising the aptamer according to claim 1.

* * * * *